US006468546B1

(12) United States Patent
Mitcham et al.

(10) Patent No.: US 6,468,546 B1
(45) **Date of Patent: *Oct. 22, 2002**

(54) COMPOSITIONS AND METHODS FOR THERAPY AND DIAGNOSIS OF OVARIAN CANCER

(75) Inventors: Jennifer L. Mitcham, Redmond; Gordon E. King, Seattle; Paul A. Algate, Issaquah, all of WA (US)

(73) Assignee: Corixa Corporation, Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/404,879

(22) Filed: Sep. 24, 1999

Related U.S. Application Data

(63) Continuation-in-part of application No. 09/338,933, filed on Jun. 23, 1999, which is a continuation-in-part of application No. 09/216,003, filed on Dec. 17, 1998, which is a continuation-in-part of application No. 09/215,681, filed on Dec. 17, 1998.

(51) Int. Cl.[7] .......................... A61K 39/00; C07K 2/00; C07K 14/435

(52) U.S. Cl. ................................ 424/277.1; 424/184.1; 424/185.1; 424/192.1; 514/2; 530/300; 530/350; 530/806; 530/853

(58) Field of Search ................................ 530/300, 350, 530/806, 853; 424/184.1, 185.1, 192.1, 277.1; 514/2

(56) References Cited

PUBLICATIONS

Bookman et al., "Biological therapy of ovarian cancer: Current directions," *Seminars in Oncology*, 25(3):381–396.

Gillespie et al., "Mage, Bage and Gage: Tumour antigen expression in benign and malignant ovarian tissue," *British Journal of Cancer*, 78(6):816–821, Sep., 1998.

Heller et al., "Discovery and analysis of inflammatory disease–related genes using cDNA microarrays," *Proc. Natl. Acad. Sci. USA 94*:2150–2155, Mar., 1997.

Ishikawa et al., "Prediction of the coding sequence of unidentified human genes. The complete sequence of 100 new cDNA clones from brain which can code for large proteins in vitro," *DNA Res.*, 5:169–176, 1998.

Jin et al., "Human T cell leukemia virus type 1 oncoprotein tax targets the human mitotic checkpoint protein MAD1," *Cell 93*:81–91, Apr. 3, 1998.

Köhler et al., "Immotherapy of Ovarian Carcinoma with the Monoclonal Anti–Idiotype Antibody ACA125—Results of the Phase LB Study," *Gebrutshilfe und Fraenheilkunde*, 58(4):180–186, Apr. 1998 + (English Abstract).

Ma et al., "Use of encapsulated single chain antibodies for induction of anti–idiotypic humoral and cellular immune responses," *Journal of Pharmaceutical Sciences*, 87(11):1375–1378, Nov., 1998.

Peoples et al., "Ovarian cancer–associated lymphocyte recognition of folate binding protein peptides," *Annals of Surgical Oncology*, 5(8):743–750, Dec., 1998.

Schena et al., "Parallel human genome analysis: Microarray–based expression monitoring of 1000 genes," *Proc. Natl. Acad. Sci.*, 93:10614–10619, Oct., 1996.

*Primary Examiner*—Mary K. Zeman
(74) *Attorney, Agent, or Firm*—Seed Intellectual Property Law Group PLLC

(57) ABSTRACT

Compositions and methods for the therapy and diagnosis of cancer, such as ovarian cancer, are disclosed. Compositions may comprise one or more ovarian carcinoma proteins, immunogenic portions thereof, polynucleotides that encode such portions or antibodies or immune system cells specific for such proteins. Such compositions may be used, for example, for the prevention and treatment of diseases such as ovarian cancer. Methods are further provided for identifying tumor antigens that are secreted from ovarian carcinomas and/or other tumors. Polypeptides and polynucleotides as provided herein may further be used for the diagnosis and monitoring of ovarian cancer.

6 Claims, 92 Drawing Sheets

11729.1 contg

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11729-45.21.21.cons1

TAGGATGTGTTGGACCCTCTGTGTCAAAAAAAACCTCACAAAGAATCCCCTGCTCATTACAGAAGAAGATGCATTT
AAAATATGGGTTATTTTCAACTTTTTATCTGAGGACAAGTATCCATTAATTATTGTGTCAGAAGAGATTGAATACC
TGCTTAAGAAGCTTACAGAAGCTATGGGAGGAGGTTGGCAGCAAGAACAATTTGAACATTATAAAATCAACTTTGA
TGACAGTAAAAATGGCCTTTCTGCATGGGAACTTATTGAGCTTATTGGAAATGGACAGTTTAGCAAAGGCATGGAC
CGGCAGACTGTGTCTATGGCAATTAATGAAGTCTTTAATGAACTTATATTAGATGTGTTAAAGCAGGGTTACATGA
TGAAAAAGGGCCACAGACGGAAAAACTGGACTGAAAGATGGTTTGTACTAAAACCCAACATAATTTCTTACTATGT
GAGTGAGGATCTGAAGGATAAGAAAGGAGACATTCTCTTGGATGAAAATTGCTGTGTAGAGTCCTTGCCTGACAAA
GATGGAAA 11729-45.21.21.cons2

TTAGAGAGGCACAGAAGGAAGAAGAGTTAAAAGCAGCAAAGCCGGGTTTTTTTGTTTTGTTTTGTTTTGTTTTGTT
TTGAGATGGAGTCTCACTCTGTTGCCCAAGCTGGAGTACAACGGCATGATCTCAGCTCGCTGCAACCTCCGCCTCC
CACGTTCAAGTGATTCTCCTGCCTCAGCCTCCCAAGTAGCTGGGATTACAGGCGCCCGCCACCACGCTCAGCTAAT
TTTTTTTGTATTTTTAGTAGAGACAGGGTTTCACCAGGTTGGCCAGGCTGCTCTTGAACTCCTGACCTCAGGTGAT
CCACCCGCCTCGGCCTCCCAAAGTGCTGGGATTACAGGCGTGAGCCACCACGCCCGGCCCCCAAAGCTGTTTCTTT
TGTCTTTAGCGTAAAGCTCTCCTGCCATGCAGTATCTACATAACTGACGTGACTGCCAGCAAGCTCAGTCACTCCG
TGGTC 11731.1contig TCTTTTTCTTTCGATTTCCTTCAATTTGTCACGTTTGATTTTATGAAGTTGTTCAAGGGCTAACTGCTGTGTATTA
TAGCTTTCTCTGAGTTCCTTCAGCTGATTGTTAAATGAATCCATTTCTGAGAGCTTAGATGCAGTTTCTTTTTCAA
GAGCATCTAATTGTTCTTTAAGTCTTTGGCATAATTCTTCCTTTTCTGATGACTTTTTATGAAGTAAACTGATCCC
TGAATCAGGTGTGTTACTGAGCTGCATGTTTTTAATTCTTTCGTTTAATAGCTGCTTCTCAGGGACCAGATAGATA
AGCTTATTTTGATATTCCTTAAGCTCTTGTTGAAGTTGTTTGATTTCCATAATTTCCAGGTCACACTGTTTATCCA
AAACTTCTAGCTCAGTCTTTTGTGTTTGCTTTCTGATTTGGACATCTTGTAGTCTGCCTGAGATCTGCTGATGXTT
TCCATTCACTGCTTCCAGTTCCAGGTGGAGACTTTXCTTTCTGGAGCTCAGCCTGACAATGCCTTCTTGXTCCCT

*Fig. 1A*

11731.2contig

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTA 11734.1contig AATAGATTTAATGCAGAGTGTCAACTTCAATTGATTGATAGTGGCTGCCTAGAGTGCTGTGTTGAGTAGGTTTCTG
AGGATGCACCCTGGCTTGAAGAGAAAGACTGGCAGGATTAACAATATCTAAAATCTCACTTGTAGGAGAAACCACA
GGCACCAGAGCTGCCACTGGTGCTGGCACCAGCTCCACCAAGGCCAGCGAAGAGCCCAAATGTGAGAGTGGCGGTC
AGGCTGGCACCAGCACTGAAGCCACCACTGGTGCTGGCACTGGCACTGGCACTGTTATTGGTACTGGTACTGGCAC
CAGTGCTGGCACTGCCACTCTCTTGGGCTTTGGCTTTAGCTTCTGCTCCCGCCTGGATCCGGGCTTTGGCCCAGGG
TCCGATATCAGCTTCGTCCCAGTTGCAGGGCCCGGCAGCATTCTCCGAGCCGAGCCCAATGCCCATTCGAGCTCTA
ATCTCGGCCCTAGCCTTGGCTTCAGCTGCAGCCTCAGCTGCAGCCTTCAAATCCGCTTCCATCGCCTCTCGGTAC 11734.2contig GCCAAGAAAGCCCGAAAGGTGAAGCATCTGGATGGGGAAGAGGATGGCAGCAGTGATCAGAGTCAGGCTTCTGGAA
CCACAGGTGGCCGAAGGGTCTCAAAGGCCCTAATGGCCTCAATGGCCCGCAGGGCTTCAAGGGGTCCCATAGCCTT
TTGGGCCCGCAGGGCATCAAGGACTCGGTTGGCTGCTTGGGCCCGGAGAGCCTTGCTCTCCCTGAGATCACCTAAA
GCCCGTAGGGGCAAGGCTCGCCGTAGAGCTGCCAAGCTCCAGTCATCCCAAGAGCCTGAAGCACCACCACCTCGGG
ATGTGGCCCTTTTGCAAGGGAGGGCAAATGATTTGGTGAAGTACCTTTTGGCTAAAGACCAGACGAAGATTCCCAT
CAAGCGCTCGGACATGCTGAAGGACATCATCAAAGAATACACTGATGTGTACCCCGAAATCATTGAACGAGCAGGC
TATTCCTTGGAGAAGGTATTTGGGATTCAATTGAAGGAAATTGATAAGAATGACCACTTGTACATTCTTCTCAGC 11736.1contg GAGGTCTCACTATGTTGCCCAGGCTGTTCTTGAACTCCTGGGATCAAGCAATCCACCCATGTTGGTCTCCAAAAGT
GCTGGGATCATAGGCGTGAGCCACCTCACCCAGCCACCAATTTTCAATCAGGAAGACTTTTTCCTTCTTCAAGAAG
TGAAGGGTTTCCAGAGTATAGCTACACTATTGCTTGCCTGAGGGTGACTACAAAATTGCTTGCTAAAAGGTTAGGA
TGGGTAAAGAATTAGATTTTCTGAATGCAAAAATAAAATGTGAACTAATGAACTTTAGGTAATACATATTCATAAA
ATAATTATTCACATATTTCCTGATTTATCACAGAAATAATGTATGAAATGCTTTGAGTTTCTTGGAGTAAACTCCA
TTACTCATCCCAAGAAACCATATTATAAGTATCACTGATAATAAGAACAACAGGACCTTGTCATAAATTCTGGATA
AGAGAAATAGTCTCTGGGTGTTTGXTCTTAATTGATAAAATTTACTTGTCCATCTTTTAGTTCAGAATCACAAAA

*Fig. 1B*

11736.2contig

AAGCGGAAATGAGAAAGGAGGGAAAATCATGTGGTATTGAGCGGAAAACTGCTGGATGACAGGGCTCAGTCCTGTT
GGAGAACTCTGGGTGGTGCTGTAGAACAGGGCCACTCACAGTGGGGTGCACAGACCAGCACGGCTCTGTGACCTGT
TTGTTACAGGTCCATGATGAGGTAAACAATACACTGAGTATAAGGGTTGGTTTAGAAACTCTTACAGCAATTTGAC
AAAGTAATCTTCTGTGCAGTGAATCTAAGAAAAAAATTGGGGCTGTATTTGTATGTTCCTTTTTTTCATTTCATGT
TCTGAGTTACCTATTTTTATTGCATTTTACAAAAGCATCCTTCCATGAAGGACCGGAAGTTAAAAACAAAGCAGGT
CCTTTATCACAGCACTGTCGTAGAACACAGTTCAGAGTTATCCACCCAAGGAGCCAGGGAGCTGGGCTAAACCAAA
GAATTTTGCTTTTGGTTAATCATCAGGTACTTGAGTTGGAATTGTTTTAATCCCATCATTACCAGGCTGGAXGTG 11739-1&2

CCGCGGCTCCTGTCCAGACCCTGACCCTCCCTCCCAAGGCTCAACCGTCCCCCAACAACCGCCAGCCTTGTACTGA
TGTCGGCTGCGAGAGCCTGTGCTTAAGTAAGAATCAGGCCTTATTGGAGACATTCAAGCAAAGGTTGGACAACTAC
TTTTCCAGAACAGAAAGGAAACTCATGCATCAGAAAAGGTGACTAATAAAGGTACCAGAAGAATATGGCTGCACAA
ATACCAGAATCTGATCAGATAAAACAGTTTAAGGAATTTCTGGGGACCTACAATAAACTTACAGAGACCTGCTTTT
TGGACTGTGTTAGAGACTTCACAACAAGAGAAGTAAAACCTGAAGAGACCACCTGTTCAGAACATTGCTTACAGAA
ATATTTAAAAATGACACAAAGAATATCCATGAGATTTCAGGAATATCATATTCAGCAGAATGAAGCCCTGGCAGCC
AAAGCAGGACTCCTTGGCCAACCACGATAGAGAAGTCCTGATGGATGAACTTTTGATGAAAGATTGCCAACAGCTG
CTTTATTGGAAATGAGGACTCATCTGATAGAATCCCCTGAAAGCAGTAGCCACCATGTTCAACCATCTGTCATGAC
TGTTTGGCAAATGGAAACCGCTGGAGAAACAAAATTGCTATTTACCAGGAATAATCACAATAGAAGGTCTTATTGT
TCAGTGAAATAATAAGATGCAACATTTGTTGAGGCCTTATGATTCAGCAGCTTGGTCACTTGATTAGAAAAATAAA
CCATTGTTTCTTCAATTGTGACTGTTAATTTTAAAGCAACTTATGTGTTCGATCATGTATGAGATAGAAAAATTTT
TATTACTCAAAGTAAAATAAATGGA 11740.1.contig GAAAAAAAATATAAAACACACTTTTGCGAAAACGGTGGCCCTAAAAGAGGAAAAGAATTTCACCAATATAAATCCA
ATTTTATGAAAACTGACAATTTAATCCAAGAATCACTTTTGTAAATGAAGCTAGCAAGTGATGATATGATAAAATA
AACGTGGAGGAAATAAAAACACAAGACTTGGCATAAGATATATCCACTTTTGATATTAAACTTGTGAAGCATATTC
TTCGACAAATTGTGAAAGCGTTCCTGATCTTGCTTGTTCTCCATTTCAAATAAGGAGGCATATCACATCCCAAGAG
TAACAGAAAAAGAAAAAAGACATTTTTGCATTTTGAGATGAACCAAAGACACAAAACAAAACGAACAAAGTGTCAT
GTCTAATTCTAGCCTCTGAAATAAACCTTGAACATCTCCTACAAGGCACCGTGATTTTTGTAATTCTAACCTGAAG
AAATGTGATGACTTTTGTGGACATGAAAATCAGATGAGAAAACTGTGGTCTTTCCAAAGCCTGAACTCCCCTGAAA
ACCTTTGCA

*Fig. 1C*

11766.1.contig

CTGGGATCATTTCTCTTGATGTCATAAAAGACTCTTCTTCTTCCTCTTCATCCTCTTCTTCATCCTCTTCTGTACA
GTGCTGCCGGGTACAACGGCTATCTTTGTCTTTATCCTGAGATGAAGATGATGCTTCTGTTTCTCCTACCATAACT
GAAGAAATTTCGCTGGAAGTCGTTTGACTGGCTGTTTCTCTGACTTCACCTTCTTTGTCAAACCTGAGTCTTTTTA
CCTCATGCCCCTCAGCTTCCACAGCATCTTCATCTGGATGTTTATTTTTCAAAGGGCTCACTGAGGAAACTTCTGA
TTCAGAGGTCGAAGAGTCACTGTGATTTTTCTCCTCATTTTGCTGCAAATTTGCCTCTTTGCTGTCTGTGCTCTCA
GGCAACCCATTTGTTGTCATGGGGGCTGACAAAGAAACCTTTGGTCGATTAAGTGGCCTGGGTGTCCCAGGCCCAT
TTATATTAGACCTCTCAGTATAGCTTGGTGAATTTCCAGGAAACATAACACCATTCATTCGATTTAAACTATTGGA
ATTGGTTTT 11766.2.contig GAGGGTTGGTGGTAGCGGCTTGGGGAGGTGCTCGCTCTGTCGGTCTTGCTCTCTCGCACGCTTCCCCCGGCTCCCT
TCGTTTCCCCCCCCCGGTCGCCTGCGTGCCGGAGTGTGTGCGAGGGAGGGGGAGGGCGTCGGGGGGGTGGGGGAG
GCGTTCCGGTCCCCAAGAGACCCGCGGAGGGAGGCGGAGGCTGTGAGGGACTCCGGGAAGCCATGGACGTCGAGAG
GCTCCAGGAGGCGCTGAAAGATTTTGAGAAGAGGGGGAAAAAGGAAGTTTGTCCTGTCCTGGATCAGTTTCTTTGT
CATGTAGCCAAGACTGGAGAAACAATGATTCAGTGGTCCCAATTTAAAGGCTATTTTATTTTCAAACTGGAGAAAG
TGATGGATGATTTCAGAACTTCAGCTCCTGAGCCAAGAGGTCCTCCCAACCCTAATGTCGA 11773.2.contig AAGCAGGCGGCTCCCGCGCTCGCAGGGCCGTGCCACCTGCCCGCCCGCCCGCTCGCTCGCTCGCCCGCCGCGCCGC
GCTGCCGACCGCCAGCATGCTGCCGAGAGTGGGCTGCCCCGCGCTGCCGXTGCCG 11775-1&2

ATCTCTTGTATGCCAAATATTTAATATAAATCTTTGAAACAAGTTCAGATGAAATAAAAATCAAAGTTTGCAAAAA
CGTGAAGATTAACTTAATTGTCAAATATTCCTCATTGCCCCAAATCAGTATTTTTTTTATTTCTATGCAAAAGTAT
GCCTTCAAACTGCTTAAATGATATATGATATGATACACAAACCAGTTTTCAAATAGTAAAGCCAGTCATCTTGCAA
TTGTAAGAAATAGGTAAAAGATTATAAGACACCTTACACACACACACACACACACACACGTGTGCACGCCAATGAC
AAAAAACAATTTGGCCTCTCCTAAAATAAGAACATGAAGACCCTTAATTGCTGCCAGGAGGGAACACTGTGTCACC
CCTCCCTACAATCCAGGTAGTTTCCTTTAATCCAATAGCAAATCTGGGCATATTTGAGAGGAGTGATTCTGACAGC
CACGTTGAAATCCTGTGGGGAACCATTCATGTCCACCCACTGGTGCCCTGAAAAAATGCCAATAATTTTTCGCTCC
CACTTCTGCTGCTGtCTCTTCCACATCCTCACATAGACCCCAGACCCGCTGGCCCCTGGCTGGGCATCGCATTGCT
GGTAGAGCAAGTCATAGGTCTCGTCTTTGACGTCACAGAAGCGATACACCAAATTGCCTGGTCGGTCATTGTCATA
ACCAGAGA

*Fig. 1D*

11777.1&2.cons

CAGACGGGGTTTCACTATGTTGGCTAGGCTGGTCTTGAACTCCTGACTTCAGGTGATCTGCCTGCCTTGGCCTCCC
AAAGTGCTGGGATTACAGGCATAAGCCACTGCGCCCGGCTGATCTGATGGTTTCATAAGGCTTTTCCCCCTTTTGC
TCAGCACTTCTCCTTCCTGCCGCCATGTGAAGAAGGACATGTTTGCTTCCCCTTCCACCACGATTGTAAGTTGTTT
CCTGAGGCCTCCCCGGCCATGCTGAACTGTGAGTCAATTAAACCTCTTTCCTTTATAAATTATCCAGTTTTGGGTA
TGTCTTTATTAGTAGAATGAGAACAGACTAATACAACCCTTAAAGGAGACTGACGGAGAGGATTCTTCCTGGATCC
CAGCACTTCCTCTGAATGCTACTGACATTCTTCTTGAGGACTTTAAACTGGGAGATAGAAAACAGATTCCATGGCT
CAGCAGCCTGAGAGCAGGGAGGGAGCCAAGCTATAGATGACATGGGCAGCCTCCCCTGAGGCCAGGTGTGGCCGAA
CCTGGGCAGTGCTGCcACCCACCCCACCAGGGCCAAGTCCTGTCCTTGGAGAGCCAAGCCTCAATCACTGCTAGCC
TCAAGTGTCCCCAAGCCACAGTGGCTAGGGGGACTCAGGGAACAGTTCCCAGTCTGCCCTACTTCTCTTACCTTTA
CCCCTCATACCTCCAAAGTAGACCATGTTCATGAGGTCCAAAGG 11779.2.contig AAGCGAGGAAGCCACTGCGGCTCCTGGCTGAAAAGCGGCGCCAGGCTCGGGAACAGAGGGAACGCGAAGAACAGGA
GCGGAAGCTGCAGGCTGAAAGGGACAAGCGAATGCGAGAGGAGCAGCTGGCCCGGGAGGCTGAAGCCCGGGCTGAA
CGTGAGGCCGAGGCGCGGAGACGGGAGGAGCAGGAGGCTCGAGAGAAGGCGCAGGCTGAGCAGGAGGAGCAGGAGC
GACTGCAGAAGCAGAAAGAGGAAGCCGAAGCCCGGTCCCGGGAAGAAGCTGAGCGCCAGCGCCAGGAGCGGGAAAA
GCACTTTCAGAAGGAGGAACAGGAGAGACAAGAGCGAAGAAAGCGGCTGGAGGAGATAATGAAGAGGACTCGGAAA
TCAGAAGCCGCCGAAACCAAGAAGCAGGATGCAAAGGAGACCGCAGCTAACAATTCCGGCCCAGACCCTTGTGAAA
GCTGTAGAGACTCGGCCCTCTGGGCTTCCAGAAAGGATTCTATTGCAGAAAGGAAGGAGCTXGGCCCCCCAXGGA 11781 & 37.cons CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACXTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAAT

CTCTGTGGAAAACTGATGAGGAATGAATTTACCATTACCCATGTTCTCATCCCCAAGCAAAGTGCTGGGTCTGATT
ACTGCAACACAGAGAACGAAGAAGAACTTTTCCTCATACAGGATCAGCAGGGCCTCATCACACTGGGCTGGATTCA
TACTCACCCCACACAGACCGCGTTTCTCTCCAGTGTCGACCTACACACTCACTGCTCTTACCAGATGATGTTGCCA
GAGTCAGTAGCCATTGTTTGCTCCCCCAAGTTCCAGGAAACTGGATTCTTTAAACTAACTGACCATGGACTAGAGG
AGATTTCTTCCTGTCGCCAGAAAGGATTTCATCCACACAGCAAGGATCCACCTCTGTTCTGTAGCTGCAGCCACGT
GACTGTTGTGGACAGAGCAGTGACCATCACAGACCTTCGATGAGCGTTTGAGTCCAACACCTTCCAAGAACAACAA
AACCATATCAGTGTACTGTAGCCCCTTAATTTAAGCTTTCTAGAAAGCTTTGGAAGTTTTTGTAGATAGTAGAAAG
GGGGGCATCACCTGAGAAAGAGCTGATTTTGTATTTCAGGTTTGAAAAGAAATAACTGAACATATTTTTTAGGCAA
GTCAGAAAGAGAACATGGTCACCCAAAAGCAACTGTAACTCAGAAATTAAGTTACTCAGAAATTAAGTAGCTCAGA
AATTAAGAAAGAATGGTATAATGAACCCCCATATACCCTTCCTTCTGGATTCACCAATTGTTAACATTTTTTTCCT
CTCAGCTATCCTTCTAATTTCTCTCTAATTTCAATTTGTTTATATTTACCTCTGGGCTCAATAAGGGCATCTGTGC
AGAAATTTGGAAGCCATTTAGAAAATCTTTTGGATTTTCCTGTGGTTTATGGCAATATGAATGGAGCTTATTACTG
GGGTGAGGGACAGCTTACTCCATTTGACCAGATTGTTTGGCTAACACATCCCGAAGAATGATTTTGTCAGGAATTA
TTGTTATTTAATAAATATTTCAGGATATTTTTCCTCTACAATAAAGTAACAATTA 11784-1 & 2

GGACGACAAGGCCATGGCGATATCGGATCCGAATTCAAGCCTTTGGAATTAAATAAACCTGGAACAGGGAAGGTGA
AAGTTGGAGTGAGATGTCTTCCATATCTATACCTTTGTGCACAGTTGAATGGGAACTGTTTGGGTTTAGGGCATCT
TAGAGTTGATTGATGGAAAAAGCAGACAGGAACTGGTGGGAGGTCAAGTGGGGAAGTTGGTGAATGTGGAATAACT
TACCTTTGTGCTCCACTTAAACCAGATGTGTTGCAGCTTTCCTGACATGCAAGGATCTACTTTAATTCCACACTCT
CATTAATAAATTGAATAAAAGGGAATGTTTTGGCACCTGATATAATCTGCCAGGCTATGTGACAGTAGGAAGGAAT
GGTTTCCCCTAACAAGCCCAATGCACTGGTCTGACTTTATAAATTATTTAATAAAATGAACTATTATC 11785.2.contig GGCAGTGACATTCACCATCATGGGAACCACCTTCCCTTTTCTTCAGGATTCTCTGTAGTGGAAGAGAGCACCCAGT
GTTGGGCTGAAAACATCTGAAAGTAGGGAGAAGAACCTAAAATAATCAGTATCTCAGAGGGCTCTAAGGTGCCAAG
AAGTCTCACTGGACATTTAAGTGCCAACAAAGGCATACTTTCGGAATCGCCAAGTCAAAACTTTCTAACTTCTGTC
TCTCTCAGAGACAAGTGAGACTCAAGAGTCTACTGCTTTAGTGGCAACTACAGAAAACTGGTGTTACCCAGAAAAA
CAGGAGCAATTAGAAATGGTTCCAATATTTCAAAGCTCCGCAAACAGGATGTGCTTTCCTTTGCCCATTTAGGGTT
TCTTCTCTTTCCTTTCTCTTTATTAACCACT

*Fig. 1F*

11718-1&2 cons

TGCGCTGAAAACAACGGCCTCCTTTACTGTTAAAATGCAGCCACAGGTGCTTAGCCGTGGGCATCTCAACCACCAG
CCTCTGTGGGGGGCAGGTGGGCGTCCCTGTGGGCCTCTGGGCCCACGTCCAGCCTCTGTCCTCTGCCTTCCGTTCT
TCGACAGTGTTCCCGGCATCCCTGGTCACTTGGTACTTGGCGTGGGCCTCCTGTGCTGCTCCAGCAGCTCCTCCAG
GXGGTCGGCCCGCTTCACCGCAGCCTCATGTTGTGTCCGGAGGCTGCTCACGGCCTCCTCCTTCCTCGCGAGGGCT
GTCTTCACCCTCCGGXGCACCTCCTCCAGCTCCAGCTGCTGGCGGGCCTGCAGCGTGGCCAGCTCGGCCTTGGCCT
GCCGCGTCTCCTCCTCARAGGCTGCCAGCCGGTCCTCGAACTCCTGGCGGATCACCTGGGCCAGGTTGCTGCGCTC
GCTAGAAAGCTGCTCGTTCACCGCCTGCGCATCCTCCAGCGCCCGCTCCTTCTGCCGCACAAGGCCCTGCAGACGC
AGATTCTCGCCCTCGGCcTCCCCAAGCTGGCCCTTCAGCTCCGAGCACCGCTCCTGAAGCTTCCGCTCCGACTGCT
CCAGCTCGGAGAGCTCGGCCTCGTACTTGTCCCGTAAGCGCTTGATGCGGCTCTCGGCAGCCTTCTCACTCTCCTC
CTTGGCCAGCGCCATGTCGGCCTCCAGCCGGTGAATGACCAGCTCAATCTCCTTGTCCCGGCCTTTCCGGATTTCT
TCCCTCAGCTCCTGTTCCCGGTTCAGCAGCCACGCCTCCTCCTTCCTGGTGCGGCCGGCCTCCCACGCCTGCCTCT
CCAGCTCCAGCTGCTGCTTCAGGGTATTCAGCTCCATCTGGCGGGCCTGCAGCGTGGCCA 13690.4

CAACTTATTACTTGAAATTATAATATAGCCTGTCCGTTTGCTGTTTCCAGGCTGTGATATATTTTCCTAGTGGTTT
GACTTTAAAAATAAATAAGGTTTAATTTTCTCCCC 13693.1

TGCAAGTCACGGGAGTTTATTTATTTAATTTTTTTCCCCAGATGGAGACTCTGTCGCCCAGGCTGGAGTGCAATGG
TGTGATCTTGGCTCACTGCAACCTCCACCTCCTGGGTTCAAGCGATTCTCCTGCCACAGCCTCCCGAGTAGCTGGG
ATTACAGGTGCCCGCCACCACACCCAGCTAATTTTTATATTTTTAGTAAAGACAGGGTTTCCCCATGTTGGCCAGG
CTGGTCTTGAACTTCTGACCTCAGGTGATCCACCTGCCTCGGCCTCCCAAAGTGTTGGGATTACAGGCGTGAGCTA
CCCGTGCCTGGCCAGCCACTGGAGTTTAAAGGACAGTCATGTTGGCTCCAGCCTAAGGCGGCATTTTCCCCCATCA
GAAAGCCCGCGGCTCCTGTACCTCAAAATAGGGCACCTGTAAAGTCAGTCAGTGAAGTCTCTGCTCTAACTGGCCA
CCCGGGGCCATTGGCNTCTGACACAGCCTTGCCAGGANGCCTGCATCTGCAAAAGAAAAGTTCACTTCCTTTCCG 13694.1

CAGAGAATCTKAGAAAGATGTCGCGTTTTCTTTTAATGAATGAGAGAAGCCCATTTGTATCCCTGAATCATTGAGA
AAAGGCGGCGGTGGCGACAGCGGCGACCTAGGGATCGATCTGGAGGGACTTGGGGAGCGTGCAGAGACCTCTAGCT
CGAGCGCGAGGGACCTCCCGCCGGGATGCCTGGGGAGCAGATGGACCCTACTGGAAGTCAGTTGGATTCAGATTTC
TCTCAGCAAGATACTCCTTGCCTGATAATTGAAGATTCTCAGCCTGAAAGCCAGGTTCTAGAGGATGATTCTGGTT
CTCACTTCAGTATGCTATCTCGACACCTTCCTAATCTCCAGACGCACAAAGAAAATCCTGTGTTGGATGTTGNGTC
CAATCCTTGAACAAACAGCTGGAGAAGAACGAGGAGACCGGTAATAGTGGGTTCAATGAACATTTGAAAGAAAACC
AGGTTGCAGACCCTG

GACTGTCCTGAACAAGGGACCTCTGACCAGAGAGCTGCAGGAGATGCAGAGTGGTGGCAGGAGTGGAAGCCAAAGA
ACACCCACCTTCCTCCCTTGAAGGAGTAGAGCAACCATCAGAAGATACTGTTTTATTGCTCTGGTCAAACAAGTCT
TCCTGAGTTGACAAAACCTCAGGCTCTGGTGACTTCTGAATCTGCAGTCCACTTTCCATAAGTTCTTGTGCAGACA
ACTGTTCTTTTGCTTCCATAGCAGCAACAGATGCTTTGGGGCTAAAAGGCATGTCCTCTGACCTTGCAGGTGGTGG
ATTTTGCTCTTTTACAACATGTACATCCTTACTGGGCTGTGCTGTCACAGGGATGTCCTTGCTGGACTGTTCTGCT
ATGGGGATATCTTCGTTGGACTGTTCTTCATGCTTAATTGCAGTATTAGCATCCACATCAGACAGCCTGGTATAAC
CAGAGTTGGTGGTTACTGATTGTAGCTGCTCTTTGTCCACTTCATATGGCACAAGTATTTTCCTCAACATCCTGGC
TCTGGGAAG 13695.1

GAAATGTATATTTAATCATTCTCTTGAACGATCAGAACTCTRAAATCAGTTTTCTATAACARCATGTAATACAGTC
ACCGTGGCTCCAAGGTCCAGGAAGGCAGTGGTTAACACATGAAGAGTGTGGGAAGGGGGCTGGAAACAAAGTATTC
TTTTCCTTCAAAGCTTCATTCCTCAAGGCCTCAATTCAAGCAGTCATTGTCCTTGCTTTCAAAAGTCTGTGTGTGC
TTCATGGAAGGTATATGTTTGTTGCCTTAATTTGAATTGTGGCCAGGAAGGGTCTGGAGATCTAAATTCAGAGTAA
GAAAACCTGAGCTAGAACTCAGGCATTTCTCTTACAGAACTTGGCTTGCAGGGTAGAATGAANGGAAAGAAACTTA
GAAGCTCAACAAGCTGAAGATAATCCCATCAGGCATTTCCCATAGGCCTTGCAACTCTGTTCACTGAGAGATGTTA
TCCTG 13695.2

AGTCTGGAGTGAGCAAACAAGAGCAAGAAACAARRAGAAGCCAAAAGCAGAAGGCTCCAATATGAACAAGATAAAT
CTATCTTCAAAGACATATTAGAAGTTGGGAAAATAATTCATGTGAACTAGACAAGTGTGTTAAGAGTGATAAGTAA
AATGCACGTGGAGACAAGTGCATCCCCAGATCTCAGGGACCTCCCCCTGCCTGTCACCTGGGGAGTGAGAGGACAG
GATAGTGCATGTTCTTTGTCTCTGAATTTTTAGTTATATGTGCTGTAATGTTGCTCTGAGGAAGCCCCTGGAAAGT
CTATCCCAACATATCCACATCTTATATTCCACAAATTAAGCTGTAGTATGTACCCTAAGACGCTGCTAATTGACTG
CCACTTCGCAACTCAGGGGCGGCTGCATTTTAGTAATGGGTCAAATGATTCACTTTTTATGATGCTTCCCAAGGTG
CCTTGGCTTCTCTTCCCAACTGACAAATGCCCAAGTTGAGAAAAATGATCATAATTTTAGCATAAACCGAGCAATC
GGCGACCCC 13697.1

TAGCTGTCTTCCTCACTCTTATGGCAATGACCCCATATCTTAATGGATTAAGATAATGAAAGTGTATTTCTTACAC
TCTGTATCTATCACCAGAAGCTGAGGTGATAGCCCGCTTGTCATTGTCATCCATATTCTGGGACTCAGGCGGGAAC
TTTCTGGAATATTGCCAGGGAGCATGGCAGAGGGGCACAGTGCATTCTGGGGGAATGCACATTGGCTCAGCCTGGG
TAATGAGTGATATACATTACCTCTGTTCACAACTCATTGCCCAGCACCAGTCACAAGGCCCCACCAAATACCAGAG
CCCAAGAAATGTAGTCCTGTTGATATGGTTTTGCTGTGTCCCAACCCAAATCTCATCTTGAATTGTAAGCTCCCAT
AATTCCCATGTGTTGTGGGAGGGACCTGGTG

ATCATGAGGATGTTACCAAAGGGATGGTACTAAACCATTTGTATTCGTCTGTTTTCACACTGCTTTGAAGATACTA
CCTGAGACTGGGTAATTTATAAACAAAAGAGATTTAATTGACTCACAGTTCTGCATGGCTGAAGAGGCCTCAGGAA
ACTTACAGTCATGGTGGAAGGCAAAGGAGGAGCAAGGCATGTCTTACATGTCAGTAGGAGAGAGAGCGAGAGCAGG
AGAACCTGCCACTTATAAACCATTCAGATCTCATAACTCCCTATCATGAGAAAAACATGGAGGAAACCACCCTCAT
GATCCAATCACCTCCCGCCAGGTCCCTCCCTCGACACGTGGGGATTATAATTCAGGATTAGAGGGACACAGAGACA
AACCATATCATCATTCATGAGAAATCCACCCTCATAGTCCAATCAGCTCCTACCAGGCCCCACCTCCAACACTGGG
GATTGCAATTCAACATGAGATTTGGATGGGGACACAGATTCAAACCATATCATAC 13699.1&2

CATGGCCTTTCTCCTTAGAGGCCAGAGGTGCTGCCCTGGCTGGGAGTGAAGCTCCAGGCACTACCAGCTTTCCTGA
TTTTCCCGTTTGGTCCATGTGAAGAGCTACCACGAGCCCCAGCCTCACAGTGTCCACTCAAGGGCAGCTTGGTCCT
CTTGTCCTGCAGAGGCAGGCTGGTGTGACCCTGGGAACTTGACCCGGGAACAACAGGTGGCCCAGAGTGAGTGTGG
CCTGGCCCCTCAACCTAGTGTCCGTCCTCCTCTCTCCTGGAGCCAGTCTTGAGTTTAAAGGCATTAAGTGTTAGAT
ACAAGCTCCTTGTGGCTGGAAAAACACCCCTCTGCTGATAAAGCTCAGGGGGCACTGAGGAAGCAGAGGCCCCTTG
GGGGTGCCCTCCTGAAGAGAGCGTCAGGCCATCAGCTCTGTCCCTCTGGTGCTCCCACGTCTGTTCCTCACCCTCC
ATCTCTGGGAGCAGCTGCACCTGACTGGCCACGCGGGGGCAGTGGAGGCACAGGCTCAGGGTGGCCGGGCTACCTG
GCACCCTATGGCTTACAAAGTAGAGTTGGCCCAGTTTCCTTCCACCTGAGGGGAGCACTCTGACTCCTAACAGTCT
TCCTTGCCCTGCCATCATCTGGGGTGGCTGGCTGTCAAGAAAGGCCGGGCATGCTTTCTAAACACAGCCACAGGAG
GCTTGTAGGGCATCTTCCAGGTGGGGAAACAGTCTTAGATAAGTAAGGTGACTTGCCTAAGGCCTCCCAGCACCCT
TGATCTTGGAGTCTCACAGCAGACTGCATGTSAACAACTGGAACCGAAAACATGCCTCAGTATAAAA 13703.3

CCAGAACCTCCTTCTCTTTGGAGAATGGGGAGGCCTCTTGGAGACACAGAGGGTTTCACCTTGGATGACCTCTAGA
GAAATTGCCCAAGAAGCCCACCTTCTGGTCCCAACCTGCAGACCCCACAGCAGTCAGTTGGTCAGGCCCTGCTGTA
GAAGGTCACTTGGCTCCATTGCCTGCTTCCAACCAATGGGCAGGAGAGAAGGCCTTTATTTCTCGCCCACCCATTC
TCCTGTACCAGCACCTCCGTTTTCAGTCAGYGTTGTCCAGCAACGGTACCGTTTACACAGTCA 13705.1

TGCATGTAGTTTTATTTATGTGTTTTSGTCTGGAAAACCAAGTGTCCCAGCAGCATGACTGAACATCACTCACTTC
CCCTACTTGATCTACAAGGCCAACGCCGAGAGCCCAGACCAGGATTCCAAACACACTGCACGAGAATATTGTGGAT
CCGCTGTCAGGTAAGTGTCCGTCACTGACCCARACGCTGTTACGTGGCACATGACTGTACAGTGCCACGTAACAGC
ACTGTACTTTTCTCCCATGAACAGTTACCTGCCATGTATCTACATGATTCAGAACATTTTGAACAGTTAATTCTGA
CACTTGAATAATCCCATCAAAAACCGTAAAATCACTTTGATGTTTGTAACGACAACATAGCATCACTTTACGACAG
AATCATCTGGAAAAACAGAACAACGAATACATACATCTTAAAAAATGCTGGGGTGGGCCAGGCACAGCTTCACGCC
TGTAATCCCAGCACTTTGGGAGGCTTAAGCGGGTG

TGGGGCGGAAAGAAGCCAAGGCCAAGGAGCTGGTGCGGCAGCTGCAGCTGGAGGCCGAGGAGCAGAGGAAGCAGAA
GAAGCGGCAGAGTGTGTCGGGCCTGCACAGATACCTTCACTTGCTGGATGGAAATGAAAATTACCCGTGTCTTGTG
GATGCAGACGGTGATGTGATTTCCTTCCCACCAATAACCAACAGTGAGAAGACAAAGGTTAAGAAAACGACTTCTG
ATTTGTTTTTGGAAGTAACAAGTGCCACCAGTCTGCAGATTTGCAAGGATGTCATGGATGCCCTCATTCTGAAAAT
GGCAAGAAATGAAAAAGTACACTTTAGAAAATAAAGAGGAAGGATCACTCTCAGATACTGAAGCCGATGCAGTCTC
TGGACAACTTCCAGATCCCACAACGAATCCCAGTGCTGGAAAGGACGGGCCCTTCCTTCTGGTGGTGGAACANGTC
CCGGTGGTGGATCTTGGAANGGAACCTGAANGTGGTGTACCCCGTCCAAGGCCGACCTTGGCCAC 13707.4

TCCCGCGCTCGCAGGGCNCGTGCCACCTGCCYGTCCGCCCGCTCGCTCGCTCGCCCGCCGCGCCGCGCTGCCGACC
GYCAGCATGCTGCCGAGAGTGGGCTGCCCCGCGCTGCCGCTGCCGCCGCCGCCGCTGCTGCCGCTGCTGCCGCTGC
TGCTGCTGC 13708.1&2

GGCGGGTAGGCATGGAACTGAGAAGAACGAAGAAGCTTTCAGACTACGTGGGGAAGAATGAAAAAACCAAAATTAT
CGCCAAGATTCAGCAAAGGGGACAGGGAGCTCCAGCCCGAGAGCCTATTATTAGCAGTGAGGAGCAGAAGCAGCTG
ATGCTGTACTATCACAGAAGACAAGAGGAGCTCAAGAGATTGGAAGAAAATGATGATGATGCCTATTTAAACTCAC
CATGGGCGGATAACACTGCTTTGAAAAGACATTTTCATGGAGTGAAAGACATAAAGTGGAGACCAAGATGAAGTTC
ACCAGCTGATGACACTTCCAAAGAGATTAGCTCACCT 13709.1

TCTGAAGGTTAAATGTTTCATCTAAATAGGGATAATGRTAAACACCTATAGCATAGAGTTGTTTGAGATTAAATGA
GATAATACATGTAAAATTATGTGCCTGGCATACAGCAAGATTGTTGTTGTTGTTGATGATGATGATGATGATGATA
ATATTTTTCTATCCCCAGTGCACAACTGCTTGAACCTATTAGATAATCAATACATGTTTCTTGAACTGAGATCAAT
TTCCCCATGTTGTCTGACTGATGAAGCCCTACATTTTCTTCTAGAGGAGATGACATTTGAGCAAGATCTTAAAGAA
AATCAGATGCCTTCACCTGACCACTGCTTGGTGATCCCATGGCACTTTGTACATCTCTCCATTAGCTCTCATCTCA
CCAGCCCATCATTATTGTATGTGCTGCCTTCTGAAGCTTGCAGCTGGCTACCATCMGGTAGAATAAAAATCATCCT
TTCATAAAATAGTGACCCTCCTTTTTTATTTGCATTTCCCAAAGCCAAGCACCGTGGGANGGTAG

TATGAAGAAGGGAAAAGAAGATAATTTGTGAAAGAAATGGGTCCAGTTACTAGTCTTTGAAAAGGGTCAGTCTGTA
GCTCTTCTTAATGAGAATAGGCAGCTTTCAGTTGCTCAGGGTCAGATTTCCTTAGTGGTGTATCTAATCACAGGAA
ACATCTGTGGTTCCCTCCAGTCTCTTTCTGGGGGACTTGGGCCCACTTCTCATTTCATTTAATTAGAGGAAATAGA
ACTCAAAGTACAATTTACTGTTGTTTAACAATGCCACAAAGACATGGTTGGGAGCTATTTCTTGATTTGTGTAAAA
TGCTGTTTTTGTGTGCTCATAATGGTTCCAAAAATTGGGTGCTGGCCAAAGAGAGATACTGTTACAGAAGCCAGCA
AGAAGACCTCTGTTCATTCACACCCCCGGGGATATCAGGAATTGACTCCAGTGTGTGCAAATCCAGTTTGGCCTAT
CTTCT 13712.1&2

TGAGGGACTGATTGGTTTGCTCTCTGCTATTCAATTCCCCAAGCCCACTTGTTCCTGCAGCGTCCTCCTTCTCATT
CCCTTTAGTTGTACCCTCTCTTTCATCTGAGACCTTTCCTTCTTGATGTCGCCTTTTCTTCTTCTTGCTTTTTCTG
ATGTTCTGCTCAGCATGTTCTGGGTGCTTCTCATCTGCATCATTCCTTTCAGATGCTGTAGCTTCTTCCTCCTCTT
TCTGCCTCCTTTTCTTTTTCTTTTTTTTGGGGGGCTTGCTCTCTGACTGCAGTTGAGGGGCCCCAGGGTCCTGGCC
TTTGAGACGAGCCAGGAAGGCCTGCTCCTGGGCCTCTAGGCGAGCAAGCTTGGCCTTCATTGTGATCCCAAGACGG
GCAGCCTTGTGTGCTGTTCGCCCCTCACAGGCTTGGAGCAGCATCTCATCAGTCAGAATCTTTGGGGACTTGGACC
CCTGGTTGTCGTCATCACTGCAGCTCTCCAAGTCTTTGTTTGGCTTCTCTCCACCTGAAGTCAATGTAGCCATCTT
CACAAACTTCTGATACAGCAAGTTGGGCTTGGGATGATTATAACGGGTGGTCTCCTTAGAAAGGCTCCTTATCTGT
ACTCCATCCTGCCCAGTTTCCACTACCAAGTTGGCCGCAGTCTTGTTGAAGAGCTCATTCCACCAGTGGTTTGTGA
ACTCCTTGGCAGGGTCATGTCCTACCCCATGAGTGTCTTGCTTCAGYGTCACCCTGAGAGCCTGAGTGATACCATT
CTCCTTCCG 13714.1&2

GACAACATGAAATAAATCCTAGAGGACAAAATTAAACTCAATAGAGTGTAGTCTAGTTAAAAACTCGAAAAATGAG
CAAGTCTGGTGGGAGTGGAGGAAGGGCTATACTATAAATCCAAGTGGGCCTCCTGATCTTAACAAGCCATGCTCAT
TATACACATCTCTGAACTGGACATACCACCTTTACGCAGGAAACAGGGCTTGGAACTTCTAAGGGAAATTAACATG
CACCACCCACATCTAACCTACCTGCCGGGTAGGTACCATCCCTGCTTCGCTGAAATCAGTGCTC 13716.1&2

TTGGAATTAAATAAACCTGGAACAGGGAAGGTGAAAGTTGGAGTGAGATGTCTTCCATATCTATACCTTTGTGCAC
AGTTGAATGGGAACTGTTTGGGTTTAGGGCATCTTAGAGTTGATTGATGGAAAAAGCAGACAGGAACTGGTGGGAG
GTCAAGTGGGGAAGTTGGTGAATGTGGAATAACTTACCTTTGTGCTCCACTTAAACCAGATGTGTTGCAGCTTTCC
TGACATGCAAGGATCTACTTTAATTCCACACTCTCATTAATAAATTGAATAAAAGGGAATGTTTTGGCACCTGATA
TAATCTGCCAGGCTATGTGACAGTAGGAAGGAATGGTTTCCCCTAACAAGCCCAATGCACTGGTCTGACTTTATAA
ATTATTTAATAAAATGAACTATTATC

AAACTGGACCTGCAACAGGGACATGAATTTACTGCARGGTCTGAGCAAGCTCAGCCCCTCTACCTCAGGGCCCCAC
AGCCATGACTACCTCCCCCAGGAGCGGGAGGGTGAAGGGGGCCTGTCTCTGCAAGTGGAGCCAGAGTGGAGGAATG
AGCTCTGAAGACACAGCACCCAGCCTTCTCGCACCAGCCAAGCCTTAACTGCCTGCCTGACCCTGAACCAGAACCC
AGCTGAACTGCCCCTCCAAGGGACAGGAAGGCTGGGGGAGGGAGTTTACAACCCAAGCCATTCCACCCCCTCCCCT
GCTGGGGAGAATGACACATCAAGCTGCTAACAATTGGGGGAAGGGGAAGGAAGAAAACTCTGAAAACAAAATCTTG
T 13722.3

CATGCGTTTCACCACTGTTGGCCAGGCTGGTCTCGAACTCCTGGCCTCAAGCAATCCACCCGCCTCAGCCTCCAAA
AGTGCTGGGATTACAGATGTGAGCCATGGCACCATGCCAAAAGGCTATATTCCTGGCTCTGTGTTTCCGAGACTGC
TTTTAATCCCAACTTCTCTACATTTAGATTAAAAAATATTTTATTCATGGTCAATCTGGAACATAATTACTGCATC
TTAAGTTTCCACTGATGTATATAGAAGGCTAAAGGCACAATTTTTATCAAATCTAGTAGAGTAACCAAACATAAAA
TCATTAATTACTTTCAACTTAATAACTAATTGACATTCCTCAAAAGAGCTGTTTTCAATCCTGATAGGTTCTTTAT
TTTTTCAAAATATATTTGCCATGGGATGCTAATTTGCAATAAGGCGCATAATGAGAATACCCCAAACTGGA 13722.4

GTTGGACCCCCAGGGACTGGAAAGACACTTCTTGCCCGAGCTGTGGCGGGAGAAGCTGATGTTCCTTTTTATTATG
CTTCTGGATCCGAATTTGATGAGATGTTTGTGGGTGTGGGAGCCAGCCGTATCAGAAATCTTTTTAGGGAAGCAAA
GGCGAATGCTCCTTGTGTTATATTTATTGATGAATTAGATTCTGTTGGTGGGAAGAGAATTGAATCTCCAATGCAT
CCATATTCAAGGCAGACCATAAATCAACTTCTTGCTGAAATGGATGGTTTTAAACCCAATGAAGGAGTTATCATAA
TAGGAGCCACAAACTTCCCAGAGGCATTAGATAATGCCTTAATACCGTCCTGGTCGTTTTGACATGCAAGTTACAG
TTCCAAGGCCAGATGTAAAAGGTCGAACAGAAATTTTGAAATGGTATCTCAATAAAATAAAGTTTGATCAATCCCG
TTGATCCAGAAATTATAGCCTCGAGGTACTGGTGGCTTTTCCGGAAGCAGAGTTGGGAGAATCTT 13724-13698-13748

GCCTACAACATCCAGAAAGAGTCTACCCTGCACCTGGTGCTSCGTCTCAGAGGTGGGATGCAGATCTTCGTGAAGA
CCCTGACTGGTAAGACCATCACTCTCGAAGTGGAGCCGAGTGACACCATYGAGAACGTCAAAGCAAAGATCCARGA
CAAGGAAGGCRTYCCTCCTGACCAGCAGAGGTTGATCTTTGCCGGAAAGCAGCTGGAAGATGGDCGCACCCTGTCT
GACTACAACATCCAGAAAGAGTCYACCCTGCACCTGGTGCTCCGTCTCAGAGGTGGGATGCARATCTTCGTGAAGA
CCCTGACTGGTAAGACCATCACCCTCGAGGTGGAGCCCAGTGACACCATCGAGAATGTCAAGGCAAAGATCCAAGA
TAAGGAAGGCATCCCTCCTGATCAGCAGAGGTTGATCTTTGCTGGGAAACAGCTGGAAGATGGACGCACCCTGTCT
GACTACAACATCCAGAAAGAGTCCACTCTGCACTTGGTCCTGCGCTTGAGGGGGGGTGTCTAAGTTTCCCCTTTTA
AGGTTTCMACAAATTTCATTGCACTTTCCTTTCAATAAAGTTGTTGCATTCCC

GAACTGGGCCCTGAGCCCAAGTCATGCCTTGTGTCCGCATCTGCCGTGTCACCTCTGTKCCTGCCCCTCACCCCTC
CCTCCTGGTCTTCTGAGCCAGCACCATCTCCAAATAGCCTATTCCTTCCTGCAAATCACACACACATGCGGGCCAC
ACATACCTGCTGCCCTGGAGATGGGGAAGTAGGAGAGATGAATAGAGGCCCATACATTGTACAGAAGGAGGGGCAG
GTGCAGATAAAAGCAGCAGACCCAGCGGCAGCTGAGGTGCATGGAGCACGGTTGGGGCCGGCATTGGGCTGAGCAC
CTGATGGGCCTCATCTCGTGAATCCTCGAGGCAGCGCCACAGCAGAGGAGTTAAGTGGCACCTGGGCCGAGCAGAG
CAGGAGACTGAGGGTCAGAGTGGAGGCTAAGCTGCCCTGGAACTCCTCAATCTTGCCTGCCCCCTAGTATGAAGCC
CCCTTCCTGCCCCTACAATTCCTGA 13732.1

ATGGATCTTACTTTGCCACCCAGGTTGGAGTGCAGTGCTGCAATCTTGGCTCACTGCAGCCTTAACCTCCCAGGCT
CAAGCTATCCTCCTGCCAAAGCCTTCCACATAGCTGGGACTACAGGTACACNGCCACCACACCCAGCTAAAATTTT
TGTATTTTTTGTAGAGACGGGATCTCGCCACGTTGCCCAGGCTGGTCCCATCCTGACCTCAAGCAGATCTGCCCAC
CTCAGCCCCCCAACGTGCTAGGATTACAGGCGTGAGCCACCGCACCCAGCCTTTGTTTTGCTTTTAATGGAATCAC
CAGTTCCCCTCCGTGTCTCAGCAGCAGCTGTGAGAAATGCTTTGCATCTGTGACCTTTATGAAGGGGAACTTCCAT
GCTGAATGAGGGTAGGATTACATGCTCCTGTTTCCCGGGGGTCAAGAAAGCCTCAGACTCCAGCATGATAAGCAGG
GTGAG 13732.2

ATAGGGGCTTTAAGGAGGGAATTCAGGTTCAATGAGGTCGTAAGGCCAGGGCTCTTATCCAGTAAGACTGGGGTCC
TTAGATGAGAAAGAGACACCCGAGGTCCTTCTCTCTGCCGTGTGAGGATGCATCAAGAAGGCGGCCGTCTGCAAGC
GAAGGAGAGGCCGCACCAGAAACCGACACCTTCATCTTGGACTTGCAGCCTCTAGAACTGAGAAAATAACTGTCTG
TTGGTTAAGCCACCCAGTTTGTAGTATTCTCTTATGGCTTCCTAAGCAGACTAACAAACAAACACCCAAAATTAAC
TGATGGCTTCGCTGTCTTCTGTAAAAATTGCTATGAGAGAACTTTTCACTCACTGTTTTGCAGTTTCTCCCTCAGT
CCCTGGTTCTTTCTTCTCACATAATCCCAATTTCAATTTATAGTTCATGGCCCAGGCAGAGTCATTCATCACGGCA
TCTCCTGAGCTAAACCAGCACCTGCTCTGCTCACTTCTTGACTGGCTGCTCATCATCAGCCCTCTTGCAGAGATTT
CATTTCCTCCCGTGCCAGGTACTTCACGCACCAAGCTCA

GGATAATGAAGTTGTTTTATTTAGCTTGGACAAAAAGGCATATTCCTCTATTTTCTTATACAACAAATATCCCCAA
AATAAAGCAAGCATATATATCTTGAATGTGTAATAATCCAGTGATAAACAAGAGCAGTACTTTAAAAGAAAAAAAA
ATATGTATTTCTGTCAGGTTAAAATGAGAATCAAAACCATTTACTCTGCTAACTCATTATTTTTTGCTTTCTTTTT
GGTTAAGAGAGGCAATGCAATACACTGAAAAAGGTTTTTATCTTATCTGGCATTGGAATTAGACATATTCAAACCC
CAGCCCCCATTTCCAAACTTTAAGACCACAAACAAGTAATTTACTTTTCTGAACATTGGTTTTTTCTGGAAAATGG
GAATTATAAAATAGACTTTGCAGACTCTTATGAGATTAAATAAGATAATGTATGAAATTCTTTCTTCTTTTTTACT
TCTTTTTCCTTTTTGAGATGGAGTCTCACCCCGTCACCCAGGCTGGAGTACAGTG 13735.2

CCACTGCACTCCAGCCTGGGTGACGGAGTGAGACTCTGTCTCAAAAAAACAAACAAACAAACAAACAAAAAACTGA
AAAGGAAATAGAGTTCCTCTTTCCTCATATATGAATATATTATTTCAACAGATTGTTGATCACCTACCATATGCTT
GGTATTGTTCTAATTGCTGGGGATACAGCAAGAGGTTCTGCAGAACTTCATGGAGCATGAAAGTAAATAAACAAAG
TTAATTTCAAGGCCAGGCATGGTTGCTCACACCTTTAGTCCCAGCACTTTGGGAGGCTGAGGCAGGTGGATCACTT
GGGCCCAGGAGTTCAAGGCTGCAGTGAGCCAAGATTGTGCCACTACTCTCCAGGCTGGGCAACAGAGCAAGACCCT
GTCTCAGGGGGAACAAAAAGTTAATTTCAGATTTTGTTAAGTGCTGTAAAGGAAGTAAATAGGTTGATATTCAAGA
GAGCACCTGAAGGCCAGGCGTGGTGGCTCACGCCTGTGGTCTAACGCTTTGGGAAGCCCGAGCGGGCGGATCACAA
GGTCAGGAGAATTTTGGCCAGGCATGGTG 13736.1

AGAATCCATTTATTGGGTTTTAAACTAGTTACACAACTGAAATCAGTTTGGCACTACTTTATACAGGGATTACGCC
TGTGTATGCCGACACTTAAATACTGTACCAGGACCACTGCTGTGCTTAGGTCTGTATTCAGTCATTCAGCATGTAG
ATACTAAAAATATACTGTAGTGTTCCTTTAAGGAAGACTGTACAGGGTGTGTTGCAAGATGACATTCACCAATTTG
TGAATTATTTCAACCCAGAAGATACCTTTCACTCTATAAACTTGTCATAGGCAAACATGTGGTGTTAGCATTGAGA
GATGCACACAAAAATGTTACATAAAAGTTCAGACATTCTAATGATAAGTGAACTGAAAAAAAAAAAAACCCCACAT
CTCAATTTTTGTAACAAGATAAAGAAAATAATTTAAAAACACAAAAAATGGCATTCAGTGGGTACAAAGCC 13737.1&2

CAAATATTTAATATAAATCTTTGAAACAAGTTCAGAKGAAATAAAAATCAAAGTTTGCAAAAACGTGAAGATTAAC
TTAATTGTCAAATATTCCTCATTGCCCCAAATCAGTATTTTTTTTATTTCTATGCAAAAGTATGCCTTCAAACTGC
TTAAATGATATATGATATGATACACAAACCAGTTTTCAAATAGTAAAGCCAGTCATCTTGCAATTGTAAGAAATAG
GTAAAAGATTATAAGACACCTTACACACACACACACACACACACACACACGTGTGCACcGCCAATGACAAAAAACA
ATTTGGCCTCTCCTAAAATAAGAACATGAAGACCCTTAATTGCTGCCAGGAGGGAACACTGTGTCACCCCTCCCTA
CAATCCAGGTAGTTTCCTTTAATCCAATAGCAAATCTGGGCATATTTGAGAGGAGTGATTCTGACAGCCACSGTTG
AAATCCTGTGGGGAACCATTCATGTCCACCCACTGGTGCCCTGAAAAAATGCCAATAATTTTTCGCTCCCACTTCT
GCTGCTGTCTCTTCCACATCCTCACATAGACCCCAGACCCGCTGGCCCCTGGCTGGGCATCGCATTGCTGGTAGAG
CAAGTCATAGGTCTCGTCTTTGACGTCACAGAAGCGATACACCAAATTGCCTGGTCGGTCATTGTCATAACCAG

TTTGACTTTAGTAGGGGTCTGAACTATTTATTTTACTTTGCCMGTAATATTTARACCYTATATATCTTTCATTATG
CCATCTTATCTTCTAATGBCAAGGGAACAGWTGCTAAMCTGGCTTCTGCATTWATCACATTAAAAATGGCTTTCTT
GGAAAATCTTCTTGATATGAATAAAGGATCTTTTAVAGCCATCATTTAAAGCMGGNTTCTCTCCAACACGAGTCTG
CTSASGGGGGGKGAGCTGTGAACTCTGGCTGAAGGCTTTCCCATACACACTGCAATGACMTGGTTTCTGACCAGBG
TGAGTTA 13738.2

AGAGAAGCCCCATAAATGCAATCAGTGTGGGAAGGCCTTCAGTCAGAGCTCAAGCCTTTTCCTCCATCATCGGGTT
CATACTGGAGAGAAACCCTATGTATGTAATGAATGCGGCAGAGCCTTTGGTTTTAACTCTCATCTTACTGAACACG
TAAGGATTCACACAGGAGAAAAACCCTATGTTTGTAATGAGTGCGGCAAAGCCTTTCGTCGGAGTTCCACTCTTGT
TCAGCATCGAAGAGTTCACACTGGGGAGAAGCCCTACCAGTGCGTTGAATGTGGGAAAGCTTTCAGCCAGAGCTCC
CAGCTCACCCTACATCAGCCGAGTTCACACTGGAGAGAAGCCCTATGACTGTGGTGACTGTGGGAAGGCCTTCAGC
CGGAGGTCAACCCTCATTCAGCATCAGAAAGTTCACAGCGGAGAGACTCGTAAGTGCAGAAAACATGGTCCAGCCT
TTGTTCATGGCTCCAGCCTCACAGCAGATGGACAGATTCCCACTGGAGAGAAGCACGGCAGAACCTTTAACCATGG
TGCAAATCTCATTCTGCGCTGGACAGTTC 13739.1&2

GAGACAGGGTCTCACTTTGTCACCCAGGCTGGAATGCAGTGGTGCGATCTTACGTAGCTCACTGCAGCCCTGACCT
CCTGGACTCAAACAATTCTCCTGCCTCAGCCCTGCAAGTAGCTGGGACTGTGGGTGCATGCCACCATGCCTGGCTA
ACTTTTGTAGTTTTTGTAAAGATGGGGTTTTGCCATGTTGCACATGCTGGTCTTGAACTCCTGAGCTCAAACGATC
TGCCCACCTCGGCCTCCCAGAATGTTGGGATTACAGGGGTAAACCACCACGCCTGGCCCCATTAGGGTATTCTTAG
CATCCACTTGCTCACTGAGATTAATCATAAGAGATGATAAGCACTGGAAGAAAAAAATTTTTACTAGGCTTTGGAT
ATTTTTTTCCTTTTTCAGCTTTATACAGAGGATTGGATCTTTAGTTTTCCTTTAACTGATAATAAAACATTGAAAG
GAAATAAGTTTACCTGAGATTCACAGAGATAACCGGCATCACTCCCTTGCTCAATTCCAGTCTTTACCACATCAAT
TATTTTCAGAGGTGCAGGATAAAGGCCTTTAGTCTGCTTTCGCACTTTTTCTTCCACTTTTTTGTAAACCTGTTGC
CTGACAAATGGAATTGACAGCGTATGCCATGACTATTCCATTTGTCAGGCATACGCTGTCAATTTTTCCACCAATC
CCTTGTCTCTCTTTGGAGAGATCTTCTTATCAGCTAGTCCTTTGGCAAAAGTAATTGCAACTTCTTCTAGGTATTC
TATTGTCCGTTCCACTGGTGGAACCCCTGGGACCAGGACTAAAACCTCCAG 13741.1

ATCTCATATATATATTTCTTCCTGACTTTATTTGCTTGCTTCTGNCACGCATTTAAAATATCACAGAGACCAAAAT
AGAGCGGCTTTCTGGTGGAACGCATGGCAGTCACAGGACAAAATACAAAACTAGGGGGCTCTGTCTTCTCATACAT
CATACAATTTTCAAGTATTTTTTTTATGTACAAAGAGCTACTCTATCTGAAAAAAAATTAAAAAATAAATGAGACA
AGATAGTTTATGCATCCTAGGAAGAAAGAATGGGAAGAAAGAACGGGGCAGTTGGGTACAGATTCCTGTCCCCTGT
TCCCAGGGACCACTACCTTCCTGCCACTGAGTTCCCCCACAGCCTCACCCATCATGTCACAGGGCAAGTGCCAGGG
TAGGTGGGGACCAGTGGAGACAGGAACCAGCAACATACTTTGGCCTGGAAGATAAGGAGAAAGTCTCAGAAACACA
CTGGTGGGAAGCAATCCCACNGGCCGTGCCCCANGAGCTTCCCACCTGCTGCTGGCTCCCTGGGTGGCTTTGGGAA
CAGCTTGGGCAGGCCCTTTTGGGTGGGGNCCAACTGGGCCTTTGGGCCCGTGTGGAAAG

AAACATTGAGATGGAATGATAGGGTTTCCCAGAATCAGGTCCATATTTTAACTAAATGAAAATTATGATTTATAGC
CTTCTCAAATACCTGCCATACTTGATATCTCAACCAGAGCTAATTTTACCTCTTTACAAATTAAATAAGCAAGTAA
CTGGATCCACAATTTATAATACCTGTCAATTTTTTCTGTATTAAACCTCTATCATAGTTTAAGCCTATTAGGGTAC
TTAATCCTTACAAATAAACAGGTTTAAAATCACCTCAATAGGCAACTGCCCTTCTGGTTTTCTTCTTTGACTAAAC
AATCTGAATGCTTAAGATTTTCCACTTTGGGTGCTAGCAGTACACAGTGTTACACTCTGTATTCCAGACTTCTTAA
ATTATAGAAAAAGGAATGTACACTTTTTGTATTCTTTCTGAGCAGGGCCGGGAGGCAACATCATCTACCATGGTAG
GGACTTGTATGCATGGACTACTTTA 14351.1

ACTCTGTCGCCCAGGCTGGAGCCCABTGGMGCGATCTCGACTCCCTGCAAGCTMCGCCTCACAGGWTCATGCCATT
CTCCTGCCTCAGCATCTGGAGTAGCTGGGACTACAGGCGCCAGCCACCATGCCCAGCTAATTTTT 14351.2

ACCTTAAAGACATAGGAGAATTTATACTGGGAGAGAAAGCTTACAAATGTAAGGTTTCTGACAAGACTTGGGAGTG
ATTCACACCTGGAACAACATACTGGACTTCACACTGGABAGAAACCTTACAAGTGTAATGAGTGTGGCAAAGCCTT
TGGCAAGCAGTCAACACTTATTCACCATCAGGCAATTCA 14354.2

AGTCAGGATCATGATGGCTCAGTTTCCCACAGCGATGAATGGAGGGCCAAATATGTGGGCTATTACATCTGAAGAA
CGTACTAAGCATGATAAACAGTTTGATAACCTCAAACCTTCAGGAGGTTACATAACAGGTGATCAAGCCCGTACTT
TTTTCCTACAGTCAGGTCTGCCGGCCCCGGTTTTAGCTGAAATATGGGCCTTATCAGATCTGAACAAGGATGGGAA
GATGGACCAGCAAGAGTTCTCTATAGCTATGAAACTCATCAAGTTAAAGTTGCAGGGCCAACAGCTGCCTGTAGTC
CTCCCTCCTATCATGAAACAACCCCCTATGTTCTCTCCACTAATCTCTGCTCGTTTTGGGATGGGAAGCATGCCCA
ATCTGTCCATTCATCAGCCATTGCCTCCAGTTGCACCTATAGCAACACCCTTGTCTTCTGCTACTTCAGGGACCAG
TATTCCTCCCTAATGATGCCTGCT 14354.1

CTTTCGATTTCCTTCAATTTGTCACGTTTGATTTTATGAAGTTGTTCAAGGGCTAACTGCTGTGTATTATAGCTTT
CTCTGAGTTCCTTCAGCTGATTGTTAAATGAATCCATTTCTGAGAGCTTAGATGCAGTTTCTTTTTCAAGAGCATC
TAATTGTTCTTTAAGTCTTTGGCATAATTCTTCCTTTTCTGATGACTTTCTATGAAGTAAACTGATCCCTGAATCA
GGTGTGTTACTGAGCTGCATGTTTTTAATTCTTTCGTTTAATAGCTGCTTCTCAGGGACCAGATAGATAAGCTTAT
TTTGATATTCCTTAAGCTCTTGGTGAAGTTGTTCGATTTCCATAATTTCCAGGTCACACTGGTTATCCCAAACTTC
T

TGGAGGTGAAACGGAGGCAAGAAAGGGGGCTACCTCAGGAGCGAGGGACAAAGGGGGCGTGAGGCACCTAGGCCGC
GGCACCCCGGCGACAGGAAGCCGTCCTGAACCGGGCTACCGGGTAGGGGAAGGGCCCGCGTAGTCCTCGCAGGGCC
CCAGAGCTGGAGTCGGCTCCACAGCCCCGGGCCGTCGGCTTCTCACTTCCTGGACCTCCCCGGCGCCCGGGCCTGA
GGACTGGCTCGGCGGAGGGAGAAGAGGAAACAGACTTGAGCAGCTCCCCGTTGTCTCGCAACTCCACTGCCGAGGA
ACTCTCATTTCTTCCCTCGCTCCTTCACCCCCCACCTCATGTAGAAAGGTGCTGAAGCGTCCGGAGGGAAGAAGAA
CCTGGGCTACCGTCCTGGCCTTCCCMCCCCCTTCCCGGGGCGCTTTGGTGGGCGTGGAGTTGGGGTTGGGGGGGTG
GGTGGGGGTTCTTTTTTGGAGTGCTGGGGAACTTTTTTCCCTTCTTCAGGTCAGGGGAAAGGGAATGCCCAATTCA
GAGAGACATGGGGGCAAGAAGGACGGGAGTGGAGGAGCTTCTGGAACTTTGCAGCCGTCATCGGGAGGCGGCAGCT
CTAACAGCAGAGAGCGTCACCGCTTGGTATCGAAGCACAAGCGGCATAAGTCCAAACACTCCAAAGACATGGGGTT
GGTGACCCCCGAAGCAGCATCCCTGGGCACAGTTATCAAACCTTTGGTGGAGTATGATGATATCAGCTCTGATTCC
GACACCTTCTCCGATGACATGGCCTTCAAACTAGACCGAAGGGAGAACGACGAACGTCGTGGATCAGATCGGAGCG
ACCGCCTGCACAAACATCGTCACCACCAGCACAGGCGTTCCCGGGACTTACTAAAAGCTAAACAGACCG 16432-1

GACATGTTTGCCTGCAGGGGACCAGAGACAATGGGATTAGCCAGTGCTCACTGTTCTTTATGCTTCCAGAGAGGAT
GGGGACAGCTCTCAGGTCAGAATCCAGGCTGAGAAGGCCATGCTGGTTGGGGGCCCCCGGAAGCACGGTCCGGATC
CTCCCTGGCATCAGCGTAGACCCGCTGCTCAGGCTTGGGGTACCAAACTCATGCTCTGTACTGTTTTGGCCCCATG
CGGTGAGAGGAAAACCTAGAAAAAGATTGGTCGTGCTAAGGAATCAGCTGCCCCCTCATCCTCCGCATCCAATGCT
GGTGACAACATATTCCCTCTCCCAGGACACAGACTCGGTGACTCCACACTGGGCTGAGTGGCCTCTGGAGGCTCGT
GGCCTAAGGCAGGGCTCCGTAAGGCTGATCGGCTGAACTGGGTGGGGTGAGGGTTTCTGACCCTTCGCTTCCCATC
CCATAACCGCTGTCAATGAGCTCACACTGTGGTCA 16432-2

GATGGCATGGTCGTTGCTAATGTGCCTGCTGGGATGGAGCACTTCCTCCTGTGAGCCCAGGGGACCCGCCTGTCCC
TGGAGCTTGGGGCAAGGAGGGAAGAGTGATACCAGGAAGGTGGGGCTGCAGCCAGGGGCCAGAGTCAGTTCAGGGA
GTGGTCCTCGGCCCTCAAAGCTCCTCCGGGGACTGCTCAGGAGTGATGGTGCCCTGGAGTTTGCCCCAACTTCCCT
GGCCACCCTGGAAGGTGCCTGGCTGCTCCAGGCCTCTAGGCTGGGCTGATGGGTTTCTCCAGGACACAAGTATCAT
TAAAGCCACCCTCTCCTCAGCTTGTCAGGCCGCACATGTGGGACAGGCTGTGCTCACAACCCCCTCGCCTGCCCTG
CCCTCCATCAGGAGGAGCCAGTGGAACCTTCGGAAAGCTCCCAGCATCTCAGCAGCCCTCAAAAGTCGTCCTGGGG
CAAGCTCTGGTTCTCCTGACTGGAGGTCATCTGGGCTTGGCCTGCTCTCTCTCGC 17184.3

TAAAAAAGTGTAACAAAGGTTTATTTAGACTTTCTTCATGCCCCCAGATCCAGGATGTCTATGTAAACCGTTATCT
TACAAAGAAAGCACAATATTTGGTATAAACTAAGTCAGTGACTTGCTTAACTGAAATAGCGTCCATCCAAAAGTGG
GTTTAAGGTAAAACTACCTGACGATATTGGCGGGGATCCTGCAGTTTGGACTGCTTGCCGGGTTTGTCCAGGGTTC
CGGGTCTGTTCTTGGCACTCATGGGGACAGGCATCCTGCTCGTCTGTGGGGCCCCGCTGGAGCCCTTACGTGAAGC
TGAAGGTATCGACCSTAGGGGGCTCTAGGGCAGTGGGACCTTCATCCGGAACTAACAAGGGTCGGGGAGAGGCCTC
TTGGGCTATGTGGG

CAAGCGTTCCTTTATGGATGTAAATTCAAACAGTCATGCTGAGCCATCCCGGGCTGACAGTCACGTTWAAGACACT
AGGTCGGGCGCCACAGTGCCACCCAAGGAGAAGAAGAATTTGGAATTTTTCCATGAAGATGTACGGAAATCTGATG
TTGAATATGAAAATGGCCCCCAAATGGAATTCCAAAAGGTTACCACAGGGGCTGTAAGACCTAGTGACCCTCCTAA
GTGGGAAAGAGGAATGGAGAATAGTATTTCTGATGCATCAAGAACATCAGAATATAAAACTGAGATCATAATGAAG
GAAAATTCCATATCCAATATGAGTTTACTCAGAGACAGTAGAAACTATTCCCAGG 17185.1

TAGGAATAACAAATGTTTATTCAGAAATGGATAAGTAATACATAATCACCCTTCATCTCTTAATGCCCCTTCCTCT
CCTTCTGCACAGGAGACACAGATGGGTAACATAGAGGCATGGGAAGTGGAGGAGGACACAGGACTAGCCCACCACC
TTCTCTTCCCGGTCTCCCAAGATGACTGCTTATAGAGTGGAGGAGGCAAACAGGTCCCCTCAATGTACCAGATGGT
CACCTATAGCACCAGCTCCAGATGGCCACGTGGTTGCAGCTGGACTCAATGAAACTCTGTGACAACCAGAAGATAC
CTGCTTTGGGATGAGAGGGAGGATAAAGCCATGCAGGGAGGATATTTACCATCCCTACCCTAAGCACAGTGCAAGC
AGTGAGCCCCCGGCTCCCAGTACCTGAAAAACCAAGGCCTACTGNCTTTTGGATGCTCTCTTGGGCCACG 17188.2

AAGCCTCCTGCCCTGGAAATCTGGAGCCCCTTGGAGCTGAGCTGGACGGGGCAGGGAGGGGCTGAGAGGCAAGACC
GTCTCCCTCCTGCTGCAGCTGCTTCCCCAGCAGCCACTGCTGGGCACAGCAGAAACGCCAGCAGAGAAAATGGGAG
CCGAGAGTCCTTAGCCCTGGAGCTGAGGCTGCCTCTGGGCTGACCCGCTGGCTGTACGTGGCCAGAACTGGGGTTG
GCATCTGGCATCCATTTGAGGCCAGGGTGGAGGAAAGGGAGGCCAACAGAGGAAAACCTATTCCTGCTGTGACAAC
ACAGCCCTTGTCCCACGCAGCCTAAGTGCAGGGAGCGTGATGAAGTCAGGCAGCCAGTCGGGGAGGACGAGGTAAC
TCAGCAGCAATGTCACCTTGTAGCCTATGCGCTCAATGGCCCGGAGGGGCAGCAACCCCCCGCACACGTCAGCCAA
CAGCAGTGCCTCTGCAGGCACCAAGAGAGCGATGATGGACTTGAGCGCCGTGTTC 17190.1

GTTTGGCAGAAGACATGTTTAATAACATTTTCATATTTAAAAAATACAGCAACAATTCTCTATCTGTCCACCATCT
TGCCTTGCCCTTCCTGGGGCTGAGGCAGACAAAGGAAAGGTAATGAGGTTAGGGCCCCCAGGCGGGCTAAGTGCTA
TTGGCCTGCTCCTGCTCAAAGAGAGCCATAGCCAGCTGGGCACGGCCCCCTAGCCCCTCCAGGTTGCTGAGGCGGC
AGCGGTGGTAGAGTTCTTCACTGAGCCGTGGGCTGCAGTCTCGCAGGGAGAACTTCTGCACCAGCCCTGGCTCTAC
GGCCCGAAAGAGGTGGAGCCCTGAGAACCGGAGGAAAACATCCATCACCTCCAGCCCCTCCAGGGCTTCCTCCTCT
TCCTGGCCTGCCAGTTCACCTGCCAGCCGGGCTCGGGCCGCCAGGTAGTCAGCGTTGTAGAAGCAGCCCTCCGCAG
AAGCCTGCCGGTCAAATCTCCCCGCTATAGGAGCCCCCCGGGAGGGGTCAGCACC

CAAGTTGAACGTCAGGCTTGGCAGAGGTGGAGTGTAGATGAAAACAAAGGTGTGATTATGAAGAGGATGTGAGTCC
TTTGGGTGTAGGAGAGAAAGGCTGTTGAGCTTCTATTTCAAGATACTTTTACCTGTGCAAAAAGCACATTTTCCAC
CTCCTTCTCATGGCATTTGTGTAAGGTGAGTATGATTCCTATTCCATCTGCATTTTAGAGGTGAAGAATAACGTAC
AAGGGATTCAGTGATTAGCAAGGGACCCCTCACTAAGTGTTGATGGAGTTAGGACAGAGCTCAGCTGTTTGAATCT
CAGAGCCCAGGCAGCTGGAGCTGGGTAGGATCCTGGAGCTGGCACTAATGTGAGGTGCATTCCCTCCAACCCAGGC
TCAGATCCGGAACCTGACCGTGCTGACCCCCGAAGGGGAGGCAGGGCTGAGCTGGCCCGTTGGGCTCCCTGCTCCT
TTCACACCACACTCTCGCTTTGAGGTGCTGGGCTGGGACTACTTCACAGAGCAGC 17191.2&89.2

TGGCCTGGGCAGGATTGGGAGAGAGGTAGCTACCCGGATGCAGTCCTTTGGGATGAAGACTATAGGGTATGACCCC
ATCATTTCCCCAGAGGTCTCGGCCTCCTTTGGTGTTCAGCAGCTGCCCCTGGAGGAGATCTGGCCTCTCTGTGATT
TCATCACTGTGCACACTCCTCTCCTGCCCTCCACGACAGGCTTGCTGAATGACAACACCTTTGCCCAGTGCAAGAA
GGGGGTGCGTGTGGTGAACTGTGCCCGTGGAGGGATCGTGGACGAAGGCGCCCTGCTCCGGGCCCTGCAGTCTGGC
CAGTGTGCCGGGGCTGCACTGGACGTGTTTACGGAAGAGCCGCCACGGGACCGGGCCTTGGTGGACCATGAGAATG
TCATCAGCTGTCCCCACCTGGGTGCCAGCACCAAGGAGGCTCAGAGCCGCTGTGGGGAGGAAATTGCTGTTCAGTT
CGTGGACATGGTGAAGGGGAAATCTCTCACGGGGGTTGTGAATGCCCAGGCCCTT

*Fig. 1S*

AGCCAGATGGCTGAGAGCTGCAAGAAGAAGTCAGGATCATGATGGCTCAGTTTCCCACAGCGATGAATGGAGGGCC
AAATATGTGGGCTATTACATCTGAAGAACGTACTAAGCATGATAAACAGTTTGATAACCTCAAACCTTCAGGAGGT
TACATAACAGGTGATCAAGCCCGTACTTTTTTCCTACAGTCAGGTCTGCCGGCCCCGGTTTTAGCTGAAATATGGG
CCTTATCAGATCTGAACAAGGATGGGAAGATGGACCAGCAAGAGTTCTCTATAGCTATGAAACTCATCAAGTTAAA
GTTGCAGGGCCAACAGCTGCCTGTAGTCCTCCCTCCTATCATGAAACAACCCCCTATGTTCTCTCCACTAATCTCT
GCTCGTTTTGGGATGGGAAGCATGCCCAATCTGTCCATTCATCAGCCATTGCCTCCAGTTGCACCTATAGCAACAC
CCTTGTCTTCTGCTACTTCAGGGACCAGTATTCCTCCCCTAATGATGCCTGCTCCCCTAGTGCCTTCTGTTAGTAC
ATCCTCATTACCAAATGGAACTGCCAGTCTCATTCAGCCTTTATCCATTCCTTATTCTTCTTCAACATTGCCTCAT
GCATCATCTTACAGCCTGATGATGGGAGGATTTGGTGGTGCTAGTATCCAGAAGGCCCAGTCTCTGATTGATTTAG
GATCTAGTAGCTCAACTTCCTCAACTGCTTCCCTCTCAGGGAACTCACCTAAGACAGGGACCTCAGAGTGGGCAGT
TCCTCAGCCTTCAAGATTAAAGTATCGGCAAAAATTTAATAGTCTAGACAAAGGCATGAGCGGATACCTCTCAGGT
TTTCAAGCTAGAAATGCCCTTCTTCAGTCAAATCTCTCTCAAACTCAGCTAGCTACTATTTGGACTCTGGCTGACA
TCGATGGTGACGGACAGTTGAAAGCTGAAGAATTTATTCTGGCGATGCACCTCACTGACATGGCCAAAGCTGGACA
GCCACTACCACTGACGTTGCCTCCCGAGCTTGTCCCTCCATCTTTCAGAGGGGGAAAGCAAGTTGATTCTGTTAAT
GGAACTCTGCCTTCATATCAGAAAACACAAGAAGAAGAGCCTCAGAAGAAACTGCCAGTTACTTTTGAGGACAAAC
GGAAAGCCAACTATGAACGAGGAAACATGGAGCTGGAGAAGCGACGCCAAGTGTTGATGGAGCAGCAGCAGAGGGA
GGCTGAACGCAAAGCCCAGAAAGAGAAGGAAGAGTGGGAGCGGAAACAGAGAGAACTGCAAGAGCAAGAATGGAAG
AAGCAGCTGGAGTTGGAGAAACGCTTGGAGAAACAGAGAGAGCTGGAGAGACAGCGGGAGGAAGAGAGGAGAAAGG
AGATAGAAAGACGAGAGGCAGCAAAACAGGAGCTTGAGAGACAACGCCGTTTAGAATGGGAAAGACTCCGTCGGCA
GGAGCTGCTCAGTCAGAAGACCAGGGAACAAGAAGACATTGTCAGGCTGAGCTCCAGAAAGAAAAGTCTCCACCTG
GAACTGGAAGCAGTGAATGGAAAACATCAGCAGATCTCAGGCAGACTACAAGATGTCCAAATCAGAAAGCAAACAC
AAAAGACTGAGCTAGAAGTTTTGGATAAACAGTGTGACCTGGAAATTATGGAAATCAAACAACTTCAACAAGAGCT
TAAGGAATATCAAAATAAGCTTATCTATCTGGTCCCTGAGAAGCAGCTATTAAACGAAAGAATTAAAAACATGCAG
CTCAGTAACACACCTGATTCAGGGATCAGTTTACTTCATAAAAAGTCATCAGAAAAGGAAGAATTATGCCAAAGAC
TTAAAGAACAATTAGATGCTCTTGAAAAAGAAACTGCATCTAAGCTCTCAGAAATGGATTCATTTAACAATCAGCT
GAAGGAACTCAGAGAAAGCTATAATACACAGCAGTTAGCCCTTGAACAACTTCATAAAATCAAACGTGACAAATTG
AAGGAAATCGAAAGAAAAAGATTAGAGCAAAAAAAAAAAAA

*Fig. 2A*

ATGGCAGTGACATTCACCATCATGGGAACCACCTTCCCTTTTCTTCAGGATTCTCTGTAGTGGAAGAGAGCACCCA
GTGTTGGGCTGAAAACATCTGAAAGTAGGGAGAAGAACCTAAAATAATCAGTATCTCAGAGGGCTCTAAGGTGCCA
AGAAGTCTCACTGGACATTTAAGTGCCAACAAAGGCATACTTTCGGAATCGCCAAGTCAAAACTTTCTAACTTCTG
TCTCTCTCAGAGACAAGTGAGACTCAAGAGTCTACTGCTTTAGTGGCAACTACAGAAAACTGGTGTTACCCAGAAA
AACAGGAGCAATTAGAAATGGTTCCAATATTTCAAAGCTCCGCAAACAGGATGTGCTTTCCTTTGCCCATTTAGGG
TTTCTTCTCTTTCCTTTCTCTTTATTAACCACTA

*Fig. 2B*

ATATCTAGAAGTCTGGAGTGAGCAAACAAGAGCAAGAAACAAAAAGAAGCCAAAAGCAGAAGGCTCCAATATGAAC
AAGATAAATCTATCTTCAAAGACATATTAGAAGTTGGGAAAATAATTCATGTGAACTAGACAAGTGTGTTAAGAGT
GATAAGTAAAATGCACGTGGAGACAAGTGCATCCCCAGATCTCAGGGACCTCCCCCTGCCTGTCACCTGGGGAGTG
AGAGGACAGGATAGTGCATGTTCTTTGTCTCTGAATTTTTAGTTATATGTGCTGTAATGTTGCTCTGAGGAAGCCC
CTGGAAAGTCTATCCCAACATATCCACATCTTATATTCCACAAATTAAGCTGTAGTATGTACCCTAAGACGCTGCT
AATTGACTGCCACTTCGCAACTCAGGGGCGGCTGCATTTTAGTAATGGGTCAAATGATTCACTTTTTATGATGCTT
CCAAAGGTGCCTTGGCTTCTCTTCCCAACTGACAAATGCCAAAGTTGAGAAAAATGATCATAATTTTAGCATAAAC
AGAGCAGTCGGCGACACCGATTTTATAAATAAACTGAGCACCTTCTTTTTAAACAAACAAATGCGGGTTTATTTCT
CAGATGATGTTCATCCGTGAATGGTCCAGGGAAGGACCTTTCACCTTGACTATATGGCATTATGTCATCACAAGCT
CTGAGGCTTCTCCTTTCCATCCTGCGTGGACAGCTAAGACCTCAGTTTTCAATAGCATCTAGAGCAGTGGGACTCA
GCTGGGGTGATTTCGCCCCCCATCTCCGGGGGAATGTCTGAAGACAATTTTGTTACCTCAATGAGGGAGTGGAGGA
GGATACAGTGCTACTACCAACTAGTGGATAAAGGCCAGGGATGCTGCTCAACCTCCTACCATGTACAGGACGTCTC
CCCATTACAACTACCCAATCCGAAGTGTCAACTGTGTCAGGACTAAGAAACCCTGGTTTTGAGTAGAAAAGGGCCT
GGAAAGAGGGGAGCCAACAAATCTGTCTGCTTCCTCACATTAGTCATTGGCAAATAAGCATTCTGTCTCTTTGGCT
GCTGCCTCAGCACAGAGAGCCAGAACTCTATCGGGCACCAGGATAACATCTCTCAGTGAACAGAGTTGACAAGGCC
TATGGGAAATGCCTGATGGGATTATCTTCAGCTTGTTGAGCTTCTAAGTTTCTTTCCCTTCATTCTACCCTGCAAG
CCAAGTTCTGTAAGAGAAATGCCTGAGTTCTAGCTCAGGTTTTCTTACTCTGAATTTAGATCTCCAGACCCTTCCT
GGCCACAATTCAAATTAAGGCAACAAACATATACCTTCCATGAAGCACACACAGACTTTTGAAAGCAAGGACAATG
ACTGCTTGAATTGAGGCCTTGAGGAATGAAGCTTTGAAGGAAAAGAATACTTTGTTTCCAGCCCCCTTCCCACACT
CTTCATGTGTTAACCACTGCCTTCCTGGACCTTGGAGCCACGGTGACTGTATTACATGTTGTTATAGAAAACTGAT
TTTAGAGTTCTGATCGTTCAAGAGAATGATTAAATATACATTTCCTA

*Fig. 2C*

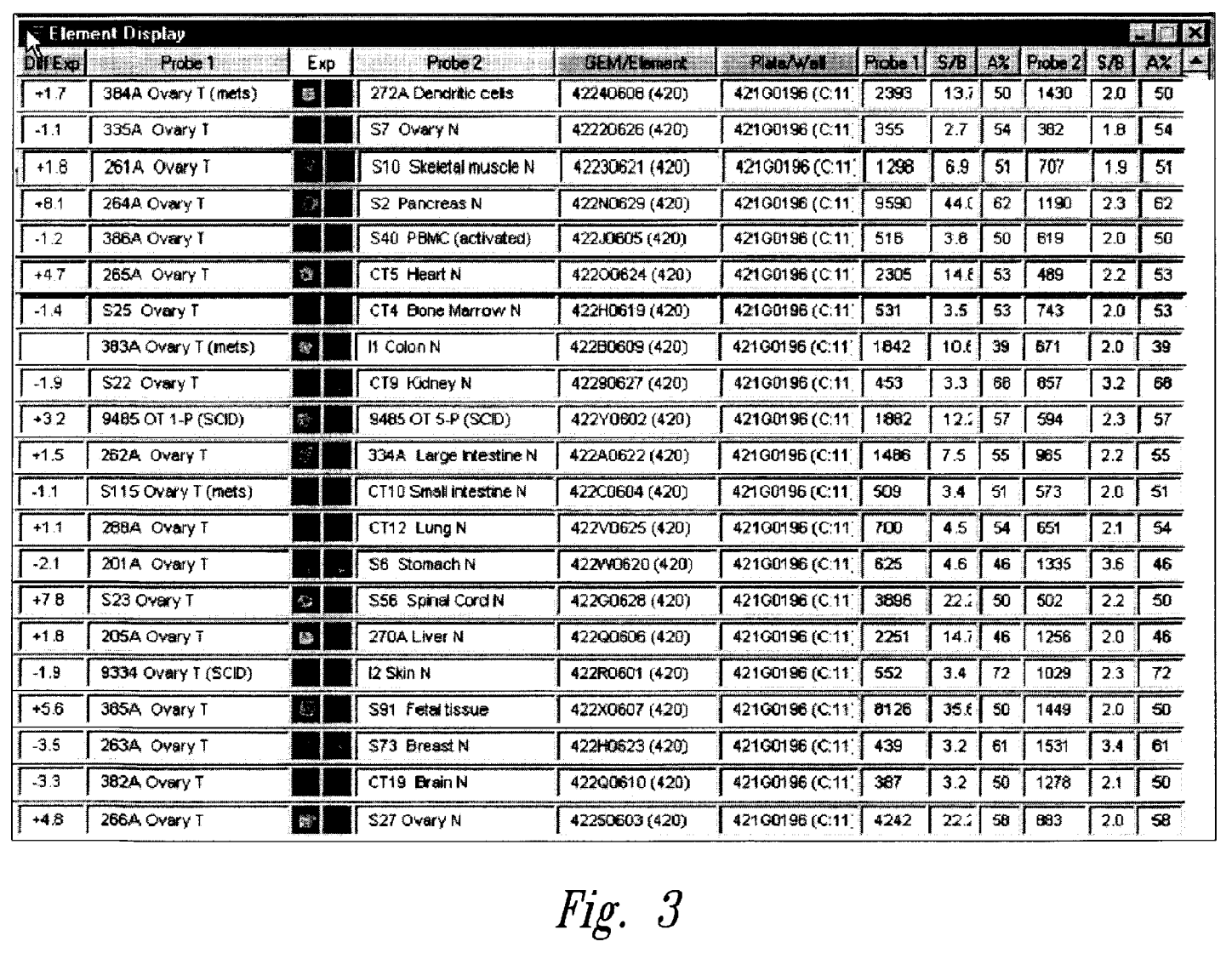

Element Display

| Diff Exp | Probe 1 | Exp | Probe 2 | GEM/Element | Plate/Well | Probe 1 | S/B | A% | Probe 2 | S/B | A% |
|---|---|---|---|---|---|---|---|---|---|---|---|
| +1.7 | 384A Ovary T (mets) | | 272A Dendritic cells | 4224O608 (420) | 421G0196 (C:11 | 2393 | 13.7 | 50 | 1430 | 2.0 | 50 |
| -1.1 | 335A Ovary T | | S7 Ovary N | 4222O626 (420) | 421G0196 (C:11 | 355 | 2.7 | 54 | 382 | 1.8 | 54 |
| +1.8 | 261A Ovary T | | S10 Skeletal muscle N | 4223O621 (420) | 421G0196 (C:11 | 1298 | 6.9 | 51 | 707 | 1.9 | 51 |
| +8.1 | 264A Ovary T | | S2 Pancreas N | 422N0629 (420) | 421G0196 (C:11 | 9590 | 44.0 | 62 | 1190 | 2.3 | 62 |
| -1.2 | 386A Ovary T | | S40 PBMC (activated) | 422J0605 (420) | 421G0196 (C:11 | 516 | 3.8 | 50 | 619 | 2.0 | 50 |
| +4.7 | 265A Ovary T | | CT5 Heart N | 422O0624 (420) | 421G0196 (C:11 | 2305 | 14.8 | 53 | 489 | 2.2 | 53 |
| -1.4 | S25 Ovary T | | CT4 Bone Marrow N | 422H0619 (420) | 421G0196 (C:11 | 531 | 3.5 | 53 | 743 | 2.0 | 53 |
| | 383A Ovary T (mets) | | I1 Colon N | 422B0609 (420) | 421G0196 (C:11 | 1842 | 10.8 | 39 | 671 | 2.0 | 39 |
| -1.9 | S22 Ovary T | | CT9 Kidney N | 4229O627 (420) | 421G0196 (C:11 | 453 | 3.3 | 68 | 657 | 3.2 | 68 |
| +3.2 | 9485 OT 1-P (SCID) | | 9485 OT 5-P (SCID) | 422Y0602 (420) | 421G0196 (C:11 | 1882 | 12.2 | 57 | 594 | 2.3 | 57 |
| +1.5 | 262A Ovary T | | 334A Large Intestine N | 422A0622 (420) | 421G0196 (C:11 | 1486 | 7.5 | 55 | 965 | 2.2 | 55 |
| -1.1 | S115 Ovary T (mets) | | CT10 Small intestine N | 422C0604 (420) | 421G0196 (C:11 | 509 | 3.4 | 51 | 573 | 2.0 | 51 |
| +1.1 | 288A Ovary T | | CT12 Lung N | 422V0625 (420) | 421G0196 (C:11 | 700 | 4.5 | 54 | 651 | 2.1 | 54 |
| -2.1 | 201A Ovary T | | S6 Stomach N | 422W0620 (420) | 421G0196 (C:11 | 625 | 4.6 | 46 | 1335 | 3.6 | 46 |
| +7.8 | S23 Ovary T | | S56 Spinal Cord N | 422G0628 (420) | 421G0196 (C:11 | 3896 | 22.2 | 50 | 502 | 2.2 | 50 |
| +1.8 | 205A Ovary T | | 270A Liver N | 422Q0606 (420) | 421G0196 (C:11 | 2251 | 14.7 | 46 | 1256 | 2.0 | 46 |
| -1.9 | 9334 Ovary T (SCID) | | I2 Skin N | 422R0601 (420) | 421G0196 (C:11 | 552 | 3.4 | 72 | 1029 | 2.3 | 72 |
| +5.6 | 385A Ovary T | | S91 Fetal tissue | 422X0607 (420) | 421G0196 (C:11 | 8126 | 35.6 | 50 | 1449 | 2.0 | 50 |
| -3.5 | 263A Ovary T | | S73 Breast N | 422H0623 (420) | 421G0196 (C:11 | 439 | 3.2 | 61 | 1531 | 3.4 | 61 |
| -3.3 | 382A Ovary T | | CT19 Brain N | 422Q0610 (420) | 421G0196 (C:11 | 387 | 3.2 | 50 | 1278 | 2.1 | 50 |
| +4.8 | 266A Ovary T | | S27 Ovary N | 4225O603 (420) | 421G0196 (C:11 | 4242 | 22.2 | 58 | 883 | 2.0 | 58 |

Fig. 3

TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 4*

TAGCGYGGTCGCGGCCGAGGYCTGCTTYTCTGTCCAGCCCAGGGCCTGTGGGGTCAGGGCGGTGGGTGCAGATGGC
ATCCACTCCGGTGGCTTCCCCATCTTTCTCTGGCCTGAGCAAGGTCAGCCTGCAGCCAGAGTACAGAGGGCCAACA
CTGGTGTTCTTGAACAAGGGCCTTAGCAGGCCCTGAAGGRCCCTCTCTGTAGTGTTGAACTTCCTGGAGCCAGGCC
ACATGTTCTCCTCATACCGCAGGYTAGYGATGGTGAAGTTGAGGGTGAAATAGTATTMANGRAGATGGCTGGCARA
CCTGCCCGGGCGGCCGCTCSAAATCC

*Fig. 5*

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

TTGGGGNTTTMGAGCGGCCGCCCGGGCAGGTACCGGGGTGGTCAGCGAGGAGCCATTCACACTGAACTTCACCATC
AACAACCTGCGGTATGAGGAGAACATGCAGCACCCTGGCTCCAGGAAGTTCAACACCACGGAGAGGGTCCTTCAGG
GCCTGCTCAGGTCCCTGTTCAAGAGCACCAGTGTTGGCCCTCTGTACTCTGGCTGCAGACTGACTTTGCTCAGACT
TGAGAAACATGGGGCAGCCACTGGAGTGGACGCCATCTGCACCCTCCGCCTTGATCCCACTGGTCCTGGACTGGAC
AGAGAGCGGCTATACTGGGAGCTGAGCCAGTCCTCTGGCGGNGACNCCNCTT

Fig. 7B

AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 7A and 7B*

TGTGGTGTTGAACTTCCTGGAGNCAGGGTGACCCATGTCCTCCCCATACTGCAGGTTGGTGATGGTGAAGTTGAGG
GTGAATGGTACCAGGAGAGGGCCAGCAGCCATAATTGTSGRGCKGSMGMSSGAGGMWGGWGTYYCWGAGGTTCYRA
RRTCCACTGTGGAGGTCCCAGGAGTGCTGGTGGTGGGCACAGAGSTCYGATGGGTGAAACCATTGACATAGAGACT
GTTCCTGTCCAGGGTGTAGGGGCCCAGCTCTTYRATGYCATTGGYCAGTTKGCTYAGCTCCCAGTACAGCCRCTCT
CKGYYGMGWCCAGSGCTTTTGGGGTCAAGATGATGGATGCAGATGGCATCCACTCCAGTGGCTGCTCCATCCTTCT
CGGACCTGAGAGAGGTCAGTCTGCAGCCAGAGTACAGAGGGCCAACACTGGTGTTCTTTGAATA

*Fig. 8*

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 9*

| Gene Name | Bal Exp | Probe 1 Name | P1 | | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|---|
| 421O0188 (D3) | +7.0 | 205A Ovary T | 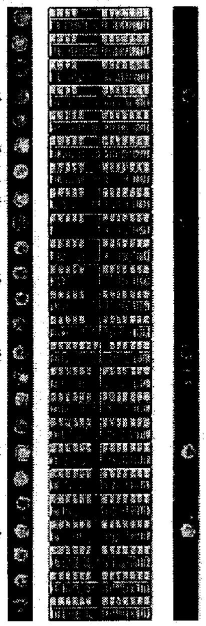 | | | 270A Liver N | 422Q0606 | 8620 | 1240 | 57.7 | 65 | 2.2 | 65 |
| 421O0188 (D3) | +5.9 | S23 Ovary T | | | | S56 Spinal Cord N | 422G0628 | 5894 | 1002 | 35.3 | 89 | 3.9 | 89 |
| 421O0188 (D3) | +5.7 | 385A Ovary T | | | | S91 Fetal tissue | 422X0607 | 12151 | 2121 | 54.3 | 73 | 2.8 | 73 |
| 421O0188 (D3) | +5.1 | 426A Ovary T (mets | | | | 415A Aorta N | 422X0611 | 7487 | 1480 | 53.0 | 73 | 9.7 | 73 |
| 421O0188 (D3) | +3.5 | 263A Ovary T | | | | S73 Breast N | 422H0623 | 7302 | 2116 | 39.2 | 84 | 4.5 | 84 |
| 421O0188 (D3) | +3.3 | 383A Ovary T (mets | | | | I1 Colon N | 422B0609 | 3714 | 1113 | 20.4 | 83 | 2.6 | 83 |
| 421O0188 (D3) | +3.0 | 9334 Ovary T (SCII | | | | I2 Skin N | 422R0601 | 2435 | 814 | 12.1 | 75 | 2.1 | 75 |
| 421O0188 (D3) | +2.6 | 384A Ovary T (mets | | | | 272A Dendritic cell | 4224O608 | 4578 | 1754 | 25.0 | 69 | 2.3 | 69 |
| 421O0188 (D3) | +2.2 | 264A Ovary T | | | | S2 Pancreas N | 422N0629 | 7904 | 3596 | 38.5 | 81 | 5.6 | 81 |
| 421O0188 (D3) | +2.0 | 386A Ovary T | | | | S40 PBMC (activat | 422J0605 | 2191 | 1081 | 14.0 | 90 | 2.9 | 90 |
| 421O0188 (D3) | +2.0 | S115 Ovary T (mets | | | | CT10 Small intestin | 422C0604 | 1979 | 971 | 10.4 | 80 | 2.7 | 80 |
| 421O0188 (D3) | +2.0 | 265A Ovary T | | | | CT5 Heart N | 422O0624 | 1911 | 964 | 13.9 | 93 | 3.4 | 93 |
| 421O0188 (D3) | +2.0 | 335A Ovary T | | | | S7 Ovary N | 42220626 | 1666 | 817 | 9.8 | 100 | 3.0 | 100 |
| 421O0188 (D3) | -1.9 | 428A Ovary T (mets | | | | 243A Esophagus N | 42240612 | 1827 | 3480 | 13.4 | 97 | 9.5 | 97 |
| 421O0188 (D3) | +1.6 | 261A Ovary T | | | | S10 Skeletal muscl | 42230621 | 5914 | 3653 | 30.4 | 86 | 6.0 | 86 |
| 421O0188 (D3) | +1.6 | 266A Ovary T | | | | S27 Ovary N | 42250603 | 2039 | 1274 | 11.9 | 50 | 2.6 | 50 |
| 421O0188 (D3) | +1.6 | S22 Ovary T | | | | CT9 Kidney N | 42290627 | 1736 | 1072 | 11.0 | 92 | 4.0 | 92 |
| 421O0188 (D3) | +1.4 | 9485 OT 1-P (SCID | | | | 9485 OT 5-P (SCID | 422Y0602 | 4204 | 3074 | 23.0 | 93 | 7.7 | 93 |
| 421O0188 (D3) | +1.4 | 262A Ovary T | | | | 334A Large Intestir | 422A0622 | 3002 | 2101 | 16.6 | 89 | 4.0 | 89 |
| 421O0188 (D3) | +1.3 | S25 Ovary T | | | | CT4 Bone Marrow | 422H0619 | 1643 | 1297 | 9.6 | 90 | 3.1 | 90 |
| 421O0188 (D3) | +1.2 | 429A Ovary T (mets | | | | 364A Ovary N | 422I0614 | 2521 | 2084 | 22.0 | 65 | 23.9 | 65 |
| 421O0188 (D3) | +1.2 | 382A Ovary T | | | | CT19 Brain N | 422Q0610 | 2072 | 1663 | 10.9 | 88 | 2.3 | 88 |
| 421O0188 (D3) | +1.2 | 288A Ovary T | | | | CT12 Lung N | 422V0625 | 1840 | 1473 | 10.7 | 87 | 3.8 | 87 |
| 421O0188 (D3) | +1.1 | 201A Ovary T | | | | S6 Stomach N | 422W0620 | 1329 | 1204 | 9.1 | 90 | 3.5 | 90 |

*Fig. 10*

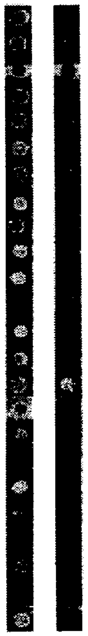

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421B0181 {C3} | +18.8 | 385A Ovary T | | | S91 Fetal tissue | 422X0607 | 26711 | 1424 | 103.3 | 54 | 2.0 | 54 |
| 421B0181 {C3} | +11.5 | S23 Ovary T | | | S56 Spinal Cord N | 422G0628 | 13559 | 1179 | 65.3 | 68 | 3.9 | 68 |
| 421B0181 {C3} | +11.1 | 426A Ovary T (mets) | | | 415A Aorta N | 422X0611 | 14125 | 1273 | 67.3 | 61 | 5.6 | 61 |
| 421B0181 {C3} | +10.8 | 205A Ovary T | | | 270A Liver N | 422Q0606 | 16121 | 1488 | 93.1 | 43 | 2.3 | 43 |
| 421B0181 {C3} | +5.1 | 263A Ovary T | | | S73 Breast N | 422H0623 | 11326 | 2235 | 58.2 | 68 | 4.4 | 68 |
| 421B0181 {C3} | +4.6 | 384A Ovary T (mets) | | | 272A Dendritic cells | 42240608 | 6583 | 1424 | 24.5 | 40 | 2.1 | 40 |
| 421B0181 {C3} | +4.4 | 264A Ovary T | | | S2 Pancreas N | 422N0629 | 9865 | 2245 | 40.9 | 64 | 3.6 | 64 |
| 421B0181 {C3} | +4.4 | 429A Ovary T (mets) | | | 364A Ovary N | 422I0614 | 2803 | 638 | 22.6 | 60 | 7.4 | 60 |
| 421B0181 {C3} | +4.2 | 261A Ovary T | | | S10 Skeletal muscle N | M2230621 | 8271 | 1949 | 39.5 | 68 | 3.6 | 68 |
| 421B0181 {C3} | +3.8 | S115 Ovary T (mets) | | | CT10 Small intestine N | M22C0604 | 2281 | 607 | 11.6 | 60 | 2.1 | 60 |
| 421B0181 {C3} | +2.5 | 265A Ovary T | | | CT5 Heart N | 422O0624 | 3192 | 1293 | 19.2 | 68 | 4.0 | 68 |
| 421B0181 {C3} | -2.3 | S22 Ovary T | | | CT9 Kidney N | 42290627 | 565 | 1276 | 3.6 | 70 | 3.9 | 70 |
| 421B0181 {C3} | +2.2 | 266A Ovary T | | | S27 Ovary N | 42250603 | 2774 | 1260 | 14.3 | 46 | 2.7 | 46 |
| 421B0181 {C3} | +2.1 | 9334 Ovary T (SCID) | | | I2 Skin N | 422R0601 | 1774 | 837 | 8.4 | 56 | 2.1 | 56 |
| 421B0181 {C3} | +1.9 | 9485 OT 1-P (SCID) | | | 9485 OT 5-P (SCID) | 422Y0602 | 6967 | 3726 | 41.5 | 70 | 9.2 | 70 |
| 421B0181 {C3} | +1.6 | 382A Ovary T | | | CT19 Brain N | 422Q0610 | 2313 | 1471 | 6.2 | 50 | 1.9 | 50 |
| 421B0181 {C3} | +1.6 | 288A Ovary T | | | CT12 Lung N | 422V0625 | 1657 | 1054 | 9.7 | 69 | 2.9 | 69 |
| 421B0181 {C3} | -1.5 | S25 Ovary T | | | CT4 Bone Marrow N | 422H0619 | 848 | 1243 | 4.5 | 65 | 2.7 | 65 |
| 421B0181 {C3} | +1.4 | 262A Ovary T | | | 334A Large Intestine N | 422A0622 | 3171 | 2214 | 16.8 | 69 | 3.8 | 69 |
| 421B0181 {C3} | +1.2 | 386A Ovary T | | | S40 PBMC (activated) | 422J0605 | 630 | 544 | 4.2 | 53 | 1.9 | 53 |
| 421B0181 {C3} | -1.2 | 335A Ovary T | | | S7 Ovary N | 42220626 | 592 | 730 | 3.7 | 75 | 2.6 | 75 |
| 421B0181 {C3} | -1.0 | 201A Ovary T | | | S6 Stomach N | 422W0620 | 1197 | 1237 | 7.8 | 65 | 3.5 | 65 |
| 421B0181 {C3} | -1.0 | 428A Ovary T (mets) | | | 243A Esophagus N | 42240612 | 783 | 797 | 4.5 | 95 | 2.4 | 95 |
| 421B0181 {C3} | | 383A Ovary T (mets) | | | I1 Colon N | 422B0609 | 3470 | 862 | 8.9 | 24 | 1.7 | 24 |

*Fig. 11*

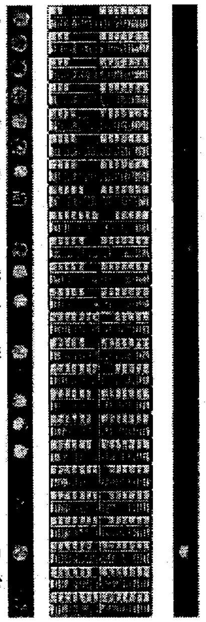

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 42110182 {H7} | +16.7 | 426A Ovary T (mets | | | 415A Aorta N | 422X0611 | 7706 | 462 | 46.3 | 75 | 3.5 | 75 |
| 42110182 {H7} | +10.7 | 205A Ovary T | | | 270A Liver N | 422Q0606 | 10171 | 950 | 61.2 | 41 | 1.8 | 41 |
| 42110182 {H7} | +9.9 | 385A Ovary T | | | S91 Fetal tissue | 422X0607 | 14415 | 1459 | 62.1 | 48 | 2.2 | 48 |
| 42110182 {H7} | +8.8 | S23 Ovary T | | | S56 Spinal Cord N | 422G0628 | 7781 | 880 | 47.3 | 73 | 3.4 | 73 |
| 42110182 {H7} | +6.4 | 383A Ovary T (mets | | | I1 Colon N | 422B0609 | 4807 | 748 | 27.6 | 47 | 2.2 | 47 |
| 42110182 {H7} | +5.1 | 263A Ovary T | | | S73 Breast N | 422H0623 | 9815 | 1909 | 57.1 | 74 | 4.2 | 74 |
| 42110182 {H7} | +4.9 | 429A Ovary T (mets | | | 364A Ovary N | 422I0614 | 2661 | 543 | 20.3 | 61 | 6.7 | 61 |
| 42110182 {H7} | +3.5 | 264A Ovary T | | | S2 Pancreas N | 422N0629 | 7934 | 2274 | 38.8 | 71 | 3.9 | 71 |
| 42110182 {H7} | -2.9 | S25 Ovary T | | | CT4 Bone Marrow | 422H0619 | 480 | 1375 | 3.5 | 80 | 3.0 | 80 |
| 42110182 {H7} | +2.8 | 261A Ovary T | | | S10 Skeletal muscl | 42230621 | 8993 | 3245 | 34.6 | 69 | 5.1 | 69 |
| 42110182 {H7} | +2.5 | S115 Ovary T (mets | | | CT10 Small intestin | 422C0604 | 1864 | 738 | 8.1 | 67 | 2.2 | 67 |
| 42110182 {H7} | +2.3 | 9334 Ovary T (SCIL | | | I2 Skin N | 422R0601 | 2552 | 1113 | 12.7 | 41 | 2.6 | 41 |
| 42110182 {H7} | -2.3 | S22 Ovary T | | | CT9 Kidney N | 42290627 | 386 | 889 | 3.2 | 69 | 3.4 | 69 |
| 42110182 {H7} | +2.2 | 384A Ovary T (mets | | | 272A Dendritic cell | 42240608 | 3516 | 1567 | 18.7 | 55 | 2.2 | 55 |
| 42110182 {H7} | -2.2 | 382A Ovary T | | | CT19 Brain N | 422Q0610 | 608 | 1320 | 4.2 | 60 | 2.3 | 60 |
| 42110182 {H7} | +1.9 | 265A Ovary T | | | CT5 Heart N | 42200624 | 2063 | 1080 | 13.6 | 87 | 3.5 | 87 |
| 42110182 {H7} | +1.8 | 266A Ovary T | | | S27 Ovary N | 42250603 | 1550 | 847 | 7.0 | 58 | 2.1 | 58 |
| 42110182 {H7} | +1.5 | 262A Ovary T | | | 334A Large Intestir | 422A0622 | 2559 | 1651 | 13.2 | 73 | 3.2 | 73 |
| 42110182 {H7} | -1.4 | 386A Ovary T | | | S40 PBMC (activat | 422J0605 | 534 | 738 | 3.9 | 62 | 2.2 | 62 |
| 42110182 {H7} | -1.3 | 288A Ovary T | | | CT12 Lung N | 422V0625 | 893 | 1120 | 5.3 | 66 | 3.1 | 66 |
| 42110182 {H7} | -1.3 | 335A Ovary T | | | S7 Ovary N | 42220626 | 440 | 567 | 3.3 | 60 | 2.2 | 60 |
| 42110182 {H7} | +1.2 | 9485 OT 1-P (SCID | | | 9485 OT 5-P (SCID | 422Y0602 | 4188 | 3529 | 21.6 | 66 | 9.5 | 66 |
| 42110182 {H7} | +1.1 | 428A Ovary T (mets | | | 243A Esophagus N | 42240612 | 725 | 689 | 6.2 | 65 | 2.8 | 65 |
| 42110182 {H7} | -1.0 | 201A Ovary T | | | S6 Stomach N | 422W0620 | 1008 | 1018 | 7.4 | 62 | 3.2 | 62 |

*Fig. 12*

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421V0189 {D1} | +33.2 | 426A Ovary T (mets | 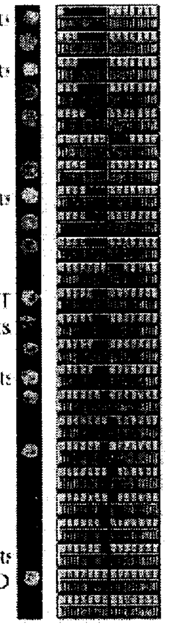 |  | 415A Aorta N | 422X0611 | 8072 | 243 | 55.2 | 67 | 2.4 | 67 |
| 421V0189 {D1} | +13.7 | S23 Ovary T | | | S56 Spinal Cord N | 422G0628 | 7367 | 537 | 42.6 | 69 | 2.5 | 69 |
| 421V0189 {D1} | +12.6 | 429A Ovary T (mets | | | 364A Ovary N | 422I0614 | 2850 | 227 | 21.7 | 64 | 3.5 | 64 |
| 421V0189 {D1} | +8.0 | 385A Ovary T | | | S91 Fetal tissue | 422X0607 | 11711 | 1469 | 54.0 | 58 | 2.2 | 58 |
| 421V0189 {D1} | +7.3 | 263A Ovary T | | | S73 Breast N | 422H0623 | 6949 | 952 | 37.8 | 69 | 2.6 | 69 |
| 421V0189 {D1} | -5.8 | S25 Ovary T | | | CT4 Bone Marrow | 422H0619 | 208 | 1210 | 2.1 | 44 | 2.9 | 44 |
| 421V0189 {D1} | +5.0 | 205A Ovary T | | | 270A Liver N | 422Q0606 | 8676 | 1737 | 52.3 | 57 | 2.6 | 57 |
| 421V0189 {D1} | +4.5 | 383A Ovary T (mets | | | 11 Colon N | 422B0609 | 3149 | 707 | 17.4 | 57 | 2.0 | 57 |
| 421V0189 {D1} | +4.4 | 261A Ovary T | | | S10 Skeletal muscl | 42230621 | 6332 | 1443 | 29.1 | 77 | 2.9 | 77 |
| 421V0189 {D1} | +4.2 | 264A Ovary T | | | S2 Pancreas N | 422N0629 | 7612 | 1809 | 38.1 | 79 | 3.3 | 79 |
| 421V0189 {D1} | -3.2 | 382A Ovary T | | | CT19 Brain N | 422Q0610 | 468 | 1508 | 3.4 | 60 | 2.3 | 60 |
| 421V0189 {D1} | +2.9 | 9334 Ovary T (SCII | | | I2 Skin N | 422R0601 | 2500 | 860 | 12.3 | 51 | 2.1 | 51 |
| 421V0189 {D1} | +2.5 | S115 Ovary T (mets | | | CT10 Small intestin | 422C0604 | 1424 | 569 | 6.7 | 61 | 2.1 | 61 |
| 421V0189 {D1} | +2.4 | 265A Ovary T | | | CT5 Heart N | 422O0624 | 1742 | 723 | 11.8 | 70 | 2.8 | 70 |
| 421V0189 {D1} | +2.3 | 384A Ovary T (mets | | | 272A Dendritic cell | 42240608 | 3083 | 1342 | 17.0 | 62 | 2.0 | 62 |
| 421V0189 {D1} | +1.9 | 266A Ovary T | | | S27 Ovary N | 42250603 | 1370 | 732 | 8.0 | 47 | 2.0 | 47 |
| 421V0189 {D1} | -1.9 | 386A Ovary T | | | S40 PBMC (activat | 422J0605 | 307 | 580 | 2.6 | 41 | 2.0 | 41 |
| 421V0189 {D1} | +1.7 | 262A Ovary T | | | 334A Large Intestir | 422A0622 | 2097 | 1202 | 11.2 | 86 | 2.7 | 86 |
| 421V0189 {D1} | -1.3 | 335A Ovary T | | | S7 Ovary N | 42220626 | 373 | 470 | 2.9 | 47 | 2.0 | 47 |
| 421V0189 {D1} | -1.1 | 288A Ovary T | | | CT12 Lung N | 422V0625 | 969 | 1094 | 5.6 | 72 | 2.9 | 72 |
| 421V0189 {D1} | +1.1 | 201A Ovary T | | | S6 Stomach N | 422W0620 | 750 | 672 | 5.6 | 62 | 2.4 | 62 |
| 421V0189 {D1} | +1.1 | 428A Ovary T (mets | | | 243A Esophagus N | 42240612 | 498 | 446 | 4.2 | 73 | 2.1 | 73 |
| 421V0189 {D1} | -1.0 | 9485 OT 1-P (SCID | | | 9485 OT 5-P (SCID | 422Y0602 | 3117 | 3174 | 16.7 | 91 | 8.2 | 91 |
| 421V0189 {D1} | | S22 Ovary T | | | CT9 Kidney N | 42290627 | 224 | 409 | 2.3 | 48 | 2.3 | 48 |

*Fig. 13*

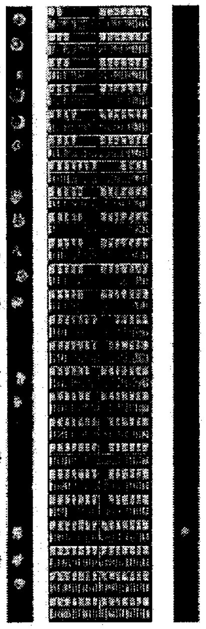

| Gene Name | Bal Exp | Probe 1 Name | P1 | P2 | Probe 2 Name | GEM ID | Probe1 Value | Probe2 Value | Probe1 S/B | Probe1 A% | Probe2 S/B | Probe2 A% |
|---|---|---|---|---|---|---|---|---|---|---|---|---|
| 421H0187 {E11} | +20.2 | 426A Ovary T (mets | | | 415A Aorta N | 422X0611 | 5441 | 270 | 36.3 | 50 | 2.3 | 50 |
| 421H0187 {E11} | +10.0 | S23 Ovary T | | | S56 Spinal Cord N | 422G0628 | 5318 | 533 | 27.1 | 56 | 2.3 | 56 |
| 421H0187 {E11} | +8.3 | 429A Ovary T (mets | | | 364A Ovary N | 422I0614 | 1252 | 150 | 10.1 | 58 | 2.5 | 58 |
| 421H0187 {E11} | +5.7 | 385A Ovary T | | | S91 Fetal tissue | 422X0607 | 9507 | 1668 | 35.8 | 45 | 2.1 | 45 |
| 421H0187 {E11} | +4.4 | 205A Ovary T | | | 270A Liver N | 422Q0606 | 5456 | 1235 | 31.1 | 50 | 2.0 | 50 |
| 421H0187 {E11} | +4.2 | 265A Ovary T | | | CT5 Heart N | 422O0624 | 1834 | 438 | 11.9 | 48 | 2.0 | 48 |
| 421H0187 {E11} | -4.1 | 382A Ovary T | | | CT19 Brain N | 422Q0610 | 309 | 1259 | 2.6 | 48 | 2.0 | 48 |
| 421H0187 {E11} | +3.6 | 261A Ovary T | | | S10 Skeletal muscl | 42230621 | 3733 | 1036 | 17.7 | 55 | 2.3 | 55 |
| 421H0187 {E11} | +3.4 | 263A Ovary T | | | S73 Breast N | 422H0623 | 4163 | 1239 | 23.0 | 62 | 3.0 | 62 |
| 421H0187 {E11} | +2.5 | S115 Ovary T (mets | | | CT10 Small intestin | 422C0604 | 1565 | 627 | 8.8 | 47 | 2.1 | 47 |
| 421H0187 {E11} | +2.1 | 264A Ovary T | | | S2 Pancreas N | 422N0629 | 3455 | 1630 | 14.9 | 60 | 3.0 | 60 |
| 421H0187 {E11} | +2.1 | 384A Ovary T (mets | | | 272A Dendritic cell | 42240608 | 2667 | 1270 | 13.4 | 44 | 1.9 | 44 |
| 421H0187 {E11} | -2.1 | S22 Ovary T | | | CT9 Kidney N | 42290627 | 291 | 605 | 2.4 | 51 | 2.5 | 51 |
| 421H0187 {E11} | -1.7 | 386A Ovary T | | | S40 PBMC (activat | 422J0605 | 410 | 687 | 3.2 | 47 | 2.0 | 47 |
| 421H0187 {E11} | +1.6 | 9334 Ovary T (SCII | | | I2 Skin N | 422R0601 | 1622 | 984 | 7.9 | 44 | 2.2 | 44 |
| 421H0187 {E11} | +1.5 | 262A Ovary T | | | 334A Large Intestir | 422A0622 | 1892 | 1245 | 10.1 | 50 | 2.6 | 50 |
| 421H0187 {E11} | -1.5 | 288A Ovary T | | | CT12 Lung N | 422V0625 | 604 | 908 | 4.1 | 62 | 2.6 | 62 |
| 421H0187 {E11} | -1.4 | 428A Ovary T (mets | | | 243A Esophagus N | 42240612 | 236 | 325 | 2.7 | 78 | 1.9 | 78 |
| 421H0187 {E11} | -1.3 | 335A Ovary T | | | S7 Ovary N | 42220626 | 382 | 501 | 2.9 | 58 | 2.0 | 58 |
| 421H0187 {E11} | -1.2 | 201A Ovary T | | | S6 Stomach N | 422W0620 | 558 | 677 | 4.2 | 58 | 2.3 | 58 |
| 421H0187 {E11} | +1.0 | 9485 OT 1-P (SCID | | | 9485 OT 5-P (SCID | 422Y0602 | 2582 | 2493 | 15.1 | 57 | 6.3 | 57 |
| 421H0187 {E11} | | 383A Ovary T (mets | | | I1 Colon N | 422B0609 | 2261 | 562 | 12.5 | 38 | 1.7 | 38 |
| 421H0187 {E11} | | 266A Ovary T | | | S27 Ovary N | 42250603 | 1739 | 965 | 9.7 | 36 | 2.2 | 36 |
| 421H0187 {E11} | | S25 Ovary T | | | CT4 Bone Marrow | 422H0619 | 283 | 845 | 2.2 | 44 | 2.2 | 44 |

ACGGTTTCAATGGACACTTTTATTGTTTACTTAATGGATCATCAATTTTGTCTCACTACCTACAAATGGAATTTCA
TCTTGTTTCCATGCTGAGTAGTGAAACAGTGACAAAGCTAATCATAATAACCTACATCAAAAGAGAACTAAGCTAA
CACTGCTCACTTTCTTTTTAACAGGCAAAATATAAATATATGCACTCTAXAATGCACAATGGTTTAGTCACTAAAA
AATTCAAATGGGATCTTGAAGAATGTATGCAAATCCAGGGTGCAGTGAAGATGAGCTGAGATGCTGTGCAACTGTT
TAAGGGTTCCTGGCACTGCATCTCTTGGCCACTAGCTGAATCTTGACATGGAAGGTTTTAGCTAATGCCAAGTGGA
GATGCAGAAAATGCTAAGTTGACTTAGGGGCTGTGCACAGGAACTAAAAGGCAGGAAAGTACTAAATATTGCTGAG
AGCATCCACCCCAGGAAGGACTTTACCTTCCAGGAGCTCCAAACTGGCACCACCCCCAGTGCTCACATGGCTGACT
TTATCCTCCGTGTTCCATTTGGCACAGCAAGTGGCAGTG 11721-2

AAGGCTGGTGGGTTTTTGATCCTGCTGGAGAACCTCCGCTTTCATGTGGAGGAAGAAGGGAAGGGAAAAGATGCTT
CTGGGAACAAGGTTAAAGCCGAGCCAGCCAAAATAGAAGCTTTCCGAGCTTCACTTTCCAAGCTAGGGGATGTCTA
TGTCAATGATGCTTTTGGCACTGCTCACAGAGCCCACAGCTCCATGGTAGGAGTCAATCTGCCACAGAAGGCTGGT
GGGTTTTTGATGAAGAAGGAGCTGAACTACTTTGCAAAGGCCTTGGAGAGCCCAGAGCGACCCTTCCTGGCCATCC
TGGGCGGAGCTAAAGTTGCAGACAAGATCCAGCTCATCAATAATATGCTGGACAAAGTCAATGAGATGATTATTGG
TGGTGGAATGGCTTTTACCTTCCTTAAGGTGCTCAACAACATGGAGATTGGCACTTCTCTGTTTGATGAAGAGGGA
GCCAAGATTGTCAAAGACCTAATGTCCAAAGCTGAGAAGAATGGTGTGAAGATTACCTTGCCTGTTGACTTTGTCA
CTGCTGACAAGTTTGATGA 11724-1

TTTGTTCCTTACATTTTTCTAAAGAGTTACTTAAATCAGTCAACTGGTCTTTGAGACTCTTAAGTTCTGATTCCAA
CTTAGCTAATTCATTCTGAGAACTGTGGTATAGGTGGCGTGTCTCTTCTAGCTGGGACAAAAGTTCTTTGTTTTCC
CCCTGTAGAGTATCACAGACCTTCTGCTGAAGCTGGACCTCTGTCTGGGCCTTGGACTCCCAAATCTGCTTGTCAT
GTTCAAGCCTGGAAATGTTAATCTTTAATTCTTCCATATGGATGGACATCTGTCTAAGTTGATCCTTTAGAACACT
GCAATTATCTTCTTTGAGTCTAATTTCTTCTTCTTTGCTTTGAATCGCATCACTAAACTTCCTCTCCCATTTCTTA
GCTTCATCTATCACCCTGTCACGATCATCCTGGAGGGAAGACATGCTCTTAGTAAAGGCTGCAAGCTGGGTCACAG
TACTGTCCAAGTTTTCCTGAAGTTGCTGAACTTCCTTGTCTTTCTTGTTCAAAGTAACCTGAATCTCTCCAATTGT
CTCTTCCAAGTGGACTTTTTCTCTGCGCAAAGCATCCAG 11724-2

TCATTGCCTGTGATGGCATCTGGAATGTGATGAGCAGCCAGGAAGTTGTAGATTTCATTCAATCAAAGGATTCAGC
ATGTGGTGGAAGCTGTGAGGCAAGAGAAACAAGAACTGTATGGCAAGTTAAGAAGCACAGAGGCAAACAAGAAGGA
GACAGAAAAGCAGTTGCAGGAAGCTGAGCAAGAAATGGAGGAAATGAAAGAAAAGATGAGAAAGTTTGCTAAATCT
AAACAGCAGAAAATCCTAGAGCTGGAAGAAGAGAATGACCGGCTTAGGGCAGAGGTGCACCCTGCAGGAGATACAG
CTAAAGAGTGTATGGAAACACTTCTTTCTTCCAATGCCAGCATGAAGGAAGAACTTGAAAGGGTCAAAATGGAGTA
TGAAACCCTTTCTAAGAAGTTTCAGTCTTTAATGTCTGAGAAAGACTCTCTAAGTGAAGAGGTTCAAGATTTAAAG
CATCAGATAGAAGGTAATGTATCTAAACAAGCTAACCTAGAGGCCACCGAGAAACATGATAACCAAACGAATGTCA
CTGAAGAGGGAACACAGTCTATACCAGGT

AAGCCAATAATCACCATTTATTACTTAATATATGCCAACCACTGTACTTGGCAGTTCACAAATTCTCACCGTTACA
ACAACCCCATGAGGTATTTATTCCCATTCTATAGATAGGGAAACCACAGCTCAAGTAAGTTAGGAAACTGAGCCAA
GTATACACAGAATACGAAGTGGCAAAACTAGAAGGAAAGACTGACACTGCTATCTGCTGGCCTCCAGTGTCCTGGC
TCTTTTCACACGGGtTCAATGTCTCCAGCGCTGCTGCTGCTGCTGCATTACCATGCCCTCATTGTTTTTCTTCCTC
TGGTGTTCAACTGCATCCTTCAAAGAATCTAACTCATTCCAGAGACCACTTATTTCTTTCTCTCTTTCTGAAATTA
CTTTTAATAATTCTTCATGAGGGGGAAAAGAAGATGCCTGTTGGTAGTTTTGTTGTTTAAGCTGCTCAATTTGGGA
CTTAAACAATTTGTTTTCATCTTGTACATCCTGTAACAGCTGTGTTTTGCTAGAAAGATCACTCTCCCTCTCTTTT
AGCATGGCTTCTAACCTCTTCAATTCATTTTCCTTTTCTTTCAACACAATCTCAAGTTCTTCAAACTGTGATGCAG
AAGAGGCCTCTTTCAAGTTATGTTGTGCTACTTCCTGAACATGTGCTTTTAAAGATTCATTTTCTTCTTGAAGATC
CTGTAACCACTTCCCTGTATTGGCTAGGTCTTTCTCTTTCTCTTCCAAAACAGCCTTCATGGTATTCATCTGTTCC
TCTTTTCCTTTTAATAAGTTCAGGAGCTTCAGAAC 11726-1&2

CAAGCTTTTTTTTTTTTTTTAAAAAGTGTTAGCATTAATGTTTTATTGTCACGCAGATGGCAACTGGGTTTATGTC
TTCATATTTTATATTTTTGTAAATTAAAAAAATTACAAGTTTTAAATAGCCAATGGCTGGTTATATTTTCAGAAAA
CATGATTAGACTAATTCATTAATGGTGGCTTCAAGCTTTTCCTTATTGGCTCCAGAAAATTCACCCACCTTTTGTC
CCTTCTTAAAAAACTGGAATGTTGGCATGCATTTGACTTCACACTCTGAAGCAACATCCTGACAGTCATCCACATC
TACTTCAAGGAATATCACGTTGGAATACTTTTCAGAGAGGGAATGAAAGAAAGGCTTGATCATTTTGCAAGGCCCA
CACCACGTGGCTGAGAAGTCAACTACTACAAGTTTATCACCTGCAGCGTCCAAGGCTTCCTGAAAAGCAGTCTTGC
TCTCGATCTGCTTCACCATCTTGGCTGCTGGAGTCTGACGAGCGGCTGTAAGGACCGATGGAAATGGATCCAAAGC
ACCAAACAGAGCTTCAAGACTCGCTGCTTGGCTTGAATTCGGATCCGATATCGCCATGGCCT 11727-1&2

AAGTGTTAGCATTAATGTTTTATTGTCACGCAGATGGCAACTGGGTTTATGTCTTCATATTTTATATTTTTGTAAA
TTAAAAAAATTMCAAGTTTTAAATAGCCAATGGCTGGTTATATTTTCAGAAAACATGATTAGACTAATTCATTAAT
GGTGGCTTCAAGCTTTTCCTTATTGGCTCCAGAAAATTCACCCACCTTTTGTCCCTTCTTAAAAAACTGGAATGTT
GGCATGCATTTGACTTCACACTCTGAAGCAACATCCTGACAGTCATCCACATCTACTTCAAGGAATATCACGTTGG
AATACTTTTCAGAGAGGGAATGAAAGAAAGGCTTGATCATTTTGCAAGGCCCACACCACGTGGCTGAGAAGTCAAC
TACTACAAGTTTATCACCTGCAGCGTCCAAGGCTTCCTGAAAAGCAGTCTTGCTCTCGATCTGCTTCACCATCTTG
GCTGCTGGAGTCTGACGAGCGGCTGTAAGGACCGATGGAAATGGATCCAAAGCACCAAACAGAGCTTCAAGACTCG
CTGCTTGGCATGAATTCGGATCCGA

TACAAACTTTATTGAAACGCACACGCGCACACACACAAACACCCCTGTGGATAGGGAAAAGCACCTGGCCACAGGG
TCCACTGAAACGGGGAGGGGATGGCAGCTTGTAATGTGGCTTTTGCCACAACCCCCTTCTGACAGGGAAGGCCTTA
GATTGAGGCCCCACCTCCCATGGTGATGGGGAGCTCAGAATGGGGTCCAGGGAGAATTTGGTTAGGGGGAGGTGCT
AGGGAGGCATGAGCAGAGGGCACCCTCCGAGTGGGGTCCCGAGGGCTGCAGAGTCTTCAGTACTGTCCCTCACAGC
AGCTGTCTCAAGGCTGGGTCCCTCAAAGGGGCGTCCCAGCGCGGGGCCTCCCTGCGCAAACACTTGGTACCCCTGG
CTGCGCAGCGGAAGCCAGCAGGACAGCAGTGGCGCCGATCAGCACAACAGACGCCCTGGCGGTAGGGACAGCAGGC
CCAGCCCTGTCGGTTGTCTCGGCAGCAGGTCTGGTTATCATGGCAGAAGTGTCCTTCCCACACTTCACGTCCTTCA
CACCCACGTGAXGGCTACXGGCCAGGAAG 11728.2.40.19.19

CCCGTGGGTGCCATCCACGGAGTTGTTACCTGATCTTTGGAAGCAGGATCGCCCGTCTGCACTGCAGTGGAAGCCC
CGTGGGCAGCAGTGATGGCCATCCCCGCATGCCACGGCCTCTGGGAAGGGGCAGCAACTGGAAGTCCCTGAGACGG
TAAAGATGCAGGAGTGGCCGGCAGAGCAGTGGGCATCAACCTGGCAGGGGCCACCCAGATGCCTGCTCAGTGTTGT
GGGCCATTTGTCCAGAAGGGGACGGCAGCAGCTGTAGCTGGCTCCTCCGGGGTCCAGGCAGCAGGCCACAGGGCAG
AACTGACCATCTGGGCACCGCGTTCCAGCCACCAGCCCTGCTGTTAAGGCCACCCAGCTCACCAGGGTCCACATGG
TCTGCCTGCGTCCGACTCCGCGGTCCTTGGGCCCTGATGGTTCTACCTGCTGTGAGCTGCCCAGTGGGAAGTATGG
CTGCTGCCAATGCCCAACGCCACCTGCTGCTCCGATCACCTGCACTGCTGCCCCAAGACACTGTGTGTGACCTGAT
CCAGAGTAAGTGCCTCTCCAAGGAGAACG 11730-1

GAATCACCTTTCTGGTTTAGCTAGTACTTTGTACAGAACAATGAGGTTTCCCACAGCGGAGTCTCCCTGGGCTCTG
TTTGGCTCTCGGTAAGGCAGGCCTACACCTTTTCCTCTCCTCTATGGAGAGGGGAATATGCATTAAGGTGAAAAGT
CACCTTCCAAAAGTGAGAAAGGGATTCGATTGCTGCTTCAGGACTGTGGAATTATTTGGAATGTTTTACAAATGGT
TGCTACAAAACAACAAAAAAGGTAATTACAAAATGTGTACATCACAACATGCTTTTTAAAGACATTATGCATTGTG
CTCACATTCCCTTAAATGTTGTTTCCAAAGGTGCTCAGCCTCTAGCCCAGCTGGATTCTCCGGGAAGAGGCAGAGA
CAGTTTGGCGAAAAAGACACAGGGAAGGAGGGGGTGGTGAAAGGAGAAAGCAGCCTTCCAGTTAAAGATCAGCCCT
CAGTTAAAGGTCAGCTTCCCGCAXGCTGGCCTCAXGCGGAGTCTGGGTCAGAGGGAGGAGCAGCAGCAGGGTGGGA
CTGGGGCGT 11730-2

AACCGGAGCGCGAGCAGTAGCTGGGTGGGCACCATGGCTGGGATCACCACCATCGAGGCGGTGAAGCGCAAGATCC
AGGTTCTGCAGCAGCAGGCAGATGATGCAGAGGAGCGAGCTGAGCGCCTCCAGCGAGAAGTTGAGGGAGAAAGGCG
GGCCCGGGAACAGGCTGAGGCTGAGGTGGCCTCCTTGAACCGTAGGATCCAGCTGGTTGAAGAAGAGCTGGACCGT
GCTCAGGAGCGCCTGGCCACTGCCCTGCAAAAGCTGGAAGAAGCTGAAAAAGCTGCTGATGAGAGTGAGAGAGGTA
TGAAGGTTATTGAAAACCGGGCCTTAAAAGATGAAGAAAAGATGGAACTCCAGGAAATCCAACTCAAAGAAGCTAA
GCACATTGCAGAAGAGGCAGATAGGAAGTATGAAGAGGTGGCTCGTAAGTTGGTGATCATTGAAGGAGACTTGGAA
CGCACAGAGGAACGAGCTGAGCTGGCAGAGTCCCGTTGCCGAGAGATGGATGAGCAGATTAGACTGATGGACCAGA
ACCTGAAGTGTCTGAGTGC

*Fig. 15C*

11732.1contig

GAGAACTTGGCCTTTATTGTGGGCCCAGGAGGGCACAAAGGTCAGGAGGCCCAAGGGAGGGATCTGGTTTTCTGGA
TAGCCAGGTCATAGCATGGGTATCAGTAGGAATCCGCTGTAGCTGCACAGGCCTCACTTGCTGCAGTTCCGGGGAG
AACACCTGCACTGCATGGCGTTGATGACCTCGTGGTACACGACAGAGCCATTGGTGCAGTGCAAGGGCACGCGCAT
GGGCTCCGTCCTCGAGGGCAGGCAGCAGGAGCATTGCTCCTGCACATCCTCGATGTCAATGGAGTACACAGCTTTG
CTGGCACACTTTCCCTGGCAGTAATGAATGTCCACTTCCTCTTGGGACTTACAATCTCCCACTTTGATGTACTGCA
CCTTGGCTGTGATGTCTTTGCAATCAGGCTCCTCACATGTGTCACAGCAGGTGCCTGGAATTTTCACGATTTTGCC
TCCTTCAGCCAGACACTTGTGTTCATCAAATGGTGGGCAGCCCGTGACCCTCTTCTCCCAGATGTACTCTCCTCT 11732.2contig GCCTGGACCTTGCCGGATCAGTGCCACACAGTGACTTGCTTGGCAAATGGCCAGACCTTGCTGCAGAGTCATCGTG
TCAATTGTGACCATGGACCCCGGCCTTCATGTGCCAACAGCCAGTCTCCTGTTCGGGTGGAGGAGACGTGTGGCTG
CCGCTGGACCTGCCCTTGTGTGTGCACGGGCAGTTCCACTCGGCACATCGTCACCTTCGATGGGCAGAATTTCAAG
CTTACTGGTAGCTGCTCCTATGTCATCTTTCAAAACAAGGAGCAGGACCTGGAAGTGCTCCTCCACAATGGGGCCT
GCAGCCCCGGGGCAAAACAAGCCTGCATGAAGTCCATTGAGATTAAGCATGCTGGCGTCTCTGCTGAGCTGCACAG
TAACATGGAGATGGCAGTGGATGGGAGACTGGTCCTTGCCCCGTACGTTGGTGAAAACATGGAAGTCAGCATCTAC
GGCGCTATCATGTATGAAGTCAGGTTTACCCATCTTGGCCACATCCTCACATACACCGCCXCAAAACAACGAGTT 11735-1-2

AGATCAACCTCTGCTGGTCAGGAGGAATGCCTTCCTTGTCTTGGATCTTTGCTTTGACGTTCTCGATAGTRWCAaC
TKKRYTSRAMSKMAAGKGYRATGRWMTTKSYWGWRASYKTMWWMRSGRARAYTTaGaCAYCCCMCCTCWgAGaCGS
AGKACCARGTGCAgAgGTGGACTCTTTCTGGATGTTGTAGTCAGACAGGGTGCGTCCATCTTCCAGCTGTTTCCCA
GCAAAGATCAACCTCTGCTGATCAGGAGGGATGCCTTCCTTATCTTGGATCTTTGCCTTGACATTCTCGATGGTGT
CACTGGGCTCCACCTCGAGGGTGATGGTCTTACCAGTCAGGGTCTTCACGAAGATYTGCATCCCACCTCTGAGACG
GAGCACCAGGTGCAGGGTRGACTCTTTCTGGATGTTGTAGTCAGACAGGGTGCGYCCATCTTCCAGCTGcTTTCCS
aGCAAAGATCAACCTCTGCTGGTCAGGAGGRATGCCTTCCTTGTCYTGGATCTTTGCYTTGACRTTCTCRATGGTG
TCACTCGGCTCCACTTCGAGAGTGATGGTCTTACCAGTCAGGGTCTTCACGAAGATCTGCATCCCACCTCTAA 11740.2.contig AAGTCACAAACAGACAAAGATTATTACCAGCTGCAAGCTATATTAGAAGCTGAACGAAGAGACAGAGGTCATGATT
CTGAGATGATTGGAGACCTTCAAGCTCGAATTACATCTTTACAAGAGGAGGTGAAGCATCTCAAACATAATCTCGA
AAAAGTGGAAGGAGAAAGAAAAGAGGCTCAAGACATGCTTAATCACTCAGAAAAGGAAAAGAATAATTTAGAGATA
GATTTAAACTACAAACTTAAATCATTACAACAACGGTTAGAACAAGAGGTAAATGAACACAAAGTAACCAAAGCTC
GTTTAACTGACAAACATCAATCTATTGAAGAGGCAAAGTCTGTGGCAATGTGTGAGATGGAAAAAAAGCTGAAAGA
AGAAAGAGAAGCTCGAGAGAAGGCTGAAAATCGGGTTGTTCAGATTGAGAAACAGTGTTCCATGCTAGACGTTGAT
CTGAAGCAATCTCAGCAGAAACTAGAACATTTGACTGGAAATAAAGAAAGGATGGAGGATGAAGTTAAGAATCTA

*Fig. 15D*

11765.2&64.2.contig

CGCCTCCACCATGTCCATCAGGGTGACCCAGAAGTCCTACAAGGTGTCCACCTCTGGCCCCCGGGCCTTCAGCAGC
CGCTCCTACACGAGTGGGCCCGGTTCCCGCATCAGCTCCTCGAGCTTCTCCCGAGTGGGCAGCAGCAACTTTCGCG
GTGGCCTGGGCGGCGGCTATGGTGGGGCCAGCGGCATGGGAGGCATCACCGCAGTTACGGTCAACCAGAGCCTGCT
GAGCCCCCTTGTCCTGGAGGTGGACCCCAACATCCAGGCCGTGCGCACCCAGGAGAAGGAGCAGATCAAGACCCTC
AACAACAAGTTTGCCTCCTTCATAGACAAGGTACGGTTCCTGGAGCAGCAGAACAAGATGCTGGAGACCAAGTGGA
GCCTCCTGCAGCAGCAGAAGACGGCTCGAAGCAACATGGACAACATGTTCGAGAGCTACATCAACARCCTTAGGCG
GCAGCTGGAGACTCTGGGCCAGGAGAAGCTGAAGCTGGAGGCGGAGCTTGGCAACATGCAGGGGCTGGTGGAGGAC
TTCAAGAACAAGTATGAGGATGAGATCAATAAGCGTACAGAGATGGAGAACGAATTTGTCCTCATCAAGAAGGATG
TGGATGAAGCTTACATGAACAAGGTAGAGCTGGAGTCTCGCCTGGAAGGGCTGACCGACGAGATCAACTTCCTCAG
GCAGCTGTATGAAGAGGAGATCCGGGAGCTGCAGTCCCAGATCTCGGACACATCTGTGGTGCTGTCCATGGACAAC
AGCCGCTCCCTGGACATGGACAGCATCATTGCTGAGGTCAAGGCACAGTACGAGGATATTGCCAACCGCAGCCGGG
CTGAGGCTGAGAGCATGTACCAGGTCAAGTATGAGGAGCTGCAGAGCCTGGCTGGGAAGCACGGGGATGACCTGCG
GCGCACAAAGACTGAGATCTCTGAGATGAACCCGGAACATCAGCCCGGCTXCAGGCTGAGATTGAGGGCCTCAAAG
GCCAGAXGGCTTXCCTGGAXGXCCGCCAT 11767.2.contig CCCGGAGCCAGCCAACGAGCGGAAAATGGCAGACAATTTTTCGCTCCATGATGCGTTATCTGGGTCTGGAAACCCA
AACCCTCAAGGATGGCCTGGCGCATGGGGGAACCAGCCTGCTGGGGCAGGGGGCTACCCAGGGGCTTCCTATCCTG
GGGCCTACCCCGGGCAGGCACCCCCAGGGGCTTATCCTGGACAGGCACCTCCAGGCGCCTACCCTGGAGCACCTGG
AGCTTATCCCGGAGCACCTGCACCTGGAGTCTACCCAGGGCCACCCAGCGGCCCTGGGGCCTACCCATCTTCTGGA
CAGCCAAGTGCCACCGGAGCCTACCCTGCCACTGGCCCCTATGGCGCCCCTGCTGGGCCACTGATTGTGCCTTATA
ACCTGCCTTTGCCTGGGGGAGTGGTGCCTCGCATGCTGATAACAATTCTGGGCACGGTGAAGCCCAATGCAAACAG
AATTGCTTTAGATTTCCAAAGAGGGAATGATGTTGCCTTCCACTTTAACCCACGCTTCAATGAGAACAACAGGAGA
GTCATTGGTTGCAATACAAAGCTGGATAA 11768-1&2

GGGAATGCAACAACTTTATTGAAAGGAAAGTGCAATGAAATTTGTTGAAACCTTAAAAGGGGAAACTTAGACACCC
CCCCTCRAgCGMAGKACCARGTGCARAgGTGGACTCTTTCTGGATGTTGTAGTCAGACAGGGTRCGWCCATCTTCC
AGCTGTTTYCCRGCAAAGATCAACCTCTGCTGATCAGGAGGRATGCCTTCCTTATCTTGGATCTTTGCCTTGACAT
TCTCGATGGTGTCACTGGGCTCCACCTCGAGGGTGATGGTCTTACCAGTCAGGGTCTTCACGAAGATYTGCATCCC
ACCTCTGAGACGGAGCACCAGGTGCAGGGTRGACTCTTTCTGGATGTTGTAGTCAGACAGGGTGCGYCCATCTTCC
AGCTGcTTTCCSaGCAAAGATCAACCTCTGCTGGTCAGGAGGRATGCCTTCCTTGTCYTGGATCTTTGCYTTGACR
TTCTCAATGGTGTCACTCGGCTCCACTTCGAGAGTGATGGTCTTACCAGTCAGGGTCTTCACGAAGATCTGCATCC
CACCTCTAAGACGGAGCACCAGGTGCAGGGTGGACTCTTTCTGGATGgTTGTAGTCAGACAGGGTGCGTCCATCTT
CCAGCTGTTTCCCAGCAAAGATCAACCT

AGGTTGATCTTTGCTGGGAAACAGCTGGAAGATGGACGCACCCTGTCTGACTACAAcCATCCAGAAAGAGTCCACC
CTGCACCTGGTGCTCCGTCTTAGAGGTGGGATGCAGATCTTCGTGAAGACCCTGACTGGTAAGACCATCACTCTCG
AAGTGGAGCCGAGTGACACCATTGAGAAYGTCAARGCAAAGATCCARGACAAGGAAGGCATYCCTCCTGACCAGCA
GAGGTTGATCTTTGCtSGGAAAgCAGCTGGAAGATGGRCGCACCCTGTCTGACTACAACATCCAGAAAGAGTCYAC
CCTGCACCTGGTGCTCCGTCTCAGAGGTGGGATGCARATCTTCGTGAAGACCCTGACTGGTAAGACCATCACCCTC
GAGGTGGAGCCCAGTGACACCATCGAGAATGTCAAGGCAAAGATCCAAGATAAGGAAGGCATCCCTCCTGATCAGC
AGAGGTTGATCTTTGCTGGGAAACAGCTGGAAGATGGACGCACCCTGTCTGACTACAACATCCAGAAAGAGTCCAC
cTYTGCACYTGGTMCTBCGtCTYaGAGGKGGGRTGcaaaTCTWMGTKWagaCaCtCaCTKKYAAGRYYaTCAMCMW
tgAKKTCgAKYSCASTKWCaCTWTCRAKAAMGTYRWWGCAWagaTCCMAGACAAGGAAGGCATTCCTCCTGACCAG
CAGAGGTTGATCT 11769.1.contig ATGGAGTCTCACTCTGTCGACCAGGCTGGAGCGCTGTGGTGCGATATCGGCTCACTGCAGTCTCCACTTCCTGGGT
TCAAGCGATCCTCCTGCCTCAGCCTCCCGAGTAGCTGGGACTACAGGCAGGCGTCACCATAATTTTTGTATTTTTA
GTAGAGACATGGTTTCGCCATGTTGGCTGGGCTGGTCTCGAACTCCTGACCTCAAGTGATCTGTCCTGGCCTCCCA
AAGTGTTGGGATTACAGGCGAAAGCCAACGCTCCCGGCCAGGGAACAACTTTAGAATGAAGGAAATATGCAAAAGA
ACATCACATCAAGGATCAATTAATTACCATCTATTAATTACTATATGTGGGTAATTATGACTATTTCCCAAGCATT
CTACGTTGACTGCTTGAGAAGATGTTTGTCCTGCATGGTGGAGAGTGGAGAAGGGCCAGGATTCTTAGGTT 11769.2.contig AGCGCGGTCTTCCGGCGCGAGAAAGCTGAAGGTGATGTGGCCGCCCTCAACCGACGCATCCAGCTCGTTGAGGAGG
AGTTGGACAGGGCTCAGGAACGACTGGCCACGGCCCTGCAGAAGCTGGAGGAGGCAGAAAAAGCTGCAGATGAGAG
TGAGAGAGGAATGAAGGTGATAGAAAACCGGGCCATGAAGGATGAGGAGAAGATGGAGATTCAGGAGATGCAGCTC
AAAGAGGCCAAGCACATTGCGGAAGAGGCTGACCGCAAATACGAGGAGGTAGCTCGTAAGCTGGTCATCCTGGAGG
GTGAGCTGGAGAGGGCAGAGGAGCGTGCGGAGGTGTCTGAACTAAAATGTGGTGACCTGGAAGAAGAACTCAAGAA
TGTTACTAACAATCTGAAATCTCTGGAGGCTGCATCTGAAAAGTATTCTGAAAAGGAGGACAAATATGAAGAAGAA
ATTAAACTTCTGTCTGACAAACTGAAAGAGGCTGAGACCCGTGCTGAATTTGCAGAGAGAACGGTTGCAAAACTGG
AAAAGACAATTGATGACCTGGAAGAGAAACTTGCCCAGC 11770.1.contig GTGCACAGGTCCCATTTATTGTAGAAAATAATAATAATTACAGTGATGAATAGCTCTTCTTAAATTACAAAACAGA
AACCACAAAGAAGGAAGAGGAAAAACCCCAGGACTTCCAAGGGTGAAGCTGTCCCCTCCTCCCTGCCACCCTCCCA
GGCTCATTAGTGTCCTTGGAAGGGGCAGAGGACTCAGAGGGGATCAGTCTCCAGGGGCCCTGGGCTGAAGCGGGTG
AGGCAGAGAGTCCTGAGGCCACAGAGCTGGGCAACCTGAGCCGCCTCTCTGGCCCCCTCCCCCACCACTGCCCAAA
CCTGTTTACAGCACCTTCGCCCCTCCCCTCTAAACCCGTCCATCCACTCTGCACTTCCCAGGCAGGTGGGTGGCC
AGGCCTCAGCCATACTCCTGGGCGCGGGTTTCGGTGAGCAAGGCACAGTCCCAGAGGTGATATCAAGGCCT

*Fig. 15F*

11770.2.contig

GCAAGGAACTGGTCTGCTCACACTTGCTGGCTTGCGCATCAGGACTGGCTTTATCTCCTGACTCACGGTGCAAAGG
TGCACTCTGCGAACGTTAAGTCCGTCCCCAGCGCTTGGAATCCTACGGCCCCCACAGCCGGATCCCCTCAGCCTTC
CAGGTCCTCAACTCCCGTGGACGCTGAACAATGGCCTCCATGGGGCTACAGGTAATGGGCATCGCGCTGGCCGTCC
TGGGCTGGCTGGCCGTCATGCTGTGCTGCGCGCTGCCCATGTGGCGCGTGACGGCCTTCATCGGCAGCAACATTGT
CACCTCGCAGACCATCTGGGAGGGCCTATGGATGAACTGCGTGGTGCAGAGCACCGGCCAGATGCAGTGCAAGGTG
TACGACTCGCTGCTGGCACTGCCGCAGGACCTGCAGGCGGCCCGCGCCCTCGTCATCATCA 11773.1.contig TGCAAAAGGGACACAGGGGTTCAAAAATAAAAATTTCTCTTCCCCCTCCCCAAACCTGTACCCCAGCTCCCCGACC
ACAACCCCCTTCCTCCCCCGGGGAAAGCAAGAAGGAGCAGGTGTGGCATCTGCAGCTGGGAAGAGAGAGGCCGGGG
AGGTGCCGAGCTCGGTGCTGGTCTCTTTCCAAATATAAATACXTGTGTCAGAACTGGAAAATCCTCCAGCACCCAC
CACCCAAGCACTCTCCGTTTTCTGCCGGTGTTTGGAGAGGGGCGGGGGGCAGGGGCGCCAGGCACCGGCTGGCTGC
GGTCTACTGCATCCGCTGGGTGTGCACCCCGCGAGCCTCCTGCTGCTCATTGTAGAAGAGATGACACTCGGGGTCC
CCCCGGATGGTGGGGGCTCCCTGGATCAGCTTCCCGGTGTTGGGGTTCACACACCAGCACTCCCCACGCTGCCCGT
TCAGAGACATCTTGCACTGTTTGAGGTTGTACAGGCCATGCTTGTCACAGTTG 11778.1.contig GGGTTGGAGGGACTGGTTCTTTATTTCAAAAAGACACTTGTCAATATTCAGTATCAAAACAGTTGCACTATTGATT
TCTCTTTCTCCCAATCGGCCCCAAAGAGACCACATAAAAGGAGAGTACATTTTAAGCCAATAAGCTGCAGGATGTA
CACCTAACAGACCTCCTAGAAACCTTACCAGAAAATGGGGACTGGGTAGGGAAGGAAACTTAAAAGATCAACAAAC
TGCCAGCCCACGGACTGCAGAGGCTGTCACAGCCAGATGGGGTGGCCAGGGTGCCACAAACCCAAAGCAAAGTTTC
AAAATAATATAAAATTTAAAAAGTTTTGTACATAAGCTATTCAAGATTTCTCCAGCACTGACTGATACAAAGCACA
ATTGAGATGGCACTTCTAGAGACAGCAGCTTCAAACCCAGAAAAGGGTGATGAGATGAGTTTCACATGGCTAAATC
AGTGGCAAAAACACAGTCTTCTTTCTTTCTTTCTTTCAAGGAGGCAGGAAAGCAATTAAGTGGTCACCTCAACATA
AGGGGGACATGATCCATTCTGTAAGCAGTTGTGAAGGGG 11778-2&30-2

CAGGAACCGGAGCGCGAGCAGTAGCTGGGTGGGCACCATGGCTGGGATCACCACCATCGAGGCGGTGAAGCGCAAG
ATCCAGGTTCTGCAGCAGCAGGCAGATGATGCAGAGGAGCGAGCTGAGCGCCTCCAGCGAGAAGTTGAGGGAGAAA
GGCGGGCCCGGGAACAGGCTGAGGCTGAGGTGGCCTCCTTGAACCGTAGGATCCAGCTGGTTGAAGAAGAGCTGGA
CCGTGCTCAGGAGCGCCTGGCCACTGCCCTGCAAAAGCTGGAAGAAGCTGAAAAAGCTGCTGATGAGAGTGAGAGA
GGTATGAAGGTTATTGAAAACCGGGCCTTAAAAGATGAAGAAAAGATGGAACTCCAGGAAATCCAACTCAAAGAAG
CTAAGCACATTGCAGAAGAGGCAGATAGGAAGTATGAAGAGGTGGCTCGTAAGTTGGTGATCATTGAAGGAGACTT
GGAACGCACAGAGGAACGAGCTGAGCTGGCAGAGTCCCGTTGCCGAGAGATGGATGAGCAGATTAGACTGATGGAC
CAGAACCTGAAGTGTCTGAGTGC

*Fig. 15G*

11782.1.contig

ATCTACGTCATCAATCAGGCTGGAGACACCATGTTCAATCGAGCTAAGCTGCTCAATATTGGCTTTCAAGAGGCCT
TGAAGGACTATGATTACAACTGCTTTGTGTTCAGTGATGTGGACCTCATTCCGATGGACGACCGTAATGCCTACAG
GTGTTTTTCGCAGCCACGGCACATTTCTGTTGCAATGGACAAGTTCGGGTTTAGCCTGCCATATGTTCAGTATTTT
GGAGGTGTCTCTGCTCTCAGTAAACAACAGTTTCTTGCCATCAATGGATTCCCTAATAATTATTGGGGTTGGGGAG
GAGAAGATGACGACATTTTTAACAGATTAGTTCATAAAGGCATGTCTATATCACGTCCAAATGCTGTAGTAGGGAG
GTGTCGAATGATCCGGCATTCAAGAGACAAGAAAAATGAGCCCAATCCTCAGAGGTTTGACCGGATCGCACATACA
AAGGAAACGATGCGCTTCGATGGTTTGAACTCACTTACCTACAAGGTGTTGGATGTCAGAGATACCCGTTATATAC
CCAAATCAC 11782.2.contig CTAGACCTCTAATTAAAAGGCACAATCATGCTGGAGAATGAACAGTCTGACCCCGAGGGCCACAGCGAATTTTAGG
GAAGGAGGCAAAGAGGTGAGAAGGGAAAGGAAAGAAGGAAGGAAGGAGAACAATAAGAACTGGAGACGTTGGGTGG
GTCAGGGAGTGTGGTGGAGGCTCGGAGAGATGGTAAACAAACCTGACTGCTATGAGTTTTCAACCCCATAGTCTAG
GGCCATGAGGGCGTCAGTTCTTGGTGGCTGAGGGTCCTTCCACCCAGCCCACCTGGGGGAGTGGAGTGGGGAGTTC
TGCCAGGTAAGCAGATGTTGTCTCCCAAGTTCCTGACCCAGATGTCTGGCAGGATAACGCTGACCTGTTCCCTCAA
CAAGGGACCTGAAAGTAATTTTGCTCTTTAC 11783-1 & 2

CCGAATTCAAGCGTCAACGATCCYTCCCTTACCATCAAATCAATTGGCCACCAATGGTACTGAACCTACGAGTACA
CCGACTACgGGCGGACTAATCTTCAACTCCTACATACTTCCCCCATTATTCCTAGAACCAGGCGACCTGCGACTCC
TTGACGTTGACAATCGAGTAGTACTCCCGATTGAAGCCCCCATTCGTATAATAATTACATCACAAGACGTCTTGCA
CTCATGAGCTGTCCCCACATTAGGCTTAAAAACAGATGCAATTCCCGGACGTCTAAGCCAAACCACTTTCACCGCT
ACACGACCGGGGGTATACTACGGTCAATGCTCTGAAATCTGTGGAGCAAACCACAGTTTCATGCCCATCGTCCTAG
AATTAATTCCCCTAAAAATCTTTGAAATAGGGCCCGTATTTACCCTATAGCACCCCCTCTACCCCCTCTAG 11786.1.contig GCTCTTCACACTTTTATTGTTAATTCTCTTCACATGGCAGATACAGAGCTGTCGTCTTGAAGACCACCACTGACCA
GGAAATGCCACTTTTACAAAATCATCCCCCCTTTTCATGATTGGAACAGTTTTCCTGACCGTCTGGGAGCGTTGAA
GGGTGACCAGCACATTTGCACATGCAAAAAAGGAGTGACCCCAAGGCCTCAACCACACTTCCCAGAGCTCACCATG
GGCTGCAGGTGACTTGCCAGGTTTGGGGTTCGTGAGCTTTCCTTGCTGCTGCGGTGGGGAGGCCCTCAAGAACTGA
GAGGCCGGGGTATGCTTCATGAGTGTTAACATTTACGGGACAAAAGCGCATCATTAGGATAAGGAACAGCCACAGC
ACTTCATGCTTGTGAGGGTTAGCTGTAGGAGCGGGTGAAAGGATTCCAGTTTATGAAAATTTAAAGCAAACAACGG
TTTTTAGCTGGGTGGGAAACAGGAAAACTGTGATGTCGGCCAATGACCACCATTTTTCTGCCCATGTGAAGGTCCC
CATGAAACC

*Fig. 15H*

11786.2.contig

CAAGCGCTTGGCGTTTGGACCCAGTTCAGTGAGGTTCTTGGGTTTTGTGCCTTTGGGGATTTTGGTTTGACCCAGG
GGTCAGCCTTAGGAAGGTCTTCAGGAGGAGGCCGAGTTCCCCTTCAGTACCACCCCTCTCTCCCCACTTTCCCTCT
CCCGGCAACATCTCTGGGAATCAACAGCATATTGACACGTTGGAGCCGAGCCTGAACATGCCCCTCGGCCCCAGCA
CATGGAAAACCCCCTTCCTTGCCTAAGGTGTCTGAGTTTCTGGCTCTTGAGGCATTTCCAGACTTGAAATTCTCAT
CAGTCCATTGCTCTTGAGTCTTTGCAGAGAACCTCAGATCAGGTGCACCTGGGAGAAAGACTTTGTCCCCACTTAC
AGATCTATCTCCTCCCTTGGGAAGGGCAGGGAATGGGGACGGTGTATGGAGGGGAAGGGATCTCCTGCGCCCTTCA
TTGCCACACTTGGTGGGACCATGAACATCTTTAGTGTCTGAGCTTCTCAAATTACTGCAATAGGA 13691.1&2

AGCGTCAAATCAGAATGGAAAAGACTCAAAACCATCATCAACACCAAGATCAAAAGGACAAGRATCCTTCAAGAAA
CAGGAAAAAACTCCTAAAACACCAAAAGGACCTAGTTCTGTAGAAGACATTAAAGCAAAAATGCAAGCAAGTATAG
AAAAAGGTGGTTCTCTTCCCAAAGTGGAAGCCAAATTCATCAATTATGTGAAGAATTGCTTCCGGATGACTGACCA
AGAGGCTATTCAAGATCTCTGGCAGTGGAGGAAGTCTCTTTAAGAAAATAGTTTAAACAATTTGTTAAAAAATTTT
CCGTCTTATTTCATTTCTGTAACAGTTGATATCTGGCTGTCCTTTTTATAATGCAGAGTGAGAACTTTCCCTACCG
TGTTTGATAAATGTTGTCCAGGTTCTATTGCCAAGAATGTGTTGTCCAAAATGCCTGTTTAGTTTTTAAAGATGGA
ACTCCACCCTTTGCTTGGTTTTAAGTATGTATGGAATGTTATGATAGGACATAGTAGTAGCGGTGGTCAGACATGG
AAATGGTGGGSMGACAAAAATATACATGTGAAATAA 13692.1&2

TCCGAATTCCAAGCGAATTATGGACAAACGATTCCTTTTAGAGGATTACTTTTTTCAATTTCGGTTTTAGTAATCT
AGGCTTTGCCTGTAAAGAATACAACGATGGATTTTAAATACTGTTTGTGGAATGTGTTTAAAGGATTGATTCTAGA
ACCTTTGTATATTTGATAGTATTTCTAACTTTCATTTCTTTACTGTTTGCAGTTAATGTTCATGTTCTGCTATGCA
ATCGTTTATATGCACGTTTCTTTAATTTTTTTAGATTTTCCTGGATGTATAGTTTAAACAACAAAAAGTCTATTTA
AAACTGTAGCAGTAGTTTACAGTTCTAGCAAAGAGGAAAGTTGTGGGGTTAAACTTTGTATTTTCTTTCTTATAGA
GGCTTCTAAAAAGGTATTTTTATATGTTCTTTTTAACAAATATTGTGTACAACCTTTAAAACATCAATGTTTGGAT
CAAAACAAGACCCAGCTTATTTTCTGC 13693.2

TGTGGTGGCGCGGGCTGAGGTGGAGGCCCAGGACTCTGACCCTGCCCCTGCCTTCAGCAAGGCCCCCGGCAGCGCC
GGCCACTACGAACTGCCGTGGGTTGAAAAATATAGGCCAGTAAAGCTGAATGAAATTGTCGGGAATGAAGACACCG
TGAGCAGGCTAGAGGTCTTTGCAAGGGAAGGAAATGTGCCCAACATCATCATTGCGGGCCCTCCAGGAACCGGCAA
GACCACAAGCATTCTGTGCTTGGCCCGGGCCCTGCTGGGCCCAGCACTCAAAGATGCCATGTTGGAACTCAATGCT
TCAAATGACAGGGGCATTGACGTTGTGAGGAATAAAATTAAAATGTTTGCTCAACAAAAAGTCACTCTTCCCAAAG
GCCGACATAAGATCATCATTCTGGATGAAGCAGACAGCATGACCGACGGAGCCCAGCAAGCCTTGAGGAGAACCAT
GGAAATCTACTCTAAAACCACTCGTTCGCCCTTGCTTGTAATGCTTCGGATAAGATCATCGAGCC

CTTTGCAAAGCTTTTATTTCATGTCTGCGGCATGGAATCCACCTGCACATGGCATCTTAGCTGTGAAGGAGAAAGC
AGTGCACGAGAAGGAATGAGTGGGCGGAACCAACGGCCTCCACAAGCTGCCTTCCAGCAGCCTGCCAAGGCCATGG
CAGAGAGAGACTGCAAACAAACACAAGCAAACAGAGTCTCTTCACAGCTGGAGTCTGAAAGCTCATAGTGGCATGT
GTGAATCTGACAAAATTAAAAGTGTGCATAGTCCATTACATGCATAAAACACTAATAATAATCCTGTTTACACGTG
ACTGCAGCAGGCAGGTCCAGCTCCACCACTGCCCTCCTGCCACATCACATCAAGTGCCATGGTTTAGAGGGTTTTT
CATATGTAATTCTTTTATTCTGTAAAAGGTAACAAAATATACAGAACAAAACTTTCCCTTTTTAAAACTAATGTTA
CAAATCTGTATTATCACTTGGATATAAATAGTATATAAGCTGATC 13700.1

CAAGGGATATATGTTGAGGGTACRGRGTGACACTGAACAGATCACAAAGCACGAGAAACATTAGTTCTCTCCCTCC
CCAGCGTCTCCTTCGTCTCCCTGGTTTTCCGATGTCCACAGAGTGAGATTGTCCCTAAGTAACTGCATGATCAGAG
TGCTGKCTTTATAAGACTCTTCATTCAGCGTATCCAATTCAGCAATTGCTTCATCAAATGCCGTTTTTGCCAGGCT
ACAGGCCTTTTCAGGAGAGTTTAGAATCTCATAGTAAAAGACTGAGAAATTTAGTGCCAGACCAAGACGAATTGGG
TGTGTAGGCTGCATTNCTTTCTTACTAATTTCAAATGCTTCCTGGTAAGCCTGCTGGGAGTTCGACACAAGTGGTT
TGTTTGTTGCTCCAGATGCCACTTCAGAAAGATACCTAAAATAATCTCCTTTCATTTTCAAAGTAGAACAC 13700.2

TCCGGAGCCGGGGTAGTCGCCGCCGCCGCCGCCGGTGCAGCCACTGCAGGCACCGCTGCCGCCGCCTGAGTAGTGG
GCTTAGGAAGGAAGAGGTCATCTCGCTCGGAGCTTCGCTCGGAAGGGTCTTTGTTCCCTGCAGCCCTCCCACGGGA
ATGACAATGGATAAAAGTGAGCTGGTACAGAAAGCCAAACTCGCTGAGCAGGCTGAGCGATATGATGATATGGCTG
CAGCCATGAAGGCAGTCACAGAACAGGGGCATGAACTCTCCAACGAAGAGAGAAATCTGCTCTCTGTTGCCTACAA
GAATGTGGTAAGGCCGCCCGCCGCTCTTCCTGGCGTGTCATCTCCAGCATTGAGCAGAAAACAGAGAGGAATGAGA
AGAAGCAGCAGATGGGCAAAGAGTACCGTGAGAAGATAGAGGCAGAACTGCAGGACATCTGCAATGATGTTCTGGA
GCTTGTTGGACAAATATCTTATTCCAATGCTACACAACCCAGAAA 13701.1

AAAAAGCAGCARGTTCAACACAAAATAGAAATCTCAAATGTAGGATAGAACAAAACCAAGTGTGTGAGGGGGGAAG
CAACAGCAAAAGGAAGAAATGAGATGTTGCAAAAAAGATGGAGGAGGGTTCCCCTCTCCTCTGGGGACTGACTCAA
ACACTGATGTGGCAGTATACACCATTCCAGAGTCAGGGGTGTTCATTCTTTTTTGGGAGTAAGAAAAGGTGGGGAT
TAAGAAGACGTTTCTGGAGGCTTAGGGACCAAGGCTGGTCTCTTTCCCCCCTCCCAACCCCCTTGATCCCTTTCTC
TGATCAGGGGAAAGGAGCTCGAATGAGGGAGGTAGAGTTGGAAAGGGAAAGGATTCCACTTGACAGAATGGGACAG
ACTCCTTCCCA

TGGCAATAGCACAGCCATCCAGGAGCTCTTCARGCGCATCTCGGAGCAGTTCACTGCCATGTTCCGCCGGAAGGCC
TTCCTCCACTGGTACACAGGCGAGGGCATGGACGAGATGGAGTTCACCGAGGCTGAGAGCAACATGAACGACCTCG
TCTCTGAGTATCAAGCAGTACCAGGATGCCACCGCAGAAGAGGAGGAGGATTTCGGTGAGGAGGCCGAAGAGGAGG
CCTAAGGCAGAGCCCCCATCACCTCAGGCTTCTCAGTTCCCTTAGCCGTCTTACTCAACTGCCCCTTTCCTCTCCC
TCAGAATTTGTGTTTGCTGCCTCTATCTTGTTTTTTGTTTTTTCTTCTGGGGGGGTCTAGAACAGTGCCTGGCACA
TAGTAGGCGCTCAATAAATACTTGGTTGNTGAATGTCTCCT 13702.2

AGCTGGCGCTAGGGCTCGGTTGTGAAATACAGCGTRGTCAGCCCTTGCGCTCAGTGTAGAAACCCACGCCTGTAAG
GTCGGTCTTCGTCCATCTGCTTTTTTCTGAAATACACTAAGAGCAGCCACAAAACTGTAACCTCAAGGAAACCATA
AAGCTTGGAGTGCCTTAATTTTTAACCAGTTTCCAATAAAACGGTTTACTACCT 13704.2-13740.2

GGAGATGAAGATGAGGAAGCTGAGTCAGCTACGGGCARGCGGGCAGCTGAAGATGATGAGGATGACGATGTCGATA
CCAAGAAGCAGAAGACCGACGAGGATGACTAGACAGCAAAAAAGGAAAAGTTAAA 13706.1

GATGAAAATTAAATACTTAAATTAATCAAAAGGCACTACGATACCACCTAAAACCTACTGCCTCAGTGGCAGTAKG
CTAAKGAAGATCAAGCTACAGSACATYATCTAATATGAATGTTAGCAATTACATAKCARGAAGCATGTTTGCTTTC
CAGAAGACTATGGNACAATGGTCATTWGGGCCCAAGAGGATATTTGGCCNGGAAAGGATCAAGATAGATNAANGTA
AAG 13706.2

GAGTAGCAACGCAAAGCGCTTGGTATTGAGTCTGTGGGSGACTTCGGTTCCGGTCTCTGCAGCAGCCGTGATCGCT
TAGTGGAGTGCTTAGGGTAGTTGGCCAGGATGCCGAATATCAAAATCTTCAGCAGGCAGCTCCCACCAGGACTTAT
CTCASAAAATTGCTGACCGCCTGGGCCTGGAGCTAGGCAAGGTGGTGACTAAGAAATTCAGCAACCAGGAGACCTG
TGTGGAAATTGGTGAAAGTGTACCGTGGAGAGGATGTCTACATTGTTCAGAGTGGNTGTGGCGAAATCAATGACAA
TTTAATGGAGCTTTTGATCATGATTAATGCCTGCAAGATTGCTTCAGCCAGCCGGGTTACTGCAGTCATCCCATGC
TTCCCTTATGCCCCGGCAGGATAAGAAAGATNAGAGCCGGGCCGCCAATCTCAGCCAAGCTTGGTGCAAATATGCT
ATCTGTAGCAGTGCAGATCATATTATCACCATGGACCTACATGCTTCTCAAATTCANGGCTTTTT

ATGCAAAAGGGGACACAGGGGGTTCAAAAATAAAAATTTCTCTTCCCCCTCCCCAAACCTGTACCCCAGCTCCCCG
ACCACAACCCCCTTCCTCCCCCGGGGAAAGCAAGAAGGAGCAGGTGTGGCATCTGCAGCTGGGAAGAGAGAGGCCG
GGGAGGTGCCGAGCTCGGTGCTGGTCTCTTTCCAAATATAAATACGTGTGTCAGAACTGGAAAATCCTCCAGCACC
CACCACCCAAGCACTCTCCGTTTTCTGCCGGTGTTTGGAGAGGGGCGGNGGGCAGGGGCGCCAGGCACCGGCTGGC
TGCGGTCTACTGCATCCGCTGGGTGTGCACCCCGCGA 13710.2

AGGTTGGAGAAGGTCATGCAGGTGCAGATTGTCCAGGSKCAGCCACAGGGTCAAGCCCAACAGGCCCAGAGTGGCA
CTGGACAGACCATGCAGGTGATGCAGCAGATCATCACTAACACAGGAGAGATCCAGCAGATCCCGGTGCAGCTGAA
TGCCGGCCAGCTGCAGTATATCCGCTTAGCCCAGCCTGTATCAGGCACTCAAGTTGTGCAGGGACAGATCCAGACA
CTTGCCACCAATGCTCAACAGATTACACAGACAGAGGTCCAGCAAGGACAGCAGCAGTTCAAGCCAGTTCACAAGA
TGGACAGCAGCTCTACCAGATCCAGCAAGTCACCATGCCTGCGGGCCANGACCTCGCCAGCCCATGTTCATCCAGT
CAAGCCAACCAGCCCTTCNACGGGCAGGCCCCCCAGGTGACCGGCGACTGAAGGGCCTGAGCTGGCAAGGCCAANG
ACACCCAACACAATTTTTGCCATACAGCCCCCAGGCAATGGGCACAGCCTTTCTTCCCAGAGGAC 13710-1

TGAGATTTATTGCATTTCATGCAGCTTGAAGTCCATGCAAAGGRGACTAGCACAGTTTTTAATGCATTTAAAAAAT
AAAAGGGAGGTGGGCAGCAAACACACAAAGTCCTAGTTTCCTGGGTCCCTGGGAGAAAAGAGTGTGGCAATGAATC
CACCCACTCTCCACAGGGAATAAATCTGTCTCTTAAATGCAAAGAATGTTTCCATGGCCTCTGGATGCAAATACAC
AGAGCTCTGGGGTCAGAGCAAGGGATGGGGAGAGGACCACGAGTGAAAAAGCAGCTACACACATTCACCTAATTCC
ATCTGAGGGCAAGAACAACGTGGCAAGTCTTGGGGGTAGCAGCTGTT 13711.1

TCCAGACATGCTCCTGTCCTAGGCGGGGAGCAGGAACCAGACCTGCTATGGGAAGCAGAAAGAGTTAAGGGAAGGT
TTCCTTTCATTCCTGTTCCTTCTCTTTTGCTTTTGAACAGTTTTTAAATATACTAATAGCTAAGTCATTTGCCAGC
CAGGTCCCGGTGAACAGTAGAGAACAAGGAGCTTGCTAAGAATTAATTTTGCTGTTTTTCACCCCATTCAAACAGA
GCTGCCCTGTTCCCTGATGGAGTTCCATTCCTGCCAGGGCACGGCTGAGTAACACGAAGCCATTCAAGAAAGGCGG
GTGTGAAATCACTGCCACCCCATGGACAGACCCCTCACTCTTCCTTCTTAGCCGCAGCGCTACTTAATAAATATAT
TTATACTTTGAAATTATGATAACCGATTTTTCCCATGCGGCATCCTAAGGGCACTTGCCAGCTCTTATCCGGACAG
TCAAGCACTGTTGTTGGACAACAGATAAAGGAAAAGAAAAAGAAGAAAACAACCGCAACTTCTGT

TGAGACGGACCACTGGCCTGGTCCCCCCTCATKTGCTGTCGTAGGACCTGACATGAAACGCAGATCTAGTGGCAGA
GAGGAAGATGATGAGGAACTTCTGAGACGTCGGCAGCTTCAAGAAGAGCAATTAATGAAGCTTAACTCAGGCCTGG
GACAGTTGATCTTGAAAGAAGAGATGGAGAAAGAGAGCCGGGAAAGGTCATCTCTGTTAGCCAGTCGCTACGATTC
TCCCATCAACTCAGCTTCACATATTCCATCATCTAAAACTGCATCTCTCCCTGGCTATGGAAGAAATGGGCTTCAC
CGGCCTGTTTCTACCGACTTCGCTCAGTATAACAGCTATGGGGATGTCAGCGGGGGAGTGCGAGATTACCAGACAC
TTCCAGATGGCCACATGCCTGCAATGAGAATGGACCGAGGAGTGTCTATGCCCAACATGTTGGAACCAAAGATATT
TCCATATGAAATGCTCATGGTGACCAACAGAGGGCCGAAACCAAATCTCAGAGAGGTGGACAGAA 13713.1&2

TCACTTTATTTTTCTTGTATAAAAACCCTATGTTGTAGCCACAGCTGGAGCCTGAGTCCGCTGCACGGAGACTCTG
GTGTGGGTCTTGACGAGGTGGTCAGTGAACTCCTGATAGGGAGACTTGGTGAATACAGTCTCCTTCCAGAGGTCGG
GGGTCAGGTAGCTGTAGGTCTTAGAAATGGCATCAAAGGTGGCCTTGGCGAAGTTGCCCAGGGTGGCAGTGCAGCC
CCGGGCTGAGGTGTAGCAGTCATCGATACCAGCCATCATGAG 13715.4

CTGGAATATAGACCCGTGATCGACAAAACTTTGAACGAGGCTGACTGTGCCACCGTCCCGCCAGCCATTCGCTCCT
ACTGATGAGACAAGATGTGGTGATGACAGAATCAGCTTTTGTAATTATGTATAATAGCTCATGCATGTGTCCATGT
CATAACTGTCTTCATACGCTTCTGCACTCTGGGGAAGAAGGAGTACATTGAAGGGAGATTGGCACCTAGTGGCTGG
GAGCTTGCCAGGAACCCAGTGGCCAGGGAGCGTGGCACTTACCTTTGTCCCTTGCTTCATTCTTGTGAGATGATAA
AACTGGGCACAGCTCTTAAATAAAATATAAATGAACA 13717.1&2

TGAATGGGGAGGAGCTGACCCAGGAAATGGAGCTTGNGGAGACCAGGCCTGCAGGGGATGGAACCTTCCAGAAGTG
GGCATCTGTGGTGGTGCCTCTTGGGAAGGAGCAGAAGTACACATGCCATGTGGAACATGAGGGGCTGCCTGAGCCC
CTCACCCTGAGATGGGGCAAGGAGGAGCCTCCTTCATCCACCAAGACTAACACAGTAATCATTGCTGTTCCGGTTG
TCCTTGGAGCTGTGGTCATCCTTGGAGCTGTGATGGCTTTTGTGATGAAGAGGAGGAGAAACACAGGTGGAAAAGG
AGGGGACTATGCTCTGGCTCCAGGCTCCCAGAGCTCTGATATGTCTCTCCCAGATTGTAAAGTGTGAAGACAGCTG
CCTGGTGTGGACTTGGTGACAGACAATGTCTTCACACATCTCCTGTGACATCCAGAGACCTCAGTTCTCTTTAGTC
AAGTGTCTGATGTTCCCTGTGAGTCTGCGGGCTCAAAGTGAAGAACTGTGGAGCCCAGTCCACCCCTGCACACCAG
GACCCTATCCCTGCACTGCCCTGTGTTCCCTTCCACAGCCAACCTTGCTGCTCCAGCCAAACATTGGTGGACATCT
GCAGCCTGTCAGCTCCATGCTACCCTGACCTTCAACTCCTCACTTCCACACTGAGAATAATAATTTGAATGTGGGT
GGCTGGAGAGATGGCTCAGCGCTGACTGCTCTTCCAAAGGTCCTGAGTTCAAATCCCAGCAACCACATGGTGGCTC
ACAACCATCTGTAATGGGATCTAATACCCTCTTCTGCAGTGTCTGAAGACASCTACAGTGTACTTACATATAATAA
TAAATAAG

GGCCGGGCGCGCGCGCCCCCGCCACACGCACGCCGGGCGTGCCAGTTTATAAAGGGAGAGAGCAAGCAGCGAGTCT
TGAAGCTCTGTTTGGTGCTTTGGATCCATTTCCATCGGTCCTTACAGCCGCTCGTCAGACTCCAGCAGCCAAGATG
GTGAAGCAGATCGAGAGCAAGACTGCTTTTCAGGAAGCCTTGGACGCTGCAGGTGATAAACTTGTAGTAGTTGACT
TCTCAGCCACGTGGTGTGGGCCTTGCAAAATGATCAAGCCTTTCTTTCATTCCCTCTCTGAAAAGTATTCCAACGT
GATATTCCTTGAAGTAGATGTGGATGACTGTCAGGATGTTGCTTCAGAGTGTGAAGTCAAATGCATGCCAACATTC
CAGTTTTTTAAGAAGGGACAAAAGGTGGGTGAATTTTCTGGAGCCAATAAGGAAAAGCTTGAAGCCACCATTAATG
AATTAGTCTAATCATGTTTTCTGAAAATATAACCAGCCATTGGCTATTTAAAACTTGTAATTTTTTTAATTTACAA
AAATATAAAATATGAAGACATAAACCCMGTTGCCATCTGCGTGACAATAAAACATTAATGCTAACACTT 13721.1

TCACATAAGAAATTTAAGCAAGTTACRCTATCTTAAAAAACACAACGAATGCATTTTAATAGAGAAACCCTTCCCT
CCCTCCACCTCCCTCCCCCACCCTCCTCATGAATTAAGAATCTAAGAGAAGAAGTAACCATAAAACCAAGTTTTGT
GGAATCCATCATCCAGAGTGCTTACATGGTGATTAGGTTAATATTGCCTTCTTACAAAATTTCTATTTTAAAAAAA
ATTATAACCTTGATTGCTTATTACAAAAAAATTCAGTACAAAAGTTCAATATATTGAAAAATGCTTTTCCCCTCCC
TCACAGCACCGTTTTATATATAGCAGAGAATAATGAAGAGATTGCTAGTCTAGATGGGGCAATCTTCAAATTACAC
CAAGACGCACAGTGGTTTATTTACCCTCCCCTTCTCATAAG 13721.2

GGAAAGGATTCAAGAATTAGAGGACTTGCTTGCTRRAGAAAAAGACAACTCTCGTCGCATGCTGACAGACAAAGAG
AGAGAGATGGCGGAAATAAGGGATCAAATGCAGCAACAGCTGAATGACTATGAACAGCTTCTTGATGTAAAGTTAG
CCCTGGACATGGAAATCAGTGCTTACAGGAAACTCTTAGAAGGCGAAGAAGAGAGGTTGAAGCTGTCTCCAAGCCC
TTCTTCCCGTGTGACAGTATCCCGAGCATCCTCAAGTCGTAGTGTACCGTACAACTAGAGGAAAGCGGAAGAGGGT
TGATGTGGAAGAATCAGAGGCGAAGTAGTAGTGTTAGCATCTCTCATTCCGCCTCAACCACTGGAAATGTTTGCAT
CGAAGAAATTGATGTTGATGGGAAATTTATCCCGCTTGAAGAACACTTCTGAACAGGATCAACCAATGGGAAGGCT
TGGGAGATGATCAGAAAAATTGGAGACACATCAGTCAGTTATAAATATACCTCAA 13723.1

CATGGGTTTCACCAGGTTGGCCAGGCTGCTCTTGAACTSCTGACCTCAGGTGATCCACCCGCCTCGGCCTCCCAAA
GTGCTGGGATTACAGGCGTGAGCCACCACGCCCGGCCCCCAAAGCTGTTTCTTTTGTCTTTAGCGTAAAGCTCTCC
TGCCATGCAGTATCTACATAACTGACGTGACTGCCAGCAAGCTCAGTCACTCCGTGGTCTTTTTCTCTTTCCAGTT
CTTCTCTCTCTCTTCAAGTTCTGCCTCAGTGAAAGCTGCAGGTCCCCAGTTAAGTGATCAGGTGAGGGTTCTTTGA
ACCTGGTTCTATCAGTCGAATTAATCCTTCATGATGG

GATGTGTTGGACCCTCTGTGTCAAAAAAAACCTCACAAAGAATCCCCTGCTCATTACAGAAGAAGATGCATTTAAA
ATATGGGTTATTTTCAACTTTTTATCTGAGGACAAGTATCCATTAATTATTGTGTCAGAAGAGATTGAATACCTGC
TTAAGAAGCTTACAGAAGCTATGGGAGGAGGTTGGCAGCAAGAACAATTTGAACATTATAAAATCAACTTTGATGA
CAGTAAAAATGGCCTTTCTGCATGGGAACTTATTGAGCTTATTGGAAATGGACAGTTTAGCAAAGGCATGGACCGG
CAGACTGTGTCTATGGCAATTAATGAAGTCTTTAATGAACTTATATTAGATGTGTTAAAGCAGGGTTACATGATGA
AAAAGGGCCACAGACGGAAAAACTGGACTGAAAGATGGTTTGTACTAAAACCCAACATAATTTCTTACTATGTGAG
TGAGGATCTGAAGGATAAGAAAGGAGACATTCTCTTGGATGAAAATTGCTGTGTAGAAGTCCTTGCCTGACAAAAG
ATGGAAAGAAATGCCTTTT 13725.1

GACTGGTTCTTTATTTCAAAAAGACACTTGTCAATATTCAGTRTCAAAACAGTTGCACTATTGATTTCTCTTTCTC
CCAATCGGCCCCAAAGAGACCACATAAAAGGAGAGTACATTTTAAGCCAATAAGCTGCAGGATGTACACCTAACAG
ACCTCCTAGAAACCTTACCAGAAAATGGGGACTGGGTAGGGAAGGAAACTTAAAAGATCAACAAACTGCCAGCCCA
CGGACTGCAGAGGCTGTCACAGCCAGATGGGGTGGCCAGGGTGCCACAAACCCAAAGCAAAGTTTCAAAATAATAT
AAAATTTAAAAAGTTTTGTACATAAGCTATTCAAGATTTCTCCAGCACTGACTGATACAAAGCACAATTGAGATGG
CACTTCTAGAGACAGCAGCTTCAAACCCAGAAAAGGGTGATGAGATGAAGTTTCACATGGCTAAATCAGTGGCAAA
AACACAGTCTTCTTTCTTTCTTTCTTTCAAGGANGCAGGAAAGCAATTAAGTGGTCACCTTAACATAAGGGGGAC 13725.2

TGGGTGGGCACCATGGCTGGGATCACCACCATCGAGGCGGTGAAGCGCAAGATCCAGGTTCTGCAGCAGCAGGCAG
ATGATGCAGAGGAGCGAGCTGAGCGCCTCCAGCGAGAAGTTGAGGGAGAAAGGCGGGCCCGGGAACAGGCTGAGGC
TGAGGTGGCCTCCTTGAACCGTAGGATCCAGCTGGTTGAAGAAGAGCTGGACCGTGCTCAGGAGCGCCTGGCCACT
GCCCTGCAAAAGCTGGAAGAAGCTGAAAAAGCTGCTGATGAGAGTGAGAGAGGTATGAAGGTTATTGAAAACCGGG
CCTTAAAAGATGAAGAAAAGATGGAACTCCAGGAAATCCAACTCAAAGAAGCTAAGCACATTGCAGAAGAGGCAGA
TAGGAAGTATGAAGAGGTGGCTCGTAAGTTGGTGATCATTGAAGGAGACTTGGAACCGCACAGAAGGAACGAGCTT
GAGCTTGGCAAAAGTCCCGTTGCCCAGAGATGGGATGAACCAGATTAGACTGATGGACCANAACC 13726.1&2

AGGGGCNGCGGGTGCGTGGGCCACTGGGTGACCGACTTAGCCTGGCCAGACTCTCAGCACCTGGAAGCGCCCCGAG
AGTGACAGCGTGAGGCTGGGAGGGAGGACTTGGCTTGAGCTTGTTAAACTCTGCTCTGAGCCTCCTTGTCGCCTGC
ATTTAGATGGCTCCCGCAAAGAAGGGTGGCGAGAAGAAAAAGGGCCGTTCTGCCATCAACGAAGTGGTAACCCGAG
AATACACCATCAACATTCACAAGCGCATCCATGGAGTGGGCTTCAAGAAGCGTGCACCTCGGGCACTCAAAGAGAT
TCGGAAATTTGCCATGAAGGAGATGGGAACTCCAGATGTGCGCATTGACACCAGGCTCAACAAAGCTGTCTGGGCC
AAAGGAATAAGGAATGTGCCATACCGAATCCGGTGTGCGGCTGTCCAGAAAACGTAATGAGGATGAAGATTCACCA
AATAAGCTATATACTTTGGTTACCTATGTACCTGTTACCACTTTCAAAAATCTACAGACAGTCAATGTGGATGAGA
ACTAATCGCTGATCGTCAGATCAAATAAAGTTATAAAAT

TCGGGAGCCACACTTGGCCCTCTTCCTCTCCAAAGSGCCAGAACCTCCTTCTCTTTGGAGAATGGGGAGGCCTCTT
GGAGACACAGAGGGTTTCACCTTGGATGACCTCTAGAGAAATTGCCCAAGAAGCCCACCTTCTGGTCCCAACCTGC
AGACCCCACAGCAGTCAGTTGGTCAGGCCCTGCTGTAGAAGGTCACTTGGCTCCATTGCCTGCTTCCAACCAATGG
GCAGGAGAGAAGGCCTTTATTTCTCGCCCACCCATTCCTCCTGTACCAGCACCTCCGTTTTCAGTCAGTGTTGTCC
AGCAACGGTACCGTTTACACAGTCACCTCAGACACACCATTTCACCTCCCTTGCCAAGCTGTTAGCCTTAGAGTGA
TTGCAGTGAACACTGTTTACACACCGTGAATCCATTCCCATCAGTCCATTCCAGTTGGCACCAGCCTGAACCATTT
GGTACCTGGTGTTAACTGGAGTCCTGTTTACAAGGTGGAGTCGGGGCTTGCTGACTTCTCTTCATTTGAGGGCAC 13727.2

ACCTAGACAGAAGGTGGGTGAGGGAGGACTGGTAGGAGGCTGAGGCAATTCCTTGGTAGTTTGTCCTGAAACCCTA
CTGGAGAAGTCAGCATGAGGCACCTACTGAGAGAAGTGCCCAGAAACTGCTGACTGCATCTGTTAAGAGTTAACAG
TAAAGAGGTAGAAGTGTGTTTCTGAATCAGAGTGGAAGCGTCTCAAGGGTCCCACAGTGGAGGTCCCTGAGCTACC
TCCCTTCCGTGAGTGGGAAGAGTGAAGCCCATGAAGAACTGAGATGAAGCAAGGATGGGGTTCCTGGGCTCCAGGC
AAGGGCTGTGCTCTCTGCAGCAGGGAGCCCCACGAGTCAGAAGAAAAGAACTAATCATTTGTTGCAAGAAACCTTG
CCCGGATACTAGCGGAAAACTGGAGGCGGNGGTGGGGGCACAGGAAAGTGGAAGTGATTTGATGGAGAGCAGAGAA
GCCTATGCACAGTGGCCGAGTCCACTTGTAAAGTG 13728.1&2

TTCAAGCAATTGTAACAAGTATATGTAGATTAGAGTGAGCAAAATCATATACAATTTTCATTTCCAGTTGCTATTT
TCCAAATTGTTCTGTAATGTCGTTAAAATTACTTAAAAATTAACAAAGCCAAAAATTATATTTATGACAAGAAAGC
CATCCCTACATTAATCTTACTTTTCCACTCACCGGCCCATCTCCTTCCTCTTTTTCCTAACTATGCCATTAAAACT
GTTCTACTGGGCCGGGCGTGTGGCTCATGCCTGTAATCCCAGCATTTTGGGAGGCCAAGGCAGGCGGATCATGAGG
TCAAGAGATTGAGACCATCCTGGCCAACATGGTGAAACCCCGCCTCGACTAAGAATACAAAAATTAGCTGGGCATG
GTGGCGCATGCCTGTAGTCTCAGCTACTCGGGAGGCTGAGGCAGAAGAATCGCTTGAACCCGGGAGGCAGAGGATG
CAGTGAGCCCCGATCGCGCCACTGCACTCTAGCCTGGGCGACAGACTGAGACTCTGCTC 13731.1&2

TGTGCCAGTCTACAGGCCTATCAGCAGCGACTCCTTCAGCAACAGATGGGGTCCCCTGTTCAGCCCAACCCCATGA
GCCCCCAGCAGCATATGCTCCCAAATCAGGCCCAGTCCCCACACCTACAAGGCCAGCAGATCCCTAATTCTCTCTC
CAATCAAGTGCGCTCTCCCCAGCCTGTCCCTTCTCCACGGCCACAGTCCCAGCCCCCCCACTCCAGTCCTTCCCCA
AGGATGCAGCCTCAGCCTTCTCCACACCACGTTTCCCCACAGACAAGTTCCCCACATCCTGGACTGGTAGTTGCCC
AGGCCAACCCCATGGAACAAGGGCATTTTGCCAGCC

TGTAAAAACTTGTTTTTAATTTTGTATAAAATAAAGGTGGTCCATGCCCACGGGGGCTGTAGGAAATCCAAGCAGACCA
GCTGGGGTGGGGGGATGTAGCCTACCTCGGGGGACTGTCTGTCCTCAAAACGGGCTGAGAAGGCCCGTCAGGGGCCCAG
GTCCCACAGAGAGGCCTGGGATACTCCCCCAACCCGAGGGGCAGACTGGGCAGTGGGGAGCCCCCATCGTGCCCCAGAG
GTGGCCACAGGCTGAAGGAGGGGCCTGAGGCACCGCAGCCTGCAACCCCCAGGGCTGCAGTCCACTAACTTTTTACAGA
ATAAAAGGAACATGGGGATGGGGAAAAAAGCACCAGGTCAGGCAGGGCCCGAGGGCCCCAGATCCCAGGAGGGCCAGGA
CTCAGGATGCCAGCACCACCCTAGCAGCTCCCACAGCTCCTGGCACAGGAGGCCGCCACGGATTGGCACAGGCCGCTGC
TGGCCATCACGCCACATTTGGAGAACTTGTCCCGACAGAGGTCAGCTCGGAGGAGCTCCTCGTGGGCACACACTGTACG
AACACAGATCTCCTTGTTAATGACGTACACACGGCGGAGGCTGCGGGGACAGGGCACGGGAGGTCTCAGCCCCACTT 13736.2

ATGGCTGCTGGATTTAGGTGGTAATAGGGGCTGTGGGCCATAAATCTGAAGCCTTGAGAACCTTGGGTCTGGAGAGCCA
TGAAGAGGGAAGGAAAAGAGGGCAAGTCCTGAACCTAACCAATGACCTGATGGATTGCTCGACCAAGACACAGAAGTGA
AGTCTGTGTCTGTGCACTTCCCACAGACTGGAGTTTTTGGTGCTGAATAGAGCCAGTTGCTAAAAAATTGGGGGTTTGG
TGAAGAAATCTGATTGTTGTGTGTATTCAATGTGTGATTTTAAAAATAAACAGCAACAACAATAAAAACCCTGACTGGC
TGTTTTTTCCCTGTATTCTTTACAACTATTTTTTGACCCTCTGAAAATTATTATACTTCACCTAAATGGAAGACTGCTG
TGTTTGTGGAAATTTTGTAATTTTTTAATTTATTTTATTCTCTCTCCTTTTTATTTTGCCTGCAGAATCCGTTGAGAGA
CTAATAAGGCTTAATATTTAATTGATTTGTTTAATATGTATATAAAT 13744.2-13696.2

GGCATGCGAGCGCACTCGGCGGACGCAAGGGCGGCGGGGAGCACACGGAGCACTGCAGGCGCCGGGTTGGGACAGCGTC
TTCGCTGCTGCTGGATAGTCGTGTTTTCGGGGATCGAGGATACTCACCAGAAACCGAAAATGCCGAAACCAATCAATGT
CCGAGTTACCACCATGGATGCAGAGCTGGAGTTTGCAATCCAGCCAAATACAACTGGAAAACAGCTTTTTGATCAGGTG
GTAAAGACTATCGGCCTCCGGGAAGTGTGGTACTTTGGCCTCCACTATGTGGATAATAAAGGATTTCCTACCTGGCTGA
AGCTGGATAAGAAGGTGTCTGCCCAGGAGGTCAGGAAGGAGAATCCCCTCCAGTTCAAGTTCCGGGCCAAaGTTCTACC
CTGAAGATGTGGCTGAGGAGCTCATCCAGGACATCACCCAGAAACTTTTCTTCCTTCAAGTGAAGGAAGGAATCCTTAG
CGATGAGATCTACTGCCCCCCTTGARACTGCCGTGCTCTTGGGGTCCTACGCTTGTGCATGCCAAGTTTGGGGACTACC
ACCAAGAAG 13746.1&2-13720.1&2

GAAGGAGTCGGGATACTCAGCATTGATGCACCCCAATTTCAAAGCGGCATTCTTCGGCAGGTCTCTGGGACAATCTCTA
GGGTCACTACCTGGAAACTCGTTAGGGTACAACTGAATGCTGAAAGGAAAGAACACCTGCAGAACCGGACAGAAATTCA
CCCCGGCGATCAGCTGATTGATCTCGGTCGACCAGAAGTCATGGCTAAAGATGACGAGGACGTTGTCAATTCCCTGGGC
TTTTCGAAGTGAGTCCAGCAGCAGTCTGAGGTATTCGGGCCGGTTATGCACCTGGACCACCAGCACCAGCTCCCGGGGG
GCCCAGGTGCCAGCCTTATCTACATTCCTCAGGGTCTGATCAAAGTTCAGCTGGTACACCAGGGACCGGTACCGCAGCG
TCAGGTTGTCCGCTCGGGCTGGGGGACCGCCGGGACCAGGGAAGCCGCCGACACGTTGGAGACCCTGCGGATGCCCACA
GCCACAGAGGGGTGGTCCCCACCGCGGCCGCCGGCACCCCGCGCGGGTTCGGCGTCCAGCAACGGTGGGGCGAGGGCCT
CGTTCTTCCTTTGTCGCCCATTGCTGCTCCAGAGGACGAAGCCGCAGGCGGCCACCACGAGCGTCAGGATTAGCACCTT
CCGTTTGTAGATGCGGAACCTCATGGTCTCCAGGGCCGGGAGCGCAGCTACAGCTCGAGCGTCGGCGCCGCCGCTAGGA
GCCGCGGCTCGGCTTCGTCTCCGTCCTCTCCATTCAGCACCACGGGTCCCGGAAAAAGCTCAGCCSCGGTCCCAACCGC
ACCCTAGCTTCGTTACCTGCGCCTCGCTTG

CAGATTTTTATTTGCAGTCGTCACTGGGGCCGTTTCTTGCTGCTTATTTGTCTGCTAGCCTGCTCTTCCAGCTGCA
TGGCCAGGCGCAAGGCCTTGATGACATCTCGCAGGGCTGAGAAATGCTTGGCTTGCTGGGCCAGAGCAGATTCCGC
TTTGTTCACAAAGGTCTCCAGGTCATAGTCTGGCTGCTCGGTCATCTCAGAGAGCTCAAGCCAGTCTGGTCCTTGC
TGTATGATCTCCTTGAGCTCTTCCATAGCCTTCTCCTCCAGCTCCCTGATCTGAGTCATGGCTTCGTTAAAGCTGG
ACATCTGGGAAGACAGTTCCTCCTCTTCCTTGGATAAATTGCCTGGAATCAGCGCCCCGTTAGAGCAGGCTTCCAT
CTCTTCTGTTTCCATTTGAATCAACTGCTCTCCACTGGGCCCACTGTGGGGGCTCAGCTCCTTGACCCTGCTGCAT
ATCTTAAGGGTGTTTAAAGGATATTCACAGGAGCTTATGCCTGGT 14347.2

CTCCTCTTGGTACATGAACCCAAGTTGAAAGTGGACTTAACAAAGTATCTGGAGAACCAAGCATTCTGCTTTGACT
TTGCATTTGATGAAACAGCTTCGAATGAAGTTGTCTACAGGTTCACAGCAAGGCCACTGGTACAGACAATCTTTGA
AGGTGGAAAAGCAACTTGTTTTGCATATGGCCAGACAGGAAGTGGCAAGACACATACTATGGGCGGAGACCTCTCT
GGGAAAGCCCAGAATGCATCCAAAGGGATCTATGCCATGGCCTTCCGGGACGTCTTCTTCTGAAGAATCAACCCTG
CTACCGGAAGTTGGGCCTGGAAGTCTATGTGACATTCTTCGAGATCTACAATGGGAAGCTGTTTGACCTGCTCAAC
AAGAAGGCCAAGCTTGCGCGTGCTGGAAGACGGCAAGCAACAGGTGCAAGTGGTGGGGGCTTGCAGGAACATCTGG
NTAACTCTGCTTGATGATGGCANTCAAGATGATCGACATGGGCAGCGCCTGCAGA 14348.2&14350.1&2

TCCCGAATTCAAGCGACAAATTGGAWAGTGAAATGGAAGATGCCTATCATGAACATCAGGCAAATCTTTTGCGCCA
AGATCTGATGAGACGACAGGAAGAATTAAGACGCATGGAAGAACTTCACAATCAAGAAATGCAGAAACGTAAAGAA
ATGCAATTGAGGCAAGAGGAGGAACGACGTAGAAGAGAGGAAGAGATGATGATTCGTCAACGTGAGATGGAAGAAC
AAATGAGGCGCCAAAGAGAGGAAAGTTACAGCCGAATGGGCTACATGGATCCACGGGAAAGAGACATGCGAATGGG
TGGCGGAGGAGCAATGAACATGGGAGATCCCTATGGTTCAGGAGGCCAGAAATTTCCACCTCTAGGAGGTGGTGGT
GGCATAGGTTATGAAGCTAATCCTGGCGTTCCACCAGCAACCATGAGTGGTTCCATGATGGGAAGTGACATGCGTA
CTGAGCGCTTTGGGCAGGGAGGTGCGGGGCCTGTGGGTGGACAGGGTCCTAGAGGAATGGGGCCTGGAACTCCAGC
AGGATATGGTAGAGGGAGAGAAGAGTACGAAGGC 14349.1&2

TTCGTGAAGACCCTGACTGGTAAGACCATCACTCTCGAAGTGGAGCCCGAGTGACACCATTGAGAATGTCAAGGCA
AAGATCCAAGACAAGGAAGGCATCCCTCCTGACCAGCAKAGGTTGATCTTTGCTGGGAAACAGCTGGAAGATGGAC
GCACCCTGTCTGACTACAACATCCAGAAAGAGTCCACCCTGCACCTGGTGCTCCGTCTCAGAGGTGGGATGCAAAT
CTTCGTGAAGACCCTGACTGGTAAGACCATCACCCTCGAGGTGGAGCCCAGTGACACCATCGAGAATGTCAAGGCA
AAGATCCAAGATAAGGAAGGCATCCCTCCTGATCAGCAGAGGTTGATCTTTGCTGGGAAACAGCTGGAAGATGGAC
GCACCCTGTCTGACTACAACATCCAGAAAGAGTCCACTCTGCACTTGGTCCTGCGCTTGAGGGGGGGTGTCTAAGT
TTCCCCTTTTAAGGTTTCAACAAATTTCATTGCACTTTCCTTTCAATAAAGTTGTTGCATTC

GCGCGGGTGCGTGGGCCACTGGGTGACCGACTTAGCCTGGCCAGACTCTCAGCACCTGGAAGCGCCCCGAGAGTGA
CAGCGTGAGGCTGGGAGGGAGGACTTGGCTTGAGCTTGTTAAACTCTGCTCTGAGCCTCCTTGTCGCCTGCATTTA
GATGGCTCCCGCAAAGAAGGGTGGCGAGAAGAAAAAGGGCCGTTCTGCCATCAACGAAGTGGTAACCCGAGAATAC
ACCATCAACATTCACAAGCGCATCCATGGAGTGGGCTTCAAGAAGCGTGCACCTCGGGCACTCAAAGAGATTCGGA
AATTTGCCATGAAGGAGATGGGAACTCCAGATGTGCGCATTGACACCAGGCTCAACAAAGCTGTCTGGGCCAAAGG
AATAAGGAATGTGCCATACCGAATCCGTGTGCGGCTGTCCAGAAAACGTAATGAGGATGAAGATTCACCAAATAAG
CTATATACTTTGGTTACCTATGTACCTGTTACCACTTTCAAAAATCTACAGACAGTCAATGTGGATGAGAACTAAT
CGCTGATCGT 14353.1

AATTCTTTATTTAAATCAACAAACTCATCTTCCTCAAGCCCCAGACCATGGTAGGCAGCCCTCCCTCTCCATCCCC
TCACCCCACCCCTTAGCCACAGTGAAGGGAATGGAAAATGAGAAGCCACGAGGGCCCCTGCCAGGGAAGGCTGCCC
CAGATGTGTGGTGAGCACAGTCAGTGCAGCTGTGGCTGGGGCAGCAGCTGCCACAGGCTCCTCCCTATAAATTAAG
TTCCTGCAGCCACAGCTGTGGGAGAAGCATACTTGTAGAAGCAAGGCCAGTCCAGCATCAGAAGGCAGAGGCAGCA
TCAGTGACTCCCAGCCATGGAATGAACGGAGGACACAGAGCTCAGAGACAGAACAGGCCAGGGGGAAGAAGGAGAG
ACAGAATAGGCCAGGGCATGGCGGTGAGGGA 14353.2

TGATGAATCTGGGTGGGCTGGCAGTAGCCCGAGATGATGGGCTCTTCTCTGGGGATCCCAACTGGTTCCCTAAGAA
ATCCAAGGAGAATCCTCGGAACTTCTCGGATAACCAGCTGCAAGAGGGCAAGAACGTGATCGGGTTACAGATGGGC
ACCAACCGCGGGGCGTCTCANGCAGGCATGACTGGCTACGGGATGCCACGCCAGATCCTCTGATCCCACCCCAGGC
CTTGCCCCTGCCCTCCCACGAATGGTTAATATATATGTAGATATATATTTTAGCAGTGACATTCCCAGAGAGCCCC
AGAGCTCTCAAGCTCCTTTCTGTCAGGGTGGGGGGTTCAAGCCTGTCCTGTCACCTCTGAAGTGCCTGCTGGCATC
CTCTCCCCCATGCTTACTAATACATTCCCTTCCCCATAGCC 17182.1&2

AGCGGAGCTCCCTCCCCTGGTGGCTACAACCCACACACGCCAGGCTCAGGCATCGAGCAGAACTCCAGCGACTGGG
TAACCACTGACATTCAGGTGAAGGTGCGGGACACCTACCTGGATACACAGGTGGTGGGACAGACAGGTGTCATCCG
CAGTGTCACGGGGGGCATGTGCTCTGTGTACCTGAAGGACAGTGAGAAGGTTGTCAGCATTTCCAGTGAGCACCTG
GAGCCTATCACCCCCACCAAGAACAACAAGGTGAAAGTGATCCTGGGCGAGGATCGGGAAGCCACGGGCGTCCTAC
TGAGCATTGATGGTGAGGATGGCATTGTCCGTATGGACCTTGATGAGCAGCTCAAGATCCTCAACCTCCGCTTCCT
GGGGAAGCTCCTGGAAGCCTGAAGCAGGCAGGGCCGGTGGACTTCGTCGGATGAAGAGTGATCCTCCTTCCTTCCC
TGGCCCTTGGCTGTGACACAAGATCCTCCTGCAGGGCTAGGCGGATTGTTCTGGATTTCCTTTTGTTTTTCCTTTT
AGGTTTCCATCTTTTCCCTCCCTGGTGCTCATTGGAATCTGAGTAGAGTCTGGGGGAGGGTCCCCACCTTCCTGTA
CCTCCTCCCCACAGCTTGCTTTTGTTGTACCGTCTTTCAATAAAAAGAAGCTGTTTGGTCTA

GGTTCACAGCACTGCTGCTTGTGTGTTGCCGGCCAGGAATTCCAGGCTCACAAGGCTATCTTAGCAGCTCGTTCTC
CGGTTTTTAGTGCCATGTTTGAACATGAAATGGAGGAGAGCAAAAAGAATCGAGTTGAAATCAATGATGTGGAGCC
TGAAGTTTTTAAGGAAATGATGTGCTTCATTTACACGGGGAAGGCTCCAAACCTCGACAAAATGGCTGATGATTTG
CTGGCAGCTGCTGACAAGTATGCCCTGGAGCGCTTAAAGGTCATGTGTGAGGATGCCCTCTGCAGTAACCTGTCCG
TGGAGAACGCTGCAGAAATTCTCATCCTGGCCGACCTCCACAGTGCAGATCAGTTGAAAACTCAGGCAGTGGATTT
CATCAACTATCATGCTTCGGATGTCTTGGAGACCTCTTGGG 17186.1&2

TCGTAGCCATTTTTCTGCTTCTTTGGAGAATGACGCCACACTGACTGCTCATTGTCGTTGGTTCCATGCCAATTGG
TGAAATAGAACCTCATCCGGTAGTGGAGCCGGAGGGACATCTTGTCATCAACGGTGATGGTGCGATTTGGAGCATA
CCAGAGCTTGGTGTTCTCGCCATACAGGGCAAAGAGGTTGTGACAAAGAGGAGAGATACGGCATGCCTGTGCAGCC
CTGATGCACAGTTCCTCTGCTGTGTACTCTCCACTGCCCAGCCGGAGGGGCTCCCTGTCCGACAGATAGAAGATCA
CTTCCACCCCTGGCTTG 17187.1&2

TGGCACACTGCTCTTAAGAAACTATGAWGATCTGAGATTTTTTTGTGTATGTTTTTGACTCTTTTGAGTGGTAATC
ATATGTGTCTTTATAGATGTACATACCTCCTTGCACAAATGGAGGGGAATTCATTTTCATCACTGGGAGTGTCCTT
AGTGTATAAAAACCATGCTGGTATATGGCTTCAAGTTGTAAAAATGAAAGTGACTTTAAAAGAAAATAGGGGATGG
TCCAGGATCTCCACTGATAAGACTGTTTTTAAGTAACTTAAGGACCTTTGGGTCTACAAGTATATGTGAAAAAAAT
GAGACTTACTGGGTGAGGAAATTCATTGTTTAAAGATGGTCGTGTGTGTGTGTGTGTGTGTGTGTGTTGTGTTGTG
TTTTGTTTTTTAAGGGAGGGAATTTATTATTTACCGTTGCTTGAAATTACTGKGTAAATATATGTYTGATAATGAT
TTGCTYTTTGVCMACTAAAATTAGGVCTGTATAAGTWCTARATGCMTCCCTGGGKGTTGATYTTCCMAGATATTGA
TGATAMCCCTTAAAATTGTAACCYGCCTTTTTCCCTTTGCTYTCMATTAAAGTCTATTCMAAAG 17191.1&89.1

GGGGGTAGGCTCTTTATTAGACGGTTATTGCTGTACTACAGGGTCAGAGTGCAGTGTAAGCAGTGTCAGAGGCCCG
CGTTCAGCCCAAGAATGTGGATTTTCTCTCCCTATTGATCACAGTGGGTGGGTTTCTTCAGAAAAGCCCCAGAGGC
AGGGACCAGTGAGCTCCAAGGTTAGAAGTGGAACTGGAAGGCTTCAGTCACATGCTGCTTCCACGCTTCCAGGCTG
GGCAGCAAGGAGGAGATGCCCATGACGTGCCAGGTCTCCCCATCTGACACCAGTGAAGTCTGGTAGGACAGCAGCC
GCACGCCTGCCTCTGCCAGGAGGCCAATCATGGTAGGCAGCATTGCAGGGTCAGAGGTCTGAGTCCGGAATAGGAG
CAGGGGCAGGTCCCTGCGGAGAGGCACTTCTGGCCTGAAGACAGCTCCATTGAGCCCCTGCAGTACAGGYGTAGTG
CCTTGGACCAAGCCCACAGCCTGGTAAGGGGCGCCTGCCAGGGCCACGGCCAGGAGGCA

TAATTTCTTAGTCGTTTGGAATCCTTAAGCATGCAAAAGCTTTGAACAGAAGGGTTCACAAAGGAACCAGGGTTGT
CTTATGGCATCCAGTTAAGCCAGAGCTGGGAATGCCTCTGGGTCATCCACATCAGGAGCAGAAGCACTTGACTTGT
CGGTCCTGCTGCCACGGTTTGGGCGCCCACCACGCCCACGTCCACCTCGTCCTCCCCTGCCGCCACGTCCTGGGCG
GCCAAGGTCTCCAAAATTGATCTCCAGCTGAGACGTTATATCATTTGCTGGCTTCCGGAAATGATGGTCCATAACC
GAATCTTCAGCATGAGCCTCTTCACTCTTTGATTTATGAAGAACAAATCCCTTCTTCCACTGCCCATCAGCACCTT
CATTTGGTTTTCGGATATTAAATTCTACTTTTGCCCGGTCCTTATTTTGAATAGCCTTCCACTCATCCAAAGTCAT
CTCTTTTGGACCCTCCTCTTTTACCTCTTCAACTTCATTCTCCTTATTTTCAGTGTCTGCCACTGGATGATGTTCT
TCACCTTCAGGTGTTTCCTCAGTCACATTTGATTGATCCAAGTCAGTTAATTCGTCTTTGACAGTTCCCCAGTTGT
GAGATCCGCTACCTCCACGTTTGTCCTCGTGCTTCAGGCCAGATCTATCACTTCCACTATGCCTATCAAATTCACG
TTTGCCACGAGAATCAAATCCATCTCCTCGGCCCATTCCACGTCCACGGCCCCCTCGACCTCTTCCAAGACCACCA
CGACCTCGAATAGGTCGGTCAATAATCGGTCTATCAACTGAAAATTCGCCTCCTTCACCCTTTTCTTCAAGTGGCT
TTTCGAATCTTCGTTCACGAGGTGGTCGCCTTTCTGGTCTTCTATCAATTATTTTCCCTTCACCCTGAAGTTGTTG
ATCAGGTCTTCTTCCAACTCGTGC

17193

AAGCGGATGGACCTGAGTCAGCCGAATCCTAGCCCCTTCCCTTGGGCCTGCTGTGGTGCTCGACATCAGTGACAGA
CGGAAGCAGCAGACCATCAAGGCTACGGGAGGCCCGGGGCGCTTGCGAAGATGAAGTTTGGCTGCCTCTCCTTCCG
GCAGCCTTATGCTGGCTTTGTCTTAAATGGAATCAAGACTGTGGAGACGCGCTGGCGTCCTCTGCTGAGCAGCCAG
CGGAACTGTACCATCGCCGTCCACATTGCTCACAGGGACTGGGAAGGCGATGCCTGTCGGGAGCTGCTGGTGGAGA
GACTCGGGATGACTCCTGCTCAGATTCAGGCCTTGCTCAGGAAAGGGGAAAAGTTTGGTCGAGGAGTGATAGCGGG
ACTCGTTGACATTGGGGAAACTTTGCAATGCCCCGAAGACTTAACTCCCGATGAGGTTGTGGAACTAGAAAATCAA
GCTGCACTGACCAACCTGAAGCAGAAGTACCTGACTGTGATTTCAAACCCCAGGTGGTTACTGGAGCCCATACCTA
GGAAAGGAGGCAAGGATGTATTCCAGGTAGACATCCCAGAGCACCTGATCCCTTTGGGGCATGAAGTGTGACAAGT
GTGGGCTCCTGAAAGGAATGTTCCRGAGAAACCAGCTAAATCATGGCACCTTCAATTTGCCATCGTGACGCAGACC
TGTATAAATTAGGTTAAAGATGAATTTCCACTGCTTTGGAGAGTCCCACCCACTAAGCACTGTGCATGTAAACAGG
TTCCTTTGCTCAGATGAAGGAAGTAGGGGGTGGGGCTTTCCTTGTGTGATGCCTCCTTAGGCACACAGGCAATGTC
TCAAGTACTTTGACCTTAGGGTAGAAGGCAAAGCTGCCAGTAAATGTCTCAGCATTGCTGCTAATTTTGGTCCTGC
TAGTTTCTGGATTGTACAAATAAATGTGTTGTAGATGA

*Fig. 15U*

16443.1.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAACCAGTCCTGGTGCANGAC
GGTGAGGACGCTNACCACACGGTACGNGCTGGTGTACTGCTCCTCCCGCGGCTTTGTCTTGGCATTATGCACCTCC
ACGCCGTCCACGTACCAATTGAACTTGACCTCAGGGTCTTCGTGGCTCACGTCCACCACCACGCATGTAACCTCAA
ANCTCGGNCGCGANCACGC 16443.2.edit AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAGCCCCGAGAACCACAGGTGTACACCCTG
CCCCCATCCCGGGAGGAGATGACCAAGAACCAGGTCAGCCTGACCTGCCTGGTCAAAGGCTTCTATCCCAGCGACA
TCGCCCGTGGAGTGGGAGAGCAATGGGCAGCCGGAGAACAACTACAAGACCACGCCTCCCGTGCTGGACTCCGACA
CCTGCCGGGCGGCCGCTCGA 16444.2.edit AGCGTGGTTNCGGCCGAGGTCCCAACCAAGGCTGCANCCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGNCGCTCGA 16445.1.edit AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGGGCGGCCGCTCGA

*Fig. 15V*

16445.2.edit

TCGAGCGGTCGCCCGGGCAGGTCCACATCGGCAGGGTCGGAGCCCTGGCCGCCATACTCGAACTGGAATCCATCGG
NCATGCTCTCGCCGAACCAGACATGCCTCTTGNCCTTGGGGTTCTTGCTGATGTACCAGNTCTTCTGGGCCACACT
GGGCTGAGTGGGGTACACGCAGGTCTCACCANTCTCCATGTTGCANAAGACTTTGATGGCATCCAGGTTGCAGCCT
TGGTTGGGGTCAATCCAGTACTCTCCACTCTTCCAGACAGAGTGGCACATCTTGAGGTCACGGCAGGTGCGGGCGG
GGTTCTTGACCTCGGTCGCGACCACGCT 16446.1.edit TCGAGCGGCCGCCCGGGCAGGTCCTCCTCAGAGCGGTAGCTGTTCTTATTGCCCCGGCAGCCTCCATAGATNAAGT
TATTGCANGAGTTCCTCTCCACGTCAAAGTACCAGCGTGGGAAGGATGCACGGCAAGGCCCAGTGACTGCGTTGGC
GGTGCAGTATTCTTCATAGTTGAACATATCGCTGGAGTGGACTTCAGAATCCTGCCTTCTGGGAGCACTTGGGACA
GAGGAATCCGCTGCATTCCTGCTGGTGGACCTCGGCCGCGACCACGCT 16446.2.edit AGCGTGGTCGCGGCCGAGGTCCACCAGCAGGAATGCAGCGGATTCCTCTGTCCCAAGTGCTCCCAGAAGGCAGGAT
TCTGAAGACCACTCCAGCGATATGTTCAACTATGAAGAATACTGCACCGCCAACGCAGTCACTGGGCCTTGCCGTG
CATCCTTCCCACGCTGGTACTTTGACGTGGAGAGGAACTCCTGCAATAACTTCATCTATGGAGGCTGCCGGGGCAA
TAAGAACAGCTACCGCTCTGAGGAGGACCTGCCCGGGCGGCCGCTCGA 16447.1.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGCCAGAATGGCACATCTTGAGGTCACGGCANGTGCGGGCGG
GGTTCTTGACCTCGGCCGCGACCACGCT

*Fig. 15W*

16447.2.edit

AGCGTGGTCGCGGCCGAGGTCAAGAAACCCCGCCCGCACCTGCCGTGACCTCAAGATGTGCCACTCTGGCTGGAAG
AGTGGAGAGTACTGGATTGACCCCAACCAAGGCTGCAACCTGGATGCCATCAAAGTCTTCTGCAACATGGAGACTG
GTGAGACCTGCGTGTACCCCACTCAGCCCAGTGTGGCCCAGAAGAACTGGTACATCAGCAAGAACCCCAAGGACAA
GAGGCATGTCTGGCTCGGCGAGAGCATGACCGATGGATTCCAGTTCGAGTATGGCGGCCAGGGCTCCGACCCTGCC
GATGTGGACCTGCCCGGGCGGCCGCTCGA 16449.1.edit AGCGTGGTCGCGGCCGAGGTCCTGTCAGAGTGGCACTGGTAGAAGNTCCAGGAACCCTGAACTGTAAGGGTTCTTC
ATCAGTGCCAACAGGATGACATGAAATGATGTACTCAGAAGTGTCCTGNAATGGGGCCCATGANATGGTTGNCTGA
GAGAGAGCTTCTTGTCCTACATTCGGCGGGTATGGTCTTGGCCTATGCCTTATGGGGGTGGCCGTTGNGGGCGGTG
NGGTCCGCCTAAAACCATGTTCCTCAAAGATCATTTGTTGCCCAACACTGGGTTGCTGACCANAAGTGCCAGGAAG
CTGAATACCATTTCCAGTGTCATACCCAGGGTGGGTGACGAAAGGGGTCTTTTGAACTGTGGAAGGAACATCCAAG
ATCTCTGNTCCATGAAGATTGGGGTGTGGAAGGGTTACCAGTTGGGGAAGCTCGCTGTCTTTTTCCTTCCAATCAN
GGGCTCGCTCTTCTGAATATTCTTCAGGGCAATGACATAAATTGTATATTCGGTTCCCGGTTCCAGGCCAG 16450.1.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGANGAACATGGNTTT
AGGCGGACCACACCGGCCACAACGGGCACCCCCATAAGGCATAGGCCAAGAACATACCCGNCGAATGTAGGACAAG
AAGCTCTNTCTCANACAANCATCTCATGGGCCCCATTCCANGACACTTCTGAGTACATCANTTCATGGCATCCTGG
TGGCACTGATAAAAACCCTTACAGTTA 16450.2.edit AGCGTGGTCGCGGGCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
NGGGCTCGCTCTTCTGATTATTCTTCAGGGCAATGACATAAATTGTATATTCGGNTCCCGGGTNCAGCCAATAATA
ATAACCCTCTGTGACACCANGGCGGGGCCGAAGGANCACT

*Fig. 15X*

16451.1.edit

AGCGTGGTCGCGGCCGAGGTCCTCACCAGAGGTACCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA 16451.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGNTGACAGAGTTGCCCACGGTAACAACCTCTTCCCGAACCTTATGCCTCTGCTGG
TCTTTCAGTGCCTCCACTATGATGTTGTAGGTGGTACCTCTGGTGAGGACCTCGGCCGCGACCACGCT 16452.1.edit AGCGTGGCCGCGGCCGAGGTCCATTGGCTGGAACGGCATCAACTTGGAAGCCAGTGATCGTCTCAGCCTTGGTTCT
CCAGCTAATGGTGATGGNGGTCTCAGTAGCATCTGTCACACGAGCCCTTCTTGGTGGGCTGACATTCTCCAGAGTG
GTGACAACACCCTGAGCTGGTCTGCTTGTCAAAGTGTCCTTAAGAGCATAGACACTCACTTCATATTTGGCGNCCA
CCATAAGTCCTGATACAACCACGGAATGACCTGTCAGGAAC 16452.2.edit TCGAGCGGCCGCCCGGGCAGGTCCTCAGACCGGGTTCTGAGTACACAGTCAGTGTGGTTGCCTTGCACGATGATAT
GGAGAGCCAGCCCCTGATTGGAACCCAGTCCACAGCTATTCCTGCACCAACTGACCTGAAGTTCACTCAGGTCACA
CCCACAAGCCTGAGCGCCCAGTGGACACCACCCAATGTTCAGCTCACTGGATATCGAGTGCGGGTGACCCCCAAGG
AGAAGACCGGACCAATGAAAGAAATCAACCTTGCTCCTGACAGCTCATCCGTGGTTGTATCAGGACTTATGGCGGC
CACCAAATATGAAGTGAGTGTCTATGCTCTTAAGGACACTTTGACAAGCAGACCAGCTCAGGGTGTTGTCACCACT
CTGGAGAATGTCAGCCCACCAAGAAGGGCTCGTGTGACAGATGCTACTGAGACCACCATCACCATTAGCTGGAGAA
CCAAGACTGAGACGATCACTGGCTTCCAAGTTGATGCCGTTCCAGCCAATGGACCTCGGCCGCGACCACGCTT

*Fig. 15Y*

16453.1.edit

AGCGTGGTCGCGGCCGAGGTCTGGCCGAACTGCCAGTGTACAGGGAAGATGTACATGTTATAGNTCTTCTCGAAGT
CCCGGGCCAGCAGCTCCACGGGGTGGTCTCCTGCCTCCAGGCGCTTCTCATTCTCATGGATCTTCTTCACCCGCAG
CTTCTGCTTCTCAGTCAGAAGGTTGTTGTCCTCATCCCTCTCATACAGGGTGACCAGGACGTTCTTGAGCCAGTCC
CGCATGCGCAGGGGGAATTCGGTCAGCTCAGAGTCCAGGCAAGGGGGGATGTATTTGCAAGGCCCGATGTAGTCCA
AGTGGAGCTTGTGGCCCTTCTTGGTGCCCTCCAAGGTGCACTTTGTGGCAAAGAAGTGGCAGGAAGAGTCGAAGGT
CTTGTTGTCATTGCTGCACACCTTCTCAAACTCGCCAATGGGGGCTGGGCAGACCTGCCCGGGCGGCCGCTCGA 16453.2.edit TCGAGCGGCCGCCCGGGCAGGTCTGCCCAGCCCCCATTGGCGAGTTTGAGAAGGNGTGCAGCAATGACAACAAGAC
CTTCGACTCTTCCTGCCACTTCTTTGCCACAAAGTGCACCCTGGAGGGCACCAAGAAGGGCCACAAGCTCCACCTG
GACTACATCGGGCCTTGCAAATACATCCCCCCTTGCCTGGACTCTGAGCTGACCGAATTCCCCCTGCGCATGCGGG
ACTGGCTCAAGAACGTCCTGGTCACCCTGTATGAGAGGGATGAGGACAACAACCTTCTGACTGAGAAGCANAAGCT
GCGGGTGAAGAANATCCATGAGAATGANAAGCGCCTGNAGGCANGAGACCACCCCGTGGAGCTGCTGGCCCGGGAC
TTCGAGAAGAACTATAACATGTACATCTTCCCTGTACACTGGCAGTTCGGCCAGACCTCGGCCGCGACCACGCT 16454.1.edit AGCGTGGNTGCGGACGACGCCCACAAAGCCATTGTATGTAGTTTTANTTCAGCTGCAAANAATACCNCCAGCATCC
ACCTTACTAACCAGCATATGCAGACA 16454.2.edit TCGAGCGGTCGCCCGGGCAGGTCTGGGCGGATAGCACCGGGCATATTTTGGAATGGATGAGGTCTGGCACCCTGAG
CAGCCCAGCGAGGACTTGGTCTTAGTTGAGCAATTTGGCTAGGAGGATAGTATGCAGCACGGTTCTGAGTCTGTGG
GATAGCTGCCATGAAGNAACCTGAAGGAGGCGCTGGCTGGTANGGGTTGATTACAGGGCTGGGAACAGCTCGTACA
CTTGCCATTCTCTGCATATACTGGNTAGTGAGGCGAGCCTGGCGCTCTTCTTTGCGCTGAGCTAAAGCTACATACA
ATGGCTTTGNGGACCTCGGCCGCGACCACGCTT

*Fig. 15Z*

16455.1.edit

TCGAGCGGCCGCCCGGGCAGGTCCATTTTCTCCCTGACGGTCCCACTTCTCTCCAATCTTGTAGTTCACACCATTG
TCATGACACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAAGTTGCCCACGGTAACAACCTCTTCCCGAACCTTATGCCTCTGCTG
GTCTTTCAAGTGCCTCCACTATGATGTTGTAGGTGGCACCTCTGGTGAGGACCTCGGCCGCGACCACGCT 16455.2.edit AGCGTGGTTTGCGGCCGAGGTCCTCACCANAGGTGCCACCTACAACATCATAGTGGAGGCACTGAAAGACCAGCAG
AGGCATAAGGTTCGGGAAGAGGTTGTTACCGTGGGCAACTCTGTCAACGAAGGCTTGAACCAACCTACGGATGACT
CGTGCTTTGACCCCTACACAGNTTCCCATTATGCCGTTGGAGATGAGTGGGAACGAATGTCTGAATCAGGCTTTAA
ACTGTTGTGCCAGTGCTTANGCTTTGGAAGTGGTCATTTCAGATGTGATTCATCTANATGGTGTCATGACAATGGT
GNGAACTACAAGATTGGAGAGAAGTGGNACCGTCAGGGGANAAAATGGACCTGCCCGGGCGGCNCGCTCGA 16456.1.edit AGCGTGGTCGCGGCCGAGGTCTGGCTTNCTGCTCANGTGATTATCCTGAACCATCCAGGCCAAATAAGCGCCGGCT
ATGCCCCTGNATTGGATTGCCACACGGCTCACATTGCATGCAAGTTTGCTGAGCTGAAGGAAAAGATTGATC 16456.2.edit TCGAGCGGCCGCCCGGGCAGGTCCAATTGAAACAAACAGTTCTGAGACCGTTCTTCCACCACTGATTAAGAGTGGG
GNGGCGGGTATTAGGGATAATATTCATTTAGCCTTCTGAGCTTTCTGGGCAGACTTGGTGACCTTGCCAGCTCCAG
CAGCCTTCTGGTCCACTGCTTTGATGACACCCACCGCAACTGTCTGTCTCATATCACGAACAGCAAAGCGACCCAA
AGGTGGATAGTCTGAGAAGCTCTCAACACACATGGGCTTGCCAGGAACCATATCAACAATGGGCAGCATCACCAGA
CTTCAAGAATTTAAGGGCCATCTTCCAGCTTTTTACCAGAACGGCGATCAATCTTTTCCTTCAGCTCAGCAAACTT
GCATGCAATGTGAGCCG

*Fig. 15A-1*

16459.1.edit

```
TCGAGCGGCCGCCCGGGCAGGTCCAGAGGGCTGTGCTGAAGTTTGCTGCTGCCACTGGAGCCACTCCAATTGCTGG
CCGCTTCACTCCTGGAACCTTCACTAACCAGATCCAGGCAGCCTTCCGGGAGCCACGGCTTCTTGTGGNTACTGAC
CCCAGGGCTGACCACCAGCCTCTCACGGAGGCATCTTATGTTAACCTACCTACCATTGCGCTGTGTAACACAGATT
CTCCTCTGCGCTATGTGGACATTGCCATCCCATGCAACAACAAGGGAGCTCACTCAGNGGGGTTTGATGTGGTGGA
TGCTGGCTCGGGAAGTTCTGCGCATGCGTGGCACCATTTCCCGTGAACACCCATGGGANGNCATGCCTGATCTGGA
CTTCTACAGAGATCCTGAAGAGATTGAAAAAGAAGAACAGGCTGNTTGCTGANAAAGCAAGTGACCAAGGANGAAA
TTTCANGGGTGAAANGGACTGCTCCCGCTCCTGAATTCACTGCTACTCAACCTGANGNTGCAGACTGGTCTTGAAG
GNGNACANGGGCCCTCTGGGCCTATTTAAGCANCTTCGGTCGCGAACACGNT
```

16459.2.edit

```
AGCGTGNGTCGCGGCCGAGGTGCTGAATAGGCACAGAGGGCACCTGTACACCTTCAGACCAGTCTGCAACCTCAGG
CTGAGTAGCAGTGAACTCAGGAGCGGGAGCAGTCCATTCACCCTGAAATTCCTCCTTGGNCACTGCCTTCTCAGCA
GCAGCCTGCTCTTCTTTTTCAATCTCTTCAGGATCTCTGTAGAAGTACAGATCAGGCATGACCTCCCATGGGTGTT
CACGGGAAATGGTGCCACGCATGCGCAGAACTTCCCGAGCCAGCATCCACCACATCAAACCCACTGAGTGAGCTCC
CTTGTTGTTGCATGGGATGGGCAATGTCCACATAGCGCAGAGGAGAATCTGTGTTACACAGCGCAATGGTAGGTAG
GTTAACATAAGATGCCTCCGCGAGAAGCTGGTGGTCAGCCCTGGGGTCAAGTAACCACAAGAAGCCGTGGCTCCCG
GAAGGCTGCCTGGATCTGGTTAGTGAAGGNTCCAGGAGTGAAGCGGCCAACAATTGGAGTGGCTTCAGTGGCAAGC
AGCAAACTTCAGCACAAGCCCTCTGGACCTGCCCGGCGGCCGCTCGA
```

16460.1.edit

```
TCGAGCGGCCGCCCGGGCAGGTCCATTTTCTCCCTGACGGNCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCNTCCCCGAACCTTATGCCTCTGCTG
GGCTTTCAGNGCCTCCACTATGATGNTGTAGGGGGGCACCTCTGGNGANGACCTCGGCCGCGACCACGCT
```

16460.2.edit

```
AGCGTGGTCGCGGCCGAGGTCCTCACCAGAGGTGCCACCTACAACATCATAGTGGAGGCACTGAAAGACCAGCAGA
GGCATAAGGCTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTANGCTTTGGAAGTGGGTCATTTCAGATGTGATTCATCTAGATGGTGCCATGACAATGGN
GNGAACTACAAGATTGGAGAGAAGTGGNACCGNCAGGGAGAAAATGGACCTGCCCGGGCGGCCGCTCGA
```

*Fig. 15B-1*

16461.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGNTGCAACCTTG
GTTGGGGTCAATCCAGTACTCTCCACTCTTCCAGCCAGAGTGGCACATCTTGAGGTCACGGCAGGTGCGGNCGGGG
GNTTTTGCGGCTGCCCTCTGGNCTTCGGNTGTNCTCNATCTGCTGGCTCA 16461.2.edit TCGAGCGGCCGCCCGGGCAGGTCTCGCGGTCGCACTGGTGATGCTGGTCCTGTTGGTCCCCCCGGCCCTCCTGGAC
CTCCTGGCCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGNCGCAAGAACCCCGCCCGCACCTGCCGTG
ACCTCAAGATGTGCCACTCTGACTGGAAGAGTGGAGAGTACTGGATTGACCCCAACCAAGCTGCAACCTGGATGCC
ATCAAAGTCTTCTGCAACATGGAGACTGGTGAGACCTGCGTGTACCCCACTCAGCCCAGTGTGGCCCAAAAGAACT
GGTACATCAGCAAGAACCCCAAGGACAAGAAGCATGTCTGGTTCGGCGAGAACATGACCGATGGATTCCAGTTCGA
GTATGGCGGGCAGGGCTCCGACCCTGCCGATGGGGACCTTGGCCGCGAACACGCT 16463.1.edit AGCGTGGNNGCGGCCGAGGTATAAATATCCAGNCCATATCCTCCCTCCACACGCTGANAGATGAAGCTGTNCAAAG
ATCTCAGGGTGGANAAAACCAT 16463.2.edit TCGAGCGGCCGCCCGGGCAGGTCCTTCAGACTTGGACTGTGTCACACTGCCAGGCTTCCAGGGCTCCAACTTGCAG
ACGGCCTGTTGTGGGACAGTCTCTGTAATCGCGAAAGCAACCATGGAAGACCTGGGGGAAAACACCATGGTTTTAT
CCACCCTGAGATCTTTGAACAACTTCATCTCTCAGCGTGCGGAGGGAGGCTCTGGACTGGATATTTCTACCTCGGC
CGCGACCACGCT

*Fig. 15C-1*

16464.1.edit

CGAGCGGGCGACCGGGCAGGTNCAGACTCCAATCCANANAACCATCAAGCCAGATGTCAGAAGCTACACCATCACA
GGTTTACAACCAGGCACTGACTACAAGANCTACCTGCACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGTACATCATCNAGTATGANAAGCCTGGGCCTCCTCCCAGAGAAGNGG
TCCCTCGGCCCCGCCCTGNTGTCCCANAGGNTACTATTACTGNGCCNGCAACCGGCAACCGATATCNATTTTGNCA
TTGGCCTTCAACAATAATTA 16464.2.edit AGCGTGGTTCGCGGCCGANGTCCTGTCAGAGTGGCACTGGTAGAAGTTCCAGGAACCCTGAACTGTAAGGGTTCTT
CATCAGNGCCAACAGGATGACATGAAATGATGTACTCAGAAGTGTCCTGGAATGGGGCCCATGAGATGGTTGTCTG
AGAGAGAGCTTCTTGNCCTGTCTTTTTCCTTCCAATCAGGGGCTCGCTCTTCTGATTATTCTTCAGGGCAATGACA
TAAATTGTATATTCGGGTCCCGGNTCCAGGCCAGTAATAGTANCCTCTGTGACACCAGGGCGGNGCCGAGGGACCA
CTTCTCTGGGAGGAGACCCAGGCTTCTCATACTTGATGATGTAACCGGTAATCCTGGCACGTGGCGGCTGCCATGA
TACCAGCAAGGAATTGGGGTGTGGTGGCCAGGAAACGCAGGTTGGATGGNGCATCAATGGCAGTGGAGGCCGTCGA
TGACCACAGGGGGAGCTCCGACATTGTCATTCAAGGTG 16465.1.edit AGCGTGGNCGCGGCCGAGGTGCAGCGCGGGCTGTGCCACCTTCTGCTCTCTGCCCAACGATAAGGAGGGTNCCTGC
CCCCAGGAGAACATTAACTNTCCCCAGCTCGGCCTCTGCCGG 16465.2.edit TCGAGCGGCCGCCCGGGCAGGTTTTTTTTGCTGAAAGTGGNTACTTTATTGGNTGGGAAAGGGAGAAGCTGTGGTC
AGCCCAAGAGGGAATACAGAGNCCCGAAAAAGGGGAGGGCAGGTGGGCTGGAACCAGACGCAGGGCCAGGCAGAAA
CTTTCTCTCCTCACTGCTCAGCCTGGTGGTGGCTGGAGCTCANAAATTGGGAGTGACACAGGACACCTTCCCACAG
CCATTGCGGCGGCATTTCATCTGGCCAGGACACTGGCTGTCCACCTGGCACTGGTCCCGACAGAAGCCCGAGCTGG
GGAAAGTTAATGTTCACCTGGGGGCAGGAACCCTCCTTATCATTGNGCAGAGAGCAGAAGGTGGCACAGCCCGCGC
TGCACCTCGGCCGCGACCACGCT 16466.2.edit TCGAGCGGCCGCCCGGGCAGGTCCACCATAAGTCCTGATACAACCACGGATGAGCTGTCAGGAGCAAGGTTGATTT
CTTTCATTGGTCCGGNCTTCTCCTTGGGGGNCACCCGCACTCGATATCCAGTGAGCTGAACATTGGGTGGCGTCCA
CTGGGCGCTCAGGCT 16467.2.edit TCGAGCGGTTCGCCCGGGCAGGTCCACCACACCCAATTCCTTGCTGGTATCATGGCAGCCGCCACGTGCCAGGATT
ACCGGCTACATCATCAAGTATGAGAAGCCTGGGTCTCCTCCCAGAGAAGCGGTCCCTCGGCCCCGCCCTGGTGTCA
CAGAGGCTACTATTACTGGCCTGGAACCGGGAACCGAATATACAATTTATGTCATTGNCCTGAAGAATAATCANNA
ANAGCGANCCCCTGATTGGAAGGA

*Fig. 15D-1*

01_16469.edit

AGCGTGGTCGCGGCCGAGGTTGTACAAGCTTTTTTTTTTTTTTTTTTTTTTTTTTTTTTTTTTTTTTTTTTTTT
TTTTTTTTTTTTTTT

02_16469.edit

TCGAGCGGNCGCCCGGGCAGGTCTGCCAACACCAAGATTGGCCCCCGCCGCATCCACACAGTCCGTGTGCGGGGAG
GTAACAAGAAATACCGTGCCCTGAGGTTGGACGTGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATCGACAGCACACCGTACCGACAGTGGTACGAGTCCCACTATGCGCTGCCCCTGGGCCGCAAGAAGGGAG
CCAAGCTGACTCCTGAGGAAGAAGAGATTTTAAACAAAAAACGATCTAANAAAAAAAAAACAAT

03_16470.edit

AGCGTGGTCGCGGCCGAGGTGAAATGGTATTCAGCTTCCTGGCACTTCTGGTCAGCAACCCAGTGTTGGGCAACAA
ATGATCTTTGAGGAACATGGTTTTAGGCGGACCACACCGCCCACAACGGCCACCCCCATAAGGCATAGGCCAAGAC
CATACCCGCCGAATGTAGGACAAGAAGCTCTCTCTCAGACAACCATCTCATGGGCCCCATTCCAGGACACTTCTGA
GTACATCATTTCATGTCATCCTGTTGGCACTGATGAAGAACCCTTACAGTTCAGGGTTCCTGGAACTTCTACCAGT
GCCACTCTGACAGGACCTGCCCGGGCGGCCGCTCGA

04_16470.edit

TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCACCTCGGCCGCGACCACGCTA

05_16471.edit

TCGAGCGGCCGCCCGGGCAGGTCTCCCTTCTTGCGGCCCAGGGGCAGCGCATAGTGGGACTCGTACCACTGTCGGT
ACGGTGTGCTGTCGATGAGCACGATGCAATTCTTCACCAGGGTCTTGGTACGAACCAGCTCGTTATTAGATGCATT
GTAGACAACATCGATGATCCTTGTTTTACGAGTACAACACTCTGAGCCCCAGGAGAAATTCCCCACGTCCAACCTC
AGGGCACGGTATTTCTTGTTACCTCCCCGCACACGGACTGTGTGGATGCGGCGGGGGCCAAGCTGACTCCTGAGGA
AGAAGAGATTTTAAACAAAAAACGATCTAAAAAAATTCAGAAGAAATATGATGAAAGGAAAAAGAATGCCAAAATC
AGCAGTCTCCTGGAGGAGCAGTTCCAGCAGGGCAAGCTTCTTGCGTGCATCGCTTCAAGGCCGGGACAGTGTGACC
GAGCAGATGGCTATGTGCTAGAGGGCAAAGAAGTGGAGTTCTATCTTAAGAAAATCAGGGCCCAGAATGGTGNGTC
TTCAACTAATCCAAAGGGGAGTTTCAGACCAGTGCAATCAGCAAAAACATTGATACTGNTGGCCAAATTTATTGGT
GCAGGGCTTGCACANTANGANNGGCTGGGTCTTGGGGCTTGGATTGGNACAAGCTTTGGCAGCCTTTTCTTTGGTT
TTGCCAAAAACCTTTTGNTGAAGANGANACCTNGGGCGGACCCCTTAACCGATTCCACNCCNGGNGGCGTTCTANG
GNCCCNCTTG

*Fig. 15E-1*

06_16471.edit

AGCGTGGTCGCGGCCGAGGTCTGCTGCTTCAGCGAAGGGTTTCTGGCATAACCAATGATAAGGCTGCCAAAGACTG
TTCCAATACCAGCACCAGAACCAGCCACTCCTACTGTTGCAGCACCTGCACCAATAAATTTGGCAGCAGTATCAAT
GTCTCTGCTGATTGCACTGGTCTGAAACTCCCTTTGGATTAGCTGAGACACACCATTCTGGGCCCTGATTTTCCTA
AGATAGAACTCCAACTCTTTGCCCTCTAGCACATAGCCATCTGCTCGGTCACACTGTCCCGGCCTTGAAGCGATGC
ACGCAAGAAGCTTGCCCTGCTGGAACTGCTCCTCCAGGAGACTGCTGATTTTGGCATTCTTTTTCCTTTCATCATA
TTTCTTCTGAATTTTTTTAGATCGTTTTTTGTTTAAAATCTCTTCTTCCTCAGGAGTCAGCTTGGCCCCCGCCGCA
TCCACACAGTCCGTGTGCGGGGAGGTAACAAGAAATACCGTGCCCTGAGGTTGGACGTGGGGAATTTCTCCTGGGG
CTCAGAGTGGTGTACTCGTAAAACAAGGATCATCGATGGTGNCTACAATGCATCTAATAACGAGCTGGGTCGGACC
CAAAGAACCTGGNGAANAAATGGATCGNCTCATCGACAGGACACCGTACCCGACAGGGGNACGANTCCCACTATGC
GCTTGCCCCTGGGCCGCAANAAAGGAAAACTGCCCGGGCGGCCNTCGAAAGCCCAATTNTGGAAAAAATCCATCAC
ACTGGGNGGCCNGTCGAGCATGCATNTANAGGGGCCCATTCCCCCTNANN

07_16472.edit

TCGAGCGGCCGCCCGGGCAGGTCCCCAACCAAGGCTGCAACCTGGATGCCATCAAAGTCTTCTGCAACATGGAGAC
TGGTGAGACCTGCGTGTACCCCACTCAGCCCAGTGTGGCCCAGAAGAACTGGTACATCAGCAAGAACCCCAAGGAC
AAGAGGCATGTCTGGTTCGGCGAGAGCATGACCGATGGATTCCAGTTCGAGTATGGCGGCCAGGGCTCCGACCCTG
CCGATGTGGACCTCGGCCGCGACCACGCT

08_16472.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGACCTGCCCGGGCGGCCGCTCGA

09_16473.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGNTTT
AGGCGGACCACACCGCCCACAACGGCCACCCCCATAAGGCATAGGCCAAGACCATACCCGCCGAATGTAGGACAAG
AAGCTNTNTNTCANACACCATNTNATGGGCCCCATTCCAGGACACTTCTGAGTACATCATTTATGNCATCTGTGGC
ACTTGATGAAAACCCTTACAGTTCAGGGTTCTGGAACTTTTACCAGGCCTNTTACAGGACTNGGCCGGACNCCTTA
AGCCNATTNCACCCTGGGGCGTTCTANGGTCCCACTCGNNCACTGGNGAAAATGGCTACTGTN

*Fig. 15F-1*

11_16474.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGNGAAACTCCNAGGACANGAGGGCTAAATTCCATGAAGTTTGTGGATGGCCTGATGATCCACAAT
CGGAGACCCTGTTAACTACTACCGTCTNACCNCCTGCTGTNCNCCCCCNTTTCTGCTNAANACATNGGGNTNNTNC
TTGNCCNTCCTTGGGTNGAANATNNAATNGCCTNCCCNTTCNTANCNCTACTNGNTCCANANTTGGCCTTTAAANA
ATCCNCCTTGCCTTNNNCACTGTTCANNTNTTTNNTCGTAAACCCTATNANTTNNATTANATNNTNNNNNNCTCAC
CCCCCTCNTCATTNANCCNATANGCTNNNAANTCCTTNANNCCTCCCNCCCNNTNCNCTCNTACTNANTNCTTCTN
NCCCATTACNNAGCTCTTTCNTTTAANATAATGNNGCCNNGCTCTNCATNTCTACNATNTGNNNAATNCCCCCNCC
CCCNANCGNNTTTTTGACCTNNNAACCTCCTTTCCTCTTCCCTNCNNAAATTNCNNANTTCCNCNTTCCNNCNTTT
CGGNTNNTCCCATNCTTTCCANNNCTTCANTCTANCNCNCTNCAACTTATTTTCCTNTCATCCCTTNTTCTTTACA
NNCCCCCTNNTCTACTCNNCNNTTNCATTANATTTGAAACTNCCACNNCTANTTNCCTCNCTCTACNNTTTTATTT
TNCGNTCNCTCTACNTAATANTTTAATNANTTNTCN

12_16474.edit

TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAAGCAGTGTCAACGTAGTAAGTTAACAGGGTCTCCGCTGTGGATCA
TCAGGCCATCCACAAACTTCATGGATTTAGCCCTCTGTCCTCGGAGTTTCCCAGACACCACAACCTCGCAGCCTTT
GGCCCCACTCTCCATGATGAACCGCAGCACACCATAGCAGGCCCTCCGCACAAGCAAGCCCTCCTAAGAATTTGTA
ACGCANANACTCTGCTGGCAATGGCACACAAACCTCTAGTGGACCTCGGNCGCGACCACGC

13_16475.edit

TCGAGCGGCCGCCCGGGCAGGTCTGGTCCAGGATAGCCTGCGAGTCCTCCTACTGCTACTCCAGACTTGACATCAT
ATGAATCATACTGGGGAGAATAGTTCTGAGGACCAGTAGGGCATGATTCACAGATTCCAGGGGGGCCAGGAGAACC
AGGGGACCCTGGTTGTCCTGGAATACCAGGGTCACCATTTCTCCCAGGAATACCAGGAGGGCCTGGATCTCCCTTG
GGGCCTTGAGGTCCTTGACCATTAGGAGGGCGAGTAGGAGCAGTTGGAGGCTGTGGGCAAACTGCACAACATTCTC
CAAATGGAATTTCTGGGTTGGGGCAGTCTAATTCTTGATCCGTCACATATTATGTCATCGCAGAGAACGGATCCTG
AGTCACAGACACATATTTGGCATGGTTCTGGCTTCCAGACATCTCTATCCGNCATAGGACTGACCAAGATGGGAAC
ATCCTCCTTCAACAAGCTTNCTGTTGTGCCAAAAATAATAGTGGGATGAAGCAGACCGAGAAGTANCCAGCTCCCC
TTTTTGCACAAAGCNTCATCATGTCTAAATATCAGACATGAGACTTCTTTGGGCAAAAAAGGAGAAAAAGAAAAAG
CAGTTCAAAGTANCCNCCATCAAGTTGGTTCCTTGCCCNTTCAGCACCCGGGCCCCGTTATAAAACACCTNGGGCC
GGACCCCCCTT

*Fig. 15G-1*

14_16475.edit

AGCGTGGTCGCGGCCGAGGTGTTTTATGACGGGCCCGGTGCTGAAGGGCAGGGAACAACTTGATGGTGCTACTTTG
AACTGCTTTTCTTTTCTCCTTTTTGCACAAAGAGTCTCATGTCTGATATTTAGACATGATGAGCTTTGTGCAAAAG
GGGAGCTGGCTACTTCTCGCTCTGCTTCATCCCACTATTATTTTGGCACAACAGGAAGCTGTTGAAGGAGGATGTT
CCCATCTTGGTCAGTCCTATGCGGATAGAGATGTCTGGAAGCCAGAACCATGCCAAATATGTGTCTGTGACTCAGG
ATCCGTTCTCTGCGATGACATAATATGTGACGATCAAGAATTAGACTGCCCCAACCCAGAAATTCCATTTGGAGAA
TGTTGTGCAGTTTGCCCACAGCCTCCAACTGCTCCTACTCGCCCTCCTAATGGTCAAGGACCTCAAGGCCCCAAGG
GAGATCCAGGCCCTCCTGGTATTCCTGGGAGAAATGGTGACCCTGGTATTCCAGGACAACCAGGGTCCCCTGGTTC
TCCTGGCCCCCCTGGAATCNGGNGAATCATGCCCTACTGGTCCTCAAACTATTCTCCCANATGATTCATATGATGT
CAAGTCTGGGATAGCNAGTANGGANGGACTCGCAGGCTATTCTGGACCANACCTGCCGGGGGGGCGTTCGAAAGCC
CGAATCTGCANANNTNCNTTCACACTGGCGGCCGTCGAGCTGCTTTAAAAGGGCCATTCCNCCTTTAGNGNGGGGG
ANTACAATTACTNGGCGGCGTTTTANANCGCGNGNCTGGGAAAT

15_16476.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAGGCTCTTGAGGGTGGTGTCCACCTCGA
GGTCACGGTCACGAACCACATTGGCATCATCAGCCCGGTAGTAGCGGCCACCATCGTGAGCCTTCTCTTGANGTGG
CTGGGGCAGGAACTGAAGTCGAAACCAGCGCTGGGAGGACCAGGGGGACCAANAGGTCCAGGAAGGGCCCGGGGGG
GACCAACAGGACCAGCATCACCAAGTGCGACCCGCGAGAACCTGCCCGGCCGNCCGCTCGAA

16_16476.edit

TCGAGCGNNCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTGAGCCAGCAGATCGAGAACATCCGGAGCCCAGAGGGCAGCCGCAAGAACCCCGCCCGCACCTGCCGTG
ACCTCAAGATGTGCCACTCTGACTGGAAGAGTGGAGAGTACTGGATTGACCCCAACCAAGGCTGCAACCTGGATGC
CATCAAAGTCTTCTGCAACATGGAGACTGGTGAGACCTGCGTGTACCCCACTCAGCCCAGTGTGGCCCAGAAGAAC
TGGTACATCAGCAAGAACCCCAAGGACAAGAGGCATGTCTGGTTCGGCGAGAGCATGACCGATGGATTCCAGTTCG
AGTATGGCGGCCAGGGCTCCCACCCTGCCGATGTGGACCTCCGGCCGCGACCACCCTT

*Fig. 15H-1*

17_16477.edit

TNGAGCGGCCGCCCGGGCAGGNTGNNAACGCTGGTCCTGCTGGTCCTCCTGGCAAGGCTGGTGAAGATGGTCACCC
TGGAAAACCCGGACGACCTGGTGAGAGAGGAGTTGTTGGACCACAGGGTGCTCGTGGTTTCCCTGGAACTCCTGGA
CTTCCTGGCTTCAAAGGCATTAGGGGACACAATGGTCTGGATGGATTGAAGGGACAGCCCGGTGCTCCTGGTGTGA
AGGGTGAACCTGGTGCCCCTGGTGAAAATGGAACTCCAGGTCAAACAGGAGCCCGTGGGCTTCCTGGTGAGAGAGG
ACCGTGTTGGTGCCCCTGGCCCANACCTCGGCCGCGACCACGCTAAGCCCGAATTTCCAGCACACTGGNGGCCGTT
ACTANTGGATCCGAGCTCGGTACCAAGCTTGGCGTAATCATGGTCATAGCTGTTTCCTGNGTGAAATTGTTATCCG
CTCACAATTTCACACANCATACGAAGCCGGAAAGCATAAAGTGTAAAGCCTTGGGGTGCTAATGAGTGAGCTAACT
CNCATTAAATTGCGTTGCGCTCACTGCCCGCTTTTCCANNNGGGAAACCNTGGCNTNGCCNGCTTGCNTTAANTGA
AATCCGCCNACCCCCGGGGAAAAGNCGGTTTGCNGTATTGGGGCNCTTTTTCCCTTTCCTCGGNTTACTTGANTTA
NTGGGCTTTGGNCGNTTCGGGTTGNGGCGANCNGGTTCAACNTCACNCCAAAGGNGGNAANACGGTTTTCCCANAA
TCCGGGGGNTANCCCAANGNAAAACATNNGNCNAANGGGCT

18_16477.edit

AGCGTGGTTNGCGGCCGAGGTCTGGGCCAGGGGCACCAACACGTCCTCTCTCACCAGGAAGCCCACGGGCTCCTGT
TTGACCTGGAGTTCCATTTTCACCAGGGGCACCAGGTTCACCCTTCACACCAGGAGCACCGGGCTGTCCCTTCAAT
CCATNCAGACCATTGTGNCCCCTAATGCCTTTGAAGCCAGGAAGTCCAGGAGTTCCAGGGAAACCACCGAGCACCC
TGTGGTCCAACAACTCCTCTCTCACCAGGTCGTCCGGGTTTTCCAGGGTGACCATCTTCACCAGCCTTGCCAGGAG
GACCAGCAGGACCAGCGTTACCAACCTGCCCGGGCGGCCGCTCGA

21_16479.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

22_16479.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAAGATGTGATTCATCTAGATGGTGCCATGACAATGGT
GTGAACTACAAGATTGGAGAGAAGTGGGACCGTCAGGGAGAAAATGGACCTGCCCGGGCCGGCCGCTCGA

*Fig. 15I-1*

24_16480.edit

TCGAGCGNNCGCCCGGGCAGGTCCAGTAGTGCCTTCGGGACTGGGTTCACCCCCAGGTCTGCGGCAGTTGTCACAG
CGCCAGCCCCGCTGGCCTCCAAAGCATGTGCAGGAGCAAATGGCACCGAGATATTCCTTCTGCCACTGTTCTCCTA
CGTGGTATGTCTTCCCATCATCGTAACACGTTGCCTCATGAGGGTCACACTTGAATTCTCCTTTTCCGTTCCCAAG
ACATGTGCAGCTCATTTGGCTGGCTCTATAGTTTGGGGAAAGTTTGTTGAAACTGTGCCACTGACCTTTACTTCCT
CCTTCTCTACTGGAGCTTTCGTACCTTCCACTTCTGCTGTTGGTAAAATGGTGGATCTTCTATCAATTTCATTGAC
AGTACCCACTTCTCCCAAACATCCAGGGAAATAGTGATTTCAGAGCGATTAGGAGAACCAAATTATGGGGCAGAAA
TAAGGGGCTTTTCCACAGGTTTTCCTTTGGAGGAAGATTTCAGTGGTGACTTTAAAAGAATACTCAACAGTGTCTT
CATCCCCATAGCAAAAGAAGAAACNGTAAATGATGGAANGCTTCTGGAGATGCCNNCATTTAAGGGACNCCCAGAA
CTTCACCATCTACAGGACCTACTTCAGTTTACANNAAGNCACATANTCTGACTCANAAAGGACCCAAGTAGCNCCA
TGGNCAGCACTTTNAGCCTTTCCCCTGGGGAAAANNTTACNTTCTTAAANCCTNGGCCNNGACCCCCTTAAGNCCA
AATTNTGGAAAANTTCCNTNCNNCTGGGGGGCNGTTCNACATGCNTTTNAAGGGCCCAATTNCCCCNT

25_16481.edit

TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGTACACCTGTGGTTCTCGGGGCTGCCCTTTGGCTTTGGAGATGGTTTTCT
CGATGGGGGCTGGGAGGGCTTTGTTGGAGACCTTGCACTTGTACTCCTTGCCATTCAGCCAGTCCTGGTGCAGGAC
GGTGAGGACGCTGACCACACGGTACGTGCTGTTGTACTGCTCCTCCCGCGGCTTTGTCTTGGCATTATGCACCTCC
ACGCCGTCCACGTACCAGTTGAACTTGACCTCAGGGTCTTCGTGGCTCACGTCCACCACCACGCATGTAACCTCAG
ACCTCGGCCGCGACCACGCT

26_16481.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GTGTGGTCAGCGTCCTCACCGTCCTGCACCAGGACTGGCTGAATGGCAAGGAGTACAAGTGCAAGGTCTCCAACAA
AGCCCTCCCAGCCCCCATCGAGAAAACCATCTCCAAAGCCAAAGGGCAAGCCCCGAGAACCACAGGTGTACACCCT
GCCCCCATCCCGGGAGGAGATGACCAAGAACCAGGTCAGCCTGACCTGCCTGGTCAAAGGCTTCTATCCCAGCGAC
ATCGCCGTGGAGTGGGAGAGCAATGGGCAGCCGGAGAACAACTACAAGACCACGCCTCCCGTGCTGGACTCCGACA
CCTGCCCGGGCGGCCGCTCGA

27_16482.edit

TCGAGCGGCCGCCCGGGCAGGTTGAATGGCTCCTCGCTGACCACCCCGGTGCTGGTGGTGGGTACAGAGCTCCGAT
GGGTGAAACCATTGACATAGAGACTGTCCCTGTCCAGGGTGTAGGGGCCCAGCTCAGTGATGCCGTGGGTCAGCTG
GCTCAGCTTCCAGTACAGCCGCTCTCTGTCCAGTCCAGGGCTTTTGGGGTCAGGACGATGGGTGCAGACAGCATCC
ACTCTGGTGGCTGCCCCATCCTTCTCAGGCCTGAGCAAGGTCAGTCTGCAACCAGAGTACAGAGAGCTGACACTGG
TGTTCTTGAACAAGGGCATAAGCAGACCCTGAAGGACACCTCGGCCGCGACCACGCT

*Fig. 15J-1*

28_16482.edit

AGCGTGGTCGCGGCCGAGGTGTCCTTCAGGGTCTGCTTATGCCCTTGTTCAAGAACACCAGTGTCAGCTCTCTGTA
CTCTGGTTGCAGACTGACCTTGCTCAGGCCTGAGAAGGATGGGGCAGCCACCAGAGTGGATGCTGTCTGCACCCAT
CGTCCTGACCCCAAAAGCCCTGGACTGGACAGAGAGCGGCTGTACTGGAAGCTGAGCCAGCTGACCCACGGCATCA
CTGAGCTGGGCCCCTACACCCTGGACAGGGACAGTCTCTATGTCAATGGTTTCACCCATCGGAGCTCTGTACCCAC
CACCAGCACCGGGGTGGTCAGCGAGGAGCCATTCAACCTGCCCGGGCGGCCGCTCGA

29_16483.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTCCCGGTTCCAGGCCAGTAATA
GTAGCCTCTGTGACACCAGGGCGGGGCCGAGGGACCCTTCTNTTGGAAGAGACCAGCTTCTCATACTTGATGATGA
GNCCGGTAATCCTGGCACGTGGNGGTTGCATGATNCCACCAAGGAAATNGGNGGGGGNGGACCTGCCCGGCGGCCG
TTCNAAAGCCCAATTCCACACACTTGGNGGCCGTACTATGGATCCCACTCNGTCCAACTTGGNGGAATATGGCATA
ACTTTT

31_16484.edit

TCGAGCGGCCGCCCGGGCAGGTCCTTGACCTTTTCAGCAAGTGGGAAGGTGTAATCCGTCTCCACAGACAAGGCCA
GGACTCGTTTGTACCCGTTGATGATAGAATGGGGTACTGATGCAACAGTTGGGTAGCCAATCTGCAGACAGACACT
GGCAACATTGCGGACACCCTCCAGGAAGCGAGAATGCAGAGTTTCCTCTGTGATATCAAGCACTTCAGGGTTGTAG
ATGCTGCCATTGTCGAACACCTGCTGGATGACCAGCCCAAAGGAGAAGGGGGAGATGTTGAGCATGTTCAGCAGCG
TGGCTTCGCTGGCTCCCACTTTGTCTCCAGTCTTGATCAGACCTCGGCCGCGACCACGCT

37_16487.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCG

*Fig. 15K-1*

38_16487.edit

CGAGCGGCCGCCCGGGCAGGTTTGGAAGGGGGATGCGGGGGAAGAGGAAGACTGACGGTCCCCCCAGGAGTTCAGG
TGCTGGGCACGGTGGGCATGTGTGAGTTTTGTCACAAGATTTGGGCTCAACTCTCTTGTCCACCTTGGTGTTGCTG
GGCTTGTGATCTACGTTGCAGGTGTAGGTCTGGGTGCCGAAGTTGCTGGAGGGCACGGTCACCACGCTGCTGAGGG
AGTAGAGTCCTGAGGACTGTAGGACAGACCTCGGCCGCGACCACGCT

39_16488.edit

NGGNNGGTCCGGNCNGNCAGGACCACTCNTCTTCGAAATA

41_16489.edit

AGCGTGGTCGCGGCCGAGGTCCTCACTTGCCTCCTGCAAAGCACCGATAGCTGCGCTCTGGAAGCGCAGATCTGTT
TTAAAGTCCTGAGCAATTTCTCGCACCAGACGCTGGAAGGGAAGTTTGCGAATCAGAAGTTCAGTGGACTTCTGAT
AACGTCTAATTTCACGGAGCGCCACAGTACCAGGACCTGCCCGGGCGGCCGCTCGA

42_16489.edit

TCGAGCGGCCGCCCGGGCAGGTCCTGGTACTGNGGCGCTCCGTGAAATTAGACGTTATCAGAAGTCCACTGAACTT
CTGATTCGCAAACTTCCCTTCCAGCGTCTGGTGCGAGAAATTGCTCAGGACTTTAAAACAGATCTGCGCTTCCAGA
GCGCAGCTATCGGTGCTTTGCAGGAGGCAAGTGAGGACCTCGGCCGCGACCACGCT

45_16491.edit

TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT

*Fig. 15L-1*

46_16491.edit

GTGGGNTTGAACCCNTTTNANCTCCGCTTGGTACCGAGCTCGGATCCACTAGTAACGGCCGCCAGTGTGCTGGAAT
TCGGCTTAGCGTGGTCGCGGCCGAGGTCAAGAACCCCGCCCGCACCTGCCGTGACCTCAAGATGTGCCACTCTGAC
TGGAAGAGTGGAGAGTACTGGATTGACCCCAACCAAGGCTGCAACCTGGATGCCATCAAAGTCTTCTGCAACATGG
AGACTGGTGAGACCTGCGTGTACCCCACTCAGCCCAGTGTGGCCCAGAAGAACTGGTACATCAGCAAGAACCCCAA
GGACAAGAGGCATGTCTGGTTCGGCGAGAGCATGACCGATGGATTCCAGTTCGAGTATGGCGGCCAGGGCTCCGAC
CCTGCCGATGTGGACCTGCCCGGGCGGCCGCTCGA

47_16492.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAAGTGT
CTATGCTCAGAATCCAAGCGGAGAGAAGTCAGCCTCTGGTTCAGACTGNAAGTAACCAACATTGATCGCCTAAAGG
ACTGGCATTCACTGATGNGGATGCCGATTCCATCAAAATTGNTTGGGAAAACCCACAGGGGCAAGTTTNCANGTCN
AGGNGGACCTACTCGAGCCCTGAGGATGGAATCCTTGACTNTTCCTTNNCCTGATGGGGAAAAAAAACCTTNAAAA
CTTGAAGGACCTGCCCGGGCGGCCGTNCAAAACCCAATTCCACCCCCTTGGGGGCGTTCTATGGGNCCCACTCGGA
CCAAACTTGGGGTAAN

48_16492.edit

TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGGCATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAGTTTTTGTTGGTCCTGGTCCATTTTTGGGAGTGGTGGTTACTCTGT
AACCAGTAACAGGGGAACTTGAAGGCAGCCACTTGACACTAATGCTGTTGTCCTGAACATCGGTCACTTGCATCTG
GGATGGTTTGTCAATTTCTGTTCGGTAATTAATGGAAATTGGCTTGCTGCTTGCGGGGCTTGTCTCCACGGCCAGT
GACAGCATACACAGTGATGGTATAATCAACTCCAGGTTTAAGCCGCTGATGGTAGCTGAAACTTTGCTCCAGGCAC
AAGTGAACTCCTGACAGGGCTATTTCCTNCTGTTCTCCGTAAGTGATCCTGTAATATCTCACTGGGACAGCAGGAN
GCATTCCAAAACTTCGGGCGNGACCCCCTAAGCCGAATTNTGCAATATNCATCACACTGGCGGGCGCTCGANCATT
CATTAAAAGGCCCAATCNCCCCTATAGGGAGTNTANTACAATTNG

*Fig. 15M-1*

49_16493.edit

TCGAGCGGCCGCCCGGGCAGGTCACTTTTGGTTTTTGGTCATGTTCGGTTGGTCAAAGATAAAAACTAAGTTTGAG
AGATGAATGCAAAGGAAAAAAATATTTTCCAAAGTCCATGTGAAATTGTCTCCCATTTTTTTGGCTTTTGAGGGGG
TTCAGTTTGGGTTGCTTGTCTGTTTCCGGGTTGGGGGGAAAGTTGGTTGGGTGGGAGGGAGCCAGGTTGGGATGGA
GGGAGTTTACAGGAAGCAGACAGGGCCAACGTCG

55_16496.edit

AGCGTGGTCGCGGCCGAGGTCCTCACCAGAGGTGCCACCTACAACATCATAGTGGAGGCACTGAAAGACCAGCAGA
GGCATAAGGTTCGGGAAGAGGTTGTTACCGTGGGCAACTCTGTCAACGAAGGCTTGAACCAACCTACGGATGACTC
GTGCTTTGACCCCTACACAGTTTCCCATTATGCCGTTGGAGATGAGTGGGAACGAATGTCTGAATCAGGCTTTAAA
CTGTTGTGCCAGTGCTTAGGCTTTGGAAGTGGTCATTTCAGATGTGATTCATCTAGATGGTGCCATGACAATGGTG
TGAACTACAAGATTGGAGAGAAGTGGGACCGTCAGGGAGAAAATGGACCTGCCCGGGCGGCCGCTCGA

56_16496.edit

TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGCCCACGGTAACAACCTCTTCCCGAACCTTATGCCTCTGCTGG
TCTTTCAGTGCCTCCACTATGATGTTGTAGGTGGCACCTCTGGTGAGGACCTCGGCCGCGACCACGCT

59_16498.edit

TCGAGCGGCCGCCCGGGCAGGTCCACCATAAGTCCTGATACAACCACGGATGAGCTGTCAGGAGCAAGGTTGATTT
CTTTCATTGGTCCGGTCTTCTCCTTGGGGGTCACCCGCACTCGATATCCAGTGAGCTGAACATTGGGTGGTGTCCA
CTGGGCGCTCAGGCTTGTGGGTGTGACCTGAGTGAACTTCAGGTCAGTTGGTGCAGGAATAGTGGTTACTGCAGTC
TGAACCAGAGGCTGACTCTCTCCGCTTGGATTCTGAGCATAGACACTAACCACATACTCCACTGTGGGCTGCAAGC
CTTCAATAGTCATTTCTGTTTGATCTGGACCTGCAGTTTTAGTTTTTGTTGGTCCTGGTCCATTTTTGGGAGTGGT
GGTTACTCTGTAACCAGTAACAGGGGAACTTGAAGGCAGCCACTTGACACTAATGCTGTTGTCCTGAACATCGGTC
ACTTGCATCTGGGATGGTTTGNCAATTTCTGTTCGGTAATTAATGGAAATTGGCTTGCTGCTTGCGGGGCTGTCTC
CACGGCCAGTGACAGCATACACAGNGATGGNATNATCAACTCCAAGTTTAAGGCCCTGATGGTAACTTTAAACTTG
CTCCCAGCCAGNGAACTTCCGGACAGGGTATTTCTTCTGGTTTTCCGAAAGNGANCCTGGAATNNTCTCCTTGGAN
CAGAAGGANCNTCCAAAACTTGGGCCGGAACCCCTT

*Fig. 15N-1*

60_16473.edit

AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTACATTCGGCGGGTATGGTCTTGGCCTATGCCTTATGGGGGTGGCCGTTGTGGGCGGTG
TGGTCCGCCTAAAACCATGTTCCTCAAAGATCATTTGTTGCCCAACACTGGGTTGCTGACCAGAAGTGCCAGGAAG
CTGAATACCATTTCCAGTGTCATACCCAGGGTGGGTGACGAAAGGGGTCTTTTGAACTGTGGAAGGAACATCCAAG
ATCTCTGGTCCATGAAGATTGGGGTGTGGAAGGGTTACCAGTTGGGGAAGCTCGTCTGTCTTTTTCCTTCCAATCA
GGGGCTCGCTCTTCTGATTATTCTTCAGGGCAATGACATAAATTGTATATTCGGTTCCCGGTTCCAGGCCAGTAAT
AGTAGCCTCTTGTGACACCAGGCGGGGCCCANGGACCACTTCTCTGGGANGAGACCCAGCTTCTCATACTTGATGA
TGTAACCCGGTAATCCTGCACGTGGCGGCTGNCATGATACCANCAAGGAATTGGGTGNGGNGGACCTGCCCGGCGG
CCCTCNA

60_16498.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGACCAGGACCAACAAAAAC
TAAAACTGCAGGTCCAGATCAAACAGAAATGACTATTGAAGGCTTGCAGCCCACAGTGGAGTATGTGGTTAGTGTC
TATGCTCAGAATCCAAGCGGAGAGAGTCAGCCTCTGGTTCAGACTGCAGTAACCACTATTCCTGCACCAACTGACC
TGAAGTTCACTCAGGTCACACCCACAAGCCTGAGCCGCCAGTGGACACCACCCAATGTTCACTCACTGGATATCGA
GTGCGGGTGACCCCCAAGGAGAAGACCCGGACCCATGAAAGAAATCAACCTTGCTCCTGACAGCTCATCCGNGGGT
GTATCAGGACTTATGGGGGACTGCCCCGGCNGGCCGNTCGAAANCGAATTNTGAAATTTCCTTCNCACTGGGNGGC
GNTTCGAGCTTNCTTNTANANGGCCCAATTCNCCTNTAGNGGGTCGTN

61_16499.edit

AGCGTGGTCGCGGCCGAGGTCNAGG

62_16483.edit

TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGTCACCCACCCTGGGTATGACACTGGAAA
TGGTATTCAGCTTCCTGGCACTTCTGGTCAGCAACCCAGTGTTGGGCAACAAATGATCTTTGAGGAACATGGTTTT
AGGCGGACCACACCGCCCACAACGGGCACCCCCATAAGGNATAGGCCAAGACCATACCCCGCCGAATGTAGGACAA
GAAGCTCTNTCTCAACAACCATCTCATGGGCCCCATTCCAGGACACTTCTGAGTACATCATTTCATGTCATCCTGG
TGGGCACTTGATGAANAACCCTTACAGTTCAGGGTTCCTGGAACTTCTACCAGNGCCACTTCTGACAGGANCTTGG
GCGNGACCACCCT

*Fig. 15O-1*

63_16500.edit

AGCGTGGTCGCGGCCGAGGTCCATTTTCTCCCTGACGGTCCCACTTCTCTCCAATCTTGTAGTTCACACCATTGTC
ATGGCACCATCTAGATGAATCACATCTGAAATGACCACTTCCAAAGCCTAAGCACTGGCACAACAGTTTAAAGCCT
GATTCAGACATTCGTTCCCACTCATCTCCAACGGCATAATGGGAAACTGTGTAGGGGTCAAAGCACGAGTCATCCG
TAGGTTGGTTCAAGCCTTCGTTGACAGAGTTGCCCACGGTAACAACCTCTTCCCGAACCTTATGCCTCTGCTGGTC
TTTCAGTGCCTCCACTATGATGTTGTAGGTGGCACCTCTGGTGAGGACCTGCCCGGGCGGCCCGCTCGA

64_16493.edit

AGCGTGGTCGCGGCCGAGGTGTGCCCCAGACCAGGAATTCGGCTTCGACGTTGGCCCTGTCTGCTTCCTGTAAACT
CCCTCCATCCCAACCTGGCTCCCTCCCACCCAACCAACTTTCCCCCCAACCCGGAAACAGACAAGCAACCCAAACT
GAACCCCCTCAAAAGCCAAAAAAATGGGAGACAATTTCACATGGACTTTGGAAAATATTTTTTTCCTTTGCATTCA
TCTCTCAAACTTAGTTTTTATCTTTGACCAACCGAACATGACCAAAAACCAAAAGTGACCTGCCCGGGCGGCCGCT
CGA

64_16500.edit

TCGAGCGGCCGCCCGGGCAGGTCCTCACCAGAGGTGCCACCTACAACATCATAGTGGAGGCACTGAAAGACCAGCA
GAGGCATAAGGTTCGGGAAGAGGTTGTTACCGTGGGCAACTCTGTCAACGAAGGCTTGAACCAACCTACGGATGAC
TCGTGCTTTGACCCCTACACAGTTTCCCATTATGCCGTTGGAGATGAGTGGGAACGAATGTCTGAATCAGGCTTTA
AACTGTTGTGCCAGTGCTTAGGCTTTGGAAGTGGTCATTTCAGATGTGATTCATCTAGATGGTGCCATGACAATGG
TGTGAACTACAAGATTGGAGAGAAGTGGGACCGTCAGGGAGAAAATGGACCTCGGCCGCGACCACGCT

*Fig. 15P-1*

16501.edit

TCGAGCGGCCGCCCGGGCAGGTACCGGGGTGGTCAGCGAGGAGCCATTCACACTGAACTTCACCATCAACAACCTG
CGGTATGAGGAGAACATGCAGCACCCTGGCTCCAGGAAGTTCAACACCACGGAGAGGGTCCTTCAGGGCCTGCTCA
GGTCCCTGTTCAAGAGCACCAGTGTTGGCCCTCTGTACTCTGGCTGCAGACTGACTTTGCTCAGACCTGAGAAACA
TGGGGCAGCCACTGGAGTGGACGCCATCTGCACCCTCCGCCTTGATCCCACTGGTNCTGGACTGGACANANAGCGG
CTATACTTGGGAGCTGANCCNAACCTTTGGCGGNGACNCCNCTT 16501.2.edit GAGGACTGGCTCAGCTCCCAGTATAGCCGCTCTCTGTCCAGTCCAGGACCAGTGGGATCAAGGCGGAGGGTGCAGA
TGGCGTCCACTCCAGTGGCTGCCCCATGTTTCTCAAGTCTGAGCAAAGNCAGTCTGCAGCCAGAGTACAGAGGGCC
AACACTGGTGCTCTTGAACAGGGACCTGAGCAGGCCCTGAAGGACCCTCTCCGTGGTGTTGAACTTCCTGGAGCCA
GGGTGCTGCATGTTCTCCTCATACCGCAGGTTGTTGATGGTGAAGTTCAGTGTGAATGGCTCCTCGCTGACCACCC 16502.1.edit AGCGTGGTCGCGGCCGAGGTCCACCACACCCAATTCCTTGCTGGTATCATGGCAGCCGCCACGTGCCAGGATTACC
GGCTACATCATCAAGTATGAGAAGCCTGGGTCTCCTCCCAGAGAAGTGGTCCCTCGGCCCCGCCCTGGTGTCACAG
AGGCTACTATTACTGGCCTGGAACCGGGAACCGAATATACAATTTATGTCATTGCCCTGAAGAATAATCAGAAGAG
CGAGCCCCTGATTGGAAGGAAAAAGACAGACGAGCTTCCCCAACTGGTAACCCTTCCACACCCCAATCTTCATGGA
CCANANANCTTGGATNGTCCTTTCACNGGTTNAAAAAACCCTTTTCGCCCCCCCACCTTGGGGATTAACCTTGGGA
AANGGGGATTTNACCNTTCC 16502.2.edit TCGAGCGGCCGCCCGGGCAGGTCCTGTCAGAGTGGCACTGGTAGAAGTTCCAGGAACCCTGAACTGTAAGGGTTCT
TCATCAGTGCCAACAGGATGACATGAAATGATGTACTCAGAAGTGTCCTGGAATGGGGCCCATGAGATGGTTGTCT
GAGAGAGAGCTTCTTGTCCTACATTCGGCGGGTATGGTCTTGGCCTATGCCTTATGGGGGTGGCCGTTGTGGGCGG
TGTGGTCCGCCTAAAACCATGTTCCTCAAAGATCATTTGTTGCCCAACACTGGGTTGCTGACCAGAAGTGCCAGGA
AGCTGAATACCATTTCCAGTGTCATACCCAGGGNGGGTGACCAAAGGGGGTCNTTTNGACCTGGNGAAAGGAACCA
TCCAAAANCTCTGNCCCATG

*Fig. 15Q-1*

16503.1.edit

AGCGTGGNCGCGGCCGAGGTCTGAGGATGTAAACTCTTCCCAGGGGAAGGCTGAAGTGCTGACCATGGTGCTACTG
GGTCCTTCTGAGTCAGATATGTGACTGATGNGAACTGAAGTAGGTACTGTAGATGGTGAAGTCTGGGTGTCCCTAA
ATGCTGCATCTCCAGAGCCTTCCATCATTACCGTTTCTTCTTTTGCTATGGGATGAGACACTGTTGAGTATTCTCT
AAAGTCACCACTGAAATCTTCCTCCAAAGGAAAACCTGTGGAAAAGCCCCTTATTTCTGCCCCATAATTTGGTTCT
CCTAATCNCTCTGAAATCACTATTTCCCTGGAANGTTTGGGAAAAANNGGGCNACCTGNCANTGGAAANTGGATAN
AAAGATCCCACCATTTTACCCAACNAGCAGAAAGTGGGAANGGTACCGAAAAGCTCCAAGTAANAAAAAGGAGGGA
AGTAAAGGTCAAGTGGGCACCAGTTTCAAACAAAACTTTCCCCAAACTATANAACCCA 16503.2.edit AAGCGGCCGCCCGGGCAGGNNCAGNAGTGCCTTCGGGACTGGGNTCACCCCCAGGTCTGCGGCAGTTGTCACAGCG
CCAGCCCCGCTGGCCTCCAAAGCATGTGCAGGAGCAAATGGCACCGAGATATTCCTTCTGCCACTGTTCTCCTACG
TGGTATGTCTTCCCATCATCGTAACACGTTGCCTCATGAGGGTCACACTTGAATTCTCCTTTTCCGTTCCCAAGAC
ATGTGCAGCTCATTTGGCTGGCTCTATAGTTTGGGGAAAGTTTGTTGAAACTGTGCCACTGACCTTTACTTCCTCC
TTCTCTACTGGAGCTTTCCGTACCTTCCACTTCTGCTGNTGGNAAAAAGGGNGGAACNTCTTATCAATTTCATTGG
ACAGTANCCCNCTTTCTNCCCAAAACATNCAAGGGAAAATATTGATTNCNAGAGCGGATTAAGGAACAACCCNAAT
TATGGGGGCCAGAAATAAAGGGGGCTTTTCCACAGGTNTTTTCCT 16504.1.edit TCGAGCGGCCGCCCGGGCAGGTCTGCAGGCTATTGTAAGTGTTCTGAGCACATATGAGATAACCTGGGCCAAGCTA
TGATGTTCGATACGTTAGGTGTATTAAATGCACTTTTGACTGCCATCTCAGTGGATGACAGCCTTCTCACTGACAG
CAGAGATCTTCCTCACTGTGCCAGTGGGCAGGAGAAAGAGCATGCTGCGACTGGACCTCGGCCGCGACCACGCT 16504.2.edit AGCGTGGTCGCGGCCGAGGTCCAGTCGCAGCATGCTCTTTCTCCTGCCCACTGGCACAGTGAGGAAGATCTCTGCT
GTCAGTGAGAAGGCTGTCATCCACTGAGATGGCAGTCAAAAGTGCATTTAATACACCTAACGTATCGAACATCATA
GCTTGGCCCAGGTTATCTCATATGTGCTCAGAACACTTACAATAGCCTGCAGACCTGCCCGGGCGGCCGCTCGA

*Fig. 15R-1*

16505.1.edit

CGAGCGGCCGCCCGGGCAGGTCCAGACTCCAATCCAGAGAACCACCAAGCCAGATGTCAGAAGCTACACCATCACA
GGTTTACAACCAGGCACTGACTACAAGATCTACCTGTACACCTTGAATGACAATGCTCGGAGCTCCCCTGTGGTCA
TCGACGCCTCCACTGCCATTGATGCACCATCCAACCTGCGTTTCCTGGCCACCACACCCAATTCCTTGCTGGTATC
ATGGCAGCCGCCACGTGCCAGGATTACCGGCTACATCATCAAGTATGAGAAGCCTGGGTCTCCTCCCAGAGAAGTG
GTCCCTCGGCCCCGCCCTGGTGNCACAGAAGCTACTATTACTGGCCTGGAACCGGGAACCGAATATACAATTTATG
TCATTGCCCTGAAGAATAATCANAAGAGCGAGCCCCTGATTGGAAGG 16505.2.edit AGCGTGGTCGCGGCCGAGGTCCTGTCAGAGTGGCACTGGTAGAAGTTCCAGGAACCCTGAACTGTAAGGGTTCTTC
ATCAGTGCCAACAGGATGACATGAAATGATGTACTCAGAAGTGTCCTGGAATGGGGCCCATGAGATGGTTGTCTGA
GAGAGAGCTTCTTGTCCTGTCTTTTTCCTTCCAATCAGGGGCTCGCTCTTCTGATTATTCTTCAGGGCAATGACAT
AAATTGTATATTCGGTTCCCGGTTCCAGGCCAGTAATAGTAGCCTCTGTGACACCAGGGCGGGGCCGAGGGACCAC
TTCTCTGGGAGGAGACCCAGGCTTCTCATACTTGATGATGTANCCGGTAATCCTGGCACCGTGGCGGCTGCCATGA
TACCAGCAAGGAATTGGGTGTGGTGGCCAAGAAACGCAGGTTGGATGGTGCATCAATGGCAGTGGAGGCGTCGATN
ACCACAGGGGAGCTCCGANCATTGTCATTCAAGGTGGACAGGTAGAATCTTGTAATCAGGTGCCTGGTTTGTAAAC
CTG 16506.1.edit TCGAGCGGCCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGCCCAGAAGAACTGGTACATCAGCAAGAACC
CCAAGGACAAGAAGCATGTCTGGTTCGGCGAAAGCATGACCGATGGATTCCAGTTCGAGTATGGCGGCCAGGGCTC
CGACCCTGCCGATGTGGACCTCGGCCGCGACCACGCTAAGCCCGAATTCCAGCACACTGGCGGCCGTTACTAGTGG
GATCCGAGCTTCGGTACCAAGCTTGGCGTAATCATGGGNCATAGCTGTTTCCTGNGTGAAAATGGTATTCCGCTTC
ACAATTTCCCAC 16506.2.edit AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAGTGGCACATCTTGAGGTCACGGCAGGTGCGGGCGGGG
TTCTTGCGGCTGCCCTCTGGGCTCCGGATGTTCTCGATCTGCTGGCTCAAGCTCTTGAAGGGTGGTGTCCACCTCG
AGGTCACGGTCACGAAACCTGCCCGGGCGGCCGCTCGA

*Fig. 15S 1*

16507.1.edit

AGCGTGGTCGCGGCCGAGGTCAAGAACCCCGCCCGCACCTGCCGTGACCTCAAGATGTGCCACTCTGACTGGAAGA
GTGGAGAGTACTGGATTGACCCCAACCAAGGCTGCAACCTGGATGCCATCAAAGTCTTCTGCAACATGGAGACTGG
TGAGACCTGCGTGTACCCCACTCAGCCCAGTGTGGCCCAGAAGAACTGGTACATCAGCAAGAACCCCAAGGACAAG
AGGCATGTCTGGTTCGGCGAGAGCATGACCGATGGATTCCAGTTCGAGTATGGCGGCCAGGGCTCCGACCCTGCCG
ATGTGGACCTGCCCGNGCCGGNCCGCTCGAAAAGCCCNAATTTCCAGNCACACTTGGCCGGCCGTTACTACTG 16507.2.edit TCGAGCGGCCGCCCGGGCAGGTCCACATCGGCAGGGTCGGAGCCCTGGCCGCCATACTCGAACTGGAATCCATCGG
TCATGCTCTCGCCGAACCAGACATGCCTCTTGTCCTTGGGGTTCTTGCTGATGTACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCTCGGCCGCGACCACGCT 16508.1.edit CGAGCGGCCGCCCGGGCAGGTCCCCCCCCTTTTTTTTTTTTTTTTTTTTTTTTTTTTTTTTTTTTTTTTTTTTTTT
TTTTTTTTTTTTTTTTTT 16508.2.edit AGCGTGGTCGCGGCCGAGGTCTGGCATTCCTTCGACTTCTCTCCAGCCGAGCTTCCCAGAACATCACATATCACTG
CAAAAATAGCATTGCATACATGGATCAGGCCAGTGGAAATGTAAAGAAGGCCCTGAAGCTGATGGGGTCAAATGAA
GGTGAATTCAAGGCTGAAGGAAATAGCAAATTCACCTACACAGTTCTGGAGGATGGTTGCACGAAACACACTGGGG
AATGGAGCAAAACAGTCTTTGAATATCGAACACGCAAGGCTGTGAGACTACCTATTGTAGATATTGCACCCTATGA
CATTGGTGGTCCTGATCAAGAATTTGGTGTGGACGTTGGCCCTGTTTGCTTTTTATAAACCAAACTCTATCTGAAA
TCCCAACAAAAAAAATTTAACTCCATATGTGNTCCTCTTGTTCTAATCTTGGCAACCAGTGCAAGTGACCGACAAA
ATTCCAGTTATTTATTTCCAAAATGTTTGGAAACAGTATAATTTGACAAAGAAAAAAGGATACTTCTCTTTTTTTG
GCTGGTCCACCAAATACAATTCAAAAGGCTTTTTGGTTTTATTTTTTTANCCAATTCCAATTTCAAAATGTCTCAA
TGGNGCTTATAATAAAATAAACTTTCACCCTTNTTTTNTGAT

*Fig. 15T-1*

16509.1.edit

AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAAGTAACCACCACTCCCAAAAATGGACCAGGACCAACAAAAA
CTAAAACTGCAGGTCCAGATCAAACAGAAAATGGACTATTGAAGGCTTGCAGCCCACAGTGGAAGTATGTGGNTAG
GNGTCTATGCTCAGAATCCCAAGCCGGAGAAAGTCAGCCTTCTGGTTTAGACTGCAGTAACCAACATTGATCGCCC
TAAAGGACTGGNCATTCACTTGGATGGTGGATGTCCAATTC 16509.2.edit TCGAGCGGCCGCCCGGGCAGGTCCTTGCAGCTCTGCAGNGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGNGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGGTGGTCCTGNCCCATTTTTGGGAAGTGGGGGGTTACTC
TGTAACCAGTAACAGGGGAACTTGAAGGCAGCCACTTGACACTAATGCTGTTGTCCTGAACATCGGTCACTTGCAT
CTGGGGATGGTTTTGACAATTTCTGGTTCGGCAAATTAATGGAAATTGGCTTGCTGCTTGGCGGGGCTGNCTCCAC
GGGCCAGTGACAGCATAC 16510.1.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGTCTGAACCAGAGG
CTGACTCTCTCCGCTTGGATTCTGAGCATAGACACTAACCACATACTCCACTGTGGGCTGCAAGCCTTCAATAGTC
ATTTCTGTTTGATCTGGACCTGCAGTTTTAAGTTTTTGTTGGNCCTGNNCCATTTTTGGGGAAGGGGTGGTTACTC
TTGTAACCAGTAACAGGGGAACTTGAAGCAGCCACTTGACACTAATGCTGGTGGCCTGAACATCGGTCACTTGCAT
CTGGGATGGTTTGGTCAATTTCTGTTCGGTAATTAATGGGAAATTGGCTTACTGGCTTGCGGGGGCTGTCTCCACG
GNCAGTGACAAGCATACACAGGNGATGGGTATAATCAACTCCAGGTTTAAGGCCNCTGATGGTA 16510.2.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGTAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGTTCCCCTGTTACTGGTTACAGAGTAACCACCACTCCCAAAAATGGGACCAGGACCAACAAAAA
ACTAAAACTGCANGGTCCAGATCAAACAGAAATGACTATTGAAGGCTTGCAGCCCACAGTGGAGTATGTGGGTTAG
TGTCTATGCTCAGAATNCCAAGCGGAGAGAGTCAGCCTCTGGTTCAGACT

*Fig. 15U-1*

16511.1.edit

```
TCGAGCGGCCGCCCGGGCAGGTCAGCGCTCTCAGGACGTCACCACCATGGCCTGGGCTCTGCTCCTCCTCACCCTC
CTCACTCAGGGCACAGGGTCCTGGGCCCAGTCTGCCCTGACTCAGCCTCCCTCCGCGTCCGGGTCTCCTGGACAGT
CAGTCACCATCTCCTGCACTGGAACCAGCAGTGACGTTGGTGCTTATGAATTTGTCTCCTGGTACCAACAACACCC
AGGCAAGGCCCCCAAACTCATGATTTCTGAGGTCACTAAGCGGCCCTCAGGGGTCCCTGATCGCTTCTCTGGCTCC
AAGTCTGGCAACACGGCCTCCCTGACCGTCTCTGGGCTCCANGCTGAGGATGANGCTGATTATTACTGGAAGCTCA
TATGCAGGCAACAACAATTGGGTGTTCGGCGGAAGGGACCAAGCTGACCGTNCTAAGGTCAAGCCCAAGGCTTGCC
CCCCTCGGTCACTCTGTTCCCACCCTCCTCTGAAGAAGCTTTCAAGCCAACAANGNCACACTGGGTGTGTCTCATA
AGTGGACTTTCTACCC
```

16511.2.edit

```
AGCGTGGTCGCGGCCGAGGTCTGTAGCTTCTGTGGGACTTCCACTGCTCAGGCGTCAGGCTCAGGTAGCTGCTGGC
CGCGTACTTGTTGTTGCTTTGNTTGGAGGGTGTGGTGGTCTCCACTCCCGCCTTGACGGGGCTGCTATCTGCCTTC
CAGGCCACTGTCACGGCTCCCGGGTAGAAGTCACTTATGAGACACACCAGTGTGGCCTTGTTGGCTTGAAGCTCCT
CAGAGGAGGGTGGGAACAGAGTGACCGAGGGGGCAGCCTTGGGCTGACCTAGGACGGTCAGCTTGGTCCCTCCGCC
GAACACCCAATTGTTGTTGCCTGCATATGAGCTGCAGTAATAATCAGCCTCATCCTCAGCCTGGAGCCCAGAGACN
GTCAAGGGAGGCCCGTGTTTGCCAAGACTTGGAAGCCAGANAAGCGATCAGGGACCCCTGAGGGCCGCTTTACNGA
CCTCAAAAAATCATGAATTTGGGGGGCCTTTGCCTGGGNGTTGGTTGGTNACCAGNAAAACAAAATTTCATAAAGC
ACCAACGTCACTGCTGGTTTCCAGTGCANGAANATGGTGAACTGAANTGTCC
```

16512.1.edit

```
AGCGTGGTCGCGGCCGAGGTCCAGCATCAGGAGCCCCGCCTTGCCGGCTCTGGTCATCGCCTTTCTTTTTGTGGCC
TGAAACGATGTCATCAATTCGCAGTAGCAGAACTGCCGTCTCCACTGCTGTCTTATAAGTCTGCAGCTTCACAGCC
AATGGCTCCCATATGCCCAGTTCCTTCATGTCCACCAAAGTACCCGTCTCACCATTTACACCCCAGGTCTCACAGT
TCTCCTGGGTGTGCTTGGCCCGAAGGGAGGTAAGTANACGGATGGTGCTGGTCCCACAGTTCTGGATCAGGGTACG
AGGAATGACCTCTAGGGCCTGGGCNACAAGCCCTGTATGGACCTGCCCGGGCGGGCCCGCTCGA
```

16512.2.edit

```
TCGAGCGGCCGCCCGGGCAGGTCCATACAGGGCTGTTGCCCAGGCCCTAGAGGNCATTCCTTGTACCCTGATCCAG
AACTGTGGGACCAGCACCATCCGTCTACTTACCTCCCTTCGGGCCAAGCACACCCAGGAGAACTGTGAGACCTGGG
GTGTAAATGGNGAGACGGGTACTTTGGTGGACATGAAGGAACTGGGCATATGGGAGCCATTGGCTGNGAAGCTGCA
NACTTATAAGACAGCAGTGGAGACGGCAGTTCTGCTACTGCGAATTGATGACATCGTTTCAGGCCACAAAAAGAAA
GGCGATGACCANAGCCGGCAAGGCGGGGCTTCCTGATGCTGGACCTCGGCCGCCGACCACGCTT
```

*Fig. 15V-1*

16514.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTGCTGTGCGCCACGTGTTGCTCANACAGGGTGTGCTGGGCATCAAGGTG
AAGATCATGCTGCCCTGGGACCCANCTGGCAAAAATGGCCCTTAAAAACCCCTTGCCNTGACCACGTGAACCATTT
GTGNGAACCCCAAGATGAANATACTTGCCCACCACCCCCCATTC 16514.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAGTGTCAACGTAGTAGTTAACAGGGTCTCCGCTGTGGATCATC
AGGCCATCCACAAACTTCATGGATTTAGCCCTCTGTCCTCGGAGTTTCCCAAAACACCACAACCTCGCCAGCCTTT
GGGCCCCACTTCTTCATGAATGAAACCGCAGCACACCATTANCAAGGCCCTTCCGCACAGGNAAGCCCTTCCTAAG
GAGTTTTGTAAACGCAAAAAACTCTTGCCTGGGGCAAATGGGCACACAGACCTNTANTNGGACCTTGGNCCGCGAA
CCACCGCTT 16515.1.edit AGCGTGGTCGCGGCCGAGGTCTGGCCCTCCTGGCAAGGCTGGTGAAGATGGTCACCCTGGAAAACCCGGACGACCT
GGTGAGAGAGGAGTTGTTGGACCACAGGGTGCTCGTGGTTTCCCTGGAACTCCTGGACTTCCTGGCTTCAAAGGCA
TTAGGGGACACAATGGTCTGGATGGATTGAAGGGACAGCCCGGTGCTCCTGGTGTGAAGGGTGAACCTGGNGCCCC
TGGTGAAAATGGAACTCCAGGTCAAACAGGAGCCCGNGGGCTTCCTGGNGAGAGAGGACGTGTTGGTGCCCCTGGC
CCANACCTGCCCGGGCGGCCGCTCNAAAAGCCGAAATCCAGNACACTGGCGGCCGNTACTANTGGAATCCGAACTT
CGGTACCAAAGCTTGGCCGTAATCATGGCCATAGCTTGTTCCCTGGGGNGGAAATTGGTATTCCGCTNCCAATTCC
ACACAACATACCGAACCCGGAAAGCATTAAAGTGTAAAAGCCCTGGGGGGGCCTAAATGANGTGAGCNTAACTCNC
ATTTAATTGGCGTTGCGCTTCACTGCCCCGCTTTTCCAGTCCGGGNA 16515.2.edit TCGAGCGGCCGCCCGGGCAGGTCTGGGCCAGGGGCACCAACACGTCCTCTCTCACCAGGAAGCCCACGGGCTCCTG
TTTGACCTGGAGTTCCATTTTCACCAGGGGCACCAGGTTCACCCTTCACACCAGGAGCACCGGGCTGTCCCTTCAA
TCCATCCAGACCATTGTGNCCCCTAATGCCTTTGAAGCCAGGAAGTCCAGGAGTTCCAGGGAAACCACGAGCACCC
TGTGGTCCAACAACTCCTCTCTCACCAGGTCGTCCGGGTTTTCCAGGGTGACCATCTTCACCAGCCTTGCCAGGAG
GGCCAGACCTCGGCCGCGACCACGCT

*Fig. 15W-1*

16516.1.edit

ANCGTGGTCGCGGCCGAGGTCCTCACCAGAGGTGNCACCTACAACATCATAGTGGAGGCACTGAAAGACCANCAGA
GGCATAAGGTTCGGGAAGAGG 16516.2.edit TCGAGCGGCCGCCCGGGCAGGTCCATTTTCTCCCTGACGGTCCCACTTCTCTCCAATCTTGTAGTTCACACCATTG
TCATGGCACCATCTAGATGAATCACATCTGAAATGACCACTTCCAAAGCCTAAGCACTGGCACAACAGTTTAAAGC
CTGATTCAGACATTCGTTCCCACTCATCTCCAACGGCATAATGGGAAACTGTGTAGGGGTCAAAGCACGAGTCATC
CGTAGGTTGGTTCAAGCCTTCGTTGACAGAGTTGTCCACGGTAACAACCTCTTCCCGAACCTTATGCCTCTGCTGG
TCTTTCAGTGCCTCCACTATGATGTTGTAGGTGGCACCTCTGGTGAGGACCTCNGNCCNGAACAACGCTTAAGCCC
GNATTCTGCAGAATAATCCCATCACACTTGGCGGCCGCTTCGANCATGCATCNTAAAAGGGGCCCCAATTTCCCCC
TTATAAGNGAANCCGTATTTNCCAATTTCACTGGNCCCGCCGNTTTTACAAACGNCGGTGAACTGGGGAAAAACCC
TGGCGGTTACCCAACTTTAATCGCCNTTGGCAGCACAATCCCCCCTTTTCGNCCANCNTGGGCGTAAATAACCGAA
AA 16517.1.edit

ANCGNGGTCGCGGCCGANGTNTTTTTTCTTNTTTTTTT 16518.1.edit

AGCGTGGTCGCGGCCGAGGTCTGAGGTTACATGCGTGGTGGTGGACGTGAGCCACGAAGACCCTGAGGTCAAGTTC
AACTGGTACGTGGACGGCGTGGAGGTGCATAATGCCAAGACAAAGCCGCGGGAGGAGCAGTACAACAGCACGTACC
GGGNGGTCAGCGTCCTCACCGTCCTGCACCAGAATTGGTTGAATGGCAAGGAGTACAAGNGCAAGGTTTCCAACAA
AGCCNTCCCAGCCCCCNTCGAAAAAACCATTTCCAAAGCCAAAGGGCAGCCCCGAGAACCACAGGTGTACACCCTG
CCCCCATCCCGGGAGGAAAAGANCAANAACCNGGTTCAGCCTTAACTTGCTTGGTCNAANGCTTTTTATCCCAACG
NACTTCCCCCNTGGAANTGGGAAAAACCAATGGGCCAANCCGAAAAACAATTACAANAACCCC 16518.2.edit TCGAGCGGCCGCCCGGGCAGGTGTCGGAGTCCAGCACGGGAGGCGTGGTCTTGTAGTTGTTCTCCGGCTGCCCATT
GCTCTCCCACTCCACGGCGATGTCGCTGGGATAGAAGCCTTTGACCAGGCAGGTCAGGCTGACCTGGTTCTTGGTC
ATCTCCTCCCGGGATGGGGGCAGGGTGAACACCTGGGGTTCTCGGGGCTTGCCCTTTGGTTTTGAANATGGTTTTC
TCGATGGGGGCTGGAAGGGCTTTGTTGNAAACCTTGCACTTGACTCCTTGCCATTCACCCAGNCCTGGNGCAGGAC
GGNGAGGACNCTNACCACACGGAACCGGGCTGGTGGACTGCTCC

*Fig. 15X-1*

16519.1.edit

AGCGTGGTCGCGGACGANGTCCTGTCAGAGTGGNACTGGTAGAAGTTCCANGAACCCTGAACTGTAAGGGTTCTTC
ATCAGTGCCAACAGGATGACATGAAATGATGTACTCAGAAGNGNCCTGGAATGGGGCCCATGANATGGTTGCC 16519.2.edit TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAGAATAATCAGAAG
AGCGAGCCCCTGATTGGAAGGAAAAAGACAGACGAGCTTCCCCAACTGGTAACCCTTCCACACCCCAATCTTCATG
GACCAGAGATCTTGGATGTTCCTTCCACAGTTCAAAAGACCCCTTTCGGCACCCCCCCTGGGTATGAACCTGGGAA
AANGGNANTTAANCTTTCCTGGCA 16520.1.edit AGCGTGGTCGCGGCCGAGGTCTGGGATGCTCCTGCTGTCACAGTGAGATATTACAGGATCACTTACGGAGAAACAG
GAGGAAATAGCCCTGTCCAGGAGTTCACTGTGCCTGGGAGCAAGTCTACAGCTACCATCAGCGGCCTTAAACCTGG
AGTTGATTATACCATCACTGTGTATGCTGTCACTGGCCGTGGAGACAGCCCCGCAAGCAGCAAGCCAATTTCCATT
AATTACCGAACAGAAATTGACAAACCATCCCAGATGCAAGTGACCGATGTTCAGGACAACAGCATTAGTGTCAAGT
GGCTGCCTTCAAGGTNCCCTGGTACTGGGTTACAGANTAACCACCACTCCCAAAAATGGACCAGGAACCACAAAAA
CTTAAACTGCAGGGTCCAGATCAAAACAGAAATGACTATTGAANGCTTGCAGCCCACAGTGGGAGTATGNGGGTAG
TGNCTATGCTTCAGAATCCAAGCGGAAAAANGTCAAGCCTTNTGGGTTCAA 16520.2.edit TCGAGCGGCCGCCCGGGCAGGTCCTTGCAGCTCTGCAGTGTCTTCTTCACCATCAGGTGCAGGGAATAGCTCATGG
ATTCCATCCTCAGGGCTCGAGTAGGTCACCCTGTACCTGGAAACTTGCCCCTGTGGGCTTTCCCAAGCAATTTTGA
TGGAATCGACATCCACATCAGTGAATGCCAGTCCTTTAGGGCGATCAATGTTGGTTACTGCAGNCTGAACCAGAGG
CTGACTCTCTCCGCTTGGATTCTGAGCATAGACACTAACCACATACTCCACTGTGGGCTGCAANCCTTCAATAANN
CATTTCTGTTTGATCTGGACC 16521.2.edit TCGAGCGGCCGCCCGGGCAGGTCTGGTGGGGTCCTGGCACACGCACATGGGGGNGTTGNTCTNATCCAGCTGCCCA
GCCCCCATTGGCGAGTTTGAGAAGGTGTGCAGCAATGACAACAANACCTTCGACTCTTCCTGCCACTTCTTTGCCA
CAAAGTGCACCCTGGAGGGCACCAAGAAGGGCCACAAGCTCCACCTGGACTACATCGGGCCTTGCAAATACATCCC
CCCTTGCCTGGACTCTGAGCTGACCGAATTCCCCCTTGCGCATGCGGGACTGGCTCAAGAACCGTCCTGGCACCCT
TGTATGANAGGGATGAAGACACNACCC

*Fig. 15Y-1*

16522.1.edit

AGCGTGGTCGCGGCCGAGGTCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGTGGACAAGAGAGTTG
AGCCCAAATCTTGTGACAAAACTCACACATGCCCACCGTGCCCAGCACCTGAACTCCTGGGGGGACCGTCAGTCTT
CCTCTTCCCCCGCATCCCCCTTCCAAACCTGCCCGGGCGGCCGCTCGAAAGCCGAATTCCAGCACACTGGCGGCCG
GTACTAGTGGANCCNAACTTGGNANCCAACCTGGNGGAANTAATGGGCATAANCTGTTTCTGGGGGGAAATTGGTA
TCCNGTTTACAATTCCCNCACAACATACGAGCCGGAAGCATAAAAGNGTAAAAGCCTGGGGGNGGCCTANTGAAGT
GAAGCTAAACTCACATTAATTNGCGTTGCCGCTCACTGGCCCGCTTTTCCAGC 16522.2.edit TCGAGCGGCCGCCCGGGCAGGTTTGGAAGGGGGATGCGGGGGAAGAGGAAGACTGACGGTCCCCCCAGGAGTTCAG
GTGCTGGGCACGGTGGGCATGTGTGAGTTTTGTCACAAGATTTGGGCTCAACTCTCTTGTCCACCTTGGTGTTGCT
GGGCTTGTGATCTACGTTGCAGGTGTAGGTCTGGGNGCCGAAGTTGCTGGAGGGCACGGTCACCACGCTGCTGAGG
GAGTAGAGTCCTGAGGACTGTANGACAGACCTCGGCCGNGACCACGCTAAGCCGAATTCTGCAGATATCCATCACA
CTGGCGGCCGCTCCGAGCATGCATTTTAGAGG 16523.1.edit

AGCGTGGNCGCGGACGANGACAACAACCCC 16523.2.edit

TCGAGCGGCCGCCCGGGCAGGNCCACATCGGCAGGGTCGGAGCCCTGGCCGCCATACTCGAACTGGAATCCATCGG
TCATGCTCTTGCCGAACCAGACATGCCTCTTGTCCTTGGGGTTCTTGCTGATGNACCAGTTCTTCTGGGCCACACT
GGGCTGAGTGGGGTACACGCAGGTCTCACCAGTCTCCATGTTGCAGAAGACTTTGATGGCATCCAGGTTGCAGCCT
TGGTTGGGGTCAATCCAGTACTCTCCACTCTTCCAGTCAGAGTGGCACATCTTGAGGTCACGGCAGGTGCGGGCGG
GGTTCTTGACCT 16524.1.edit AGCGTGGTCGCGGCCGAGGTCCAGCCTGGAGATAANGGTGAAGGTGGTGCCCCCGGACTTCCAGGTATAGCTGGAC
CTCGTGGTAGCCCTGGTGAGAGAGGTGAAACTGGCCCTCCAGGACCTGCTGGTTTCCCTGGTGCTCCTGGACAGAA
TGGTGAACCTGGNGGTAAAGGAGAAAGAGGGGCTCCGGNTGANAAAGGTGAAGGAGGCCCTCCTGNATTGGCAGGG
GCCCCANGACTTAGAGGTGGAGCTGGCCCCCCTGGCCCCGAAGGAGGAAAGGGTGCTGCTGGTCCTCCTGGGCCAC
CTGG

*Fig. 15Z-1*

16524.2.edit

```
TCGAGCGGCCGCCCGGGCAGGTCTGGGCCAGGAGGACCAATAGGACCAGTAGGACCCCTTGGGCCATCTTTCCCTG
GGACACCATCAGCACCTGGACCGCCTGGTTCACCCTTGTCACCCTTTGGACCAGGACTTCCAAGACCTCCTCTTTC
TCCAGGCATTCCTTGCAGACCAGGAGTACCANCAGCACCAGGTGGCCCAGGAGGACCAGCAGCACCCTTTCCTCCT
TCGGGACCAGGGGGACCAGCTCCACCTCTAAGTCCTGGGGCCCCTGCCAATCCAGGAGGGCCTCCTTCACCTTTCT
CACCCGGAGCCCCTCTTTCT
```

16526.1.edit

```
TCGAGCGGCCGCCCGGGCAGGTCCACCGGGATATTCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGACAACCGGAG
GCTGGAGAGCAAAATCCGGGAGCACTTGGAGAAGAAGGGACCCCAGGTCAGAGACTGGAGCCATTACTTCAAGATC
ATCGAGGACCTGAGGGCTCANATCTTCGCAAATACTGCNGACAATGCCCG
```

16526.2.edit

```
ATGCGNGGTCGCGGCCGANGACCANCTCTGGCTCATACTTGACTCTAAAGNCNTCACCAGNANTTACGGNCATTGC
CAATCTGCAGAACGATGCGGGCATTGTCCGCANTATTTGCGAAGATCTGAGCCCTCAGGNCCTCGATGATCTTGAA
GTAANGGCTCCAGTCTCTGACCTGGGGTCCCTTCTTCTCCAAGTGCTCCCGGATTTTGCTCTCCAGCCTCCGGTTC
TCGGTCTCCAAGNCTTCTCACTCTGTCCAGGAAAAGAGGCCAGGCGGNCGATCAGGGCTTTTGCATGGACT
```

16527.1.edit

```
AGCGTGGTCGCGGCCGAGGTTGTACAAGCTTTTTTTTTTTTTTTTTTTTTTTTTTTTTTTTTTTTTTTTTTTTTTT
TTTTTTTTTTTTTTTTTTTTTTTT
```

16527.2.edit

```
TCGAGCGGCCGCCCGGGCAGGTCTGCCAACACCAAGATTGGCCCCCGCCGCATCCACACAGTTNGTGTGCGGGGAG
GTAACAAGAAATACCGTGCCCTGAGGNTGGACGNGGGGAATTTCTCCTGGGGCTCAGAGTGTTGTACTCGTAAAAC
AAGGATCATCGATGTTGTCTACAATGCATCTAATAACGAGCTGGTTCGTACCAAGACCCTGGTGAAGAATTGCATC
GTGCTCATNGACAGCACACCGTACCGACAGTGGGTACCGAAGTCCCACTATGCNCCT
```

*Fig. 15A-2*

16528.1.edit

```
TCGAGCGGCCGCCCGGGCAGGTCCACCACACCCAATTCCTTGCTGGTATCATGGCAGCCGCCACGTGCCAGGATTA
CCGGCTACATCATCAAGTATGAGAAGCCTGGGTCTCCTCCCAGAGAAGTGGTCCCTCGGCCCCGCCCTGGTGTCAC
AGAGGCTACTATTACTGGCCTGGAACCGGGAACCGAATATACAATTTATGTCATTGCCCTGAAG
```

16528.2.edit

```
AGCGTGNTCNCGGCCGAGGATGGGGAAGCTCGNCTGTCTTTTTCCTTCCAATCAGGGGCTNNNTCTTCTGATTATT
CTTCAGGGCAANGACATAAATTGTATATTCGGNTCCCGGTTCCAGNCCAGTAATAGTAGCCTCTGTGACACCAGGG
CGGGGCCGAGGGACCACTTCTCTGGGAGGAGACCCAGGCTTCTCATACTTGATGATGAAGCCGGTAATCCTGGCAC
GTGGGCGGCTGCCATGATACCACCAANGAATTGGGTGTGGTGGACCTGCCCGGGCGGGCCGCTCGAAAANCCGAAT
TCNTGCAAGAATATCCATCACACTTGGGCGGGCCGNTCGAACCATGCATCNTAAAAGGGCCCCAATTTCCCCCCTA
TTAGGNGAAGCCNCATTTAACAAATTCCACTTGG
```

16529.1.edit

```
TCGAGCGGCCGCCCGGGCAGGTCTCGCGGTCGCACTGGTGATGCTGGTCCTGTTGGTCCCCCCGGCCCTCCTGGAC
CTCCTGGTCCCCCTGGTCCTCCCAGCGCTGGTTTCGACTTCAGCTTCCTGCCCCAGCCACCTCAAGAGAAGGCTCA
CGATGGTGGCCGCTACTACCGGGCTGATGATGCCAATGTGGTTCGTGACCGTGACCTCGAGGTGGACACCACCCTC
AAGAGCCTTGAGCCAGCAGAATCGAAAACATTCGGAACCCAAGAAGGGCAAGCCCGCAAAGAAACCCCGCCCGCAC
CTGGCCGNGAACCTCCAAGAANGTGCCCACNTCTTGACTGGGAAAAAAAGGGAAAANTACTTGGAATTGGAC
```

16529.2.edit

```
AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACGCAGGTCTCACCAGTCTCCATGTTGCAGAAGACTTTGATGGCATCCAGGTTGCAGCCTTG
GTTGGGGTCAATCCAGTACTCTCCACTCTTCCAGTCAGAAGTGGCACATCTTGAGGTCACGGCAGGGTGCGGGCGG
GGTTCTTGCGGGCTGCCCTTCTGGGCTCCCGGAATGTTCTNNGAACTTGCTGG
```

*Fig. 15B-2*

16530.1.edit

AGCGTGGTCGCGGCCGAGGTCCACTAGAGGTCTGTGTGCCATTGCCCAGGCAGAGTCTCTGCGTTACAAACTCCTA
GGAGGGCTTGCTGTGCGGAGGGCCTGCTATGGTGTGCTGCGGTTCATCATGGAGAGTGGGGCCAAAGGCTGCGAGG
TTGTGGTGTCTGGGAAACTCCGAGGACAGAGGGCTAAATCCATGAAGTTTGTGGATGGCCTGATGATCCACAGCGG
AGACCCTGTTAACTACTACGTTGACACTTGCTTGTGCGCCACGTGTTGCTCANACANGGGTGGGCTGGGCATCAAG
GNG 16530.2.edit TCGAGCGGCCGCCCGGGCAGGTCTGCCAAGGAGACCCTGTTATGCTGTGGGGACTGGCTGGGGCATGGCAGGCGGC
TCTGGCTTCCCACCCTTCTGTTCTGAGATGGGGGTGGTGGGCAGTATCTCATCTTTGGGTTCCACAATGCTCACGT
GGTCAGGCAGGGGCTTCTTAGGGCCAATCTTACCAGTTGGGTCCCAGGGCAGCATGATCTTCACCTTGATGCCCAG
CACACCCTGTCTGAGCAACACGTGGCGCACAGCAAGTGTCAACGTAAGTAAGTTAACAGGGTCTCCGCTGTGGATC
ATCAGGCCATCCACAAACTTCATGGATTTAACCCTCTGTCCTCGGAG 16531.1.edit TCGAGCGGCCGCCCGGGCAGGTGTTTCAGAGGTTCCAAGGTCCACTGTGGAGGTCCCAGGAGTGCTGGTGGTGGGC
ACAGAGGTCCGATGGGTGAAACCATTGACATAGAGACTGTTCCTGTCCAGGGTGTAGGGGCCCAGCTCTTTGATGC
CATTGGCCAGTTGGCTCAGCTCCCAGTACAGCCGCTCTCTGTTGAGTCCAGGGCTTTTGGGGTCAAGATGATGGAT
GCAGATGGCATCCACTCCAGTGGCTGCTCCATCCTTCTCGGACCTGAGAGAGGTCAGTCTGCAGCCAGAGTACAGA
GGGCCAACACTGGTGTTCTTTGAATA 16531.2.edit AGCGTGGTCGCGGCCGAGGTCTGTACTGGGAGCTAAGCAAACTGACCAATGACATTGAAGAGCTGGGCCCCTACAC
CCTGGACAGGAACAGTCTCTATGTCAATGGTTTCACCCATCAGAGCTCTGTGNCCACCACCAGCACTCCTGGGACC
TCCACAGTGGATTTCAGAACCTCAGGGACTCCATCCTCCCTCTCCAGCCCCACAATTATGGCTGCTGGCCCTCTCC
TGGTACCATTCACCCTCAACTTCACCATCACCAACCTGCAGTATGGGGAGGACATGGGTCACCCTGNCTCCAGGAA
GTTCAACACCACA 16532.1.edit TCGAGCGGCCGCCCGGACAGGTCTGGGCGGATAGCACCGGGCATATTTTGGAATGGATGAGGTCTGGCACCCTGAG
CAGTCCAGCGAGGACTTGGTCTTAGTTGAGCAATTTGGCTAGGAGGATAGTATGCAGCACGGNTCTGAGNCTGTGG
GATAGCTGCCATGAAGTAACCTGAAGGAGGTGCTGGCTGGTANGGGTTGATTACAGGGTTGGGAACAGCTCGTACA
CTTGCCATTCTCTGCATATACTGGTTAGTGAGGTGAGCCTGGCCCTCTTCTTTTG

*Fig. 15C-2*

01_16558.3.edit

AGCGTGGTCGCGGCCGAGGTGAGCCACAGGTGACCGGGGCTGAAGCTGGGGCTGCTGGNCCTGCTGGTCCTG

02_16558.4.edit

CAGCNGCTCCNACGGGGCCTGNGGGACCAACAACACCGTTTTCACCCTTAGGCCCTTTGGCTCCTCTTTCTCCTTT
AGCACCAGGTTGACCAGCAGCNCCANCAGGACCAGCAAATCCATTGGGGCCAGCAGGACCGACCTCACCACGTTCA
CCAGGGCTTCCCCGAGGACCAGCAGGACCAGCAGGACCAGCAGCCCCAGCTTCGCCCCGGTCACCTGTGGCTCACC
TCGGCCGCGACCACGCT

03_16535.1.edit

TCGAGCGGTCGCCCGGGCAGGTCCACCGGGATAGCCGGGGGTCTGGCAGGAATGGGAGGCATCCAGAACGAGAAGG
AGACCATGCAAAGCCTGAACGACCGCCTGGCCTCTTACCTGGACAGAGTGAGGAGCCTGGAGACCGANAACCGGAG
GCTGGANAGCAAAATCCGGGAGCACTTGGAGAAGAAGGGACCCCAGGTCAAGAGACTGGAGCCATTACTTCAAGAT
CATCGAGGGACCTGGAGG

04_16535.2.edit

AGCGNGGTCGCGGCCGAGGTCCAGCTCTGTCTCATACTTGACTCTAAAGTCATCAGCAGCAAGACGGGCATTGTCA
ATCTGCAGAACGATGCGGGCATTGTCCGCAGTATTTGCGAAGATCTGAGCCCTCAGGTCCTCGATGATCTTGAAGT
AATGGCTCCAGTCTCTGACCTGGGGTCCCTTCTTCTCCAAGTGCTCCCGGATTTTGCTCTCCAGCCTCCGGTTCTC
GGTCTCCAGGCTCCTCACTCTGTCCAGGTAAGAAGGCCCAGGCGGTCGTTCAGGCTTTGCATGGTCTCCTTCTCGT
TCTGGATGCCTCCCATTCCTGCCAGACCC

05_16536.1.edit

TCGAGCGGCCGCCCGGGCAGGTCAGGAAGCACATTGGTCTTAGAGCCACTGCCTCCTGGATTCCACCTGTGCTGCG
GACATCTCCAGGGAGTGCAGAAGGGAAGCAGGTCAAACTGCTCAGATCAGTCAGACTGGCTGTTCTCAGTTCTCAC
CTGAGCAAGGTCAGTCTGCAGCCAGAGTACAGAGGGCCAACACTGGTGTTCTTGAACAAGGGCTTGAGCAGACCCT
GCAGAACCCTCTTCCGTGGTGTTGAACTTCCTGGAAACCAGGGTGTTGCATGTTTTTCCTCATAATGCAAGGTTGG
TGATGG

*Fig. 15D-2*

07_16537.1.edit

AGCGTGGTCGCGGCCGAGGTCCACATCGGCAGGGTCGGAGCCCTGGCCGCCATACTCGAACTGGAATCCATCGGTC
ATGCTCTCGCCGAACCAGACATGCCTCTTGTCCTTGGGGTTCTTGCTGATGTACCAGTTCTTCTGGGCCACACTGG
GCTGAGTGGGGTACACCGCAGGTCTCACCAGTCTCCATGTTGCAGAAGACTTTGATGGCATCCAGGTTGCAGCCTT
GGTTGGGGTCAATCCAGTACTCTCCACTCTTCCAGTCAGAAGTGGGCACATCTTGAGGTCACCGGCAGGTGCCGGG
CCGGGGGTTCTTGCGGCTTGCCCTCTGGGCTCCGGATGTTCTCGATCTGCTTGGCTCAGGCTCTTGAGGGTGGGTG
TCCACCTCGAGGTCACGGTCACCGAAACCTGCCCGGGCGGCCCGCTCGA

08_16537.2.edit

TCGAGCGGTCGCCCGGGCAGGTTTCGTGACCGTGACCTCGAGGTGGACACCACCCTCAAGAGCCTGAGCCAGCAGA
TCGAGAACATCCGGAGCCCAGAGGGCAGCCGCAAGAACCCCGCCCGCACCTGCCGTGACCTCAAGATGTGCCACTC
TGACTGGAAGAGTGGAGAGTACTGGATTGACCCCAACCAAGGCTGCAACCTGGATGCCATCAAAGTCTTCTGCAAC
ATGGAGACTGGTGAGACCTGCGTGTACCCCACTCAGCCCAGTGTGGGCCCAGAAGAAACTGGTACATCAGCAAGGA
ACCCCAAGGACAAGAGGCATTGTCTTGGTTCGGCGAGNAGCATGACCCGATGGATTCCAGTTTCGAGTATTGGCGG
CCAGGGCTTCCCGACCCTTGCCGATGTGGACCTCGGCCGCGACCACCGCT

*Fig. 15E-2*

COMPOSITIONS AND METHODS FOR THERAPY AND DIAGNOSIS OF OVARIAN CANCER

CROSS REFERENCE TO RELATED APPLICATIONS

This application is a continuation-in-part of U.S. application Ser. No. 09/338,933, filed Jun. 23, 1999, which is a continuation-in-part of U.S. application Ser. No. 09/216,003, filed Dec. 17, 1998, hereby incorporated by reference in their entirety which is a CIP of 09/215,681 filed Dec. 17, 1998.

TECHNICAL FIELD

The present invention relates generally to ovarian cancer therapy. The invention is more specifically related to polypeptides comprising at least a portion of an ovarian carcinoma protein, and to polynucleotides encoding such polypeptides, as well as antibodies and immune system cells that specifically recognize such polypeptides. Such polypeptides, polynucleotides, antibodies and cells may be used in vaccines and pharmaceutical compositions for treatment of ovarian cancer.

BACKGROUND OF THE INVENTION

Ovarian cancer is a significant health problem for women in the United States and throughout the world. Although advances have been made in detection and therapy of this cancer, no vaccine or other universally successful method for prevention or treatment is currently available. Management of the disease currently relies on a combination of early diagnosis and aggressive treatment, which may include one or more of a variety of treatments such as surgery, radiotherapy, chemotherapy and hormone therapy. The course of treatment for a particular cancer is often selected based on a variety of prognostic parameters, including an analysis of specific tumor markers. However, the use of established markers often leads to a result that is difficult to interpret, and high mortality continues to be observed in many cancer patients.

Immunotherapies have the potential to substantially improve cancer treatment and survival. Such therapies may involve the generation or enhancement of an immune response to an ovarian carcinoma antigen. However, to date, relatively few ovarian carcinoma antigens are known and the generation of an immune response against such antigens has not been shown to be therapeutically beneficial.

Accordingly, there is a need in the art for improved methods for identifying ovarian tumor antigens and for using such antigens in the therapy of ovarian cancer. The present invention fulfills these needs and further provides other related advantages.

SUMMARY OF THE INVENTION

Briefly stated, this invention provides compositions and methods for the therapy of cancer, such as ovarian cancer. In one aspect, the present invention provides polypeptides comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished. Within certain embodiments, the ovarian carcinoma protein comprises a sequence that is encoded by a polynucleotide sequence selected from the group consisting of SEQ ID NOs:1–81, 313–331, 359, 366, 379, 385–387, 391 and complements of such polynucleotides.

The present invention further provides polynucleotides that encode a polypeptide as described above or a portion thereof, expression vectors comprising such polynucleotides and host cells transformed or transfected with such expression vectors.

Within other aspects, the present invention provides pharmaceutical compositions and vaccines. Pharmaceutical compositions may comprise a physiologically acceptable carrier or excipient in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–81, 313–331, 359, 366, 379, 385–387 or 391; (ii) a polynucleotide encoding such a polypeptide; (iii) an antibody that specifically binds to such a polypeptide; (iv) an antigen-presenting cell that expresses such a polypeptide and/or (v) a T cell that specifically reacts with such a polypeptide. Vaccines may comprise a non-specific immune response enhancer in combination with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–81, 313–331, 359, 366, 379, 385–387 or 391; (ii) a polynucleotide encoding such a polypeptide; (iii) an anti-idiotypic antibody that is specifically bound by an antibody that specifically binds to such a polypeptide; (iv) an antigen-presenting cell that expresses such a polypeptide and/or (v) a T cell that specifically reacts with such a polypeptide.

The present invention further provides, in other aspects, fusion proteins that comprise at least one polypeptide as described above, as well as polynucleotides encoding such fusion proteins.

Within related aspects, pharmaceutical compositions comprising a fusion protein or polynucleotide encoding a fusion protein in combination with a physiologically acceptable carrier are provided.

Vaccines are further provided, within other aspects, comprising a fusion protein or polynucleotide encoding a fusion protein in combination with a non-specific immune response enhancer.

Within further aspects, the present invention provides methods for inhibiting the development of a cancer in a patient, comprising administering to a patient a pharmaceutical composition or vaccine as recited above.

The present invention further provides, within other aspects, methods for stimulating and/or expanding T cells, comprising contacting T cells with (a) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs:1–387 or 391; (b) a polynucleotide encoding such a polypeptide and/or (c) an antigen presenting cell that expresses such a polypeptide under conditions and for a time sufficient to permit the stimulation and/or expansion of T cells. Such polypeptide, polynucleotide and/or antigen presenting cell(s) may be present within a pharmaceutical composition or vaccine, for use in stimulating and/or expanding T cells in a mammal.

Within other aspects, the present invention provides methods for inhibiting the development of ovarian cancer in a patient, comprising administering to a patient T cells prepared as described above.

Within further aspects, the present invention provides methods for inhibiting the development of ovarian cancer in a patient, comprising the steps of: (a) incubating $CD4^+$ and/or $CD8^+$ T cells isolated from a patient with one or more of: (i) a polypeptide comprising an immunogenic portion of an ovarian carcinoma protein, or a variant thereof that differs in one or more substitutions, deletions, additions and/or insertions such that the ability of the variant to react with ovarian carcinoma protein-specific antisera is not substantially diminished, wherein the ovarian carcinoma protein comprises an amino acid sequence encoded by a polynucleotide that comprises a sequence recited in any one of SEQ ID NOs: 1–387 or 391; (ii) a polynucleotide encoding such a polypeptide; or (iii) an antigen-presenting cell that expresses such a polypeptide; such that T cells proliferate; and (b) administering to the patient an effective amount of the proliferated T cells, and thereby inhibiting the development of ovarian cancer in the patient. The proliferated cells may be cloned prior to administration to the patient.

The present invention also provides, within other aspects, methods for identifying secreted tumor antigens. Such methods comprise the steps of: (a) implanting tumor cells in an immunodeficient mammal; (b) obtaining serum from the immunodeficient mammal after a time sufficient to permit secretion of tumor antigens into the serum; (c) immunizing an immunocompetent mammal with the serum; (d) obtaining antiserum from the immunocompetent mammal; and (e) screening a tumor expression library with the antiserum, and therefrom identifying a secreted tumor antigen. A preferred method for identifying a secreted ovarian carcinoma antigen comprises the steps of: (a) implanting ovarian carcinoma cells in a SCID mouse; (b) obtaining serum from the SCID mouse after a time sufficient to permit secretion of ovarian carcinoma antigens into the serum; (c) immunizing an immunocompetent mouse with the serum; (d) obtaining antiserum from the immunocompetent mouse; and (e) screening an ovarian carcinoma expression library with the antiserum, and therefrom identifying a secreted ovarian carcinoma antigen.

These and other aspects of the present invention will become apparent upon reference to the following detailed description and attached drawings. All references disclosed herein are hereby incorporated by reference in their entirety as if each was incorporated individually.

BRIEF DESCRIPTION OF THE DRAWINGS

FIGS. 1A–1S (SEQ ID NOs:1–71) depict partial sequences of polynucleotides encoding representative secreted ovarian carcinoma antigens.

FIGS. 2A–2C depict full insert sequences for three of the clones of FIG. 1. FIG. 2A shows the sequence designated 07E (11731; SEQ ID NO:72), FIG. 2B shows the sequence designated 09E (11785; SEQ ID NO:73) and FIG. 2C shows the sequence designated 08E (13695; SEQ ID NO:74).

FIG. 3 presents results of microarray expression analysis of the ovarian carcinoma sequence designated 08E.

FIG. 4 presents a partial sequence of a polynucleotide (designated 3*g*; SEQ ID NO:75) encoding an ovarian carcinoma sequence that is a splice fusion between the human T-cell leukemia virus type I oncoprotein TAX and osteonectin.

FIG. 5 presents the ovarian carcinoma polynucleotide designated 3*f* (SEQ ID NO:76).

FIG. 6 presents the ovarian carcinoma polynucleotide designated 6*b* (SEQ ID NO:77).

FIGS. 7A and 7B present the ovarian carcinoma polynucleotides designated 8*e* (SEQ ID NO:78) and 8*h* (SEQ ID NO:79).

FIG. 8 presents the ovarian carcinoma polynucleotide designated 12*c* (SEQ ID NO:80).

FIG. 9 presents the ovarian carcinoma polynucleotide designated 12*h* (SEQ ID NO:81).

FIG. 10 is a chart which depicts results of microarray expression analysis of the ovarian carcinoma sequence designated 3*f*.

FIG. 11 is a chart which depicts results of microarray expression analysis of the ovarian carcinoma sequence designated 6*b*.

FIG. 12 is a chart which depicts results of microarray expression analysis of the ovarian carcinoma sequence designated 8*e*.

FIG. 13 is a chart which depicts results of microarray expression analysis of the ovarian carcinoma sequence designated 12*c*.

FIG. 14 is a chart which depicts results of microarray expression analysis of the ovarian carcinoma sequence designated 12*h*.

FIGS. 15A–15E-2 depict partial sequences of additional polynucleotides encoding representative secreted ovarian carcinoma antigens (SEQ ID NOs:82–310).

DETAILED DESCRIPTION OF THE INVENTION

Figure 16:
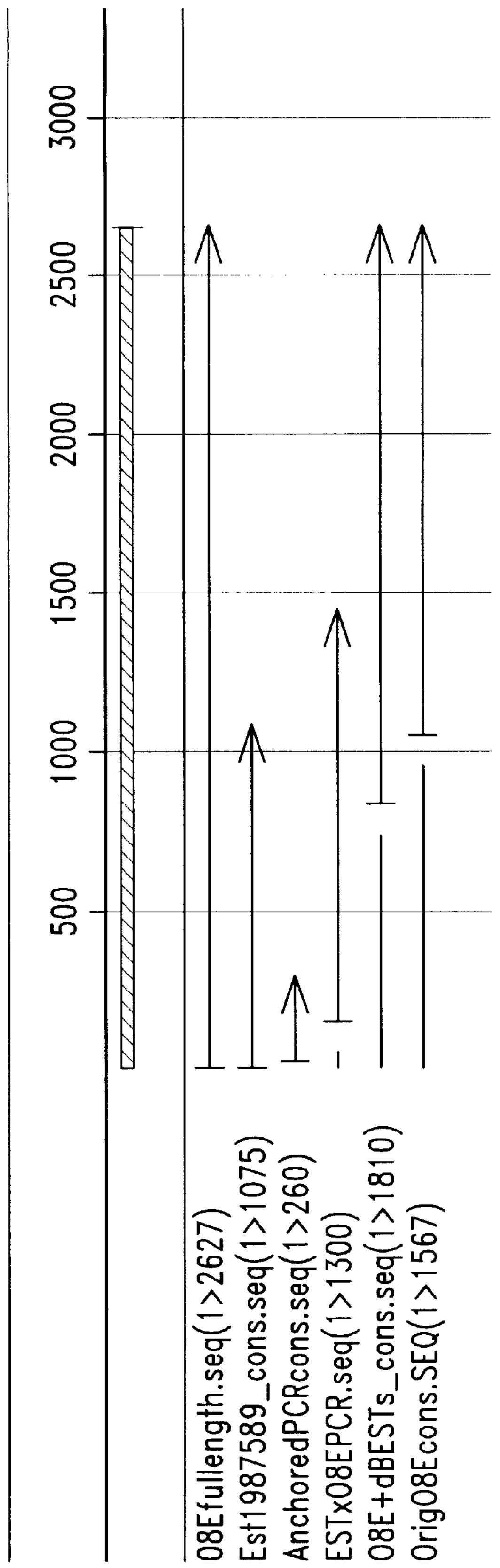
FIG. 16 is a diagram illustrating the location of various partial 08E sequences within the full length sequence.

As noted above, the present invention is generally directed to compositions and methods for the therapy of cancer, such as ovarian cancer. The compositions described herein may include immunogenic polypeptides, polynucleotides encoding such polypeptides, binding agents such as antibodies that bind to a polypeptide, antigen presenting cells (APCs) and/or immune system cells (e.g., T cells).

Polypeptides of the present invention generally comprise at least an immunogenic portion of an ovarian carcinoma protein or a variant thereof. Certain ovarian carcinoma proteins have been identified using an immunoassay technique, and are referred to herein as ovarian carcinoma antigens. An "ovarian carcinoma antigen" is a protein that is expressed by ovarian tumor cells (preferably human cells) at a level that is at least two fold higher than the level in normal ovarian cells. Certain ovarian carcinoma antigens react detectably (within an immunoassay, such as an ELISA or Western blot) with antisera generated against serum from an immunodeficient animal implanted with a human ovarian tumor. Such ovarian carcinoma antigens are shed or secreted from an ovarian tumor into the sera of the immunodeficient animal. Accordingly, certain ovarian carcinoma antigens provided herein are secreted antigens. Certain nucleic acid sequences of the subject invention generally comprise a DNA or RNA sequence that encodes all or a portion of such a polypeptide, or that is complementary to such a sequence.

The present invention further provides ovarian carcinoma sequences that are identified using techniques to evaluate altered expression within an ovarian tumor. Such sequences may be polynucleotide or protein sequences. Ovarian carcinoma sequences are generally expressed in an ovarian tumor at a level that is at least two fold, and preferably at least five fold, greater than the level of expression in normal ovarian tissue, as determined using a representative assay provided herein. Certain partial ovarian carcinoma polynucleotide sequences are presented herein. Proteins encoded by genes comprising such polynucleotide sequences (or complements thereof) are also considered ovarian carcinoma proteins.

Antibodies are generally immune system proteins, or antigen-binding fragments thereof, that are capable of binding to at least a portion of an ovarian carcinoma polypeptide as described herein. T cells that may be employed within the compositions provided herein are generally T cells (e.g., $CD4^+$ and/or $CD8^+$) that are specific for such a polypeptide. Certain methods described herein further employ antigen-presenting cells (such as dendritic cells or macrophages) that express an ovarian carcinoma polypeptide as provided herein.

Ovarian Carcinoma Polynucleotides

Any polynucleotide that encodes an ovarian carcinoma protein or a portion or other variant thereof as described herein is encompassed by the present invention. Preferred polynucleotides comprise at least 15 consecutive nucleotides, preferably at least 30 consecutive nucleotides, and more preferably at least 45 consecutive nucleotides, that encode a portion of an ovarian carcinoma protein. More preferably, a polynucleotide encodes an immunogenic portion of an ovarian carcinoma protein, such as an ovarian carcinoma antigen. Polynucleotides complementary to any such sequences are also encompassed by the present invention. Polynucleotides may be single-stranded (coding or antisense) or double-stranded, and may be DNA (genomic, cDNA or synthetic) or RNA molecules. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an ovarian carcinoma protein or a portion thereof) or may comprise a variant of such a sequence. Polynucleotide variants may contain one or more substitutions, additions, deletions and/or insertions such that the immunogenicity of the encoded polypeptide is not diminished, relative to a native ovarian carcinoma protein. The effect on the immunogenicity of the encoded polypeptide may generally be assessed as described herein. Variants preferably exhibit at least about 70% identity, more preferably at least about 80% identity and most preferably at least about 90% identity to a polynucleotide sequence that encodes a native ovarian carcinoma protein or a portion thereof.

The percent identity for two polynucleotide or polypeptide sequences may be readily determined by comparing sequences using computer algorithms well known to those of ordinary skill in the art, such as Megalign, using default parameters. Comparisons between two sequences are typically performed by comparing the sequences over a comparison window to identify and compare local regions of sequence similarity. A "comparison window" as used herein, refers to a segment of at least about 20 contiguous positions, usually 30 to about 75, or 40 to about 50, in which a sequence may be compared to a reference sequence of the same number of contiguous positions after the two sequences are optimally aligned. Optimal alignment of sequences for comparison may be conducted, for example, using the Megalign program in the Lasergene suite of bioinformatics software (DNASTAR, Inc., Madison, Wis.), using default parameters. Preferably, the percentage of sequence identity is determined by comparing two optimally aligned sequences over a window of comparison of at least 20 positions, wherein the portion of the polynucleotide or polypeptide sequence in the window may comprise additions or deletions (i e., gaps) of 20% or less, usually 5 to 15%, or 10 to 12%, relative to the reference sequence (which does not contain additions or deletions). The percent identity may be calculated by determining the number of positions at which the identical nucleic acid bases or amino acid residue occurs in both sequences to yield the number of matched positions, dividing the number of matched positions by the total number of positions in the reference sequence (i.e., the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native ovarian carcinoma protein (or a complementary sequence). Suitable moderately stringent conditions include prewashing in a solution of 5×SSC, 0.5% SDS, 1.0 mM EDTA (pH 8.0); hybridizing at 50° C.–65° C., 5×SSC, overnight; followed by washing twice at 65° C. for 20 minutes with each of 2×, 0.5× and 0.2×SSC containing 0.1% SDS.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

Polynucleotides may be prepared using any of a variety of techniques. For example, an ovarian carcinoma polynucleotide may be identified, as described in more detail below, by screening a late passage ovarian tumor expression library with antisera generated against sera of immunocompetent mice after injection of such mice with sera from SCID mice implanted with late passage ovarian tumors. Ovarian carcinoma polynucleotides may also be identified using any of a variety of techniques designed to evaluate differential gene expression. Alternatively, polynucleotides may be amplified from cDNA prepared from ovarian tumor cells. Such polynucleotides may be amplified via polymerase chain reaction (PCR). For this approach, sequence-specific primers may be designed based on the sequences provided herein, and may be purchased or synthesized.

An amplified portion may be used to isolate a full length gene from a suitable library (e.g., an ovarian carcinoma cDNA library) using well known techniques. Within such techniques, a library (cDNA or genomic) is screened using one or more polynucleotide probes or primers suitable for amplification. Preferably, a library is size-selected to include larger molecules. Random primed libraries may also be preferred for identifying 5' and upstream regions of genes. Genomic libraries are preferred for obtaining introns and extending 5' sequences.

For hybridization techniques, a partial sequence may be labeled (e.g., by nick-translation or end-labeling with $^{32}P$) using well known techniques. A bacterial or bacteriophage library is then screened by hybridizing filters containing denatured bacterial colonies (or lawns containing phage plaques) with the labeled probe (see Sambrook et al., *Molecular Cloning: A Laboratory Manual*, Cold Spring Harbor Laboratories, Cold Spring Harbor, N.Y. 1989). Hybridizing colonies or plaques are selected and expanded, and the DNA is isolated for further analysis. cDNA clones may be analyzed to determine the amount of additional sequence by, for example, PCR using a primer from the partial sequence and a primer from the vector. Restriction maps and partial sequences may be generated to identify one or more overlapping clones. The complete sequence may then be determined using standard techniques, which may involve generating a series of deletion clones. The resulting overlapping sequences are then assembled into a single contiguous sequence. A full length cDNA molecule can be generated by ligating suitable fragments, using well known techniques.

Alternatively, there are numerous amplification techniques for obtaining a full length coding sequence from a partial cDNA sequence. Within such techniques, amplification is generally performed via PCR. Any of a variety of commercially available kits may be used to perform the amplification step. Primers may be designed using, for example, software well known in the art. Primers are preferably 22–30 nucleotides in length, have a GC content of at least 50% and anneal to the target sequence at temperatures of about 68° C. to 72° C. The amplified region may be sequenced as described above, and overlapping sequences assembled into a contiguous sequence.

One such amplification technique is inverse PCR (see Triglia et al., *Nucl Acids Res.* 16:8186, 1988), which uses restriction enzymes to generate a fragment in the known region of the gene. The fragment is then circularized by intramolecular ligation and used as a template for PCR with divergent primers derived from the known region. Within an alternative approach, sequences adjacent to a partial sequence may be retrieved by amplification with a primer to a linker sequence and a primer specific to a known region. The amplified sequences are typically subjected to a second round of amplification with the same linker primer and a second primer specific to the known region. A variation on this procedure, which employs two primers that initiate extension in opposite directions from the known sequence, is described in WO 96/38591. Additional techniques include capture PCR (Lagerstrom et al., *PCR Methods Applic.* 1:111–19, 1991) and walking PCR (Parker et al., *Nucl Acids. Res.* 19:3055–60, 1991). Other methods employing amplification may also be employed to obtain a full length cDNA sequence.

In certain instances, it is possible to obtain a full length cDNA sequence by analysis of sequences provided in an expressed sequence tag (EST) database, such as that available from GenBank. Searches for overlapping ESTs may generally be performed using well known programs (e.g., NCBI BLAST searches), and such ESTs may be used to generate a contiguous full length sequence.

Certain nucleic acid sequences of cDNA molecules encoding portions of ovarian carcinoma antigens are provided in FIGS. 1A–1S (SEQ ID NOS: 1 to 71) and FIGS. 15A to 15EEE (SEQ ID NOs:82 to 310). The sequences provided in FIGS. 1A–1S appear to be novel. For sequences in FIGS. 15A–15EEE, database searches revealed matches having substantial identity. These polynucleotides were isolated by serological screening of an ovarian tumor cDNA expression library, using a technique designed to identify secreted tumor antigens. Briefly, a late passage ovarian tumor expression library was prepared from a SCID-derived human ovarian tumor (OV9334) in the vector λ-screen (Novagen). The sera used for screening were obtained by injecting immunocompetent mice with sera from SCID mice implanted with one late passage ovarian tumors. This technique permits the identification of cDNA molecules that encode immunogenic portions of secreted tumor antigens.

The polynucleotides recited herein, as well as full length polynucleotides comprising such sequences, other portions of such full length polynucleotides, and sequences complementary to all or a portion of such full length molecules, are specifically encompassed by the present invention. It will be apparent to those of ordinary skill in the art that this technique can also be applied to the identification of antigens that are secreted from other types of tumors.

Other nucleic acid sequences of cDNA molecules encoding portions of ovarian carcinoma proteins are provided in FIGS. 4–9 (SEQ ID NOs:75–81), as well as SEQ ID NOs:313–384. These sequences were identified by screening a microarray of cDNAs for tumor-associated expression (i.e., expression that is at least five fold greater in an ovarian tumor than in normal ovarian tissue, as determined using a representative assay provided herein). Such screens were performed using a Synteni microarray (Palo Alto, Calif.) according to the manufacturer's instructions (and essentially as described by Schena et al., *Proc. Natl. Acad Sci. USA* 93:10614–10619, 1996 and Heller et al., *Proc. Natl. Acad. Sci. USA* 94:2150–2155, 1997). SEQ ID NOs:311 and 391 provide full length sequences incorporating certain of these nucleic acid sequences.

Any of a variety of well known techniques may be used to evaluate tumor-associated expression of a cDNA. For example, hybridization techniques using labeled polynucleotide probes may be employed. Alternatively, or in addition, amplification techniques such as real-time PCR may be used (see Gibson et al., *Genome Research* 6:995–1001, 1996; Heid et al., *Genome Research* 6:986–994, 1996). Real-time PCR is a technique that evaluates the level of PCR product accumulation during amplification. This technique permits quantitative evaluation of mRNA levels in multiple samples. Briefly, mRNA is extracted from tumor and normal tissue and cDNA is prepared using standard techniques. Real-time PCR may be performed, for example, using a Perkin Elmer/Applied Biosystems (Foster City, Calif.) 7700 Prism instrument. Matching primers and fluorescent probes may be designed for genes of interest using, for example, the primer express program provided by Perkin Elmer/Applied Biosystems (Foster City, Calif.). Optimal concentrations of primers and probes may be initially determined by those of ordinary skill in the art, and control (e.g., β-actin) primers and probes may be obtained commercially from, for example, Perkin Elmer/Applied Biosystems (Foster City, Calif.). To quantitate the amount of specific RNA in a sample, a standard curve is generated alongside using a plasmid containing the gene of interest. Standard curves may be generated using the Ct values determined in the real-time PCR, which are related to the initial cDNA concentration used in the assay. Standard dilutions ranging from $10–10^6$ copies of the gene of interest are generally sufficient. In addition, a standard curve is generated for the control sequence. This permits standardization of initial RNA content of a tissue sample to the amount of control for comparison purposes.

Polynucleotide variants may generally be prepared by any method known in the art, including chemical synthesis by, for example, solid phase phosphoramidite chemical synthesis. Modifications in a polynucleotide sequence may also be introduced using standard mutagenesis techniques, such as oligonucleotide-directed site-specific mutagenesis (see Adelman et al., *DNA* 2:183, 1983). Alternatively, RNA molecules may be generated by in vitro or in vivo transcription of DNA sequences encoding an ovarian carcinoma antigen, or portion thereof, provided that the DNA is incorporated into a vector with a suitable RNA polymerase promoter (such as T7 or SP6). Certain portions may be used to prepare an encoded polypeptide, as described herein. In addition, or alternatively, a portion may be administered to a patient such that the encoded polypeptide is generated in vivo.

A portion of a sequence complementary to a coding sequence (i.e., an antisense polynucleotide) may also be used as a probe or to modulate gene expression. cDNA constructs that can be transcribed into antisense RNA may also be introduced into cells or tissues to facilitate the production of antisense RNA. An antisense polynucleotide may be used, as described herein, to inhibit expression of an ovarian carcinoma protein. Antisense technology can be used to control gene expression through triple-helix formation, which compromises the ability of the double helix to open sufficiently for the binding of polymerases, transcription factors or regulatory molecules (see Gee et al., In Huber and Carr, *Molecular and Immunologic Approaches*, Futura Publishing Co. (Mt. Kisco, N.Y.; 1994). Alternatively, an antisense molecule may be designed to hybridize with a control region of a gene (e.g., promoter, enhancer or transcription initiation site), and block transcription of the gene; or to block translation by inhibiting binding of a transcript to ribosomes.

Any polynucleotide may be further modified to increase stability in vivo. Possible modifications include, but are not limited to, the addition of flanking sequences at the 5' and/or 3' ends; the use of phosphorothioate or 2' O-methyl rather than phosphodiesterase linkages in the backbone; and/or the inclusion of nontraditional bases such as inosine, queosine and wybutosine, as well as acetyl- methyl-, thio- and other modified forms of adenine, cytidine, guanine, thymine and uridine.

Nucleotide sequences as described herein may be joined to a variety of other nucleotide sequences using established recombinant DNA techniques. For example, a polynucleotide may be cloned into any of a variety of cloning vectors, including plasmids, phagemids, lambda phage derivatives and cosmids. Vectors of particular interest include expression vectors, replication vectors, probe generation vectors and sequencing vectors. In general, a vector will contain an origin of replication functional in at least one organism, convenient restriction endonuclease sites and one or more selectable markers. Other elements will depend upon the desired use, and will be apparent to those of ordinary skill in the art.

Within certain embodiments, polynucleotides may be formulated so as to permit entry into a cell of a mammal, and expression therein. Such formulations are particularly useful for therapeutic purposes, as described below. Those of ordinary skill in the art will appreciate that there are many ways to achieve expression of a polynucleotide in a target cell, and any suitable method may be employed. For example, a polynucleotide may be incorporated into a viral vector such as, but not limited to, adenovirus, adeno-associated virus, retrovirus, or vaccinia or other pox virus (e.g., avian pox virus). Techniques for incorporating DNA into such vectors are well known to those of ordinary skill in the art. A retroviral vector may additionally transfer or incorporate a gene for a selectable marker (to aid in the identification or selection of transduced cells) and/or a targeting moiety, such as a gene that encodes a ligand for a receptor on a specific target cell, to render the vector target specific. Targeting may also be accomplished using an antibody, by methods known to those of ordinary skill in the art.

Other formulations for therapeutic purposes include colloidal dispersion systems, such as macromolecule complexes, nanocapsules, microspheres, beads, and lipid-based systems including oil-in-water emulsions, micelles, mixed micelles, and liposomes. A preferred colloidal system for use as a delivery vehicle in vitro and in vivo is a liposome (i.e., an artificial membrane vesicle). The preparation and use of such systems is well known in the art.

Ovarian Carcinoma Polypeptides

Within the context of the present invention, polypeptides may comprise at least an immunogenic portion of an ovarian carcinoma protein or a variant thereof, as described herein. As noted above, certain ovarian carcinoma proteins are ovarian carcinoma antigens that are expressed by ovarian tumor cells and react detectably within an immunoassay (such as an ELISA) with antisera generated against serum from an immunodeficient animal implanted with an ovarian tumor. Other ovarian carcinoma proteins are encoded by ovarian carcinoma polynucleotides recited herein. Polypeptides as described herein may be of any length. Additional sequences derived from the native protein and/or heterologous sequences may be present, and such sequences may (but need not) possess further immunogenic or antigenic properties.

An "immunogenic portion," as used herein is a portion of an antigen that is recognized (i.e., specifically bound) by a B-cell and/or T-cell surface antigen receptor. Such immunogenic portions generally comprise at least 5 amino acid residues, more preferably at least 10, and still more preferably at least 20 amino acid residues of an ovarian carcinoma protein or a variant thereof. Preferred immunogenic portions are encoded by cDNA molecules isolated as described herein. Further immunogenic portions may generally be identified using well known techniques, such as those summarized in Paul, *Fundamental Immunology,* 3rd ed., 243–247 (Raven Press, 1993) and references cited therein. Such techniques include screening polypeptides for the ability to react with ovarian carcinoma protein-specific antibodies, antisera and/or T-cell lines or clones. As used herein, antisera and antibodies are "ovarian carcinoma protein-specific" if they specifically bind to an ovarian carcinoma protein (i.e., they react with the ovarian carcinoma protein in an ELISA or other immunoassay, and do not react detectably with unrelated proteins). Such antisera, antibodies and T cells may be prepared as described herein, and using well known techniques. An immunogenic portion of a native ovarian carcinoma protein is a portion that reacts with such antisera, antibodies and/or T-cells at a level that is not substantially less than the reactivity of the full length polypeptide (e.g., in an ELISA and/or T-cell reactivity assay). Such immunogenic portions may react within such assays at a level that is similar to or greater than the reactivity of the full length protein. Such screens may generally be performed using methods well known to those of ordinary skill in the art, such as those described in Harlow and Lane, *Antibodies: A Laboraoy Manual*, Cold Spring Harbor Laboratory, 1988. For example, a polypeptide may be immobilized on a solid support and contacted with patient sera to allow binding of antibodies within the sera to the immobilized polypeptide. Unbound sera may then be removed and bound antibodies detected using, for example, $^{125}$I-labeled Protein A.

As noted above, a composition may comprise a variant of a native ovarian carcinoma protein. A polypeptide "variant," as used herein, is a polypeptide that differs from a native ovarian carcinoma protein in one or more substitutions, deletions, additions and/or insertions, such that the immunogenicity of the polypeptide is not substantially diminished. In other words, the ability of a variant to react with ovarian carcinoma protein-specific antisera may be enhanced or unchanged, relative to the native ovarian carcinoma protein, or may be diminished by less than 50%, and preferably less than 20%, relative to the native ovarian carcinoma protein. Such variants may generally be identified by modifying one of the above polypeptide sequences and evaluating the reactivity of the modified polypeptide with ovarian carcinoma protein-specific antibodies or antisera as described herein. Preferred variants include those in which one or more portions, such as an N-terminal leader sequence or transmembrane domain, have been removed. Other preferred variants include variants in which a small portion (e.g., 1–30 amino acids, preferably 5–15 amino acids) has been removed from the N- and/or C-terminal of the mature protein.

Polypeptide variants preferably exhibit at least about 70%, more preferably at least about 90% and most preferably at least about 95% identity to the native polypeptide. Preferably, a variant contains conservative substitutions. A "conservative substitution" is one in which an amino acid is substituted for another amino acid that has similar properties, such that one skilled in the art of peptide chemistry would expect the secondary structure and hydropathic nature of the polypeptide to be substantially unchanged. Amino acid substitutions may generally be made on the basis of similarity in polarity, charge, solubility, hydrophobicity, hydrophilicity and/or the amphipathic nature of the residues. For example, negatively charged amino acids include aspartic acid and glutamic acid; positively charged amino acids include lysine and arginine; and amino acids with uncharged polar head groups having similar hydrophilicity values include leucine, isoleucine and valine; glycine and alanine; asparagine and glutamine; and serine, threonine, phenylalanine and tyrosine. Other groups of amino acids that may represent conservative changes include: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. A variant may also, or alternatively, contain nonconservative changes. Variants may also (or alternatively) be modified by, for example, the deletion or addition of amino acids that have minimal influence on the immunogenicity, secondary structure and hydropathic nature of the polypeptide.

As noted above, polypeptides may comprise a signal (or leader) sequence at the N-terminal end of the protein which co-translationally or post-translationally directs transfer of the protein. The polypeptide may also be conjugated to a linker or other sequence for ease of synthesis, purification or identification of the polypeptide (e.g., poly-His), or to enhance binding of the polypeptide to a solid support. For example, a polypeptide may be conjugated to an immunoglobulin Fc region.

Polypeptides may be prepared using any of a variety of well known techniques. Recombinant polypeptides encoded by DNA sequences as described above may be readily prepared from the DNA sequences using any of a variety of expression vectors known to those of ordinary skill in the art. Expression may be achieved in any appropriate host cell that has been transformed or transfected with an expression vector containing a DNA molecule that encodes a recombinant polypeptide. Suitable host cells include prokaryotes, yeast and higher eukaryotic cells. Preferably, the host cells employed are *E coli*, yeast or a mammalian cell line such as COS or CHO. Supernatants from suitable host/vector systems which secrete recombinant protein or polypeptide into culture media may be first concentrated using a commercially available filter. Following concentration, the concentrate may be applied to a suitable purification matrix such as an affinity matrix or an ion exchange resin. Finally, one or more reverse phase HPLC steps can be employed to further purify a recombinant polypeptide.

Portions and other variants having fewer than about 100 amino acids, and generally fewer than about 50 amino acids, may also be generated by synthetic means, using techniques well known to those of ordinary skill in the art. For example, such polypeptides may be synthesized using any of the commercially available solid-phase techniques, such as the Merrifield solid-phase synthesis method, where amino acids are sequentially added to a growing amino acid chain. See Merrifield, *J. Am. Chem. Soc.* 85:2149–2146, 1963. Equipment for automated synthesis of polypeptides is commercially available from suppliers such as Applied BioSystems, Inc. (Foster City, Calif.), and may be operated according to the manufacturer's instructions.

Within certain specific embodiments, a polypeptide may be a fusion protein that comprises multiple polypeptides as described herein, or that comprises one polypeptide as described herein and a known tumor antigen, such as an ovarian carcinoma protein or a variant of such a protein. A fusion partner may, for example, assist in providing T helper epitopes (an immunological fusion partner), preferably T helper epitopes recognized by humans, or may assist in expressing the protein (an expression enhancer) at higher yields than the native recombinant protein. Certain preferred fusion partners are both immunological and expression enhancing fusion partners. Other fusion partners may be selected so as to increase the solubility of the protein or to enable the protein to be targeted to desired intracellular compartments. Still further fusion partners include affinity tags, which facilitate purification of the protein.

Fusion proteins may generally be prepared using standard techniques, including chemical conjugation. Preferably, a fusion protein is expressed as a recombinant protein, allowing the production of increased levels, relative to a non-fused protein, in an expression system. Briefly, DNA sequences encoding the polypeptide components may be assembled separately, and ligated into an appropriate expression vector. The 3' end of the DNA sequence encoding one polypeptide component is ligated, with or without a peptide linker, to the 5' end of a DNA sequence encoding the second polypeptide component so that the reading frames of the sequences are in phase. This permits translation into a single fusion protein that retains the biological activity of both component polypeptides.

A peptide linker sequence may be employed to separate the first and the second polypeptide components by a distance sufficient to ensure that each polypeptide folds into its secondary and tertiary structures. Such a peptide linker sequence is incorporated into the fusion protein using standard techniques well known in the art. Suitable peptide linker sequences may be chosen based on the following factors: (1) their ability to adopt a flexible extended conformation; (2) their inability to adopt a secondary structure that could interact with functional epitopes on the first and second polypeptides; and (3) the lack of hydrophobic or charged residues that might react with the polypeptide functional epitopes. Preferred peptide linker sequences contain Gly, Asn and Ser residues. Other near neutral amino acids, such as Thr and Ala may also be used in the linker sequence. Amino acid sequences which may be usefully employed as linkers include those disclosed in Maratea et al., *Gene* 40:39–46, 1985; Murphy et al., *Proc. Natl. Acad Sci. USA* 83:8258–8262, 1986; U.S. Pat. No. 4,935,233 and U.S. Pat. No. 4,751,180. The linker sequence may generally be from 1 to about 50 amino acids in length. Linker sequences are not required when the first and second polypeptides have non-essential N-terminal amino acid regions that can be used to separate the functional domains and prevent steric interference.

The ligated DNA sequences are operably linked to suitable transcriptional or translational regulatory elements. The regulatory elements responsible for expression of DNA are located only 5' to the DNA sequence encoding the first polypeptides. Similarly, stop codons required to end translation and transcription termination signals are only present 3' to the DNA sequence encoding the second polypeptide.

Fusion proteins are also provided that comprise a polypeptide of the present invention together with an unrelated immunogenic protein. Preferably the immunogenic protein is capable of eliciting a recall response. Examples of such proteins include tetanus, tuberculosis and hepatitis proteins (see, for example, Stoute et al. *New Engl. J. Med.,* 336:86–91, 1997).

Within preferred embodiments, an immunological fusion partner is derived from protein D, a surface protein of the gram-negative bacterium Haemophilus influenza B (WO 91/18926). Preferably, a protein D derivative comprises approximately the first third of the protein (e.g., the first N-terminal 100–110 amino acids), and a protein D derivative may be lipidated. Within certain preferred embodiments, the first 109 residues of a Lipoprotein D fusion partner is included on the N-terminus to provide the polypeptide with additional exogenous T-cell epitopes and to increase the expression level in *E. coli* (thus functioning as an expression enhancer). The lipid tail ensures optimal presentation of the antigen to antigen present cells. Other fusion partners include the non-structural protein from influenzae virus, NS1 (hemaglutinin). Typically, the N-terminal 81 amino acids are used, although different fragments that include T-helper epitopes may be used.

In another embodiment, the immunological fusion partner is the protein known as LYTA, or a portion thereof (preferably a C-terminal portion). LYTA is derived from *Streptococcus pneumoniae*, which synthesizes an N-acetyl-L-alanine amidase known as amidase LYTA (encoded by the LytA gene; *Gene* 43:265–292, 1986). LYTA is an autolysin that specifically degrades certain bonds in the peptidoglycan backbone. The C-terminal domain of the LYTA protein is responsible for the affinity to the choline or to some choline analogues such as DEAE. This property has been exploited for the development of *E. coli* C-LYTA expressing plasmids useful for expression of fusion proteins. Purification of hybrid proteins containing the C-LYTA fragment at the amino terminus has been described (see *Biotechnology* 10:795–798, 1992). Within a preferred embodiment, a repeat portion of LYTA may be incorporated into a fusion protein. A repeat portion is found in the C-terminal region starting at residue 178. A particularly preferred repeat portion incorporates residues 188–305.

In general, polypeptides (including fusion proteins) and polynucleotides as described herein are isolated. An "isolated" polypeptide or polynucleotide is one that is removed from its original environment. For example, a naturally-occurring protein is isolated if it is separated from some or all of the coexisting materials in the natural system. Preferably, such polypeptides are at least about 90% pure, more preferably at least about 95% pure and most preferably at least about 99% pure. A polynucleotide is considered to be isolated if, for example, it is cloned into a vector that is not a part of the natural environment.

Binding Agents

The present invention further provides agents, such as antibodies and antigen-binding fragments thereof, that specifically bind to an ovarian carcinoma protein. As used herein, an antibody, or antigen-binding fragment thereof, is said to "specifically bind" to an ovarian carcinoma protein if it reacts at a detectable level (within, for example, an ELISA) with an ovarian carcinoma protein, and does not react detectably with unrelated proteins under similar conditions. As used herein, "binding" refers to a noncovalent association between two separate molecules such that a "complex" is formed. The ability to bind may be evaluated by, for example, determining a binding constant for the formation of the complex. The binding constant is the value obtained when the concentration of the complex is divided by the product of the component concentrations. In general, two compounds are said to "bind," in the context of the present invention, when the binding constant for complex formation exceeds about $10^3$ L/mol. The binding constant maybe determined using methods well known in the art.

Binding agents may be further capable of differentiating between patients with and without a cancer, such as ovarian cancer, using the representative assays provided herein. In other words, antibodies or other binding agents that bind to a ovarian carcinoma antigen will generate a signal indicating the presence of a cancer in at least about 20% of patients with the disease, and will generate a negative signal indicating the absence of the disease in at least about 90% of individuals without the cancer. To determine whether a binding agent satisfies this requirement, biological samples (e.g., blood, sera, leukophoresis, urine and/or tumor biopsies) from patients with and without a cancer (as determined using standard clinical tests) may be assayed as described herein for the presence of polypeptides that bind to the binding agent. It will be apparent that a statistically significant number of samples with and without the disease should be assayed. Each binding agent should satisfy the above criteria, however, those of ordinary skill in the art will recognize that binding agents may be used in combination to improve sensitivity.

Any agent that satisfies the above requirements may be a binding agent. For example, a binding agent may be a ribosome, with or without a peptide component, an RNA molecule or a polypeptide. In a preferred embodiment, a binding agent is an antibody or an antigen-binding fragment thereof. Antibodies may be prepared by any of a variety of techniques known to those of ordinary skill in the art. See, e.g., Harlow and Lane, *Antibodies: A Laboratory Manual*, Cold Spring Harbor Laboratory, 1988. In general, antibodies can be produced by cell culture techniques, including the generation of monoclonal antibodies as described herein, or via transfection of antibody genes into suitable bacterial or mammalian cell hosts, in order to allow for the production of recombinant antibodies. In one technique, an immunogen comprising the polypeptide is initially injected into any of a wide variety of mammals (e.g., mice, rats, rabbits, sheep or goats). In this step, the polypeptides of this invention may serve as the immunogen without modification. Alternatively, particularly for relatively short polypeptides, a superior immune response may be elicited if the polypeptide is joined to a carrier protein, such as bovine serum albumin or keyhole limpet hemocyanin. The immunogen is injected into the animal host, preferably according to a predetermined schedule incorporating one or more booster immunizations, and the animals are bled periodically. Polyclonal antibodies specific for the polypeptide may then be purified from such antisera by, for example, affinity chromatography using the polypeptide coupled to a suitable solid support.

Monoclonal antibodies specific for an antigenic polypeptide of interest may be prepared, for example, using the technique of Kohler and Milstein, *Eur. J. Immunol.* 6:511–519, 1976, and improvements thereto. Briefly, these methods involve the preparation of immortal cell lines capable of producing antibodies having the desired specificity (i.e., reactivity with the polypeptide of interest). Such cell lines may be produced, for example, from spleen cells obtained from an animal immunized as described above. The spleen cells are then immortalized by, for example, fusion with a myeloma cell fusion partner, preferably one that is syngeneic with the immunized animal. A variety of fusion techniques may be employed. For example, the spleen cells and myeloma cells may be combined with a nonionic detergent for a few minutes and then plated at low density on a selective medium that supports the growth of hybrid cells, but not myeloma cells. A preferred selection technique uses HAT (hypoxanthine, aminopterin, thymidine) selection. After a sufficient time, usually about 1 to 2 weeks, colonies of hybrids are observed. Single colonies are selected and their culture supernatants tested for binding activity against the polypeptide. Hybridomas having high reactivity and specificity are preferred.

Monoclonal antibodies may be isolated from the supernatants of growing hybridoma colonies. In addition, various techniques may be employed to enhance the yield, such as injection of the hybridoma cell line into the peritoneal cavity of a suitable vertebrate host, such as a mouse. Monoclonal antibodies may then be harvested from the ascites fluid or the blood. Contaminants may be removed from the antibodies by conventional techniques, such as chromatography, gel filtration, precipitation, and extraction. The polypeptides of this invention may be used in the purification process in, for example, an affinity chromatography step.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988) and digested by papain to yield Fab and Fc fragments. The Fab and Fc fragments may be separated by affinity chromatography on protein A bead columns.

Monoclonal antibodies of the present invention may be coupled to one or more therapeutic agents. Suitable agents in this regard include radionuclides, differentiation inducers, drugs, toxins, and derivatives thereof. Preferred radionuclides include $^{90}Y$, $^{123}I$, $^{125}I$, $^{131}I$, $^{186}Re$, $^{188}Re$, $^{211}At$, and $^{212}Bi$. Preferred drugs include methotrexate, and pyrimidine and purine analogs. Preferred differentiation inducers include phorbol esters and butyric acid. Preferred toxins include ricin, abrin, diptheria toxin, cholera toxin, gelonin, Pseudomonas exotoxin, Shigella toxin, and pokeweed antiviral protein.

A therapeutic agent may be coupled (e.g., covalently bonded) to a suitable monoclonal antibody either directly or indirectly (e.g., via a linker group). A direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

Alternatively, it may be desirable to couple a therapeutic agent and an antibody via a linker group. A linker group can function as a spacer to distance an antibody from an agent in order to avoid interference with binding capabilities. A linker group can also serve to increase the chemical reactivity of a substituent on an agent or an antibody, and thus increase the coupling efficiency. An increase in chemical reactivity may also facilitate the use of agents, or functional groups on agents, which otherwise would not be possible.

It will be evident to those skilled in the art that a variety of bifunctional or polyfunctional reagents, both homo- and hetero-functional (such as those described in the catalog of the Pierce Chemical Co., Rockford, Ill.), may be employed as the linker group. Coupling may be effected, for example, through amino groups, carboxyl groups, sulfhydryl groups or oxidized carbohydrate residues. There are numerous references describing such methodology, e.g., U.S. Pat. No. 4,671,958, to Rodwell et al.

Where a therapeutic agent is more potent when free from the antibody portion of the immunoconjugates of the present invention, it may be desirable to use a linker group which is cleavable during or upon internalization into a cell. A number of different cleavable linker groups have been described. The mechanisms for the intracellular release of an agent from these linker groups include cleavage by reduction of a disulfide bond (e.g., U.S. Pat. No. 4,489,710, to Spitler), by irradiation of a photolabile bond (e.g., U.S. Pat. No. 4,625,014, to Senter et al.), by hydrolysis of derivatized amino acid side chains (e.g., U.S. Pat. No. 4,638,045, to Kohn et al.), by serum complement-mediated hydrolysis (e.g., U.S. Pat. No. 4,671,958, to Rodwell et al.), and acid-catalyzed hydrolysis (e.g., U.S. Pat. No. 4,569,789, to Blattler et al.).

It may be desirable to couple more than one agent to an antibody. In one embodiment, multiple molecules of an agent are coupled to one antibody molecule. In another embodiment, more than one type of agent may be coupled to one antibody. Regardless of the particular embodiment, immunoconjugates with more than one agent may be prepared in a variety of ways. For example, more than one agent may be coupled directly to an antibody molecule, or linkers which provide multiple sites for attachment can be used. Alternatively, a carrier can be used.

A carrier may bear the agents in a variety of ways, including covalent bonding either directly or via a linker group. Suitable carriers include proteins such as albumins (e.g., U.S. Pat. No. 4,507,234, to Kato et al.), peptides and polysaccharides such as aminodextran (e.g., U.S. Pat. No. 4,699,784, to Shih et al.). A carrier may also bear an agent by noncovalent bonding or by encapsulation, such as within a liposome vesicle (e.g., U.S. Pat. Nos. 4,429,008 and 4,873,088). Carriers specific for radionuclide agents include radiohalogenated small molecules and chelating compounds. For example, U.S. Pat. No. 4,735,792 discloses representative radiohalogenated small molecules and their synthesis. A radionuclide chelate may be formed from chelating compounds that include those containing nitrogen and sulfur atoms as the donor atoms for binding the metal, or metal oxide, radionuclide. For example, U.S. Pat. No. 4,673,562, to Davison et al. discloses representative chelating compounds and their synthesis.

A variety of routes of administration for the antibodies and immunoconjugates may be used. Typically, administration will be intravenous, intramuscular, subcutaneous or in the bed of a resected tumor. It will be evident that the precise dose of the antibody/immunoconjugate will vary depending upon the antibody used, the antigen density on the tumor, and the rate of clearance of the antibody.

Also provided herein are anti-idiotypic antibodies that mimic an immunogenic portion of an ovarian carcinoma protein. Such antibodies may be raised against an antibody, or antigen-binding fragment thereof, that specifically binds to an immunogenic portion of an ovarian carcinoma protein, using well known techniques. Anti-idiotypic antibodies that mimic an immunogenic portion of an ovarian carcinoma protein are those antibodies that bind to an antibody, or antigen-binding fragment thereof, that specifically binds to an immunogenic portion of an ovarian carcinoma protein, as described herein.

T Cells

Immunotherapeutic compositions may also, or alternatively, comprise T cells specific for an ovarian carcinoma protein. Such cells may generally be prepared in vitro or ex vivo, using standard procedures. For example, T cells may be present within (or isolated from) bone marrow, peripheral blood or a fraction of bone marrow or peripheral blood of a mammal, such as a patient, using a commercially available cell separation system, such as the CEPRATE™ system, available from CellPro Inc., Bothell Wash. (see also U.S. Pat. No. 5,240,856; U.S. Pat. No. 5,215,926; WO 89/06280; WO 91/16116 and WO 92/07243). Alternatively, T cells may be derived from related or unrelated humans, non-human animals, cell lines or cultures.

T cells may be stimulated with an ovarian carcinoma polypeptide, polynucleotide encoding an ovarian carcinoma polypeptide and/or an antigen presenting cell (APC) that expresses such a polypeptide. Such stimulation is performed under conditions and for a time sufficient to permit the generation of T cells that are specific for the polypeptide. Preferably, an ovarian carcinoma polypeptide or polynucleotide is present within a delivery vehicle, such as a microsphere, to facilitate the generation of specific T cells.

T cells are considered to be specific for an ovarian carcinoma polypeptide if the T cells kill target cells coated with an ovarian carcinoma polypeptide or expressing a gene encoding such a polypeptide. T cell specificity may be evaluated using any of a variety of standard techniques. For example, within a chromium release assay or proliferation assay, a stimulation index of more than two fold increase in lysis and/or proliferation, compared to negative controls, indicates T cell specificity. Such assays may be performed, for example, as described in Chen et al., *Cancer Res.* 54:1065–1070, 1994. Alternatively, detection of the proliferation of T cells may be accomplished by a variety of known techniques. For example, T cell proliferation can be detected by measuring an increased rate of DNA synthesis (e.g., by pulse-labeling cultures of T cells with tritiated thymidine and measuring the amount of tritiated thymidine incorporated into DNA). Contact with an ovarian carcinoma polypeptide (200 ng/ml–100 $\mu$g/ml, preferably 100 ng/ml–25 $\mu$g/ml) for 3–7 days should result in at least a two fold increase in proliferation of the T cells and/or contact as described above for 2–3 hours should result in activation of the T cells, as measured using standard cytokine assays in which a two fold increase in the level of cytokine release (e.g., TNF or IFN-$\gamma$) is indicative of T cell activation (see Coligan et al., Current Protocols in Immunology, vol. 1, Wiley Interscience (Greene 1998). T cells that have been activated in response to an ovarian carcinoma polypeptide, polynucleotide or ovarian carcinoma polypeptide-expressing APC may be $CD4^+$ and/or $CD8^+$. Ovarian carcinoma polypeptide-specific T cells may be expanded using standard techniques. Within preferred embodiments, the T cells are derived from a patient or a related or unrelated donor and are administered to the patient following stimulation and expansion.

For therapeutic purposes, $CD4^+$ or $CD8^+$ T cells that proliferate in response to an ovarian carcinoma polypeptide, polynucleotide or APC can be expanded in number either in vitro or in vivo. Proliferation of such T cells in vitro may be accomplished in a variety of ways. For example, the T cells can be re-exposed to an ovarian carcinoma polypeptide, with or without the addition of T cell growth factors, such as interleukin-2, and/or stimulator cells that synthesize an ovarian carcinoma polypeptide. Alternatively, one or more T cells that proliferate in the presence of an ovarian carcinoma polypeptide can be expanded in number by cloning. Methods for cloning cells are well known in the art, and include limiting dilution. Following expansion, the cells may be administered back to the patient as described, for example, by Chang et al., *Crit. Rev. Oncol. Hematol.* 22:213, 1996.

Pharmaceutical Compositions and Vaccines

Within certain aspects, polypeptides, polynucleotides, binding agents and/or immune system cells as described herein may be incorporated into pharmaceutical compositions or vaccines. Pharmaceutical compositions comprise one or more such compounds or cells and a physiologically acceptable carrier. Vaccines may comprise one or more such compounds or cells and a non-specific immune response enhancer. A non-specific immune response enhancer may be any substance that enhances an immune response to an exogenous antigen. Examples of non-specific immune response enhancers include adjuvants, biodegradable microspheres (e.g., polylactic galactide) and liposomes (into which the compound is incorporated; see e.g., Fullerton, U.S. Pat. No. 4,235,877). Vaccine preparation is generally described in, for example, M. F. Powell and M. J. Newman, eds., "Vaccine Design (the subunit and adjuvant approach)," Plenum Press (NY, 1995). Pharmaceutical compositions and vaccines within the scope of the present invention may also contain other compounds, which may be biologically active or inactive. For example, one or more immunogenic portions of other tumor antigens may be present, either incorporated into a fusion polypeptide or as a separate compound within the composition or vaccine.

A pharmaceutical composition or vaccine may contain DNA encoding one or more of the polypeptides as described above, such that the polypeptide is generated in situ. As noted above, the DNA may be present within any of a variety of delivery systems known to those of ordinary skill in the art, including nucleic acid expression systems, bacteria and viral expression systems. Appropriate nucleic acid expression systems contain the necessary DNA sequences for expression in the patient (such as a suitable promoter and terminating signal). Bacterial delivery systems involve the administration of a bacterium (such as Bacillus-Calmette- Guerrin) that expresses an immunogenic portion of the polypeptide on its cell surface. In a preferred embodiment, the DNA may be introduced using a viral expression system (e.g., vaccinia or other pox virus, retrovirus, or adenovirus), which may involve the use of a non-pathogenic (defective), replication competent virus. Suitable systems are disclosed, for example, in Fisher-Hoch et al., *PNAS* 86:317–321, 1989; Flexner et al., *Ann. N.Y. Acad. Sci.* 569:86–103, 1989; Flexner et al., *Vaccine* 8:17–21, 1990; U.S. Pat. Nos. 4,603,112, 4,769,330, and 5,017,487; WO 89/01973; U.S. Pat. No. 4,777,127; GB 2,200,651; EP 0,345,242; WO 91/02805; Berkner, *Biotechniques* 6:616–627, 1988; Rosenfeld et al., *Science* 252:431–434, 1991; Kolls et al., *PNAS* 91:215–219, 1994; Kass-Eisler et al., *PNAS* 90:11498–11502, 1993; Guzman et al., *Circulation* 88:2838–2848, 1993; and Guzman et al., *Cir. Res.* 73:1202–1207, 1993. Techniques for incorporating DNA into such expression systems are well known to those of ordinary skill in the art. The DNA may also be "naked," as described, for example, in Ulmer et al., *Science* 259:1745–1749, 1993 and reviewed by Cohen, *Science* 259:1691–1692, 1993. The uptake of naked DNA may be increased by coating the DNA onto biodegradable beads, which are efficiently transported into the cells.

While any suitable carrier known to those of ordinary skill in the art may be employed in the pharmaceutical compositions of this invention, the type of carrier will vary depending on the mode of administration. Compositions of the present invention may be formulated for any appropriate manner of administration, including for example, topical, oral, nasal, intravenous, intracranial, intraperitoneal, subcutaneous or intramuscular administration. For parenteral administration, such as subcutaneous injection, the carrier preferably comprises water, saline, alcohol, a fat, a wax or a buffer. For oral administration, any of the above carriers or a solid carrier, such as mannitol, lactose, starch, magnesium stearate, sodium saccharine, talcum, cellulose, glucose, sucrose, and magnesium carbonate, may be employed. Biodegradable microspheres (e.g., polylactate polyglycolate) may also be employed as carriers for the pharmaceutical compositions of this invention. Suitable biodegradable microspheres are disclosed, for example, in U.S. Pat. Nos. 4,897,268 and 5,075,109.

Such compositions may also comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Alternatively, compositions of the present invention may be formulated as a lyophilizate. Compounds may also be encapsulated within liposomes using well known technology.

Any of a variety of non-specific immune response enhancers may be employed in the vaccines of this invention. For example, an adjuvant may be included. Most adjuvants contain a substance designed to protect the antigen from rapid catabolism, such as aluminum hydroxide or mineral oil, and a stimulator of immune responses, such as lipid A, *Bortadella pertussis* or *Mycobacterium tuberculosis* derived proteins. Suitable adjuvants are commercially available as, for example, Freund's Incomplete Adjuvant and Complete Adjuvant (Difco Laboratories, Detroit, Mich.), Merck Adjuvant 65 (Merck and Company, Inc., Rahway, N.J.), alum, biodegradable microspheres, monophosphoryl lipid A and quil A. Cytokines, such as GM-CSF or interleukin-2, -7, or -12, may also be used as adjuvants.

Within the vaccines provided herein, the adjuvant composition is preferably designed to induce an immune response predominantly of the Th1 type. High levels of Th1-type cytokines (e.g., IFN-γ, IL-2 and IL-12) tend to favor the induction of cell mediated immune responses to an administered antigen. In contrast, high levels of Th2-type cytokines (e.g., IL-4, IL-5, IL-6, IL-10 and TNF-β) tend to favor the induction of humoral immune responses. Following application of a vaccine as provided herein, a patient will support an immune response that includes Th1- and Th2-type responses. Within a preferred embodiment, in which a response is predominantly Th1-type, the level of Th1-type cytokines will increase to a greater extent than the level of Th2-type cytokines. The levels of these cytokines may be readily assessed using standard assays. For a review of the families of cytokines, see Mosmann and Coffman, *Ann. Rev. Immunol.* 7:145–173, 1989.

Preferred adjuvants for use in eliciting a predominantly Th1-type response include, for example, a combination of monophosphoryl lipid A, preferably 3-de-O-acylated monophosphoryl lipid A (3D-MPL), together with an aluminum salt. MPL adjuvants are available from Ribi ImmunoChem Research Inc. (Hamilton, Mont.; see U.S. Pat. Nos. 4,436,727; 4,877,611; 4,866,034 and 4,912,094). Also preferred is AS-2 (SmithKline Beecham). CpG-containing oligonucleotides (in which the CpG dinucleotide is unmethylated) also induce a predominantly Th1 response. Such oligonucleotides are well known and are described, for example, in WO 96/02555. Another preferred adjuvant is a saponin, preferably QS21, which may be used alone or in combination with other adjuvants. For example, an enhanced system involves the combination of a monophosphoryl lipid A and saponin derivative, such as the combination of QS21 and 3D-MPL as described in WO 94/00153, or a less reactogenic composition where the QS21 is quenched with cholesterol, as described in WO 96/33739. Other preferred formulations comprises an oil-in-water emulsion and tocopherol. A particularly potent adjuvant formulation involving QS21, 3D-MPL and tocopherol in an oil-in-water emulsion is described in WO 95/17210. Any vaccine provided herein may be prepared using well known methods that result in a combination of antigen, immune response enhancer and a suitable carrier or excipient.

The compositions described herein may be administered as part of a sustained release formulation (i.e., a formulation such as a capsule or sponge that effects a slow release of compound following administration). Such formulations may generally be prepared using well known technology and administered by, for example, oral, rectal or subcutaneous implantation, or by implantation at the desired target site. Sustained-release formulations may contain a polypeptide, polynucleotide or antibody dispersed in a carrier matrix and/or contained within a reservoir surrounded by a rate controlling membrane. Carriers for use within such formulations are biocompatible, and may also be biodegradable; preferably the formulation provides a relatively constant level of active component release. The amount of active compound contained within a sustained release formulation depends upon the site of implantation, the rate and expected duration of release and the nature of the condition to be treated or prevented.

Any of a variety of delivery vehicles may be employed within pharmaceutical compositions and vaccines to facilitate production of an antigen-specific immune response that targets tumor cells. Delivery vehicles include antigen presenting cells (APCs), such as dendritic cells, macrophages, B cells, monocytes and other cells that may be engineered to be efficient APCs. Such cells may, but need not, be genetically modified to increase the capacity for presenting the antigen, to improve activation and/or maintenance of the T cell response, to have anti-tumor effects per se and/or to be immunologically compatible with the receiver (i.e., matched HLA haplotype). APCs may generally be isolated from any of a variety of biological fluids and organs, including tumor and peritumoral tissues, and may be autologous, allogeneic, syngeneic or xenogeneic cells.

Certain preferred embodiments of the present invention use dendritic cells or progenitors thereof as antigen-presenting cells. Dendritic cells are highly potent APCs (Banchereau and Steinman, *Nature* 392:245–251, 1998) and have been shown to be effective as a physiological adjuvant for eliciting prophylactic or therapeutic antitumor immunity (see Timmerman and Levy, *Ann. Rev. Med.* 50:507–529, 1999). In general, dendritic cells may be identified based on their typical shape (stellate in situ, with marked cytoplasmic processes (dendrites) visible in vitro) and based on the lack of differentiation markers of B cells (CD19 and CD20), T cells (CD3), monocytes (CD14) and natural killer cells (CD56), as determined using standard assays. Dendritic cells may, of course, be engineered to express specific cell-surface receptors or ligands that are not commonly found on dendritic cells in vivo or ex vivo, and such modified dendritic cells are contemplated by the present invention. As an alternative to dendritic cells, secreted vesicles antigen-loaded dendritic cells (called exosomes) may be used within a vaccine (see Zitvogel et al., *Nature Med* 4:594–600, 1998).

Dendritic cells and progenitors may be obtained from peripheral blood, bone marrow, tumor-infiltrating cells, peritumoral tissues-infiltrating cells, lymph nodes, spleen, skin, umbilical cord blood or any other suitable tissue or fluid. For example, dendritic cells may be differentiated ex vivo by adding a combination of cytokines such as GM-CSF, IL-4, IL-13 and/or TNFα to cultures of monocytes harvested from peripheral blood. Alternatively, CD34 positive cells harvested from peripheral blood, umbilical cord blood or bone marrow may be differentiated into dendritic cells by adding to the culture medium combinations of GM-CSF, IL-3, TNFα, CD40 ligand, LPS, flt3 ligand and/or other compound(s) that induce maturation and proliferation of dendritic cells.

Dendritic cells are conveniently categorized as “immature” and “mature” cells, which allows a simple way to discriminate between two well characterized phenotypes. However, this nomenclature should not be construed to exclude all possible intermediate stages of differentiation. Immature dendritic cells are characterized as APC with a high capacity for antigen uptake and processing, which correlates with the high expression of Fcγ receptor, mannose receptor and DEC-205 marker. The mature phenotype is typically characterized by a lower expression of these markers, but a high expression of cell surface molecules responsible for T cell activation such as class I and class II MHC, adhesion molecules (e.g., CD54 and CD11) and costimulatory molecules (e.g., CD40, CD80 and CD86).

APCs may generally be transfected with a polynucleotide encoding a ovarian carcinoma antigen (or portion or other variant thereof) such that the antigen, or an immunogenic portion thereof, is expressed on the cell surface. Such transfection may take place ex vivo, and a composition or vaccine comprising such transfected cells may then be used for therapeutic purposes, as described herein. Alternatively, a gene delivery vehicle that targets a dendritic or other antigen presenting cell may be administered to a patient, resulting in transfection that occurs in vivo. In vivo and ex vivo transfection of dendritic cells, for example, may generally be performed using any methods known in the art, such as those described in WO 97/24447, or the gene gun approach described by Mahvi et al., *Immunology and cell Biology* 75:456–460, 1997. Antigen loading of dendritic cells may be achieved by incubating dendritic cells or progenitor cells with the polypeptide, DNA (naked or within a plasmid vector) or RNA; or with antigen-expressing recombinant bacterium or viruses (e.g., vaccinia, fowlpox, adenovirus or lentivirus vectors). Prior to loading, the polypeptide may be covalently conjugated to an immunological partner that provides T cell help (e.g., a carrier molecule). Alternatively, a dendritic cell may be pulsed with a non-conjugated immunological partner, separately or in the presence of the polypeptide.

Cancer Therapy

In further aspects of the present invention, the compositions described herein may be used for immunotherapy of cancer, such as ovarian cancer. Within such methods, pharmaceutical compositions and vaccines are typically administered to a patient. As used herein, a “patient” refers to any warm-blooded animal, preferably a human. A patient may or may not be afflicted with cancer. Accordingly, the above pharmaceutical compositions and vaccines may be used to prevent the development of a cancer or to treat a patient afflicted with a cancer. Within certain preferred embodiments, a patient is afflicted with ovarian cancer. Such cancer may be diagnosed using criteria generally accepted in the art, including the presence of a malignant tumor. Pharmaceutical compositions and vaccines may be administered either prior to or following surgical removal of primary tumors and/or treatment such as administration of radiotherapy or conventional chemotherapeutic drugs.

Within certain embodiments, immunotherapy may be active immunotherapy, in which treatment relies on the in vivo stimulation of the endogenous host immune system to react against tumors with the administration of immuno response-modifying agents (such as tumor vaccines, bacterial adjuvants and/or cytokines).

Within other embodiments, immunotherapy may be passive immunotherapy, in which treatment involves the delivery of agents with established tumor-immune reactivity (such as effector cells or antibodies) that can directly or indirectly mediate antitumor effects and does not necessarily depend on an intact host immune system. Examples of effector cells include T lymphocytes (such as $CD8^+$ cytotoxic T lymphocytes and $CD4^+$ T-helper tumor-infiltrating lymphocytes), killer cells (such as Natural Killer cells and lymphokine-activated killer cells), B cells and antigen-presenting cells (such as dendritic cells and macrophages) expressing a polypeptide provided herein. T cell receptors and antibody receptors specific for the polypeptides recited herein may be cloned, expressed and transferred into other vectors or effector cells for adoptive immunotherapy. The polypeptides provided herein may also be used to generate antibodies or anti-idiotypic antibodies (as described above and in U.S. Pat. No. 4,918,164) for passive immunotherapy.

Effector cells may generally be obtained in sufficient quantities for adoptive immunotherapy by growth in vitro, as described herein. Culture conditions for expanding single antigen-specific effector cells to several billion in number with retention of antigen recognition in vivo are well known in the art. Such in vitro culture conditions typically use intermittent stimulation with antigen, often in the presence of cytokines (such as IL-2) and non-dividing feeder cells. As noted above, immunoreactive polypeptides as provided herein may be used to rapidly expand antigen-specific T cell cultures in order to generate a sufficient number of cells for immunotherapy. In particular, antigen-presenting cells, such as dendritic, macrophage or B cells, may be pulsed with immunoreactive polypeptides or transfected with one or more polynucleotides using standard techniques well known in the art. For example, antigen-presenting cells can be transfected with a polynucleotide having a promoter appropriate for increasing expression in a recombinant virus or other expression system. Cultured effector cells for use in therapy must be able to grow and distribute widely, and to survive long term in vivo. Studies have shown that cultured effector cells can be induced to grow in vivo and to survive long term in substantial numbers by repeated stimulation with antigen supplemented with IL-2 (see, for example, Cheever et al., *Immunological Reviews* 157:177, 1997).

Alternatively, a vector expressing a polypeptide recited herein may be introduced into stem cells taken from a patient and clonally propagated in vitro for autologous transplant back into the same patient.

Routes and frequency of administration, as well as dosage, will vary from individual to individual, and may be readily established using standard techniques. In general, the pharmaceutical compositions and vaccines may be administered by injection (e.g., intracutaneous, intramuscular, intravenous or subcutaneous), intranasally (e.g., by aspiration), orally or in the bed of a resected tumor. Preferably, between 1 and 10 doses may be administered over a 52 week period. Preferably, 6 doses are administered, at intervals of 1 month, and booster vaccinations may be given periodically thereafter. Alternate protocols may be appropriate for individual patients. A suitable dose is an amount of a compound that, when administered as described above, is capable of promoting an anti-tumor immune response, and is at least 10–50% above the basal (i.e., untreated) level. Such response can be monitored by measuring the anti-tumor antibodies in a patient or by vaccine-dependent generation of cytolytic effector cells capable of killing the patient's tumor cells in vitro. Such vaccines should also be capable of causing an immune response that leads to an improved clinical outcome (e.g., more frequent remissions, complete or partial or longer disease-free survival) in vaccinated patients as compared to non-vaccinated patients. In general, for pharmaceutical compositions and vaccines comprising one or more polypeptides, the amount of each polypeptide present in a dose ranges from about 100 $\mu$g to 5 mg per kg of host. Suitable dose sizes will vary with the size of the patient, but will typically range from about 0.1 mL to about 5 mL.

In general, an appropriate dosage and treatment regimen provides the active compound(s) in an amount sufficient to provide therapeutic and/or prophylactic benefit. Such a response can be monitored by establishing an improved clinical outcome (e.g., more frequent remissions, complete or partial, or longer disease-free survival) in treated patients as compared to non-treated patients. Increases in preexisting immune responses to an ovarian carcinoma antigen generally correlate with an improved clinical outcome. Such immune responses may generally be evaluated using standard proliferation, cytotoxicity or cytokine assays, which may be performed using samples obtained from a patient before and after treatment.

Screens for Identifying Secreted Ovarian Carcinoma Antigens

The present invention provides methods for identifying secreted tumor antigens. Within such methods, tumors are implanted into immunodeficient animals such as SCID mice and maintained for a time sufficient to permit secretion of tumor antigens into serum. In general, tumors may be implanted subcutaneously or within the gonadal fat pad of an immunodeficient animal and maintained for 1–9 months, preferably 1–4 months. Implantation may generally be performed as described in WO 97/18300. The serum containing secreted antigens is then used to prepare antisera in immunocompetent mice, using standard techniques and as described herein. Briefly, 50–100 $\mu$L of sera (pooled from three sets of immunodeficient mice, each set bearing a different SCID-derived human ovarian tumor) may be mixed 1:1 (vol:vol) with an appropriate adjuvant, such as RIBI-MPL or MPL+TDM (Sigma Chemical Co., St. Louis, Mo.) and injected intraperitoneally into syngeneic immunocompetent animals at monthly intervals for a total of 5 months. Antisera from animals immunized in such a manner may be obtained by drawing blood after the third, fourth and fifth immunizations. The resulting antiserum is generally precleared of *E. coli* and phage antigens and used (generally following dilution, such as 1:200) in a serological expression screen.

The library is typically an expression library containing cDNAs from one or more tumors of the type that was implanted into SCID mice. This expression library may be prepared in any suitable vector, such as λ-screen (Novagen). cDNAs that encode a polypeptide that reacts with the antiserum may be identified using standard techniques, and sequenced. Such cDNA molecules may be further characterized to evaluate expression in tumor and normal tissue, and to evaluate antigen secretion in patients.

The methods provided herein have advantages over other methods for tumor antigen discovery. In particular, all antigens identified by such methods should be secreted or released through necrosis of the tumor cells. Such antigens may be present on the surface of tumor cells for an amount of time sufficient to permit targeting and killing by the immune system, following vaccination.

Methods for Detecting Cancer

In general, a cancer may be detected in a patient based on the presence of one or more ovarian carcinoma proteins and/or polynucleotides encoding such proteins in a biological sample (such as blood, sera, urine and/or tumor biopsies) obtained from the patient. In other words, such proteins may be used as markers to indicate the presence or absence of a cancer such as ovarian cancer. In addition, such proteins may be useful for the detection of other cancers. The binding agents provided herein generally permit detection of the level of protein that binds to the agent in the biological sample. Polynucleotide primers and probes may be used to detect the level of mRNA encoding a tumor protein, which is also indicative of the presence or absence of a cancer. In general, an ovarian carcinoma-associated sequence should be present at a level that is at least three fold higher in tumor tissue than in normal tissue There are a variety of assay formats known to those of ordinary skill in the art for using a binding agent to detect polypeptide markers in a sample. See, e.g., Harlow and Lane, *Antibodies: A Laboratory Manual*, Cold Spring Harbor Laboratory, 1988. In general, the presence or absence of a cancer in a patient may be determined by (a) contacting a biological sample obtained from a patient with a binding agent; (b) detecting in the sample a level of polypeptide that binds to the binding agent; and (c) comparing the level of polypeptide with a predetermined cut-off value.

In a preferred embodiment, the assay involves the use of binding agent immobilized on a solid support to bind to and remove the polypeptide from the remainder of the sample. The bound polypeptide may then be detected using a detection reagent that contains a reporter group and specifically binds to the binding agent/polypeptide complex. Such detection reagents may comprise, for example, a binding agent that specifically binds to the polypeptide or an antibody or other agent that specifically binds to the binding agent, such as an anti-immunoglobulin, protein G, protein A or a lectin. Alternatively, a competitive assay may be utilized, in which a polypeptide is labeled with a reporter group and allowed to bind to the immobilized binding agent after incubation of the binding agent with the sample. The extent to which components of the sample inhibit the binding of the labeled polypeptide to the binding agent is indicative of the reactivity of the sample with the immobilized binding agent. Suitable polypeptides for use within such assays include full length ovarian carcinoma proteins and portions thereof to which the binding agent binds, as described above.

The solid support may be any material known to those of ordinary skill in the art to which the tumor protein may be attached. For example, the solid support may be a test well in a microtiter plate or a nitrocellulose or other suitable membrane. Alternatively, the support may be a bead or disc, such as glass, fiberglass, latex or a plastic material such as polystyrene or polyvinylchloride. The support may also be a magnetic particle or a fiber optic sensor, such as those disclosed, for example, in U.S. Pat. No. 5,359,681. The binding agent may be immobilized on the solid support using a variety of techniques known to those of skill in the art, which are amply described in the patent and scientific literature. In the context of the present invention, the term "immobilization" refers to both noncovalent association, such as adsorption, and covalent attachment (which may be a direct linkage between the agent and functional groups on the support or may be a linkage by way of a cross-linking agent). Immobilization by adsorption to a well in a microtiter plate or to a membrane is preferred. In such cases, adsorption may be achieved by contacting the binding agent, in a suitable buffer, with the solid support for a suitable amount of time. The contact time varies with temperature, but is typically between about 1 hour and about 1 day. In general, contacting a well of a plastic microtiter plate (such as polystyrene or polyvinylchloride) with an amount of binding agent ranging from about 10 ng to about 10 μg, and preferably about 100 ng to about 1 μg, is sufficient to immobilize an adequate amount of binding agent.

Covalent attachment of binding agent to a solid support may generally be achieved by first reacting the support with a bifunctional reagent that will react with both the support and a functional group, such as a hydroxyl or amino group, on the binding agent. For example, the binding agent may be covalently attached to supports having an appropriate polymer coating using benzoquinone or by condensation of an aldehyde group on the support with an amine and an active hydrogen on the binding partner (see, e.g., Pierce Immunotechnology Catalog and Handbook, 1991, at A12–A13).

In certain embodiments, the assay is a two-antibody sandwich assay. This assay may be performed by first contacting an antibody that has been immobilized on a solid support, commonly the well of a microtiter plate, with the sample, such that polypeptides within the sample are allowed to bind to the immobilized antibody. Unbound sample is then removed from the immobilized polypeptide-antibody complexes and a detection reagent (preferably a second antibody capable of binding to a different site on the polypeptide) containing a reporter group is added. The amount of detection reagent that remains bound to the solid support is then determined using a method appropriate for the specific reporter group.

More specifically, once the antibody is immobilized on the support as described above, the remaining protein binding sites on the support are typically blocked. Any suitable blocking agent known to those of ordinary skill in the art, such as bovine serum albumin or Tween 20™ (Sigma Chemical Co., St. Louis, Mo.). The immobilized antibody is then incubated with the sample, and polypeptide is allowed to bind to the antibody. The sample may be diluted with a suitable diluent, such as phosphate-buffered saline (PBS) prior to incubation. In general, an appropriate contact time (i.e., incubation time) is a period of time that is sufficient to detect the presence of polypeptide within a sample obtained from an individual with ovarian cancer. Preferably, the contact time is sufficient to achieve a level of binding that is at least about 95% of that achieved at equilibrium between bound and unbound polypeptide. Those of ordinary skill in the art will recognize that the time necessary to achieve equilibrium may be readily determined by assaying the level of binding that occurs over a period of time. At room temperature, an incubation time of about 30 minutes is generally sufficient.

Unbound sample may then be removed by washing the solid support with an appropriate buffer, such as PBS containing 0.1% Tween 20™. The second antibody, which contains a reporter group, may then be added to the solid support. Preferred reporter groups include those groups recited above.

The detection reagent is then incubated with the immobilized antibody-polypeptide complex for an amount of time sufficient to detect the bound polypeptide. An appropriate amount of time may generally be determined by assaying the level of binding that occurs over a period of time. Unbound detection reagent is then removed and bound detection reagent is detected using the reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products.

To determine the presence or absence of a cancer, such as ovarian cancer, the signal detected from the reporter group that remains bound to the solid support is generally compared to a signal that corresponds to a predetermined cut-off value. In one preferred embodiment, the cut-off value for the detection of a cancer is the average mean signal obtained when the immobilized antibody is incubated with samples from patients without the cancer. In general, a sample generating a signal that is three standard deviations above the predetermined cut-off value is considered positive for the cancer. In an alternate preferred embodiment, the cut-off value is determined using a Receiver Operator Curve, according to the method of Sackett et al., *Clinical Epidemiology: A Basic Science for Clinical Medicine*, Little Brown and Co., 1985, p. 106–7. Briefly, in this embodiment, the cut-off value may be determined from a plot of pairs of true positive rates (i.e., sensitivity) and false positive rates (100%-specificity) that correspond to each possible cut-off value for the diagnostic test result. The cut-off value on the plot that is the closest to the upper left-hand corner (i.e., the value that encloses the largest area) is the most accurate cut-off value, and a sample generating a signal that is higher than the cut-off value determined by this method may be considered positive. Alternatively, the cut-off value may be shifted to the left along the plot, to minimize the false positive rate, or to the right, to minimize the false negative rate. In general, a sample generating a signal that is higher than the cut-off value determined by this method is considered positive for a cancer.

In a related embodiment, the assay is performed in a flow-through or strip test format, wherein the binding agent is immobilized on a membrane, such as nitrocellulose. In the flow-through test, polypeptides within the sample bind to the immobilized binding agent as the sample passes through the membrane. A second, labeled binding agent then binds to the binding agent-polypeptide complex as a solution containing the second binding agent flows through the membrane. The detection of bound second binding agent may then be performed as described above. In the strip test format, one end of the membrane to which binding agent is bound is immersed in a solution containing the sample. The sample migrates along the membrane through a region containing second binding agent and to the area of immobilized binding agent. Concentration of second binding agent at the area of immobilized antibody indicates the presence of a cancer. Typically, the concentration of second binding agent at that site generates a pattern, such as a line, that can be read visually. The absence of such a pattern indicates a negative result. In general, the amount of binding agent immobilized on the membrane is selected to generate a visually discernible pattern when the biological sample contains a level of polypeptide that would be sufficient to generate a positive signal in the two-antibody sandwich assay, in the format discussed above. Preferred binding agents for use in such assays are antibodies and antigen-binding fragments thereof Preferably, the amount of antibody immobilized on the membrane ranges from about 25 ng to about 1 $\mu$g, and more preferably from about 50 ng to about 500 ng. Such tests can typically be performed with a very small amount of biological sample.

Of course, numerous other assay protocols exist that are suitable for use with the tumor proteins or binding agents of the present invention. The above descriptions are intended to be exemplary only. For example, it will be apparent to those of ordinary skill in the art that the above protocols may be readily modified to use ovarian carcinoma polypeptides to detect antibodies that bind to such polypeptides in a biological sample. The detection of such ovarian carcinoma protein specific antibodies may correlate with the presence of a cancer.

A cancer may also, or alternatively, be detected based on the presence of T cells that specifically react with an ovarian carcinoma protein in a biological sample. Within certain methods, a biological sample comprising $CD4^+$ and/or $CD8^+$ T cells isolated from a patient is incubated with an ovarian carcinoma protein, a polynucleotide encoding such a polypeptide and/or an APC that expresses at least an immunogenic portion of such a polypeptide, and the presence or absence of specific activation of the T cells is detected. Suitable biological samples include, but are not limited to, isolated T cells. For example, T cells may be isolated from a patient by routine techniques (such as by Ficoll/Hypaque density gradient centrifugation of peripheral blood lymphocytes). T cells may be incubated in vitro for 2–9 days (typically 4 days) at 37° C. with an ovarian carcinoma protein (e.g, 5–25 $\mu$g/ml). It may be desirable to incubate another aliquot of a T cell sample in the absence of ovarian carcinoma protein to serve as a control. For $CD4^+$ T cells, activation is preferably detected by evaluating proliferation of the T cells. For $CD8^+$ T cells, activation is preferably detected by evaluating cytolytic activity. A level of proliferation that is at least two fold greater and/or a level of cytolytic activity that is at least 20% greater than in disease-free patients indicates the presence of a cancer in the patient.

As noted above, a cancer may also, or alternatively, be detected based on the level of mRNA encoding an ovarian carcinoma protein in a biological sample. For example, at least two oligonucleotide primers may be employed in a polymerase chain reaction (PCR) based assay to amplify a portion of an ovarian carcinoma protein cDNA derived from a biological sample, wherein at least one of the oligonucleotide primers is specific for (i.e., hybridizes to) a polynucleotide encoding the ovarian carcinoma protein. The amplified cDNA is then separated and detected using techniques well known in the art, such as gel electrophoresis. Similarly, oligonucleotide probes that specifically hybridize to a polynucleotide encoding an ovarian carcinoma protein may be used in a hybridization assay to detect the presence of polynucleotide encoding the tumor protein in a biological sample.

To permit hybridization under assay conditions, oligonucleotide primers and probes should comprise an oligonucleotide sequence that has at least about 60%, preferably at least about 75% and more preferably at least about 90%, identity to a portion of a polynucleotide encoding an ovarian carcinoma protein that is at least 10 nucleotides, and preferably at least 20 nucleotides, in length. Preferably, oligonucleotide primers and/or probes hybridize to a polynucleotide encoding a polypeptide described herein under moderately stringent conditions, as defined above. Oligonucleotide primers and/or probes which may be usefully employed in the diagnostic methods described herein preferably are at least 10–40 nucleotides in length. In a preferred embodiment, the oligonucleotide primers comprise at least 10 contiguous nucleotides, more preferably at least 15 contiguous nucleotides, of a DNA molecule having a sequence provided herein. Techniques for both PCR based assays and hybridization assays are well known in the art (see, for example, Mullis et al., *Cold Spring Harbor Symp. Quant. Biol.,* 51:263, 1987; Erlich ed., *PCR Technology*, Stockton Press, NY, 1989).

One preferred assay employs RT-PCR, in which PCR is applied in conjunction with reverse transcription. Typically, RNA is extracted from a biological sample such as a biopsy tissue and is reverse transcribed to produce cDNA molecules. PCR amplification using at least one specific primer generates a cDNA molecule, which may be separated and visualized using, for example, gel electrophoresis. Amplification may be performed on biological samples taken from a test patient and from an individual who is not afflicted with a cancer. The amplification reaction may be performed on several dilutions of cDNA spanning two orders of magnitude. A two-fold or greater increase in expression in several dilutions of the test patient sample as compared to the same dilutions of the non-cancerous sample is typically considered positive.

In another embodiment, ovarian carcinoma proteins and polynucleotides encoding such proteins may be used as markers for monitoring the progression of cancer. In this embodiment, assays as described above for the diagnosis of a cancer may be performed over time, and the change in the level of reactive polypeptide(s) evaluated. For example, the assays may be performed every 24–72 hours for a period of 6 months to 1 year, and thereafter performed as needed. In general, a cancer is progressing in those patients in whom the level of polypeptide detected by the binding agent increases over time. In contrast, the cancer is not progressing when the level of reactive polypeptide either remains constant or decreases with time.

Certain in vivo diagnostic assays may be performed directly on a tumor. One such assay involves contacting tumor cells with a binding agent. The bound binding agent may then be detected directly or indirectly via a reporter group. Such binding agents may also be used in histological applications. Alternatively, polynucleotide probes may be used within such applications.

As noted above, to improve sensitivity, multiple ovarian carcinoma protein markers may be assayed within a given sample. It will be apparent that binding agents specific for different proteins provided herein may be combined within a single assay. Further, multiple primers or probes may be used concurrently. The selection of tumor protein markers may be based on routine experiments to determine combinations that results in optimal sensitivity. In addition, or alternatively, assays for tumor proteins provided herein may be combined with assays for other known tumor antigens.

Diagnostic Kits

The present invention further provides kits for use within any of the above diagnostic methods. Such kits typically comprise two or more components necessary for performing a diagnostic assay. Components may be compounds, reagents, containers and/or equipment. For example, one container within a kit may contain a monoclonal antibody or fragment thereof that specifically binds to an ovarian carcinoma protein. Such antibodies or fragments may be provided attached to a support material, as described above. One or more additional containers may enclose elements, such as reagents or buffers, to be used in the assay. Such kits may also, or alternatively, contain a detection reagent as described above that contains a reporter group suitable for direct or indirect detection of antibody binding.

Alternatively, a kit may be designed to detect the level of mRNA encoding an ovarian carcinoma protein in a biological sample. Such kits generally comprise at least one oligonucleotide probe or primer, as described above, that hybridizes to a polynucleotide encoding an ovarian carcinoma protein. Such an oligonucleotide may be used, for example, within a PCR or hybridization assay. Additional components that may be present within such kits include a second oligonucleotide and/or a diagnostic reagent or container to facilitate the detection of a polynucleotide encoding an ovarian carcinoma protein.

The following Examples are offered by way of illustration and not by way of limitation.

EXAMPLES

Example 1

Identification of Representative Ovarian Carcinoma Protein cDNAs

This Example illustrates the identification of cDNA molecules encoding ovarian carcinoma proteins.

Anti-SCID mouse sera (generated against sera from SCID mice carrying late passage ovarian carcinoma) was precleared of *E. coli* and phage antigens and used at a 1:200 dilution in a serological expression screen. The library screened was made from a SCID-derived human ovarian tumor (OV9334) using a directional RH oligo(dT) priming cDNA library construction kit and the λScreen vector (Novagen). A bacteriophage lambda screen was employed. Approximately 400,000 pfu of the amplified OV9334 library were screened.

196 positive clones were isolated. Certain sequences that appear to be novel are provided in FIGS. 1A–1S and SEQ ID NOs:1 to 71. Three complete insert sequences are shown in FIGS. 2A–2C (SEQ ID NOs:72 to 74). Other clones having known sequences are presented in FIGS. 15A–15EEE (SEQ ID NOs:82 to 310). Database searches identified the following sequences that were substantially identical to the sequences presented in FIGS. 15A–15EEE.

These clones were further characterized using microarray technology to determine mRNA expression levels in a variety of tumor and normal tissues. Such analyses were performed using a Synteni (Palo Alto, Calif.) microarray, according to the manufacturer's instructions. PCR amplification products were arrayed on slides, with each product occupying a unique location in the array. mRNA was extracted from the tissue sample to be tested, reverse transcribed and fluorescent-labeled cDNA probes were generated. The microarrays were probed with the labeled cDNA probes and the slides were scanned to measure fluorescence intensity. Data was analyzed using Synteni's provided GEMtools software. The results for one clone (13695, also referred to as O8E) are shown in FIG. 3.

Example 2

Identification of Ovarian Carcinoma cDNAs using Microarray Technology

This Example illustrates the identification of ovarian carcinoma polynucleotides by PCR subtraction and microarray analysis. Microarrays of cDNAs were analyzed for ovarian tumor-specific expression using a Synteni (Palo Alto, Calif.) microarray, according to the manufacturer's instructions (and essentially as described by Schena et al., *Proc. Natl. Acad. Sci. USA* 93:10614–10619, 1996 and Heller et al., *Proc. Natl. Acad. Sci. USA* 94:2150–2155, 1997).

A PCR subtraction was performed using a tester comprising cDNA of four ovarian tumors (three of which were metastatic tumors) and a driver of cDNA form five normal tissues (adrenal gland, lung, pancreas, spleen and brain). cDNA fragments recovered from this subtraction were subjected to DNA microarray analysis where the fragments were PCR amplified, adhered to chips and hybridized with fluorescently labeled probes derived from mRNAs of human ovarian tumors and a variety of normal human tissues. In this analysis, the slides were scanned and the fluorescence intensity was measured, and the data were analyzed using Synteni's GEMtools software. In general, sequences showing at least a 5-fold increase in expression in tumor cells (relative to normal cells) were considered ovarian tumor antigens. The fluorescent results were analyzed and clones that displayed increased expression in ovarian tumors were further characterized by DNA sequencing and database searches to determine the novelty of the sequences.

Using such assays, an ovarian tumor antigen was identified that is a splice fusion between the human T-cell leukemia virus type I oncoprotein TAX (see Jin et al., *Cell* 93:81–91, 1998) and an extracellular matrix protein called osteonectin. A splice junction sequence exists at the fusion point. The sequence of this clone is presented in FIG. 4 and SEQ ID NO:75. Osteonectin, unspliced and unaltered, was also identified from such assays independently.

Further clones identified by this method are referred to herein as 3*f*, 6*b*, 8*e*, 8*h*, 12*c* and 12*h*. Sequences of these clones are shown in FIGS. 5 to 9 and SEQ ID NOs:76 to 81. Microarray analyses were performed as described above, and are presented in FIGS. 10 to 14. A full length sequence encompassing clones 3*f*, 6*b*, 8*e* and 12*h* was obtained by screening an ovarian tumor (SCID-derived) cDNA library.

This 2996 base pair sequence (designated O772P) is presented in SEQ ID NO:311, and the encoded 914 amino acid protein sequence is shown in SEQ ID NO:312. PSORT analysis indicates a Type 1a transmembrane protein localized to the plasma membrane.

In addition to certain of the sequences described above, this screen identified the following sequences:

TABLE 1

Ovarian Carcinoma cDNAs Identified by Microarray Analysis

| Sequence | Comments |
|---|---|
| OV4vG11 (SEQ ID NO: 313) | human clone 1119D9 on chromosome 20p12 |
| OV4vB11 (SEQ ID NO: 314) | human UWGC:y14c094 from chromosome 6p21 |
| OV4vD9 (SEQ ID NO: 315) | human clone 1049G16 chromosome 20q12-13.2 |
| OV4vD5 (SEQ ID NO: 316) | human KIAA0014 gene |
| OV4vC2 (SEQ ID NO: 317) | human KIAA0084 gene |
| OV4vF3 (SEQ ID NO: 318) | human chromosome 19 cosmid R31167 |
| OV4VC1 (SEQ ID NO: 319) | novel |
| OV4vH3 (SEQ ID NO: 320) | novel |
| OV4vD2 (SEQ ID NO: 321) | novel |
| O815P (SEQ ID NO: 322) | novel |
| OV4vC12 (SEQ ID NO: 323) | novel |
| OV4vA4 (SEQ ID NO: 324) | novel |
| OV4vA3 (SEQ ID NO: 325) | novel |
| OV4v2A5 (SEQ ID NO: 326) | novel |
| O819P (SEQ LD NO: 327) | novel |
| O818P (SEQ ID NO: 328) | novel |
| O817P (SEQ ID NO: 329) | novel |
| O816P (SEQ ID NO: 330) | novel |
| Ov4vC5 (SEQ ID NO: 331) | novel |
| 21721 (SEQ ID NO: 332) | human lumican |
| 21719 (SEQ ID NO: 333) | human retinoic acid-binding protein II |
| 21717 (SEQ ID NO: 334) | human 26S proteasome ATPase subunit |
| 21654 (SEQ ID NO: 335) | human copine I |
| 21627 (SEQ ID NO: 336) | human neuron specific gamma-2 enolase |
| 21623 (SEQ ID NO: 337) | human geranylgeranyl transferase II |
| 21621 (SEQ ID NO: 338) | human cyclin-dependent protein kinase |
| 21616 (SEQ ID NO: 339) | human prepro-megakaryocyte potentiating factor |
| 21612 (SEQ ID NO: 340) | human UPH1 |
| 21558 (SEQ ID NO: 341) | human RalGDS-like 2 (RGL2) |
| 21555 (SEQ ID NO: 342) | human autoantigen P542 |
| 21548 (SEQ ID NO: 343) | human actin-related protein (ARP2) |
| 21462 (SEQ ID NO: 344) | human huntingtin interacting protein |
| 21441 (SEQ ID NO: 345) | human 90K product (tumor associated antigen) |
| 21439 (SEQ ID NO: 346) | human guanine nucleotide regulator protein (tim1) |
| 21438 (SEQ ID NO: 347) | human Ku autoimmune (p70/p80) antigen |
| 21237 (SEQ ID NO: 348) | human S-laminin |
| 21436 (SEQ ID NO: 349) | human ribophorin I |
| 21435 (SEQ ID NO: 350) | human cytoplasmic chaperonin hTRiC5 |
| 21425 (SEQ ID NO: 351) | human EMX2 |
| 21423 (SEQ ID NO: 352) | human p87/p89 gene |
| 21419 (SEQ ID NO: 353) | human HPBRII-7 |
| 21252 (SEQ ID NO: 354) | human T1-227H |
| 21251 (SEQ ID NO: 355) | human cullin I |
| 21247 (SEQ ID NO: 356) | kunitz type protease inhibitor (KOP) |
| 21244-1 (SEQ ID NO: 357) | human protein tyrosine phosphatase receptor F (PTPRF) |
| 21718 (SEQ ID NO: 358) | human LTR repeat |
| OV2-90 (SEQ ID NO: 359) | novel |
| Human zinc finger (SEQ ID NO: 360) | |
| Human polyA binding protein (SEQ ID NO: 361) | |
| Human pleitrophin (SEQ ID NO: 362) | |
| Human PAC clone 278C19 (SEQ ID NO: 363) | |
| Human LLRep3 (SEQ ID NO: 364) | |
| Human Kunitz type protease inhib (SEQ ID NO: 365) | |
| Human KIAA0106 gene (SEQ ID NO: 366) | |
| Human keratin (SEQ ID NO: 367) | |
| Human HIV-1TAR (SEQ ID NO: 368) | |
| Human glia derived nexin (SEQ ID NO: 369) | |
| Human fibronectin (SEQ ID NO: 370) | |
| Human ECMproBM40 (SEQ ID NO: 371) | |
| Human collagen (SEQ ID NO: 372) | |
| Human alpha enolase (SEQ ID NO: 373) | |
| Human aldolase (SEQ ID NO: 374) | |
| Human transf growth factor BIG H3 (SEQ ID NO: 375) | |
| Human SPARC osteonectin (SEQ ID NO: 376) | |
| Human SLP1 leucocyte protease (SEQ ID NO: 377) | |
| Human mitochondrial ATP synth (SEQ ID NO: 378) | |
| Human DNA seq clone 461P17 (SEQ ID NO: 379) | |
| Human dbpB pro Y box (SEQ ID NO: 380) | |
| Human 40 kDa keratin (SEQ ID NO: 381) | |
| Human arginosuccinate synth (SEQ ID NO: 382) | |
| Human acidic ribosomal phosphoprotein (SEQ ID NO: 383) | |
| Human colon carcinoma laminin binding pro (SEQ ID NO: 384) | |

This screen further identified multiple forms of the clone O772P, referred to herein as 21013, 21003 and 21008. PSORT analysis indicates that 21003 (SEQ ID NO:386; translated as SEQ ID NO:389) and 21008 (SEQ ID NO:387; translated as SEQ ID NO:390) represent Type 1a transmembrane protein forms of O772P. 21013 (SEQ ID NO:385; translated as SEQ ID NO:388) appears to be a truncated form of the protein and is predicted by PSORT analysis to be a secreted protein.

Additional sequence analysis resulted in a full length clone for O8E (2627 bp, which agrees with the message size observed by Northern analysis; SEQ ID NO:391). This nucleotide sequence was obtained as follows: the original O8E sequence (OrigO8Econs) was found to overlap by 33 nucleotides with a sequence from an EST clone (IMAGE#1987589). This clone provided 1042 additional nucleotides upstream of the original O8E sequence. The link between the EST and O8E was confirmed by sequencing multiple PCR fragments generated from an ovary primary tumor library using primers to the unique EST and the O8E sequence (ESTxO8EPCR). Full length status was further indicated when anchored PCR from the ovary tumor library gave several clones (AnchoredPCR cons) that all terminated upstream of the putative start methionine, but failed to yield any additional sequence information. FIG. 16 presents a diagram that illustrates the location of each partial sequence within the full length O8E sequence.

Two protein sequences may be translated from the full length O8E. For "a" (SEQ ID NO:393) begins with a putative start methionine. A second form "b" (SEQ ID NO:392) includes 27 additional upstream residues to the 5' end of the nucleotide sequence.

From the foregoing it will be appreciated that, although specific embodiments of the invention have been described herein for purposes of illustration, various modifications may be made without deviating from the spirit and scope of the invention. Accordingly, the invention is not limited except as by the appended claims.

SUMMARY OF SEQUENCE LISTING

SEQ ID NOs:1–71 are ovarian carcinoma antigen polynucleotides shown in FIGS. 1A–1S.

SEQ ID NOs:72–74 are ovarian carcinoma antigen polynucleotides shown in FIGS. 2A–2C.

SEQ ID NO:75 is the ovarian carcinoma polynucleotide 3*g* (FIG. 4).

SEQ ID NO:76 is the ovarian carcinoma polynucleotide 3*f* (FIG. 5).

SEQ ID NO:77 is the ovarian carcinoma polynucleotide 6*b* (FIG. 6).

SEQ ID NO:78 is the ovarian carcinoma polynucleotide 8*e* (FIG. 7A).

SEQ ID NO:79 is the ovarian carcinoma polynucleotide 8*h* (FIG. 7B).

SEQ ID NO:80 is the ovarian carcinoma polynucleotide 12*e* (FIG. 8).

SEQ ID NO:81 is the ovarian carcinoma polynucleotide 12*h* (FIG. 9).

SEQ ID NOs:82–310 are ovarian carcinoma antigen polynucleotides shown in FIGS. 15A–15EEE.

SEQ ID NO:311 is a full length sequence of ovarian carcinoma polynucleotide O772P.

SEQ ID NO:312 is the O772P amino acid sequence.

SEQ ID NOs:313–384 are ovarian carcinoma antigen polynucleotides.

SEQ ID NOs:385–390 present sequences of O772P forms.

SEQ ID NO:391 is a full length sequence of ovarian carcinoma polynucleotide O8E.

SEQ ID NOs:392–393 are protein sequences encoded by O8E.

What is claimed is:

1. An isolated polypeptide comprising SEQ ID NO:390.

2. An isolated polypeptide comprising at least a 20 amino acid portion of SEQ ID NO:390.

3. An isolated polypeptide comprising at least a 20 amino acid portion of SEQ ID NO:390, wherein said polypeptide binds an antibody having specificity for a polypeptide comprising SEQ ID NO:390.

4. A fusion polypeptide comprising a polypeptide according to any one of claims 1–3.

5. A composition comprising a polypeptide according to any one of claims 1–3 and at least one physiologically acceptable excipient.

6. A composition comprising a polypeptide according to any one of claims 1–3 and at least one adjuvant.

* * * * *

SEQUENCE LISTING

<160> NUMBER OF SEQ ID NOS: 393

<210> SEQ ID NO 1
<211> LENGTH: 461
<212> TYPE: DNA
<213> ORGANISM: Homo sapien

<400> SEQUENCE: 1

```
ttagagaggc acagaaggaa gaagagttaa aagcagcaaa gccgggtttt tttgttttgt     60
tttgttttgt tttgttttga gatggagtct cactctgttg cccaagctgg agtacaacgg    120
catgatctca gctcgctgca acctccgcct cccacgttca agtgattctc ctgcctcagc    180
ctcccaagta gctgggatta caggcgcccg ccaccacgct cagctaattt tttttgtatt    240
tttagtagag acagggtttc accaggttgg ccaggctgct cttgaactcc tgacctcagg    300
tgatccaccc gcctcggcct cccaaagtgc tgggattaca ggcgtgagcc accacgcccg    360
gcccccaaag ctgtttcttt tgtctttagc gtaaagctct cctgccatgc agtatctaca    420
taactgacgt gactgccagc aagctcagtc actccgtggt c                         461
```

<210> SEQ ID NO 2
<211> LENGTH: 540
<212> TYPE: DNA
<213> ORGANISM: Homo sapien

<400> SEQUENCE: 2

```
taggatgtgt tggaccctct gtgtcaaaaa aaacctcaca aagaatcccc tgctcattac     60
agaagaagat gcatttaaaa tatgggttat tttcaacttt ttatctgagg acaagtatcc    120
attaattatt gtgtcagaag agattgaata cctgcttaag aagcttacag aagctatggg    180
aggaggttgg cagcaagaac aatttgaaca ttataaaatc aactttgatg acagtaaaaa    240
tggcctttct gcatgggaac ttattgagct tattggaaat ggacagttta gcaaaggcat    300
ggaccggcag actgtgtcta tggcaattaa tgaagtcttt aatgaactta tattagatgt    360
```

-continued gttaaagcag ggttacatga tgaaaaaggg ccacagacgg aaaaactgga ctgaaagatg 420
gtttgtacta aaacccaaca taatttctta ctatgtgagt gaggatctga aggataagaa 480
aggagacatt ctcttggatg aaaattgctg tgtagagtcc ttgcctgaca aagatggaaa 540

<210> SEQ ID NO 3
<211> LENGTH: 461
<212> TYPE: DNA
<213> ORGANISM: Homo sapien

<400> SEQUENCE: 3
ttagagaggc acagaaggaa gaagagttaa aagcagcaaa gccgggtttt tttgttttgt 60
tttgttttgt tttgttttga gatggagtct cactctgttg cccaagctgg agtacaacgg 120
catgatctca gctcgctgca acctccgcct cccacgttca agtgattctc ctgcctcagc 180
ctcccaagta gctgggatta caggcgcccg ccaccacgct cagctaattt tttttgtatt 240
tttagtagag acagggtttc accaggttgg ccaggctgct cttgaactcc tgacctcagg 300
tgatccaccc gcctcggcct cccaaagtgc tgggattaca ggcgtgagcc accacgcccg 360
gcccccaaag ctgtttcttt tgtctttagc gtaaagctct cctgccatgc agtatctaca 420
taactgacgt gactgccagc aagctcagtc actccgtggt c 461

<210> SEQ ID NO 4
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 4
tctttttctt tcgatttcct tcaatttgtc acgtttgatt ttatgaagtt gttcaagggc 60
taactgctgt gtattatagc tttctctgag ttccttcagc tgattgttaa atgaatccat 120
ttctgagagc ttagatgcag tttctttttc aagagcatct aattgttctt taagtctttg 180
gcataattct tccttttctg atgacttttt atgaagtaaa ctgatccctg aatcaggtgt 240
gttactgagc tgcatgtttt taattctttc gtttaatagc tgcttctcag ggaccagata 300
gataagctta ttttgatatt ccttaagctc ttgttgaagt tgtttgattt ccataatttc 360
caggtcacac tgtttatcca aaacttctag ctcagtcttt tgtgtttgct ttctgatttg 420
gacatcttgt agtctgcctg agatctgctg atgntttcca ttcactgctt ccagttccag 480
gtggagactt tnctttctgg agctcagcct gacaatgcct tcttgntccc t 531

<210> SEQ ID NO 5
<211> LENGTH: 531
<212> TYPE: DNA
<213> ORGANISM: Homo sapien

<400> SEQUENCE: 5
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300

-continued

```
taaagttgca gggccaacag ctgcctgtag tcctccctcc tatcatgaaa caacccccta    360

tgttctctcc actaatctct gctcgttttg ggatgggaag catgcccaat ctgtccattc    420

atcagccatt gcctccagtt gcacctatag caacaccctt gtcttctgct acttcaggga    480

ccagtattcc tcccctaatg atgcctgctc ccctagtgcc ttctgttagt a             531


<210> SEQ ID NO 6
<211> LENGTH: 531
<212> TYPE: DNA
<213> ORGANISM: Homo sapien

<400> SEQUENCE: 6

aatagattta atgcagagtg tcaacttcaa ttgattgata gtggctgcct agagtgctgt     60

gttgagtagg tttctgagga tgcaccctgg cttgaagaga aagactggca ggattaacaa    120

tatctaaaat ctcacttgta ggagaaacca caggcaccag agctgccact ggtgctggca    180

ccagctccac caaggccagc gaagagccca aatgtgagag tggcggtcag gctggcacca    240

gcactgaagc caccactggt gctggcactg gcactggcac tgttattggt actggtactg    300

gcaccagtgc tggcactgcc actctcttgg gctttggctt tagcttctgc tcccgcctgg    360

atccgggctt tggcccaggg tccgatatca gcttcgtccc agttgcaggg cccggcagca    420

ttctccgagc cgagcccaat gcccattcga gctctaatct cggccctagc cttggcttca    480

gctgcagcct cagctgcagc cttcaaatcc gcttccatcg cctctcggta c             531


<210> SEQ ID NO 7
<211> LENGTH: 531
<212> TYPE: DNA
<213> ORGANISM: Homo sapien

<400> SEQUENCE: 7

gccaagaaag cccgaaaggt gaagcatctg gatggggaag aggatggcag cagtgatcag     60

agtcaggctt ctggaaccac aggtggccga agggtctcaa aggccctaat ggcctcaatg    120

gcccgcaggg cttcaagggg tcccatagcc ttttgggccc gcagggcatc aaggactcgg    180

ttggctgctt gggcccggag agccttgctc tccctgagat cacctaaagc ccgtaggggc    240

aaggctcgcc gtagagctgc caagctccag tcatcccaag agcctgaagc accaccacct    300

cgggatgtgg cccttttgca agggagggca aatgatttgg tgaagtacct tttggctaaa    360

gaccagacga agattcccat caagcgctcg gacatgctga aggacatcat caaagaatac    420

actgatgtgt accccgaaat cattgaacga gcaggctatt ccttggagaa ggtatttggg    480

attcaattga aggaaattga taagaatgac cacttgtaca ttcttctcag c             531


<210> SEQ ID NO 8
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 8

gaggtctcac tatgttgccc aggctgttct tgaactcctg ggatcaagca atccacccat     60

gttggtctcc aaaagtgctg ggatcatagg cgtgagccac ctcacccagc caccaatttt    120

caatcaggaa gactttttcc ttcttcaaga agtgaagggt ttccagagta tagctacact    180

attgcttgcc tgagggtgac tacaaaattg cttgctaaaa ggttaggatg ggtaaagaat    240
```

-continued tagattttct gaatgcaaaa ataaaatgtg aactaatgaa ctttaggtaa tacatattca 300
taaaataatt attcacatat ttcctgattt atcacagaaa taatgtatga aatgctttga 360
gtttcttgga gtaaactcca ttactcatcc caagaaacca tattataagt atcactgata 420
ataagaacaa caggaccttg tcataaattc tggataagag aaatagtctc tgggtgtttg 480
ntcttaattg ataaaattta cttgtccatc ttttagttca gaatcacaaa a 531

<210> SEQ ID NO 9
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 9
aagcggaaat gagaaaggag ggaaaatcat gtggtattga gcggaaaact gctggatgac 60
agggctcagt cctgttggag aactctgggt ggtgctgtag aacagggcca ctcacagtgg 120
ggtgcacaga ccagcacggc tctgtgacct gtttgttaca ggtccatgat gaggtaaaca 180
atacactgag tataagggtt ggtttagaaa ctcttacagc aatttgacaa agtaatcttc 240
tgtgcagtga atctaagaaa aaaattgggg ctgtatttgt atgttccttt ttttcatttc 300
atgttctgag ttacctattt ttattgcatt ttacaaaagc atccttccat gaaggaccgg 360
aagttaaaaa caaagcaggt cctttatcac agcactgtcg tagaacacag ttcagagtta 420
tccacccaag gagccaggga gctgggctaa accaaagaat tttgcttttg gttaatcatc 480
aggtacttga gttggaattg ttttaatccc atcattacca ggctggangt g 531

<210> SEQ ID NO 10
<211> LENGTH: 861
<212> TYPE: DNA
<213> ORGANISM: Homo sapien

<400> SEQUENCE: 10
ccgcggctcc tgtccagacc ctgaccctcc ctcccaaggc tcaaccgtcc cccaacaacc 60
gccagccttg tactgatgtc ggctgcgaga gcctgtgctt aagtaagaat caggccttat 120
tggagacatt caagcaaagg ttggacaact actttttccag aacagaaagg aaactcatgc 180
atcagaaaag gtgactaata aaggtaccag aagaatatgg ctgcacaaat accagaatct 240
gatcagataa aacagtttaa ggaatttctg gggacctaca ataaacttac agagacctgc 300
tttttggact gtgttagaga cttcacaaca agagaagtaa aacctgaaga gaccacctgt 360
tcagaacatt gcttacagaa atatttaaaa atgacacaaa gaatatccat gagatttcag 420
gaatatcata ttcagcagaa tgaagccctg gcagccaaag caggactcct tggccaacca 480
cgatagagaa gtcctgatgg atgaactttt gatgaaagat tgccaacagc tgctttattg 540
gaaatgagga ctcatctgat agaatcccct gaaagcagta gccaccatgt tcaaccatct 600
gtcatgactg tttggcaaat ggaaaccgct ggagaaacaa aattgctatt taccaggaat 660
aatcacaata gaaggtctta ttgttcagtg aaataataag atgcaacatt tgttgaggcc 720
ttatgattca gcagcttggt cacttgatta gaaaaataaa ccattgtttc ttcaattgtg 780
actgttaatt ttaaagcaac ttatgtgttc gatcatgtat gagatagaaa aatttttatt 840
actcaaagta aaataaatgg a 861

-continued

<210> SEQ ID NO 11
<211> LENGTH: 541
<212> TYPE: DNA
<213> ORGANISM: Homo sapien

<400> SEQUENCE: 11
gaaaaaaaat ataaaacaca cttttgcgaa aacggtggcc ctaaaagagg aaaagaattt 60
caccaatata aatccaattt tatgaaaact gacaatttaa tccaagaatc acttttgtaa 120
atgaagctag caagtgatga tatgataaaa taaacgtgga ggaaataaaa acacaagact 180
tggcataaga tatatccact tttgatatta aacttgtgaa gcatattctt cgacaaattg 240
tgaaagcgtt cctgatcttg cttgttctcc atttcaaata aggaggcata tcacatccca 300
agagtaacag aaaaagaaaa aagacatttt tgcattttga gatgaaccaa agacacaaaa 360
caaaacgaac aaagtgtcat gtctaattct agcctctgaa ataaaccttg aacatctcct 420
acaaggcacc gtgatttttg taattctaac ctgaagaaat gtgatgactt ttgtggacat 480
gaaaatcaga tgagaaaact gtggtctttc caaagcctga actcccctga aaacctttgc 540
a 541

<210> SEQ ID NO 12
<211> LENGTH: 541
<212> TYPE: DNA
<213> ORGANISM: Homo sapien

<400> SEQUENCE: 12
ctgggatcat ttctcttgat gtcataaaag actcttcttc ttcctcttca tcctcttctt 60
catcctcttc tgtacagtgc tgccgggtac aacggctatc tttgtcttta tcctgagatg 120
aagatgatgc ttctgtttct cctaccataa ctgaagaaat ttcgctggaa gtcgtttgac 180
tggctgtttc tctgacttca ccttctttgt caaacctgag tctttttacc tcatgcccct 240
cagcttccac agcatcttca tctggatgtt tatttttcaa agggctcact gaggaaactt 300
ctgattcaga ggtcgaagag tcactgtgat ttttctcctc attttgctgc aaatttgcct 360
ctttgctgtc tgtgctctca ggcaacccat ttgttgtcat gggggctgac aaagaaacct 420
ttggtcgatt aagtggcctg ggtgtcccag gcccatttat attagacctc tcagtatagc 480
ttggtgaatt tccaggaaac ataacaccat tcattcgatt taaactattg gaattggttt 540
t 541

<210> SEQ ID NO 13
<211> LENGTH: 441
<212> TYPE: DNA
<213> ORGANISM: Homo sapien

<400> SEQUENCE: 13
gagggttggt ggtagcggct tggggaggtg ctcgctctgt cggtcttgct ctctcgcacg 60
cttcccccgg ctcccttcgt ttcccccccc cggtcgcctg cgtgccggag tgtgtgcgag 120
ggagggggag ggcgtcgggg gggtgggggg aggcgttccg gtccccaaga gacccgcgga 180
gggaggcgga ggctgtgagg gactccggga agccatggac gtcgagaggc tccaggaggc 240
gctgaaagat tttgagaaga gggggaaaaa ggaagtttgt cctgtcctgg atcagtttct 300
ttgtcatgta gccaagactg gagaaacaat gattcagtgg tcccaattta aaggctattt 360
tattttcaaa ctggagaaag tgatggatga tttcagaact tcagctcctg agccaagagg 420
tcctcccaac cctaatgtcg a 441

-continued

<210> SEQ ID NO 14
<211> LENGTH: 131
<212> TYPE: DNA
<213> ORGANISM: Homo sapien
<220> FEATURE:
<221> NAME/KEY: misc_feature
<222> LOCATION: (1)...(131)
<223> OTHER INFORMATION: n = A,T,C or G

<400> SEQUENCE: 14
aagcaggcgg ctcccgcgct cgcagggccg tgccacctgc ccgcccgccc gctcgctcgc 60
tcgcccgccg cgccgcgctg ccgaccgcca gcatgctgcc gagagtgggc tgccccgcgc 120
tgccgntgcc g 131

<210> SEQ ID NO 15
<211> LENGTH: 692
<212> TYPE: DNA
<213> ORGANISM: Homo sapien

<400> SEQUENCE: 15
atctcttgta tgccaaatat ttaatataaa tctttgaaac aagttcagat gaaataaaaa 60
tcaaagtttg caaaaacgtg aagattaact taattgtcaa atattcctca ttgccccaaa 120
tcagtatttt ttttatttct atgcaaaagt atgccttcaa actgcttaaa tgatatatga 180
tatgatacac aaaccagttt tcaaatagta aagccagtca tcttgcaatt gtaagaaata 240
ggtaaaagat tataagacac cttacacaca cacacacaca cacacacgtg tgcacgccaa 300
tgacaaaaaa caatttggcc tctcctaaaa taagaacatg aagaccctta attgctgcca 360
ggagggaaca ctgtgtcacc cctccctaca atccaggtag tttcctttaa tccaatagca 420
aatctgggca tatttgagag gagtgattct gacagccacg ttgaaatcct gtggggaacc 480
attcatgtcc acccactggt gccctgaaaa aatgccaata atttttcgct cccacttctg 540
ctgctgtctc ttccacatcc tcacatagac cccagacccg ctggcccctg gctgggcatc 600
gcattgctgg tagagcaagt cataggtctc gtctttgacg tcacagaagc gatacaccaa 660
attgcctggt cggtcattgt cataaccaga ga 692

<210> SEQ ID NO 16
<211> LENGTH: 728
<212> TYPE: DNA
<213> ORGANISM: Homo sapien

<400> SEQUENCE: 16
cagacggggt ttcactatgt tggctaggct ggtcttgaac tcctgacttc aggtgatctg 60
cctgccttgg cctcccaaag tgctgggatt acaggcataa gccactgcgc ccggctgatc 120
tgatggtttc ataaggcttt tccccctttt gctcagcact tctccttcct gccgccatgt 180
gaagaaggac atgtttgctt ccccttccac cacgattgta agttgtttcc tgaggcctcc 240
ccggccatgc tgaactgtga gtcaattaaa cctctttcct ttataaatta tccagttttg 300
ggtatgtctt tattagtaga atgagaacag actaatacaa cccttaaagg agactgacgg 360
agaggattct tcctggatcc cagcacttcc tctgaatgct actgacattc ttcttgagga 420
ctttaaactg ggagatagaa aacagattcc atggctcagc agcctgagag cagggaggga 480
gccaagctat agatgacatg ggcagcctcc cctgaggcca ggtgtggccg aacctgggca 540
gtgctgccac ccaccccacc agggccaagt cctgtccttg gagagccaag cctcaatcac 600

-continued

```
tgctagcctc aagtgtcccc aagccacagt ggctaggggg actcagggaa cagttcccag    660

tctgccctac ttctcttacc tttacccctc atacctccaa agtagaccat gttcatgagg    720

tccaaagg                                                             728


<210> SEQ ID NO 17
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 17

aagcgaggaa gccactgcgg ctcctggctg aaaagcggcg ccaggctcgg gaacagaggg     60

aacgcgaaga acaggagcgg aagctgcagg ctgaaaggga caagcgaatg cgagaggagc    120

agctggcccg ggaggctgaa gcccgggctg aacgtgaggc cgaggcgcgg agacgggagg    180

agcaggaggc tcgagagaag gcgcaggctg agcaggagga gcaggagcga ctgcagaagc    240

agaaagagga agccgaagcc cggtcccggg aagaagctga gcgccagcgc caggagcggg    300

aaaagcactt tcagaaggag gaacaggaga gacaagagcg aagaaagcgg ctggaggaga    360

taatgaagag gactcggaaa tcagaagccg ccgaaaccaa gaagcaggat gcaaaggaga    420

ccgcagctaa caattccggc ccagaccctt gtgaaagctg tagagactcg gccctctggg    480

cttccagaaa ggattctatt gcagaaagga aggagctngg ccccccangg a             531


<210> SEQ ID NO 18
<211> LENGTH: 1041
<212> TYPE: DNA
<213> ORGANISM: Homo sapien
<220> FEATURE:
<221> NAME/KEY: misc_feature
<222> LOCATION: (1)...(1041)
<223> OTHER INFORMATION: n = A,T,C or G

<400> SEQUENCE: 18

ctctgtggaa aactgatgag gaatgaattt accattaccc atgttctcat ccccaagcaa     60

agtgctgggt ctgattactg caacacagag aacgaagaag aacttttcct catacaggat    120

cagcagggcc tcatcacact gggctggatt catactcacc ccacacagac cgcgtttctc    180

tccagtgtcg acctacacac tcactgctct taccagatga tgttgccaga gtcagtagcc    240

attgtttgct cccccaagtt ccaggaaact ggattcttta aactaactga ccatggacta    300

gaggagattt cttcctgtcg ccagaaagga tttcatccac acagcaagga tccacctctg    360

ttctgtagct gcagccacgt gactgttgtg gacagagcag tgaccatcac agaccttcga    420

tgagcgtttg agtccaacac cttccaagaa caacaaaacc atatcagtgt actgtagccc    480

cttaatttaa gctttctaga aagctttgga agtttttgta gatagtagaa agggggggcat   540

cacntgagaa agagctgatt ttgtatttca ggtttgaaaa gaaataactg aacatatttt    600

ttaggcaagt cagaaagaga acatggtcac ccaaaagcaa ctgtaactca gaaattaagt    660

tactcagaaa ttaagtagct cagaaattaa gaaagaatgg tataatgaac cccatatac     720

ccttccttct ggattcacca attgttaaca tttttttcct ctcagctatc cttctaattt    780

ctctctaatt tcaatttgtt tatatttacc tctgggctca ataagggcat ctgtgcagaa    840

atttggaagc catttagaaa atcttttgga ttttcctgtg gtttatggca atatgaatgg    900

agcttattac tggggtgagg gacagcttac tccatttgac cagattgttt ggctaacaca    960
```

-continued tcccgaagaa tgattttgtc aggaattatt gttatttaat aaatatttca ggatattttt 1020
cctctacaat aaagtaacaa t 1041

<210> SEQ ID NO 19
<211> LENGTH: 1043
<212> TYPE: DNA
<213> ORGANISM: Homo sapien

<400> SEQUENCE: 19
ctctgtggaa aactgatgag gaatgaattt accattaccc atgttctcat ccccaagcaa 60
agtgctgggt ctgattactg caacacagag aacgaagaag aacttttcct catacaggat 120
cagcagggcc tcatcacact gggctggatt catactcacc ccacacagac cgcgtttctc 180
tccagtgtcg acctacacac tcactgctct taccagatga tgttgccaga gtcagtagcc 240
attgtttgct cccccaagtt ccaggaaact ggattcttta aactaactga ccatggacta 300
gaggagattt cttcctgtcg ccagaaagga tttcatccac acagcaagga tccacctctg 360
ttctgtagct gcagccacgt gactgttgtg gacagagcag tgaccatcac agaccttcga 420
tgagcgtttg agtccaacac cttccaagaa caacaaaacc atatcagtgt actgtagccc 480
cttaatttaa gctttctaga aagctttgga agtttttgta gatagtagaa agggggggcat 540 cacctgagaa agagctgatt ttgtatttca ggtttgaaaa gaaataactg aacatatttt 600
ttaggcaagt cagaaagaga acatggtcac ccaaaagcaa ctgtaactca gaaattaagt 660
tactcagaaa ttaagtagct cagaaattaa gaaagaatgg tataatgaac cccccatatac 720 ccttccttct ggattcacca attgttaaca tttttttcct ctcagctatc cttctaattt 780
ctctctaatt tcaatttgtt tatatttacc tctgggctca ataagggcat ctgtgcagaa 840
atttggaagc catttagaaa atcttttgga ttttcctgtg gtttatggca atatgaatgg 900
agcttattac tggggtgagg gacagcttac tccatttgac cagattgttt ggctaacaca 960
tcccgaagaa tgattttgtc aggaattatt gttatttaat aaatatttca ggatattttt 1020
cctctacaat aaagtaacaa tta 1043

<210> SEQ ID NO 20
<211> LENGTH: 448
<212> TYPE: DNA
<213> ORGANISM: Homo sapien

<400> SEQUENCE: 20
ggacgacaag gccatggcga tatcggatcc gaattcaagc ctttggaatt aaataaacct 60
ggaacaggga aggtgaaagt tggagtgaga tgtcttccat atctatacct ttgtgcacag 120
ttgaatggga actgtttggg tttagggcat cttagagttg attgatggaa aaagcagaca 180
ggaactggtg ggaggtcaag tggggaagtt ggtgaatgtg gaataactta cctttgtgct 240
ccacttaaac cagatgtgtt gcagctttcc tgacatgcaa ggatctactt taattccaca 300
ctctcattaa taaattgaat aaaagggaat gttttggcac ctgatataat ctgccaggct 360
atgtgacagt aggaaggaat ggtttcccct aacaagccca atgcactggt ctgactttat 420
aaattattta ataaaatgaa ctattatc 448

<210> SEQ ID NO 21
<211> LENGTH: 411
<212> TYPE: DNA
<213> ORGANISM: Homo sapien -continued

<400> SEQUENCE: 21
ggcagtgaca ttcaccatca tgggaaccac cttccctttt cttcaggatt ctctgtagtg 60
gaagagagca cccagtgttg ggctgaaaac atctgaaagt agggagaaga acctaaaata 120
atcagtatct cagagggctc taaggtgcca agaagtctca ctggacattt aagtgccaac 180
aaaggcatac tttcggaatc gccaagtcaa aactttctaa cttctgtctc tctcagagac 240
aagtgagact caagagtcta ctgctttagt ggcaactaca gaaaactggt gttacccaga 300
aaaacaggag caattagaaa tggttccaat atttcaaagc tccgcaaaca ggatgtgctt 360
tcctttgccc atttagggtt tcttctcttt cctttctctt tattaaccac t 411

<210> SEQ ID NO 22
<211> LENGTH: 896
<212> TYPE: DNA
<213> ORGANISM: Homo sapien
<220> FEATURE:
<221> NAME/KEY: misc_feature
<222> LOCATION: (1)...(896)
<223> OTHER INFORMATION: n = A,T,C or G

<400> SEQUENCE: 22
tgcgctgaaa acaacggcct cctttactgt taaaatgcag ccacaggtgc ttagccgtgg 60
gcatctcaac caccagcctc tgtgggggc aggtgggcgt ccctgtgggc ctctgggccc 120
acgtccagcc tctgtcctct gccttccgtt cttcgacagt gttcccggca tccctggtca 180
cttggtactt ggcgtgggcc tcctgtgctg ctccagcagc tcctccaggn ggtcggcccg 240
cttcaccgca gcctcatgtt gtgtccggag gctgctcacg gcctcctcct tcctcgcgag 300
ggctgtcttc accctccggn gcacctcctc cagctccagc tgctggcggg cctgcagcgt 360
ggccagctcg gccttggcct gccgcgtctc ctcctcarag gctgccagcc ggtcctcgaa 420
ctcctggcgg atcacctggg ccaggttgct gcgctcgcta gaaagctgct cgttcaccgc 480
ctgcgcatcc tccagcgccc gctccttctg ccgcacaagg ccctgcagac gcagattctc 540
gccctcggcc tccccaagct ggcccttcag ctccgagcac cgctcctgaa gcttccgctc 600
cgactgctcc agctcggaga gctcggcctc gtacttgtcc cgtaagcgct tgatgcggct 660
ctcggcagcc ttctcactct cctccttggc cagcgccatg tcggcctcca gccggtgaat 720
gaccagctca atctccttgt cccggccttt ccggatttct tccctcagct cctgttcccg 780
gttcagcagc cacgcctcct ccttcctggt gcggccggcc tcccacgcct gcctctccag 840
ctccagctgc tgcttcaggg tattcagctc catctggcgg gcctgcagcg tggcca 896

<210> SEQ ID NO 23
<211> LENGTH: 111
<212> TYPE: DNA
<213> ORGANISM: Homo sapien

<400> SEQUENCE: 23
caacttatta cttgaaatta taatatagcc tgtccgtttg ctgtttccag gctgtgatat 60
attttcctag tggtttgact ttaaaaataa ataaggttta attttctccc c 111

<210> SEQ ID NO 24
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G -continued

<400> SEQUENCE: 24
tgcaagtcac gggagtttat ttatttaatt tttttcccca gatggagact ctgtcgccca 60
ggctggagtg caatggtgtg atcttggctc actgcaacct ccacctcctg ggttcaagcg 120
attctcctgc cacagcctcc cgagtagctg ggattacagg tgcccgccac cacacccagc 180
taatttttat atttttagta aagacagggt ttccccatgt tggccaggct ggtcttgaac 240
ttctgacctc aggtgatcca cctgcctcgg cctcccaaag tgttgggatt acaggcgtga 300
gctacccgtg cctggccagc cactggagtt taaaggacag tcatgttggc tccagcctaa 360
ggcggcattt tcccccatca gaaagcccgc ggctcctgta cctcaaaata gggcacctgt 420
aaagtcagtc agtgaagtct ctgctctaac tggccacccg gggccattgg cntctgacac 480
agccttgcca ggangcctgc atctgcaaaa gaaaagttca cttcctttcc g 531

<210> SEQ ID NO 25
<211> LENGTH: 471
<212> TYPE: DNA
<213> ORGANISM: Homo sapien
<220> FEATURE:
<221> NAME/KEY: misc_feature
<222> LOCATION: (1)...(471)
<223> OTHER INFORMATION: n = A,T,C or G

<400> SEQUENCE: 25
cagagaatct kagaaagatg tcgcgttttc ttttaatgaa tgagagaagc ccatttgtat 60
ccctgaatca ttgagaaaag gcggcggtgg cgacagcggc gacctaggga tcgatctgga 120
gggacttggg gagcgtgcag agacctctag ctcgagcgcg agggacctcc cgccgggatg 180
cctggggagc agatggaccc tactggaagt cagttggatt cagatttctc tcagcaagat 240
actccttgcc tgataattga agattctcag cctgaaagcc aggttctaga ggatgattct 300
ggttctcact tcagtatgct atctcgacac cttcctaatc tccagacgca caaagaaaat 360
cctgtgttgg atgttgngtc caatccttga acaaacagct ggagaagaac gaggagaccg 420
gtaatagtgg gttcaatgaa catttgaaag aaaaccaggt tgcagaccct g 471

<210> SEQ ID NO 26
<211> LENGTH: 541
<212> TYPE: DNA
<213> ORGANISM: Homo sapien

<400> SEQUENCE: 26
gactgtcctg aacaagggac ctctgaccag agagctgcag gagatgcaga gtggtggcag 60
gagtggaagc caaagaacac ccaccttcct cccttgaagg agtagagcaa ccatcagaag 120
atactgtttt attgctctgg tcaaacaagt cttcctgagt tgacaaaacc tcaggctctg 180
gtgacttctg aatctgcagt ccactttcca taagttcttg tgcagacaac tgttcttttg 240
cttccatagc agcaacagat gctttggggc taaaaggcat gtcctctgac cttgcaggtg 300
gtggattttg ctcttttaca acatgtacat ccttactggg ctgtgctgtc acagggatgt 360
ccttgctgga ctgttctgct atggggatat cttcgttgga ctgttcttca tgcttaattg 420
cagtattagc atccacatca gacagcctgg tataaccaga gttggtggtt actgattgta 480
gctgctcttt gtccacttca tatggcacaa gtattttcct caacatcctg gctctgggaa 540
g 541

<210> SEQ ID NO 27

-continued

<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 27
gaaatgtata tttaatcatt ctcttgaacg atcagaactc traaatcagt tttctataac 60
arcatgtaat acagtcaccg tggctccaag gtccaggaag gcagtggtta acacatgaag 120
agtgtgggaa gggggctgga aacaaagtat tcttttcctt caaagcttca ttcctcaagg 180
cctcaattca agcagtcatt gtccttgctt tcaaaagtct gtgtgtgctt catggaaggt 240
atatgtttgt tgccttaatt tgaattgtgg ccaggaaggg tctggagatc taaattcaga 300
gtaagaaaac ctgagctaga actcaggcat ttctcttaca gaacttggct tgcagggtag 360
aatgaangga aagaaactta gaagctcaac aagctgaaga taatcccatc aggcatttcc 420
cataggcctt gcaactctgt tcactgagag atgttatcct g 461

<210> SEQ ID NO 28
<211> LENGTH: 541
<212> TYPE: DNA
<213> ORGANISM: Homo sapien

<400> SEQUENCE: 28
agtctggagt gagcaaacaa gagcaagaaa caarragaag ccaaaagcag aaggctccaa 60
tatgaacaag ataaatctat cttcaaagac atattagaag ttgggaaaat aattcatgtg 120
aactagacaa gtgtgttaag agtgataagt aaaatgcacg tggagacaag tgcatcccca 180
gatctcaggg acctccccct gcctgtcacc tggggagtga gaggacagga tagtgcatgt 240
tctttgtctc tgaattttta gttatatgtg ctgtaatgtt gctctgagga agcccctgga 300
aagtctatcc caacatatcc acatcttata ttccacaaat taagctgtag tatgtaccct 360
aagacgctgc taattgactg ccacttcgca actcaggggc ggctgcattt tagtaatggg 420
tcaaatgatt cactttttat gatgcttccc aaggtgcctt ggcttctctt cccaactgac 480
aaatgcccaa gttgagaaaa atgatcataa ttttagcata aaccgagcaa tcggcgaccc 540
c 541

<210> SEQ ID NO 29
<211> LENGTH: 411
<212> TYPE: DNA
<213> ORGANISM: Homo sapien

<400> SEQUENCE: 29
tagctgtctt cctcactctt atggcaatga ccccatatct taatggatta agataatgaa 60
agtgtatttc ttacactctg tatctatcac cagaagctga ggtgatagcc cgcttgtcat 120
tgtcatccat attctgggac tcaggcggga actttctgga atattgccag ggagcatggc 180
agaggggcac agtgcattct gggggaatgc acattggctc agcctgggta atgagtgata 240
tacattacct ctgttcacaa ctcattgccc agcaccagtc acaaggcccc accaaatacc 300
agagcccaag aaatgtagtc ctgttgatat ggttttgctg tgtcccaacc caaatctcat 360
cttgaattgt aagctcccat aattcccatg tgttgtggga gggacctggt g 411

<210> SEQ ID NO 30
<211> LENGTH: 511

-continued

<212> TYPE: DNA
<213> ORGANISM: Homo sapien

<400> SEQUENCE: 30
atcatgagga tgttaccaaa gggatggtac taaaccattt gtattcgtct gttttcacac 60
tgctttgaag atactacctg agactgggta atttataaac aaaagagatt taattgactc 120
acagttctgc atggctgaag aggcctcagg aaacttacag tcatggtgga aggcaaagga 180
ggagcaaggc atgtcttaca tgtcagtagg agagagagcg agagcaggag aacctgccac 240
ttataaacca ttcagatctc ataactccct atcatgagaa aaacatggag gaaaccaccc 300
tcatgatcca atcacctccc gccaggtccc tccctcgaca cgtggggatt ataattcagg 360
attagaggga cacagagaca aaccatatca tcattcatga gaaatccacc ctcatagtcc 420
aatcagctcc taccaggccc cacctccaac actggggatt gcaattcaac atgagatttg 480
gatggggaca cagattcaaa ccatatcata c 511

<210> SEQ ID NO 31
<211> LENGTH: 827
<212> TYPE: DNA
<213> ORGANISM: Homo sapien

<400> SEQUENCE: 31
catggccttt ctccttagag gccagaggtg ctgccctggc tgggagtgaa gctccaggca 60
ctaccagctt tcctgatttt cccgtttggt ccatgtgaag agctaccacg agccccagcc 120
tcacagtgtc cactcaaggg cagcttggtc ctcttgtcct gcagaggcag gctggtgtga 180
ccctgggaac ttgacccggg aacaacaggt ggcccagagt gagtgtggcc tggcccctca 240
acctagtgtc cgtcctcctc tctcctggag ccagtcttga gtttaaaggc attaagtgtt 300
agatacaagc tccttgtggc tggaaaaaca cccctctgct gataaagctc agggggcact 360
gaggaagcag aggccccttg gggtgccct cctgaagaga gcgtcaggcc atcagctctg 420
tccctctggt gctcccacgt ctgttcctca ccctccatct ctgggagcag ctgcacctga 480
ctggccacgc gggggcagtg gaggcacagg ctcagggtgg ccgggctacc tggcacccta 540
tggcttacaa agtagagttg gcccagtttc cttccacctg aggggagcac tctgactcct 600
aacagtcttc cttgccctgc catcatctgg ggtggctggc tgtcaagaaa ggccgggcat 660
gctttctaaa cacagccaca ggaggcttgt agggcatctt ccaggtgggg aaacagtctt 720
agataagtaa ggtgacttgc ctaaggcctc ccagcaccct tgatcttgga gtctcacagc 780
agactgcatg tsaacaactg gaaccgaaaa catgcctcag tataaaa 827

<210> SEQ ID NO 32
<211> LENGTH: 291
<212> TYPE: DNA
<213> ORGANISM: Homo sapien

<400> SEQUENCE: 32
ccagaacctc cttctctttg gagaatgggg aggcctcttg gagacacaga gggtttcacc 60
ttggatgacc tctagagaaa ttgcccaaga agcccacctt ctggtcccaa cctgcagacc 120
ccacagcagt cagttggtca ggccctgctg tagaaggtca cttggctcca ttgcctgctt 180
ccaaccaatg ggcaggagag aaggccttta tttctcgccc acccattctc ctgtaccagc 240
acctccgttt tcagtcagyg ttgtccagca acggtaccgt ttacacagtc a 291

<210> SEQ ID NO 33

-continued

<211> LENGTH: 491
<212> TYPE: DNA
<213> ORGANISM: Homo sapien

<400> SEQUENCE: 33

```
tgcatgtagt tttatttatg tgttttsgtc tggaaaacca agtgtcccag cagcatgact     60

gaacatcact cacttcccct acttgatcta caaggccaac gccgagagcc cagaccagga    120

ttccaaacac actgcacgag aatattgtgg atccgctgtc aggtaagtgt ccgtcactga    180

cccaracgct gttacgtggc acatgactgt acagtgccac gtaacagcac tgtacttttc    240

tcccatgaac agttacctgc catgtatcta catgattcag aacattttga acagttaatt    300

ctgacacttg aataatccca tcaaaaaccg taaaatcact ttgatgtttg taacgacaac    360

atagcatcac tttacgacag aatcatctgg aaaaacagaa caacgaatac atacatctta    420

aaaaatgctg ggtgggccca ggcacagctt cacgcctgta atcccagcac tttgggaggc    480

ttaagcgggt g                                                          491
```

<210> SEQ ID NO 34
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 34

```
tggggcggaa agaagccaag gccaaggagc tggtgcggca gctgcagctg gaggccgagg     60

agcagaggaa gcagaagaag cggcagagtg tgtcgggcct gcacagatac cttcacttgc    120

tggatggaaa tgaaaattac ccgtgtcttg tggatgcaga cggtgatgtg atttccttcc    180

caccaataac caacagtgag aagacaaagg ttaagaaaac gacttctgat ttgtttttgg    240

aagtaacaag tgccaccagt ctgcagattt gcaaggatgt catggatgcc ctcattctga    300

aaatggcaag aaatgaaaaa gtacacttta gaaaataaag aggaaggatc actctcagat    360

actgaagccg atgcagtctc tggacaactt ccagatccca caacgaatcc cagtgctgga    420

aaggacgggc ccttccttct ggtggtggaa cangtcccgg tggtggatct tggaanggaa    480

cctgaangtg gtgtaccccg tccaaggccg accttggcca c                         521
```

<210> SEQ ID NO 35
<211> LENGTH: 161
<212> TYPE: DNA
<213> ORGANISM: Homo sapien
<220> FEATURE:
<221> NAME/KEY: misc_feature
<222> LOCATION: (1)...(161)
<223> OTHER INFORMATION: n = A,T,C or G

<400> SEQUENCE: 35

```
tcccgcgctc gcagggcncg tgccacctgc cygtccgccc gctcgctcgc tcgcccgccg     60

cgccgcgctg ccgaccgyca gcatgctgcc gagagtgggc tgccccgcgc tgccgctgcc    120

gccgccgccg ctgctgccgc tgctgccgct gctgctgctg c                         161
```

<210> SEQ ID NO 36
<211> LENGTH: 341
<212> TYPE: DNA
<213> ORGANISM: Homo sapien

<400> SEQUENCE: 36

-continued

```
ggcgggtagg catggaactg agaagaacga agaagctttc agactacgtg gggaagaatg     60

aaaaaaccaa aattatcgcc aagattcagc aaaggggaca gggagctcca gcccgagagc    120

ctattattag cagtgaggag cagaagcagc tgatgctgta ctatcacaga agacaagagg    180

agctcaagag attggaagaa aatgatgatg atgcctattt aaactcacca tgggcggata    240

acactgcttt gaaaagacat tttcatggag tgaaagacat aaagtggaga ccaagatgaa    300

gttcaccagc tgatgacact tccaaagaga ttagctcacc t                        341
```

<210> SEQ ID NO 37
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 37

```
tctgaaggtt aaatgtttca tctaaatagg gataatgrta aacacctata gcatagagtt     60

gtttgagatt aaatgagata atacatgtaa aattatgtgc ctggcataca gcaagattgt    120

tgttgttgtt gatgatgatg atgatgatga taatattttt ctatccccag tgcacaactg    180

cttgaaccta ttagataatc aatacatgtt tcttgaactg agatcaattt ccccatgttg    240

tctgactgat gaagccctac attttcttct agaggagatg acatttgagc aagatcttaa    300

agaaaatcag atgccttcac ctgaccactg cttggtgatc ccatggcact ttgtacatct    360

ctccattagc tctcatctca ccagcccatc attattgtat gtgctgcctt ctgaagcttg    420

cagctggcta ccatcmggta gaataaaaat catcctttca taaaatagtg accctccttt    480

tttatttgca tttcccaaag ccaagcaccg tgggangta g                         521
```

<210> SEQ ID NO 38
<211> LENGTH: 461
<212> TYPE: DNA
<213> ORGANISM: Homo sapien

<400> SEQUENCE: 38

```
tatgaagaag ggaaaagaag ataatttgtg aaagaaatgg gtccagttac tagtctttga     60

aaagggtcag tctgtagctc ttcttaatga gaataggcag ctttcagttg ctcagggtca    120

gatttcctta gtggtgtatc taatcacagg aaacatctgt ggttccctcc agtctctttc    180

tgggggactt gggcccactt ctcatttcat ttaattagag gaaatagaac tcaaagtaca    240

atttactgtt gtttaacaat gccacaaaga catggttggg agctatttct tgatttgtgt    300

aaaatgctgt ttttgtgtgc tcataatggt tccaaaaatt gggtgctggc caaagagaga    360

tactgttaca gaagccagca agaagacctc tgttcattca cacccccggg gatatcagga    420

attgactcca gtgtgtgcaa atccagtttg gcctatcttc t                        461
```

<210> SEQ ID NO 39
<211> LENGTH: 769
<212> TYPE: DNA
<213> ORGANISM: Homo sapien

<400> SEQUENCE: 39

```
tgagggactg attggtttgc tctctgctat tcaattcccc aagcccactt gttcctgcag     60

cgtcctcctt ctcattccct ttagttgtac cctctctttc atctgagacc tttccttctt    120
```

-continued

```
gatgtcgcct tttcttcttc ttgctttttc tgatgttctg ctcagcatgt tctgggtgct    180

tctcatctgc atcattcctt tcagatgctg tagcttcttc ctcctctttc tgcctccttt    240

tctttttctt ttttttgggg ggcttgctct ctgactgcag ttgaggggcc ccagggtcct    300

ggcctttgag acgagccagg aaggcctgct cctgggcctc taggcgagca agcttggcct    360

tcattgtgat cccaagacgg gcagccttgt gtgctgttcg cccctcacag gcttggagca    420

gcatctcatc agtcagaatc tttggggact tggacccctg gttgtcgtca tcactgcagc    480

tctccaagtc tttgtttggc ttctctccac ctgaagtcaa tgtagccatc ttcacaaact    540

tctgatacag caagttgggc ttgggatgat tataacgggt ggtctcctta gaaaggctcc    600

ttatctgtac tccatcctgc ccagtttcca ctaccaagtt ggccgcagtc ttgttgaaga    660

gctcattcca ccagtggttt gtgaactcct tggcagggtc atgtcctacc ccatgagtgt    720

cttgcttcag ygtcaccctg agagcctgag tgataccatt ctccttccg                769
```

```
<210> SEQ ID NO 40
<211> LENGTH: 292
<212> TYPE: DNA
<213> ORGANISM: Homo sapien

<400> SEQUENCE: 40

gacaacatga aataaatcct agaggacaaa attaaactca atagagtgta gtctagttaa     60

aaactcgaaa aatgagcaag tctggtggga gtggaggaag ggctatacta taaatccaag    120

tgggcctcct gatcttaaca agccatgctc attatacaca tctctgaact ggacatacca    180

cctttacgca ggaaacaggg cttggaactt ctaagggaaa ttaacatgca ccacccacat    240

ctaacctacc tgccgggtag gtaccatccc tgcttcgctg aaatcagtgc tc            292
```

```
<210> SEQ ID NO 41
<211> LENGTH: 406
<212> TYPE: DNA
<213> ORGANISM: Homo sapien

<400> SEQUENCE: 41

ttggaattaa ataaacctgg aacagggaag gtgaaagttg gagtgagatg tcttccatat     60

ctataccttt gtgcacagtt gaatgggaac tgtttgggtt tagggcatct tagagttgat    120

tgatggaaaa agcagacagg aactggtggg aggtcaagtg gggaagttgg tgaatgtgga    180

ataacttacc tttgtgctcc acttaaacca gatgtgttgc agctttcctg acatgcaagg    240

atctacttta attccacact ctcattaata aattgaataa aagggaatgt tttggcacct    300

gatataatct gccaggctat gtgacagtag gaaggaatgg tttcccctaa caagcccaat    360

gcactggtct gactttataa attatttaat aaaatgaact attatc                   406
```

```
<210> SEQ ID NO 42
<211> LENGTH: 381
<212> TYPE: DNA
<213> ORGANISM: Homo sapien

<400> SEQUENCE: 42

aaactggacc tgcaacaggg acatgaattt actgcarggt ctgagcaagc tcagcccctc     60

tacctcaggg ccccacagcc atgactacct cccccaggag cgggagggtg aagggggcct    120

gtctctgcaa gtggagccag agtggaggaa tgagctctga agacacagca cccagccttc    180

tcgcaccagc caagccttaa ctgcctgcct gaccctgaac cagaacccag ctgaactgcc    240

cctccaaggg acaggaaggc tgggggaggg agtttacaac ccaagccatt ccacccccctc    300
```

-continued ccctgctggg gagaatgaca catcaagctg ctaacaattg ggggaagggg aaggaagaaa 360
actctgaaaa caaaatcttg t 381

<210> SEQ ID NO 43
<211> LENGTH: 451
<212> TYPE: DNA
<213> ORGANISM: Homo sapien

<400> SEQUENCE: 43
catgcgtttc accactgttg gccaggctgg tctcgaactc ctggcctcaa gcaatccacc 60
cgcctcagcc tccaaaagtg ctgggattac agatgtgagc catggcacca tgccaaaagg 120
ctatattcct ggctctgtgt ttccgagact gcttttaatc ccaacttctc tacatttaga 180
ttaaaaaata ttttattcat ggtcaatctg gaacataatt actgcatctt aagtttccac 240
tgatgtatat agaaggctaa aggcacaatt tttatcaaat ctagtagagt aaccaaacat 300
aaaatcatta attactttca acttaataac taattgacat tcctcaaaag agctgttttc 360
aatcctgata ggttctttat tttttcaaaa tatatttgcc atgggatgct aatttgcaat 420
aaggcgcata atgagaatac cccaaactgg a 451

<210> SEQ ID NO 44
<211> LENGTH: 521
<212> TYPE: DNA
<213> ORGANISM: Homo sapien

<400> SEQUENCE: 44
gttggacccc cagggactgg aaagacactt cttgcccgag ctgtggcggg agaagctgat 60
gttccttttt attatgcttc tggatccgaa tttgatgaga tgtttgtggg tgtgggagcc 120
agccgtatca gaaatctttt tagggaagca aaggcgaatg ctccttgtgt tatatttatt 180
gatgaattag attctgttgg tgggaagaga attgaatctc caatgcatcc atattcaagg 240
cagaccataa atcaacttct tgctgaaatg gatggtttta aacccaatga aggagttatc 300
ataataggag ccacaaactt cccagaggca ttagataatg ccttaatacc gtcctggtcg 360
ttttgacatg caagttacag ttccaaggcc agatgtaaaa ggtcgaacag aaattttgaa 420
atggtatctc aataaaataa agtttgatca atcccgttga tccagaaatt atagcctcga 480
ggtactggtg gcttttccgg aagcagagtt gggagaatct t 521

<210> SEQ ID NO 45
<211> LENGTH: 585
<212> TYPE: DNA
<213> ORGANISM: Homo sapien

<400> SEQUENCE: 45
gcctacaaca tccagaaaga gtctaccctg cacctggtgc tscgtctcag aggtgggatg 60
cagatcttcg tgaagaccct gactggtaag accatcactc tcgaagtgga gccgagtgac 120
accatygaga acgtcaaagc aaagatccar gacaaggaag gcrtycctcc tgaccagcag 180
aggttgatct ttgccggaaa gcagctggaa gatggdcgca ccctgtctga ctacaacatc 240
cagaaagagt cyaccctgca cctggtgctc cgtctcagag gtgggatgca ratcttcgtg 300
aagaccctga ctggtaagac catcaccctc gaggtggagc ccagtgacac catcgagaat 360
gtcaaggcaa agatccaaga taaggaaggc atccctcctg atcagcagag gttgatcttt 420
gctgggaaac agctggaaga tggacgcacc ctgtctgact acaacatcca gaaagagtcc 480

-continued actctgcact tggtcctgcg cttgaggggg ggtgtctaag tttccccttt taaggtttcm 540
acaaatttca ttgcactttc ctttcaataa agttgttgca ttccc 585

<210> SEQ ID NO 46
<211> LENGTH: 481
<212> TYPE: DNA
<213> ORGANISM: Homo sapien

<400> SEQUENCE: 46
gaactgggcc ctgagcccaa gtcatgcctt gtgtccgcat ctgccgtgtc acctctgtkc 60
ctgcccctca cccctccctc ctggtcttct gagccagcac catctccaaa tagcctattc 120
cttcctgcaa atcacacaca catgcgggcc acacatacct gctgccctgg agatggggaa 180
gtaggagaga tgaatagagg cccatacatt gtacagaagg aggggcaggt gcagataaaa 240
gcagcagacc cagcggcagc tgaggtgcat ggagcacggt tggggccggc attgggctga 300
gcacctgatg ggcctcatct cgtgaatcct cgaggcagcg ccacagcaga ggagttaagt 360
ggcacctggg ccgagcagag caggagactg agggtcagag tggaggctaa gctgccctgg 420
aactcctcaa tcttgcctgc cccctagtat gaagccccct tcctgcccct acaattcctg 480
a 481

<210> SEQ ID NO 47
<211> LENGTH: 461
<212> TYPE: DNA
<213> ORGANISM: Homo sapien
<220> FEATURE:
<221> NAME/KEY: misc_feature
<222> LOCATION: (1)...(461)
<223> OTHER INFORMATION: n = A,T,C or G

<400> SEQUENCE: 47
atggatctta ctttgccacc caggttggag tgcagtgctg caatcttggc tcactgcagc 60
cttaacctcc caggctcaag ctatcctcct gccaaagcct tccacatagc tgggactaca 120
ggtacacngc caccacaccc agctaaaatt tttgtatttt ttgtagagac gggatctcgc 180
cacgttgccc aggctggtcc catcctgacc tcaagcagat ctgcccacct cagcccccca 240
acgtgctagg attacaggcg tgagccaccg cacccagcct ttgttttgct tttaatggaa 300
tcaccagttc ccctccgtgt ctcagcagca gctgtgagaa atgctttgca tctgtgacct 360
ttatgaaggg gaacttccat gctgaatgag ggtaggatta catgctcctg tttcccgggg 420
gtcaagaaag cctcagactc cagcatgata agcagggtga g 461

<210> SEQ ID NO 48
<211> LENGTH: 571
<212> TYPE: DNA
<213> ORGANISM: Homo sapien

<400> SEQUENCE: 48
ataggggctt taaggaggga attcaggttc aatgaggtcg taaggccagg gctcttatcc 60
agtaagactg gggtccttag atgagaaaga gacacccgag gtccttctct ctgccgtgtg 120
aggatgcatc aagaaggcgg ccgtctgcaa gcgaaggaga ggccgcacca gaaaccgaca 180
ccttcatctt ggacttgcag cctctagaac tgagaaaata actgtctgtt ggttaagcca 240
cccagtttgt agtattctct tatggcttcc taagcagact aacaaacaaa cacccaaaat 300
taactgatgg cttcgctgtc ttctgtaaaa attgctatga gagaactttt cactcactgt 360
tttgcagttt ctccctcagt ccctggttct ttcttctcac ataatcccaa tttcaattta 420

-continued

```
tagttcatgg cccaggcaga gtcattcatc acggcatctc ctgagctaaa ccagcacctg    480

ctctgctcac ttcttgactg gctgctcatc atcagccctc ttgcagagat ttcatttcct    540

cccgtgccag gtacttcacg caccaagctc a                                   571
```

<210> SEQ ID NO 49
<211> LENGTH: 511
<212> TYPE: DNA
<213> ORGANISM: Homo sapien

<400> SEQUENCE: 49

```
ggataatgaa gttgttttat ttagcttgga caaaaaggca tattcctcta ttttcttata     60

caacaaatat ccccaaaata aagcaagcat atatatcttg aatgtgtaat aatccagtga    120

taaacaagag cagtacttta aaagaaaaaa aaatatgtat ttctgtcagg ttaaaatgag    180

aatcaaaacc atttactctg ctaactcatt attttttgct ttctttttgg ttaagagagg    240

caatgcaata cactgaaaaa ggtttttatc ttatctggca ttggaattag acatattcaa    300

accccagccc ccatttccaa actttaagac cacaaacaag taatttactt ttctgaacat    360

tggtttttttc tggaaaatgg gaattataaa atagactttg cagactctta tgagattaaa   420

taagataatg tatgaaattc tttcttcttt tttacttctt tttccttttt gagatggagt    480

ctcaccccgt cacccaggct ggagtacagt g                                   511
```

<210> SEQ ID NO 50
<211> LENGTH: 561
<212> TYPE: DNA
<213> ORGANISM: Homo sapien

<400> SEQUENCE: 50

```
ccactgcact ccagcctggg tgacggagtg agactctgtc tcaaaaaaac aaacaaacaa     60

acaaacaaaa aactgaaaag gaaatagagt tcctctttcc tcatatatga atatattatt    120

tcaacagatt gttgatcacc taccatatgc ttggtattgt tctaattgct ggggatacag    180

caagaggttc tgcagaactt catggagcat gaaagtaaat aaacaaagtt aatttcaagg    240

ccaggcatgg ttgctcacac ctttagtccc agcactttgg gaggctgagg caggtggatc    300

acttgggccc aggagttcaa ggctgcagtg agccaagatt gtgccactac tctccaggct    360

gggcaacaga gcaagaccct gtctcagggg gaacaaaaag ttaatttcag attttgttaa    420

gtgctgtaaa ggaagtaaat aggttgatat tcaagagagc acctgaaggc caggcgtggt    480

ggctcacgcc tgtggtctaa cgctttggga agcccgagcg ggcggatcac aaggtcagga    540

gaattttggc caggcatggt g                                              561
```

<210> SEQ ID NO 51
<211> LENGTH: 451
<212> TYPE: DNA
<213> ORGANISM: Homo sapien

<400> SEQUENCE: 51

```
agaatccatt tattgggttt taaactagtt acacaactga aatcagtttg gcactacttt     60

atacagggat tacgcctgtg tatgccgaca cttaaatact gtaccaggac cactgctgtg    120

cttaggtctg tattcagtca ttcagcatgt agatactaaa aatatactgt agtgttcctt    180

taaggaagac tgtacagggt gtgttgcaag atgacattca ccaatttgtg aattatttca    240

acccagaaga tacctttcac tctataaact tgtcataggc aaacatgtgg tgttagcatt    300
```

-continued

```
gagagatgca cacaaaaatg ttacataaaa gttcagacat tctaatgata agtgaactga    360

aaaaaaaaaa aaccccacat ctcaattttt gtaacaagat aaagaaaata atttaaaaac    420

acaaaaaatg gcattcagtg ggtacaaagc c                                   451
```

<210> SEQ ID NO 52
<211> LENGTH: 682
<212> TYPE: DNA
<213> ORGANISM: Homo sapien

<400> SEQUENCE: 52

```
caaatattta atataaatct ttgaaacaag ttcagakgaa ataaaaatca aagtttgcaa     60

aaacgtgaag attaacttaa ttgtcaaata ttcctcattg ccccaaatca gtattttttt    120

tatttctatg caaaagtatg ccttcaaact gcttaaatga tatatgatat gatacacaaa    180

ccagttttca aatagtaaag ccagtcatct tgcaattgta agaaataggt aaaagattat    240

aagacacctt acacacacac acacacacac acacacacgt gtgcaccgcc aatgacaaaa    300

aacaatttgg cctctcctaa aataagaaca tgaagaccct taattgctgc caggagggaa    360

cactgtgtca cccctcccta caatccaggt agtttccttt aatccaatag caaatctggg    420

catatttgag aggagtgatt ctgacagcca csgttgaaat cctgtgggga accattcatg    480

tccacccact ggtgccctga aaaaatgcca ataatttttc gctcccactt ctgctgctgt    540

ctcttccaca tcctcacata gaccccagac ccgctggccc ctggctgggc atcgcattgc    600

tggtagagca agtcataggt ctcgtctttg acgtcacaga agcgatacac caaattgcct    660

ggtcggtcat tgtcataacc ag                                             682
```

<210> SEQ ID NO 53
<211> LENGTH: 311
<212> TYPE: DNA
<213> ORGANISM: Homo sapien
<220> FEATURE:
<221> NAME/KEY: misc_feature
<222> LOCATION: (1)...(311)
<223> OTHER INFORMATION: n = A,T,C or G

<400> SEQUENCE: 53

```
tttgacttta gtaggggtct gaactattta ttttactttg ccmgtaatat ttaraccyta     60

tatatctttc attatgccat cttatcttct aatgbcaagg gaacagwtgc taamctggct    120

tctgcattwa tcacattaaa aatggctttc ttggaaaatc ttcttgatat gaataaagga    180

tcttttavag ccatcattta aagcmggntt ctctccaaca cgagtctgct sasggggggk    240

gagctgtgaa ctctggctga aggctttccc atacacactg caatgacmtg gtttctgacc    300

agbgtgagtt a                                                         311
```

<210> SEQ ID NO 54
<211> LENGTH: 561
<212> TYPE: DNA
<213> ORGANISM: Homo sapien

<400> SEQUENCE: 54

```
agagaagccc cataaatgca atcagtgtgg gaaggccttc agtcagagct caagcctttt     60

cctccatcat cgggttcata ctggagagaa accctatgta tgtaatgaat gcggcagagc    120

ctttggtttt aactctcatc ttactgaaca cgtaaggatt cacacaggag aaaaacccta    180

tgtttgtaat gagtgcggca aagcctttcg tcggagttcc actcttgttc agcatcgaag    240

agttcacact ggggagaagc cctaccagtg cgttgaatgt gggaaagctt tcagccagag    300
```

-continued

```
ctcccagctc accctacatc agccgagttc acactggaga gaagccctat gactgtggtg    360

actgtgggaa ggccttcagc cggaggtcaa ccctcattca gcatcagaaa gttcacagcg    420

gagagactcg taagtgcaga aaacatggtc cagcctttgt tcatggctcc agcctcacag    480

cagatggaca gattcccact ggagagaagc acggcagaac ctttaaccat ggtgcaaatc    540

tcattctgcg ctggacagtt c                                             561
```

<210> SEQ ID NO 55
<211> LENGTH: 811
<212> TYPE: DNA
<213> ORGANISM: Homo sapien

<400> SEQUENCE: 55

```
gagacagggt ctcactttgt cacccaggct ggaatgcagt ggtgcgatct tacgtagctc     60

actgcagccc tgacctcctg gactcaaaca attctcctgc ctcagccctg caagtagctg    120

ggactgtggg tgcatgccac catgcctggc taacttttgt agtttttgta aagatggggt    180

tttgccatgt tgcacatgct ggtcttgaac tcctgagctc aaacgatctg cccacctcgg    240

cctcccagaa tgttgggatt acaggggtaa accaccacgc ctggccccat tagggtattc    300

ttagcatcca cttgctcact gagattaatc ataagagatg ataagcactg gaagaaaaaa    360

atttttacta ggctttggat atttttttcc tttttcagct ttatacagag gattggatct    420

ttagttttcc tttaactgat aataaaacat tgaaaggaaa taagtttacc tgagattcac    480

agagataacc ggcatcactc ccttgctcaa ttccagtctt taccacatca attattttca    540

gaggtgcagg ataaaggcct ttagtctgct ttcgcacttt ttcttccact tttttgtaaa    600

cctgttgcct gacaaatgga attgacagcg tatgccatga ctattccatt tgtcaggcat    660

acgctgtcaa tttttccacc aatcccttgt ctctctttgg agagatcttc ttatcagcta    720

gtcctttggc aaaagtaatt gcaacttctt ctaggtattc tattgtccgt tccactggtg    780

gaacccctgg gaccaggact aaaacctcca g                                   811
```

<210> SEQ ID NO 56
<211> LENGTH: 591
<212> TYPE: DNA
<213> ORGANISM: Homo sapien
<220> FEATURE:
<221> NAME/KEY: misc_feature
<222> LOCATION: (1)...(591)
<223> OTHER INFORMATION: n = A,T,C or G

<400> SEQUENCE: 56

```
atctcatata tatatttctt cctgacttta tttgcttgct tctgncacgc atttaaaata     60

tcacagagac caaaatagag cggctttctg gtggaacgca tggcagtcac aggacaaaat    120

acaaaactag gggctctgt cttctcatac atcatacaat tttcaagtat ttttttttatg    180

tacaaagagc tactctatct gaaaaaaaat taaaaaataa atgagacaag atagtttatg    240

catcctagga agaaagaatg ggaagaaaga acggggcagt tgggtacaga ttcctgtccc    300

ctgttcccag ggaccactac cttcctgcca ctgagttccc ccacagcctc acccatcatg    360

tcacagggca agtgccaggg taggtgggga ccagtggaga caggaaccag caacatactt    420

tggcctggaa gataaggaga aagtctcaga aacacactgg tgggaagcaa tcccacnggc    480

cgtgccccan gagcttccca cctgctgctg gctccctggg tggctttggg aacagcttgg    540

gcaggccctt ttgggtgggg nccaactggg cctttgggcc cgtgtggaaa g             591
```

-continued

<210> SEQ ID NO 57
<211> LENGTH: 481
<212> TYPE: DNA
<213> ORGANISM: Homo sapien

<400> SEQUENCE: 57
aaacattgag atggaatgat agggtttccc agaatcaggt ccatatttta actaaatgaa 60
aattatgatt tatagccttc tcaaatacct gccatacttg atatctcaac cagagctaat 120
tttacctctt tacaaattaa ataagcaagt aactggatcc acaatttata atacctgtca 180
attttttctg tattaaacct ctatcatagt ttaagcctat tagggtactt aatccttaca 240
aataaacagg tttaaaatca cctcaatagg caactgccct tctggttttc ttctttgact 300
aaacaatctg aatgcttaag attttccact ttgggtgcta gcagtacaca gtgttacact 360
ctgtattcca gacttcttaa attatagaaa aaggaatgta cactttttgt attctttctg 420
agcagggccg ggaggcaaca tcatctacca tggtagggac ttgtatgcat ggactacttt 480
a 481

<210> SEQ ID NO 58
<211> LENGTH: 141
<212> TYPE: DNA
<213> ORGANISM: Homo sapien

<400> SEQUENCE: 58
actctgtcgc ccaggctgga gcccabtggm gcgatctcga ctccctgcaa gctmcgcctc 60
acaggwtcat gccattctcc tgcctcagca tctggagtag ctgggactac aggcgccagc 120
caccatgccc agctaatttt t 141

<210> SEQ ID NO 59
<211> LENGTH: 191
<212> TYPE: DNA
<213> ORGANISM: Homo sapien

<400> SEQUENCE: 59
accttaaaga cataggagaa tttatactgg gagagaaagc ttacaaatgt aaggtttctg 60
acaagacttg ggagtgattc acacctggaa caacatactg gacttcacac tggabagaaa 120
ccttacaagt gtaatgagtg tggcaaagcc tttggcaagc agtcaacact tattcaccat 180
caggcaattc a 191

<210> SEQ ID NO 60
<211> LENGTH: 480
<212> TYPE: DNA
<213> ORGANISM: Homo sapien

<400> SEQUENCE: 60
agtcaggatc atgatggctc agtttcccac agcgatgaat ggagggccaa atatgtgggc 60
tattacatct gaagaacgta ctaagcatga taaacagttt gataacctca aaccttcagg 120
aggttacata acaggtgatc aagcccgtac ttttttccta cagtcaggtc tgccggcccc 180
ggttttagct gaaatatggg ccttatcaga tctgaacaag gatgggaaga tggaccagca 240
agagttctct atagctatga aactcatcaa gttaaagttg cagggccaac agctgcctgt 300
agtcctccct cctatcatga aacaaccccc tatgttctct ccactaatct ctgctcgttt 360
tgggatggga agcatgccca atctgtccat tcatcagcca ttgcctccag ttgcacctat 420
agcaacaccc ttgtcttctg ctacttcagg gaccagtatt cctccctaat gatgcctgct 480

-continued

<210> SEQ ID NO 61
<211> LENGTH: 381
<212> TYPE: DNA
<213> ORGANISM: Homo sapien

<400> SEQUENCE: 61

```
ctttcgattt ccttcaattt gtcacgtttg attttatgaa gttgttcaag ggctaactgc     60
tgtgtattat agctttctct gagttccttc agctgattgt taaatgaatc catttctgag    120
agcttagatg cagtttcttt ttcaagagca tctaattgtt ctttaagtct ttggcataat    180
tcttcctttt ctgatgactt tctatgaagt aaactgatcc ctgaatcagg tgtgttactg    240
agctgcatgt ttttaattct ttcgtttaat agctgcttct cagggaccag atagataagc    300
ttattttgat attccttaag ctcttggtga agttgttcga tttccataat ttccaggtca    360
cactggttat cccaaacttc t                                              381
```

<210> SEQ ID NO 62
<211> LENGTH: 906
<212> TYPE: DNA
<213> ORGANISM: Homo sapien

<400> SEQUENCE: 62

```
gtggaggtga aacggaggca agaaaggggg ctacctcagg agcgagggac aaagggggcg     60
tgaggcacct aggccgcggc accccggcga caggaagccg tcctgaaccg ggctaccggg    120
taggggaagg gcccgcgtag tcctcgcagg gccccagagc tggagtcggc tccacagccc    180
cgggccgtcg gcttctcact tcctggacct ccccggcgcc cgggcctgag gactggctcg    240
gcggagggag aagaggaaac agacttgagc agctccccgt tgtctcgcaa ctccactgcc    300
gaggaactct catttcttcc ctcgctcctt caccccccac ctcatgtaga aaggtgctga    360
agcgtccgga gggaagaaga acctgggcta ccgtcctggc cttcccmccc ccttcccggg    420
gcgctttggt gggcgtggag ttggggttgg gggggtgggt gggggttctt ttttggagtg    480
ctggggaact tttttccctt cttcaggtca ggggaaaggg aatgcccaat tcagagagac    540
atgggggcaa gaaggacggg agtggaggag cttctggaac tttgcagccg tcatcgggag    600
gcggcagctc taacagcaga gagcgtcacc gcttggtatc gaagcacaag cggcataagt    660
ccaaacactc caaagacatg ggggttggtga cccccgaagc agcatccctg ggcacagtta    720
tcaaaccttt ggtggagtat gatgatatca gctctgattc cgacaccttc tccgatgaca    780
tggccttcaa actagaccga agggagaacg acgaacgtcg tggatcagat cggagcgacc    840
gcctgcacaa acatcgtcac caccagcaca ggcgttcccg ggacttacta aaagctaaac    900
agaccg                                                               906
```

<210> SEQ ID NO 63
<211> LENGTH: 491
<212> TYPE: DNA
<213> ORGANISM: Homo sapien

<400> SEQUENCE: 63

```
gacatgtttg cctgcagggg accagagaca atgggattag ccagtgctca ctgttcttta     60
tgcttccaga gaggatgggg acagctctca ggtcagaatc caggctgaga aggccatgct    120
ggttgggggc ccccggaagc acggtccgga tcctccctgg catcagcgta gacccgctgc    180
tcaggcttgg ggtaccaaac tcatgctctg tactgttttg gccccatgcg gtgagaggaa    240
```

-continued

```
aacctagaaa aagattggtc gtgctaagga atcagctgcc ccctcatcct ccgcatccaa    300

tgctggtgac aacatattcc ctctcccagg acacagactc ggtgactcca cactgggctg    360

agtggcctct ggaggctcgt ggcctaaggc agggctccgt aaggctgatc ggctgaactg    420

ggtggggtga gggtttctga cccttcgctt cccatcccat aaccgctgtc aatgagctca    480

cactgtggtc a                                                         491


<210> SEQ ID NO 64
<211> LENGTH: 511
<212> TYPE: DNA
<213> ORGANISM: Homo sapien

<400> SEQUENCE: 64

gatggcatgg tcgttgctaa tgtgcctgct gggatggagc acttcctcct gtgagcccag     60

gggacccgcc tgtccctgga gcttggggca aggagggaag agtgatacca ggaaggtggg    120

gctgcagcca ggggccagag tcagttcagg gagtggtcct cggccctcaa agctcctccg    180

gggactgctc aggagtgatg gtgccctgga gtttgcccca acttccctgg ccaccctgga    240

aggtgcctgg ctgctccagg cctctaggct gggctgatgg gtttctccag gacacaagta    300

tcattaaagc caccctctcc tcagcttgtc aggccgcaca tgtgggacag gctgtgctca    360

caaccccctc gcctgccctg ccctccatca ggaggagcca gtggaacctt cggaaagctc    420

ccagcatctc agcagccctc aaaagtcgtc ctggggcaag ctctggttct cctgactgga    480

ggtcatctgg gcttggcctg ctctctctcg c                                   511


<210> SEQ ID NO 65
<211> LENGTH: 394
<212> TYPE: DNA
<213> ORGANISM: Homo sapien

<400> SEQUENCE: 65

taaaaaagtg taacaaaggt ttatttagac tttcttcatg cccccagatc caggatgtct     60

atgtaaaccg ttatcttaca aagaaagcac aatatttggt ataaactaag tcagtgactt    120

gcttaactga aatagcgtcc atccaaaagt gggtttaagg taaaactacc tgacgatatt    180

ggcggggatc ctgcagtttg gactgcttgc cgggtttgtc cagggttccg ggtctgttct    240

tggcactcat ggggacaggc atcctgctcg tctgtggggc cccgctggag cccttacgtg    300

aagctgaagg tatcgaccst agggggctct agggcagtgg gaccttcatc cggaactaac    360

aagggtcggg gagaggcctc ttgggctatg tggg                                394


<210> SEQ ID NO 66
<211> LENGTH: 359
<212> TYPE: DNA
<213> ORGANISM: Homo sapien

<400> SEQUENCE: 66

caagcgttcc tttatggatg taaattcaaa cagtcatgct gagccatccc gggctgacag     60

tcacgttwaa gacactaggt cgggcgccac agtgccaccc aaggagaaga agaatttgga    120

atttttccat gaagatgtac ggaaatctga tgttgaatat gaaaatggcc cccaaatgga    180

attccaaaag gttaccacag gggctgtaag acctagtgac cctcctaagt gggaaagagg    240

aatggagaat agtatttctg atgcatcaag aacatcagaa tataaaactg agatcataat    300

gaaggaaaat tccatatcca atatgagttt actcagagac agtagaaact attcccagg     359
```

-continued

<210> SEQ ID NO 67
<211> LENGTH: 450
<212> TYPE: DNA
<213> ORGANISM: Homo sapien
<220> FEATURE:
<221> NAME/KEY: misc_feature
<222> LOCATION: (1)...(450)
<223> OTHER INFORMATION: n = A,T,C or G

<400> SEQUENCE: 67

```
taggaataac aaatgtttat tcagaaatgg ataagtaata cataatcacc cttcatctct     60
taatgcccct tcctctcctt ctgcacagga gacacagatg ggtaacatag aggcatggga    120
agtggaggag gacacaggac tagcccacca ccttctcttc ccggtctccc aagatgactg    180
cttatagagt ggaggaggca aacaggtccc ctcaatgtac cagatggtca cctatagcac    240
cagctccaga tggccacgtg gttgcagctg gactcaatga aactctgtga caaccagaag    300
atacctgctt tgggatgaga gggaggataa agccatgcag ggaggatatt taccatccct    360
accctaagca cagtgcaagc agtgagcccc cggctcccag tacctgaaaa accaaggcct    420
actgnctttt ggatgctctc ttgggccacg                                     450
```

<210> SEQ ID NO 68
<211> LENGTH: 511
<212> TYPE: DNA
<213> ORGANISM: Homo sapien

<400> SEQUENCE: 68

```
aagcctcctg ccctggaaat ctggagcccc ttggagctga gctggacggg gcagggaggg     60
gctgagaggc aagaccgtct ccctcctgct gcagctgctt ccccagcagc cactgctggg    120
cacagcagaa acgccagcag agaaaatggg agccgagagt ccttagccct ggagctgagg    180
ctgcctctgg gctgacccgc tggctgtacg tggccagaac tggggttggc atctggcatc    240
catttgaggc cagggtggag gaaagggagg ccaacagagg aaaacctatt cctgctgtga    300
caacacagcc cttgtcccac gcagcctaag tgcagggagc gtgatgaagt caggcagcca    360
gtcggggagg acgaggtaac tcagcagcaa tgtcaccttg tagcctatgc gctcaatggc    420
ccggaggggc agcaaccccc cgcacacgtc agccaacagc agtgcctctg caggcaccaa    480
gagagcgatg atggacttga gcgccgtgtt c                                   511
```

<210> SEQ ID NO 69
<211> LENGTH: 511
<212> TYPE: DNA
<213> ORGANISM: Homo sapien

<400> SEQUENCE: 69

```
gtttggcaga agacatgttt aataacattt tcatatttaa aaaatacagc aacaattctc     60
tatctgtcca ccatcttgcc ttgcccttcc tggggctgag gcagacaaag gaaaggtaat    120
gaggttaggg cccccaggcg ggctaagtgc tattggcctg ctcctgctca aagagagcca    180
tagccagctg ggcacggccc cctagcccct ccaggttgct gaggcggcag cggtggtaga    240
gttcttcact gagccgtggg ctgcagtctc gcagggagaa cttctgcacc agccctggct    300
ctacggcccg aaagaggtgg agccctgaga accggaggaa aacatccatc acctccagcc    360
cctccagggc ttcctcctct tcctggcctg ccagttcacc tgccagccgg gctcgggccg    420
ccaggtagtc agcgttgtag aagcagccct ccgcagaagc ctgccggtca aatctccccg    480
ctataggagc cccccgggag gggtcagcac c                                   511
```

-continued

<210> SEQ ID NO 70
<211> LENGTH: 511
<212> TYPE: DNA
<213> ORGANISM: Homo sapien

<400> SEQUENCE: 70
caagttgaac gtcaggcttg gcagaggtgg agtgtagatg aaaacaaagg tgtgattatg 60
aagaggatgt gagtcctttg ggtgtaggag agaaaggctg ttgagcttct atttcaagat 120
acttttacct gtgcaaaaag cacattttcc acctccttct catggcattt gtgtaaggtg 180
agtatgattc ctattccatc tgcattttag aggtgaagaa taacgtacaa gggattcagt 240
gattagcaag ggacccctca ctaagtgttg atggagttag gacagagctc agctgtttga 300
atctcagagc ccaggcagct ggagctgggt aggatcctgg agctggcact aatgtgaggt 360
gcattccctc caacccaggc tcagatccgg aacctgaccg tgctgacccc cgaaggggag 420
gcagggctga gctggcccgt tgggctccct gctcctttca caccacactc tcgctttgag 480
gtgctgggct gggactactt cacagagcag c 511

<210> SEQ ID NO 71
<211> LENGTH: 511
<212> TYPE: DNA
<213> ORGANISM: Homo sapien

<400> SEQUENCE: 71
tggcctgggc aggattggga gagaggtagc tacccggatg cagtcctttg ggatgaagac 60
tatagggtat gaccccatca tttccccaga ggtctcggcc tcctttggtg ttcagcagct 120
gcccctggag gagatctggc ctctctgtga tttcatcact gtgcacactc ctctcctgcc 180
ctccacgaca ggcttgctga atgacaacac ctttgcccag tgcaagaagg gggtgcgtgt 240
ggtgaactgt gcccgtggag ggatcgtgga cgaaggcgcc ctgctccggg ccctgcagtc 300
tggccagtgt gccggggctg cactggacgt gtttacggaa gagccgccac gggaccgggc 360
cttggtggac catgagaatg tcatcagctg tccccacctg ggtgccagca ccaaggaggc 420
tcagagccgc tgtggggagg aaattgctgt tcagttcgtg gacatggtga aggggaaatc 480
tctcacgggg gttgtgaatg cccaggccct t 511

<210> SEQ ID NO 72
<211> LENGTH: 2017
<212> TYPE: DNA
<213> ORGANISM: Homo sapien

<400> SEQUENCE: 72
agccagatgg ctgagagctg caagaagaag tcaggatcat gatggctcag tttcccacag 60
cgatgaatgg agggccaaat atgtgggcta ttacatctga agaacgtact aagcatgata 120
aacagtttga taacctcaaa ccttcaggag gttacataac aggtgatcaa gcccgtactt 180
ttttcctaca gtcaggtctg ccggccccgg ttttagctga aatatgggcc ttatcagatc 240
tgaacaagga tgggaagatg gaccagcaag agttctctat agctatgaaa ctcatcaagt 300
taaagttgca gggccaacag ctgcctgtag tcctccctcc tatcatgaaa caacccccta 360
tgttctctcc actaatctct gctcgttttg ggatgggaag catgcccaat ctgtccattc 420
atcagccatt gcctccagtt gcacctatag caacaccctt gtcttctgct acttcaggga 480
ccagtattcc tcccctaatg atgcctgctc ccctagtgcc ttctgttagt acatcctcat 540
taccaaatgg aactgccagt ctcattcagc ctttatccat tccttattct tcttcaacat 600

-continued tgcctcatgc atcatcttac agcctgatga tgggaggatt tggtggtgct agtatccaga 660
aggcccagtc tctgattgat ttaggatcta gtagctcaac ttcctcaact gcttccctct 720
cagggaactc acctaagaca gggacctcag agtgggcagt tcctcagcct tcaagattaa 780
agtatcggca aaaatttaat agtctagaca aaggcatgag cggatacctc tcaggttttc 840
aagctagaaa tgcccttctt cagtcaaatc tctctcaaac tcagctagct actatttgga 900
ctctggctga catcgatggt gacggacagt tgaaagctga agaatttatt ctggcgatgc 960
acctcactga catggccaaa gctggacagc cactaccact gacgttgcct cccgagcttg 1020
tccctccatc tttcagaggg ggaaagcaag ttgattctgt taatggaact ctgccttcat 1080
atcagaaaac acaagaagaa gagcctcaga agaaactgcc agttactttt gaggacaaac 1140
ggaaagccaa ctatgaacga ggaaacatgg agctggagaa gcgacgccaa gtgttgatgg 1200
agcagcagca gagggaggct gaacgcaaag cccagaaaga gaaggaagag tgggagcgga 1260
aacagagaga actgcaagag caagaatgga agaagcagct ggagttggag aaacgcttgg 1320
agaaacagag agagctggag agacagcggg aggaagagag gagaaaggag atagaaagac 1380
gagaggcagc aaaacaggag cttgagagac aacgccgttt agaatgggaa agactccgtc 1440
ggcaggagct gctcagtcag aagaccaggg aacaagaaga cattgtcagg ctgagctcca 1500
gaaagaaaag tctccacctg gaactggaag cagtgaatgg aaaacatcag cagatctcag 1560
gcagactaca agatgtccaa atcagaaagc aaacacaaaa gactgagcta gaagttttgg 1620
ataaacagtg tgacctggaa attatggaaa tcaaacaact tcaacaagag cttaaggaat 1680
atcaaaataa gcttatctat ctggtccctg agaagcagct attaaacgaa agaattaaaa 1740
acatgcagct cagtaacaca cctgattcag ggatcagttt acttcataaa aagtcatcag 1800
aaaaggaaga attatgccaa agacttaaag aacaattaga tgctcttgaa aaagaaactg 1860
catctaagct ctcagaaatg gattcattta acaatcagct gaaggaactc agagaaagct 1920
ataatacaca gcagttagcc cttgaacaac ttcataaaat caaacgtgac aaattgaagg 1980
aaatcgaaag aaaaagatta gagcaaaaaa aaaaaaa 2017

<210> SEQ ID NO 73
<211> LENGTH: 414
<212> TYPE: DNA
<213> ORGANISM: Homo sapien

<400> SEQUENCE: 73
atggcagtga cattcaccat catgggaacc accttccctt ttcttcagga ttctctgtag 60
tggaagagag cacccagtgt tgggctgaaa acatctgaaa gtagggagaa gaacctaaaa 120
taatcagtat ctcagagggc tctaaggtgc caagaagtct cactggacat ttaagtgcca 180
acaaaggcat actttcggaa tcgccaagtc aaaactttct aacttctgtc tctctcagag 240
acaagtgaga ctcaagagtc tactgcttta gtggcaacta cagaaaactg gtgttaccca 300
gaaaaacagg agcaattaga aatggttcca atatttcaaa gctccgcaaa caggatgtgc 360
tttcctttgc ccatttaggg tttcttctct ttcctttctc tttattaacc acta 414

<210> SEQ ID NO 74
<211> LENGTH: 1567
<212> TYPE: DNA
<213> ORGANISM: Homo sapien

<400> SEQUENCE: 74

-continued

```
atatctagaa gtctggagtg agcaaacaag agcaagaaac aaaaagaagc caaaagcaga     60
aggctccaat atgaacaaga taaatctatc ttcaaagaca tattagaagt tgggaaaata    120
attcatgtga actagacaag tgtgttaaga gtgataagta aaatgcacgt ggagacaagt    180
gcatccccag atctcaggga cctccccctg cctgtcacct ggggagtgag aggacaggat    240
agtgcatgtt ctttgtctct gaatttttag ttatatgtgc tgtaatgttg ctctgaggaa    300
gcccctggaa agtctatccc aacatatcca catcttatat tccacaaatt aagctgtagt    360
atgtacccta agacgctgct aattgactgc cacttcgcaa ctcaggggcg gctgcatttt    420
agtaatgggt caaatgattc actttttatg atgcttccaa aggtgccttg gcttctcttc    480
ccaactgaca aatgccaaag ttgagaaaaa tgatcataat tttagcataa acagagcagt    540
cggcgacacc gattttataa ataaactgag caccttcttt ttaaacaaac aaatgcgggt    600
ttatttctca gatgatgttc atccgtgaat ggtccaggga aggacctttc accttgacta    660
tatggcatta tgtcatcaca agctctgagg cttctccttt ccatcctgcg tggacagcta    720
agacctcagt tttcaatagc atctagagca gtgggactca gctggggtga tttcgccccc    780
catctccggg ggaatgtctg aagacaattt tgttacctca atgagggagt ggaggaggat    840
acagtgctac taccaactag tggataaagg ccagggatgc tgctcaacct cctaccatgt    900
acaggacgtc tccccattac aactacccaa tccgaagtgt caactgtgtc aggactaaga    960
aaccctggtt ttgagtagaa aagggcctgg aaagagggga gccaacaaat ctgtctgctt   1020
cctcacatta gtcattggca aataagcatt ctgtctcttt ggctgctgcc tcagcacaga   1080
gagccagaac tctatcgggc accaggataa catctctcag tgaacagagt tgacaaggcc   1140
tatgggaaat gcctgatggg attatcttca gcttgttgag cttctaagtt tctttccctt   1200
cattctaccc tgcaagccaa gttctgtaag agaaatgcct gagttctagc tcaggttttc   1260
ttactctgaa tttagatctc cagacccttc ctggccacaa ttcaaattaa ggcaacaaac   1320
atataccttc catgaagcac acacagactt ttgaaagcaa ggacaatgac tgcttgaatt   1380
gaggccttga ggaatgaagc tttgaaggaa aagaatactt tgtttccagc cccottccca   1440
cactcttcat gtgttaacca ctgccttcct ggaccttgga gccacggtga ctgtattaca   1500
tgttgttata gaaaactgat tttagagttc tgatcgttca agagaatgat taaatataca   1560
tttccta                                                             1567

<210> SEQ ID NO 75
<211> LENGTH: 240
<212> TYPE: DNA
<213> ORGANISM: Homo sapien

<400> SEQUENCE: 75

tcgagcggcc gcccgggcag gtccttcaga cttggactgt gtcacactgc caggcttcca     60
gggctccaac ttgcagacgg cctgttgtgg gacagtctct gtaatcgcga aagcaaccat    120
ggaagacctg ggggaaaaca ccatggtttt atccaccctg agatctttga acaacttcat    180
ctctcagcgt gcggagggag gctctggact ggatatttct acctcggccg cgaccacgct    240

<210> SEQ ID NO 76
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G
```

-continued

<400> SEQUENCE: 76
tagcgyggtc gcggccgagg yctgcttytc tgtccagccc agggcctgtg gggtcagggc 60
ggtgggtgca gatggcatcc actccggtgg cttccccatc tttctctggc ctgagcaagg 120
tcagcctgca gccagagtac agagggccaa cactggtgtt cttgaacaag ggccttagca 180
ggccctgaag grccctctct gtagtgttga acttcctgga gccaggccac atgttctcct 240
cataccgcag gytagygatg gtgaagttga gggtgaaata gtattmangr agatggctgg 300
caracctgcc cgggcggccg ctcsaaatcc 330

<210> SEQ ID NO 77
<211> LENGTH: 361
<212> TYPE: DNA
<213> ORGANISM: Homo sapien

<400> SEQUENCE: 77
agcgtggtcg cggccgaggt gtccttcagg gtctgcttat gcccttgttc aagaacacca 60
gtgtcagctc tctgtactct ggttgcagac tgaccttgct caggcctgag aaggatgggg 120
cagccaccag agtggatgct gtctgcaccc atcgtcctga ccccaaaagc cctggactgg 180
acagagagcg gctgtactgg aagctgagcc agctgaccca cggcatcact gagctgggcc 240
cctacaccct ggacagggac agtctctatg tcaatggttt cacccatcgg agctctgtac 300
ccaccaccag caccggggtg gtcagcgagg agccattcaa cctgcccggg cggccgctcg 360
a 361

<210> SEQ ID NO 78
<211> LENGTH: 356
<212> TYPE: DNA
<213> ORGANISM: Homo sapien
<220> FEATURE:
<221> NAME/KEY: misc_feature
<222> LOCATION: (1)...(356)
<223> OTHER INFORMATION: n = A,T,C or G

<400> SEQUENCE: 78
ttggggnttt mgagcggccg cccgggcagg taccggggtg gtcagcgagg agccattcac 60
actgaacttc accatcaaca acctgcggta tgaggagaac atgcagcacc ctggctccag 120
gaagttcaac accacggaga gggtccttca gggcctgctc aggtccctgt tcaagagcac 180
cagtgttggc cctctgtact ctggctgcag actgactttg ctcagacttg agaaacatgg 240
ggcagccact ggagtggacg ccatctgcac cctccgcctt gatcccactg gtcctggact 300
ggacagagag cggctatact gggagctgag ccagtcctct ggcggngacn ccnctt 356

<210> SEQ ID NO 79
<211> LENGTH: 226
<212> TYPE: DNA
<213> ORGANISM: Homo sapien

<400> SEQUENCE: 79
agcgtggtcg cggccgaggt ccagtcgcag catgctcttt ctcctgccca ctggcacagt 60
gaggaagatc tctgctgtca gtgagaaggc tgtcatccac tgagatggca gtcaaaagtg 120
catttaatac acctaacgta tcgaacatca tagcttggcc caggttatct catatgtgct 180
cagaacactt acaatagcct gcagacctgc ccgggcggcc gctcga 226

<210> SEQ ID NO 80

-continued

<211> LENGTH: 444
<212> TYPE: DNA
<213> ORGANISM: Homo sapien
<220> FEATURE:
<221> NAME/KEY: misc_feature
<222> LOCATION: (1)...(444)
<223> OTHER INFORMATION: n = A,T,C or G

<400> SEQUENCE: 80
tgtggtgttg aacttcctgg agncagggtg acccatgtcc tccccatact gcaggttggt 60
gatggtgaag ttgagggtga atggtaccag gagagggcca gcagccataa ttgtsgrgck 120
gsmgmssgag gmwggwgtyy cwgaggttcy rarrtccact gtggaggtcc caggagtgct 180
ggtggtgggc acagagstcy gatgggtgaa accattgaca tagagactgt tcctgtccag 240
ggtgtagggg cccagctctt yratgycatt ggycagttkg ctyagctccc agtacagccr 300
ctctckgyyg mgwccagsgc ttttggggtc aagatgatgg atgcagatgg catccactcc 360
agtggctgct ccatccttct cggacctgag agaggtcagt ctgcagccag agtacagagg 420
gccaacactg gtgttctttg aata 444

<210> SEQ ID NO 81
<211> LENGTH: 310
<212> TYPE: DNA
<213> ORGANISM: Homo sapien

<400> SEQUENCE: 81
tcgagcggcc gcccgggcag gtcaggaagc acattggtct tagagccact gcctcctgga 60
ttccacctgt gctgcggaca tctccaggga gtgcagaagg gaagcaggtc aaactgctca 120
gatcagtcag actggctgtt ctcagttctc acctgagcaa ggtcagtctg cagccagagt 180
acagagggcc aacactggtg ttcttgaaca agggcttgag cagaccctgc agaaccctct 240
tccgtggtgt tgaacttcct ggaaaccagg gtgttgcatg tttttcctca taatgcaagg 300
ttggtgatgg 310

<210> SEQ ID NO 82
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 82
acggtttcaa tggacacttt tattgtttac ttaatggatc atcaattttg tctcactacc 60
tacaaatgga atttcatctt gtttccatgc tgagtagtga aacagtgaca aagctaatca 120
taataaccta catcaaaaga gaactaagct aacactgctc actttctttt taacaggcaa 180
aatataaata tatgcactct anaatgcaca atggtttagt cactaaaaaa ttcaaatggg 240
atcttgaaga atgtatgcaa atccagggtg cagtgaagat gagctgagat gctgtgcaac 300
tgtttaaggg ttcctggcac tgcatctctt ggccactagc tgaatcttga catggaaggt 360
tttagctaat gccaagtgga gatgcagaaa atgctaagtt gacttagggg ctgtgcacag 420
gaactaaaag gcaggaaagt actaaatatt gctgagagca tccaccccag gaaggacttt 480
accttccagg agctccaaac tggcaccacc cccagtgctc acatggctga ctttatcctc 540
cgtgttccat ttggcacagc aagtggcagt g 571

-continued

<210> SEQ ID NO 83
<211> LENGTH: 551
<212> TYPE: DNA
<213> ORGANISM: Homo sapien

<400> SEQUENCE: 83
aaggctggtg ggtttttgat cctgctggag aacctccgct ttcatgtgga ggaagaaggg 60
aagggaaaag atgcttctgg gaacaaggtt aaagccgagc cagccaaaat agaagctttc 120
cgagcttcac tttccaagct aggggatgtc tatgtcaatg atgcttttgg cactgctcac 180
agagcccaca gctccatggt aggagtcaat ctgccacaga aggctggtgg gtttttgatg 240
aagaaggagc tgaactactt tgcaaaggcc ttggagagcc cagagcgacc cttcctggcc 300
atcctgggcg gagctaaagt tgcagacaag atccagctca tcaataatat gctggacaaa 360
gtcaatgaga tgattattgg tggtggaatg gcttttacct tccttaaggt gctcaacaac 420
atggagattg gcacttctct gtttgatgaa gagggagcca agattgtcaa agacctaatg 480
tccaaagctg agaagaatgg tgtgaagatt accttgcctg ttgactttgt cactgctgac 540
aagtttgatg a 551

<210> SEQ ID NO 84
<211> LENGTH: 571
<212> TYPE: DNA
<213> ORGANISM: Homo sapien

<400> SEQUENCE: 84
tttgttcctt acatttttct aaagagttac ttaaatcagt caactggtct ttgagactct 60
taagttctga ttccaactta gctaattcat tctgagaact gtggtatagg tggcgtgtct 120
cttctagctg ggacaaaagt tctttgtttt ccccctgtag agtatcacag accttctgct 180
gaagctggac ctctgtctgg gccttggact cccaaatctg cttgtcatgt tcaagcctgg 240
aaatgttaat ctttaattct tccatatgga tggacatctg tctaagttga tcctttagaa 300
cactgcaatt atcttctttg agtctaattt cttcttcttt gctttgaatc gcatcactaa 360
acttcctctc ccatttctta gcttcatcta tcaccctgtc acgatcatcc tggagggaag 420
acatgctctt agtaaaggct gcaagctggg tcacagtact gtccaagttt tcctgaagtt 480
gctgaacttc cttgtctttc ttgttcaaag taacctgaat ctctccaatt gtctcttcca 540
agtggacttt ttctctgcgc aaagcatcca g 571

<210> SEQ ID NO 85
<211> LENGTH: 561
<212> TYPE: DNA
<213> ORGANISM: Homo sapien

<400> SEQUENCE: 85
tcattgcctg tgatggcatc tggaatgtga tgagcagcca ggaagttgta gatttcattc 60
aatcaaagga ttcagcatgt ggtggaagct gtgaggcaag agaaacaaga actgtatggc 120
aagttaagaa gcacagaggc aaacaagaag gagacagaaa agcagttgca ggaagctgag 180
caagaaatgg aggaaatgaa agaaaagatg agaaagtttg ctaaatctaa acagcagaaa 240
atcctagagc tggaagaaga gaatgaccgg cttagggcag aggtgcaccc tgcaggagat 300
acagctaaag agtgtatgga aacacttctt tcttccaatg ccagcatgaa ggaagaactt 360
gaaagggtca aaatggagta tgaaaccctt tctaagaagt ttcagtcttt aatgtctgag 420
aaagactctc taagtgaaga ggttcaagat ttaaagcatc agatagaagg taatgtatct 480

-continued

```
aaacaagcta acctagaggc caccgagaaa catgataacc aaacgaatgt cactgaagag    540

ggaacacagt ctataccagg t                                              561


<210> SEQ ID NO 86
<211> LENGTH: 795
<212> TYPE: DNA
<213> ORGANISM: Homo sapien

<400> SEQUENCE: 86

aagccaataa tcaccattta ttacttaata tatgccaacc actgtacttg gcagttcaca     60

aattctcacc gttacaacaa ccccatgagg tatttattcc cattctatag atagggaaac    120

cacagctcaa gtaagttagg aaactgagcc aagtatacac agaatacgaa gtggcaaaac    180

tagaaggaaa gactgacact gctatctgct ggcctccagt gtcctggctc ttttcacacg    240

ggttcaatgt ctccagcgct gctgctgctg ctgcattacc atgccctcat tgtttttctt    300

cctctggtgt tcaactgcat ccttcaaaga atctaactca ttccagagac cacttatttc    360

tttctctctt tctgaaatta cttttaataa ttcttcatga gggggaaaag aagatgcctg    420

ttggtagttt tgttgtttaa gctgctcaat ttgggactta aacaatttgt tttcatcttg    480

tacatcctgt aacagctgtg ttttgctaga aagatcactc tccctctctt ttagcatggc    540

ttctaacctc ttcaattcat tttccttttc tttcaacaca atctcaagtt cttcaaactg    600

tgatgcagaa gaggcctctt tcaagttatg ttgtgctact tcctgaacat gtgcttttaa    660

agattcattt tcttcttgaa gatcctgtaa ccacttccct gtattggcta ggtctttctc    720

tttctcttcc aaaacagcct tcatggtatt catctgttcc tcttttcctt ttaataagtt    780

caggagcttc agaac                                                     795


<210> SEQ ID NO 87
<211> LENGTH: 594
<212> TYPE: DNA
<213> ORGANISM: Homo sapien

<400> SEQUENCE: 87

caagcttttt tttttttttt aaaaagtgtt agcattaatg ttttattgtc acgcagatgg     60

caactgggtt tatgtcttca tattttatat ttttgtaaat taaaaaaatt acaagtttta    120

aatagccaat ggctggttat attttcagaa aacatgatta gactaattca ttaatggtgg    180

cttcaagctt ttccttattg gctccagaaa attcacccac cttttgtccc ttcttaaaaa    240

actggaatgt tggcatgcat ttgacttcac actctgaagc aacatcctga cagtcatcca    300

catctacttc aaggaatatc acgttggaat acttttcaga gagggaatga aagaaaggct    360

tgatcatttt gcaaggccca caccacgtgg ctgagaagtc aactactaca agtttatcac    420

ctgcagcgtc caaggcttcc tgaaaagcag tcttgctctc gatctgcttc accatcttgg    480

ctgctggagt ctgacgagcg gctgtaagga ccgatggaaa tggatccaaa gcaccaaaca    540

gagcttcaag actcgctgct tggcttgaat tcggatccga tatcgccatg gcct          594


<210> SEQ ID NO 88
<211> LENGTH: 557
<212> TYPE: DNA
<213> ORGANISM: Homo sapien

<400> SEQUENCE: 88

aagtgttagc attaatgttt tattgtcacg cagatggcaa ctgggtttat gtcttcatat     60

tttatatttt tgtaaattaa aaaaattmca agttttaaat agccaatggc tggttatatt    120
```

-continued

```
ttcagaaaac atgattagac taattcatta atggtggctt caagcttttc cttattggct    180

ccagaaaatt cacccacctt ttgtcccttc ttaaaaaact ggaatgttgg catgcatttg    240

acttcacact ctgaagcaac atcctgacag tcatccacat ctacttcaag gaatatcacg    300

ttggaatact tttcagagag ggaatgaaag aaaggcttga tcatttttgca aggcccacac   360

cacgtggctg agaagtcaac tactacaagt ttatcacctg cagcgtccaa ggcttcctga    420

aaagcagtct tgctctcgat ctgcttcacc atcttggctg ctggagtctg acgagcggct    480

gtaaggaccg atggaaatgg atccaaagca ccaaacagag cttcaagact cgctgcttgg    540

catgaattcg gatccga                                                    557
```

<210> SEQ ID NO 89
<211> LENGTH: 561
<212> TYPE: DNA
<213> ORGANISM: Homo sapien
<220> FEATURE:
<221> NAME/KEY: misc_feature
<222> LOCATION: (1)...(561)
<223> OTHER INFORMATION: n = A,T,C or G

<400> SEQUENCE: 89

```
tacaaacttt attgaaacgc acacgcgcac acacacaaac acccctgtgg atagggaaaa     60

gcacctggcc acagggtcca ctgaaacggg gaggggatgg cagcttgtaa tgtggctttt    120

gccacaaccc ccttctgaca gggaaggcct tagattgagg ccccacctcc catggtgatg    180

gggagctcag aatggggtcc agggagaatt tggttagggg gaggtgctag ggaggcatga    240

gcagagggca ccctccgagt ggggtcccga gggctgcaga gtcttcagta ctgtccctca    300

cagcagctgt ctcaaggctg ggtccctcaa aggggcgtcc cagcgcgggg cctccctgcg    360

caaacacttg gtacccctgg ctgcgcagcg gaagccagca ggacagcagt ggcgccgatc    420

agcacaacag acgccctggc ggtagggaca gcaggcccag ccctgtcggt tgtctcggca    480

gcaggtctgg ttatcatggc agaagtgtcc ttcccacact tcacgtcctt cacacccacg    540

tganggctac nggccaggaa g                                               561
```

<210> SEQ ID NO 90
<211> LENGTH: 561
<212> TYPE: DNA
<213> ORGANISM: Homo sapien

<400> SEQUENCE: 90

```
cccgtgggtg ccatccacgg agttgttacc tgatctttgg aagcaggatc gcccgtctgc     60

actgcagtgg aagccccgtg ggcagcagtg atggccatcc ccgcatgcca cggcctctgg    120

gaaggggcag caactggaag tccctgagac ggtaaagatg caggagtggc cggcagagca    180

gtgggcatca acctggcagg ggccacccag atgcctgctc agtgttgtgg gccatttgtc    240

cagaagggga cggcagcagc tgtagctggc tcctccgggg tccaggcagc aggccacagg    300

gcagaactga ccatctgggc accgcgttcc agccaccagc cctgctgtta aggccaccca    360

gctcaccagg gtccacatgg tctgcctgcg tccgactccg cggtccttgg gccctgatgg    420

ttctacctgc tgtgagctgc ccagtgggaa gtatggctgc tgccaatgcc caacgccacc    480

tgctgctccg atcacctgca ctgctgcccc aagacactgt gtgtgacctg atccagagta    540

agtgcctctc caaggagaac g                                               561
```

<210> SEQ ID NO 91

-continued

<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 91
gaatcacctt tctggtttag ctagtacttt gtacagaaca atgaggtttc ccacagcgga 60
gtctccctgg gctctgtttg gctctcggta aggcaggcct acaccttttc ctctcctcta 120
tggagagggg aatatgcatt aaggtgaaaa gtcaccttcc aaaagtgaga aagggattcg 180
attgctgctt caggactgtg gaattatttg gaatgtttta caaatggttg ctacaaaaca 240
acaaaaaagg taattacaaa atgtgtacat cacaacatgc tttttaaaga cattatgcat 300
tgtgctcaca ttcccttaaa tgttgtttcc aaaggtgctc agcctctagc ccagctggat 360
tctccgggaa gaggcagaga cagtttggcg aaaaagacac agggaaggag ggggtggtga 420
aaggagaaag cagccttcca gttaaagatc agccctcagt taaaggtcag cttcccgcan 480
gctggcctca ngcggagtct gggtcagagg gaggagcagc agcagggtgg gactggggcg 540
t 541

<210> SEQ ID NO 92
<211> LENGTH: 551
<212> TYPE: DNA
<213> ORGANISM: Homo sapien

<400> SEQUENCE: 92
aaccggagcg cgagcagtag ctgggtgggc accatggctg ggatcaccac catcgaggcg 60
gtgaagcgca agatccaggt tctgcagcag caggcagatg atgcagagga gcgagctgag 120
cgcctccagc gagaagttga gggagaaagg cgggcccggg aacaggctga ggctgaggtg 180
gcctccttga accgtaggat ccagctggtt gaagaagagc tggaccgtgc tcaggagcgc 240
ctggccactg ccctgcaaaa gctggaagaa gctgaaaaag ctgctgatga gagtgagaga 300
ggtatgaagg ttattgaaaa ccgggcctta aaagatgaag aaaagatgga actccaggaa 360
atccaactca aagaagctaa gcacattgca gaagaggcag ataggaagta tgaagaggtg 420
gctcgtaagt tggtgatcat tgaaggagac ttggaacgca cagaggaacg agctgagctg 480
gcagagtccc gttgccgaga gatggatgag cagattagac tgatggacca gaacctgaag 540
tgtctgagtg c 551

<210> SEQ ID NO 93
<211> LENGTH: 531
<212> TYPE: DNA
<213> ORGANISM: Homo sapien

<400> SEQUENCE: 93
gagaacttgg cctttattgt gggcccagga gggcacaaag gtcaggaggc ccaagggagg 60
gatctggttt tctggatagc caggtcatag catgggtatc agtaggaatc cgctgtagct 120
gcacaggcct cacttgctgc agttccgggg agaacacctg cactgcatgg cgttgatgac 180
ctcgtggtac acgacagagc cattggtgca gtgcaagggc acgcgcatgg gctccgtcct 240
cgagggcagg cagcaggagc attgctcctg cacatcctcg atgtcaatgg agtacacagc 300
tttgctggca cactttccct ggcagtaatg aatgtccact tcctcttggg acttacaatc 360
tcccactttg atgtactgca ccttggctgt gatgtctttg caatcaggct cctcacatgt 420

-continued gtcacagcag gtgcctggaa ttttcacgat tttgcctcct tcagccagac acttgtgttc 480
atcaaatggt gggcagcccg tgaccctctt ctcccagatg tactctcctc t 531

<210> SEQ ID NO 94
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 94
gcctggacct tgccggatca gtgccacaca gtgacttgct tggcaaatgg ccagaccttg 60
ctgcagagtc atcgtgtcaa ttgtgaccat ggaccccggc cttcatgtgc caacagccag 120
tctcctgttc gggtggagga gacgtgtggc tgccgctgga cctgcccttg tgtgtgcacg 180
ggcagttcca ctcggcacat cgtcaccttc gatgggcaga atttcaagct tactggtagc 240
tgctcctatg tcatctttca aaacaaggag caggacctgg aagtgctcct ccacaatggg 300
gcctgcagcc ccggggcaaa acaagcctgc atgaagtcca ttgagattaa gcatgctggc 360
gtctctgctg agctgcacag taacatggag atggcagtgg atgggagact ggtccttgcc 420
ccgtacgttg gtgaaaacat ggaagtcagc atctacggcg ctatcatgta tgaagtcagg 480
tttacccatc ttggccacat cctcacatac accgccncaa aacaacgagt t 531

<210> SEQ ID NO 95
<211> LENGTH: 605
<212> TYPE: DNA
<213> ORGANISM: Homo sapien

<400> SEQUENCE: 95
agatcaacct ctgctggtca ggaggaatgc cttccttgtc ttggatcttt gctttgacgt 60
tctcgatagt rwcaactkkr ytsramskma agkgyratgr wmttksywgw rasyktmwwm 120
rsgraraytt agacayccm cctcwgagac gsagkaccar gtgcagaggt ggactctttc 180
tggatgttgt agtcagacag ggtgcgtcca tcttccagct gtttcccagc aaagatcaac 240
ctctgctgat caggagggat gccttcctta tcttggatct ttgccttgac attctcgatg 300
gtgtcactgg gctccacctc gagggtgatg gtcttaccag tcagggtctt cacgaagaty 360
tgcatcccac ctctgagacg gagcaccagg tgcagggtrg actctttctg gatgttgtag 420
tcagacaggg tgcgyccatc ttccagctgc tttccsagca aagatcaacc tctgctggtc 480
aggaggratg ccttccttgt cytggatctt tgcyttgacr ttctcratgg tgtcactcgg 540
ctccacttcg agagtgatgg tcttaccagt cagggtcttc acgaagatct gcatcccacc 600
tctaa 605

<210> SEQ ID NO 96
<211> LENGTH: 531
<212> TYPE: DNA
<213> ORGANISM: Homo sapien

<400> SEQUENCE: 96
aagtcacaaa cagacaaaga ttattaccag ctgcaagcta tattagaagc tgaacgaaga 60
gacagaggtc atgattctga gatgattgga gaccttcaag ctcgaattac atctttacaa 120
gaggaggtga agcatctcaa acataatctc gaaaaagtgg aaggagaaag aaaagaggct 180

-continued

```
caagacatgc ttaatcactc agaaaaggaa aagaataatt tagagataga tttaaactac    240

aaacttaaat cattacaaca acggttagaa caagaggtaa atgaacacaa agtaaccaaa    300

gctcgtttaa ctgacaaaca tcaatctatt gaagaggcaa agtctgtggc aatgtgtgag    360

atggaaaaaa agctgaaaga agaaagagaa gctcgagaga aggctgaaaa tcgggttgtt    420

cagattgaga aacagtgttc catgctagac gttgatctga agcaatctca gcagaaacta    480

gaacatttga ctggaaataa agaaaggatg gaggatgaag ttaagaatct a             531
```

<210> SEQ ID NO 97
<211> LENGTH: 1017
<212> TYPE: DNA
<213> ORGANISM: Homo sapien
<220> FEATURE:
<221> NAME/KEY: misc_feature
<222> LOCATION: (1)...(1017)
<223> OTHER INFORMATION: n = A,T,C or G

<400> SEQUENCE: 97

```
cgcctccacc atgtccatca gggtgaccca gaagtcctac aaggtgtcca cctctggccc     60

ccgggccttc agcagccgct cctacacgag tgggcccggt tcccgcatca gctcctcgag    120

cttctcccga gtgggcagca gcaactttcg cggtggcctg ggcggcggct atggtggggc    180

cagcggcatg ggaggcatca ccgcagttac ggtcaaccag agcctgctga gccccccttgt   240

cctggaggtg gaccccaaca tccaggccgt gcgcacccag gagaaggagc agatcaagac    300

cctcaacaac aagtttgcct ccttcataga caaggtacgg ttcctggagc agcagaacaa    360

gatgctggag accaagtgga gcctcctgca gcagcagaag acggctcgaa gcaacatgga    420

caacatgttc gagagctaca tcaacarcct taggcggcag ctggagactc tgggccagga    480

gaagctgaag ctggaggcgg agcttggcaa catgcagggg ctggtggagg acttcaagaa    540

caagtatgag gatgagatca ataagcgtac agagatggag aacgaatttg tcctcatcaa    600

gaaggatgtg gatgaagctt acatgaacaa ggtagagctg gagtctcgcc tggaagggct    660

gaccgacgag atcaacttcc tcaggcagct gtatgaagag gagatccggg agctgcagtc    720

ccagatctcg gacacatctg tggtgctgtc catggacaac agccgctccc tggacatgga    780

cagcatcatt gctgaggtca aggcacagta cgaggatatt gccaaccgca gccgggctga    840

ggctgagagc atgtaccagg tcaagtatga ggagctgcag agcctggctg ggaagcacgg    900

ggatgacctg cggcgcacaa agactgagat ctctgagatg aacccggaac atcagcccgg    960

ctncaggctg agattgaggg cctcaaaggc caganggctt ncctggangn ccgccat      1017
```

<210> SEQ ID NO 98
<211> LENGTH: 561
<212> TYPE: DNA
<213> ORGANISM: Homo sapien

<400> SEQUENCE: 98

```
cccggagcca gccaacgagc ggaaaatggc agacaatttt tcgctccatg atgcgttatc     60

tgggtctgga aacccaaacc ctcaaggatg gcctggcgca tgggggaacc agcctgctgg    120

ggcagggggc tacccagggg cttcctatcc tggggcctac cccgggcagg cacccccagg    180

ggcttatcct ggacaggcac ctccaggcgc ctaccctgga gcacctggag cttatcccgg    240

agcacctgca cctggagtct acccagggcc acccagcggc cctggggcct acccatcttc    300

tggacagcca agtgccaccg gagcctaccc tgccactggc ccctatggcg cccctgctgg    360

gccactgatt gtgccttata acctgccttt gcctggggga gtggtgcctc gcatgctgat    420
```

-continued aacaattctg ggcacggtga agcccaatgc aaacagaatt gctttagatt tccaaagagg 480
gaatgatgtt gccttccact ttaacccacg cttcaatgag aacaacagga gagtcattgg 540
ttgcaataca aagctggata a 561

<210> SEQ ID NO 99
<211> LENGTH: 636
<212> TYPE: DNA
<213> ORGANISM: Homo sapien

<400> SEQUENCE: 99
gggaatgcaa caactttatt gaaaggaaag tgcaatgaaa tttgttgaaa ccttaaaagg 60
ggaaacttag acacccccc tcragcgmag kaccargtgc araggtggac tctttctgga 120
tgttgtagtc agacagggtr cgwccatctt ccagctgttt yccrgcaaag atcaacctct 180
gctgatcagg aggratgcct tccttatctt ggatctttgc cttgacattc tcgatggtgt 240
cactgggctc cacctcgagg gtgatggtct taccagtcag ggtcttcacg aagatytgca 300
tcccacctct gagacggagc accaggtgca gggtrgactc tttctggatg ttgtagtcag 360
acagggtgcg yccatcttcc agctgctttc csagcaaaga tcaacctctg ctggtcagga 420
ggratgcctt ccttgtcytg gatctttgcy ttgacrttct caatggtgtc actcggctcc 480
acttcgagag tgatggtctt accagtcagg gtcttcacga agatctgcat cccacctcta 540
agacggagca ccaggtgcag ggtggactct ttctggatgg ttgtagtcag acagggtgcg 600
tccatcttcc agctgtttcc cagcaaagat caacct 636

<210> SEQ ID NO 100
<211> LENGTH: 697
<212> TYPE: DNA
<213> ORGANISM: Homo sapien

<400> SEQUENCE: 100
aggttgatct ttgctgggaa acagctggaa gatggacgca ccctgtctga ctacaaccat 60
ccagaaagag tccaccctgc acctggtgct ccgtcttaga ggtgggatgc agatcttcgt 120
gaagaccctg actggtaaga ccatcactct cgaagtggag ccgagtgaca ccattgagaa 180
ygtcaargca aagatccarg acaaggaagg catycctcct gaccagcaga ggttgatctt 240
tgctsggaaa gcagctggaa gatggrcgca ccctgtctga ctacaacatc cagaaagagt 300
cyaccctgca cctggtgctc cgtctcagag gtgggatgca ratcttcgtg aagaccctga 360
ctggtaagac catcaccctc gaggtggagc ccagtgacac catcgagaat gtcaaggcaa 420
agatccaaga taaggaaggc atccctcctg atcagcagag gttgatcttt gctgggaaac 480
agctggaaga tggacgcacc ctgtctgact acaacatcca gaaagagtcc acctytgcac 540
ytggtmctbc gtctyagagg kgggrtgcaa atctwmgtkw agacactcac tkkyaagryy 600
atcamcmwtg akktcgakys castkwcact wtcrakaamg tyrwwgcawa gatccmagac 660
aaggaaggca ttcctcctga ccagcagagg ttgatct 697

<210> SEQ ID NO 101
<211> LENGTH: 451
<212> TYPE: DNA
<213> ORGANISM: Homo sapien

<400> SEQUENCE: 101
atggagtctc actctgtcga ccaggctgga gcgctgtggt gcgatatcgg ctcactgcag 60

-continued

```
tctccacttc ctgggttcaa gcgatcctcc tgcctcagcc tcccgagtag ctgggactac    120

aggcaggcgt caccataatt tttgtatttt tagtagagac atggtttcgc catgttggct    180

gggctggtct cgaactcctg acctcaagtg atctgtcctg gcctcccaaa gtgttgggat    240

tacaggcgaa agccaacgct cccggccagg gaacaacttt agaatgaagg aaatatgcaa    300

aagaacatca catcaaggat caattaatta ccatctatta attactatat gtgggtaatt    360

atgactattt cccaagcatt ctacgttgac tgcttgagaa gatgtttgtc ctgcatggtg    420

gagagtggag aagggccagg attcttaggt t                                   451
```

<210> SEQ ID NO 102
<211> LENGTH: 571
<212> TYPE: DNA
<213> ORGANISM: Homo sapien

<400> SEQUENCE: 102

```
agcgcggtct tccggcgcga gaaagctgaa ggtgatgtgg ccgccctcaa ccgacgcatc     60

cagctcgttg aggaggagtt ggacagggct caggaacgac tggccacggc cctgcagaag    120

ctggaggagg cagaaaaagc tgcagatgag agtgagagag gaatgaaggt gatagaaaac    180

cgggccatga aggatgagga gaagatggag attcaggaga tgcagctcaa agaggccaag    240

cacattgcgg aagaggctga ccgcaaatac gaggaggtag ctcgtaagct ggtcatcctg    300

gagggtgagc tggagagggc agaggagcgt gcggaggtgt ctgaactaaa atgtggtgac    360

ctggaagaag aactcaagaa tgttactaac aatctgaaat ctctggaggc tgcatctgaa    420

aagtattctg aaaaggagga caaatatgaa gaagaaatta aacttctgtc tgacaaactg    480

aaagaggctg agacccgtgc tgaatttgca gagagaacgg ttgcaaaact ggaaaagaca    540

attgatgacc tggaagagaa acttgcccag c                                   571
```

<210> SEQ ID NO 103
<211> LENGTH: 451
<212> TYPE: DNA
<213> ORGANISM: Homo sapien

<400> SEQUENCE: 103

```
gtgcacaggt cccatttatt gtagaaaata ataataatta cagtgatgaa tagctcttct     60

taaattacaa aacagaaacc acaaagaagg aagaggaaaa accccaggac ttccaagggt    120

gaagctgtcc cctcctccct gccaccctcc caggctcatt agtgtccttg gaaggggcag    180

aggactcaga ggggatcagt ctccaggggc cctgggctga agcgggtgag gcagagagtc    240

ctgaggccac agagctgggc aacctgagcc gcctctctgg ccccctcccc caccactgcc    300

caaacctgtt tacagcacct tcgcccctcc cctctaaacc cgtccatcca ctctgcactt    360

cccaggcagg tgggtgggcc aggcctcagc catactcctg ggcgcgggtt tcggtgagca    420

aggcacagtc ccagaggtga tatcaaggcc t                                   451
```

<210> SEQ ID NO 104
<211> LENGTH: 441
<212> TYPE: DNA
<213> ORGANISM: Homo sapien

<400> SEQUENCE: 104

```
gcaaggaact ggtctgctca cacttgctgg cttgcgcatc aggactggct ttatctcctg     60

actcacggtg caaaggtgca ctctgcgaac gttaagtccg tccccagcgc ttggaatcct    120

acggccccca cagccggatc ccctcagcct tccaggtcct caactcccgt ggacgctgaa    180
```

-continued caatggcctc catggggcta caggtaatgg gcatcgcgct ggccgtcctg ggctggctgg 240
ccgtcatgct gtgctgcgcg ctgcccatgt ggcgcgtgac ggccttcatc ggcagcaaca 300
ttgtcacctc gcagaccatc tgggagggcc tatggatgaa ctgcgtggtg cagagcaccg 360
gccagatgca gtgcaaggtg tacgactcgc tgctggcact gccgcaggac ctgcaggcgg 420
cccgcgccct cgtcatcatc a 441

<210> SEQ ID NO 105
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 105
tgcaaaaggg acacaggggt tcaaaaataa aaatttctct tccccctccc caaacctgta 60
ccccagctcc ccgaccacaa ccccccttcct cccccgggga aagcaagaag gagcaggtgt 120
ggcatctgca gctgggaaga gagaggccgg ggaggtgccg agctcggtgc tggtctcttt 180
ccaaatataa atacntgtgt cagaactgga aaatcctcca gcacccacca cccaagcact 240
ctccgttttc tgccggtgtt tggagagggg cggggggcag gggcgccagg caccggctgg 300
ctgcggtcta ctgcatccgc tgggtgtgca ccccgcgagc ctcctgctgc tcattgtaga 360
agagatgaca ctcggggtcc ccccggatgg tgggggctcc ctggatcagc ttcccggtgt 420
tggggttcac acaccagcac tccccacgct gcccgttcag agacatcttg cactgtttga 480
ggttgtacag gccatgcttg tcacagttg 509

<210> SEQ ID NO 106
<211> LENGTH: 571
<212> TYPE: DNA
<213> ORGANISM: Homo sapien

<400> SEQUENCE: 106
gggttggagg gactggttct ttatttcaaa aagacacttg tcaatattca gtatcaaaac 60
agttgcacta ttgatttctc tttctcccaa tcggccccaa agagaccaca taaaaggaga 120
gtacatttta agccaataag ctgcaggatg tacacctaac agacctccta gaaaccttac 180
cagaaaatgg ggactgggta gggaaggaaa cttaaaagat caacaaactg ccagcccacg 240
gactgcagag gctgtcacag ccagatgggg tggccagggt gccacaaacc caaagcaaag 300
tttcaaaata atataaaatt taaaaagttt tgtacataag ctattcaaga tttctccagc 360
actgactgat acaaagcaca attgagatgg cacttctaga gacagcagct tcaaacccag 420
aaaagggtga tgagatgagt ttcacatggc taaatcagtg gcaaaaacac agtcttcttt 480
ctttctttct ttcaaggagg caggaaagca attaagtggt cacctcaaca taagggggac 540
atgatccatt ctgtaagcag ttgtgaaggg g 571

<210> SEQ ID NO 107
<211> LENGTH: 555
<212> TYPE: DNA
<213> ORGANISM: Homo sapien

<400> SEQUENCE: 107
caggaaccgg agcgcgagca gtagctgggt gggcaccatg gctgggatca ccaccatcga 60

-continued ggcggtgaag cgcaagatcc aggttctgca gcagcaggca gatgatgcag aggagcgagc 120
tgagcgcctc cagcgagaag ttgagggaga aaggcgggcc cgggaacagg ctgaggctga 180
ggtggcctcc ttgaaccgta ggatccagct ggttgaagaa gagctggacc gtgctcagga 240
gcgcctggcc actgccctgc aaaagctgga agaagctgaa aaagctgctg atgagagtga 300
gagaggtatg aaggttattg aaaaccgggc cttaaaagat gaagaaaaga tggaactcca 360
ggaaatccaa ctcaaagaag ctaagcacat tgcagaagag gcagatagga agtatgaaga 420
ggtggctcgt aagttggtga tcattgaagg agacttggaa cgcacagagg aacgagctga 480
gctggcagag tcccgttgcc gagagatgga tgagcagatt agactgatgg accagaacct 540
gaagtgtctg agtgc 555

<210> SEQ ID NO 108
<211> LENGTH: 541
<212> TYPE: DNA
<213> ORGANISM: Homo sapien

<400> SEQUENCE: 108
atctacgtca tcaatcaggc tggagacacc atgttcaatc gagctaagct gctcaatatt 60
ggctttcaag aggccttgaa ggactatgat tacaactgct ttgtgttcag tgatgtggac 120
ctcattccga tggacgaccg taatgcctac aggtgttttt cgcagccacg gcacatttct 180
gttgcaatgg acaagttcgg gtttagcctg ccatatgttc agtattttgg aggtgtctct 240
gctctcagta aacaacagtt tcttgccatc aatggattcc ctaataatta ttggggttgg 300
ggaggagaag atgacgacat ttttaacaga ttagttcata aaggcatgtc tatatcacgt 360
ccaaatgctg tagtagggag gtgtcgaatg atccggcatt caagagacaa gaaaaatgag 420
cccaatcctc agaggtttga ccggatcgca catacaaagg aaacgatgcg cttcgatggt 480
ttgaactcac ttacctacaa ggtgttggat gtcagagata cccgttatat acccaaatca 540
c 541

<210> SEQ ID NO 109
<211> LENGTH: 411
<212> TYPE: DNA
<213> ORGANISM: Homo sapien

<400> SEQUENCE: 109
ctagacctct aattaaaagg cacaatcatg ctggagaatg aacagtctga ccccgagggc 60
cacagcgaat tttagggaag gaggcaaaga ggtgagaagg gaaaggaaag aaggaaggaa 120
ggagaacaat aagaactgga gacgttgggt gggtcaggga gtgtggtgga ggctcggaga 180
gatggtaaac aaacctgact gctatgagtt ttcaacccca tagtctaggg ccatgagggc 240
gtcagttctt ggtggctgag ggtccttcca cccagcccac ctgggggagt ggagtgggga 300
gttctgccag gtaagcagat gttgtctccc aagttcctga cccagatgtc tggcaggata 360
acgctgacct gttccctcaa caagggacct gaaagtaatt ttgctcttta c 411

<210> SEQ ID NO 110
<211> LENGTH: 451
<212> TYPE: DNA
<213> ORGANISM: Homo sapien

<400> SEQUENCE: 110
ccgaattcaa gcgtcaacga tccytccctt accatcaaat caattggcca ccaatggtac 60
tgaacctacg agtacaccga ctacgggcgg actaatcttc aactcctaca tacttccccc 120

-continued

```
attattccta gaaccaggcg acctgcgact ccttgacgtt gacaatcgag tagtactccc    180

gattgaagcc cccattcgta taataattac atcacaagac gtcttgcact catgagctgt    240

ccccacatta ggcttaaaaa cagatgcaat tcccggacgt ctaagccaaa ccactttcac    300

cgctacacga ccgggggtat actacggtca atgctctgaa atctgtggag caaaccacag    360

tttcatgccc atcgtcctag aattaattcc cctaaaaatc tttgaaatag ggcccgtatt    420

taccctatag cacccccctct accccctcta g                                    451
```

<210> SEQ ID NO 111
<211> LENGTH: 541
<212> TYPE: DNA
<213> ORGANISM: Homo sapien

<400> SEQUENCE: 111

```
gctcttcaca cttttattgt taattctctt cacatggcag atacagagct gtcgtcttga     60

agaccaccac tgaccaggaa atgccacttt tacaaaatca tcccccctttt tcatgattgg    120

aacagttttc ctgaccgtct gggagcgttg aagggtgacc agcacatttg cacatgcaaa    180

aaaggagtga ccccaaggcc tcaaccacac ttcccagagc tcaccatggg ctgcaggtga    240

cttgccaggt ttggggttcg tgagctttcc ttgctgctgc ggtggggagg ccctcaagaa    300

ctgagaggcc ggggtatgct tcatgagtgt taacatttac gggacaaaag cgcatcatta    360

ggataaggaa cagccacagc acttcatgct tgtgagggtt agctgtagga gcgggtgaaa    420

ggattccagt ttatgaaaat ttaaagcaaa caacggtttt tagctgggtg ggaaacagga    480

aaactgtgat gtcggccaat gaccaccatt tttctgccca tgtgaaggtc cccatgaaac    540

c                                                                     541
```

<210> SEQ ID NO 112
<211> LENGTH: 521
<212> TYPE: DNA
<213> ORGANISM: Homo sapien

<400> SEQUENCE: 112

```
caagcgcttg gcgtttggac ccagttcagt gaggttcttg ggttttgtgc ctttggggat     60

tttggtttga cccaggggtc agccttagga aggtcttcag gaggaggccg agttcccctt    120

cagtaccacc cctctctccc cactttccct ctcccggcaa catctctggg aatcaacagc    180

atattgacac gttggagccg agcctgaaca tgcccctcgg ccccagcaca tggaaaaccc    240

ccttccttgc ctaaggtgtc tgagtttctg gctcttgagg catttccaga cttgaaattc    300

tcatcagtcc attgctcttg agtctttgca gagaacctca gatcaggtgc acctgggaga    360

aagactttgt ccccacttac agatctatct cctcccttgg gaagggcagg gaatggggac    420

ggtgtatgga ggggaaggga tctcctgcgc ccttcattgc cacacttggt gggaccatga    480

acatctttag tgtctgagct tctcaaatta ctgcaatagg a                         521
```

<210> SEQ ID NO 113
<211> LENGTH: 568
<212> TYPE: DNA
<213> ORGANISM: Homo sapien

<400> SEQUENCE: 113

```
agcgtcaaat cagaatggaa aagactcaaa accatcatca acaccaagat caaaaggaca     60

agratccttc aagaaacagg aaaaaactcc taaaacacca aaaggaccta gttctgtaga    120
```

-continued agacattaaa gcaaaaatgc aagcaagtat agaaaaaggt ggttctcttc ccaaagtgga 180
agccaaattc atcaattatg tgaagaattg cttccggatg actgaccaag aggctattca 240
agatctctgg cagtggagga agtctcttta agaaaatagt ttaaacaatt tgttaaaaaa 300
ttttccgtct tatttcattt ctgtaacagt tgatatctgg ctgtcctttt tataatgcag 360
agtgagaact ttccctaccg tgtttgataa atgttgtcca ggttctattg ccaagaatgt 420
gttgtccaaa atgcctgttt agtttttaaa gatggaactc caccctttgc ttggttttaa 480
gtatgtatgg aatgttatga taggacatag tagtagcggt ggtcagacat ggaaatggtg 540
ggsmgacaaa aatatacatg tgaaataa 568

<210> SEQ ID NO 114
<211> LENGTH: 483
<212> TYPE: DNA
<213> ORGANISM: Homo sapien

<400> SEQUENCE: 114
tccgaattcc aagcgaatta tggacaaacg attcctttta gaggattact tttttcaatt 60
tcggttttag taatctaggc tttgcctgta aagaatacaa cgatggattt taaatactgt 120
ttgtggaatg tgtttaaagg attgattcta gaacctttgt atatttgata gtatttctaa 180
ctttcatttc tttactgttt gcagttaatg ttcatgttct gctatgcaat cgtttatatg 240
cacgtttctt taattttttt agattttcct ggatgtatag tttaaacaac aaaaagtcta 300
tttaaaactg tagcagtagt ttacagttct agcaaagagg aaagttgtgg ggttaaactt 360
tgtattttct ttcttataga ggcttctaaa aaggtatttt tatatgttct ttttaacaaa 420
tattgtgtac aacctttaaa acatcaatgt ttggatcaaa acaagaccca gcttattttc 480
tgc 483

<210> SEQ ID NO 115
<211> LENGTH: 521
<212> TYPE: DNA
<213> ORGANISM: Homo sapien

<400> SEQUENCE: 115
tgtggtggcg cgggctgagg tggaggccca ggactctgac cctgcccctg ccttcagcaa 60
ggcccccggc agcgccggcc actacgaact gccgtgggtt gaaaaatata ggccagtaaa 120
gctgaatgaa attgtcggga atgaagacac cgtgagcagg ctagaggtct ttgcaaggga 180
aggaaatgtg cccaacatca tcattgcggg ccctccagga accggcaaga ccacaagcat 240
tctgtgcttg gcccgggccc tgctgggccc agcactcaaa gatgccatgt tggaactcaa 300
tgcttcaaat gacaggggca ttgacgttgt gaggaataaa attaaaatgt ttgctcaaca 360
aaaagtcact cttcccaaag gccgacataa gatcatcatt ctggatgaag cagacagcat 420
gaccgacgga gcccagcaag ccttgaggag aaccatggaa atctactcta aaaccactcg 480
ttcgcccttg cttgtaatgc ttcggataag atcatcgagc c 521

<210> SEQ ID NO 116
<211> LENGTH: 501
<212> TYPE: DNA
<213> ORGANISM: Homo sapien

<400> SEQUENCE: 116
ctttgcaaag cttttatttc atgtctgcgg catggaatcc acctgcacat ggcatcttag 60
ctgtgaagga gaaagcagtg cacgagaagg aatgagtggg cggaaccaac ggcctccaca 120

-continued agctgccttc cagcagcctg ccaaggccat ggcagagaga gactgcaaac aaacacaagc 180
aaacagagtc tcttcacagc tggagtctga aagctcatag tggcatgtgt gaatctgaca 240
aaattaaaag tgtgcatagt ccattacatg cataaaacac taataataat cctgtttaca 300
cgtgactgca gcaggcaggt ccagctccac cactgccctc ctgccacatc acatcaagtg 360
ccatggttta gagggttttt catatgtaat tcttttattc tgtaaaaggt aacaaaatat 420
acagaacaaa actttccctt tttaaaacta atgttacaaa tctgtattat cacttggata 480
taaatagtat ataagctgat c 501

<210> SEQ ID NO 117
<211> LENGTH: 451
<212> TYPE: DNA
<213> ORGANISM: Homo sapien
<220> FEATURE:
<221> NAME/KEY: misc_feature
<222> LOCATION: (1)...(451)
<223> OTHER INFORMATION: n = A,T,C or G

<400> SEQUENCE: 117
caagggatat atgttgaggg tacrgrgtga cactgaacag atcacaaagc acgagaaaca 60
ttagttctct ccctccccag cgtctccttc gtctccctgg ttttccgatg tccacagagt 120
gagattgtcc ctaagtaact gcatgatcag agtgctgkct ttataagact cttcattcag 180
cgtatccaat tcagcaattg cttcatcaaa tgccgttttt gccaggctac aggccttttc 240
aggagagttt agaatctcat agtaaaagac tgagaaattt agtgccagac caagacgaat 300
tgggtgtgta ggctgcattn ctttcttact aatttcaaat gcttcctggt aagcctgctg 360
ggagttcgac acaagtggtt tgtttgttgc tccagatgcc acttcagaaa gatacctaaa 420
ataatctcct ttcattttca aagtagaaca c 451

<210> SEQ ID NO 118
<211> LENGTH: 501
<212> TYPE: DNA
<213> ORGANISM: Homo sapien

<400> SEQUENCE: 118
tccggagccg gggtagtcgc cgccgccgcc gccggtgcag ccactgcagg caccgctgcc 60
gccgcctgag tagtgggctt aggaaggaag aggtcatctc gctcggagct tcgctcggaa 120
gggtctttgt tccctgcagc cctcccacgg gaatgacaat ggataaaagt gagctggtac 180
agaaagccaa actcgctgag caggctgagc gatatgatga tatggctgca gccatgaagg 240
cagtcacaga acaggggcat gaactctcca acgaagagag aaatctgctc tctgttgcct 300
acaagaatgt ggtaaggccg cccgccgctc ttcctggcgt gtcatctcca gcattgagca 360
gaaaacagag aggaatgaga agaagcagca gatgggcaaa gagtaccgtg agaagataga 420
ggcagaactg caggacatct gcaatgatgt tctggagctt gttggacaaa tatcttattc 480
caatgctaca caacccagaa a 501

<210> SEQ ID NO 119
<211> LENGTH: 391
<212> TYPE: DNA
<213> ORGANISM: Homo sapien

<400> SEQUENCE: 119
aaaaagcagc argttcaaca caaaatagaa atctcaaatg taggatagaa caaaaccaag 60

-continued

```
tgtgtgaggg gggaagcaac agcaaaagga agaaatgaga tgttgcaaaa aagatggagg    120

agggttcccc tctcctctgg ggactgactc aaacactgat gtggcagtat acaccattcc    180

agagtcaggg gtgttcattc ttttttggga gtaagaaaag gtggggatta agaagacgtt    240

tctggaggct tagggaccaa ggctggtctc tttccccct cccaaccccc ttgatccctt    300

tctctgatca ggggaaagga gctcgaatga gggaggtaga gttggaaagg gaaaggattc    360

cacttgacag aatgggacag actccttccc a                                   391
```

```
<210> SEQ ID NO 120
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 120

tggcaatagc acagccatcc aggagctctt cargcgcatc tcggagcagt tcactgccat     60

gttccgccgg aaggccttcc tccactggta cacaggcgag ggcatggacg agatggagtt    120

caccgaggct gagagcaaca tgaacgacct cgtctctgag tatcaagcag taccaggatg    180

ccaccgcaga agaggaggag gatttcggtg aggaggccga agaggaggcc taaggcagag    240

cccccatcac ctcaggcttc tcagttccct tagccgtctt actcaactgc ccctttcctc    300

tccctcagaa tttgtgtttg ctgcctctat cttgtttttt gttttttctt ctgggggggt    360

ctagaacagt gcctggcaca tagtaggcgc tcaataaata cttggttgnt gaatgtctcc    420

t                                                                    421
```

```
<210> SEQ ID NO 121
<211> LENGTH: 206
<212> TYPE: DNA
<213> ORGANISM: Homo sapien

<400> SEQUENCE: 121

agctggcgct agggctcggt tgtgaaatac agcgtrgtca gcccttgcgc tcagtgtaga     60

aacccacgcc tgtaaggtcg gtcttcgtcc atctgctttt ttctgaaata cactaagagc    120

agccacaaaa ctgtaacctc aaggaaacca taaagcttgg agtgccttaa tttttaacca    180

gtttccaata aaacggttta ctacct                                         206
```

```
<210> SEQ ID NO 122
<211> LENGTH: 131
<212> TYPE: DNA
<213> ORGANISM: Homo sapien

<400> SEQUENCE: 122

ggagatgaag atgaggaagc tgagtcagct acgggcargc gggcagctga agatgatgag     60

gatgacgatg tcgataccaa gaagcagaag accgacgagg atgactagac agcaaaaaag    120

gaaaagttaa a                                                         131
```

```
<210> SEQ ID NO 123
<211> LENGTH: 231
<212> TYPE: DNA
<213> ORGANISM: Homo sapien
<220> FEATURE:
<221> NAME/KEY: misc_feature
<222> LOCATION: (1)...(231)
<223> OTHER INFORMATION: n = A,T,C or G
```

-continued

<400> SEQUENCE: 123
gatgaaaatt aaatacttaa attaatcaaa aggcactacg ataccaccta aaacctactg 60
cctcagtggc agtakgctaa kgaagatcaa gctacagsac atyatctaat atgaatgtta 120
gcaattacat akcargaagc atgtttgctt tccagaagac tatggnacaa tggtcattwg 180
ggcccaagag gatatttggc cnggaaagga tcaagataga tnaangtaaa g 231

<210> SEQ ID NO 124
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 124
gagtagcaac gcaaagcgct tggtattgag tctgtgggsg acttcggttc cggtctctgc 60
agcagccgtg atcgcttagt ggagtgctta gggtagttgg ccaggatgcc gaatatcaaa 120
atcttcagca ggcagctccc accaggactt atctcasaaa attgctgacc gcctgggcct 180
ggagctaggc aaggtggtga ctaagaaatt cagcaaccag gagacctgtg tggaaattgg 240
tgaaagtgta ccgtggagag gatgtctaca ttgttcagag tggntgtggc gaaatcaatg 300
acaatttaat ggagcttttg atcatgatta atgcctgcaa gattgcttca gccagccggg 360
ttactgcagt catcccatgc ttcccttatg ccccggcagg ataagaaaga tnagagccgg 420
gccgccaatc tcagccaagc ttggtgcaaa tatgctatct gtagcagtgc agatcatatt 480
atcaccatgg acctacatgc ttctcaaatt canggctttt t 521

<210> SEQ ID NO 125
<211> LENGTH: 341
<212> TYPE: DNA
<213> ORGANISM: Homo sapien
<220> FEATURE:
<221> NAME/KEY: misc_feature
<222> LOCATION: (1)...(341)
<223> OTHER INFORMATION: n = A,T,C or G

<400> SEQUENCE: 125
atgcaaaagg ggacacaggg ggttcaaaaa taaaaatttc tcttccccct ccccaaacct 60
gtaccccagc tccccgacca caaccccctt cctcccccgg ggaaagcaag aaggagcagg 120
tgtggcatct gcagctggga agagagaggc cggggaggtg ccgagctcgg tgctggtctc 180
tttccaaata taaatacgtg tgtcagaact ggaaaatcct ccagcaccca ccacccaagc 240
actctccgtt ttctgccggt gtttggagag gggcggnggg caggggcgcc aggcaccggc 300
tggctgcggt ctactgcatc cgctgggtgt gcaccccgcg a 341

<210> SEQ ID NO 126
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 126
aggttggaga aggtcatgca ggtgcagatt gtccaggskc agccacaggg tcaagcccaa 60

-continued

```
caggcccaga gtggcactgg acagaccatg caggtgatgc agcagatcat cactaacaca    120

ggagagatcc agcagatccc ggtgcagctg aatgccggcc agctgcagta tatccgctta    180

gcccagcctg tatcaggcac tcaagttgtg cagggacaga tccagacact tgccaccaat    240

gctcaacaga ttacacagac agaggtccag caaggacagc agcagttcaa gccagttcac    300

aagatggaca gcagctctac cagatccagc aagtcaccat gcctgcgggc cangacctcg    360

ccagcccatg ttcatccagt caagccaacc agcccttcna cgggcaggcc ccccaggtga    420

ccggcgactg aagggcctga gctggcaagg ccaangacac ccaacacaat ttttgccata    480

cagcccccag gcaatgggca cagcctttct tcccagagga c                        521
```

<210> SEQ ID NO 127
<211> LENGTH: 351
<212> TYPE: DNA
<213> ORGANISM: Homo sapien

<400> SEQUENCE: 127

```
tgagatttat tgcatttcat gcagcttgaa gtccatgcaa aggrgactag cacagttttt     60

aatgcattta aaaaataaaa gggaggtggg cagcaaacac acaaagtcct agtttcctgg    120

gtccctggga gaaaagagtg tggcaatgaa tccacccact ctccacaggg aataaatctg    180

tctcttaaat gcaaagaatg tttccatggc ctctggatgc aaatacacag agctctgggg    240

tcagagcaag ggatggggag aggaccacga gtgaaaaagc agctacacac attcacctaa    300

ttccatctga gggcaagaac aacgtggcaa gtcttggggg tagcagctgt t             351
```

<210> SEQ ID NO 128
<211> LENGTH: 521
<212> TYPE: DNA
<213> ORGANISM: Homo sapien

<400> SEQUENCE: 128

```
tccagacatg ctcctgtcct aggcggggag caggaaccag acctgctatg ggaagcagaa     60

agagttaagg gaaggtttcc tttcattcct gttccttctc ttttgctttt gaacagtttt    120

taaatatact aatagctaag tcatttgcca gccaggtccc ggtgaacagt agagaacaag    180

gagcttgcta agaattaatt ttgctgtttt tcaccccatt caaacagagc tgccctgttc    240

cctgatggag ttccattcct gccagggcac ggctgagtaa cacgaagcca ttcaagaaag    300

gcgggtgtga aatcactgcc accccatgga cagacccctc actcttcctt cttagccgca    360

gcgctactta ataaatatat ttatactttg aaattatgat aaccgatttt tcccatgcgg    420

catcctaagg gcacttgcca gctcttatcc ggacagtcaa gcactgttgt tggacaacag    480

ataaaggaaa agaaaaagaa gaaaacaacc gcaacttctg t                        521
```

<210> SEQ ID NO 129
<211> LENGTH: 521
<212> TYPE: DNA
<213> ORGANISM: Homo sapien

<400> SEQUENCE: 129

```
tgagacggac cactggcctg gtcccccctc atktgctgtc gtaggacctg acatgaaacg     60

cagatctagt ggcagagagg aagatgatga ggaacttctg agacgtcggc agcttcaaga    120

agagcaatta atgaagctta actcaggcct gggacagttg atcttgaaag aagagatgga    180

gaaagagagc cgggaaaggt catctctgtt agccagtcgc tacgattctc ccatcaactc    240

agcttcacat attccatcat ctaaaactgc atctctccct ggctatggaa gaaatgggct    300
```

-continued

```
tcaccggcct gtttctaccg acttcgctca gtataacagc tatggggatg tcagcggggg    360

agtgcgagat taccagacac ttccagatgg ccacatgcct gcaatgagaa tggaccgagg    420

agtgtctatg cccaacatgt tggaaccaaa gatatttcca tatgaaatgc tcatggtgac    480

caacagaggg ccgaaaccaa atctcagaga ggtggacaga a                        521
```

<210> SEQ ID NO 130
<211> LENGTH: 270
<212> TYPE: DNA
<213> ORGANISM: Homo sapien

<400> SEQUENCE: 130

```
tcactttatt tttcttgtat aaaaacccta tgttgtagcc acagctggag cctgagtccg     60

ctgcacggag actctggtgt gggtcttgac gaggtggtca gtgaactcct gatagggaga    120

cttggtgaat acagtctcct tccagaggtc gggggtcagg tagctgtagg tcttagaaat    180

ggcatcaaag gtggccttgg cgaagttgcc cagggtggca gtgcagcccc gggctgaggt    240

gtagcagtca tcgataccag ccatcatgag                                     270
```

<210> SEQ ID NO 131
<211> LENGTH: 341
<212> TYPE: DNA
<213> ORGANISM: Homo sapien

<400> SEQUENCE: 131

```
ctggaatata gacccgtgat cgacaaaact ttgaacgagg ctgactgtgc caccgtcccg     60

ccagccattc gctcctactg atgagacaag atgtggtgat gacagaatca gcttttgtaa    120

ttatgtataa tagctcatgc atgtgtccat gtcataactg tcttcatacg cttctgcact    180

ctggggaaga aggagtacat tgaagggaga ttggcaccta gtggctggga gcttgccagg    240

aacccagtgg ccagggagcg tggcacttac ctttgtccct tgcttcattc ttgtgagatg    300

ataaaactgg gcacagctct taaataaaat ataaatgaac a                        341
```

<210> SEQ ID NO 132
<211> LENGTH: 844
<212> TYPE: DNA
<213> ORGANISM: Homo sapien
<220> FEATURE:
<221> NAME/KEY: misc_feature
<222> LOCATION: (1)...(844)
<223> OTHER INFORMATION: n = A,T,C or G

<400> SEQUENCE: 132

```
tgaatgggga ggagctgacc caggaaatgg agcttgngga gaccaggcct gcaggggatg     60

gaaccttcca gaagtgggca tctgtggtgg tgcctcttgg gaaggagcag aagtacacat    120

gccatgtgga acatgagggg ctgcctgagc ccctcaccct gagatggggc aaggaggagc    180

ctccttcatc caccaagact aacacagtaa tcattgctgt tccggttgtc cttggagctg    240

tggtcatcct tggagctgtg atggcttttg tgatgaagag gaggagaaac acaggtggaa    300

aaggaggggga ctatgctctg gctccaggct cccagagctc tgatatgtct ctcccagatt    360

gtaaagtgtg aagacagctg cctggtgtgg acttggtgac agacaatgtc ttcacacatc    420

tcctgtgaca tccagagacc tcagttctct ttagtcaagt gtctgatgtt ccctgtgagt    480

ctgcgggctc aaagtgaaga actgtggagc ccagtccacc cctgcacacc aggaccctat    540

ccctgcactg ccctgtgttc ccttccacag ccaaccttgc tgctccagcc aaacattggt    600
```

-continued

```
ggacatctgc agcctgtcag ctccatgcta ccctgacctt caactcctca cttccacact    660

gagaataata atttgaatgt gggtggctgg agagatggct cagcgctgac tgctcttcca    720

aaggtcctga gttcaaatcc cagcaaccac atggtggctc acaaccatct gtaatgggat    780

ctaataccct cttctgcagt gtctgaagac asctacagtg tacttacata taataataaa    840

taag                                                                  844
```

<210> SEQ ID NO 133
<211> LENGTH: 601
<212> TYPE: DNA
<213> ORGANISM: Homo sapien

<400> SEQUENCE: 133

```
ggccgggcgc gcgcgccccc gccacacgca cgccgggcgt gccagtttat aaagggagag     60

agcaagcagc gagtcttgaa gctctgtttg gtgctttgga tccatttcca tcggtcctta    120

cagccgctcg tcagactcca gcagccaaga tggtgaagca gatcgagagc aagactgctt    180

ttcaggaagc cttggacgct gcaggtgata aacttgtagt agttgacttc tcagccacgt    240

ggtgtgggcc ttgcaaaatg atcaagcctt tctttcattc cctctctgaa aagtattcca    300

acgtgatatt ccttgaagta gatgtggatg actgtcagga tgttgcttca gagtgtgaag    360

tcaaatgcat gccaacattc cagtttttta agaagggaca aaaggtgggt gaattttctg    420

gagccaataa ggaaaagctt gaagccacca ttaatgaatt agtctaatca tgttttctga    480

aaatataacc agccattggc tatttaaaac ttgtaatttt tttaatttac aaaaatataa    540

aatatgaaga cataaacccm gttgccatct gcgtgacaat aaaacattaa tgctaacact    600

t                                                                     601
```

<210> SEQ ID NO 134
<211> LENGTH: 421
<212> TYPE: DNA
<213> ORGANISM: Homo sapien

<400> SEQUENCE: 134

```
tcacataaga aatttaagca agttacrcta tcttaaaaaa cacaacgaat gcattttaat     60

agagaaaccc ttccctccct ccacctccct cccccaccct cctcatgaat taagaatcta    120

agagaagaag taaccataaa accaagtttt gtggaatcca tcatccagag tgcttacatg    180

gtgattaggt taatattgcc ttcttacaaa atttctattt taaaaaaaat tataaccttg    240

attgcttatt acaaaaaaat tcagtacaaa agttcaatat attgaaaaat gcttttcccc    300

tccctcacag caccgtttta tatatagcag agaataatga agagattgct agtctagatg    360

gggcaatctt caaattacac caagacgcac agtggtttat ttaccctccc cttctcataa    420

g                                                                     421
```

<210> SEQ ID NO 135
<211> LENGTH: 511
<212> TYPE: DNA
<213> ORGANISM: Homo sapien

<400> SEQUENCE: 135

```
ggaaaggatt caagaattag aggacttgct tgctrragaa aaagacaact ctcgtcgcat     60

gctgacagac aaagagagag agatggcgga aataagggat caaatgcagc aacagctgaa    120

tgactatgaa cagcttcttg atgtaaagtt agccctggac atggaaatca gtgcttacag    180

gaaactctta gaaggcgaag aagagaggtt gaagctgtct ccaagccctt cttcccgtgt    240
```

-continued

```
gacagtatcc cgagcatcct caagtcgtag tgtaccgtac aactagagga aagcggaaga    300

gggttgatgt ggaagaatca gaggcgaagt agtagtgtta gcatctctca ttccgcctca    360

accactggaa atgtttgcat cgaagaaatt gatgttgatg ggaaatttat cccgcttgaa    420

gaacacttct gaacaggatc aaccaatggg aaggcttggg agatgatcag aaaaattgga    480

gacacatcag tcagttataa atatacctca a                                   511
```

<210> SEQ ID NO 136
<211> LENGTH: 341
<212> TYPE: DNA
<213> ORGANISM: Homo sapien

<400> SEQUENCE: 136

```
catgggtttc accaggttgg ccaggctgct cttgaactsc tgacctcagg tgatccaccc     60

gcctcggcct cccaaagtgc tgggattaca ggcgtgagcc accacgcccg gcccccaaag    120

ctgtttcttt tgtctttagc gtaaagctct cctgccatgc agtatctaca taactgacgt    180

gactgccagc aagctcagtc actccgtggt ctttttctct ttccagttct tctctctctc    240

ttcaagttct gcctcagtga aagctgcagg tccccagtta agtgatcagg tgagggttct    300

ttgaacctgg ttctatcagt cgaattaatc cttcatgatg g                        341
```

<210> SEQ ID NO 137
<211> LENGTH: 551
<212> TYPE: DNA
<213> ORGANISM: Homo sapien

<400> SEQUENCE: 137

```
gatgtgttgg accctctgtg tcaaaaaaaa cctcacaaag aatcccctgc tcattacaga     60

agaagatgca tttaaaatat gggttatttt caacttttta tctgaggaca agtatccatt    120

aattattgtg tcagaagaga ttgaatacct gcttaagaag cttacagaag ctatgggagg    180

aggttggcag caagaacaat ttgaacatta taaaatcaac tttgatgaca gtaaaaatgg    240

cctttctgca tgggaactta ttgagcttat tggaaatgga cagtttagca aaggcatgga    300

ccggcagact gtgtctatgg caattaatga agtctttaat gaacttatat tagatgtgtt    360

aaagcagggt tacatgatga aaaagggcca cagacggaaa aactggactg aaagatggtt    420

tgtactaaaa cccaacataa tttcttacta tgtgagtgag gatctgaagg ataagaaagg    480

agacattctc ttggatgaaa attgctgtgt agaagtcctt gcctgacaaa agatggaaag    540

aaatgccttt t                                                         551
```

<210> SEQ ID NO 138
<211> LENGTH: 531
<212> TYPE: DNA
<213> ORGANISM: Homo sapien
<220> FEATURE:
<221> NAME/KEY: misc_feature
<222> LOCATION: (1)...(531)
<223> OTHER INFORMATION: n = A,T,C or G

<400> SEQUENCE: 138

```
gactggttct ttatttcaaa aagacacttg tcaatattca gtrtcaaaac agttgcacta     60

ttgatttctc tttctcccaa tcggccccaa agagaccaca taaaaggaga gtacatttta    120

agccaataag ctgcaggatg tacacctaac agacctccta gaaaccttac cagaaaatgg    180

ggactgggta gggaaggaaa cttaaaagat caacaaactg ccagcccacg gactgcagag    240
```

-continued

```
gctgtcacag ccagatgggg tggccagggt gccacaaacc caaagcaaag tttcaaaata    300

atataaaatt taaaaagttt tgtacataag ctattcaaga tttctccagc actgactgat    360

acaaagcaca attgagatgg cacttctaga gacagcagct tcaaacccag aaaagggtga    420

tgagatgaag tttcacatgg ctaaatcagt ggcaaaaaca cagtcttctt tctttctttc    480

tttcaaggan gcaggaaagc aattaagtgg tcaccttaac ataaggggga c             531
```

<210> SEQ ID NO 139
<211> LENGTH: 521
<212> TYPE: DNA
<213> ORGANISM: Homo sapien
<220> FEATURE:
<221> NAME/KEY: misc_feature
<222> LOCATION: (1)...(521)
<223> OTHER INFORMATION: n = A,T,C or G

<400> SEQUENCE: 139

```
tgggtgggca ccatggctgg gatcaccacc atcgaggcgg tgaagcgcaa gatccaggtt     60

ctgcagcagc aggcagatga tgcagaggag cgagctgagc gcctccagcg agaagttgag    120

ggagaaaggc gggcccggga acaggctgag gctgaggtgg cctccttgaa ccgtaggatc    180

cagctggttg aagaagagct ggaccgtgct caggagcgcc tggccactgc cctgcaaaag    240

ctggaagaag ctgaaaaagc tgctgatgag agtgagagag gtatgaaggt tattgaaaac    300

cgggccttaa aagatgaaga aaagatggaa ctccaggaaa tccaactcaa agaagctaag    360

cacattgcag aagaggcaga taggaagtat gaagaggtgg ctcgtaagtt ggtgatcatt    420

gaaggagact tggaaccgca cagaaggaac gagcttgagc ttggcaaaag tcccgttgcc    480

cagagatggg atgaaccaga ttagactgat ggaccanaac c                        521
```

<210> SEQ ID NO 140
<211> LENGTH: 571
<212> TYPE: DNA
<213> ORGANISM: Homo sapien
<220> FEATURE:
<221> NAME/KEY: misc_feature
<222> LOCATION: (1)...(571)
<223> OTHER INFORMATION: n = A,T,C or G

<400> SEQUENCE: 140

```
aggggcngcg ggtgcgtggg ccactgggtg accgacttag cctggccaga ctctcagcac     60

ctggaagcgc cccgagagtg acagcgtgag gctgggaggg aggacttggc ttgagcttgt    120

taaactctgc tctgagcctc cttgtcgcct gcatttagat ggctcccgca aagaagggtg    180

gcgagaagaa aaagggccgt tctgccatca acgaagtggt aacccgagaa tacaccatca    240

acattcacaa gcgcatccat ggagtgggct tcaagaagcg tgcacctcgg gcactcaaag    300

agattcggaa atttgccatg aaggagatgg gaactccaga tgtgcgcatt gacaccaggc    360

tcaacaaagc tgtctgggcc aaaggaataa ggaatgtgcc ataccgaatc cggtgtgcgg    420

ctgtccagaa aacgtaatga ggatgaagat tcaccaaata agctatatac tttggttacc    480

tatgtacctg ttaccacttt caaaaatcta cagacagtca atgtggatga gaactaatcg    540

ctgatcgtca gatcaaataa agttataaaa t                                   571
```

<210> SEQ ID NO 141
<211> LENGTH: 531
<212> TYPE: DNA
<213> ORGANISM: Homo sapien

<400> SEQUENCE: 141

-continued tcgggagcca cacttggccc tcttcctctc caaagsgcca gaacctcctt ctctttggag 60
aatggggagg cctcttggag acacagaggg tttcaccttg gatgacctct agagaaattg 120
cccaagaagc ccaccttctg gtcccaacct gcagacccca cagcagtcag ttggtcaggc 180
cctgctgtag aaggtcactt ggctccattg cctgcttcca accaatgggc aggagagaag 240
gcctttattt ctcgcccacc cattcctcct gtaccagcac ctccgttttc agtcagtgtt 300
gtccagcaac ggtaccgttt acacagtcac ctcagacaca ccatttcacc tcccttgcca 360
agctgttagc cttagagtga ttgcagtgaa cactgtttac acaccgtgaa tccattccca 420
tcagtccatt ccagttggca ccagcctgaa ccatttggta cctggtgtta actggagtcc 480
tgtttacaag gtggagtcgg ggcttgctga cttctcttca tttgagggca c 531

<210> SEQ ID NO 142
<211> LENGTH: 491
<212> TYPE: DNA
<213> ORGANISM: Homo sapien
<220> FEATURE:
<221> NAME/KEY: misc_feature
<222> LOCATION: (1)...(491)
<223> OTHER INFORMATION: n = A,T,C or G

<400> SEQUENCE: 142
acctagacag aaggtgggtg agggaggact ggtaggaggc tgaggcaatt ccttggtagt 60
ttgtcctgaa accctactgg agaagtcagc atgaggcacc tactgagaga agtgcccaga 120
aactgctgac tgcatctgtt aagagttaac agtaaagagg tagaagtgtg tttctgaatc 180
agagtggaag cgtctcaagg gtcccacagt ggaggtccct gagctacctc ccttccgtga 240
gtgggaagag tgaagcccat gaagaactga gatgaagcaa ggatggggtt cctgggctcc 300
aggcaagggc tgtgctctct gcagcaggga gccccacgag tcagaagaaa agaactaatc 360
atttgttgca agaaaccttg cccggatact agcggaaaac tggaggcggn ggtgggggca 420
caggaaagtg gaagtgattt gatggagagc agagaagcct atgcacagtg gccgagtcca 480
cttgtaaagt g 491

<210> SEQ ID NO 143
<211> LENGTH: 515
<212> TYPE: DNA
<213> ORGANISM: Homo sapien

<400> SEQUENCE: 143
ttcaagcaat tgtaacaagt atatgtagat tagagtgagc aaaatcatat acaattttca 60
tttccagttg ctattttcca aattgttctg taatgtcgtt aaaattactt aaaaattaac 120
aaagccaaaa attatattta tgacaagaaa gccatcccta cattaatctt acttttccac 180
tcaccggccc atctccttcc tctttttcct aactatgcca ttaaaactgt tctactgggc 240
cgggcgtgtg gctcatgcct gtaatcccag cattttggga ggccaaggca ggcggatcat 300
gaggtcaaga gattgagacc atcctggcca acatggtgaa accccgcctc gactaagaat 360
acaaaaatta gctgggcatg gtggcgcatg cctgtagtct cagctactcg ggaggctgag 420
gcagaagaat cgcttgaacc cgggaggcag aggatgcagt gagccccgat cgcgccactg 480
cactctagcc tgggcgacag actgagactc tgctc 515

<210> SEQ ID NO 144
<211> LENGTH: 340
<212> TYPE: DNA

-continued

<213> ORGANISM: Homo sapien

<400> SEQUENCE: 144
tgtgccagtc tacaggccta tcagcagcga ctccttcagc aacagatggg gtcccctgtt 60
cagcccaacc ccatgagccc ccagcagcat atgctcccaa atcaggccca gtccccacac 120
ctacaaggcc agcagatccc taattctctc tccaatcaag tgcgctctcc ccagcctgtc 180
ccttctccac ggccacagtc ccagcccccc cactccagtc cttccccaag gatgcagcct 240
cagccttctc cacaccacgt ttccccacag acaagttccc cacatcctgg actggtagtt 300
gcccaggcca accccatgga acaagggcat tttgccagcc 340

<210> SEQ ID NO 145
<211> LENGTH: 630
<212> TYPE: DNA
<213> ORGANISM: Homo sapien

<400> SEQUENCE: 145
tgtaaaaact tgtttttaat tttgtataaa ataaaggtgg tccatgccca cgggggctgt 60
aggaaatcca agcagaccag ctggggtggg gggatgtagc ctacctcggg ggactgtctg 120
tcctcaaaac gggctgagaa ggcccgtcag gggcccaggt cccacagaga ggcctgggat 180
actcccccaa cccgaggggc agactgggca gtggggagcc cccatcgtgc cccagaggtg 240
gccacaggct gaaggagggg cctgaggcac cgcagcctgc aacccccagg gctgcagtcc 300
actaactttt tacagaataa aaggaacatg ggatggggga aaaaagcacc aggtcaggca 360
gggcccgagg gccccagatc ccaggagggc caggactcag gatgccagca ccaccctagc 420
agctcccaca gctcctggca caggaggccg ccacggattg gcacaggccg ctgctggcca 480
tcacgccaca tttggagaac ttgtcccgac agaggtcagc tcggaggagc tcctcgtggg 540
cacacactgt acgaacacag atctccttgt taatgacgta cacacggcgg aggctgcggg 600
gacagggcac gggaggtctc agccccactt 630

<210> SEQ ID NO 146
<211> LENGTH: 521
<212> TYPE: DNA
<213> ORGANISM: Homo sapien

<400> SEQUENCE: 146
atggctgctg gatttaggtg gtaatagggg ctgtgggcca taaatctgaa gccttgagaa 60
ccttgggtct ggagagccat gaagagggaa ggaaaagagg gcaagtcctg aacctaacca 120
atgacctgat ggattgctcg accaagacac agaagtgaag tctgtgtctg tgcacttccc 180
acagactgga gtttttggtg ctgaatagag ccagttgcta aaaaattggg ggtttggtga 240
agaaatctga ttgttgtgtg tattcaatgt gtgattttaa aaataaacag caacaacaat 300
aaaaaccctg actggctgtt ttttccctgt attctttaca actatttttt gaccctctga 360
aaattattat acttcaccta aatggaagac tgctgtgttt gtggaaattt tgtaattttt 420
taatttattt tattctctct cctttttatt ttgcctgcag aatccgttga gagactaata 480
aggcttaata tttaattgat ttgtttaata tgtatataaa t 521

<210> SEQ ID NO 147
<211> LENGTH: 562
<212> TYPE: DNA
<213> ORGANISM: Homo sapien

<400> SEQUENCE: 147

-continued ggcatgcgag cgcactcggc ggacgcaagg gcggcgggga gcacacggag cactgcaggc 60
gccgggttgg gacagcgtct tcgctgctgc tggatagtcg tgttttcggg gatcgaggat 120
actcaccaga aaccgaaaat gccgaaacca atcaatgtcc gagttaccac catggatgca 180
gagctggagt ttgcaatcca gccaaataca actggaaaac agctttttga tcaggtggta 240
aagactatcg gcctccggga agtgtggtac tttggcctcc actatgtgga taataaagga 300
tttcctacct ggctgaagct ggataagaag gtgtctgccc aggaggtcag gaaggagaat 360
cccctccagt tcaagttccg ggccaaagtt ctaccctgaa gatgtggctg aggagctcat 420
ccaggacatc acccagaaac ttttcttcct tcaagtgaag gaaggaatcc ttagcgatga 480
gatctactgc ccccttgar actgccgtgc tcttggggtc ctacgcttgt gcatgccaag 540
tttggggact accaccaaga ag 562

<210> SEQ ID NO 148
<211> LENGTH: 820
<212> TYPE: DNA
<213> ORGANISM: Homo sapien

<400> SEQUENCE: 148
gaaggagtcg ggatactcag cattgatgca ccccaatttc aaagcggcat tcttcggcag 60
gtctctggga caatctctag ggtcactacc tggaaactcg ttagggtaca actgaatgct 120
gaaaggaaag aacacctgca gaaccggaca gaaattcacc ccggcgatca gctgattgat 180
ctcggtcgac cagaagtcat ggctaaagat gacgaggacg ttgtcaattc cctgggcttt 240
tcgaagtgag tccagcagca gtctgaggta ttcgggccgg ttatgcacct ggaccaccag 300
caccagctcc cggggggccc aggtgccagc cttatctaca ttcctcaggg tctgatcaaa 360
gttcagctgg tacaccaggg accggtaccg cagcgtcagg ttgtccgctc gggctggggg 420
accgccggga ccagggaagc cgccgacacg ttggagaccc tgcggatgcc cacagccaca 480
gaggggtggt ccccaccgcg gccgccggca ccccgcgcgg gttcggcgtc cagcaacggt 540
ggggcgaggg cctcgttctt cctttgtcgc ccattgctgc tccagaggac gaagccgcag 600
gcggccacca cgagcgtcag gattagcacc ttccgtttgt agatgcggaa cctcatggtc 660
tccagggccg ggagcgcagc tacagctcga gcgtcggcgc cgccgctagg agccgcggct 720
cggcttcgtc tccgtcctct ccattcagca ccacgggtcc cggaaaaagc tcagccscgg 780
tcccaaccgc accctagctt cgttacctgc gcctcgcttg 820

<210> SEQ ID NO 149
<211> LENGTH: 501
<212> TYPE: DNA
<213> ORGANISM: Homo sapien

<400> SEQUENCE: 149
cagattttta tttgcagtcg tcactggggc cgtttcttgc tgcttatttg tctgctagcc 60
tgctcttcca gctgcatggc caggcgcaag gccttgatga catctcgcag ggctgagaaa 120
tgcttggctt gctgggccag agcagattcc gctttgttca caaaggtctc caggtcatag 180
tctggctgct cggtcatctc agagagctca agccagtctg gtccttgctg tatgatctcc 240
ttgagctctt ccatagcctt ctcctccagc tccctgatct gagtcatggc ttcgttaaag 300
ctggacatct gggaagacag ttcctcctct tccttggata aattgcctgg aatcagcgcc 360
ccgttagagc aggcttccat ctcttctgtt tccatttgaa tcaactgctc tccactgggc 420

-continued

```
ccactgtggg ggctcagctc cttgaccctg ctgcatatct taagggtgtt taaaggatat    480

tcacaggagc ttatgcctgg t                                              501
```

<210> SEQ ID NO 150
<211> LENGTH: 511
<212> TYPE: DNA
<213> ORGANISM: Homo sapien
<220> FEATURE:
<221> NAME/KEY: misc_feature
<222> LOCATION: (1)...(511)
<223> OTHER INFORMATION: n = A,T,C or G

<400> SEQUENCE: 150

```
ctcctcttgg tacatgaacc caagttgaaa gtggacttaa caaagtatct ggagaaccaa     60

gcattctgct ttgactttgc atttgatgaa acagcttcga atgaagttgt ctacaggttc    120

acagcaaggc cactggtaca gacaatcttt gaaggtggaa aagcaacttg ttttgcatat    180

ggccagacag gaagtggcaa gacacatact atgggcggag acctctctgg gaaagcccag    240

aatgcatcca aagggatcta tgccatggcc ttccgggacg tcttcttctg aagaatcaac    300

cctgctaccg gaagttgggc ctggaagtct atgtgacatt cttcgagatc tacaatggga    360

agctgtttga cctgctcaac aagaaggcca agcttgcgcg tgctggaaga cggcaagcaa    420

caggtgcaag tggtgggggc ttgcaggaac atctggntaa ctctgcttga tgatggcant    480

caagatgatc gacatgggca gcgcctgcag a                                   511
```

<210> SEQ ID NO 151
<211> LENGTH: 566
<212> TYPE: DNA
<213> ORGANISM: Homo sapien

<400> SEQUENCE: 151

```
tcccgaattc aagcgacaaa ttggawagtg aaatggaaga tgcctatcat gaacatcagg     60

caaatctttt gcgccaagat ctgatgagac gacaggaaga attaagacgc atggaagaac    120

ttcacaatca agaaatgcag aaacgtaaag aaatgcaatt gaggcaagag gaggaacgac    180

gtagaagaga ggaagagatg atgattcgtc aacgtgagat ggaagaacaa atgaggcgcc    240

aaagagagga aagttacagc cgaatgggct acatggatcc acgggaaaga gacatgcgaa    300

tgggtggcgg aggagcaatg aacatgggag atccctatgg ttcaggaggc cagaaatttc    360

cacctctagg aggtggtggt ggcataggtt atgaagctaa tcctggcgtt ccaccagcaa    420

ccatgagtgg ttccatgatg ggaagtgaca tgcgtactga gcgctttggg cagggaggtg    480

cggggcctgt gggtggacag ggtcctagag gaatggggcc tggaactcca gcaggatatg    540

gtagagggag agaagagtac gaaggc                                         566
```

<210> SEQ ID NO 152
<211> LENGTH: 518
<212> TYPE: DNA
<213> ORGANISM: Homo sapien

<400> SEQUENCE: 152

```
ttcgtgaaga ccctgactgg taagaccatc actctcgaag tggagcccga gtgacaccat     60

tgagaatgtc aaggcaaaga tccaagacaa ggaaggcatc cctcctgacc agcakaggtt    120

gatctttgct gggaaacagc tggaagatgg acgcaccctg tctgactaca acatccagaa    180

agagtccacc ctgcacctgg tgctccgtct cagaggtggg atgcaaatct tcgtgaagac    240

cctgactggt aagaccatca ccctcgaggt ggagcccagt gacaccatcg agaatgtcaa    300
```

-continued

```
ggcaaagatc caagataagg aaggcatccc tcctgatcag cagaggttga tctttgctgg    360

gaaacagctg gaagatggac gcaccctgtc tgactacaac atccagaaag agtccactct    420

gcacttggtc ctgcgcttga ggggggtgt ctaagtttcc ccttttaagg tttcaacaaa    480

tttcattgca ctttcctttc aataaagttg ttgcattc                           518
```

```
<210> SEQ ID NO 153
<211> LENGTH: 542
<212> TYPE: DNA
<213> ORGANISM: Homo sapien

<400> SEQUENCE: 153

gcgcgggtgc gtgggccact gggtgaccga cttagcctgg ccagactctc agcacctgga     60

agcgccccga gagtgacagc gtgaggctgg gagggaggac ttggcttgag cttgttaaac    120

tctgctctga gcctccttgt cgcctgcatt tagatggctc ccgcaaagaa gggtggcgag    180

aagaaaaagg gccgttctgc catcaacgaa gtggtaaccc gagaatacac catcaacatt    240

cacaagcgca tccatggagt gggcttcaag aagcgtgcac ctcgggcact caaagagatt    300

cggaaatttg ccatgaagga gatgggaact ccagatgtgc gcattgacac caggctcaac    360

aaagctgtct gggccaaagg aataaggaat gtgccatacc gaatccgtgt gcggctgtcc    420

agaaaacgta atgaggatga agattcacca aataagctat atactttggt tacctatgta    480

cctgttacca ctttcaaaaa tctacagaca gtcaatgtgg atgagaacta atcgctgatc    540

gt                                                                   542
```

```
<210> SEQ ID NO 154
<211> LENGTH: 411
<212> TYPE: DNA
<213> ORGANISM: Homo sapien

<400> SEQUENCE: 154

aattctttat ttaaatcaac aaactcatct tcctcaagcc ccagaccatg gtaggcagcc     60

ctccctctcc atcccctcac cccacccctt agccacagtg aagggaatgg aaaatgagaa    120

gccacgaggg cccctgccag ggaaggctgc cccagatgtg tggtgagcac agtcagtgca    180

gctgtggctg gggcagcagc tgccacaggc tcctccctat aaattaagtt cctgcagcca    240

cagctgtggg agaagcatac ttgtagaagc aaggccagtc cagcatcaga aggcagaggc    300

agcatcagtg actcccagcc atggaatgaa cggaggacac agagctcaga gacagaacag    360

gccaggggga agaaggagag acagaatagg ccagggcatg gcggtgaggg a             411
```

```
<210> SEQ ID NO 155
<211> LENGTH: 421
<212> TYPE: DNA
<213> ORGANISM: Homo sapien
<220> FEATURE:
<221> NAME/KEY: misc_feature
<222> LOCATION: (1)...(421)
<223> OTHER INFORMATION: n = A,T,C or G

<400> SEQUENCE: 155

tgatgaatct gggtgggctg gcagtagccc gagatgatgg gctcttctct ggggatccca     60

actggttccc taagaaatcc aaggagaatc ctcggaactt ctcggataac cagctgcaag    120

agggcaagaa cgtgatcggg ttacagatgg gcaccaaccg cggggcgtct cangcaggca    180

tgactggcta cgggatgcca cgccagatcc tctgatccca ccccaggcct tgcccctgcc    240
```

-continued

```
ctcccacgaa tggttaatat atatgtagat atatatttta gcagtgacat tcccagagag    300

ccccagagct ctcaagctcc tttctgtcag ggtgggggt tcaagcctgt cctgtcacct    360

ctgaagtgcc tgctggcatc ctctccccca tgcttactaa tacattccct tccccatagc    420

c                                                                    421
```

<210> SEQ ID NO 156
<211> LENGTH: 670
<212> TYPE: DNA
<213> ORGANISM: Homo sapien

<400> SEQUENCE: 156

```
agcggagctc cctcccctgg tggctacaac ccacacacgc caggctcagg catcgagcag     60

aactccagcg actgggtaac cactgacatt caggtgaagg tgcgggacac ctacctggat    120

acacaggtgg tgggacagac aggtgtcatc cgcagtgtca cggggggcat gtgctctgtg    180

tacctgaagg acagtgagaa ggttgtcagc atttccagtg agcacctgga gcctatcacc    240

cccaccaaga acaacaaggt gaaagtgatc ctgggcgagg atcgggaagc cacgggcgtc    300

ctactgagca ttgatggtga ggatggcatt gtccgtatgg accttgatga gcagctcaag    360

atcctcaacc tccgcttcct ggggaagctc ctggaagcct gaagcaggca gggccggtgg    420

acttcgtcgg atgaagagtg atcctccttc cttccctggc ccttggctgt gacacaagat    480

cctcctgcag ggctaggcgg attgttctgg atttcctttt gtttttcctt ttaggtttcc    540

atcttttccc tccctggtgc tcattggaat ctgagtagag tctgggggag ggtccccacc    600

ttcctgtacc tcctccccac agcttgcttt tgttgtaccg tctttcaata aaaagaagct    660

gtttggtcta                                                           670
```

<210> SEQ ID NO 157
<211> LENGTH: 421
<212> TYPE: DNA
<213> ORGANISM: Homo sapien

<400> SEQUENCE: 157

```
ggttcacagc actgctgctt gtgtgttgcc ggccaggaat tccaggctca caaggctatc     60

ttagcagctc gttctccggt ttttagtgcc atgtttgaac atgaaatgga ggagagcaaa    120

aagaatcgag ttgaaatcaa tgatgtggag cctgaagttt ttaaggaaat gatgtgcttc    180

atttacacgg ggaaggctcc aaacctcgac aaaatggctg atgatttgct ggcagctgct    240

gacaagtatg ccctggagcg cttaaaggtc atgtgtgagg atgccctctg cagtaacctg    300

tccgtggaga acgctgcaga aattctcatc ctggccgacc tccacagtgc agatcagttg    360

aaaactcagg cagtggattt catcaactat catgcttcgg atgtcttgga gacctcttgg    420

g                                                                    421
```

<210> SEQ ID NO 158
<211> LENGTH: 321
<212> TYPE: DNA
<213> ORGANISM: Homo sapien

<400> SEQUENCE: 158

```
tcgtagccat ttttctgctt ctttggagaa tgacgccaca ctgactgctc attgtcgttg     60

gttccatgcc aattggtgaa atagaacctc atccggtagt ggagccggag ggacatcttg    120

tcatcaacgg tgatggtgcg atttggagca taccagagct tggtgttctc gccatacagg    180

gcaaagaggt tgtgacaaag aggagagata cggcatgcct gtgcagccct gatgcacagt    240
```

-continued tcctctgctg tgtactctcc actgcccagc cggaggggct ccctgtccga cagatagaag 300
atcacttcca cccctggctt g 321

<210> SEQ ID NO 159
<211> LENGTH: 596
<212> TYPE: DNA
<213> ORGANISM: Homo sapien

<400> SEQUENCE: 159
tggcacactg ctcttaagaa actatgawga tctgagattt ttttgtgtat gtttttgact 60
cttttgagtg gtaatcatat gtgtctttat agatgtacat acctccttgc acaaatggag 120
gggaattcat tttcatcact gggagtgtcc ttagtgtata aaaaccatgc tggtatatgg 180
cttcaagttg taaaaatgaa agtgacttta aaagaaaata ggggatggtc caggatctcc 240
actgataaga ctgtttttaa gtaacttaag gacctttggg tctacaagta tatgtgaaaa 300
aaatgagact tactgggtga ggaaattcat tgtttaaaga tggtcgtgtg tgtgtgtgtg 360
tgtgtgtgtg ttgtgttgtg ttttgttttt taagggaggg aatttattat ttaccgttgc 420
ttgaaattac tgkgtaaata tatgtytgat aatgatttgc tytttgvcma ctaaaattag 480
gvctgtataa gtwctaratg cmtccctggg kgttgatytt ccmagatatt gatgatamcc 540
cttaaaattg taaccygcct ttttcccttt gctytcmatt aaagtctatt cmaaag 596

<210> SEQ ID NO 160
<211> LENGTH: 515
<212> TYPE: DNA
<213> ORGANISM: Homo sapien

<400> SEQUENCE: 160
gggggtaggc tctttattag acggttattg ctgtactaca gggtcagagt gcagtgtaag 60
cagtgtcaga ggcccgcgtt cagcccaaga atgtggattt tctctcccta ttgatcacag 120
tgggtgggtt tcttcagaaa agccccagag gcagggacca gtgagctcca aggttagaag 180
tggaactgga aggcttcagt cacatgctgc ttccacgctt ccaggctggg cagcaaggag 240
gagatgccca tgacgtgcca ggtctcccca tctgacacca gtgaagtctg gtaggacagc 300
agccgcacgc ctgcctctgc caggaggcca atcatggtag gcagcattgc agggtcagag 360
gtctgagtcc ggaataggag caggggcagg tccctgcgga gaggcacttc tggcctgaag 420
acagctccat tgagcccctg cagtacaggy gtagtgcctt ggaccaagcc cacagcctgg 480
taaggggcgc ctgccagggc cacggccagg aggca 515

<210> SEQ ID NO 161
<211> LENGTH: 936
<212> TYPE: DNA
<213> ORGANISM: Homo sapien

<400> SEQUENCE: 161
taatttctta gtcgtttgga atccttaagc atgcaaaagc tttgaacaga agggttcaca 60
aaggaaccag ggttgtctta tggcatccag ttaagccaga gctgggaatg cctctgggtc 120
atccacatca ggagcagaag cacttgactt gtcggtcctg ctgccacggt ttgggcgccc 180
accacgccca cgtccacctc gtcctcccct gccgccacgt cctgggcggc caaggtctcc 240
aaaattgatc tccagctgag acgttatatc atttgctggc ttccggaaat gatggtccat 300
aaccgaatct tcagcatgag cctcttcact ctttgattta tgaagaacaa atcccttctt 360

-continued

```
ccactgccca tcagcacctt catttggttt tcggatatta aattctactt ttgcccggtc    420

cttattttga atagccttcc actcatccaa agtcatctct tttggaccct cctcttttac    480

ctcttcaact tcattctcct tattttcagt gtctgccact ggatgatgtt cttcaccttc    540

aggtgtttcc tcagtcacat ttgattgatc caagtcagtt aattcgtctt tgacagttcc    600

ccagttgtga gatccgctac ctccacgttt gtcctcgtgc ttcaggccag atctatcact    660

tccactatgc ctatcaaatt cacgtttgcc acgagaatca aatccatctc ctcggcccat    720

tccacgtcca cggcccccctc gacctcttcc aagaccacca cgacctcgaa taggtcggtc    780

aataatcggt ctatcaactg aaaattcgcc tccttcaccc ttttcttcaa gtggcttttc    840

gaatcttcgt tcacgaggtg gtcgcctttc tggtcttcta tcaattattt tcccttcacc    900

ctgaagttgt tgatcaggtc ttcttccaac tcgtgc                              936
```

```
<210> SEQ ID NO 162
<211> LENGTH: 950
<212> TYPE: DNA
<213> ORGANISM: Homo sapien

<400> SEQUENCE: 162

aagcggatgg acctgagtca gccgaatcct agccccttcc cttgggcctg ctgtggtgct     60

cgacatcagt gacagacgga agcagcagac catcaaggct acgggaggcc cggggcgctt    120

gcgaagatga agtttggctg cctctccttc cggcagcctt atgctggctt tgtcttaaat    180

ggaatcaaga ctgtggagac gcgctggcgt cctctgctga gcagccagcg gaactgtacc    240

atcgccgtcc acattgctca cagggactgg gaaggcgatg cctgtcggga gctgctggtg    300

gagagactcg ggatgactcc tgctcagatt caggccttgc tcaggaaagg ggaaaagttt    360

ggtcgaggag tgatagcggg actcgttgac attggggaaa ctttgcaatg ccccgaagac    420

ttaactcccg atgaggttgt ggaactagaa aatcaagctg cactgaccaa cctgaagcag    480

aagtacctga ctgtgatttc aaaccccagg tggttactgg agcccatacc taggaaagga    540

ggcaaggatg tattccaggt agacatccca gagcacctga tccctttggg gcatgaagtg    600

tgacaagtgt gggctcctga aaggaatgtt ccrgagaaac cagctaaatc atggcacctt    660

caatttgcca tcgtgacgca gacctgtata aattaggtta aagatgaatt tccactgctt    720

tggagagtcc cacccactaa gcactgtgca tgtaaacagg ttcctttgct cagatgaagg    780

aagtaggggg tggggctttc cttgtgtgat gcctccttag gcacacaggc aatgtctcaa    840

gtactttgac cttagggtag aaggcaaagc tgccagtaaa tgtctcagca ttgctgctaa    900

ttttggtcct gctagtttct ggattgtaca aataaatgtg ttgtagatga               950
```

```
<210> SEQ ID NO 163
<211> LENGTH: 475
<212> TYPE: DNA
<213> ORGANISM: Homo sapien
<220> FEATURE:
<221> NAME/KEY: misc_feature
<222> LOCATION: (1)...(475)
<223> OTHER INFORMATION: n = A,T,C or G

<400> SEQUENCE: 163

tcgagcggcc gcccgggcag gtgtcggagt ccagcacggg aggcgtggtc ttgtagttgt     60

tctccggctg cccattgctc tcccactcca cggcgatgtc gctgggatag aagcctttga    120

ccaggcaggt caggctgacc tggttcttgg tcatctcctc ccgggatggg ggcagggtgt    180

acacctgtgg ttctcggggc tgccctttgg ctttggagat ggttttctcg atgggggctg    240
```

-continued

```
ggagggcttt gttggagacc ttgcacttgt actccttgcc attcaaccag tcctggtgca    300

ngacggtgag gacgctnacc acacggtacg ngctggtgta ctgctcctcc cgcggctttg    360

tcttggcatt atgcacctcc acgccgtcca cgtaccaatt gaacttgacc tcagggtctt    420

cgtggctcac gtccaccacc acgcatgtaa cctcaaanct cggncgcgan cacgc         475


<210> SEQ ID NO 164
<211> LENGTH: 476
<212> TYPE: DNA
<213> ORGANISM: Homo sapien

<400> SEQUENCE: 164

agcgtggtcg cggccgaggt ctgaggttac atgcgtggtg gtggacgtga gccacgaaga     60

ccctgaggtc aagttcaact ggtacgtgga cggcgtggag gtgcataatg ccaagacaaa    120

gccgcgggag gagcagtaca acagcacgta ccgtgtggtc agcgtcctca ccgtcctgca    180

ccaggactgg ctgaatggca aggagtacaa gtgcaaggtc tccaacaaag ccctcccagc    240

cccatcgag aaaaccatct ccaaagccaa agggcagccc cgagaaccac aggtgtacac    300

cctgccccca tcccgggagg agatgaccaa gaaccaggtc agcctgacct gcctggtcaa    360

aggcttctat cccagcgaca tcgcccgtgg agtgggagag caatgggcag ccggagaaca    420

actacaagac cacgcctccc gtgctggact ccgacacctg ccgggcggcc gctcga        476


<210> SEQ ID NO 165
<211> LENGTH: 256
<212> TYPE: DNA
<213> ORGANISM: Homo sapien
<220> FEATURE:
<221> NAME/KEY: misc_feature
<222> LOCATION: (1)...(256)
<223> OTHER INFORMATION: n = A,T,C or G

<400> SEQUENCE: 165

agcgtggttn cggccgaggt cccaaccaag gctgcancct ggatgccatc aaagtcttct     60

gcaacatgga gactggtgag acctgcgtgt accccactca gcccagtgtg gcccagaaga    120

actggtacat cagcaagaac cccaaggaca agaggcatgt ctggttcggc gagagcatga    180

ccgatggatt ccagttcgag tatggcggcc agggctccga ccctgccgat gtggacctgc    240

ccgggcggnc gctcga                                                    256


<210> SEQ ID NO 166
<211> LENGTH: 332
<212> TYPE: DNA
<213> ORGANISM: Homo sapien

<400> SEQUENCE: 166

agcgtggtcg cggccgaggt caagaacccc gcccgcacct gccgtgacct caagatgtgc     60

cactctgact ggaagagtgg agagtactgg attgacccca accaaggctg caacctggat    120

gccatcaaag tcttctgcaa catggagact ggtgagacct gcgtgtaccc cactcagccc    180

agtgtggccc agaagaactg gtacatcagc aagaacccca aggacaagag gcatgtctgg    240

ttcggcgaga gcatgaccga tggattccag ttcgagtatg gcggccaggg ctccgaccct    300

gccgatgtgg acctgcccgg gcggccgctc ga                                  332


<210> SEQ ID NO 167
<211> LENGTH: 332
<212> TYPE: DNA
```

-continued

<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 167
tcgagcggtc gcccgggcag gtccacatcg gcagggtcgg agccctggcc gccatactcg 60
aactggaatc catcggncat gctctcgccg aaccagacat gcctcttgnc cttggggttc 120
ttgctgatgt accagntctt ctgggccaca ctgggctgag tggggtacac gcaggtctca 180
ccantctcca tgttgcanaa gactttgatg gcatccaggt tgcagccttg gttggggtca 240
atccagtact ctccactctt ccagacagag tggcacatct tgaggtcacg gcaggtgcgg 300
gcggggttct tgacctcggt cgcgaccacg ct 332

<210> SEQ ID NO 168
<211> LENGTH: 276
<212> TYPE: DNA
<213> ORGANISM: Homo sapien
<220> FEATURE:
<221> NAME/KEY: misc_feature
<222> LOCATION: (1)...(276)
<223> OTHER INFORMATION: n = A,T,C or G

<400> SEQUENCE: 168
tcgagcggcc gcccgggcag gtcctcctca gagcggtagc tgttcttatt gccccggcag 60
cctccataga tnaagttatt gcangagttc ctctccacgt caaagtacca gcgtgggaag 120
gatgcacggc aaggcccagt gactgcgttg gcggtgcagt attcttcata gttgaacata 180
tcgctggagt ggacttcaga atcctgcctt ctgggagcac ttgggacaga ggaatccgct 240
gcattcctgc tggtggacct cggccgcgac cacgct 276

<210> SEQ ID NO 169
<211> LENGTH: 276
<212> TYPE: DNA
<213> ORGANISM: Homo sapien

<400> SEQUENCE: 169
agcgtggtcg cggccgaggt ccaccagcag gaatgcagcg gattcctctg tcccaagtgc 60
tcccagaagg caggattctg aagaccactc cagcgatatg ttcaactatg aagaatactg 120
caccgccaac gcagtcactg ggccttgccg tgcatccttc ccacgctggt actttgacgt 180
ggagaggaac tcctgcaata acttcatcta tggaggctgc cggggcaata agaacagcta 240
ccgctctgag gaggacctgc ccgggcggcc gctcga 276

<210> SEQ ID NO 170
<211> LENGTH: 332
<212> TYPE: DNA
<213> ORGANISM: Homo sapien
<220> FEATURE:
<221> NAME/KEY: misc_feature
<222> LOCATION: (1)...(332)
<223> OTHER INFORMATION: n = A,T,C or G

<400> SEQUENCE: 170
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240

-continued atccagtact ctccactctt ccagccagaa tggcacatct tgaggtcacg gcangtgcgg 300
gcggggttct tgacctcggc cgcgaccacg ct 332

<210> SEQ ID NO 171
<211> LENGTH: 333
<212> TYPE: DNA
<213> ORGANISM: Homo sapien

<400> SEQUENCE: 171
agcgtggtcg cggccgaggt caagaaaccc cgcccgcacc tgccgtgacc tcaagatgtg 60
ccactctggc tggaagagtg gagagtactg gattgacccc aaccaaggct gcaacctgga 120
tgccatcaaa gtcttctgca acatggagac tggtgagacc tgcgtgtacc ccactcagcc 180
cagtgtggcc cagaagaact ggtacatcag caagaacccc aaggacaaga ggcatgtctg 240
gctcggcgag agcatgaccg atggattcca gttcgagtat ggcggccagg gctccgaccc 300
tgccgatgtg gacctgcccg ggcggccgct cga 333

<210> SEQ ID NO 172
<211> LENGTH: 527
<212> TYPE: DNA
<213> ORGANISM: Homo sapien
<220> FEATURE:
<221> NAME/KEY: misc_feature
<222> LOCATION: (1)...(527)
<223> OTHER INFORMATION: n = A,T,C or G

<400> SEQUENCE: 172
agcgtggtcg cggccgaggt cctgtcagag tggcactggt agaagntcca ggaaccctga 60
actgtaaggg ttcttcatca gtgccaacag gatgacatga aatgatgtac tcagaagtgt 120
cctgnaatgg ggcccatgan atggttgnct gagagagagc ttcttgtcct acattcggcg 180
ggtatggtct tggcctatgc cttatggggg tggccgttgn gggcggtgng gtccgcctaa 240
aaccatgttc ctcaaagatc atttgttgcc caacactggg ttgctgacca naagtgccag 300
gaagctgaat accatttcca gtgtcatacc cagggtgggt gacgaaaggg gtcttttgaa 360
ctgtggaagg aacatccaag atctctgntc catgaagatt ggggtgtgga agggttacca 420
gttggggaag ctcgctgtct ttttccttcc aatcangggc tcgctcttct gaatattctt 480
cagggcaatg acataaattg tatattcggt tcccggttcc aggccag 527

<210> SEQ ID NO 173
<211> LENGTH: 635
<212> TYPE: DNA
<213> ORGANISM: Homo sapien
<220> FEATURE:
<221> NAME/KEY: misc_feature
<222> LOCATION: (1)...(635)
<223> OTHER INFORMATION: n = A,T,C or G

<400> SEQUENCE: 173
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agacccctt cgtcacccac 360

-continued

```
cctgggtatg acactggaaa tggtattcag cttcctggca cttctggtca gcaacccagt    420

gttgggcaac aaatgatctt tgangaacat ggntttaggc ggaccacacc ggccacaacg    480

ggcacccccca taaggcatag gccaagaaca tacccgncga atgtaggaca agaagctctn    540

tctcanacaa ncatctcatg ggccccattc cangacactt ctgagtacat canttcatgg    600

catcctggtg gcactgataa aaacccttac agtta                               635
```

```
<210> SEQ ID NO 174
<211> LENGTH: 572
<212> TYPE: DNA
<213> ORGANISM: Homo sapien
<220> FEATURE:
<221> NAME/KEY: misc_feature
<222> LOCATION: (1)...(572)
<223> OTHER INFORMATION: n = A,T,C or G

<400> SEQUENCE: 174

agcgtggtcg cgggcgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300

gaagctgaat accatttcca gtgtcatacc cagggtgggt gacgaaaggg gtcttttgaa    360

ctgtggaagg aacatccaag atctctggtc catgaagatt ggggtgtgga agggttacca    420

gttggggaag ctcgtctgtc tttttccttc caatcanggg ctcgctcttc tgattattct    480

tcagggcaat gacataaatt gtatattcgg ntcccgggtn cagccaataa taataaccct    540

ctgtgacacc anggcggggc cgaagganca ct                                  572
```

```
<210> SEQ ID NO 175
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 175

agcgtggtcg cggccgaggt cctcaccaga ggtaccacct acaacatcat agtggaggca     60

ctgaaagacc agcagaggca taaggttcgg gaagaggttg ttaccgtggg caactctgtc    120

aacgaaggct tgaaccaacc tacggatgac tcgtgctttg acccctacac agtttcccat    180

tatgccgttg gagatgagtg ggaacgaatg tctgaatcag gctttaaact gttgtgccag    240

tgcttangct ttggaagtgg tcatttcaga tgtgattcat ctagatggtg ccatgacaat    300

ggtgtgaact acaagattgg agagaagtgg gaccgtcagg gagaaaatgg acctgcccgg    360

gcggccgctc ga                                                        372
```

```
<210> SEQ ID NO 176
<211> LENGTH: 372
<212> TYPE: DNA
<213> ORGANISM: Homo sapien
<220> FEATURE:
<221> NAME/KEY: misc_feature
<222> LOCATION: (1)...(372)
<223> OTHER INFORMATION: n = A,T,C or G

<400> SEQUENCE: 176
```

-continued

```
tcgagcggcc gcccgggcag gtccattttc tccctgacgg tcccacttct ctccaatctt     60

gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ntgacagagt tgcccacggt aacaacctct tcccgaacct tatgcctctg    300

ctggtctttc agtgcctcca ctatgatgtt gtaggtggta cctctggtga ggacctcggc    360

cgcgaccacg ct                                                        372


<210> SEQ ID NO 177
<211> LENGTH: 269
<212> TYPE: DNA
<213> ORGANISM: Homo sapien
<220> FEATURE:
<221> NAME/KEY: misc_feature
<222> LOCATION: (1)...(269)
<223> OTHER INFORMATION: n = A,T,C or G

<400> SEQUENCE: 177

agcgtggccg cggccgaggt ccattggctg gaacggcatc aacttggaag ccagtgatcg     60

tctcagcctt ggttctccag ctaatggtga tggnggtctc agtagcatct gtcacacgag    120

cccttcttgg tgggctgaca ttctccagag tggtgacaac accctgagct ggtctgcttg    180

tcaaagtgtc cttaagagca tagacactca cttcatattt ggcgnccacc ataagtcctg    240

atacaaccac ggaatgacct gtcaggaac                                      269


<210> SEQ ID NO 178
<211> LENGTH: 529
<212> TYPE: DNA
<213> ORGANISM: Homo sapien

<400> SEQUENCE: 178

tcgagcggcc gcccgggcag gtcctcagac cgggttctga gtacacagtc agtgtggttg     60

ccttgcacga tgatatggag agccagcccc tgattggaac ccagtccaca gctattcctg    120

caccaactga cctgaagttc actcaggtca cacccacaag cctgagcgcc cagtggacac    180

cacccaatgt tcagctcact ggatatcgag tgcgggtgac ccccaaggag aagaccggac    240

caatgaaaga aatcaacctt gctcctgaca gctcatccgt ggttgtatca ggacttatgg    300

cggccaccaa atatgaagtg agtgtctatg ctcttaagga cactttgaca agcagaccag    360

ctcagggtgt tgtcaccact ctggagaatg tcagcccacc aagaagggct cgtgtgacag    420

atgctactga gaccaccatc accattagct ggagaaccaa gactgagacg atcactggct    480

tccaagttga tgccgttcca gccaatggac ctcggccgcg accacgctt                529


<210> SEQ ID NO 179
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 179

agcgtggtcg cggccgaggt ctggccgaac tgccagtgta cagggaagat gtacatgtta     60

tagntcttct cgaagtcccg ggccagcagc tccacggggt ggtctcctgc ctccaggcgc    120
```

-continued

```
ttctcattct catggatctt cttcacccgc agcttctgct tctcagtcag aaggttgttg    180

tcctcatccc tctcatacag ggtgaccagg acgttcttga gccagtcccg catgcgcagg    240

gggaattcgg tcagctcaga gtccaggcaa ggggggatgt atttgcaagg cccgatgtag    300

tccaagtgga gcttgtggcc cttcttggtg ccctccaagg tgcactttgt ggcaaagaag    360

tggcaggaag agtcgaaggt cttgttgtca ttgctgcaca ccttctcaaa ctcgccaatg    420

ggggctgggc agacctgccc gggcggccgc tcga                                454


<210> SEQ ID NO 180
<211> LENGTH: 454
<212> TYPE: DNA
<213> ORGANISM: Homo sapien
<220> FEATURE:
<221> NAME/KEY: misc_feature
<222> LOCATION: (1)...(454)
<223> OTHER INFORMATION: n = A,T,C or G

<400> SEQUENCE: 180

tcgagcggcc gcccgggcag gtctgcccag cccccattgg cgagtttgag aaggngtgca     60

gcaatgacaa caagaccttc gactcttcct gccacttctt tgccacaaag tgcaccctgg    120

agggcaccaa gaagggccac aagctccacc tggactacat cgggccttgc aaatacatcc    180

ccccttgcct ggactctgag ctgaccgaat tccccctgcg catgcgggac tggctcaaga    240

acgtcctggt caccctgtat gagagggatg aggacaacaa ccttctgact gagaagcana    300

agctgcgggt gaagaanatc catgagaatg anaagcgcct gnaggcanga gaccaccccg    360

tggagctgct ggcccgggac ttcgagaaga actataacat gtacatcttc cctgtacact    420

ggcagttcgg ccagacctcg gccgcgacca cgct                                454


<210> SEQ ID NO 181
<211> LENGTH: 102
<212> TYPE: DNA
<213> ORGANISM: Homo sapien
<220> FEATURE:
<221> NAME/KEY: misc_feature
<222> LOCATION: (1)...(102)
<223> OTHER INFORMATION: n = A,T,C or G

<400> SEQUENCE: 181

agcgtggntg cggacgacgc ccacaaagcc attgtatgta gttttanttc agctgcaaan     60

aataccncca gcatccacct tactaaccag catatgcaga ca                       102


<210> SEQ ID NO 182
<211> LENGTH: 337
<212> TYPE: DNA
<213> ORGANISM: Homo sapien
<220> FEATURE:
<221> NAME/KEY: misc_feature
<222> LOCATION: (1)...(337)
<223> OTHER INFORMATION: n = A,T,C or G

<400> SEQUENCE: 182

tcgagcggtc gcccgggcag gtctgggcgg atagcaccgg gcatattttg gaatggatga     60

ggtctggcac cctgagcagc ccagcgagga cttggtctta gttgagcaat ttggctagga    120

ggatagtatg cagcacggtt ctgagtctgt gggatagctg ccatgaagna acctgaagga    180

ggcgctggct ggtangggtt gattacaggg ctgggaacag ctcgtacact tgccattctc    240

tgcatatact ggntagtgag gcgagcctgg cgctcttctt tgcgctgagc taaagctaca    300

tacaatggct ttgnggacct cggccgcgac cacgctt                             337
```

<210> SEQ ID NO 183
<211> LENGTH: 374
<212> TYPE: DNA
<213> ORGANISM: Homo sapien

<400> SEQUENCE: 183
tcgagcggcc gcccgggcag gtccattttc tccctgacgg tcccacttct ctccaatctt 60
gtagttcaca ccattgtcat gacaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagaag ttgcccacgg taacaacctc ttcccgaacc ttatgcctct 300
gctggtcttt caagtgcctc cactatgatg ttgtaggtgg cacctctggt gaggacctcg 360
gccgcgacca cgct 374

<210> SEQ ID NO 184
<211> LENGTH: 375
<212> TYPE: DNA
<213> ORGANISM: Homo sapien
<220> FEATURE:
<221> NAME/KEY: misc_feature
<222> LOCATION: (1)...(375)
<223> OTHER INFORMATION: n = A,T,C or G

<400> SEQUENCE: 184
agcgtggttt gcggccgagg tcctcaccan aggtgccacc tacaacatca tagtggaggc 60
actgaaagac cagcagaggc ataaggttcg ggaagaggtt gttaccgtgg gcaactctgt 120
caacgaaggc ttgaaccaac ctacggatga ctcgtgcttt gacccctaca cagnttccca 180
ttatgccgtt ggagatgagt gggaacgaat gtctgaatca ggctttaaac tgttgtgcca 240
gtgcttangc tttggaagtg gtcatttcag atgtgattca tctanatggt gtcatgacaa 300
tggtgngaac tacaagattg gagagaagtg gnaccgtcag gggananaaat ggacctgccc 360 gggcggcncg ctcga 375

<210> SEQ ID NO 185
<211> LENGTH: 148
<212> TYPE: DNA
<213> ORGANISM: Homo sapien
<220> FEATURE:
<221> NAME/KEY: misc_feature
<222> LOCATION: (1)...(148)
<223> OTHER INFORMATION: n = A,T,C or G

<400> SEQUENCE: 185
agcgtggtcg cggccgaggt ctggcttnct gctcangtga ttatcctgaa ccatccaggc 60
caaataagcg ccggctatgc ccctgnattg gattgccaca cggctcacat tgcatgcaag 120
tttgctgagc tgaaggaaaa gattgatc 148

<210> SEQ ID NO 186
<211> LENGTH: 397
<212> TYPE: DNA
<213> ORGANISM: Homo sapien
<220> FEATURE:
<221> NAME/KEY: misc_feature
<222> LOCATION: (1)...(397)
<223> OTHER INFORMATION: n = A,T,C or G

<400> SEQUENCE: 186

-continued

```
tcgagcggcc gcccgggcag gtccaattga aacaaacagt tctgagaccg ttcttccacc     60

actgattaag agtggggngg cgggtattag ggataatatt catttagcct tctgagcttt    120

ctgggcagac ttggtgacct tgccagctcc agcagccttc tggtccactg ctttgatgac    180

acccaccgca actgtctgtc tcatatcacg aacagcaaag cgacccaaag gtggatagtc    240

tgagaagctc tcaacacaca tgggcttgcc aggaaccata tcaacaatgg gcagcatcac    300

cagacttcaa gaatttaagg gccatcttcc agctttttac cagaacggcg atcaatcttt    360

tccttcagct cagcaaactt gcatgcaatg tgagccg                             397
```

```
<210> SEQ ID NO 187
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 187

tcgagcggcc gcccgggcag gtccagaggg ctgtgctgaa gtttgctgct gccactggag     60

ccactccaat tgctggccgc ttcactcctg gaaccttcac taaccagatc caggcagcct    120

tccgggagcc acggcttctt gtggntactg accccagggc tgaccaccag cctctcacgg    180

aggcatctta tgttaaccta cctaccattg cgctgtgtaa cacagattct cctctgcgct    240

atgtggacat tgccatccca tgcaacaaca agggagctca ctcagngggg tttgatgtgg    300

tggatgctgg ctcgggaagt tctgcgcatg cgtggcacca tttcccgtga acacccatgg    360

gangncatgc ctgatctgga cttctacaga gatcctgaag agattgaaaa agaagaacag    420

gctgnttgct ganaaagcaa gtgaccaagg angaaatttc angggtgaaa nggactgctc    480

ccgctcctga attcactgct actcaacctg angntgcaga ctggtcttga aggngnacan    540

gggccctctg ggcctattta agcancttcg gtcgcgaaca cgnt                     584
```

```
<210> SEQ ID NO 188
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 188

agcgtgngtc gcggccgagg tgctgaatag gcacagaggg cacctgtaca ccttcagacc     60

agtctgcaac ctcaggctga gtagcagtga actcaggagc gggagcagtc cattcaccct    120

gaaattcctc cttggncact gccttctcag cagcagcctg ctcttctttt tcaatctctt    180

caggatctct gtagaagtac agatcaggca tgacctccca tgggtgttca cgggaaatgg    240

tgccacgcat gcgcagaact tcccgagcca gcatccacca catcaaaccc actgagtgag    300

ctcccttgtt gttgcatggg atgggcaatg tccacatagc gcagaggaga atctgtgtta    360

cacagcgcaa tggtaggtag gttaacataa gatgcctccg cgagaagctg gtggtcagcc    420

ctggggtcaa gtaaccacaa gaagccgtgg ctcccggaag gctgcctgga tctggttagt    480

gaaggntcca ggagtgaagc ggccaacaat tggagtggct tcagtggcaa gcagcaaact    540

tcagcacaag ccctctggac ctgcccggcg gccgctcga                           579
```

-continued

<210> SEQ ID NO 189
<211> LENGTH: 374
<212> TYPE: DNA
<213> ORGANISM: Homo sapien
<220> FEATURE:
<221> NAME/KEY: misc_feature
<222> LOCATION: (1)...(374)
<223> OTHER INFORMATION: n = A,T,C or G

<400> SEQUENCE: 189
tcgagcggcc gcccgggcag gtccattttc tccctgacgg ncccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctcn tccccgaacc ttatgcctct 300
gctgggcttt cagngcctcc actatgatgn tgtagggggg cacctctggn gangacctcg 360
gccgcgacca cgct 374

<210> SEQ ID NO 190
<211> LENGTH: 373
<212> TYPE: DNA
<213> ORGANISM: Homo sapien
<220> FEATURE:
<221> NAME/KEY: misc_feature
<222> LOCATION: (1)...(373)
<223> OTHER INFORMATION: n = A,T,C or G

<400> SEQUENCE: 190
agcgtggtcg cggccgaggt cctcaccaga ggtgccacct acaacatcat agtggaggca 60
ctgaaagacc agcagaggca taaggctcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttangct ttggaagtgg gtcatttcag atgtgattca tctagatggt gccatgacaa 300
tggngngaac tacaagattg gagagaagtg gnaccgncag ggagaaaatg gacctgcccg 360
ggcggccgct cga 373

<210> SEQ ID NO 191
<211> LENGTH: 354
<212> TYPE: DNA
<213> ORGANISM: Homo sapien
<220> FEATURE:
<221> NAME/KEY: misc_feature
<222> LOCATION: (1)...(354)
<223> OTHER INFORMATION: n = A,T,C or G

<400> SEQUENCE: 191
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggntg caaccttggt tggggtcaat 240
ccagtactct ccactcttcc agccagagtg gcacatcttg aggtcacggc aggtgcggnc 300
gggggntttt gcggctgccc tctggncttc ggntgtnctc natctgctgg ctca 354

<210> SEQ ID NO 192
<211> LENGTH: 587
<212> TYPE: DNA

-continued

<213> ORGANISM: Homo sapien
<220> FEATURE:
<221> NAME/KEY: misc_feature
<222> LOCATION: (1)...(587)
<223> OTHER INFORMATION: n = A,T,C or G

<400> SEQUENCE: 192
tcgagcggcc gcccgggcag gtctcgcggt cgcactggtg atgctggtcc tgttggtccc 60
cccggccctc ctggacctcc tggccccct ggtcctccca gcgctggttt cgacttcagc 120
ttcctgcccc agccacctca agagaaggct cacgatggtg gccgctacta ccgggctgat 180
gatgccaatg tggttcgtga ccgtgacctc gaggtggaca ccaccctcaa gagcctgagc 240
cagcagatcg agaacatccg gagcccagag ggcagncgca agaaccccgc ccgcacctgc 300
cgtgacctca agatgtgcca ctctgactgg aagagtggag agtactggat tgaccccaac 360
caagctgcaa cctggatgcc atcaaagtct tctgcaacat ggagactggt gagacctgcg 420
tgtaccccac tcagcccagt gtggcccaaa agaactggta catcagcaag aaccccaagg 480
acaagaagca tgtctggttc ggcgagaaca tgaccgatgg attccagttc gagtatggcg 540
ggcagggctc cgaccctgcc gatggggacc ttggccgcga acacgct 587

<210> SEQ ID NO 193
<211> LENGTH: 98
<212> TYPE: DNA
<213> ORGANISM: Homo sapien
<220> FEATURE:
<221> NAME/KEY: misc_feature
<222> LOCATION: (1)...(98)
<223> OTHER INFORMATION: n = A,T,C or G

<400> SEQUENCE: 193
agcgtggnng cggccgaggt ataaatatcc agnccatatc ctccctccac acgctganag 60
atgaagctgt ncaaagatct cagggtggan aaaaccat 98

<210> SEQ ID NO 194
<211> LENGTH: 240
<212> TYPE: DNA
<213> ORGANISM: Homo sapien

<400> SEQUENCE: 194
tcgagcggcc gcccgggcag gtccttcaga cttggactgt gtcacactgc caggcttcca 60
gggctccaac ttgcagacgg cctgttgtgg gacagtctct gtaatcgcga aagcaaccat 120
ggaagacctg ggggaaaaca ccatggtttt atccaccctg agatctttga acaacttcat 180
ctctcagcgt gcggagggag gctctggact ggatatttct acctcggccg cgaccacgct 240

<210> SEQ ID NO 195
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 195
cgagcgggcg accgggcagg tncagactcc aatccanana accatcaagc cagatgtcag 60
aagctacacc atcacaggtt tacaaccagg cactgactac aaganctacc tgcacacctt 120
gaatgacaat gctcggagct cccctgtggt catcgacgcc tccactgcca ttgatgcacc 180
atccaacctg cgtttcctgg ccaccacacc caattccttg ctggtatcat ggcagccgcc 240

-continued

```
acgtgccagg attaccggta catcatcnag tatganaagc ctgggcctcc tcccagagaa    300

gnggtccctc ggccccgccc tgntgtccca naggntacta ttactgngcc ngcaaccggc    360

aaccgatatc nattttgnca ttggccttca acaataatta                          400


<210> SEQ ID NO 196
<211> LENGTH: 494
<212> TYPE: DNA
<213> ORGANISM: Homo sapien
<220> FEATURE:
<221> NAME/KEY: misc_feature
<222> LOCATION: (1)...(494)
<223> OTHER INFORMATION: n = A,T,C or G

<400> SEQUENCE: 196

agcgtggttc gcggccgang tcctgtcaga gtggcactgg tagaagttcc aggaaccctg     60

aactgtaagg gttcttcatc agngccaaca ggatgacatg aaatgatgta ctcagaagtg    120

tcctggaatg gggcccatga gatggttgtc tgagagagag cttcttgncc tgtctttttc    180

cttccaatca ggggctcgct cttctgatta ttcttcaggg caatgacata aattgtatat    240

tcgggtcccg gntccaggcc agtaatagta ncctctgtga caccagggcg gngccgaggg    300

accacttctc tgggaggaga cccaggcttc tcatacttga tgatgtaacc ggtaatcctg    360

gcacgtggcg gctgccatga taccagcaag gaattggggt gtggtggcca ggaaacgcag    420

gttggatggn gcatcaatgg cagtggaggc cgtcgatgac cacaggggga gctccgacat    480

tgtcattcaa ggtg                                                      494


<210> SEQ ID NO 197
<211> LENGTH: 118
<212> TYPE: DNA
<213> ORGANISM: Homo sapien
<220> FEATURE:
<221> NAME/KEY: misc_feature
<222> LOCATION: (1)...(118)
<223> OTHER INFORMATION: n = A,T,C or G

<400> SEQUENCE: 197

agcgtggncg cggccgaggt gcagcgcggg ctgtgccacc ttctgctctc tgcccaacga     60

taaggagggt ncctgccccc aggagaacat taactntccc cagctcggcc tctgccgg      118


<210> SEQ ID NO 198
<211> LENGTH: 403
<212> TYPE: DNA
<213> ORGANISM: Homo sapien
<220> FEATURE:
<221> NAME/KEY: misc_feature
<222> LOCATION: (1)...(403)
<223> OTHER INFORMATION: n = A,T,C or G

<400> SEQUENCE: 198

tcgagcggcc gcccgggcag gtttttttg ctgaaagtgg ntactttatt ggntgggaaa      60

gggagaagct gtggtcagcc caagagggaa tacagagncc cgaaaaaggg gagggcaggt    120

gggctggaac cagacgcagg gccaggcaga aactttctct cctcactgct cagcctggtg    180

gtggctggag ctcanaaatt gggagtgaca caggacacct tcccacagcc attgcggcgg    240

catttcatct ggccaggaca ctggctgtcc acctggcact ggtcccgaca gaagcccgag    300

ctggggaaag ttaatgttca cctgggggca ggaaccctcc ttatcattgn gcagagagca    360

gaaggtggca cagcccgcgc tgcacctcgg ccgcgaccac gct                      403
```

-continued

<210> SEQ ID NO 199
<211> LENGTH: 167
<212> TYPE: DNA
<213> ORGANISM: Homo sapien
<220> FEATURE:
<221> NAME/KEY: misc_feature
<222> LOCATION: (1)...(167)
<223> OTHER INFORMATION: n = A,T,C or G

<400> SEQUENCE: 199
tcgagcggcc gcccgggcag gtccaccata agtcctgata caaccacgga tgagctgtca 60
ggagcaaggt tgatttcttt cattggtccg gncttctcct tgggggncac ccgcactcga 120
tatccagtga gctgaacatt gggtggcgtc cactgggcgc tcaggct 167

<210> SEQ ID NO 200
<211> LENGTH: 252
<212> TYPE: DNA
<213> ORGANISM: Homo sapien
<220> FEATURE:
<221> NAME/KEY: misc_feature
<222> LOCATION: (1)...(252)
<223> OTHER INFORMATION: n = A,T,C or G

<400> SEQUENCE: 200
tcgagcggtt cgcccgggca ggtccaccac acccaattcc ttgctggtat catggcagcc 60
gccacgtgcc aggattaccg gctacatcat caagtatgag aagcctgggt ctcctcccag 120
agaagcggtc cctcggcccc gccctggtgt cacagaggct actattactg gcctggaacc 180
gggaaccgaa tatacaattt atgtcattgn cctgaagaat aatcannaan agcgancccc 240
tgattggaag ga 252

<210> SEQ ID NO 201
<211> LENGTH: 91
<212> TYPE: DNA
<213> ORGANISM: Homo sapien

<400> SEQUENCE: 201
agcgtggtcg cggccgaggt tgtacaagct tttttttttt tttttttttt tttttttttt 60
tttttttttt tttttttttt tttttttttt t 91

<210> SEQ ID NO 202
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 202
tcgagcggnc gcccgggcag gtctgccaac accaagattg gcccccgccg catccacaca 60
gtccgtgtgc ggggaggtaa caagaaatac cgtgccctga ggttggacgt ggggaatttc 120
tcctggggct cagagtgttg tactcgtaaa acaaggatca tcgatgttgt ctacaatgca 180
tctaataacg agctggttcg taccaagacc ctggtgaaga attgcatcgt gctcatcgac 240
agcacaccgt accgacagtg gtacgagtcc cactatgcgc tgcccctggg ccgcaagaag 300
ggagccaagc tgactcctga ggaagaagag attttaaaca aaaaacgatc taanaaaaaa 360
aaaacaat 368

-continued

<210> SEQ ID NO 203
<211> LENGTH: 340
<212> TYPE: DNA
<213> ORGANISM: Homo sapien

<400> SEQUENCE: 203
agcgtggtcg cggccgaggt gaaatggtat tcagcttcct ggcacttctg gtcagcaacc 60
cagtgttggg caacaaatga tctttgagga acatggtttt aggcggacca caccgcccac 120
aacggccacc cccataaggc ataggccaag accatacccg ccgaatgtag gacaagaagc 180
tctctctcag acaaccatct catgggcccc attccaggac acttctgagt acatcatttc 240
atgtcatcct gttggcactg atgaagaacc cttacagttc agggttcctg gaacttctac 300
cagtgccact ctgacaggac ctgcccgggc ggccgctcga 340

<210> SEQ ID NO 204
<211> LENGTH: 341
<212> TYPE: DNA
<213> ORGANISM: Homo sapien

<400> SEQUENCE: 204
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc acctcggccg cgaccacgct a 341

<210> SEQ ID NO 205
<211> LENGTH: 770
<212> TYPE: DNA
<213> ORGANISM: Homo sapien
<220> FEATURE:
<221> NAME/KEY: misc_feature
<222> LOCATION: (1)...(770)
<223> OTHER INFORMATION: n = A,T,C or G

<400> SEQUENCE: 205
tcgagcggcc gcccgggcag gtctcccttc ttgcggccca ggggcagcgc atagtgggac 60
tcgtaccact gtcggtacgg tgtgctgtcg atgagcacga tgcaattctt caccagggtc 120
ttggtacgaa ccagctcgtt attagatgca ttgtagacaa catcgatgat ccttgtttta 180
cgagtacaac actctgagcc ccaggagaaa ttccccacgt ccaacctcag ggcacggtat 240
ttcttgttac ctccccgcac acggactgtg tggatgcggc gggggccaag ctgactcctg 300
aggaagaaga gattttaaac aaaaaacgat ctaaaaaaat tcagaagaaa tatgatgaaa 360
ggaaaaagaa tgccaaaatc agcagtctcc tggaggagca gttccagcag ggcaagcttc 420
ttgcgtgcat cgcttcaagg ccgggacagt gtgaccgagc agatggctat gtgctagagg 480
gcaaagaagt ggagttctat cttaagaaaa tcagggccca gaatggtgng tcttcaacta 540
atccaaaggg gagtttcaga ccagtgcaat cagcaaaaac attgatactg ntggccaaat 600
ttattggtgc agggcttgca cantangann ggctgggtct tggggcttgg attggnacaa 660
gctttggcag ccttttcttt ggttttgcca aaaacctttt gntgaagang anacctnggg 720
cggacccctt aaccgattcc acnccnggng gcgttctang gncccncttg 770

<210> SEQ ID NO 206

-continued

<211> LENGTH: 810
<212> TYPE: DNA
<213> ORGANISM: Homo sapien
<220> FEATURE:
<221> NAME/KEY: misc_feature
<222> LOCATION: (1)...(810)
<223> OTHER INFORMATION: n = A,T,C or G

<400> SEQUENCE: 206
agcgtggtcg cggccgaggt ctgctgcttc agcgaagggt ttctggcata accaatgata 60
aggctgccaa agactgttcc aataccagca ccagaaccag ccactcctac tgttgcagca 120
cctgcaccaa taaatttggc agcagtatca atgtctctgc tgattgcact ggtctgaaac 180
tccctttgga ttagctgaga cacaccattc tgggccctga ttttcctaag atagaactcc 240
aactctttgc cctctagcac atagccatct gctcggtcac actgtcccgg ccttgaagcg 300
atgcacgcaa gaagcttgcc ctgctggaac tgctcctcca ggagactgct gattttggca 360
ttctttttcc tttcatcata tttcttctga atttttttag atcgtttttt gtttaaaatc 420
tcttcttcct caggagtcag cttggccccc gccgcatcca cacagtccgt gtgcggggag 480
gtaacaagaa ataccgtgcc ctgaggttgg acgtggggaa tttctcctgg ggctcagagt 540
ggtgtactcg taaaacaagg atcatcgatg gtgnctacaa tgcatctaat aacgagctgg 600
gtcggaccca aagaacctgg ngaanaaatg gatcgnctca tcgacaggac accgtacccg 660
acaggggnac gantcccact atgcgcttgc ccctgggccg caanaaagga aaactgcccg 720
ggcggccntc gaaagcccaa ttntggaaaa aatccatcac actgggnggc cngtcgagca 780
tgcatntana ggggcccatt cccccctnann 810

<210> SEQ ID NO 207
<211> LENGTH: 257
<212> TYPE: DNA
<213> ORGANISM: Homo sapien

<400> SEQUENCE: 207
tcgagcggcc gcccgggcag gtccccaacc aaggctgcaa cctggatgcc atcaaagtct 60
tctgcaacat ggagactggt gagacctgcg tgtaccccac tcagcccagt gtggcccaga 120
agaactggta catcagcaag aaccccaagg acaagaggca tgtctggttc ggcgagagca 180
tgaccgatgg attccagttc gagtatggcg gccagggctc cgaccctgcc gatgtggacc 240
tcggccgcga ccacgct 257

<210> SEQ ID NO 208
<211> LENGTH: 257
<212> TYPE: DNA
<213> ORGANISM: Homo sapien

<400> SEQUENCE: 208
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggacctg 240
cccgggcggc cgctcga 257

<210> SEQ ID NO 209
<211> LENGTH: 747
<212> TYPE: DNA
<213> ORGANISM: Homo sapien -continued
<220> FEATURE:
<221> NAME/KEY: misc_feature
<222> LOCATION: (1)...(747)
<223> OTHER INFORMATION: n = A,T,C or G

<400> SEQUENCE: 209
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cgtcacccac 360
cctgggtatg acactggaaa tggtattcag cttcctggca cttctggtca gcaacccagt 420
gttgggcaac aaatgatctt tgaggaacat ggntttaggc ggaccacacc gcccacaacg 480
gccaccccca taaggcatag gccaagacca tacccgccga atgtaggaca agaagctntn 540
tntcanacac catntnatgg gccccattcc aggacacttc tgagtacatc atttatgnca 600
tctgtggcac ttgatgaaaa cccttacagt tcagggttct ggaactttta ccaggcctnt 660
tacaggactn ggccggacnc cttaagccna ttncaccctg ggcgttcta nggtcccact 720 cgnncactgg ngaaaatggc tactgtn 747

<210> SEQ ID NO 210
<211> LENGTH: 872
<212> TYPE: DNA
<213> ORGANISM: Homo sapien
<220> FEATURE:
<221> NAME/KEY: misc_feature
<222> LOCATION: (1)...(872)
<223> OTHER INFORMATION: n = A,T,C or G

<400> SEQUENCE: 210
agcgtggtcg cggccgaggt ccactagagg tctgtgtgcc attgcccagg cagagtctct 60
gcgttacaaa ctcctaggag ggcttgctgt gcggagggcc tgctatggtg tgctgcggtt 120
catcatggag agtggggcca aaggctgcga ggttgtggtg tctgngaaac tccnaggaca 180
ngagggctaa attccatgaa gtttgtggat ggcctgatga tccacaatcg gagaccctgt 240
taactactac cgtctnaccn cctgctgtnc ncccccnttt ctgctnaana catngggntn 300
ntncttgncc ntccttgggt ngaanatnna atngcctncc cnttcntanc nctactngnt 360
ccananttgg cctttaaana atccnccttg ccttnnncac tgttcanntn tttnntcgta 420
aaccctatna nttnnattan atnntnnnnn nctcaccccc ctcntcattn anccnatang 480
ctnnnaantc cttnannccct cccnccccnnt ncnctcntac tnantncttc tnncccatta 540
cnnagctctt tcntttaana taatgnngcc nngctctnca tntctacnat ntgnnnaatn 600
cccccncccc cnancgnntt tttgacctnn naacctcctt tcctcttccc tncnnaaatt 660
ncnnanttcc ncnttccnnc ntttcggntn ntcccatnct ttccannnct tcantctanc 720
ncnctncaac ttattttcct ntcatccctt nttctttaca nncccccctnn tctactcnnc 780 nnttncatta natttgaaac tnccacnnct anttncctcn ctctacnntt ttattttncg 840
ntcnctctac ntaatanttt aatnanttnt cn 872

<210> SEQ ID NO 211
<211> LENGTH: 517
<212> TYPE: DNA

-continued

<213> ORGANISM: Homo sapien
<220> FEATURE:
<221> NAME/KEY: misc_feature
<222> LOCATION: (1)...(517)
<223> OTHER INFORMATION: n = A,T,C or G

<400> SEQUENCE: 211
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacaa gcagtgtcaa cgtagtaagt taacagggtc tccgctgtgg 300
atcatcaggc catccacaaa cttcatggat ttagccctct gtcctcggag tttcccagac 360
accacaacct cgcagccttt ggccccactc tccatgatga accgcagcac accatagcag 420
gccctccgca caagcaagcc ctcctaagaa tttgtaacgc ananactctg ctggcaatgg 480
cacacaaacc tctagtggac ctcggncgcg accacgc 517

<210> SEQ ID NO 212
<211> LENGTH: 695
<212> TYPE: DNA
<213> ORGANISM: Homo sapien
<220> FEATURE:
<221> NAME/KEY: misc_feature
<222> LOCATION: (1)...(695)
<223> OTHER INFORMATION: n = A,T,C or G

<400> SEQUENCE: 212
tcgagcggcc gcccgggcag gtctggtcca ggatagcctg cgagtcctcc tactgctact 60
ccagacttga catcatatga atcatactgg ggagaatagt tctgaggacc agtagggcat 120
gattcacaga ttccaggggg gccaggagaa ccaggggacc ctggttgtcc tggaatacca 180
gggtcaccat ttctcccagg aataccagga gggcctggat ctcccttggg gccttgaggt 240
ccttgaccat taggagggcg agtaggagca gttggaggct gtgggcaaac tgcacaacat 300
tctccaaatg gaatttctgg gttggggcag tctaattctt gatccgtcac atattatgtc 360
atcgcagaga acggatcctg agtcacagac acatatttgg catggttctg gcttccagac 420
atctctatcc gncataggac tgaccaagat gggaacatcc tccttcaaca agcttnctgt 480
tgtgccaaaa ataatagtgg gatgaagcag accgagaagt anccagctcc cctttttgca 540
caaagcntca tcatgtctaa atatcagaca tgagacttct ttgggcaaaa aaggagaaaa 600
agaaaaagca gttcaaagta nccnccatca agttggttcc ttgcccnttc agcacccggg 660
ccccgttata aaacacctng ggccggaccc ccctt 695

<210> SEQ ID NO 213
<211> LENGTH: 804
<212> TYPE: DNA
<213> ORGANISM: Homo sapien
<220> FEATURE:
<221> NAME/KEY: misc_feature
<222> LOCATION: (1)...(804)
<223> OTHER INFORMATION: n = A,T,C or G

<400> SEQUENCE: 213
agcgtggtcg cggccgaggt gttttatgac gggcccggtg ctgaagggca gggaacaact 60
tgatggtgct actttgaact gcttttcttt tctccttttt gcacaaagag tctcatgtct 120
gatatttaga catgatgagc tttgtgcaaa aggggagctg gctacttctc gctctgcttc 180

-continued

```
atcccactat tattttggca caacaggaag ctgttgaagg aggatgttcc catcttggtc    240

agtcctatgc ggatagagat gtctggaagc cagaaccatg ccaaatatgt gtctgtgact    300

caggatccgt tctctgcgat gacataatat gtgacgatca agaattagac tgccccaacc    360

cagaaattcc atttggagaa tgttgtgcag tttgcccaca gcctccaact gctcctactc    420

gccctcctaa tggtcaagga cctcaaggcc ccaagggaga tccaggccct cctggtattc    480

ctgggagaaa tggtgaccct ggtattccag gacaaccagg gtcccctggt tctcctggcc    540

cccctggaat cnggngaatc atgccctact ggtcctcaaa ctattctccc anatgattca    600

tatgatgtca agtctgggat agcnagtang ganggactcg caggctattc tggaccanac    660

ctgccggggg ggcgttcgaa agcccgaatc tgcananntn cnttcacact ggcggccgtc    720

gagctgcttt aaaagggcca ttccnccttt agngnggggg antacaatta ctnggcggcg    780

ttttanancg cgngnctggg aaat                                            804
```

<210> SEQ ID NO 214
<211> LENGTH: 594
<212> TYPE: DNA
<213> ORGANISM: Homo sapien
<220> FEATURE:
<221> NAME/KEY: misc_feature
<222> LOCATION: (1)...(594)
<223> OTHER INFORMATION: n = A,T,C or G

<400> SEQUENCE: 214

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagagtg gcacatcttg aggtcacggc aggtgcgggc    300

ggggttcttg cggctgccct ctgggctccg gatgttctcg atctgctggc tcaggctctt    360

gagggtggtg tccacctcga ggtcacggtc acgaaccaca ttggcatcat cagcccggta    420

gtagcggcca ccatcgtgag ccttctcttg angtggctgg ggcaggaact gaagtcgaaa    480

ccagcgctgg gaggaccagg gggaccaana ggtccaggaa gggcccgggg gggaccaaca    540

ggaccagcat caccaagtgc gacccgcgag aacctgcccg gccgnccgct cgaa          594
```

<210> SEQ ID NO 215
<211> LENGTH: 590
<212> TYPE: DNA
<213> ORGANISM: Homo sapien
<220> FEATURE:
<221> NAME/KEY: misc_feature
<222> LOCATION: (1)...(590)
<223> OTHER INFORMATION: n = A,T,C or G

<400> SEQUENCE: 215

```
tcgagcgnnc gcccgggcag gtctcgcggt cgcactggtg atgctggtcc tgttggtccc     60

cccggccctc ctggacctcc tggtccccct ggtcctccca gcgctggttt cgacttcagc    120

ttcctgcccc agccacctca agagaaggct cacgatggtg gccgctacta ccgggctgat    180

gatgccaatg tggttcgtga ccgtgacctc gaggtggaca ccaccctcaa gagcctgagc    240

cagcagatcg agaacatccg gagcccagag ggcagccgca agaaccccgc ccgcacctgc    300

cgtgacctca agatgtgcca ctctgactgg aagagtggag agtactggat tgaccccaac    360
```

-continued

```
caaggctgca acctggatgc catcaaagtc ttctgcaaca tggagactgg tgagacctgc    420

gtgtacccca ctcagcccag tgtggcccag aagaactggt acatcagcaa gaaccccaag    480

gacaagaggc atgtctggtt cggcgagagc atgaccgatg gattccagtt cgagtatggc    540

ggccagggct cccaccctgc cgatgtggac ctccggccgc gaccaccctt               590


<210> SEQ ID NO 216
<211> LENGTH: 801
<212> TYPE: DNA
<213> ORGANISM: Homo sapien
<220> FEATURE:
<221> NAME/KEY: misc_feature
<222> LOCATION: (1)...(801)
<223> OTHER INFORMATION: n = A,T,C or G

<400> SEQUENCE: 216

tngagcggcc gcccgggcag gntgnnaacg ctggtcctgc tggtcctcct ggcaaggctg     60

gtgaagatgg tcaccctgga aaacccggac gacctggtga gagaggagtt gttggaccac    120

agggtgctcg tggtttccct ggaactcctg gacttcctgg cttcaaaggc attaggggac    180

acaatggtct ggatggattg aagggacagc ccggtgctcc tggtgtgaag ggtgaacctg    240

gtgcccctgg tgaaaatgga actccaggtc aaacaggagc ccgtgggctt cctggtgaga    300

gaggaccgtg ttggtgcccc tggcccanac ctcggccgcg accacgctaa gcccgaattt    360

ccagcacact ggnggccgtt actantggat ccgagctcgg taccaagctt ggcgtaatca    420

tggtcatagc tgtttcctgn gtgaaattgt tatccgctca caatttcaca cancatacga    480

agccggaaag cataaagtgt aaagccttgg ggtgctaatg agtgagctaa ctcncattaa    540

attgcgttgc gctcactgcc cgcttttcca nnngggaaac cntggcntng ccngcttgcn    600

ttaantgaaa tccgccnacc cccggggaaa agncggtttg cngtattggg gcncttttc     660

cctttcctcg gnttacttga nttantgggc tttggncgnt tcgggttgng gcgancnggt    720

tcaacntcac nccaaaggng gnaanacggt tttcccanaa tccgggggnt ancccaangn    780

aaaacatnng ncnaangggc t                                              801


<210> SEQ ID NO 217
<211> LENGTH: 349
<212> TYPE: DNA
<213> ORGANISM: Homo sapien
<220> FEATURE:
<221> NAME/KEY: misc_feature
<222> LOCATION: (1)...(349)
<223> OTHER INFORMATION: n = A,T,C or G

<400> SEQUENCE: 217

agcgtggttn gcggccgagg tctgggccag gggcaccaac acgtcctctc tcaccaggaa     60

gcccacgggc tcctgtttga cctggagttc cattttcacc aggggcacca ggttcaccct    120

tcacaccagg agcaccgggc tgtcccttca atccatncag accattgtgn cccctaatgc    180

ctttgaagcc aggaagtcca ggagttccag ggaaaccacc gagcaccctg tggtccaaca    240

actcctctct caccaggtcg tccgggtttt ccagggtgac catcttcacc agccttgcca    300

ggaggaccag caggaccagc gttaccaacc tgcccgggcg gccgctcga                349


<210> SEQ ID NO 218
<211> LENGTH: 372
<212> TYPE: DNA
<213> ORGANISM: Homo sapien

<400> SEQUENCE: 218
```

-continued tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgcccacggt aacaacctct tcccgaacct tatgcctctg 300
ctggtctttc agtgcctcca ctatgatgtt gtaggtggca cctctggtga ggacctcggc 360
cgcgaccacg ct 372

<210> SEQ ID NO 219
<211> LENGTH: 374
<212> TYPE: DNA
<213> ORGANISM: Homo sapien

<400> SEQUENCE: 219
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaag atgtgattca tctagatggt gccatgacaa 300
tggtgtgaac tacaagattg gagagaagtg ggaccgtcag ggagaaaatg gacctgcccg 360
ggccggccgc tcga 374

<210> SEQ ID NO 220
<211> LENGTH: 828
<212> TYPE: DNA
<213> ORGANISM: Homo sapien
<220> FEATURE:
<221> NAME/KEY: misc_feature
<222> LOCATION: (1)...(828)
<223> OTHER INFORMATION: n = A,T,C or G

<400> SEQUENCE: 220
tcgagcgnnc gcccgggcag gtccagtagt gccttcggga ctgggttcac ccccaggtct 60
gcggcagttg tcacagcgcc agccccgctg gcctccaaag catgtgcagg agcaaatggc 120
accgagatat tccttctgcc actgttctcc tacgtggtat gtcttcccat catcgtaaca 180
cgttgcctca tgagggtcac acttgaattc tccttttccg ttcccaagac atgtgcagct 240
catttggctg gctctatagt ttggggaaag tttgttgaaa ctgtgccact gacctttact 300
tcctccttct ctactggagc tttcgtacct tccacttctg ctgttggtaa aatggtggat 360
cttctatcaa tttcattgac agtacccact tctcccaaac atccagggaa atagtgattt 420
cagagcgatt aggagaacca aattatgggg cagaaataag gggcttttcc acaggttttc 480
ctttggagga agatttcagt ggtgacttta aaagaatact caacagtgtc ttcatcccca 540
tagcaaaaga agaaacngta aatgatggaa ngcttctgga gatgccnnca tttaagggac 600
ncccagaact tcaccatcta caggacctac ttcagtttac annaagncac atantctgac 660
tcanaaagga cccaagtagc nccatggnca gcactttnag cctttcccct ggggaaaann 720
ttacnttctt aaancctngg ccnngacccc cttaagncca aattntggaa aanttccntn 780
cnnctggggg gcngttcnac atgcntttna agggcccaat tnccccnt 828

<210> SEQ ID NO 221

-continued

<211> LENGTH: 476
<212> TYPE: DNA
<213> ORGANISM: Homo sapien

<400> SEQUENCE: 221
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtgt 180
acacctgtgg ttctcggggc tgccctttgg ctttggagat ggttttctcg atgggggctg 240
ggagggcttt gttggagacc ttgcacttgt actccttgcc attcagccag tcctggtgca 300
ggacggtgag gacgctgacc acacggtacg tgctgttgta ctgctcctcc cgcggctttg 360
tcttggcatt atgcacctcc acgccgtcca cgtaccagtt gaacttgacc tcagggtctt 420
cgtggctcac gtccaccacc acgcatgtaa cctcagacct cggccgcgac cacgct 476

<210> SEQ ID NO 222
<211> LENGTH: 477
<212> TYPE: DNA
<213> ORGANISM: Homo sapien

<400> SEQUENCE: 222
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgtgtggtc agcgtcctca ccgtcctgca 180
ccaggactgg ctgaatggca aggagtacaa gtgcaaggtc tccaacaaag ccctcccagc 240
ccccatcgag aaaaccatct ccaaagccaa agggcaagcc ccgagaacca caggtgtaca 300
ccctgccccc atcccgggag gagatgacca agaaccaggt cagcctgacc tgcctggtca 360
aaggcttcta tcccagcgac atcgccgtgg agtgggagag caatgggcag ccggagaaca 420
actacaagac cacgcctccc gtgctggact ccgacacctg cccgggcggc cgctcga 477

<210> SEQ ID NO 223
<211> LENGTH: 361
<212> TYPE: DNA
<213> ORGANISM: Homo sapien

<400> SEQUENCE: 223
tcgagcggcc gcccgggcag gttgaatggc tcctcgctga ccaccccggt gctggtggtg 60
ggtacagagc tccgatgggt gaaaccattg acatagagac tgtccctgtc cagggtgtag 120
gggcccagct cagtgatgcc gtgggtcagc tggctcagct tccagtacag ccgctctctg 180
tccagtccag ggcttttggg gtcaggacga tgggtgcaga cagcatccac tctggtggct 240
gccccatcct tctcaggcct gagcaaggtc agtctgcaac cagagtacag agagctgaca 300
ctggtgttct tgaacaaggg cataagcaga ccctgaagga cacctcggcc gcgaccacgc 360
t 361

<210> SEQ ID NO 224
<211> LENGTH: 361
<212> TYPE: DNA
<213> ORGANISM: Homo sapien

<400> SEQUENCE: 224
agcgtggtcg cggccgaggt gtccttcagg gtctgcttat gcccttgttc aagaacacca 60
gtgtcagctc tctgtactct ggttgcagac tgaccttgct caggcctgag aaggatgggg 120

-continued

```
cagccaccag agtggatgct gtctgcaccc atcgtcctga ccccaaaagc cctggactgg    180

acagagagcg gctgtactgg aagctgagcc agctgaccca cggcatcact gagctgggcc    240

cctacaccct ggacagggac agtctctatg tcaatggttt cacccatcgg agctctgtac    300

ccaccaccag caccggggtg gtcagcgagg agccattcaa cctgcccggg cggccgctcg    360

a                                                                     361
```

<210> SEQ ID NO 225
<211> LENGTH: 766
<212> TYPE: DNA
<213> ORGANISM: Homo sapien
<220> FEATURE:
<221> NAME/KEY: misc_feature
<222> LOCATION: (1)...(766)
<223> OTHER INFORMATION: n = A,T,C or G

<400> SEQUENCE: 225

```
agcgtggtcg cggccgaggt cctgtcagag tggcactggt agaagttcca ggaaccctga     60

actgtaaggg ttcttcatca gtgccaacag gatgacatga aatgatgtac tcagaagtgt    120

cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300

gaagctgaat accatttcca gtgtcatacc cagggtgggt gacgaaaggg gtcttttgaa    360

ctgtggaagg aacatccaag atctctggtc catgaagatt ggggtgtgga agggttacca    420

gttggggaag ctcgtctgtc tttttccttc caatcagggg ctcgctcttc tgattattct    480

tcagggcaat gacataaatt gtatattcgg tcccggttcc aggccagtaa tagtagcctc    540

tgtgacacca gggcggggcc gagggaccct tctnttggaa gagaccagct tctcatactt    600

gatgatgagn ccggtaatcc tggcacgtgg nggttgcatg atnccaccaa ggaaatnggn    660

gggggnggac ctgcccggcg gccgttcnaa agcccaattc cacacacttg gnggccgtac    720

tatggatccc actcngtcca acttggngga atatggcata actttt                   766
```

<210> SEQ ID NO 226
<211> LENGTH: 364
<212> TYPE: DNA
<213> ORGANISM: Homo sapien

<400> SEQUENCE: 226

```
tcgagcggcc gcccgggcag gtccttgacc ttttcagcaa gtgggaaggt gtaatccgtc     60

tccacagaca aggccaggac tcgtttgtac ccgttgatga tagaatgggg tactgatgca    120

acagttgggt agccaatctg cagacagaca ctggcaacat tgcggacacc ctccaggaag    180

cgagaatgca gagtttcctc tgtgatatca agcacttcag ggttgtagat gctgccattg    240

tcgaacacct gctggatgac cagcccaaag gagaaggggg agatgttgag catgttcagc    300

agcgtggctt cgctggctcc cactttgtct ccagtcttga tcagacctcg gccgcgacca    360

cgct                                                                  364
```

<210> SEQ ID NO 227
<211> LENGTH: 275
<212> TYPE: DNA
<213> ORGANISM: Homo sapien

<400> SEQUENCE: 227

-continued

```
agcgtggtcg cggccgaggt ctgtcctaca gtcctcagga ctctactccc tcagcagcgt     60

ggtgaccgtg ccctccagca acttcggcac ccagacctac acctgcaacg tagatcacaa    120

gcccagcaac accaaggtgg acaagagagt tgagcccaaa tcttgtgaca aaactcacac    180

atgcccaccg tgcccagcac ctgaactcct gggggggaccg tcagtcttcc tcttccccccg    240

catcccccctt ccaaacctgc ccgggcggcc gctcg                               275
```

<210> SEQ ID NO 228
<211> LENGTH: 275
<212> TYPE: DNA
<213> ORGANISM: Homo sapien

<400> SEQUENCE: 228

```
cgagcggccg cccgggcagg tttggaaggg ggatgcgggg gaagaggaag actgacggtc     60

cccccaggag ttcaggtgct gggcacggtg ggcatgtgtg agttttgtca caagatttgg    120

gctcaactct cttgtccacc ttggtgttgc tgggcttgtg atctacgttg caggtgtagg    180

tctgggtgcc gaagttgctg gagggcacgg tcaccacgct gctgagggag tagagtcctg    240

aggactgtag gacagacctc ggccgcgacc acgct                               275
```

<210> SEQ ID NO 229
<211> LENGTH: 40
<212> TYPE: DNA
<213> ORGANISM: Homo sapien
<220> FEATURE:
<221> NAME/KEY: misc_feature
<222> LOCATION: (1)...(40)
<223> OTHER INFORMATION: n = A,T,C or G

<400> SEQUENCE: 229

```
nggnnggtcc ggncngncag gaccactcnt cttcgaaata                           40
```

<210> SEQ ID NO 230
<211> LENGTH: 208
<212> TYPE: DNA
<213> ORGANISM: Homo sapien

<400> SEQUENCE: 230

```
agcgtggtcg cggccgaggt cctcacttgc ctcctgcaaa gcaccgatag ctgcgctctg     60

gaagcgcaga tctgttttaa agtcctgagc aatttctcgc accagacgct ggaagggaag    120

tttgcgaatc agaagttcag tggacttctg ataacgtcta atttcacgga gcgccacagt    180

accaggacct gcccgggcgg ccgctcga                                       208
```

<210> SEQ ID NO 231
<211> LENGTH: 208
<212> TYPE: DNA
<213> ORGANISM: Homo sapien
<220> FEATURE:
<221> NAME/KEY: misc_feature
<222> LOCATION: (1)...(208)
<223> OTHER INFORMATION: n = A,T,C or G

<400> SEQUENCE: 231

```
tcgagcggcc gcccgggcag gtcctggtac tgnggcgctc cgtgaaatta gacgttatca     60

gaagtccact gaacttctga ttcgcaaact tcccttccag cgtctggtgc gagaaattgc    120

tcaggacttt aaaacagatc tgcgcttcca gagcgcagct atcggtgctt tgcaggaggc    180

aagtgaggac ctcggccgcg accacgct                                       208
```

-continued

<210> SEQ ID NO 232
<211> LENGTH: 332
<212> TYPE: DNA
<213> ORGANISM: Homo sapien

<400> SEQUENCE: 232
tcgagcggcc gcccgggcag gtccacatcg gcagggtcgg agccctggcc gccatactcg 60
aactggaatc catcggtcat gctctcgccg aaccagacat gcctcttgtc cttggggttc 120
ttgctgatgt accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacctcggc cgcgaccacg ct 332

<210> SEQ ID NO 233
<211> LENGTH: 415
<212> TYPE: DNA
<213> ORGANISM: Homo sapien
<220> FEATURE:
<221> NAME/KEY: misc_feature
<222> LOCATION: (1)...(415)
<223> OTHER INFORMATION: n = A,T,C or G

<400> SEQUENCE: 233
gtgggnttga acccntttna nctccgcttg gtaccgagct cggatccact agtaacggcc 60
gccagtgtgc tggaattcgg cttagcgtgg tcgcggccga ggtcaagaac cccgcccgca 120
cctgccgtga cctcaagatg tgccactctg actggaagag tggagagtac tggattgacc 180
ccaaccaagg ctgcaacctg gatgccatca aagtcttctg caacatggag actggtgaga 240
cctgcgtgta ccccactcag cccagtgtgg cccagaagaa ctggtacatc agcaagaacc 300
ccaaggacaa gaggcatgtc tggttcggcg agagcatgac cgatggattc cagttcgagt 360
atggcggcca gggctccgac cctgccgatg tggacctgcc cgggcggccg ctcga 415

<210> SEQ ID NO 234
<211> LENGTH: 776
<212> TYPE: DNA
<213> ORGANISM: Homo sapien
<220> FEATURE:
<221> NAME/KEY: misc_feature
<222> LOCATION: (1)...(776)
<223> OTHER INFORMATION: n = A,T,C or G

<400> SEQUENCE: 234
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
ggaccaggac caacaaaaac taaaactgca ggtccagatc aaacagaaat gactattgaa 420
ggcttgcagc ccacagtgga gtatgtggtt aagtgtctat gctcagaatc caagcggaga 480
gaagtcagcc tctggttcag actgnaagta accaacattg atcgcctaaa ggactggcat 540
tcactgatgn ggatgccgat tccatcaaaa ttgnttggga aaacccacag gggcaagttt 600
ncangtcnag gnggacctac tcgagccctg aggatggaat ccttgactnt tccttnncct 660

-continued gatggggaaa aaaaaccttn aaaacttgaa ggacctgccc gggcggccgt ncaaaaccca 720
attccacccc cttgggggcg ttctatgggn cccactcgga ccaaacttgg ggtaan 776

<210> SEQ ID NO 235
<211> LENGTH: 805
<212> TYPE: DNA
<213> ORGANISM: Homo sapien
<220> FEATURE:
<221> NAME/KEY: misc_feature
<222> LOCATION: (1)...(805)
<223> OTHER INFORMATION: n = A,T,C or G

<400> SEQUENCE: 235
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg gcatccacat cagtgaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttagttttt gttggtcctg gtccattttt 360
gggagtggtg gttactctgt aaccagtaac aggggaactt gaaggcagcc acttgacact 420
aatgctgttg tcctgaacat cggtcacttg catctgggat ggtttgtcaa tttctgttcg 480
gtaattaatg gaaattggct tgctgcttgc ggggcttgtc tccacggcca gtgacagcat 540
acacagtgat ggtataatca actccaggtt taagccgctg atggtagctg aaactttgct 600
ccaggcacaa gtgaactcct gacagggcta tttcctnctg ttctccgtaa gtgatcctgt 660
aatatctcac tgggacagca ggangcattc caaaacttcg ggcgngaccc cctaagccga 720
attntgcaat atncatcaca ctggcgggcg ctcgancatt cattaaaagg cccaatcncc 780
cctataggga gtntantaca attng 805

<210> SEQ ID NO 236
<211> LENGTH: 262
<212> TYPE: DNA
<213> ORGANISM: Homo sapien

<400> SEQUENCE: 236
tcgagcggcc gcccgggcag gtcacttttg gtttttggtc atgttcggtt ggtcaaagat 60
aaaaactaag tttgagagat gaatgcaaag gaaaaaaata ttttccaaag tccatgtgaa 120
attgtctccc atttttttgg cttttgaggg ggttcagttt gggttgcttg tctgtttccg 180
ggttgggggg aaagttggtt gggtgggagg gagccaggtt gggatggagg gagtttacag 240
gaagcagaca gggccaacgt cg 262

<210> SEQ ID NO 237
<211> LENGTH: 372
<212> TYPE: DNA
<213> ORGANISM: Homo sapien

<400> SEQUENCE: 237
agcgtggtcg cggccgaggt cctcaccaga ggtgccacct acaacatcat agtggaggca 60
ctgaaagacc agcagaggca taaggttcgg gaagaggttg ttaccgtggg caactctgtc 120
aacgaaggct tgaaccaacc tacggatgac tcgtgctttg acccctacac agtttcccat 180
tatgccgttg gagatgagtg ggaacgaatg tctgaatcag gctttaaact gttgtgccag 240
tgcttaggct ttggaagtgg tcatttcaga tgtgattcat ctagatggtg ccatgacaat 300

-continued

```
ggtgtgaact acaagattgg agagaagtgg gaccgtcagg gagaaaatgg acctgcccgg    360

gcggccgctc ga                                                        372
```

<210> SEQ ID NO 238
<211> LENGTH: 372
<212> TYPE: DNA
<213> ORGANISM: Homo sapien

<400> SEQUENCE: 238

```
tcgagcggcc gcccgggcag gtccattttc tccctgacgg tcccacttct ctccaatctt     60

gtagttcaca ccattgtcat ggcaccatct agatgaatca catctgaaat gaccacttcc    120

aaagcctaag cactggcaca acagtttaaa gcctgattca gacattcgtt cccactcatc    180

tccaacggca taatgggaaa ctgtgtaggg gtcaaagcac gagtcatccg taggttggtt    240

caagccttcg ttgacagagt tgcccacggt aacaacctct tcccgaacct tatgcctctg    300

ctggtctttc agtgcctcca ctatgatgtt gtaggtggca cctctggtga ggacctcggc    360

cgcgaccacg ct                                                        372
```

<210> SEQ ID NO 239
<211> LENGTH: 720
<212> TYPE: DNA
<213> ORGANISM: Homo sapien
<220> FEATURE:
<221> NAME/KEY: misc_feature
<222> LOCATION: (1)...(720)
<223> OTHER INFORMATION: n = A,T,C or G

<400> SEQUENCE: 239

```
tcgagcggcc gcccgggcag gtccaccata agtcctgata caaccacgga tgagctgtca     60

ggagcaaggt tgatttcttt cattggtccg gtcttctcct tgggggtcac ccgcactcga    120

tatccagtga gctgaacatt gggtggtgtc cactgggcgc tcaggcttgt gggtgtgacc    180

tgagtgaact tcaggtcagt tggtgcagga atagtggtta ctgcagtctg aaccagaggc    240

tgactctctc cgcttggatt ctgagcatag acactaacca catactccac tgtgggctgc    300

aagccttcaa tagtcatttc tgtttgatct ggacctgcag ttttagtttt tgttggtcct    360

ggtccatttt tgggagtggt ggttactctg taaccagtaa caggggaact tgaaggcagc    420

cacttgacac taatgctgtt gtcctgaaca tcggtcactt gcatctggga tggtttgnca    480

atttctgttc ggtaattaat ggaaattggc ttgctgcttg cggggctgtc tccacggcca    540

gtgacagcat acacagngat ggnatnatca actccaagtt taaggccctg atggtaactt    600

taaacttgct cccagccagn gaacttccgg acagggtatt tcttctggtt ttccgaaagn    660

gancctggaa tnntctcctt ggancagaag gancntccaa aacttgggcc ggaacccctt    720
```

<210> SEQ ID NO 240
<211> LENGTH: 691
<212> TYPE: DNA
<213> ORGANISM: Homo sapien
<220> FEATURE:
<221> NAME/KEY: misc_feature
<222> LOCATION: (1)...(691)
<223> OTHER INFORMATION: n = A,T,C or G

<400> SEQUENCE: 240

```
agcgtggtcg cggccgaggt cctgtcagag tggcactggt agaagttcca ggaaccctga     60

actgtaaggg ttcttcatca gtgccaacag gatgacatga aatgatgtac tcagaagtgt    120
```

-continued

```
cctggaatgg ggcccatgag atggttgtct gagagagagc ttcttgtcct acattcggcg    180

ggtatggtct tggcctatgc cttatggggg tggccgttgt gggcggtgtg gtccgcctaa    240

aaccatgttc ctcaaagatc atttgttgcc caacactggg ttgctgacca gaagtgccag    300

gaagctgaat accatttcca gtgtcatacc cagggtgggt gacgaaaggg gtcttttgaa    360

ctgtggaagg aacatccaag atctctggtc catgaagatt ggggtgtgga agggttacca    420

gttggggaag ctcgtctgtc tttttccttc caatcagggg ctcgctcttc tgattattct    480

tcagggcaat gacataaatt gtatattcgg ttcccggttc caggccagta atagtagcct    540

cttgtgacac caggcggggc ccanggacca cttctctggg angagaccca gcttctcata    600

cttgatgatg taacccggta atcctgcacg tggcggctgn catgatacca ncaaggaatt    660

gggtgnggng gacctgcccg gcggccctcn a                                   691
```

<210> SEQ ID NO 241
<211> LENGTH: 808
<212> TYPE: DNA
<213> ORGANISM: Homo sapien
<220> FEATURE:
<221> NAME/KEY: misc_feature
<222> LOCATION: (1)...(808)
<223> OTHER INFORMATION: n = A,T,C or G

<400> SEQUENCE: 241

```
agcgtggtcg cggccgaggt ctgggatgct cctgctgtca cagtgagata ttacaggatc     60

acttacggag aaacaggagg aaatagccct gtccaggagt tcactgtgcc tgggagcaag    120

tctacagcta ccatcagcgg ccttaaacct ggagttgatt ataccatcac tgtgtatgct    180

gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaagttc ccctgttact ggttacagag taaccaccac tcccaaaaat    360

ggaccaggac caacaaaaac taaaactgca ggtccagatc aaacagaaat gactattgaa    420

ggcttgcagc ccacagtgga gtatgtggtt agtgtctatg ctcagaatcc aagcggagag    480

agtcagcctc tggttcagac tgcagtaacc actattcctg caccaactga cctgaagttc    540

actcaggtca cacccacaag cctgagccgc cagtggacac cacccaatgt tcactcactg    600

gatatcgagt gcgggtgacc cccaaggaga agacccggac ccatgaaaga aatcaacctt    660

gctcctgaca gctcatccgn gggtgtatca ggacttatgg gggactgccc cggcnggccg    720

ntcgaaancg aattntgaaa tttccttcnc actgggnggc gnttcgagct tncttntana    780

nggcccaatt cncctntagn gggtcgtn                                       808
```

<210> SEQ ID NO 242
<211> LENGTH: 26
<212> TYPE: DNA
<213> ORGANISM: Homo sapien
<220> FEATURE:
<221> NAME/KEY: misc_feature
<222> LOCATION: (1)...(26)
<223> OTHER INFORMATION: n = A,T,C or G

<400> SEQUENCE: 242

```
agcgtggtcg cggccgaggt cnagga                                          26
```

<210> SEQ ID NO 243
<211> LENGTH: 697
<212> TYPE: DNA
<213> ORGANISM: Homo sapien -continued
<220> FEATURE:
<221> NAME/KEY: misc_feature
<222> LOCATION: (1)...(697)
<223> OTHER INFORMATION: n = A,T,C or G

<400> SEQUENCE: 243

```
tcgagcggcc gcccgggcag gtccaccaca cccaattcct tgctggtatc atggcagccg     60
ccacgtgcca ggattaccgg ctacatcatc aagtatgaga agcctgggtc tcctcccaga    120
gaagtggtcc ctcggccccg ccctggtgtc acagaggcta ctattactgg cctggaaccg    180
ggaaccgaat atacaattta tgtcattgcc ctgaagaata atcagaagag cgagcccctg    240
attggaagga aaaagacaga cgagcttccc caactggtaa cccttccaca ccccaatctt    300
catggaccag agatcttgga tgttccttcc acagttcaaa agaccccttt cgtcacccac    360
cctgggtatg acactggaaa tggtattcag cttcctggca cttctggtca gcaacccagt    420
gttgggcaac aaatgatctt tgaggaacat ggttttaggc ggaccacacc gcccacaacg    480
ggcaccccca taaggnatag gccaagacca taccccgccg aatgtaggac aagaagctct    540
ntctcaacaa ccatctcatg ggccccattc caggacactt ctgagtacat catttcatgt    600
catcctggtg ggcacttgat gaanaaccct tacagttcag ggttcctgga acttctacca    660
gngccacttc tgacagganc ttgggcgnga ccaccct                             697
```

<210> SEQ ID NO 244
<211> LENGTH: 373
<212> TYPE: DNA
<213> ORGANISM: Homo sapien

<400> SEQUENCE: 244

```
agcgtggtcg cggccgaggt ccattttctc cctgacggtc ccacttctct ccaatcttgt     60
agttcacacc attgtcatgg caccatctag atgaatcaca tctgaaatga ccacttccaa    120
agcctaagca ctggcacaac agtttaaagc ctgattcaga cattcgttcc cactcatctc    180
caacggcata atgggaaact gtgtaggggt caaagcacga gtcatccgta ggttggttca    240
agccttcgtt gacagagttg cccacggtaa caacctcttc ccgaacctta tgcctctgct    300
ggtctttcag tgcctccact atgatgttgt aggtggcacc tctggtgagg acctgcccgg    360
gcggcccgct cga                                                       373
```

<210> SEQ ID NO 245
<211> LENGTH: 307
<212> TYPE: DNA
<213> ORGANISM: Homo sapien

<400> SEQUENCE: 245

```
agcgtggtcg cggccgaggt gtgccccaga ccaggaattc ggcttcgacg ttggccctgt     60
ctgcttcctg taaactccct ccatcccaac ctggctccct cccacccaac caactttccc    120
cccaacccgg aaacagacaa gcaacccaaa ctgaaccccc tcaaaagcca aaaaaatggg    180
agacaatttc acatggactt tggaaaatat ttttttcctt tgcattcatc tctcaaactt    240
agtttttatc tttgaccaac cgaacatgac caaaaaccaa aagtgacctg cccgggcggc    300
cgctcga                                                              307
```

<210> SEQ ID NO 246
<211> LENGTH: 372
<212> TYPE: DNA
<213> ORGANISM: Homo sapien

```
<400> SEQUENCE: 246

tcgagcggcc gcccgggcag gtcctcacca gaggtgccac ctacaacatc atagtggagg      60

cactgaaaga ccagcagagg cataaggttc gggaagaggt tgttaccgtg ggcaactctg     120

tcaacgaagg cttgaaccaa cctacggatg actcgtgctt tgacccctac acagtttccc    180

attatgccgt tggagatgag tgggaacgaa tgtctgaatc aggctttaaa ctgttgtgcc    240

agtgcttagg ctttggaagt ggtcatttca gatgtgattc atctagatgg tgccatgaca    300

atggtgtgaa ctacaagatt ggagagaagt gggaccgtca gggagaaaat ggacctcggc    360

cgcgaccacg ct                                                        372

<210> SEQ ID NO 247
<211> LENGTH: 348
<212> TYPE: DNA
<213> ORGANISM: Homo sapien
<220> FEATURE:
<221> NAME/KEY: misc_feature
<222> LOCATION: (1)...(348)
<223> OTHER INFORMATION: n = A,T,C or G

<400> SEQUENCE: 247

tcgagcggcc gcccgggcag gtaccggggt ggtcagcgag gagccattca cactgaactt     60

caccatcaac aacctgcggt atgaggagaa catgcagcac cctggctcca ggaagttcaa    120

caccacggag agggtccttc agggcctgct caggtccctg ttcaagagca ccagtgttgg    180

ccctctgtac tctggctgca gactgacttt gctcagacct gagaaacatg gggcagccac    240

tggagtggac gccatctgca ccctccgcct tgatcccact ggtnctggac tggacanana    300

gcggctatac ttgggagctg anccnaacct ttggcggnga cnccnctt                 348

<210> SEQ ID NO 248
<211> LENGTH: 304
<212> TYPE: DNA
<213> ORGANISM: Homo sapien
<220> FEATURE:
<221> NAME/KEY: misc_feature
<222> LOCATION: (1)...(304)
<223> OTHER INFORMATION: n = A,T,C or G

<400> SEQUENCE: 248

gaggactggc tcagctccca gtatagccgc tctctgtcca gtccaggacc agtgggatca     60

aggcggaggg tgcagatggc gtccactcca gtggctgccc catgtttctc aagtctgagc    120

aaagncagtc tgcagccaga gtacagaggg ccaacactgg tgctcttgaa cagggacctg    180

agcaggccct gaaggaccct ctccgtggtg ttgaacttcc tggagccagg gtgctgcatg    240

ttctcctcat accgcaggtt gttgatggtg aagttcagtg tgaatggctc ctcgctgacc    300

accc                                                                 304

<210> SEQ ID NO 249
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 249

agcgtggtcg cggccgaggt ccaccacacc caattccttg ctggtatcat ggcagccgcc     60

acgtgccagg attaccggct acatcatcaa gtatgagaag cctgggtctc ctcccagaga    120
```

-continued agtggtccct cggccccgcc ctggtgtcac agaggctact attactggcc tggaaccggg 180
aaccgaatat acaatttatg tcattgccct gaagaataat cagaagagcg agcccctgat 240
tggaaggaaa aagacagacg agcttcccca actggtaacc cttccacacc ccaatcttca 300
tggaccanan ancttggatn gtcctttcac nggttnaaaa aaccctttttc gcccccccac 360 cttggggatt aaccttggga aangggggatt tnaccnttcc 400

<210> SEQ ID NO 250
<211> LENGTH: 400
<212> TYPE: DNA
<213> ORGANISM: Homo sapien
<220> FEATURE:
<221> NAME/KEY: misc_feature
<222> LOCATION: (1)...(400)
<223> OTHER INFORMATION: n = A,T,C or G

<400> SEQUENCE: 250
tcgagcggcc gcccgggcag gtcctgtcag agtggcactg gtagaagttc caggaaccct 60
gaactgtaag ggttcttcat cagtgccaac aggatgacat gaaatgatgt actcagaagt 120
gtcctggaat ggggcccatg agatggttgt ctgagagaga gcttcttgtc ctacattcgg 180
cgggtatggt cttggcctat gccttatggg ggtggccgtt gtgggcggtg tggtccgcct 240
aaaaccatgt tcctcaaaga tcatttgttg cccaacactg ggttgctgac cagaagtgcc 300
aggaagctga ataccatttc cagtgtcata cccagggngg gtgaccaaag gggtcnttt 360 ngacctggng aaaggaacca tccaaaanct ctgncccatg 400

<210> SEQ ID NO 251
<211> LENGTH: 514
<212> TYPE: DNA
<213> ORGANISM: Homo sapien
<220> FEATURE:
<221> NAME/KEY: misc_feature
<222> LOCATION: (1)...(514)
<223> OTHER INFORMATION: n = A,T,C or G

<400> SEQUENCE: 251
agcgtggncg cggccgaggt ctgaggatgt aaactcttcc caggggaagg ctgaagtgct 60
gaccatggtg ctactgggtc cttctgagtc agatatgtga ctgatgngaa ctgaagtagg 120
tactgtagat ggtgaagtct gggtgtccct aaatgctgca tctccagagc cttccatcat 180
taccgtttct tcttttgcta tgggatgaga cactgttgag tattctctaa agtcaccact 240
gaaatcttcc tccaaaggaa aacctgtgga aaagcccctt atttctgccc cataatttgg 300
ttctcctaat cnctctgaaa tcactatttc cctggaangt ttgggaaaaa nngggcnacc 360
tgncantgga aantggatan aaagatccca ccattttacc caacnagcag aaagtgggaa 420
nggtaccgaa aagctccaag taanaaaaag gagggaagta aaggtcaagt gggcaccagt 480
ttcaaacaaa actttcccca aactatanaa ccca 514

<210> SEQ ID NO 252
<211> LENGTH: 501
<212> TYPE: DNA
<213> ORGANISM: Homo sapien
<220> FEATURE:
<221> NAME/KEY: misc_feature
<222> LOCATION: (1)...(501)
<223> OTHER INFORMATION: n = A,T,C or G

<400> SEQUENCE: 252

-continued

```
aagcggccgc ccgggcaggn ncagnagtgc cttcgggact gggntcaccc ccaggtctgc     60

ggcagttgtc acagcgccag ccccgctggc ctccaaagca tgtgcaggag caaatggcac    120

cgagatattc cttctgccac tgttctccta cgtggtatgt cttcccatca tcgtaacacg    180

ttgcctcatg agggtcacac ttgaattctc cttttccgtt cccaagacat gtgcagctca    240

tttggctggc tctatagttt ggggaaagtt tgttgaaact gtgccactga cctttacttc    300

ctccttctct actggagctt tccgtacctt ccacttctgc tgntggnaaa aagggnggaa    360

cntcttatca atttcattgg acagtanccc nctttctncc caaaacatnc aagggaaaat    420

attgattncn agagcggatt aaggaacaac ccnaattatg ggggccagaa ataaaggggg    480

cttttccaca ggtnttttcc t                                              501
```

```
<210> SEQ ID NO 253
<211> LENGTH: 226
<212> TYPE: DNA
<213> ORGANISM: Homo sapien

<400> SEQUENCE: 253

tcgagcggcc gcccgggcag gtctgcaggc tattgtaagt gttctgagca catatgagat     60

aacctgggcc aagctatgat gttcgatacg ttaggtgtat taaatgcact tttgactgcc    120

atctcagtgg atgacagcct tctcactgac agcagagatc ttcctcactg tgccagtggg    180

caggagaaag agcatgctgc gactggacct cggccgcgac cacgct                   226
```

```
<210> SEQ ID NO 254
<211> LENGTH: 226
<212> TYPE: DNA
<213> ORGANISM: Homo sapien

<400> SEQUENCE: 254

agcgtggtcg cggccgaggt ccagtcgcag catgctcttt ctcctgccca ctggcacagt     60

gaggaagatc tctgctgtca gtgagaaggc tgtcatccac tgagatggca gtcaaaagtg    120

catttaatac acctaacgta tcgaacatca tagcttggcc caggttatct catatgtgct    180

cagaacactt acaatagcct gcagacctgc ccgggcggcc gctcga                   226
```

```
<210> SEQ ID NO 255
<211> LENGTH: 427
<212> TYPE: DNA
<213> ORGANISM: Homo sapien
<220> FEATURE:
<221> NAME/KEY: misc_feature
<222> LOCATION: (1)...(427)
<223> OTHER INFORMATION: n = A,T,C or G

<400> SEQUENCE: 255

cgagcggccg cccgggcagg tccagactcc aatccagaga accaccaagc cagatgtcag     60

aagctacacc atcacaggtt tacaaccagg cactgactac aagatctacc tgtacacctt    120

gaatgacaat gctcggagct cccctgtggt catcgacgcc tccactgcca ttgatgcacc    180

atccaacctg cgtttcctgg ccaccacacc caattccttg ctggtatcat ggcagccgcc    240

acgtgccagg attaccggct acatcatcaa gtatgagaag cctgggtctc ctcccagaga    300

agtggtccct cggccccgcc ctggtgncac agaagctact attactggcc tggaaccggg    360

aaccgaatat acaatttatg tcattgccct gaagaataat canaagagcg agcccctgat    420

tggaagg                                                              427
```

-continued

<210> SEQ ID NO 256
<211> LENGTH: 535
<212> TYPE: DNA
<213> ORGANISM: Homo sapien
<220> FEATURE:
<221> NAME/KEY: misc_feature
<222> LOCATION: (1)...(535)
<223> OTHER INFORMATION: n = A,T,C or G

<400> SEQUENCE: 256
agcgtggtcg cggccgaggt cctgtcagag tggcactggt agaagttcca ggaaccctga 60
actgtaaggg ttcttcatca gtgccaacag gatgacatga aatgatgtac tcagaagtgt 120
cctggaatgg ggcccatgag atggttgtct gagagagagc ttcttgtcct gtctttttcc 180
ttccaatcag gggctcgctc ttctgattat tcttcagggc aatgacataa attgtatatt 240
cggttcccgg ttccaggcca gtaatagtag cctctgtgac accagggcgg ggccgaggga 300
ccacttctct gggaggagac ccaggcttct catacttgat gatgtanccg gtaatcctgg 360
caccgtggcg gctgccatga taccagcaag gaattgggtg tggtggccaa gaaacgcagg 420
ttggatggtg catcaatggc agtggaggcg tcgatnacca caggggagct ccgancattg 480
tcattcaagg tggacaggta gaatcttgta atcaggtgcc tggtttgtaa acctg 535

<210> SEQ ID NO 257
<211> LENGTH: 544
<212> TYPE: DNA
<213> ORGANISM: Homo sapien
<220> FEATURE:
<221> NAME/KEY: misc_feature
<222> LOCATION: (1)...(544)
<223> OTHER INFORMATION: n = A,T,C or G

<400> SEQUENCE: 257
tcgagcggcc gcccgggcag gtttcgtgac cgtgacctcg aggtggacac caccctcaag 60
agcctgagcc agcagatcga gaacatccgg agcccagagg gcagccgcaa gaaccccgcc 120
cgcacctgcc gtgacctcaa gatgtgccac tctgactgga agagtggaga gtactggatt 180
gaccccaacc aaggctgcaa cctggatgcc atcaaagtct tctgcaacat ggagactggt 240
gagacctgcg tgtaccccac tcagcccagt gtggcccaga agaactggta catcagcaag 300
aaccccaagg acaagaagca tgtctggttc ggcgaaagca tgaccgatgg attccagttc 360
gagtatggcg gccagggctc cgaccctgcc gatgtggacc tcggccgcga ccacgctaag 420
cccgaattcc agcacactgg cggccgttac tagtgggatc cgagcttcgg taccaagctt 480
ggcgtaatca tgggncatag ctgtttcctg ngtgaaaatg gtattccgct tcacaatttc 540
ccac 544

<210> SEQ ID NO 258
<211> LENGTH: 418
<212> TYPE: DNA
<213> ORGANISM: Homo sapien

<400> SEQUENCE: 258
agcgtggtcg cggccgaggt ccacatcggc agggtcggag ccctggccgc catactcgaa 60
ctggaatcca tcggtcatgc tctcgccgaa ccagacatgc ctcttgtcct tggggttctt 120
gctgatgtac cagttcttct gggccacact gggctgagtg gggtacacgc aggtctcacc 180
agtctccatg ttgcagaaga ctttgatggc atccaggttg cagccttggt tggggtcaat 240
ccagtactct ccactcttcc agtcagagtg gcacatcttg aggtcacggc aggtgcgggc 300

-continued

```
ggggttcttg cggctgccct ctgggctccg gatgttctcg atctgctggc tcaagctctt    360

gaagggtggt gtccacctcg aggtcacggt cacgaaacct gcccgggcgg ccgctcga      418


<210> SEQ ID NO 259
<211> LENGTH: 377
<212> TYPE: DNA
<213> ORGANISM: Homo sapien
<220> FEATURE:
<221> NAME/KEY: misc_feature
<222> LOCATION: (1)...(377)
<223> OTHER INFORMATION: n = A,T,C or G

<400> SEQUENCE: 259

agcgtggtcg cggccgaggt caagaacccc gcccgcacct gccgtgacct caagatgtgc     60

cactctgact ggaagagtgg agagtactgg attgacccca accaaggctg caacctggat    120

gccatcaaag tcttctgcaa catggagact ggtgagacct gcgtgtaccc cactcagccc    180

agtgtggccc agaagaactg gtacatcagc aagaacccca aggacaagag gcatgtctgg    240

ttcggcgaga gcatgaccga tggattccag ttcgagtatg gcggccaggg ctccgaccct    300

gccgatgtgg acctgccccgn gccggnccgc tcgaaaagcc cnaatttcca gncacacttg    360

gccggccgtt actactg                                                   377


<210> SEQ ID NO 260
<211> LENGTH: 332
<212> TYPE: DNA
<213> ORGANISM: Homo sapien

<400> SEQUENCE: 260

tcgagcggcc gcccgggcag gtccacatcg gcagggtcgg agccctggcc gccatactcg     60

aactggaatc catcggtcat gctctcgccg aaccagacat gcctcttgtc cttggggttc    120

ttgctgatgt accagttctt ctgggccaca ctgggctgag tggggtacac gcaggtctca    180

ccagtctcca tgttgcagaa gactttgatg gcatccaggt tgcagccttg gttggggtca    240

atccagtact ctccactctt ccagtcagag tggcacatct tgaggtcacg gcaggtgcgg    300

gcggggttct tgacctcggc cgcgaccacg ct                                  332


<210> SEQ ID NO 261
<211> LENGTH: 94
<212> TYPE: DNA
<213> ORGANISM: Homo sapien

<400> SEQUENCE: 261

cgagcggccg cccgggcagg tcccccccct tttttttttt tttttttttt tttttttttt     60

tttttttttt tttttttttt tttttttttt tttt                                 94


<210> SEQ ID NO 262
<211> LENGTH: 650
<212> TYPE: DNA
<213> ORGANISM: Homo sapien
<220> FEATURE:
<221> NAME/KEY: misc_feature
<222> LOCATION: (1)...(650)
<223> OTHER INFORMATION: n = A,T,C or G

<400> SEQUENCE: 262

agcgtggtcg cggccgaggt ctggcattcc ttcgacttct ctccagccga gcttcccaga     60

acatcacata tcactgcaaa aatagcattg catacatgga tcaggccagt ggaaatgtaa    120

agaaggccct gaagctgatg gggtcaaatg aaggtgaatt caaggctgaa ggaaatagca    180
```

aattcaccta cacagttctg gaggatggtt gcacgaaaca cactggggaa tggagcaaaa 240
cagtctttga atatcgaaca cgcaaggctg tgagactacc tattgtagat attgcaccct 300
atgacattgg tggtcctgat caagaatttg gtgtggacgt tggccctgtt tgctttttat 360
aaaccaaact ctatctgaaa tcccaacaaa aaaaatttaa ctccatatgt gntcctcttg 420
ttctaatctt ggcaaccagt gcaagtgacc gacaaaattc cagttattta tttccaaaat 480
gtttggaaac agtataattt gacaaagaaa aaaggatact tctctttttt tggctggtcc 540
accaaataca attcaaaagg ctttttggtt ttattttttt anccaattcc aatttcaaaa 600
tgtctcaatg gngcttataa taaaataaac tttcaccctt nttttntgat 650

<210> SEQ ID NO 263
<211> LENGTH: 573
<212> TYPE: DNA
<213> ORGANISM: Homo sapien
<220> FEATURE:
<221> NAME/KEY: misc_feature
<222> LOCATION: (1)...(573)
<223> OTHER INFORMATION: n = A,T,C or G

<400> SEQUENCE: 263
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agcaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagaa gtaaccacca ctcccaaaaa 360
tggaccagga ccaacaaaaa ctaaaactgc aggtccagat caaacagaaa atggactatt 420
gaaggcttgc agcccacagt ggaagtatgt ggntaggngt ctatgctcag aatcccaagc 480
cggagaaagt cagccttctg gtttagactg cagtaaccaa cattgatcgc cctaaaggac 540
tggncattca cttggatggt ggatgtccaa ttc 573

<210> SEQ ID NO 264
<211> LENGTH: 550
<212> TYPE: DNA
<213> ORGANISM: Homo sapien
<220> FEATURE:
<221> NAME/KEY: misc_feature
<222> LOCATION: (1)...(550)
<223> OTHER INFORMATION: n = A,T,C or G

<400> SEQUENCE: 264
tcgagcggcc gcccgggcag gtccttgcag ctctgcagng tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagngaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tggtggtcct gncccatttt 360
tgggaagtgg ggggttactc tgtaaccagt aacaggggaa cttgaaggca gccacttgac 420
actaatgctg ttgtcctgaa catcggtcac ttgcatctgg ggatggtttt gacaatttct 480
ggttcggcaa attaatggaa attggcttgc tgcttggcgg ggctgnctcc acgggccagt 540

-continued gacagcatac 550

<210> SEQ ID NO 265
<211> LENGTH: 596
<212> TYPE: DNA
<213> ORGANISM: Homo sapien
<220> FEATURE:
<221> NAME/KEY: misc_feature
<222> LOCATION: (1)...(596)
<223> OTHER INFORMATION: n = A,T,C or G

<400> SEQUENCE: 265
tcgagcggcc gcccgggcag gtccttgcag ctctgcagtg tcttcttcac catcaggtgc 60
agggaatagc tcatggattc catcctcagg gctcgagtag gtcaccctgt acctggaaac 120
ttgcccctgt gggctttccc aagcaatttt gatggaatcg acatccacat cagtgaatgc 180
cagtccttta gggcgatcaa tgttggttac tgcagtctga accagaggct gactctctcc 240
gcttggattc tgagcataga cactaaccac atactccact gtgggctgca agccttcaat 300
agtcatttct gtttgatctg gacctgcagt tttaagtttt tgttggncct gnnccatttt 360
tggggaaggg gtggttactc ttgtaaccag taacagggga acttgaagca gccacttgac 420
actaatgctg gtggcctgaa catcggtcac ttgcatctgg gatggtttgg tcaatttctg 480
ttcggtaatt aatgggaaat tggcttactg gcttgcgggg gctgtctcca cggncagtga 540
caagcataca caggngatgg gtataatcaa ctccaggttt aaggccnctg atggta 596

<210> SEQ ID NO 266
<211> LENGTH: 506
<212> TYPE: DNA
<213> ORGANISM: Homo sapien
<220> FEATURE:
<221> NAME/KEY: misc_feature
<222> LOCATION: (1)...(506)
<223> OTHER INFORMATION: n = A,T,C or G

<400> SEQUENCE: 266
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180
gtcactggcc gtggagacag ccccgcaagc agtaagccaa tttccattaa ttaccgaaca 240
gaaattgaca aaccatccca gatgcaagtg accgatgttc aggacaacag cattagtgtc 300
aagtggctgc cttcaagttc ccctgttact ggttacagag taaccaccac tcccaaaaat 360
gggaccagga ccaacaaaaa actaaaactg canggtccag atcaaacaga aatgactatt 420
gaaggcttgc agcccacagt ggagtatgtg ggttagtgtc tatgctcaga atnccaagcg 480
gagagagtca gcctctggtt cagact 506

<210> SEQ ID NO 267
<211> LENGTH: 548
<212> TYPE: DNA
<213> ORGANISM: Homo sapien
<220> FEATURE:
<221> NAME/KEY: misc_feature
<222> LOCATION: (1)...(548)
<223> OTHER INFORMATION: n = A,T,C or G

<400> SEQUENCE: 267
tcgagcggcc gcccgggcag gtcagcgctc tcaggacgtc accaccatgg cctgggctct 60
gctcctcctc accctcctca ctcagggcac agggtcctgg gcccagtctg ccctgactca 120

-continued

```
gcctccctcc gcgtccgggt ctcctggaca gtcagtcacc atctcctgca ctggaaccag    180

cagtgacgtt ggtgcttatg aatttgtctc ctggtaccaa caacacccag gcaaggcccc    240

caaactcatg atttctgagg tcactaagcg gccctcaggg gtccctgatc gcttctctgg    300

ctccaagtct ggcaacacgg cctccctgac cgtctctggg ctccangctg aggatgangc    360

tgattattac tggaagctca tatgcaggca acaacaattg ggtgttcggc ggaagggacc    420

aagctgaccg tnctaaggtc aagcccaagg cttgcccccc tcggtcactc tgttcccacc    480

ctcctctgaa gaagctttca agccaacaan gncacactgg gtgtgtctca taagtggact    540

ttctaccc                                                              548
```

<210> SEQ ID NO 268
<211> LENGTH: 584
<212> TYPE: DNA
<213> ORGANISM: Homo sapien
<220> FEATURE:
<221> NAME/KEY: misc_feature
<222> LOCATION: (1)...(584)
<223> OTHER INFORMATION: n = A,T,C or G

<400> SEQUENCE: 268

```
agcgtggtcg cggccgaggt ctgtagcttc tgtgggactt ccactgctca ggcgtcaggc     60

tcaggtagct gctggccgcg tacttgttgt tgctttgntt ggagggtgtg gtggtctcca    120

ctcccgcctt gacggggctg ctatctgcct tccaggccac tgtcacggct cccgggtaga    180

agtcacttat gagacacacc agtgtggcct tgttggcttg aagctcctca gaggagggtg    240

ggaacagagt gaccgagggg gcagccttgg gctgacctag gacggtcagc ttggtccctc    300

cgccgaacac ccaattgttg ttgcctgcat atgagctgca gtaataatca gcctcatcct    360

cagcctggag cccagagacn gtcaagggag gcccgtgttt gccaagactt ggaagccaga    420

naagcgatca gggacccctg agggccgctt tacngacctc aaaaaatcat gaatttgggg    480

ggcctttgcc tgggngttgg ttggtnacca gnaaaacaaa atttcataaa gcaccaacgt    540

cactgctggt ttccagtgca ngaanatggt gaactgaant gtcc                     584
```

<210> SEQ ID NO 269
<211> LENGTH: 368
<212> TYPE: DNA
<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 269

```
agcgtggtcg cggccgaggt ccagcatcag gagccccgcc ttgccggctc tggtcatcgc     60

ctttcttttt gtggcctgaa acgatgtcat caattcgcag tagcagaact gccgtctcca    120

ctgctgtctt ataagtctgc agcttcacag ccaatggctc ccatatgccc agttccttca    180

tgtccaccaa agtacccgtc tcaccattta caccccaggt ctcacagttc tcctgggtgt    240

gcttggcccg aagggaggta agtanacgga tggtgctggt cccacagttc tggatcaggg    300

tacgaggaat gacctctagg gcctgggcna caagccctgt atggacctgc ccgggcgggc    360

ccgctcga                                                              368
```

<210> SEQ ID NO 270
<211> LENGTH: 368
<212> TYPE: DNA

-continued

<213> ORGANISM: Homo sapien
<220> FEATURE:
<221> NAME/KEY: misc_feature
<222> LOCATION: (1)...(368)
<223> OTHER INFORMATION: n = A,T,C or G

<400> SEQUENCE: 270

```
tcgagcggcc gcccgggcag gtccatacag ggctgttgcc caggccctag aggncattcc     60

ttgtaccctg atccagaact gtgggaccag caccatccgt ctacttacct cccttcgggc    120

caagcacacc caggagaact gtgagacctg ggtgtaaat ggngagacgg gtactttggt    180

ggacatgaag gaactgggca tatgggagcc attggctgng aagctgcana cttataagac    240

agcagtggag acggcagttc tgctactgcg aattgatgac atcgtttcag gccacaaaaa    300

gaaaggcgat gaccanagcc ggcaaggcgg ggcttcctga tgctggacct cggccgccga    360

ccacgctt                                                             368
```

<210> SEQ ID NO 271
<211> LENGTH: 424
<212> TYPE: DNA
<213> ORGANISM: Homo sapien
<220> FEATURE:
<221> NAME/KEY: misc_feature
<222> LOCATION: (1)...(424)
<223> OTHER INFORMATION: n = A,T,C or G

<400> SEQUENCE: 271

```
agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgggaaac tccgaggaca    180

gagggctaaa tccatgaagt ttgtggatgg cctgatgatc cacagcggag accctgttaa    240

ctactacgtt gacactgctg tgcgccacgt gttgctcana cagggtgtgc tgggcatcaa    300

ggtgaagatc atgctgccct gggacccanc tggcaaaaat ggcccttaaa aaccccttgc    360

cntgaccacg tgaaccattt gtgngaaccc caagatgaan atacttgccc accaccccc     420

attc                                                                 424
```

<210> SEQ ID NO 272
<211> LENGTH: 541
<212> TYPE: DNA
<213> ORGANISM: Homo sapien
<220> FEATURE:
<221> NAME/KEY: misc_feature
<222> LOCATION: (1)...(541)
<223> OTHER INFORMATION: n = A,T,C or G

<400> SEQUENCE: 272

```
tcgagcggcc gcccgggcag gtctgccaag gagaccctgt tatgctgtgg ggactggctg     60

gggcatggca ggcggctctg gcttcccacc cttctgttct gagatggggg tggtgggcag    120

tatctcatct ttgggttcca caatgctcac gtggtcaggc aggggcttct tagggccaat    180

cttaccagtt gggtcccagg gcagcatgat cttcaccttg atgcccagca caccctgtct    240

gagcaacacg tggcgcacag cagtgtcaac gtagtagtta acagggtctc cgctgtggat    300

catcaggcca tccacaaact tcatggattt agccctctgt cctcggagtt tcccaaaaca    360

ccacaacctc gccagccttt gggccccact tcttcatgaa tgaaaccgca gcacaccatt    420

ancaaggccc ttccgcacag gnaagccctt cctaaggagt tttgtaaacg caaaaaactc    480

ttgcctgggg caaatgggca cacagacctn tantnggacc ttggnccgcg aaccaccgct    540
```

-continued

```
t                                                                   541


<210> SEQ ID NO 273
<211> LENGTH: 579
<212> TYPE: DNA
<213> ORGANISM: Homo sapien
<220> FEATURE:
<221> NAME/KEY: misc_feature
<222> LOCATION: (1)...(579)
<223> OTHER INFORMATION: n = A,T,C or G

<400> SEQUENCE: 273

agcgtggtcg cggccgaggt ctggccctcc tggcaaggct ggtgaagatg gtcaccctgg     60

aaaacccgga cgacctggtg agagaggagt tgttggacca cagggtgctc gtggtttccc    120

tggaactcct ggacttcctg gcttcaaagg cattagggga cacaatggtc tggatggatt    180

gaagggacag cccggtgctc ctggtgtgaa gggtgaacct ggngcccctg gtgaaaatgg    240

aactccaggt caaacaggag cccgngggct tcctggngag agaggacgtg ttggtgcccc    300

tggcccanac ctgcccgggc ggccgctcna aaagccgaaa tccagnacac tggcggccgn    360

tactantgga atccgaactt cggtaccaaa gcttggccgt aatcatggcc atagcttgtt    420

ccctggggng gaaattggta ttccgctncc aattccacac aacataccga acccggaaag    480

cattaaagtg taaaagccct gggggggcct aaatgangtg agcntaactc ncatttaatt    540

ggcgttgcgc ttcactgccc cgcttttcca gtccgggna                           579


<210> SEQ ID NO 274
<211> LENGTH: 330
<212> TYPE: DNA
<213> ORGANISM: Homo sapien
<220> FEATURE:
<221> NAME/KEY: misc_feature
<222> LOCATION: (1)...(330)
<223> OTHER INFORMATION: n = A,T,C or G

<400> SEQUENCE: 274

tcgagcggcc gcccgggcag gtctgggcca ggggcaccaa cacgtcctct ctcaccagga     60

agcccacggg ctcctgtttg acctggagtt ccattttcac caggggcacc aggttcaccc    120

ttcacaccag gagcaccggg ctgtcccttc aatccatcca gaccattgtg ncccctaatg    180

cctttgaagc caggaagtcc aggagttcca gggaaaccac gagcaccctg tggtccaaca    240

actcctctct caccaggtcg tccgggtttt ccagggtgac catcttcacc agccttgcca    300

ggagggccag acctcggccg cgaccacgct                                     330


<210> SEQ ID NO 275
<211> LENGTH: 97
<212> TYPE: DNA
<213> ORGANISM: Homo sapien
<220> FEATURE:
<221> NAME/KEY: misc_feature
<222> LOCATION: (1)...(97)
<223> OTHER INFORMATION: n = A,T,C or G

<400> SEQUENCE: 275

ancgtggtcg cggccgaggt cctcaccaga ggtgncacct acaacatcat agtggaggca     60

ctgaaagacc ancagaggca taaggttcgg gaagagg                              97


<210> SEQ ID NO 276
<211> LENGTH: 610
<212> TYPE: DNA
```

-continued

<213> ORGANISM: Homo sapien
<220> FEATURE:
<221> NAME/KEY: misc_feature
<222> LOCATION: (1)...(610)
<223> OTHER INFORMATION: n = A,T,C or G

<400> SEQUENCE: 276
tcgagcggcc gcccgggcag gtccattttc tccctgacgg tcccacttct ctccaatctt 60
gtagttcaca ccattgtcat ggcaccatct agatgaatca catctgaaat gaccacttcc 120
aaagcctaag cactggcaca acagtttaaa gcctgattca gacattcgtt cccactcatc 180
tccaacggca taatgggaaa ctgtgtaggg gtcaaagcac gagtcatccg taggttggtt 240
caagccttcg ttgacagagt tgtccacggt aacaacctct tcccgaacct tatgcctctg 300
ctggtctttc agtgcctcca ctatgatgtt gtaggtggca cctctggtga ggacctcngn 360
ccngaacaac gcttaagccc gnattctgca gaataatccc atcacacttg gcggccgctt 420
cgancatgca tcntaaaagg ggccccaatt tccccccttat aagngaancc gtatttncca 480
atttcactgg ncccgccgnt tttacaaacg ncggtgaact ggggaaaaac cctggcggtt 540
acccaacttt aatcgccntt ggcagcacaa tcccccctttt tcgnccancn tgggcgtaaa 600
taaccgaaaa 610

<210> SEQ ID NO 277
<211> LENGTH: 38
<212> TYPE: DNA
<213> ORGANISM: Homo sapien
<220> FEATURE:
<221> NAME/KEY: misc_feature
<222> LOCATION: (1)...(38)
<223> OTHER INFORMATION: n = A,T,C or G

<400> SEQUENCE: 277
ancgnggtcg cggccgangt nttttttctt ntttttt 38

<210> SEQ ID NO 278
<211> LENGTH: 443
<212> TYPE: DNA
<213> ORGANISM: Homo sapien
<220> FEATURE:
<221> NAME/KEY: misc_feature
<222> LOCATION: (1)...(443)
<223> OTHER INFORMATION: n = A,T,C or G

<400> SEQUENCE: 278
agcgtggtcg cggccgaggt ctgaggttac atgcgtggtg gtggacgtga gccacgaaga 60
ccctgaggtc aagttcaact ggtacgtgga cggcgtggag gtgcataatg ccaagacaaa 120
gccgcgggag gagcagtaca acagcacgta ccgggnggtc agcgtcctca ccgtcctgca 180
ccagaattgg ttgaatggca aggagtacaa gngcaaggtt tccaacaaag ccntcccagc 240
ccccntcgaa aaaaccattt ccaaagccaa agggcagccc cgagaaccac aggtgtacac 300 cctgcccccca tcccgggagg aaaagancaa naaccnggtt cagccttaac ttgcttggtc 360
naangctttt tatcccaacg nacttccccc ntggaantgg gaaaaaccaa tgggccaanc 420
cgaaaaacaa ttacaanaac ccc 443

<210> SEQ ID NO 279
<211> LENGTH: 348
<212> TYPE: DNA
<213> ORGANISM: Homo sapien
<220> FEATURE:
<221> NAME/KEY: misc_feature -continued
<222> LOCATION: (1)...(348)
<223> OTHER INFORMATION: n = A,T,C or G

<400> SEQUENCE: 279
tcgagcggcc gcccgggcag gtgtcggagt ccagcacggg aggcgtggtc ttgtagttgt 60
tctccggctg cccattgctc tcccactcca cggcgatgtc gctgggatag aagcctttga 120
ccaggcaggt caggctgacc tggttcttgg tcatctcctc ccgggatggg ggcagggtga 180
acacctgggg ttctcggggc ttgccctttg gttttgaana tggttttctc gatgggggct 240
ggaagggctt tgttgnaaac cttgcacttg actccttgcc attcacccag ncctggngca 300
ggacggngag gacnctnacc acacggaacc gggctggtgg actgctcc 348

<210> SEQ ID NO 280
<211> LENGTH: 149
<212> TYPE: DNA
<213> ORGANISM: Homo sapien
<220> FEATURE:
<221> NAME/KEY: misc_feature
<222> LOCATION: (1)...(149)
<223> OTHER INFORMATION: n = A,T,C or G

<400> SEQUENCE: 280
agcgtggtcg cggacgangt cctgtcagag tggnactggt agaagttcca ngaaccctga 60
actgtaaggg ttcttcatca gtgccaacag gatgacatga aatgatgtac tcagaagngn 120
cctggaatgg ggcccatgan atggttgcc 149

<210> SEQ ID NO 281
<211> LENGTH: 404
<212> TYPE: DNA
<213> ORGANISM: Homo sapien
<220> FEATURE:
<221> NAME/KEY: misc_feature
<222> LOCATION: (1)...(404)
<223> OTHER INFORMATION: n = A,T,C or G

<400> SEQUENCE: 281
tcgagcggcc gcccgggcag gtccaccaca cccaattcct tgctggtatc atggcagccg 60
ccacgtgcca ggattaccgg ctacatcatc aagtatgaga agcctgggtc tcctcccaga 120
gaagtggtcc ctcggccccg ccctggtgtc acagaggcta ctattactgg cctggaaccg 180
ggaaccgaat atacaattta tgtcattgcc ctgaagaata atcagaagag cgagcccctg 240
attggaagga aaaagacaga cgagcttccc caactggtaa cccttccaca ccccaatctt 300
catggaccag agatcttgga tgttccttcc acagttcaaa agaccccttt cggcaccccc 360
cctgggtatg aacctgggaa aanggnantt aanctttcct ggca 404

<210> SEQ ID NO 282
<211> LENGTH: 507
<212> TYPE: DNA
<213> ORGANISM: Homo sapien
<220> FEATURE:
<221> NAME/KEY: misc_feature
<222> LOCATION: (1)...(507)
<223> OTHER INFORMATION: n = A,T,C or G

<400> SEQUENCE: 282
agcgtggtcg cggccgaggt ctgggatgct cctgctgtca cagtgagata ttacaggatc 60
acttacggag aaacaggagg aaatagccct gtccaggagt tcactgtgcc tgggagcaag 120
tctacagcta ccatcagcgg ccttaaacct ggagttgatt ataccatcac tgtgtatgct 180

-continued

```
gtcactggcc gtggagacag ccccgcaagc agcaagccaa tttccattaa ttaccgaaca    240

gaaattgaca aaccatccca gatgcaagtg accgatgttc aggacaacag cattagtgtc    300

aagtggctgc cttcaaggtn ccctggtact gggttacaga ntaaccacca ctcccaaaaa    360

tggaccagga accacaaaaa cttaaactgc agggtccaga tcaaaacaga aatgactatt    420

gaangcttgc agcccacagt gggagtatgn gggtagtgnc tatgcttcag aatccaagcg    480

gaaaaangtc aagccttntg ggttcaa                                        507
```

<210> SEQ ID NO 283
<211> LENGTH: 325
<212> TYPE: DNA
<213> ORGANISM: Homo sapien
<220> FEATURE:
<221> NAME/KEY: misc_feature
<222> LOCATION: (1)...(325)
<223> OTHER INFORMATION: n = A,T,C or G

<400> SEQUENCE: 283

```
tcgagcggcc gcccgggcag gtccttgcag ctctgcagtg tcttcttcac catcaggtgc     60

agggaatagc tcatggattc catcctcagg gctcgagtag gtcaccctgt acctggaaac    120

ttgcccctgt gggctttccc aagcaatttt gatggaatcg acatccacat cagtgaatgc    180

cagtccttta gggcgatcaa tgttggttac tgcagnctga accagaggct gactctctcc    240

gcttggattc tgagcataga cactaaccac atactccact gtgggctgca anccttcaat    300

aanncatttc tgtttgatct ggacc                                          325
```

<210> SEQ ID NO 284
<211> LENGTH: 331
<212> TYPE: DNA
<213> ORGANISM: Homo sapien
<220> FEATURE:
<221> NAME/KEY: misc_feature
<222> LOCATION: (1)...(331)
<223> OTHER INFORMATION: n = A,T,C or G

<400> SEQUENCE: 284

```
tcgagcggcc gcccgggcag gtctggtggg gtcctggcac acgcacatgg gggngttgnt     60

ctnatccagc tgcccagccc ccattggcga gtttgagaag gtgtgcagca atgacaacaa    120

naccttcgac tcttcctgcc acttctttgc cacaaagtgc accctggagg gcaccaagaa    180

gggccacaag ctccacctgg actacatcgg gccttgcaaa tacatccccc cttgcctgga    240

ctctgagctg accgaattcc cccttgcgca tgcgggactg gctcaagaac cgtcctggca    300

cccttgtatg anagggatga agacacnacc c                                   331
```

<210> SEQ ID NO 285
<211> LENGTH: 509
<212> TYPE: DNA
<213> ORGANISM: Homo sapien
<220> FEATURE:
<221> NAME/KEY: misc_feature
<222> LOCATION: (1)...(509)
<223> OTHER INFORMATION: n = A,T,C or G

<400> SEQUENCE: 285

```
agcgtggtcg cggccgaggt ctgtcctaca gtcctcagga ctctactccc tcagcagcgt     60

ggtgaccgtg ccctccagca acttcggcac ccagacctac acctgcaacg tagatcacaa    120

gcccagcaac accaaggtgg acaagagagt tgagcccaaa tcttgtgaca aaactcacac    180

atgcccaccg tgcccagcac ctgaactcct gggggggaccg tcagtcttcc tcttcccccg    240
```

-continued catccccctt ccaaacctgc ccgggcggcc gctcgaaagc cgaattccag cacactggcg 300
gccggtacta gtgganccna acttggnanc caacctggng gaantaatgg gcataanctg 360
tttctggggg gaaattggta tccngtttac aattcccnca caacatacga gccggaagca 420
taaaagngta aaagcctggg ggnggcctan tgaagtgaag ctaaactcac attaattngc 480
gttgccgctc actggcccgc ttttccagc 509

<210> SEQ ID NO 286
<211> LENGTH: 336
<212> TYPE: DNA
<213> ORGANISM: Homo sapien
<220> FEATURE:
<221> NAME/KEY: misc_feature
<222> LOCATION: (1)...(336)
<223> OTHER INFORMATION: n = A,T,C or G

<400> SEQUENCE: 286
tcgagcggcc gcccgggcag gtttggaagg gggatgcggg ggaagaggaa gactgacggt 60
ccccccagga gttcaggtgc tgggcacggt gggcatgtgt gagttttgtc acaagatttg 120
ggctcaactc tcttgtccac cttggtgttg ctgggcttgt gatctacgtt gcaggtgtag 180
gtctgggngc cgaagttgct ggagggcacg gtcaccacgc tgctgaggga gtagagtcct 240
gaggactgta ngacagacct cggccgngac cacgctaagc cgaattctgc agatatccat 300
cacactggcg gccgctccga gcatgcattt tagagg 336

<210> SEQ ID NO 287
<211> LENGTH: 30
<212> TYPE: DNA
<213> ORGANISM: Homo sapien
<220> FEATURE:
<221> NAME/KEY: misc_feature
<222> LOCATION: (1)...(30)
<223> OTHER INFORMATION: n = A,T,C or G

<400> SEQUENCE: 287
agcgtggncg cggacganga caacaacccc 30

<210> SEQ ID NO 288
<211> LENGTH: 316
<212> TYPE: DNA
<213> ORGANISM: Homo sapien
<220> FEATURE:
<221> NAME/KEY: misc_feature
<222> LOCATION: (1)...(316)
<223> OTHER INFORMATION: n = A,T,C or G

<400> SEQUENCE: 288
tcgagcggcc gcccgggcag gnccacatcg gcagggtcgg agccctggcc gccatactcg 60
aactggaatc catcggtcat gctcttgccg aaccagacat gcctcttgtc cttggggttc 120
ttgctgatgn accagttctt ctgggccaca ctgggctgag tggggtacac gcaggtctca 180
ccagtctcca tgttgcagaa gactttgatg gcatccaggt tgcagccttg gttggggtca 240
atccagtact ctccactctt ccagtcagag tggcacatct tgaggtcacg gcaggtgcgg 300
gcggggttct tgacct 316

<210> SEQ ID NO 289
<211> LENGTH: 308
<212> TYPE: DNA
<213> ORGANISM: Homo sapien
<220> FEATURE:

-continued

<221> NAME/KEY: misc_feature
<222> LOCATION: (1)...(308)
<223> OTHER INFORMATION: n = A,T,C or G

<400> SEQUENCE: 289
agcgtggtcg cggccgaggt ccagcctgga gataanggtg aaggtggtgc ccccggactt 60
ccaggtatag ctggacctcg tggtagccct ggtgagagag gtgaaactgg ccctccagga 120
cctgctggtt tccctggtgc tcctggacag aatggtgaac ctggnggtaa aggagaaaga 180
ggggctccgg ntganaaagg tgaaggaggc cctcctgnat tggcaggggc cccangactt 240
agaggtggag ctggcccccc tggccccgaa ggaggaaagg gtgctgctgg tcctcctggg 300
ccacctgg 308

<210> SEQ ID NO 290
<211> LENGTH: 324
<212> TYPE: DNA
<213> ORGANISM: Homo sapien
<220> FEATURE:
<221> NAME/KEY: misc_feature
<222> LOCATION: (1)...(324)
<223> OTHER INFORMATION: n = A,T,C or G

<400> SEQUENCE: 290
tcgagcggcc gcccgggcag gtctgggcca ggaggaccaa taggaccagt aggacccctt 60
gggccatctt tccctgggac accatcagca cctggaccgc ctggttcacc cttgtcaccc 120
tttggaccag gacttccaag acctcctctt tctccaggca ttccttgcag accaggagta 180
ccancagcac caggtggccc aggaggacca gcagcaccct ttcctccttc gggaccaggg 240
ggaccagctc cacctctaag tcctggggcc cctgccaatc caggagggcc tccttcacct 300
ttctcacccg gagcccctct ttct 324

<210> SEQ ID NO 291
<211> LENGTH: 278
<212> TYPE: DNA
<213> ORGANISM: Homo sapien
<220> FEATURE:
<221> NAME/KEY: misc_feature
<222> LOCATION: (1)...(278)
<223> OTHER INFORMATION: n = A,T,C or G

<400> SEQUENCE: 291
tcgagcggcc gcccgggcag gtccaccggg atattcgggg gtctggcagg aatgggaggc 60
atccagaacg agaaggagac catgcaaagc ctgaacgacc gcctggcctc ttacctggac 120
agagtgagga gcctggagac cgacaaccgg aggctggaga gcaaaatccg ggagcacttg 180
gagaagaagg gaccccaggt cagagactgg agccattact tcaagatcat cgaggacctg 240
agggctcana tcttcgcaaa tactgcngac aatgcccg 278

<210> SEQ ID NO 292
<211> LENGTH: 299
<212> TYPE: DNA
<213> ORGANISM: Homo sapien
<220> FEATURE:
<221> NAME/KEY: misc_feature
<222> LOCATION: (1)...(299)
<223> OTHER INFORMATION: n = A,T,C or G

<400> SEQUENCE: 292
atgcgnggtc gcggccgang accanctctg gctcatactt gactctaaag ncntcaccag 60
nanttacggn cattgccaat ctgcagaacg atgcgggcat tgtccgcant atttgcgaag 120

-continued

```
atctgagccc tcaggncctc gatgatcttg aagtaanggc tccagtctct gacctggggt    180

cccttcttct ccaagtgctc ccggattttg ctctccagcc tccggttctc ggtctccaag    240

ncttctcact ctgtccagga aaagaggcca ggcggncgat cagggctttt gcatggact     299


<210> SEQ ID NO 293
<211> LENGTH: 101
<212> TYPE: DNA
<213> ORGANISM: Homo sapien

<400> SEQUENCE: 293

agcgtggtcg cggccgaggt tgtacaagct tttttttttt tttttttttt tttttttttt     60

tttttttttt tttttttttt tttttttttt tttttttttt t                        101


<210> SEQ ID NO 294
<211> LENGTH: 285
<212> TYPE: DNA
<213> ORGANISM: Homo sapien
<220> FEATURE:
<221> NAME/KEY: misc_feature
<222> LOCATION: (1)...(285)
<223> OTHER INFORMATION: n = A,T,C or G

<400> SEQUENCE: 294

tcgagcggcc gcccgggcag gtctgccaac accaagattg gcccccgccg catccacaca     60

gttngtgtgc ggggaggtaa caagaaatac cgtgccctga ggntggacgn ggggaatttc    120

tcctggggct cagagtgttg tactcgtaaa acaaggatca tcgatgttgt ctacaatgca    180

tctaataacg agctggttcg taccaagacc ctggtgaaga attgcatcgt gctcatngac    240

agcacaccgt accgacagtg ggtaccgaag tcccactatg cncct                    285


<210> SEQ ID NO 295
<211> LENGTH: 216
<212> TYPE: DNA
<213> ORGANISM: Homo sapien

<400> SEQUENCE: 295

tcgagcggcc gcccgggcag gtccaccaca cccaattcct tgctggtatc atggcagccg     60

ccacgtgcca ggattaccgg ctacatcatc aagtatgaga agcctgggtc tcctcccaga    120

gaagtggtcc ctcggccccg ccctggtgtc acagaggcta ctattactgg cctggaaccg    180

ggaaccgaat atacaattta tgtcattgcc ctgaag                              216


<210> SEQ ID NO 296
<211> LENGTH: 414
<212> TYPE: DNA
<213> ORGANISM: Homo sapien
<220> FEATURE:
<221> NAME/KEY: misc_feature
<222> LOCATION: (1)...(414)
<223> OTHER INFORMATION: n = A,T,C or G

<400> SEQUENCE: 296

agcgtgntcn cggccgagga tggggaagct cgnctgtctt tttccttcca atcaggggct     60

nnntcttctg attattcttc agggcaanga cataaattgt atattcggnt cccggttcca    120

gnccagtaat agtagcctct gtgacaccag ggcggggccg agggaccact tctctgggag    180

gagacccagg cttctcatac ttgatgatga agccggtaat cctggcacgt gggcggctgc    240

catgatacca ccaangaatt gggtgtggtg gacctgcccg ggcgggccgc tcgaaaancc    300
```

-continued

```
gaattcntgc aagaatatcc atcacacttg ggcgggccgn tcgaaccatg catcntaaaa    360

gggccccaat ttccccccta ttaggngaag ccncatttaa caaattccac ttgg          414


<210> SEQ ID NO 297
<211> LENGTH: 376
<212> TYPE: DNA
<213> ORGANISM: Homo sapien
<220> FEATURE:
<221> NAME/KEY: misc_feature
<222> LOCATION: (1)...(376)
<223> OTHER INFORMATION: n = A,T,C or G

<400> SEQUENCE: 297

tcgagcggcc gcccgggcag gtctcgcggt cgcactggtg atgctggtcc tgttggtccc     60

cccggccctc ctggacctcc tggtccccct ggtcctccca gcgctggttt cgacttcagc    120

ttcctgcccc agccacctca agagaaggct cacgatggtg gccgctacta ccgggctgat    180

gatgccaatg tggttcgtga ccgtgacctc gaggtggaca ccaccctcaa gagccttgag    240

ccagcagaat cgaaaacatt cggaacccaa gaagggcaag cccgcaaaga aaccccgccc    300

gcacctggcc gngaacctcc aagaangtgc ccacntcttg actgggaaaa aaagggaaaa    360

ntacttggaa ttggac                                                    376


<210> SEQ ID NO 298
<211> LENGTH: 357
<212> TYPE: DNA
<213> ORGANISM: Homo sapien
<220> FEATURE:
<221> NAME/KEY: misc_feature
<222> LOCATION: (1)...(357)
<223> OTHER INFORMATION: n = A,T,C or G

<400> SEQUENCE: 298

agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacacgc aggtctcacc    180

agtctccatg ttgcagaaga ctttgatggc atccaggttg cagccttggt tggggtcaat    240

ccagtactct ccactcttcc agtcagaagt ggcacatctt gaggtcacgg cagggtgcgg    300

gcggggttct tgcgggctgc ccttctgggc tcccggaatg ttctnngaac ttgctgg       357


<210> SEQ ID NO 299
<211> LENGTH: 307
<212> TYPE: DNA
<213> ORGANISM: Homo sapien
<220> FEATURE:
<221> NAME/KEY: misc_feature
<222> LOCATION: (1)...(307)
<223> OTHER INFORMATION: n = A,T,C or G

<400> SEQUENCE: 299

agcgtggtcg cggccgaggt ccactagagg tctgtgtgcc attgcccagg cagagtctct     60

gcgttacaaa ctcctaggag ggcttgctgt gcggagggcc tgctatggtg tgctgcggtt    120

catcatggag agtggggcca aaggctgcga ggttgtggtg tctgggaaac tccgaggaca    180

gagggctaaa tccatgaagt ttgtggatgg cctgatgatc cacagcggag accctgttaa    240

ctactacgtt gacacttgct tgtgcgccac gtgttgctca nacangggtg ggctgggcat    300

caaggng                                                              307
```

-continued

<210> SEQ ID NO 300
<211> LENGTH: 351
<212> TYPE: DNA
<213> ORGANISM: Homo sapien

<400> SEQUENCE: 300
tcgagcggcc gcccgggcag gtctgccaag gagaccctgt tatgctgtgg ggactggctg 60
gggcatggca ggcggctctg gcttcccacc cttctgttct gagatggggg tggtgggcag 120
tatctcatct ttgggttcca caatgctcac gtggtcaggc aggggcttct tagggccaat 180
cttaccagtt gggtcccagg gcagcatgat cttcaccttg atgcccagca caccctgtct 240
gagcaacacg tggcgcacag caagtgtcaa cgtaagtaag ttaacagggt ctccgctgtg 300
gatcatcagg ccatccacaa acttcatgga tttaaccctc tgtcctcgga g 351

<210> SEQ ID NO 301
<211> LENGTH: 330
<212> TYPE: DNA
<213> ORGANISM: Homo sapien

<400> SEQUENCE: 301
tcgagcggcc gcccgggcag gtgtttcaga ggttccaagg tccactgtgg aggtcccagg 60
agtgctggtg gtgggcacag aggtccgatg ggtgaaacca ttgacataga gactgttcct 120
gtccagggtg taggggccca gctctttgat gccattggcc agttggctca gctcccagta 180
cagccgctct ctgttgagtc cagggctttt ggggtcaaga tgatggatgc agatggcatc 240
cactccagtg gctgctccat ccttctcgga cctgagagag gtcagtctgc agccagagta 300
cagagggcca acactggtgt tctttgaata 330

<210> SEQ ID NO 302
<211> LENGTH: 317
<212> TYPE: DNA
<213> ORGANISM: Homo sapien
<220> FEATURE:
<221> NAME/KEY: misc_feature
<222> LOCATION: (1)...(317)
<223> OTHER INFORMATION: n = A,T,C or G

<400> SEQUENCE: 302
agcgtggtcg cggccgaggt ctgtactggg agctaagcaa actgaccaat gacattgaag 60
agctgggccc ctacaccctg gacaggaaca gtctctatgt caatggtttc acccatcaga 120
gctctgtgnc caccaccagc actcctggga cctccacagt ggatttcaga acctcaggga 180
ctccatcctc cctctccagc cccacaatta tggctgctgg ccctctcctg gtaccattca 240
ccctcaactt caccatcacc aacctgcagt atggggagga catgggtcac cctgnctcca 300
ggaagttcaa caccaca 317

<210> SEQ ID NO 303
<211> LENGTH: 283
<212> TYPE: DNA
<213> ORGANISM: Homo sapien
<220> FEATURE:
<221> NAME/KEY: misc_feature
<222> LOCATION: (1)...(283)
<223> OTHER INFORMATION: n = A,T,C or G

<400> SEQUENCE: 303
tcgagcggcc gcccggacag gtctgggcgg atagcaccgg gcatattttg gaatggatga 60
ggtctggcac cctgagcagt ccagcgagga cttggtctta gttgagcaat ttggctagga 120

-continued

```
ggatagtatg cagcacggnt ctgagnctgt gggatagctg ccatgaagta acctgaagga    180

ggtgctggct ggtangggtt gattacaggg ttgggaacag ctcgtacact tgccattctc    240

tgcatatact ggttagtgag gtgagcctgg ccctcttctt ttg                      283


<210> SEQ ID NO 304
<211> LENGTH: 72
<212> TYPE: DNA
<213> ORGANISM: Homo sapien
<220> FEATURE:
<221> NAME/KEY: misc_feature
<222> LOCATION: (1)...(72)
<223> OTHER INFORMATION: n = A,T,C or G

<400> SEQUENCE: 304

agcgtggtcg cggccgaggt gagccacagg tgaccggggc tgaagctggg gctgctggnc     60

ctgctggtcc tg                                                         72


<210> SEQ ID NO 305
<211> LENGTH: 245
<212> TYPE: DNA
<213> ORGANISM: Homo sapien
<220> FEATURE:
<221> NAME/KEY: misc_feature
<222> LOCATION: (1)...(245)
<223> OTHER INFORMATION: n = A,T,C or G

<400> SEQUENCE: 305

cagcngctcc nacggggcct gngggaccaa caacaccgtt ttcaccctta ggccctttgg     60

ctcctctttc tcctttagca ccaggttgac cagcagcncc ancaggacca gcaaatccat    120

tggggccagc aggaccgacc tcaccacgtt caccagggct tccccgagga ccagcaggac    180

cagcaggacc agcagcccca gcttcgcccc ggtcacctgt ggctcacctc ggccgcgacc    240

acgct                                                                245


<210> SEQ ID NO 306
<211> LENGTH: 246
<212> TYPE: DNA
<213> ORGANISM: Homo sapien
<220> FEATURE:
<221> NAME/KEY: misc_feature
<222> LOCATION: (1)...(246)
<223> OTHER INFORMATION: n = A,T,C or G

<400> SEQUENCE: 306

tcgagcggtc gcccgggcag gtccaccggg atagccgggg gtctggcagg aatgggaggc     60

atccagaacg agaaggagac catgcaaagc ctgaacgacc gcctggcctc ttacctggac    120

agagtgagga gcctggagac cganaaccgg aggctggana gcaaaatccg ggagcacttg    180

gagaagaagg gaccccaggt caagagactg gagccattac ttcaagatca tcgagggacc    240

tggagg                                                               246


<210> SEQ ID NO 307
<211> LENGTH: 333
<212> TYPE: DNA
<213> ORGANISM: Homo sapien
<220> FEATURE:
<221> NAME/KEY: misc_feature
<222> LOCATION: (1)...(333)
<223> OTHER INFORMATION: n = A,T,C or G

<400> SEQUENCE: 307

agcgnggtcg cggccgaggt ccagctctgt ctcatacttg actctaaagt catcagcagc     60
```

-continued

```
aagacgggca ttgtcaatct gcagaacgat gcgggcattg tccgcagtat ttgcgaagat    120

ctgagccctc aggtcctcga tgatcttgaa gtaatggctc cagtctctga cctggggtcc    180

cttcttctcc aagtgctccc ggattttgct ctccagcctc cggttctcgg tctccaggct    240

cctcactctg tccaggtaag aaggcccagg cggtcgttca ggctttgcat ggtctccttc    300

tcgttctgga tgcctcccat tcctgccaga ccc                                 333
```

<210> SEQ ID NO 308
<211> LENGTH: 310
<212> TYPE: DNA
<213> ORGANISM: Homo sapien

<400> SEQUENCE: 308

```
tcgagcggcc gcccgggcag gtcaggaagc acattggtct tagagccact gcctcctgga     60

ttccacctgt gctgcggaca tctccaggga gtgcagaagg gaagcaggtc aaactgctca    120

gatcagtcag actggctgtt ctcagttctc acctgagcaa ggtcagtctg cagccagagt    180

acagagggcc aacactggtg ttcttgaaca agggcttgag cagaccctgc agaaccctct    240

tccgtggtgt tgaacttcct ggaaaccagg gtgttgcatg tttttcctca taatgcaagg    300

ttggtgatgg                                                           310
```

<210> SEQ ID NO 309
<211> LENGTH: 429
<212> TYPE: DNA
<213> ORGANISM: Homo sapien

<400> SEQUENCE: 309

```
agcgtggtcg cggccgaggt ccacatcggc agggtcggag ccctggccgc catactcgaa     60

ctggaatcca tcggtcatgc tctcgccgaa ccagacatgc ctcttgtcct tggggttctt    120

gctgatgtac cagttcttct gggccacact gggctgagtg gggtacaccg caggtctcac    180

cagtctccat gttgcagaag actttgatgg catccaggtt gcagccttgg ttggggtcaa    240

tccagtactc tccactcttc cagtcagaag tgggcacatc ttgaggtcac cggcaggtgc    300

cgggccgggg gttcttgcgg cttgccctct gggctccgga tgttctcgat ctgcttggct    360

caggctcttg agggtgggtg tccacctcga ggtcacggtc accgaaacct gcccgggcgg    420

cccgctcga                                                            429
```

<210> SEQ ID NO 310
<211> LENGTH: 430
<212> TYPE: DNA
<213> ORGANISM: Homo sapien
<220> FEATURE:
<221> NAME/KEY: misc_feature
<222> LOCATION: (1)...(430)
<223> OTHER INFORMATION: n = A,T,C or G

<400> SEQUENCE: 310

```
tcgagcggtc gcccgggcag gtttcgtgac cgtgacctcg aggtggacac caccctcaag     60

agcctgagcc agcagatcga gaacatccgg agcccagagg gcagccgcaa gaaccccgcc    120

cgcacctgcc gtgacctcaa gatgtgccac tctgactgga agagtggaga gtactggatt    180

gaccccaacc aaggctgcaa cctggatgcc atcaaagtct tctgcaacat ggagactggt    240

gagacctgcg tgtaccccac tcagcccagt gtgggcccag aagaaactgg tacatcagca    300

aggaacccca aggacaagag gcattgtctt ggttcggcga gnagcatgac ccgatggatt    360
```

-continued

```
ccagtttcga gtattggcgg ccagggcttc ccgacccttg ccgatgtgga cctcggccgc    420

gaccaccgct                                                           430


<210> SEQ ID NO 311
<211> LENGTH: 2996
<212> TYPE: DNA
<213> ORGANISM: Homo sapien

<400> SEQUENCE: 311

cagccaccgg agtggatgcc atctgcaccc accgccctga ccccacaggc cctgggctgg     60

acagagagca gctgtatttg gagctgagcc agctgaccca cagcatcact gagctgggcc    120

cctacaccct ggacagggac agtctctatg tcaatggttt cacacagcgg agctctgtgc    180

ccaccactag cattcctggg acccccacag tggacctggg aacatctggg actccagttt    240

ctaaacctgg tccctcggct gccagccctc tcctggtgct attcactctc aacttcacca    300

tcaccaacct gcggtatgag gagaacatgc agcaccctgg ctccaggaag ttcaacacca    360

cggagagggt ccttcagggc ctggtccctg ttcaagagca ccagtgttgg ccctctgtac    420

tctggctgca gactgacttt gctcaggcct gaaaaggatg ggacagccac tggagtggat    480

gccatctgca cccaccaccc tgaccccaaa agccctaggc tggacagaga gcagctgtat    540

tgggagctga gccagctgac ccacaatatc actgagctgg gcccctatgc cctggacaac    600

gacagcctct ttgtcaatgg tttcactcat cggagctctg tgtccaccac cagcactcct    660

gggaccccca cagtgtatct gggagcatct aagactccag cctcgatatt tggcccttca    720

gctgccagcc atctcctgat actattcacc ctcaacttca ccatcactaa cctgcggtat    780

gaggagaaca tgtggcctgg ctccaggaag ttcaacacta cagagagggt ccttcagggc    840

ctgctaaggc ccttgttcaa gaacaccagt gttggccctc tgtactctgg ctgcaggctg    900

accttgctca ggccagagaa agatggggaa gccaccggag tggatgccat ctgcacccac    960

cgccctgacc ccacaggccc tgggctggac agagagcagc tgtatttgga gctgagccag   1020

ctgacccaca gcatcactga gctgggcccc tacacactgg acagggacag tctctatgtc   1080

aatggtttca cccatcggag ctctgtaccc accaccagca ccggggtggt cagcgaggag   1140

ccattcacac tgaacttcac catcaacaac ctgcgctaca tggcggacat gggccaaccc   1200

ggctccctca agttcaacat cacagacaac gtcatgaagc acctgctcag tcctttgttc   1260

cagaggagca gcctgggtgc acggtacaca ggctgcaggg tcatcgcact aaggtctgtg   1320

aagaacggtg ctgagacacg ggtggacctc ctctgcacct acctgcagcc cctcagcggc   1380

ccaggtctgc ctatcaagca ggtgttccat gagctgagcc agcagaccca tggcatcacc   1440

cggctgggcc cctactctct ggacaaagac agcctctacc ttaacggtta caatgaacct   1500

ggtccagatg agcctcctac aactcccaag ccagccacca cattcctgcc tcctctgtca   1560

gaagccacaa cagccatggg gtaccacctg aagaccctca cactcaactt caccatctcc   1620

aatctccagt attcaccaga tatgggcaag ggctcagcta cattcaactc caccgagggg   1680

gtccttcagc acctgctcag acccttgttc cagaagagca gcatgggccc cttctacttg   1740

ggttgccaac tgatctccct caggcctgag aaggatgggg cagccactgg tgtggacacc   1800

acctgcacct accaccctga ccctgtgggc cccgggctgg acatacagca gctttactgg   1860

gagctgagtc agctgaccca tggtgtcacc caactgggct tctatgtcct ggacagggat   1920

agcctcttca tcaatggcta tgcaccccag aatttatcaa tccggggcga gtaccagata   1980

aatttccaca ttgtcaactg gaacctcagt aatccagacc ccacatcctc agagtacatc   2040
```

-continued

```
accctgctga gggacatcca ggacaaggtc accacactct acaaaggcag tcaactacat   2100

gacacattcc gcttctgcct ggtcaccaac ttgacgatgg actccgtgtt ggtcactgtc   2160

aaggcattgt tctcctccaa tttggacccc agcctggtgg agcaagtctt tctagataag   2220

accctgaatg cctcattcca ttggctgggc tccacctacc agttggtgga catccatgtg   2280

acagaaatgg agtcatcagt ttatcaacca acaagcagct ccagcaccca gcacttctac   2340

ctgaatttca ccatcaccaa cctaccatat tcccaggaca aagcccagcc aggcaccacc   2400

aattaccaga ggaacaaaag gaatattgag gatgcgctca accaactctt ccgaaacagc   2460

agcatcaaga gttatttttc tgactgtcaa gtttcaacat tcaggtctgt ccccaacagg   2520

caccacaccg gggtggactc cctgtgtaac ttctcgccac tggctcggag agtagacaga   2580

gttgccatct atgaggaatt tctgcggatg acccggaatg gtacccagct gcagaacttc   2640

accctggaca ggagcagtgt ccttgtggat gggtattttc ccaacagaaa tgagccctta   2700

actgggaatt ctgaccttcc cttctgggct gtcatcctca tcggcttggc aggactcctg   2760

ggactcatca catgcctgat ctgcggtgtc ctggtgacca cccgccggcg gaagaaggaa   2820

ggagaataca acgtccagca acagtgccca ggctactacc agtcacacct agacctggag   2880

gatctgcaat gactggaact tgccggtgcc tggggtgcct ttcccccagc cagggtccaa   2940

agaagcttgg ctggggcaga aataaaccat attggtcgga cacaaaaaaa aaaaaa       2996
```

<210> SEQ ID NO 312
<211> LENGTH: 914
<212> TYPE: PRT
<213> ORGANISM: Homo sapien

<400> SEQUENCE: 312

```
Met Ser Met Val Ser His Ser Gly Ala Leu Cys Pro Pro Leu Ala Phe
 1               5                  10                  15

Leu Gly Pro Pro Gln Trp Thr Trp Glu His Leu Gly Leu Gln Phe Leu
            20                  25                  30

Asn Leu Val Pro Arg Leu Pro Ala Leu Ser Trp Cys Tyr Ser Leu Ser
        35                  40                  45

Thr Ser Pro Ser Pro Thr Cys Gly Met Arg Arg Thr Cys Ser Thr Leu
    50                  55                  60

Ala Pro Gly Ser Ser Thr Pro Arg Arg Gly Ser Phe Arg Ala Trp Ser
65                  70                  75                  80

Leu Phe Lys Ser Thr Ser Val Gly Pro Leu Tyr Ser Gly Cys Arg Leu
                85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205
```

-continued

```
Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300

Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620
```

-continued

```
Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Ser Thr Gln His Phe Tyr Leu Asn Phe Thr Ile
                725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Leu Asn Gln Leu Phe
        755                 760                 765

Arg Asn Ser Ser Ile Lys Ser Tyr Phe Ser Asp Cys Gln Val Ser Thr
    770                 775                 780

Phe Arg Ser Val Pro Asn Arg His His Thr Gly Val Asp Ser Leu Cys
785                 790                 795                 800

Asn Phe Ser Pro Leu Ala Arg Arg Val Asp Arg Val Ala Ile Tyr Glu
                805                 810                 815

Glu Phe Leu Arg Met Thr Arg Asn Gly Thr Gln Leu Gln Asn Phe Thr
            820                 825                 830

Leu Asp Arg Ser Ser Val Leu Val Asp Gly Tyr Phe Pro Asn Arg Asn
        835                 840                 845

Glu Pro Leu Thr Gly Asn Ser Asp Leu Pro Phe Trp Ala Val Ile Leu
    850                 855                 860

Ile Gly Leu Ala Gly Leu Leu Gly Leu Ile Thr Cys Leu Ile Cys Gly
865                 870                 875                 880

Val Leu Val Thr Thr Arg Arg Arg Lys Lys Glu Gly Glu Tyr Asn Val
                885                 890                 895

Gln Gln Gln Cys Pro Gly Tyr Tyr Gln Ser His Leu Asp Leu Glu Asp
            900                 905                 910

Leu Gln
```

```
<210> SEQ ID NO 313
<211> LENGTH: 656
<212> TYPE: DNA
<213> ORGANISM: Homo sapiens

<400> SEQUENCE: 313

acagccagtc ggagctgcaa gtgttctggg tggatcgcgy atatgcactc aaaatgctct      60

ttgtaaagga aagccacaac atgtccaagg gacctgaggc gacttggagg ctgagcaaag     120

tgcagtttgt ctacgactcc tcggagaaaa cccacttcaa agacgcagtc agtgctggga     180

agcacacagc caactcgcac cacctctctg ccttggtcac ccccgctggg aagtcctatg     240

agtgtcaagc tcaacaaacc atttcactgg cctctagtga tccgcagaag acggtcacca     300

tgatcctgtc tgcggtccac atccaacctt ttgacattat ctcagatttt gtcttcagtg     360

aagagcataa atgcccagtg gatgagcggg agcaactgga agaaaccttg ccccctgattt     420

tggggctcat cttgggcctc gtcatcatgg taacactcgc gatttaccac gtccaccaca     480
```

-continued aaatgactgc caaccaggtg cagatccctc gggacagatc ccagtataag cacatgggct 540
agaggccgtt aggcaggcac cccctattcc tgctccccca actggatcag gtagaacaac 600
aaaagcactt ttccatcttg tacacgagat acaccaacat agctacaatc aaacag 656

<210> SEQ ID NO 314
<211> LENGTH: 519
<212> TYPE: DNA
<213> ORGANISM: Homo sapiens

<400> SEQUENCE: 314
tgtgcgtgga ccagtcagct tccgggtgtg actggagcag ggcttgtcgt cttcttcaga 60
gtcactttgc aggggttggt gaagctgctc ccatccatgt acagctccca gtctactgat 120
gtttaaggat ggtctcggtg gttaggccca ctagaataaa ctgagtccaa tacctctaca 180
cagttatgtt taactgggct ctctgacacc gggaggaagg tggcggggtt taggtgttgc 240
aaacttcaat ggttatgcgg ggatgttcac agagcaagct ttggtatcta gctagtctag 300
cattcattag ctaatggtgt cctttggtat ttattaaaat caccacagca taggggggact 360 ttatgtttag gttttgtcta agagttagct tatctgcttc ttgtgctaac agggctattg 420
ctaccaggga ctttggacat gggggccagc gtttggaaac ctcatctagt ttttttgaga 480
gataggccac tggccttgga cctcggccgc gaccacgct 519

<210> SEQ ID NO 315
<211> LENGTH: 441
<212> TYPE: DNA
<213> ORGANISM: Homo sapiens

<400> SEQUENCE: 315
cacagagcgt ttattgacac caccactcct gaaaattggg atttcttatt aggttcccct 60
aaaagttccc atgttgatta catgtaaata gtcacatata tacaatgaag gcagtttctt 120
cagaggcaac cagggtttat agtgctaggt aaatgtcatc tcttttgtgc tactgactca 180
ttgtcaaacg tctctgcact gttttcagcc tctccacgtt gcctctgtcc tgcttcttag 240
ttccttcttt gtgacaaacc aaaagaataa gaggatttag aacaggactg cttttcccct 300
atgatttaaa aattccaatg actttcgccc ttgggagaaa tttccaagga aatctctctc 360
gctcgctctc tccgttttcc tttgtgagct tctgggggag ggttagtggt gactttttga 420
tacgaaaaaa tgcattttgt g 441

<210> SEQ ID NO 316
<211> LENGTH: 247
<212> TYPE: DNA
<213> ORGANISM: Homo sapiens

<400> SEQUENCE: 316
tggcgcggct gctggatttc accttcttgc acctgccggt gagcgcctgg ggtctaaagg 60
ggcgggatac tccattatgg cccctcgccc tgtagggctg gaatagttag aaaaggcaac 120
ccagtctagc ttggtaagaa gagagacatg cccccaacct cggcgccctt tttcctcacg 180
atctgctgtc cttacttcag cgactgcagg agcttcacct gcaagaaaac agcattgagc 240
tgctgac 247

<210> SEQ ID NO 317
<211> LENGTH: 409
<212> TYPE: DNA

-continued

<213> ORGANISM: Homo sapiens

<400> SEQUENCE: 317
tgacagggct cctggagttg ttaagtcacc aagtagctgc aggggatgga cactgcccca 60
cacgatgtgg gatgaacagc agccttggtt tgtagcccag ggtgtccatg gatttgaccc 120
gaatgctccc tggaggccct gtggcgagga caggcactgg atggtccaga ccctctggct 180
ggaggagtgg tggagccagg actgggcctt cagccatgag ggctagaata acctgacctc 240
ttgcattcta acactgggtc attaatgaca cctttccagt ggatgttgca aaaaccaaca 300
ctgtcaggaa cctggccctg ggagggctca ggtgagctca caaggagagg tcaagccaag 360
ccaaagggta ggkaacacac aacaccaggg gaaaccagcc cccaaacca 409

<210> SEQ ID NO 318
<211> LENGTH: 320
<212> TYPE: DNA
<213> ORGANISM: Homo sapiens
<220> FEATURE:
<221> NAME/KEY: misc_feature
<222> LOCATION: (1)...(320)
<223> OTHER INFORMATION: n = A,T,C or G

<400> SEQUENCE: 318
caaggnagat cttaagnggg gtcntatgta agtgtgctcc tggctccagg gttcctggag 60
cctcacgagg tcaggggaac ccttgtagaa ctccaccagc agcatcatct cgtgaaggat 120
gtcattggtc aggaagctgt cctggacgta ggccatctcc acatccatgg ggatgccata 180
gtcactgggc ctttgctcgg gaggaggcat cacccagaaa ggcgagatct tggactcggg 240
gcctgggttg ccagaatagt aaggggagca nagcagggcg aggcagggct ggaagccatt 300
gctggagccc tgcagccgca 320

<210> SEQ ID NO 319
<211> LENGTH: 212
<212> TYPE: DNA
<213> ORGANISM: Homo sapiens
<220> FEATURE:
<221> NAME/KEY: misc_feature
<222> LOCATION: (1)...(212)
<223> OTHER INFORMATION: n = A,T,C or G

<400> SEQUENCE: 319
tgaagcaata gcgcccccat tttacaggcg gagcatggaa gccagagagg tgggtggggg 60
agggggtcct tccctggctc aggcagatgg gaagatgagg aagccgctga agacgctgtc 120
ggcctcagag ccctggtaaa tgtgaccctt tttggggtct ttttcaaccc anacctggtc 180
accctgctgc agacctcggc cgcgaccacg ct 212

<210> SEQ ID NO 320
<211> LENGTH: 769
<212> TYPE: DNA
<213> ORGANISM: Homo sapiens

<400> SEQUENCE: 320
tggaggtgta gcagtgagag gagatytcag gcaagagtgt cacagcagag ccctaaascc 60
tccaactcac cagtgagaga tgagactgcc cagtactcag ccttcatctc ctgggccacc 120
tggagggcgt ctttctccat cagcgcatac tgagcagggg tactcagatc cttcttggaa 180
cctacaagga agagaagcac actggaaggg tcattctcct tcagggcatc ggccagccac 240
tgcctgccat gggaggtgga aagtaaggga tgagtgagtc tgcagggccc ctcccactga 300

-continued

```
cattcatagg cccaattacc ccctctctgg tcctacatgc attcttcttc ttcctgacca    360

cccctctgtt ctgaaccctc tcttcccgga gcctcccatt atattgcagg atgctcactt    420

acttggtatg ttccagagat gccacatcat tcaggttgaa gacaatgatg atggcttgga    480

agagtggcag aaacagcccc aggttgacag ggaagacact actgctcatt tccccaatcc    540

ttccagctcc atatgagaaa gccatgtgca ctctgagacc cacctacccc acttcaccca    600

gcccccttacc ttgagctcct ctatagtagg ttgatgcaat gcatttgaac ctctcctgcc    660

cagcggtatc ccaactggaa ggaaggaaga gtgaagcaca ggtatgtatc ttggggggtg    720

tgggtgctgg ggagaaggga tagctggaag gggtgtggaa gcactcaca                769
```

```
<210> SEQ ID NO 321
<211> LENGTH: 690
<212> TYPE: DNA
<213> ORGANISM: Homo sapiens
<220> FEATURE:
<221> NAME/KEY: misc_feature
<222> LOCATION: (1)...(690)
<223> OTHER INFORMATION: n = A,T,C or G

<400> SEQUENCE: 321

tgggctgtgg gcggcacctg tgctctgcag gccagacagc gatagaagcc tttgtctgtg     60

cctactcccc cggaggcaac tgggaggtca acgggaagac aatcatcccc tataagaagg    120

gtgcctggtg ttcgctctgc acagccagtg tctcaggctg cttcaaagcc tgggaccatg    180

cagggggggct ctgtgaggtc cccaggaatc cttgtcgcat gagctgccag aaccatggac    240

gtctcaacat cagcacctgc cactgccact gtccccctgg ctacacgggc agatactgcc    300

aagtgaggtg cagcctgcag tgtgtgcacg gccggttccg ggaggaggag tgctcgtgcg    360

tctgtgacat cggctacggg ggagcccagt gtgccaccaa ggtgcatttt cccttccaca    420

cctgtgacct gaggatcgac ggagactgct tcatggtgtc ttcagaggca gacacctatt    480

acagaagcca ggatgaaatg tcagaggaat ggcggggtgc tggcccagat caagagccag    540

aaagtgcagg acatcctcgc cttctatctg ggccgcctgg agaccaccaa cgaggtgact    600

gacagtgact ttgagaccag gaacttctgg atngggctca cctacaagac cgccaaggac    660

tccttncgct gggccacagg ggagcaccag                                     690
```

```
<210> SEQ ID NO 322
<211> LENGTH: 104
<212> TYPE: DNA
<213> ORGANISM: Homo sapiens

<400> SEQUENCE: 322

gtcgcaagcc ggagcaccac catgtagcct ttcccgaagt accggacctt ctcctcctcc     60

acgctcacat cacggacatc atggagcagg accaccacct ggtc                     104
```

```
<210> SEQ ID NO 323
<211> LENGTH: 118
<212> TYPE: DNA
<213> ORGANISM: Homo sapiens

<400> SEQUENCE: 323

gggccctggg cgcttccaaa tgacccagga ggtggtctgc gacgaatgcc ctaatgtcaa     60

actagtgaat gaagaacgaa cactggaagt agaaatagag cctggggtga gagacgga      118
```

```
<210> SEQ ID NO 324
```

-continued

<211> LENGTH: 354
<212> TYPE: DNA
<213> ORGANISM: Homo sapiens

<400> SEQUENCE: 324
tgctctccgg gagcttgaag aagaaactgg ctacaaaggg gacattgccg aatgttctcc 60
agcggtctgt atggacccag gcttgtcaaa ctgtactata cacatcgtga cagtcaccat 120
taacggagat gatgccgaaa acgcaaggcc gaagccaaag ccaggggatg gagagtttgt 180
ggaagtcatt tctttaccca agaatgacct gctgcagaga cttgatgctc tggtagctga 240
agaacatctc acagtggacg ccagggtcta ttcctacgct ctagcgctga aacatgcaaa 300
tgcaaagcca tttgaagtgc ccttcttgaa attttaagcc caaatatgac actg 354

<210> SEQ ID NO 325
<211> LENGTH: 642
<212> TYPE: DNA
<213> ORGANISM: Homo sapiens
<220> FEATURE:
<221> NAME/KEY: misc_feature
<222> LOCATION: (1)...(642)
<223> OTHER INFORMATION: n = A,T,C or G

<400> SEQUENCE: 325
ncatgcttga atgggctcct ggtgagagat tgccccctgg tggtgaaaca atcgtgtgtg 60
cccactgata ccaagaccaa tgaaagagac acagttaagc agcaatccat ctcatttcca 120
ggcacttcaa taggtcgctg attggtcctt gcaccagcag tggtagtcgt acctatttca 180
gagaggtctg aaattcaggt tcttagtttg ccagggacag gccctacctt atattttttt 240
ccatcttcat catccacttc tgcttacagt ttgctgctta caataactta atgatggatt 300
gagttatctg ggtggtctct agccatctgg gcagtgtggt tctgtctaac caaagggcat 360
tggcctcaaa ccctgcattt ggtttagggg ctaacagagc tcctcagata atcttcacac 420
acatgtaact gctggagatc ttattctatt atgaataaga aacgagaagt ttttccaaag 480
tgttagtcag gatctgaagg ctgtcattca gataacccag cttttccttt tggcttttag 540
cccattcaga ctttgccaga gtcaagccaa ggattgcttt tttgctacag ttttctgcca 600
aatggcctag ttcctgagta cctggaaacc agagagaaag ag 642

<210> SEQ ID NO 326
<211> LENGTH: 455
<212> TYPE: DNA
<213> ORGANISM: Homo sapiens

<400> SEQUENCE: 326
tccgtgagga tgagcttcga gtccttcacc aggcactgca ggggcacagt cacgtcaatc 60
accttcacct tctcgctctt cctgctcttg tcattgacaa acttcccgta ccaggcattg 120
acgatgatga ggcccattct ggactcttct gcctcaatta tccttcggac agattcctgc 180
atcagccgga cagcggactc cgcctcttgc ttcttctgca gcacatcggt ggcggcgctt 240
tccctctgct tctccaattc cttctctttc tgagccctga ggtatggttt gatgatcaga 300
cggtgcatgg caaagtagac cactagaggc cccacggtgg catagaacat ggcgctgggc 360
agaagctggt ccgtcaagtg aatagggaag aagtatgtct gactggccct gttgagcttg 420
actttgagag aaacgccctg tggaactcca acgct 455

<210> SEQ ID NO 327
<211> LENGTH: 321

-continued

<212> TYPE: DNA
<213> ORGANISM: Homo sapiens

<400> SEQUENCE: 327
ttcactgtga actcgcagtc ctcgatgaac tcgcacagat gtgacagccc tgtctccttg 60
ctctctgagt tctcttcaat gatgctgatg atgcagtcca cgatagcgcg cttatactca 120
aagccaccct cttcccgcag catggtgaac aggaagttca taaggacggc gtgtttgcga 180
ggatatttct gacacagggc actgatggcc tggacaacca ccaccttgaa ttcatccgag 240
atttctgaca tgaaggagga gatctgcttc atgaggcggt cgatgctgct ctcgctgccc 300
gtcttaagga gggtggtgat g 321

<210> SEQ ID NO 328
<211> LENGTH: 476
<212> TYPE: DNA
<213> ORGANISM: Homo sapiens
<220> FEATURE:
<221> NAME/KEY: misc_feature
<222> LOCATION: (1)...(476)
<223> OTHER INFORMATION: n = A,T,C or G

<400> SEQUENCE: 328
tgcaggaggg gccatggggg ctgtgaatgg gatgcagccc catggtgtcc ctgataaatc 60
cagtgtgcag tctgatgaag tctgggtggg tgtggtctac gggctggcag ctaccatgat 120
ccaagaggta atgcactcct tttcccatct ctccaccatc tgtatcctgg ccmagaaaaa 180
cttcccttca aaccaaccaa aatttccttt caaaggcata acccaaatgc catccttggt 240
ccggtctaat aaagcctccc ccatttttcc cctggtatgc attcccaggc tccctggcct 300
tncagggctt nctgtctgtg ggtcatagtt tatctcctcc cacttgctgg gagctccttg 360
aaggcaaaga ctctactgcc tccatctatc cagtggaagt ggctcttcag agggtgccaa 420
gttagtatgt atgactgtca tctctcccaa cagggcctga cttggsaggg cttcca 476

<210> SEQ ID NO 329
<211> LENGTH: 340
<212> TYPE: DNA
<213> ORGANISM: Homo sapiens

<400> SEQUENCE: 329
cgagggagat tgccagcacc ctgatggaga gtgagatgat ggagatcttg tcagtgctag 60
ctaagggtga ccacagccct gtcacaaggg ctgctgcagc ctgcctggac aaagcagtgg 120
aatatgggct tatccaaccc aaccaagatg gagagtgagg gggttgtccc tgggcccaag 180
gctcatgcac acgctaccta ttgtggcacg gagagtaagg acggaagcag ctttggctgg 240
tggtggctgg catgcccaat actcttgccc atcctcgctt gctgccctag gatgtcctct 300
gttctgagtc agcggccacg ttcagtcaca cagccctgct 340

<210> SEQ ID NO 330
<211> LENGTH: 277
<212> TYPE: DNA
<213> ORGANISM: Homo sapiens

<400> SEQUENCE: 330
tgtcaccatc acattggtgc caaataccca gaagacatcg tagatgaaga gtccgcccag 60
caggatgcag ccagtgctga cattgttgag gtgcaggagc tctactccat taagggagaa 120
ggccaggcca aaaaggttgt tggcaatcca gtgcttcctc agcaggtacc agacgccaac 180

-continued

```
gatgctgctc aggcccaggc acaccaggtc cttggtgtca aattcataat tgatgatctc    240

ctccttgttt tcccagaacc ctgtgtgaag agcagac                             277


<210> SEQ ID NO 331
<211> LENGTH: 136
<212> TYPE: DNA
<213> ORGANISM: Homo sapiens

<400> SEQUENCE: 331

ttgcttccca cctcctttct ctgtcctctc ctgaggttct gccttacaat ggggacactg     60

atacaaacca cacacacaat gaggatgaaa acagataaca ggtaaaatga cctcacctgc    120

ccgggcggcc gctcga                                                    136


<210> SEQ ID NO 332
<211> LENGTH: 184
<212> TYPE: DNA
<213> ORGANISM: Homo sapiens

<400> SEQUENCE: 332

ttgtgagata aacgcagata ctgcaatgca ttaaaacgct tgaaatactc atcagggatg     60

ttgctgatct tattgttgtc taagtagaga gttagaagag agacagggag accagaaggc    120

agtctggcta tctgattgaa gctcaagtca aggtattcga gtgatttaag acctttaaaa    180

gcag                                                                 184


<210> SEQ ID NO 333
<211> LENGTH: 384
<212> TYPE: DNA
<213> ORGANISM: Homo sapiens

<400> SEQUENCE: 333

cggaaaactt cgaggaattg ctcaaagtgc tgggggtgaa tgtgatgctg aggaagattg     60

ctgtggctgc agcgtccaag ccagcagtgg agatcaaaca ggagggagac actttctaca    120

tcaaaacctc caccaccgtg cgcaccacag agattaactt caaggttggg gaggagtttg    180

aggagcagac tgtggatggg aggccctgta agagcctggt gaaatgggag agtgagaata    240

aaatggtctg tgagcagaag ctcctgaagg gagagggccc caagacctcg tggaccagag    300

aactgaccaa cgatggggaa ctgatcctga ccatgacggc ggatgacgtt gtgtgcacca    360

gggtctacgt ccgagagtga gcgg                                           384


<210> SEQ ID NO 334
<211> LENGTH: 169
<212> TYPE: DNA
<213> ORGANISM: Homo sapiens
<220> FEATURE:
<221> NAME/KEY: misc_feature
<222> LOCATION: (1)...(169)
<223> OTHER INFORMATION: n = A,T,C or G

<400> SEQUENCE: 334

cnacaaacag agcagacacc ctggatccgg tcctgctact ggccaggacg gctggaccgt     60

aaaattgaat ttccacttcc tgaccgccgc cagaagagat tgattttctc cactatcact    120

agcaagatga acctctctga ggaggttgac ttggaagact atgtngccc                169


<210> SEQ ID NO 335
<211> LENGTH: 185
<212> TYPE: DNA
<213> ORGANISM: Homo sapiens
```

-continued

<400> SEQUENCE: 335
ccaggtttgc agcccaggct gcacatcagg ggactgcctc gcaatacttc atgctgttgc 60
tgctgactga tggtgctgtg acggatgtgg aagccacacg tgaggctgtg gtgcgtgcct 120
cgaacctgcc catgtcagtg atcattgtgg gtgtgggtgg tgctgacttt gaggccatgg 180
agcag 185

<210> SEQ ID NO 336
<211> LENGTH: 358
<212> TYPE: DNA
<213> ORGANISM: Homo sapiens
<220> FEATURE:
<221> NAME/KEY: misc_feature
<222> LOCATION: (1)...(358)
<223> OTHER INFORMATION: n = A,T,C or G

<400> SEQUENCE: 336
ctgcccctgc cttacggcgg ccaganacac acccaggatg gcattggccc caaacttgga 60
tttgttctca gtcccatcca actccagcat caggttgtcc agtttctctt gctccaccac 120
agagagacct gagctgatga gggctggcgc gatggtggag ttgatgtggt ccactgcctt 180
caggacacct ttgcctaagt aacgctgttt gtctccatcc ctcagctcca gggcctcata 240
gatgcccgta gaggctccac tgggcactgc agcccggaaa agacctttgg cagtatagag 300
atccacctcc actgtggggt tcccgcggga gtccaggatc tcccgggccc agatcttc 358

<210> SEQ ID NO 337
<211> LENGTH: 271
<212> TYPE: DNA
<213> ORGANISM: Homo sapiens
<220> FEATURE:
<221> NAME/KEY: misc_feature
<222> LOCATION: (1)...(271)
<223> OTHER INFORMATION: n = A,T,C or G

<400> SEQUENCE: 337
cacaaagcca ccagccnggg aaatcagaat ttacttgatg caactgactt gtaatagcca 60
gaaatcctgc ccagcatggg attcagaacc tggtctgcaa ccaaatccac cgtcaaagtt 120
catacaggat aaaacaaatt caattgcctt ttccacatta atagcatcaa gcttccccaa 180
caaagccaaa gttgccaccg cacaaaaaga gaatcttgtg tcaatttctc cctactttat 240
aaaagtagat ttttcacatc ccatgaagca g 271

<210> SEQ ID NO 338
<211> LENGTH: 326
<212> TYPE: DNA
<213> ORGANISM: Homo sapiens
<220> FEATURE:
<221> NAME/KEY: misc_feature
<222> LOCATION: (1)...(326)
<223> OTHER INFORMATION: n = A,T,C or G

<400> SEQUENCE: 338
ctgtgctccc gactngnnca tctcaggtac caccgactgc actgggcggg gccctctggg 60
gggaaaggct ccacggggca gggatacatc tcgaggccag tcatcctctg gaggcagccc 120
aatcaggtca aagattttgc ccaactggtc ggcttcagag tttccacaga agagaggctt 180
tcgacgaaac atctctgcaa agatacagcc aacactccac atgtccacag gtgttgcata 240
tgtggactgc agaagaactt cgggagctcg gtaccagagt gtaacaacca cgggtgtaag 300

-continued tgccatctgg tagctgtaga ttctgg 326

<210> SEQ ID NO 339
<211> LENGTH: 260
<212> TYPE: DNA
<213> ORGANISM: Homo sapiens
<220> FEATURE:
<221> NAME/KEY: misc_feature
<222> LOCATION: (1)...(260)
<223> OTHER INFORMATION: n = A,T,C or G

<400> SEQUENCE: 339
ttcacctgag gactcatttc gtgccctttg ttgacttcaa gcaaagncct tcanggtctn 60
caaggacgnc acatttccac ttgcgaatgn nctcanggct catcttgaag aanaagnanc 120
ccaagtgctg gatcccagac tcgggggtaa ccttgtgggt aagagctcat ccagtttatg 180
ctttaggacg tccanctact cgggggagct ggaagcctgc gtggatgcgg ccctgctgga 240
cctcggccgc gaccacgcta 260

<210> SEQ ID NO 340
<211> LENGTH: 220
<212> TYPE: DNA
<213> ORGANISM: Homo sapiens
<220> FEATURE:
<221> NAME/KEY: misc_feature
<222> LOCATION: (1)...(220)
<223> OTHER INFORMATION: n = A,T,C or G

<400> SEQUENCE: 340
ctggaagccc ggctnggnct ggcagcggaa ggagccaggc aggttcacgc agcggtgctg 60
gcagtagcgg tagcggcact cgtctatgtc cacacactcg ggcccgatct tgcggtaacc 120
atcagggcag gtgcactgat aggagccagg caagttatgg cagtcctggc tggggcgaca 180
gtcgtgcagg gcctgggcac actcgtccac atccacacag 220

<210> SEQ ID NO 341
<211> LENGTH: 384
<212> TYPE: DNA
<213> ORGANISM: Homo sapiens

<400> SEQUENCE: 341
ctgctaccag gggagcgaga gctgactatc ccagcctcgg ctaatgtatt ctacgccatg 60
gatggagctt cacacgattt cctcctgcgg cagcggcgaa ggtcctctac tgctacaccg 120
ggcgtcacca gtggcccgtc tgcctcagga actcctccga gtgagggagg agggggctcc 180
tttcccagga tcaaggccac agggaggaag attgcacggg cactgttctg aggaggaagc 240
cccgttggct tacagaagtc atggtgttca taccagatgt gggtagccat cctgaatggt 300
ggcaattata tcacattgag acagaaattc agaaagggag ccagccaccc tggggcagtg 360
aagtgccact ggtttaccag acag 384

<210> SEQ ID NO 342
<211> LENGTH: 245
<212> TYPE: DNA
<213> ORGANISM: Homo sapiens

<400> SEQUENCE: 342
ctggctaagc tcatcattgt tactggtggg caccatgtcc ttgaagcttc aggcaagcaa 60
tgtaaccaac aagaatgacc ccaagtccat caactctcga gtcttcattg gaaacctcaa 120
cacagctctg gtgaagaaat cagatgtgga gaccatcttc tctaagtatg gccgtgtggc 180

-continued

```
cggctgttct gtgcacaagg gctatgcctt tgttcagtac tccaatgagc gccatgcccg    240

ggcag                                                                245


<210> SEQ ID NO 343
<211> LENGTH: 611
<212> TYPE: DNA
<213> ORGANISM: Homo sapiens

<400> SEQUENCE: 343

ccaaaaaaat caagatttaa ttttttttatt tgcactgaaa aactaatcat aactgttaat    60

tctcagccat ctttgaagct tgaaagaaga gtctttggta ttttgtaaac gttagcagac    120

tttcctgcca gtgtcagaaa atcctattta tgaatcctgt cggtattcct tggtatctga    180

aaaaaatacc aaatagtacc atacatgagt tatttctaag tttgaaaaat aaaaagaaat    240

tgcatcacac taattacaaa atacaagttc tggaaaaaat atttttcttc attttaaaac    300

ttttttaac taataatggc tttgaaagaa gaggcttaat ttgggggtgg taactaaaat    360

caaaagaaat gattgacttg agggtctctg tttggtaaga atacatcatt agcttaaata    420

agcagcagaa ggttagtttt aattatgtag cttctgttaa tattaagtgt tttttgtctg    480

ttttacctca atttgaacag ataagtttgc ctgcatgctg gacatgcctc agaaccatga    540

atagcccgta ctagatcttg ggaacatgga tcttagagtc ctttggaata agttcttata    600

taaatacccc c                                                         611


<210> SEQ ID NO 344
<211> LENGTH: 311
<212> TYPE: DNA
<213> ORGANISM: Homo sapiens
<220> FEATURE:
<221> NAME/KEY: misc_feature
<222> LOCATION: (1)...(311)
<223> OTHER INFORMATION: n = A,T,C or G

<400> SEQUENCE: 344

nctcgaaaaa gcccaagaca gcagaagcag acacctccag tgaactagca aagaaaagca    60

aagaagtatt cagaaaagag atgtcccagt tcatcgtcca gtgcctgaac ccttaccgga    120

aacctgactg caaagtggga agaattacca caactgaaga ctttaaacat ctggctcgca    180

agctgactca cggtgttatg aataaggagc tgaagtactg taagaatcct gaggacctgg    240

agtgcaatga gaatgtgaaa cacaaaacca aggantacat taanaagtac atgcannaan    300

tttggggctt g                                                         311


<210> SEQ ID NO 345
<211> LENGTH: 201
<212> TYPE: DNA
<213> ORGANISM: Homo sapiens

<400> SEQUENCE: 345

cacacggtca tcccgactgc caacctggag gcccaggccc tgtggaagga gccgggcagc    60

aatgtcacca tgagtgtgga tgctgagtgt gtgcccatgg tcagggacct tctcaggtac    120

ttctactccc gaaggattga catcaccctg tcgtcagtca agtgcttcca caagctggcc    180

tctgcctatg gggccaggca g                                              201


<210> SEQ ID NO 346
<211> LENGTH: 370
<212> TYPE: DNA
```

-continued

<213> ORGANISM: Homo sapiens

<400> SEQUENCE: 346
ctgctccagg gcgtggtgtg ccttcgtggc ctctgcctcc tccgaggagc caggctgtgt 60
tctcttcaga atgttctgga gcagcagttt gaggcgggtg atgcgttgga agggcagaat 120
cagaaaggac ttgagggaaa ggcgctggca gacggggtcg ctctccagct tctccaagac 180
ctcccggaaa ttgctgttgc tattcatcag gctctggaag gtgcgttcct gataggtctg 240
gttggtgaca taaggcaggt agacccggcg gaagtctggg gcgtggttca ggactacgtc 300
acatacttgg aaggagaaga tattgttctc aaagttctct tccaggtctg aaaggaacgt 360
ggcgctgacg 370

<210> SEQ ID NO 347
<211> LENGTH: 416
<212> TYPE: DNA
<213> ORGANISM: Homo sapiens
<220> FEATURE:
<221> NAME/KEY: misc_feature
<222> LOCATION: (1)...(416)
<223> OTHER INFORMATION: n = A,T,C or G

<400> SEQUENCE: 347
ctgttgtgct gtgtatggac gtgggcttta ccatgagtaa ctccattcct ggtatagaat 60
ccccatttga acaagcaaag aaggtgataa ccatgtttgt acagcgacag gtgtttgctg 120
agaacaagga tgagattgct ttagtcctgt ttggtacaga tggcactgac aatccccttt 180
ctggtgggga tcagtatcag aacatcacag tgcacagaca tctgatgcta ccagattttg 240
atttgctgga ggacattgaa agcaaaatcc aaccaggttc tcaacaggct gacttcctgg 300
atgcactaat cgtgagcatg gatgtgattc aacatgaaac aataggaaag aagtttggag 360
aagaggcata ttgaaatatt cactgacctc aagcagcccg attcagcaaa agtcan 416

<210> SEQ ID NO 348
<211> LENGTH: 351
<212> TYPE: DNA
<213> ORGANISM: Homo sapiens

<400> SEQUENCE: 348
gtacaggaga ggatggcagg tgcagagcgg gcactgagct ctgcaggtga aagggctcgg 60
cagttggatg ctctcctgga ggctctgaaa ttgaaacggg caggaaatag tctggcagcc 120
tctacagcag aagaaacggc aggcagtgcc cagggacgag caggagacag atgccttcct 180
cttgtctcaa ctgcaaagag gcgttccttc ctctttcact aatcctcctc agcacagacc 240
ctttacgggt gtcaggctgg gggacagtaa ggtctttccc ttcccacaag gccatatctc 300
aggctgtctc agtgggggga aaccttggac aatacccggg ctttcttggg c 351

<210> SEQ ID NO 349
<211> LENGTH: 207
<212> TYPE: DNA
<213> ORGANISM: Homo sapiens
<220> FEATURE:
<221> NAME/KEY: misc_feature
<222> LOCATION: (1)...(207)
<223> OTHER INFORMATION: n = A,T,C or G

<400> SEQUENCE: 349
nccgggacat ctccaccctc aacagtggca agaagagcct ggagactgaa cacaaggcct 60
tgaccagtga gattgcactg ctgcagtcca ggctgaagac agagggctct gatctgtgcg 120

-continued acagagtgag cgaaatgcag aagctggatg cacaggtcaa ggagctggtg ctgaagtcgg 180
cggtggaggc tgagcgcctg gtggctg 207

<210> SEQ ID NO 350
<211> LENGTH: 323
<212> TYPE: DNA
<213> ORGANISM: Homo sapiens

<400> SEQUENCE: 350
ccatacaggg ctgttgccca ggccctagag gtcattcctc gtaccctgat ccagaactgt 60
ggggccagca ccatccgtct acttacctcc cttcgggcca agcacaccca ggagaactgt 120
gagacctggg gtgtaaatgg tgagacgggt actttggtgg acatgaagga actgggcata 180
tgggagccat tggctgtgaa gctgcagact tataagacag cagtggagac ggcagttctg 240
ctactgcgaa ttgatgacat cgtttcaggc cacgaaaaga aaggcgatga ccagagccgg 300
caaggcgggg ctcctgatgc tgg 323

<210> SEQ ID NO 351
<211> LENGTH: 353
<212> TYPE: DNA
<213> ORGANISM: Homo sapiens
<220> FEATURE:
<221> NAME/KEY: misc_feature
<222> LOCATION: (1)...(353)
<223> OTHER INFORMATION: n = A,T,C or G

<400> SEQUENCE: 351
cgccgcatcc cntggtccct tccantccct tttcctttnt cngggaacgt gtatgcggtt 60
tgtttttgtt ttgtagggtt tttttccttc tccacctctc cctgtctctt ttgctccatg 120
ttgtccgttt ctgtggggtt aggtttatgt ttttaatcat ctgaggtcac gtctatttcc 180
tccggactcg cctgcttggt ggcgattctc caccggttaa tatggtgcgt ccctttttttc 240 ttttgttgcg aatctgagcc ttcttcctcc agcttctgcc ttttgaactt tgttcttcgg 300
ttctgaaacc atacttttac ctgagtttcc gtgaggctga ggctgtgtgc caa 353

<210> SEQ ID NO 352
<211> LENGTH: 467
<212> TYPE: DNA
<213> ORGANISM: Homo sapiens

<400> SEQUENCE: 352
ctgcccacac tgatcacttg cgagatgtcc ttagggtaca agaacaggaa ttgaagtctg 60
aatttgagca gaacctgtct gagaaactct ctgaacaaga attacaattt cgtcgtctca 120
gtcaagagca agttgacaac tttactctgg atataaatac tgcctatgcc agactcagag 180
gaatcgaaca ggctgttcag agccatgcag ttgctgaaga ggaagccaga aaagcccacc 240
aactctggct ttcagtggag gcattaaagt acagcatgaa gacctcatct gcagaaacac 300
ctactatccc gctgggtagt gcagttgagg ccatcaaagc caactgttct gataatgaat 360
tcacccaagc tttaaccgca gctatccctc cagagtccct gacccgtggg gtgtacagtg 420
aagagaccct tagagcccgt ttctatgctg ttcaaaaact ggcccga 467

<210> SEQ ID NO 353
<211> LENGTH: 350
<212> TYPE: DNA
<213> ORGANISM: Homo sapiens -continued

<400> SEQUENCE: 353
ctgctgcagc cacagtagtt cctcccatgg tgggtggccc tcctggtcct gctggcccag 60
gaaatctgtc cccaccagga acagcccctg gaaaacggcc ccgtcctcta ccaccttgtg 120
gaaatgctgc acgggaactg cctcctggag gaccagcttt accttcccca gacatttgtc 180
ctgattgtgt agttttcctg gactgcattt caaattgact caggaactgt ttattgcatg 240
gagttacaac aggattctga ccatgaagtt ctcttttagg taacagatcc attaactttt 300
ttgaagatgc ttcagatcca acaccaacaa gggcaaaccc ctttgactgg 350

<210> SEQ ID NO 354
<211> LENGTH: 351
<212> TYPE: DNA
<213> ORGANISM: Homo sapiens

<400> SEQUENCE: 354
atttagatga gatctgaggc atggagacat ggagacagta tacagactcc tagatttaag 60
ttttaggttt tttgcttttc taatcaccaa ttcttatata caatgtatat tttagactcg 120
agcagatgat catcttcatc ttaagtcatt cctttttgact gagtatggca ggattagagg 180
gaatggcagt atagatcaat gtctttttct gtaaagtata ggaaaaacca gagaggaaaa 240
aaagagctga caattggaag gtagtagaaa attgacgata atttcttctt aacaaataat 300
agttgtatat acaaggaggc tagtcaacca gattttattt gttgagggcg a 351

<210> SEQ ID NO 355
<211> LENGTH: 308
<212> TYPE: DNA
<213> ORGANISM: Homo sapiens

<400> SEQUENCE: 355
ttttggcgca agttttacag attttattaa agtcgaagct attggtcttg gaagatgaaa 60
atgcaaatgt tgatgaggtg gaattgaagc cagatacctt aataaaatta tatcttggtt 120
ataaaaataa gaaattaagg gttaacatca atgtgccaat gaaaaccgaa cagaagcagg 180
aacaagaaac cacacacaaa aacatcgagg aagaccgcaa actactgatt caggcggcca 240
tcgtgagaat catgaagatg aggaaggttc tgaaacacca gcagttactt ggcgaggtcc 300
tcactcag 308

<210> SEQ ID NO 356
<211> LENGTH: 207
<212> TYPE: DNA
<213> ORGANISM: Homo sapiens

<400> SEQUENCE: 356
ctgtcccaag tgctcccaga aggcaggatt ctgaagacca ctccagcgat atgttcaact 60
atgaagaata ctgcaccgcc aacgcagtca ctgggccttg ccgtgcatcc ttcccacgct 120
ggtactttga cgtggagagg aactcctgca ataacttcat ctatggaggc tgccggggca 180
ataagaacag ctaccgctct gaggagg 207

<210> SEQ ID NO 357
<211> LENGTH: 188
<212> TYPE: DNA
<213> ORGANISM: Homo sapiens
<220> FEATURE:
<221> NAME/KEY: misc_feature
<222> LOCATION: (1)...(188)
<223> OTHER INFORMATION: n = A,T,C or G -continued

<400> SEQUENCE: 357
tcgaccacgc cctcgtagcg catgngctnc aggacgatgc tcagagtgat gaacaccccg 60
gtgcggccca cgccagcact gcagtgcacc gtgataggcc catcctgtcc aaactgctcc 120
ttggtcttat gcacctgccc gatgaagtca atgaatccct cgcctgtctt gggcacgccc 180
tgctctgg 188

<210> SEQ ID NO 358
<211> LENGTH: 291
<212> TYPE: DNA
<213> ORGANISM: Homo sapiens

<400> SEQUENCE: 358
ctgggagcat cggcaagcta ctgccttaaa atccgatctc cccgagtgca caatttctgt 60
cccttttaag ggttcacaac actaaagatt tcacatgaaa gggttgtgat tgatttgagc 120
aggcaggcgg tacgtgacag gggctgcatg caccggtggt cagagagaaa cagaacaggg 180
cagggaattt cacaatgttc ttctatacaa tggctggaat ctatgaataa catcagtttc 240
taagttatgg gttgattttt aactactggg tttaggccag gcaggcccag g 291

<210> SEQ ID NO 359
<211> LENGTH: 117
<212> TYPE: DNA
<213> ORGANISM: Homo sapiens
<220> FEATURE:
<221> NAME/KEY: misc_feature
<222> LOCATION: (1)...(117)
<223> OTHER INFORMATION: n = A,T,C or G

<400> SEQUENCE: 359
gccaccacac tccagcctgg gcaatacagc aagactgtct caaaaaaaaa aaaaaaaaaa 60
cccaaaaaaa ctcaaaaang taatgaatga tacccaangn gccttttcta gaaaaag 117

<210> SEQ ID NO 360
<211> LENGTH: 394
<212> TYPE: DNA
<213> ORGANISM: Homo sapiens

<400> SEQUENCE: 360
ctgttcctct ggggtggtcc agttctagag tgggagaaag ggagtcaggc gcattgggaa 60
tcgtggttcc agtctggttg cagaatctgc acatttgcca agaaattttc cctgtttgga 120
aagtttgccc cagctttccc gggcacacca ccttttgtcc caagtgtctg ccggtcgacc 180
aatctgcctg ccacacattg accaagccag acccggttca cccagctcga ggatcccagg 240
ttgaagagtg gccccttgag gccctggaaa gaccaatcac tggacttctt cccttgagag 300
tcagaggtca cccgtgattc tgcctgcacc ttatcattga tctgcagtga tttctgcaaa 360
tcaagagaaa ctctgcaggg cactcccctg tttc 394

<210> SEQ ID NO 361
<211> LENGTH: 394
<212> TYPE: DNA
<213> ORGANISM: Homo sapiens
<220> FEATURE:
<221> NAME/KEY: misc_feature
<222> LOCATION: (1)...(394)
<223> OTHER INFORMATION: n = A,T,C or G

<400> SEQUENCE: 361

-continued

```
ctgggcggat agcaccgggc atattttntt natggatgag gtctggcacc ctgagcagtc     60

cagcgaggac ttggtcttag ttgagcaatt tggctaggag gatagtatgc agcacggttc    120

tgagtctgtg ggatagctgc catgaagtaa cctgaaggag gtgctggctg gtaggggttg    180

attacagggt tgggaacagc tcgtacactt gccattctct gcatatactg gttagtgagg    240

tgagcctggc gctcttcttt gcgctgagct aaagctacat acaatggctt tgtggacctc    300

ggccgcgacc acgctaagcc gaattccagc acactggcgg ccgttactag tggatccgag    360

ctcggtacca agcttggcgt aatcatggtc atag                                394
```

<210> SEQ ID NO 362
<211> LENGTH: 268
<212> TYPE: DNA
<213> ORGANISM: Homo sapiens

<400> SEQUENCE: 362

```
ctgcgcgtgg accagtcagc ttccgggtgt gactggagca gggcttgtcg tcttcttcag     60

agtcactttg caggggttgg tgaagctgct cccatccatg tacagctccc agtctactga    120

tgtttaagga tggtctcggt ggttaggccc actagaataa actgagtcca atacctctac    180

acagttatgt ttaactgggc tctctgacac cgggaggaag gtggcggggt ttaggtgttg    240

caaacttcaa tggttatgcg gggatgtt                                       268
```

<210> SEQ ID NO 363
<211> LENGTH: 323
<212> TYPE: DNA
<213> ORGANISM: Homo sapiens

<400> SEQUENCE: 363

```
ccttgacctt ttcagcaagt gggaaggtgt aatccgtctc cacagacaag gccaggactc     60

gtttgtaccc gttgatgata gaatggggta ctgatgcaac agttgggtag ccaatctgca    120

gacagacact ggcaacattg cggacaccct ccaggaagcg agaatgcaga gtttcctctg    180

tgatatcaag cacttcaggg ttgtagatgc tgccattgtc gaacacctgc tggatgacca    240

gcccaaagga gaagggggag atgttgagca tgttcagcag cgtggcttcg ctggctccca    300

ctttgtctcc agtcttgatc aga                                            323
```

<210> SEQ ID NO 364
<211> LENGTH: 393
<212> TYPE: DNA
<213> ORGANISM: Homo sapiens
<220> FEATURE:
<221> NAME/KEY: misc_feature
<222> LOCATION: (1)...(393)
<223> OTHER INFORMATION: n = A,T,C or G

<400> SEQUENCE: 364

```
ccaagctctc catcgtcccc gtgcgcagng gctactgggg gaacaagatc ggcaagcccc     60

acactgtccc ttgcaaggtg acaggccgct gcggctctgt gctggtacgc ctcatcactg    120

cacccagggg cactggcatc gtctccgcac ctgtgcctaa gaagctgctc atgatggctg    180

gcatcgatga ctgctacacc tcagcccggg gctgcactgc caccctgggc aacttcgcca    240

aggccacctt tgatgccatt tctaagacct acagctacct gacccccgac ctctggaagg    300

agactgtatt caccaagtct ccctatcagg agttcactga ccacctcgtc aagacccaca    360

ccagagtctc cgtgcagcgg actcaggctc cag                                 393
```

-continued

<210> SEQ ID NO 365
<211> LENGTH: 371
<212> TYPE: DNA
<213> ORGANISM: Homo sapiens

<400> SEQUENCE: 365
cctcctcaga gcggtagctg ttcttattgc cccggcagcc tccatagatg aagttattgc 60
aggagttcct ctccacgtca aagtaccagc gtgggaagga tgcacggcaa ggcccagtga 120
ctgcgttggc ggtgcagtat tcttcatagt tgaacatatc gctggagtgg tcttcagaat 180
cctgccttct gggagcactt gggacagagg aatccgctgc attcctgctg gtggacctcg 240
gccgcgacca cgctaagccg aattccagca cactggcggc cgttactagt ggatccgagc 300
tcggtaccaa gcttggcgta atcatggtca tagctgtttc ctgtgtgaaa ttgttatccg 360
ctcacaattc c 371

<210> SEQ ID NO 366
<211> LENGTH: 393
<212> TYPE: DNA
<213> ORGANISM: Homo sapiens

<400> SEQUENCE: 366
atttcttgcc agatgggagc tctttggtga agactccttt cgggaaaagt tttttggctt 60
cttcttcagg gatggttgga aggaccatca cactatcccc atccttccaa tcaactgggg 120
tggcaaccct tttttctgct gtcagctgga gagagatgac taccctgaga atctcatcaa 180
agttcctgcc agtggtagct gggtagagga tagacagctt cagcttctta tcaggaccaa 240
aaacaaacac cacacgagct gccacaggca tgccctttc atccttctct gctggatcca 300
gcatgcccaa caggatggca agctcccgat tcctatcatc gatgatggga aaaggtaact 360
tttctgtggg ctcttcacaa ttgtaagcat tga 393

<210> SEQ ID NO 367
<211> LENGTH: 327
<212> TYPE: DNA
<213> ORGANISM: Homo sapiens
<220> FEATURE:
<221> NAME/KEY: misc_feature
<222> LOCATION: (1)...(327)
<223> OTHER INFORMATION: n = A,T,C or G

<400> SEQUENCE: 367
ccagctctgt ctcatacttg actctaaagt cttnagcagc aagacgggca ttgnnaatct 60
gcagaacgat gcgggcattg tccacagtat ttgcgaagat ctgagccctc aggtcctcga 120
tgatcttgaa gtaatggctc cagtctctga cctggggtcc cttcttctcc aagtgctccc 180
ggattttgct ctccagcctc cggttctcgg tctccaggct cctcactctg tccaggtaag 240
aggccaggcg gtcgttcagg ctttgcatgg tctccttctc gttctggatg cctcccattc 300
ctgccagacc cccggctatc ccggtgg 327

<210> SEQ ID NO 368
<211> LENGTH: 306
<212> TYPE: DNA
<213> ORGANISM: Homo sapiens
<220> FEATURE:
<221> NAME/KEY: misc_feature
<222> LOCATION: (1)...(306)
<223> OTHER INFORMATION: n = A,T,C or G

<400> SEQUENCE: 368

-continued

```
ctggagaagg acttcagcag tttnaagaag tactgccaag tcatccgtgt cattgcccac     60

acccagatgc gcctgcttcc tctgcgccag aagaaggccc acctgatgga gatccaggtg    120

aacggaggca ctgtggccga gaagctggac tgggcccgcg agaggcttga gcagcaggta    180

cctgtgaacc aagtgtttgg gcaggatgag atgatcgacg tcatcggggt gaccaagggc    240

aaaggctaca aaggggtcac cagtcgttgg cacaccaaga agctgccccg caagacccac    300

cgagga                                                               306
```

<210> SEQ ID NO 369
<211> LENGTH: 394
<212> TYPE: DNA
<213> ORGANISM: Homo sapiens

<400> SEQUENCE: 369

```
tcgacccaca ccggaacacg gagagctggg ccagcattgg cacttgatag gatttcccgt     60

cggctgccac gaaagtgcgt ttctttgtgt tctcgggttg gaaccgtgat ttccacagac    120

ccttgaaata cactgcgttg acgaggacca gtctggtgag cacaccatca ataagatctg    180

gggacagcag attgtcaatc atatccctgg tttcattttt aacccatgca ttgatggaat    240

cacaggcaga ggctggatcc tcaaagttca cattccggac ctcacactgg aacacatctt    300

tgttccttgt aacaaaaggc acttcaattt cagaggcatt cttaacaaac acggcgttag    360

ccactgtcac aatgtcttta ttcttcttgg agac                                394
```

<210> SEQ ID NO 370
<211> LENGTH: 653
<212> TYPE: DNA
<213> ORGANISM: Homo sapiens

<400> SEQUENCE: 370

```
ccaccacacc caattccttg ctggtatcat ggcagccgcc acgtgccagg attaccggct     60

acatcatcaa gtatgagaag cctgggtctc ctcccagaga agtggtccct cggccccgcc    120

ctggtgtcac agaggctact attactggcc tggaaccggg aaccgaatat acaatttatg    180

tcattgccct gaagaataat cagaagagcg agcccctgat tggaaggaaa aagacagacg    240

agcttcccca actggtaacc cttccacacc ccaatcttca tggaccagag atcttggatg    300

ttccttccac agttcaaaag accccttttcg tcacccaccc tgggtatgac actggaaatg    360

gtattcagct tcctggcact tctggtcagc aacccagtgt tgggcaacaa atgatctttg    420

aggaacatgg ttttaggcgg accacaccgc ccacaacggc cacccccata aggcataggc    480

caagaccata cccgccgaat gtaggacaag aagctctctc tcagacaacc atctcatggg    540

ccccattcca ggacacttct gagtacatca tttcatgtca tcctgttggc actgatgaag    600

aacccttaca gttcagggtt cctggaactt ctaccagtgc cactctgaca gga           653
```

<210> SEQ ID NO 371
<211> LENGTH: 268
<212> TYPE: DNA
<213> ORGANISM: Homo sapiens

<400> SEQUENCE: 371

```
ctgcccagcc cccattggcg agtttgagaa ggtgtgcagc aatgacaaca agaccttcga     60

ctcttcctgc cacttctttg ccacaaagtg caccctggag ggcaccaaga agggccacaa    120

gctccacctg gactacatcg ggccttgcaa atacatcccc ccttgcctgg actctgagct    180

gaccgaattc cccctgcgca tgcgggactg gctcaagaac gtcctggtca ccctgtatga    240
```

-continued

```
gagggatgag gacaacaacc ttctgact                                          268


<210> SEQ ID NO 372
<211> LENGTH: 392
<212> TYPE: DNA
<213> ORGANISM: Homo sapiens

<400> SEQUENCE: 372

gctggtgccc ctggtgaacg tggacctcct ggattggcag gggccccagg acttagaggt      60

ggaactggtc cccctggtcc cgaaggagga aagggtgctg ctggtcctcc tgggccacct     120

ggtgctgctg gtactcctgg tctgcaagga atgcctggag aaagaggagg tcttggaagt     180

cctggtccaa agggtgacaa gggtgaacca ggcggtccag gtgctgatgg tgtcccaggg     240

aaagatggcc caaggggtcc tactggtcct attggtcctc ctggcccagc tggccagcct     300

ggagataagg gtgaaggtgg tgccccccgga cttccaggta tagctggacc tcgtggtagc    360

cctggtgaga gaggtgaaac ctcggccgcg ac                                   392


<210> SEQ ID NO 373
<211> LENGTH: 388
<212> TYPE: DNA
<213> ORGANISM: Homo sapiens
<220> FEATURE:
<221> NAME/KEY: misc_feature
<222> LOCATION: (1)...(388)
<223> OTHER INFORMATION: n = A,T,C or G

<400> SEQUENCE: 373

ccaagcgctc agatcggcaa ggggcaccan ttttgatctg cccagtgcac agccccacaa      60

ccaggtcagc gatgaaggta tcttcagtct cccccgaacg atgagacacc atgacgcccc     120

aaccattggc ctgggccagc ttgcacgcct gaagagactc ggtcacggag ccaatctggt     180

tgactttgag caggaggcag ttgcaggact tctcgttcac ggccttggcg atcctctttg     240

ggttggtcac tgtgagatca tcccccacta cctggattcc tgcactggct gtgaacttct     300

gccaagctcc ccagtcatcc tggtcaaagg gatcttcgat agacaccact gggtagtcct     360

tgatgaagga cttgtacagg tcagccag                                        388


<210> SEQ ID NO 374
<211> LENGTH: 393
<212> TYPE: DNA
<213> ORGANISM: Homo sapiens

<400> SEQUENCE: 374

ctgacgaccg cgtgaacccc tgcattgggg gtgtcatcct cttccatgag acactctacc      60

agaaggcgga tgatgggcgt cccttccccc aagttatcaa atccaagggc ggtgttgtgg     120

gcatcaaggt agacaagggc gtggtccccc tggcagggac aaatggcgag actaccaccc     180

aagggttgga tgggctgtct gagcgctgtg cccagtacaa gaaggacgga gctgacttcg     240

ccaagtggcg ttgtgtgctg aagattgggg aacacacccc ctcagccctc gccatcatgg     300

aaaatgccaa tgttctggcc cgttatgcca gtatctgcca gcagaatggc attgtgccca     360

tcgtggagcc tgagatcctc cctgatgggg acc                                  393


<210> SEQ ID NO 375
<211> LENGTH: 394
<212> TYPE: DNA
<213> ORGANISM: Homo sapiens
<220> FEATURE:
```

-continued

<221> NAME/KEY: misc_feature
<222> LOCATION: (1)...(394)
<223> OTHER INFORMATION: n = A,T,C or G

<400> SEQUENCE: 375
ccacaaatgg cgtggtccat gtcatcaccn ttnttctgca gcctccagcc aacagacctc 60
aggaaagagg ggatgaactt gcagactctg cgcttgagat cttcaaacaa gcatcagcgt 120
tttccagggc ttcccagagg tctgtgcgac tagcccctgt ctatcaaaag ttattagaga 180
ggatgaagca ttagcttgaa gcactacagg aggaatgcac cacggcagct ctccgccaat 240
ttctctcaga tttccacaga gactgtttga atgttttcaa aaccaagtat cacactttaa 300
tgtacatggg ccgcaccata atgagatgtg agccttgtgc atgtggggga ggagggagag 360
agatgtactt tttaaatcat gttcccccta aaca 394

<210> SEQ ID NO 376
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 376
ctgcccagcc cccattggcg agtttgattn ggtgtgcagc aatgacaaca agaccttcga 60
ctcttcctgc cacttctttg ccacaaagtg caccctggag ggcaccaaga agggccacaa 120
gctccacctg gactacatcg ggccttgcaa atacatcccc ccttgcctgg actctgagct 180
gaccgaattc cccctgcgca tgcgggactg gctcaagaac gtcctggtca ccctgtatga 240
gagggatgag gacaacaacc ttctgactga gaagcagaag ctgcgggtga agaagatcca 300
tgagaatgag aagcgcctgg aggcaggaga ccaccccgtg gagctgctgg cccgggactt 360
cgagaagaac tataacatgt acatcttccc tg 392

<210> SEQ ID NO 377
<211> LENGTH: 292
<212> TYPE: DNA
<213> ORGANISM: Homo sapiens

<400> SEQUENCE: 377
caatgtttga tgcttaaccc ccccaatttc tgtgagatgg atggccagtg caagcgtgac 60
ttgaagtgtt gcatgggcat gtgtgggaaa tcctgcgttt cccctgtgaa agcttgattc 120
ctgccatatg gaggaggctc tggagtcctg ctctgtgtgg tccaggtcct ttccaccctg 180
agacttggct ccaccactga tatcctcctt tggggaaagg cttggcacac agcaggcttt 240
caagaagtgc cagttgatca atgaataaat aaacgagcct atttctcttt gc 292

<210> SEQ ID NO 378
<211> LENGTH: 395
<212> TYPE: DNA
<213> ORGANISM: Homo sapiens

<400> SEQUENCE: 378
ctgctgcttc agcgaagggt ttctggcata tccaatgata aggctgccaa agactgttcc 60
aataccagca ccagaaccag ccactcctac tgttgcagca cctgcaccaa taaatttggc 120
agcagtatca atgtctctgc tgattgcact ggtctgaaac tccctttgga ttagctgaga 180
cacaccattc tgggccctga ttttcctaag atagaactcc aactctttgc cctctagcac 240

-continued atagccatct gctcggccac actgtcccgg ccttgaagcg atgcacgcaa gaagcttgcc 300
ctgctggaac tgctcctcca ggagactgct gattttggca ttctttttcc tttcatcata 360
tttcttctga attttttaga tcgttttttg tttaa 395

<210> SEQ ID NO 379
<211> LENGTH: 223
<212> TYPE: DNA
<213> ORGANISM: Homo sapiens

<400> SEQUENCE: 379
ccagatgaaa tgctgccgca atggctgtgg gaaggtgtcc tgtgtcactc ccaatttctg 60
agctccagcc accaccaggc tgagcagtga ggagagaaag tttctgcctg gccctgcatc 120
tggttccagc ccacctgccc tccccttttt cgggactctg tattccctct tgggctgacc 180
acagcttctc cctttcccaa ccaataaagt aaccactttc agc 223

<210> SEQ ID NO 380
<211> LENGTH: 317
<212> TYPE: DNA
<213> ORGANISM: Homo sapiens
<220> FEATURE:
<221> NAME/KEY: misc_feature
<222> LOCATION: (1)...(317)
<223> OTHER INFORMATION: n = A,T,C or G

<400> SEQUENCE: 380
tcgaccacag tattccaacc ctcctgtgcn tngagaagtg atggagggtg ctgacaacca 60
gggtgcagga gaacaaggta gaccagtgag gcagaatatg tatcggggat atagaccacg 120
attccgcagg ggccctcctc gccaaagaca gcctagagag gacggcaatg aagaagataa 180
agaaaatcaa ggagatgaga cccaaggtca gcagccacct caacgtcggt accgccgcaa 240
cttcaattac cgacgcagac gcccagaaaa ccctaaacca caagatggca aagagacaaa 300
agcagccgat ccaccag 317

<210> SEQ ID NO 381
<211> LENGTH: 392
<212> TYPE: DNA
<213> ORGANISM: Homo sapiens
<220> FEATURE:
<221> NAME/KEY: misc_feature
<222> LOCATION: (1)...(392)
<223> OTHER INFORMATION: n = A,T,C or G

<400> SEQUENCE: 381
cctgaaggaa gagctggcct acctgaatnn naaccatgag gaggaaatca gtacgctgag 60
gggccaagtg ggaggccagg tcagtgtgga ggtggattcc gctccgggca ccgatctcgc 120
caagatcctg agtgacatgc gaagccaata tgaggtcatg gccgagcaga accggaagga 180
tgctgaagcc tggttcacca gccggactga agaattgaac cgggaggtcg ctggccacac 240
ggagcagctc cagatgagca ggtccgaggt tactgacctg cggcgcaccc ttcagggtct 300
tgagattgag ctgcagtcac agacctcggc cgcgaccacg ctaagccgaa ttccagcaca 360
ctggcggccg ttactagtgg atccgagctc gg 392

<210> SEQ ID NO 382
<211> LENGTH: 234
<212> TYPE: DNA
<213> ORGANISM: Homo sapiens -continued

<400> SEQUENCE: 382
cctcgatgtc taaatgagcg tggtaaagga tggtgcctgc tggggtctcg tagatacctc 60
gggacttcat tccaatgaag cggttctcca cgatgtcaat acggcccacg ccatgcttgc 120
ccgcgacttc gttcaggtac atgaagagct ccaaggaggt ctggtgggtg gtgccatcct 180
tgacgttggt caccttcaca gggacccctt ttttgaactc catctccaga atgt 234

<210> SEQ ID NO 383
<211> LENGTH: 396
<212> TYPE: DNA
<213> ORGANISM: Homo sapiens
<220> FEATURE:
<221> NAME/KEY: misc_feature
<222> LOCATION: (1)...(396)
<223> OTHER INFORMATION: n = A,T,C or G

<400> SEQUENCE: 383
ccttgacctt ttcagcaagt gggaaggtgt tttccgtctc cacagacaag gccaggactc 60
gtttgnaccc gttgatgata gaatggggta ctgatgcaac agttgggtag ccaatctgca 120
gacagacact ggcaacattg cggacaccca ggatttcaat ggtgcccctg gagattttag 180
tggtgatacc taaagcctgg aaaaaggagg tcttctcggg cccgagacca gtgttctggg 240
ctggcacagt gacttcacat ggggcaatgg caccagcacg ggcagcagac ctgcccgggc 300
ggccgctcga aagccgaatt ccagcacact ggcggccgtt actagtggat ccgagctcgg 360
taccaagctt ggcgtaatca tggtcatagc tgtttc 396

<210> SEQ ID NO 384
<211> LENGTH: 396
<212> TYPE: DNA
<213> ORGANISM: Homo sapiens

<400> SEQUENCE: 384
gctgaatagg cacagagggc acctgtacac cttcagacca gtctgcaacc tcaggctgag 60
tagcagtgaa ctcaggagcg ggagcagtcc attcaccctg aaattcctcc ttggtcactg 120
ccttctcagc agcagcctgc tcttcttttt caatctcttc aggatctctg tagaagtaca 180
gatcaggcat gacctcccat gggtgttcac gggaaatggt gccacgcatg cgcagaactt 240
cccgagccag catccaccac atcaaaccca ctgagtgagc tcccttgttg ttgcatggga 300
tggcaatgtc cacatagcgc agaggagaat ctgtgttaca cagcgcaatg gtaggtaggt 360
taacataaga tgcctccgtg agaggctggt ggtcag 396

<210> SEQ ID NO 385
<211> LENGTH: 2943
<212> TYPE: DNA
<213> ORGANISM: Homo sapiens

<400> SEQUENCE: 385
cagccaccgg agtggatgcc atctgcaccc accgccctga ccccacaggc cctgggctgg 60
acagagagca gctgtatttg gagctgagcc agctgaccca cagcatcact gagctgggcc 120
cctacaccct ggacagggac agtctctatg tcaatggttt cacacagcgg agctctgtgc 180
ccaccactag cattcctggg acccccacag tggacctggg aacatctggg actccagttt 240
ctaaacctgg tccctcggct gccagccctc tcctggtgct attcactctc aacttcacca 300
tcaccaacct gcggtatgag gagaacatgc agcaccctgg ctccaggaag ttcaacacca 360
cggagagggt ccttcagggc ctggtccctg ttcaagagca ccagtgttgg ccctctgtac 420

-continued

```
tctggctgca gactgacttt gctcaggcct gaaaaggatg ggacagccac tggagtggat    480
gccatctgca cccaccaccc tgaccccaaa agccctaggc tggacagaga gcagctgtat    540
tgggagctga gccagctgac ccacaatatc actgagctgg gcccctatgc cctggacaac    600
gacagcctct ttgtcaatgg tttcactcat cggagctctg tgtccaccac cagcactcct    660
gggacccccca cagtgtatct gggagcatct aagactccag cctcgatatt tggcccttca    720
gctgccagcc atctcctgat actattcacc ctcaacttca ccatcactaa cctgcggtat    780
gaggagaaca tgtggcctgg ctccaggaag ttcaacacta cagagagggt ccttcagggc    840
ctgctaaggc ccttgttcaa gaacaccagt gttggccctc tgtactctgg ctgcaggctg    900
accttgctca ggccagagaa agatggggaa gccaccggag tggatgccat ctgcacccac    960
cgccctgacc ccacaggccc tgggctggac agagagcagc tgtatttgga gctgagccag   1020
ctgacccaca gcatcactga gctgggcccc tacacactgg acagggacag tctctatgtc   1080
aatggtttca cccatcggag ctctgtaccc accaccagca ccggggtggt cagcgaggag   1140
ccattcacac tgaacttcac catcaacaac ctgcgctaca tggcggacat gggccaaccc   1200
ggctccctca agttcaacat cacagacaac gtcatgaagc acctgctcag tcctttgttc   1260
cagaggagca gcctgggtgc acggtacaca ggctgcaggg tcatcgcact aaggtctgtg   1320
aagaacggtg ctgagacacg ggtggacctc ctctgcacct acctgcagcc cctcagcggc   1380
ccaggtctgc ctatcaagca ggtgttccat gagctgagcc agcagaccca tggcatcacc   1440
cggctgggcc cctactctct ggacaaagac agcctctacc ttaacggtta caatgaacct   1500
ggtccagatg agcctcctac aactcccaag ccagccacca cattcctgcc tcctctgtca   1560
gaagccacaa cagccatggg gtaccacctg aagaccctca cactcaactt caccatctcc   1620
aatctccagt attcaccaga tatgggcaag ggctcagcta cattcaactc caccgagggg   1680
gtccttcagc acctgctcag acccttgttc cagaagagca gcatgggccc cttctacttg   1740
ggttgccaac tgatctccct caggcctgag aaggatgggg cagccactgg tgtggacacc   1800
acctgcacct accaccctga ccctgtgggc cccgggctgg acatacagca gctttactgg   1860
gagctgagtc agctgaccca tggtgtcacc caactgggct tctatgtcct ggacagggat   1920
agcctcttca tcaatggcta tgcaccccag aatttatcaa tccggggcga gtaccagata   1980
aatttccaca ttgtcaactg gaacctcagt aatccagacc ccacatcctc agagtacatc   2040
accctgctga gggacatcca ggacaaggtc accacactct acaaaggcag tcaactacat   2100
gacacattcc gcttctgcct ggtcaccaac ttgacgatgg actccgtgtt ggtcactgtc   2160
aaggcattgt tctcctccaa tttggacccc agcctggtgg agcaagtctt tctagataag   2220
accctgaatg cctcattcca ttggctgggc tccacctacc agttggtgga catccatgtg   2280
acagaaatgg agtcatcagt ttatcaacca acaagcagct ccagcaccca gcacttctac   2340
ctgaatttca ccatcaccaa cctaccatat tcccaggaca aagcccagcc aggcaccacc   2400
aattaccaga ggaacaaaag gaatattgag gatgcggcac cacaccgggg tggactccct   2460
gtgtaacttc tcgccactgg ctcggagagt agacagagtt gccatctatg aggaatttct   2520
gcggatgacc cggaatggta cccagctgca gaacttcacc ctggacagga gcagtgtcct   2580
tgtggatggg tattttccca acagaaatga gcccttaact gggaattctg accttccctt   2640
ctgggctgtc atcctcatcg gcttggcagg actcctggga ctcatcacat gcctgatctg   2700
cggtgtcctg gtgaccaccc gccggcggaa gaaggaagga gaatacaacg tccagcaaca   2760
```

-continued gtgcccaggc tactaccagt cacacctaga cctggaggat ctgcaatgac tggaacttgc 2820
cggtgcctgg ggtgcctttc ccccagccag ggtccaaaga agcttggctg gggcagaaat 2880
aaaccatatt ggtcggaaaa aaaaaaaaaa aaaaaaaaaa aaaaaaaaaa aaaaaaaaaa 2940
aaa 2943

<210> SEQ ID NO 386
<211> LENGTH: 2608
<212> TYPE: DNA
<213> ORGANISM: Homo sapiens

<400> SEQUENCE: 386
gttcaagagc accagtgttg gccctctgta ctctggctgc agactgactt tgctcaggcc 60
tgaaaaggat gggacagcca ctggagtgga tgccatctgc acccaccacc ctgaccccaa 120
aagccctagg ctggacagag agcagctgta ttgggagctg agccagctga cccacaatat 180
cactgagctg ggcccctatg ccctggacaa cgacagcctc tttgtcaatg gtttcactca 240
tcggagctct gtgtccacca ccagcactcc tgggaccccc acagtgtatc tgggagcatc 300
taagactcca gcctcgatat ttggcccttc agctgccagc catctcctga tactattcac 360
cctcaacttc accatcacta acctgcggta tgaggagaac atgtggcctg gctccaggaa 420
gttcaacact acagagaggg tccttcaggg cctgctaagg cccttgttca agaacaccag 480
tgttggccct ctgtactctg gctgcaggct gaccttgctc aggccagaga aagatgggga 540
agccaccgga gtggatgcca tctgcaccca ccgccctgac ccccacaggcc ctgggctgga 600 cagagagcag ctgtatttgg agctgagcca gctgacccac agcatcactg agctgggccc 660
ctacacactg gacagggaca gtctctatgt caatggtttc acccatcgga gctctgtacc 720
caccaccagc accggggtgg tcagcgagga gccattcaca ctgaacttca ccatcaacaa 780
cctgcgctac atggcggaca tgggccaacc cggctccctc aagttcaaca tcacagacaa 840
cgtcatgaag cacctgctca gtcctttgtt ccagaggagc agcctgggtg cacggtacac 900
aggctgcagg gtcatcgcac taaggtctgt gaagaacggt gctgagacac gggtggacct 960
cctctgcacc tacctgcagc ccctcagcgg cccaggtctg cctatcaagc aggtgttcca 1020
tgagctgagc cagcagaccc atggcatcac ccggctgggc ccctactctc tggacaaaga 1080
cagcctctac cttaacggtt acaatgaacc tggtccagat gagcctccta caactcccaa 1140
gccagccacc acattcctgc ctcctctgtc agaagccaca acagccatgg ggtaccacct 1200
gaagaccctc acactcaact tcaccatctc caatctccag tattcaccag atatgggcaa 1260
gggctcagct acattcaact ccaccgaggg ggtccttcag cacctgctca gacccttgtt 1320
ccagaagagc agcatgggcc ccttctactt gggttgccaa ctgatctccc tcaggcctga 1380
gaaggatggg gcagccactg gtgtggacac cacctgcacc taccaccctg accctgtggg 1440
ccccgggctg gacatacagc agctttactg ggagctgagt cagctgaccc atggtgtcac 1500
ccaactgggc ttctatgtcc tggacaggga tagcctcttc atcaatggct atgcacccca 1560
gaatttatca atccggggcg agtaccagat aaatttccac attgtcaact ggaacctcag 1620
taatccagac cccacatcct cagagtacat caccctgctg agggacatcc aggacaaggt 1680
caccacactc tacaaaggca gtcaactaca tgacacattc cgcttctgcc tggtcaccaa 1740
cttgacgatg gactccgtgt tggtcactgt caaggcattg ttctcctcca atttggaccc 1800
cagcctggtg gagcaagtct ttctagataa gaccctgaat gcctcattcc attggctggg 1860
ctccacctac cagttggtgg acatccatgt gacagaaatg gagtcatcag tttatcaacc 1920

-continued aacaagcagc tccagcaccc agcacttcta cctgaatttc accatcacca acctaccata 1980
ttcccaggac aaagcccagc caggcaccac caattaccag aggaacaaaa ggaatattga 2040
ggatgcgctc aaccaactct tccgaaacag cagcatcaag agttattttt ctgactgtca 2100
agtttcaaca ttcaggtctg tccccaacag gcaccacacc ggggtggact ccctgtgtaa 2160
cttctcgcca ctggctcgga gagtagacag agttgccatc tatgaggaat ttctgcggat 2220
gacccggaat ggtacccagc tgcagaactt caccctggac aggagcagtg tccttgtgga 2280
tgggtatttt cccaacagaa atgagccctt aactgggaat tctgaccttc ccttctgggc 2340
tgtcatcctc atcggcttgg caggactcct gggactcatc acatgcctga tctgcggtgt 2400
cctggtgacc acccgccggc ggaagaagga aggagaatac aacgtccagc aacagtgccc 2460
aggctactac cagtcacacc tagacctgga ggatctgcaa tgactggaac ttgccggtgc 2520
ctggggtgcc tttcccccag ccagggtcca aagaagcttg gctggggcag aaataaacca 2580
tattggtcgg acacaaaaaa aaaaaaaa 2608

<210> SEQ ID NO 387
<211> LENGTH: 1761
<212> TYPE: DNA
<213> ORGANISM: Homo sapiens

<400> SEQUENCE: 387
ctgaacttca ccatcaacaa cctgcgctac atggcggaca tgggccaacc cggctccctc 60
aagttcaaca tcacagacaa cgtcatgaag cacctgctca gtcctttgtt ccagaggagc 120
agcctgggtg cacggtacac aggctgcagg gtcatcgcac taaggtctgt gaagaacggt 180
gctgagacac gggtggacct cctctgcagg taggtgcaga ggaggtccac ggcatcaccc 240
ggctgggccc ctactctctg gacaaagaca gcctctacct taacgctccc aagccagcca 300
ccacattcct gcctcctctg tcagaagcca caacagccat ggggtaccac ctgaagaccc 360
tcacactcaa cttcaccatc tccaatctcc agtattcacc agatatgggc aagggctcag 420
ctacattcaa ctccaccgag gggtccttc agcacctgct cagacccttg ttccagaaga 480
gcagcatggg ccccttctac ttgggttgcc aactgatctc cctcaggcct gagaaggatg 540
gggcagccac tggtgtggac accacctgca cctaccaccc tgaccctgtg ggccccgggc 600
tggacataca gcagctttac tgggagctga gtcagctgac ccatggtgtc acccaactgg 660
gcttctatgt cctggacagg gatagcctct tcatcaatgg ctatgcaccc cagaatttat 720
caatccgggg cgagtaccag ataaatttcc acattgtcaa ctggaacctc agtaatccag 780
accccacatc ctcagagtac atcaccctgc tgagggacat ccaggacaag gtcaccacac 840
tctacaaagg cagtcaacta catgacacat tccgcttctg cctggtcacc aacttgacga 900
tggactccgt gttggtcact gtcaaggcat tgttctcctc caatttggac cccagcctgg 960
tggagcaagt ctttctagat aagaccctga atgcctcatt ccattggctg ggctccacct 1020
accagttggt ggacatccat gtgacagaaa tggagtcatc agtttatcaa ccaacaagca 1080
gctccagcac ccagcacttc tacctgaatt tcaccatcac caacctacca tattcccagg 1140
acaaagccca gccaggcacc accaattacc agaggaacaa aaggaatatt gaggatgcgc 1200
tcaaccaact cttccgaaac agcagcatca agagttattt ttctgactgt caagtttcaa 1260
cattcaggtc tgtccccaac aggcaccaca ccggggtgga ctccctgtgt aacttctcgc 1320
cactggctcg gagagtagac agagttgcca tctatgagga atttctgcgg atgacccgga 1380

-continued

```
atggtaccca gctgcagaac ttcaccctgg acaggagcag tgtccttgtg gatgggtatt   1440

ttcccaacag aaatgagccc ttaactggga attctgacct tcccttctgg gctgtcatcc   1500

tcatcggctt ggcaggactc ctgggactca tcacatgcct gatctgcggt gtcctggtga   1560

ccacccgccg gcggaagaag gaaggagaat acaacgtcca gcaacagtgc ccaggctact   1620

accagtcaca cctagacctg gaggatctgc aatgactgga acttgccggt gcctggggtg   1680

cctttccccc agccagggtc caaagaagct tggctggggc agaaataaac catattggtc   1740

ggacacaaaa aaaaaaaaaa a                                             1761
```

```
<210> SEQ ID NO 388
<211> LENGTH: 772
<212> TYPE: PRT
<213> ORGANISM: Homo sapiens

<400> SEQUENCE: 388

Met Ser Met Val Ser His Ser Gly Ala Leu Cys Pro Pro Leu Ala Phe
                  5                  10                  15

Leu Gly Pro Pro Gln Trp Thr Trp Glu His Leu Gly Leu Gln Phe Leu
             20                  25                  30

Asn Leu Val Pro Arg Leu Pro Ala Leu Ser Trp Cys Tyr Ser Leu Ser
         35                  40                  45

Thr Ser Pro Ser Pro Thr Cys Gly Met Arg Arg Thr Cys Ser Thr Leu
     50                  55                  60

Ala Pro Gly Ser Ser Thr Pro Arg Arg Gly Ser Phe Arg Ala Trp Ser
 65                  70                  75                  80

Leu Phe Lys Ser Thr Ser Val Gly Pro Leu Tyr Ser Gly Cys Arg Leu
                 85                  90                  95

Thr Leu Leu Arg Pro Glu Lys Asp Gly Thr Ala Thr Gly Val Asp Ala
            100                 105                 110

Ile Cys Thr His His Pro Asp Pro Lys Ser Pro Arg Leu Asp Arg Glu
        115                 120                 125

Gln Leu Tyr Trp Glu Leu Ser Gln Leu Thr His Asn Ile Thr Glu Leu
    130                 135                 140

Gly Pro Tyr Ala Leu Asp Asn Asp Ser Leu Phe Val Asn Gly Phe Thr
145                 150                 155                 160

His Arg Ser Ser Val Ser Thr Thr Ser Thr Pro Gly Thr Pro Thr Val
                165                 170                 175

Tyr Leu Gly Ala Ser Lys Thr Pro Ala Ser Ile Phe Gly Pro Ser Ala
            180                 185                 190

Ala Ser His Leu Leu Ile Leu Phe Thr Leu Asn Phe Thr Ile Thr Asn
        195                 200                 205

Leu Arg Tyr Glu Glu Asn Met Trp Pro Gly Ser Arg Lys Phe Asn Thr
    210                 215                 220

Thr Glu Arg Val Leu Gln Gly Leu Leu Arg Pro Leu Phe Lys Asn Thr
225                 230                 235                 240

Ser Val Gly Pro Leu Tyr Ser Gly Cys Arg Leu Thr Leu Leu Arg Pro
                245                 250                 255

Glu Lys Asp Gly Glu Ala Thr Gly Val Asp Ala Ile Cys Thr His Arg
            260                 265                 270

Pro Asp Pro Thr Gly Pro Gly Leu Asp Arg Glu Gln Leu Tyr Leu Glu
        275                 280                 285

Leu Ser Gln Leu Thr His Ser Ile Thr Glu Leu Gly Pro Tyr Thr Leu
    290                 295                 300
```

-continued

```
Asp Arg Asp Ser Leu Tyr Val Asn Gly Phe Thr His Arg Ser Ser Val
305                 310                 315                 320

Pro Thr Thr Ser Thr Gly Val Val Ser Glu Glu Pro Phe Thr Leu Asn
                325                 330                 335

Phe Thr Ile Asn Asn Leu Arg Tyr Met Ala Asp Met Gly Gln Pro Gly
            340                 345                 350

Ser Leu Lys Phe Asn Ile Thr Asp Asn Val Met Lys His Leu Leu Ser
        355                 360                 365

Pro Leu Phe Gln Arg Ser Ser Leu Gly Ala Arg Tyr Thr Gly Cys Arg
    370                 375                 380

Val Ile Ala Leu Arg Ser Val Lys Asn Gly Ala Glu Thr Arg Val Asp
385                 390                 395                 400

Leu Leu Cys Thr Tyr Leu Gln Pro Leu Ser Gly Pro Gly Leu Pro Ile
                405                 410                 415

Lys Gln Val Phe His Glu Leu Ser Gln Gln Thr His Gly Ile Thr Arg
            420                 425                 430

Leu Gly Pro Tyr Ser Leu Asp Lys Asp Ser Leu Tyr Leu Asn Gly Tyr
        435                 440                 445

Asn Glu Pro Gly Pro Asp Glu Pro Pro Thr Thr Pro Lys Pro Ala Thr
    450                 455                 460

Thr Phe Leu Pro Pro Leu Ser Glu Ala Thr Thr Ala Met Gly Tyr His
465                 470                 475                 480

Leu Lys Thr Leu Thr Leu Asn Phe Thr Ile Ser Asn Leu Gln Tyr Ser
                485                 490                 495

Pro Asp Met Gly Lys Gly Ser Ala Thr Phe Asn Ser Thr Glu Gly Val
            500                 505                 510

Leu Gln His Leu Leu Arg Pro Leu Phe Gln Lys Ser Ser Met Gly Pro
        515                 520                 525

Phe Tyr Leu Gly Cys Gln Leu Ile Ser Leu Arg Pro Glu Lys Asp Gly
    530                 535                 540

Ala Ala Thr Gly Val Asp Thr Thr Cys Thr Tyr His Pro Asp Pro Val
545                 550                 555                 560

Gly Pro Gly Leu Asp Ile Gln Gln Leu Tyr Trp Glu Leu Ser Gln Leu
                565                 570                 575

Thr His Gly Val Thr Gln Leu Gly Phe Tyr Val Leu Asp Arg Asp Ser
            580                 585                 590

Leu Phe Ile Asn Gly Tyr Ala Pro Gln Asn Leu Ser Ile Arg Gly Glu
        595                 600                 605

Tyr Gln Ile Asn Phe His Ile Val Asn Trp Asn Leu Ser Asn Pro Asp
    610                 615                 620

Pro Thr Ser Ser Glu Tyr Ile Thr Leu Leu Arg Asp Ile Gln Asp Lys
625                 630                 635                 640

Val Thr Thr Leu Tyr Lys Gly Ser Gln Leu His Asp Thr Phe Arg Phe
                645                 650                 655

Cys Leu Val Thr Asn Leu Thr Met Asp Ser Val Leu Val Thr Val Lys
            660                 665                 670

Ala Leu Phe Ser Ser Asn Leu Asp Pro Ser Leu Val Glu Gln Val Phe
        675                 680                 685

Leu Asp Lys Thr Leu Asn Ala Ser Phe His Trp Leu Gly Ser Thr Tyr
    690                 695                 700

Gln Leu Val Asp Ile His Val Thr Glu Met Glu Ser Ser Val Tyr Gln
705                 710                 715                 720

Pro Thr Ser Ser Ser Ser Thr Gln His Phe Tyr Leu Asn Phe Thr Ile
```

-continued

```
            725                 730                 735

Thr Asn Leu Pro Tyr Ser Gln Asp Lys Ala Gln Pro Gly Thr Thr Asn
            740                 745                 750

Tyr Gln Arg Asn Lys Arg Asn Ile Glu Asp Ala Ala Pro His Arg Gly
        755                 760                 765

Gly Leu Pro Val
    770


<210> SEQ ID NO 389
<211> LENGTH: 833
<212> TYPE: PRT
<213> ORGANISM: Homo sapiens

<400> SEQUENCE: 389

Phe Lys Ser Thr Ser Val Gly Pro Leu Tyr Ser Gly Cys Arg Leu Thr
                5                   10                  15

Leu Leu Arg Pro Glu Lys Asp Gly Thr Ala Thr Gly Val Asp Ala Ile
            20                  25                  30

Cys Thr His His Pro Asp Pro Lys Ser Pro Arg Leu Asp Arg Glu Gln
        35                  40                  45

Leu Tyr Trp Glu Leu Ser Gln Leu Thr His Asn Ile Thr Glu Leu Gly
    50                  55                  60

Pro Tyr Ala Leu Asp Asn Asp Ser Leu Phe Val Asn Gly Phe Thr His
65                  70                  75                  80

Arg Ser Ser Val Ser Thr Thr Ser Thr Pro Gly Thr Pro Thr Val Tyr
                85                  90                  95

Leu Gly Ala Ser Lys Thr Pro Ala Ser Ile Phe Gly Pro Ser Ala Ala
            100                 105                 110

Ser His Leu Leu Ile Leu Phe Thr Leu Asn Phe Thr Ile Thr Asn Leu
        115                 120                 125

Arg Tyr Glu Glu Asn Met Trp Pro Gly Ser Arg Lys Phe Asn Thr Thr
    130                 135                 140

Glu Arg Val Leu Gln Gly Leu Leu Arg Pro Leu Phe Lys Asn Thr Ser
145                 150                 155                 160

Val Gly Pro Leu Tyr Ser Gly Cys Arg Leu Thr Leu Leu Arg Pro Glu
                165                 170                 175

Lys Asp Gly Glu Ala Thr Gly Val Asp Ala Ile Cys Thr His Arg Pro
            180                 185                 190

Asp Pro Thr Gly Pro Gly Leu Asp Arg Glu Gln Leu Tyr Leu Glu Leu
        195                 200                 205

Ser Gln Leu Thr His Ser Ile Thr Glu Leu Gly Pro Tyr Thr Leu Asp
    210                 215                 220

Arg Asp Ser Leu Tyr Val Asn Gly Phe Thr His Arg Ser Ser Val Pro
225                 230                 235                 240

Thr Thr Ser Thr Gly Val Val Ser Glu Glu Pro Phe Thr Leu Asn Phe
                245                 250                 255

Thr Ile Asn Asn Leu Arg Tyr Met Ala Asp Met Gly Gln Pro Gly Ser
            260                 265                 270

Leu Lys Phe Asn Ile Thr Asp Asn Val Met Lys His Leu Leu Ser Pro
        275                 280                 285

Leu Phe Gln Arg Ser Ser Leu Gly Ala Arg Tyr Thr Gly Cys Arg Val
    290                 295                 300

Ile Ala Leu Arg Ser Val Lys Asn Gly Ala Glu Thr Arg Val Asp Leu
305                 310                 315                 320
```

-continued

```
Leu Cys Thr Tyr Leu Gln Pro Leu Ser Gly Pro Gly Leu Pro Ile Lys
                325                 330                 335

Gln Val Phe His Glu Leu Ser Gln Gln Thr His Gly Ile Thr Arg Leu
            340                 345                 350

Gly Pro Tyr Ser Leu Asp Lys Asp Ser Leu Tyr Leu Asn Gly Tyr Asn
        355                 360                 365

Glu Pro Gly Pro Asp Glu Pro Pro Thr Thr Pro Lys Pro Ala Thr Thr
    370                 375                 380

Phe Leu Pro Pro Leu Ser Glu Ala Thr Thr Ala Met Gly Tyr His Leu
385                 390                 395                 400

Lys Thr Leu Thr Leu Asn Phe Thr Ile Ser Asn Leu Gln Tyr Ser Pro
                405                 410                 415

Asp Met Gly Lys Gly Ser Ala Thr Phe Asn Ser Thr Glu Gly Val Leu
            420                 425                 430

Gln His Leu Leu Arg Pro Leu Phe Gln Lys Ser Ser Met Gly Pro Phe
        435                 440                 445

Tyr Leu Gly Cys Gln Leu Ile Ser Leu Arg Pro Glu Lys Asp Gly Ala
    450                 455                 460

Ala Thr Gly Val Asp Thr Thr Cys Thr Tyr His Pro Asp Pro Val Gly
465                 470                 475                 480

Pro Gly Leu Asp Ile Gln Gln Leu Tyr Trp Glu Leu Ser Gln Leu Thr
                485                 490                 495

His Gly Val Thr Gln Leu Gly Phe Tyr Val Leu Asp Arg Asp Ser Leu
            500                 505                 510

Phe Ile Asn Gly Tyr Ala Pro Gln Asn Leu Ser Ile Arg Gly Glu Tyr
        515                 520                 525

Gln Ile Asn Phe His Ile Val Asn Trp Asn Leu Ser Asn Pro Asp Pro
    530                 535                 540

Thr Ser Ser Glu Tyr Ile Thr Leu Leu Arg Asp Ile Gln Asp Lys Val
545                 550                 555                 560

Thr Thr Leu Tyr Lys Gly Ser Gln Leu His Asp Thr Phe Arg Phe Cys
                565                 570                 575

Leu Val Thr Asn Leu Thr Met Asp Ser Val Leu Val Thr Val Lys Ala
            580                 585                 590

Leu Phe Ser Ser Asn Leu Asp Pro Ser Leu Val Glu Gln Val Phe Leu
        595                 600                 605

Asp Lys Thr Leu Asn Ala Ser Phe His Trp Leu Gly Ser Thr Tyr Gln
    610                 615                 620

Leu Val Asp Ile His Val Thr Glu Met Glu Ser Ser Val Tyr Gln Pro
625                 630                 635                 640

Thr Ser Ser Ser Ser Thr Gln His Phe Tyr Leu Asn Phe Thr Ile Thr
                645                 650                 655

Asn Leu Pro Tyr Ser Gln Asp Lys Ala Gln Pro Gly Thr Thr Asn Tyr
            660                 665                 670

Gln Arg Asn Lys Arg Asn Ile Glu Asp Ala Leu Asn Gln Leu Phe Arg
        675                 680                 685

Asn Ser Ser Ile Lys Ser Tyr Phe Ser Asp Cys Gln Val Ser Thr Phe
    690                 695                 700

Arg Ser Val Pro Asn Arg His His Thr Gly Val Asp Ser Leu Cys Asn
705                 710                 715                 720

Phe Ser Pro Leu Ala Arg Arg Val Asp Arg Val Ala Ile Tyr Glu Glu
                725                 730                 735

Phe Leu Arg Met Thr Arg Asn Gly Thr Gln Leu Gln Asn Phe Thr Leu
```

-continued

```
            740                 745                 750

Asp Arg Ser Ser Val Leu Val Asp Gly Tyr Phe Pro Asn Arg Asn Glu
        755                 760                 765

Pro Leu Thr Gly Asn Ser Asp Leu Pro Phe Trp Ala Val Ile Leu Ile
    770                 775                 780

Gly Leu Ala Gly Leu Leu Gly Leu Ile Thr Cys Leu Ile Cys Gly Val
785                 790                 795                 800

Leu Val Thr Thr Arg Arg Arg Lys Lys Glu Gly Glu Tyr Asn Val Gln
                805                 810                 815

Gln Gln Cys Pro Gly Tyr Tyr Gln Ser His Leu Asp Leu Glu Asp Leu
            820                 825                 830

Gln


<210> SEQ ID NO 390
<211> LENGTH: 438
<212> TYPE: PRT
<213> ORGANISM: Homo sapiens

<400> SEQUENCE: 390

Met Gly Tyr His Leu Lys Thr Leu Thr Leu Asn Phe Thr Ile Ser Asn
                  5                  10                  15

Leu Gln Tyr Ser Pro Asp Met Gly Lys Gly Ser Ala Thr Phe Asn Ser
            20                  25                  30

Thr Glu Gly Val Leu Gln His Leu Leu Arg Pro Leu Phe Gln Lys Ser
        35                  40                  45

Ser Met Gly Pro Phe Tyr Leu Gly Cys Gln Leu Ile Ser Leu Arg Pro
     50                  55                  60

Glu Lys Asp Gly Ala Ala Thr Gly Val Asp Thr Thr Cys Thr Tyr His
 65                  70                  75                  80

Pro Asp Pro Val Gly Pro Gly Leu Asp Ile Gln Gln Leu Tyr Trp Glu
                 85                  90                  95

Leu Ser Gln Leu Thr His Gly Val Thr Gln Leu Gly Phe Tyr Val Leu
            100                 105                 110

Asp Arg Asp Ser Leu Phe Ile Asn Gly Tyr Ala Pro Gln Asn Leu Ser
        115                 120                 125

Ile Arg Gly Glu Tyr Gln Ile Asn Phe His Ile Val Asn Trp Asn Leu
    130                 135                 140

Ser Asn Pro Asp Pro Thr Ser Ser Glu Tyr Ile Thr Leu Leu Arg Asp
145                 150                 155                 160

Ile Gln Asp Lys Val Thr Thr Leu Tyr Lys Gly Ser Gln Leu His Asp
                165                 170                 175

Thr Phe Arg Phe Cys Leu Val Thr Asn Leu Thr Met Asp Ser Val Leu
            180                 185                 190

Val Thr Val Lys Ala Leu Phe Ser Ser Asn Leu Asp Pro Ser Leu Val
        195                 200                 205

Glu Gln Val Phe Leu Asp Lys Thr Leu Asn Ala Ser Phe His Trp Leu
    210                 215                 220

Gly Ser Thr Tyr Gln Leu Val Asp Ile His Val Thr Glu Met Glu Ser
225                 230                 235                 240

Ser Val Tyr Gln Pro Thr Ser Ser Ser Ser Thr Gln His Phe Tyr Leu
                245                 250                 255

Asn Phe Thr Ile Thr Asn Leu Pro Tyr Ser Gln Asp Lys Ala Gln Pro
            260                 265                 270

Gly Thr Thr Asn Tyr Gln Arg Asn Lys Arg Asn Ile Glu Asp Ala Leu
```

-continued

```
        275                 280                 285

Asn Gln Leu Phe Arg Asn Ser Ser Ile Lys Ser Tyr Phe Ser Asp Cys
    290                 295                 300

Gln Val Ser Thr Phe Arg Ser Val Pro Asn Arg His His Thr Gly Val
305                 310                 315                 320

Asp Ser Leu Cys Asn Phe Ser Pro Leu Ala Arg Arg Val Asp Arg Val
                325                 330                 335

Ala Ile Tyr Glu Glu Phe Leu Arg Met Thr Arg Asn Gly Thr Gln Leu
            340                 345                 350

Gln Asn Phe Thr Leu Asp Arg Ser Ser Val Leu Val Asp Gly Tyr Phe
        355                 360                 365

Pro Asn Arg Asn Glu Pro Leu Thr Gly Asn Ser Asp Leu Pro Phe Trp
    370                 375                 380

Ala Val Ile Leu Ile Gly Leu Ala Gly Leu Leu Gly Leu Ile Thr Cys
385                 390                 395                 400

Leu Ile Cys Gly Val Leu Val Thr Thr Arg Arg Arg Lys Lys Glu Gly
                405                 410                 415

Glu Tyr Asn Val Gln Gln Gln Cys Pro Gly Tyr Tyr Gln Ser His Leu
            420                 425                 430

Asp Leu Glu Asp Leu Gln
        435
```

<210> SEQ ID NO 391
<211> LENGTH: 2627
<212> TYPE: DNA
<213> ORGANISM: Homo sapiens

<400> SEQUENCE: 391

```
ccacgcgtcc gcccacgcgt ccggaaggca gcggcagctc cactcagcca gtacccagat     60

acgctgggaa ccttccccag ccatggcttc cctggggcag atcctcttct ggagcataat    120

tagcatcatc attattctgg ctggagcaat tgcactcatc attggctttg gtatttcagg    180

gagacactcc atcacagtca ctactgtcgc ctcagctggg aacattgggg aggatggaat    240

cctgagctgc acttttgaac ctgacatcaa actttctgat atcgtgatac aatggctgaa    300

ggaaggtgtt ttaggcttgg tccatgagtt caaagaaggc aaagatgagc tgtcggagca    360

ggatgaaatg ttcagaggcc ggacagcagt gtttgctgat caagtgatag ttggcaatgc    420

ctctttgcgg ctgaaaaacg tgcaactcac agatgctggc acctacaaat gttatatcat    480

cacttctaaa ggcaagggga atgctaacct tgagtataaa actggagcct tcagcatgcc    540

ggaagtgaat gtggactata atgccagctc agagaccttg cggtgtgagg ctccccgatg    600

gttcccccag cccacagtgg tctgggcatc ccaagttgac cagggagcca acttctcgga    660

agtctccaat accagctttg agctgaactc tgagaatgtg accatgaagg ttgtgtctgt    720

gctctacaat gttacgatca acaacacata ctcctgtatg attgaaaatg acattgccaa    780

agcaacaggg gatatcaaag tgacagaatc ggagatcaaa aggcggagtc acctacagct    840

gctaaactca aaggcttctc tgtgtgtctc ttctttcttt gccatcagct gggcacttct    900

gcctctcagc ccttacctga tgctaaaata atgtgccttg gccacaaaaa agcatgcaaa    960

gtcattgtta caacagggat ctacagaact atttcaccac cagatatgac ctagttttat   1020

atttctggga ggaaatgaat tcatatctag aagtctggag tgagcaaaca agagcaagaa   1080

acaaaaagaa gccaaaagca gaaggctcca atatgaacaa gataaatcta tcttcaaaga   1140

catattagaa gttgggaaaa taattcatgt gaactagaca agtgtgttaa gagtgataag   1200
```

-continued

```
taaaatgcac gtggagacaa gtgcatcccc agatctcagg gacctccccc tgcctgtcac   1260
ctggggagtg agaggacagg atagtgcatg ttctttgtct ctgaattttt agttatatgt   1320
gctgtaatgt tgctctgagg aagcccctgg aaagtctatc ccaacatatc cacatcttat   1380
attccacaaa ttaagctgta gtatgtaccc taagacgctg ctaattgact gccacttcgc   1440
aactcagggg cggctgcatt ttagtaatgg gtcaaatgat tcacttttta tgatgcttcc   1500
aaaggtgcct tggcttctct tcccaactga caaatgccaa agttgagaaa aatgatcata   1560
attttagcat aaacagagca gtcggcgaca ccgattttat aaataaactg agcaccttct   1620
ttttaaacaa acaaatgcgg gtttatttct cagatgatgt tcatccgtga atggtccagg   1680
gaaggacctt tcaccttgac tatatggcat tatgtcatca caagctctga ggcttctcct   1740
ttccatcctg cgtggacagc taagacctca gttttcaata gcatctagag cagtgggact   1800
cagctggggt gatttcgccc cccatctccg ggggaatgtc tgaagacaat tttggttacc   1860
tcaatgaggg agtggaggag gatacagtgc tactaccaac tagtggataa aggccaggga   1920
tgctgctcaa cctcctacca tgtacaggac gtctccccat tacaactacc caatccgaag   1980
tgtcaactgt gtcaggacta agaaaccctg gttttgagta gaaaagggcc tggaaagagg   2040
ggagccaaca aatctgtctg cttcctcaca ttagtcattg gcaaataagc attctgtctc   2100
tttggctgct gcctcagcac agagagccag aactctatcg ggcaccagga taacatctct   2160
cagtgaacag agttgacaag gcctatggga aatgcctgat gggattatct tcagcttgtt   2220
gagcttctaa gtttctttcc cttcattcta ccctgcaagc caagttctgt aagagaaatg   2280
cctgagttct agctcaggtt ttcttactct gaatttagat ctccagaccc ttcctggcca   2340
caattcaaat taaggcaaca aacatatacc ttccatgaag cacacacaga cttttgaaag   2400
caaggacaat gactgcttga attgaggcct tgaggaatga agctttgaag gaaaagaata   2460
ctttgtttcc agccccottc ccacactctt catgtgttaa ccactgcctt cctggacctt   2520
ggagccacgg tgactgtatt acatgttgtt atagaaaact gattttagag ttctgatcgt   2580
tcaagagaat gattaaatat acatttccta caccaaaaaa aaaaaaa                 2627
```

```
<210> SEQ ID NO 392
<211> LENGTH: 309
<212> TYPE: PRT
<213> ORGANISM: Homo sapiens

<400> SEQUENCE: 392

His Ala Ser Ala His Ala Ser Gly Arg Gln Arg Gln Leu His Ser Ala
                5                   10                  15

Ser Thr Gln Ile Arg Trp Glu Pro Ser Pro Ala Met Ala Ser Leu Gly
            20                  25                  30

Gln Ile Leu Phe Trp Ser Ile Ile Ser Ile Ile Ile Ile Leu Ala Gly
        35                  40                  45

Ala Ile Ala Leu Ile Ile Gly Phe Gly Ile Ser Gly Arg His Ser Ile
    50                  55                  60

Thr Val Thr Thr Val Ala Ser Ala Gly Asn Ile Gly Glu Asp Gly Ile
65                  70                  75                  80

Leu Ser Cys Thr Phe Glu Pro Asp Ile Lys Leu Ser Asp Ile Val Ile
                85                  90                  95

Gln Trp Leu Lys Glu Gly Val Leu Gly Leu Val His Glu Phe Lys Glu
            100                 105                 110

Gly Lys Asp Glu Leu Ser Glu Gln Asp Glu Met Phe Arg Gly Arg Thr
```

-continued

```
        115                 120                 125

Ala Val Phe Ala Asp Gln Val Ile Val Gly Asn Ala Ser Leu Arg Leu
    130                 135                 140

Lys Asn Val Gln Leu Thr Asp Ala Gly Thr Tyr Lys Cys Tyr Ile Ile
145                 150                 155                 160

Thr Ser Lys Gly Lys Gly Asn Ala Asn Leu Glu Tyr Lys Thr Gly Ala
                165                 170                 175

Phe Ser Met Pro Glu Val Asn Val Asp Tyr Asn Ala Ser Ser Glu Thr
            180                 185                 190

Leu Arg Cys Glu Ala Pro Arg Trp Phe Pro Gln Pro Thr Val Val Trp
        195                 200                 205

Ala Ser Gln Val Asp Gln Gly Ala Asn Phe Ser Glu Val Ser Asn Thr
    210                 215                 220

Ser Phe Glu Leu Asn Ser Glu Asn Val Thr Met Lys Val Val Ser Val
225                 230                 235                 240

Leu Tyr Asn Val Thr Ile Asn Asn Thr Tyr Ser Cys Met Ile Glu Asn
                245                 250                 255

Asp Ile Ala Lys Ala Thr Gly Asp Ile Lys Val Thr Glu Ser Glu Ile
            260                 265                 270

Lys Arg Arg Ser His Leu Gln Leu Leu Asn Ser Lys Ala Ser Leu Cys
        275                 280                 285

Val Ser Ser Phe Phe Ala Ile Ser Trp Ala Leu Leu Pro Leu Ser Pro
    290                 295                 300

Tyr Leu Met Leu Lys
305


<210> SEQ ID NO 393
<211> LENGTH: 282
<212> TYPE: PRT
<213> ORGANISM: Homo sapiens

<400> SEQUENCE: 393

Met Ala Ser Leu Gly Gln Ile Leu Phe Trp Ser Ile Ile Ser Ile Ile
                  5                  10                  15

Ile Ile Leu Ala Gly Ala Ile Ala Leu Ile Ile Gly Phe Gly Ile Ser
            20                  25                  30

Gly Arg His Ser Ile Thr Val Thr Thr Val Ala Ser Ala Gly Asn Ile
        35                  40                  45

Gly Glu Asp Gly Ile Leu Ser Cys Thr Phe Glu Pro Asp Ile Lys Leu
     50                  55                  60

Ser Asp Ile Val Ile Gln Trp Leu Lys Glu Gly Val Leu Gly Leu Val
 65                  70                  75                  80

His Glu Phe Lys Glu Gly Lys Asp Glu Leu Ser Glu Gln Asp Glu Met
                 85                  90                  95

Phe Arg Gly Arg Thr Ala Val Phe Ala Asp Gln Val Ile Val Gly Asn
            100                 105                 110

Ala Ser Leu Arg Leu Lys Asn Val Gln Leu Thr Asp Ala Gly Thr Tyr
        115                 120                 125

Lys Cys Tyr Ile Ile Thr Ser Lys Gly Lys Gly Asn Ala Asn Leu Glu
    130                 135                 140

Tyr Lys Thr Gly Ala Phe Ser Met Pro Glu Val Asn Val Asp Tyr Asn
145                 150                 155                 160

Ala Ser Ser Glu Thr Leu Arg Cys Glu Ala Pro Arg Trp Phe Pro Gln
                165                 170                 175
```

-continued

```
Pro Thr Val Val Trp Ala Ser Gln Val Asp Gln Gly Ala Asn Phe Ser
            180                 185                 190

Glu Val Ser Asn Thr Ser Phe Glu Leu Asn Ser Glu Asn Val Thr Met
        195                 200                 205

Lys Val Val Ser Val Leu Tyr Asn Val Thr Ile Asn Asn Thr Tyr Ser
    210                 215                 220

Cys Met Ile Glu Asn Asp Ile Ala Lys Ala Thr Gly Asp Ile Lys Val
225                 230                 235                 240

Thr Glu Ser Glu Ile Lys Arg Arg Ser His Leu Gln Leu Leu Asn Ser
                245                 250                 255

Lys Ala Ser Leu Cys Val Ser Ser Phe Phe Ala Ile Ser Trp Ala Leu
            260                 265                 270

Leu Pro Leu Ser Pro Tyr Leu Met Leu Lys
        275                 280
```